United States Patent
Lee et al.

(10) Patent No.: US 11,578,076 B2
(45) Date of Patent: Feb. 14, 2023

(54) HETEROCYCLIC COMPOUND AND ORGANIC LIGHT EMITTING DEVICE USING THE SAME

(71) Applicant: LG CHEM, LTD., Seoul (KR)

(72) Inventors: Jung Ha Lee, Daejeon (KR); Dong Hoon Lee, Daejeon (KR); Tae Yoon Park, Daejeon (KR); Seong Mi Cho, Daejeon (KR); Dong Uk Heo, Daejeon (KR); Min Woo Jung, Daejeon (KR)

(73) Assignee: LG CHEM, LTD., Seoul (KR)

( * ) Notice: Subject to any disclaimer, the term of this patent is extended or adjusted under 35 U.S.C. 154(b) by 681 days.

(21) Appl. No.: 16/490,014

(22) PCT Filed: Jul. 20, 2018

(86) PCT No.: PCT/KR2018/008233
§ 371 (c)(1),
(2) Date: Aug. 29, 2019

(87) PCT Pub. No.: WO2019/017731
PCT Pub. Date: Jan. 24, 2019

(65) Prior Publication Data
US 2020/0010476 A1 Jan. 9, 2020

(30) Foreign Application Priority Data

Jul. 20, 2017 (KR) .......... 10-2017-0092174
Jul. 19, 2018 (KR) .......... 10-2018-0084348

(51) Int. Cl.
*C07D 491/048* (2006.01)
*C07D 209/82* (2006.01)
(Continued)

(52) U.S. Cl.
CPC ....... *C07D 491/048* (2013.01); *C07D 209/82* (2013.01); *C07D 307/91* (2013.01);
(Continued)

(58) Field of Classification Search
CPC .. C07D 209/82; C07D 307/91; C07D 333/52; C07D 407/14; C07D 409/14;
(Continued)

(56) References Cited

U.S. PATENT DOCUMENTS

2004/0251816 A1 12/2004 Leo et al.
2011/0095282 A1 4/2011 Pflumm et al.
(Continued)

FOREIGN PATENT DOCUMENTS

CN 102077384 A 5/2011
CN 104370904 A 2/2015
(Continued)

*Primary Examiner* — Dawn L Garrett
(74) *Attorney, Agent, or Firm* — Dentons US LLP

(57) ABSTRACT

Disclosed are a heterocyclic compound represented by Formula 1 and an organic light emitting device using the same. The heterocyclic compound is used as a material for hole injection layer, hole transport layer, hole injection and transport layer, light emission layer, electron transport layer, or electron injection layer of the organic light emitting device and provides improved efficiency, low driving voltage, and improved lifetime characteristic.

[Formula 1]

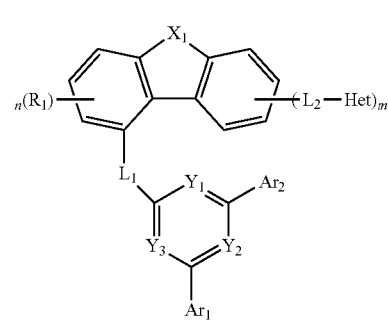

14 Claims, 1 Drawing Sheet

(51) Int. Cl.
| | |
|---|---|
| *C07D 307/91* | (2006.01) |
| *C07D 333/52* | (2006.01) |
| *C07D 495/04* | (2006.01) |
| *H01L 51/00* | (2006.01) |
| *C07D 407/14* | (2006.01) |
| *C07D 409/14* | (2006.01) |
| *C07D 471/04* | (2006.01) |
| *C07D 487/04* | (2006.01) |
| *C07D 413/14* | (2006.01) |
| *C07D 417/14* | (2006.01) |
| *H01L 51/50* | (2006.01) |

(52) U.S. Cl.
CPC ......... *C07D 333/52* (2013.01); *C07D 407/14* (2013.01); *C07D 409/14* (2013.01); *C07D 413/14* (2013.01); *C07D 417/14* (2013.01); *C07D 471/04* (2013.01); *C07D 487/04* (2013.01); *C07D 495/04* (2013.01); *H01L 51/0052* (2013.01); *H01L 51/0067* (2013.01); *H01L 51/0071* (2013.01); *H01L 51/0072* (2013.01); *H01L 51/0073* (2013.01); *H01L 51/0074* (2013.01); *H01L 51/508* (2013.01); *H01L 51/5016* (2013.01); *H01L 51/5024* (2013.01); *H01L 51/5072* (2013.01); *H01L 51/5092* (2013.01)

(58) Field of Classification Search
CPC .. C07D 413/14; C07D 417/14; C07D 471/04; C07D 487/04; C07D 491/048; C07D 495/04; H01L 2251/5384; H01L 51/0052; H01L 51/0059; H01L 51/006; H01L 51/0067; H01L 51/0071; H01L 51/0072; H01L 51/0073; H01L 51/0074; H01L 51/0085; H01L 51/5016; H01L 51/5024; H01L 51/5072; H01L 51/508; H01L 51/5092
See application file for complete search history.

(56) References Cited

U.S. PATENT DOCUMENTS

| | | |
|---|---|---|
| 2011/0309343 A1 | 12/2011 | Langer et al. |
| 2014/0291645 A1 | 10/2014 | Inoue et al. |
| 2014/0346483 A1 | 11/2014 | Yu et al. |
| 2015/0207082 A1 | 7/2015 | Dyatkin et al. |
| 2016/0093808 A1 | 3/2016 | Adamovich et al. |
| 2016/0111657 A1 | 4/2016 | Lee et al. |
| 2016/0226001 A1 | 8/2016 | Parham et al. |
| 2016/0276603 A1 | 9/2016 | Beers et al. |
| 2016/0308142 A1 | 10/2016 | Kim et al. |
| 2016/0329502 A1 | 11/2016 | Dyatkin et al. |
| 2016/0351826 A1 | 12/2016 | Kim et al. |
| 2017/0012216 A1 | 1/2017 | Kim et al. |
| 2017/0025618 A1 | 1/2017 | Zheng et al. |
| 2017/0054087 A1 | 2/2017 | Zeng et al. |
| 2017/0179403 A1* | 6/2017 | Kim ................ H01L 51/0058 |
| 2017/0186965 A1 | 6/2017 | Parham et al. |
| 2017/0186971 A1* | 6/2017 | Kanamoto ......... C07D 491/048 |
| 2017/0200903 A1 | 7/2017 | Park et al. |
| 2017/0207399 A1 | 7/2017 | Parham et al. |
| 2017/0237017 A1 | 8/2017 | Parham et al. |
| 2018/0037546 A1 | 2/2018 | Sugino et al. |
| 2018/0162843 A1 | 6/2018 | Parham et al. |
| 2018/0166641 A1 | 6/2018 | Inoue et al. |
| 2020/0058877 A1 | 2/2020 | Cha et al. |
| 2020/0144511 A1 | 5/2020 | Bae et al. |
| 2020/0259098 A1 | 8/2020 | Lee et al. |

FOREIGN PATENT DOCUMENTS

| | | |
|---|---|---|
| CN | 105189455 A | 12/2015 |
| CN | 105934436 A | 9/2016 |
| CN | 106459018 A | 2/2017 |
| CN | 106565433 A | 4/2017 |
| CN | 106661006 A | 5/2017 |
| CN | 108250189 A | 7/2018 |
| CN | 108884086 A | 11/2018 |
| CN | 108884087 A | 11/2018 |
| CN | 110268036 A | 9/2019 |
| CN | 110313078 A | 10/2019 |
| CN | 110869372 A | 3/2020 |
| CN | 111183204 A | 5/2020 |
| JP | 2013-131518 A | 7/2013 |
| JP | 5831654 B1 | 12/2015 |
| JP | 6128119 B2 | 5/2017 |
| JP | 2017-098561 A | 6/2017 |
| JP | 2017-107992 A | 6/2017 |
| KR | 10-2010-0007143 A | 1/2010 |
| KR | 10-2010-0077675 A | 7/2010 |
| KR | 10-2010-0118690 A | 11/2010 |
| KR | 10-2012-0033017 A | 4/2012 |
| KR | 10-2013-0036048 A | 4/2013 |
| KR | 10-2013-0069431 A | 6/2013 |
| KR | 10-2013-0073537 A | 7/2013 |
| KR | 10-2014-0065863 A | 5/2014 |
| KR | 10-2015-0074603 A | 7/2015 |
| KR | 10-2015-0084657 A | 7/2015 |
| KR | 10-2015-0121394 A | 10/2015 |
| KR | 10-2015-0129282 A | 11/2015 |
| KR | 10-2015-0136942 A | 12/2015 |
| KR | 10-2016-0026661 A | 3/2016 |
| KR | 10-2016-0028524 A | 3/2016 |
| KR | 1020160045507 A | 4/2016 |
| KR | 10-2017-0003502 A | 1/2017 |
| KR | 10-2017-0039209 A | 4/2017 |
| KR | 10-2018-0055698 A | 5/2018 |
| KR | 10-1857703 B1 | 5/2018 |
| KR | 1020180068869 A | 6/2018 |
| KR | 10-2018-0133376 A | 12/2018 |
| WO | 2003/012890 A2 | 2/2003 |
| WO | 2006/128800 A1 | 12/2006 |
| WO | 2009/069442 A1 | 6/2009 |
| WO | 2010/015306 A1 | 2/2010 |
| WO | 2010/126270 A1 | 11/2010 |
| WO | 2011/126224 A1 | 10/2011 |
| WO | 2011/157790 A1 | 12/2011 |
| WO | 2011/158204 A1 | 12/2011 |
| WO | 2013/168534 A1 | 11/2013 |
| WO | 2014/042420 A1 | 3/2014 |
| WO | 2014/123369 A1 | 8/2014 |
| WO | 2014/178532 A1 | 11/2014 |
| WO | 2015/014434 A1 | 2/2015 |
| WO | 2015/036080 A1 | 3/2015 |
| WO | 2015/083974 A1 | 6/2015 |
| WO | 2015/169412 A1 | 11/2015 |
| WO | 2016/012075 A1 | 1/2016 |
| WO | 2016/013735 A1 | 1/2016 |
| WO | 2016/015810 A1 | 2/2016 |
| WO | 2016/023608 A1 | 2/2016 |
| WO | 2016/027938 A1 | 2/2016 |
| WO | 2016/129672 A1 | 8/2016 |
| WO | 2016/198144 A1 | 12/2016 |
| WO | 2017/016630 A1 | 2/2017 |
| WO | 2017/178311 A1 | 10/2017 |

* cited by examiner

[FIG. 1]
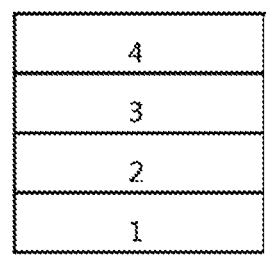
[FIG. 2]
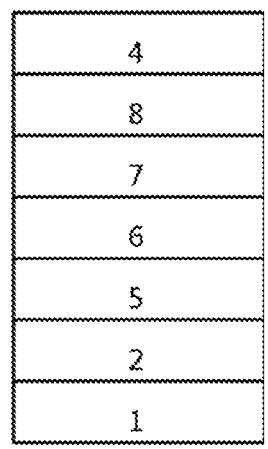

HETEROCYCLIC COMPOUND AND ORGANIC LIGHT EMITTING DEVICE USING THE SAME

CROSS-REFERENCE TO RELATED APPLICATION(S)

This application is a National Phase entry pursuant to 35 U.S.C. § 371 of PCT/KR2018/008233 filed on Jul. 20, 2018, and claims priority to and the benefit of Korean Patent Application No. 10-2017-0092174 filed on Jul. 20, 2017 and Korean Patent Application No. 10-2018-0084348 filed on Jul. 19, 2018 with the Korean Intellectual Property Office, the disclosures of which are incorporated herein by reference in their entirety.

TECHNICAL FIELD

The present disclosure relates to a novel heterocyclic compound and an organic light emitting device including the same.

BACKGROUND ART

In general, an organic light emitting phenomenon refers to a phenomenon where electrical energy is converted into light energy by an organic material. The organic light emitting device using the organic light emitting phenomenon has characteristics such as a wide viewing angle, excellent contrast, a fast response time, and excellent luminance, driving voltage, and response speed, and thus many studies about it have proceeded.

The organic light emitting device generally has a structure which includes an anode, a cathode, and an organic material layer interposed between the anode and the cathode. The organic material layer may has a multilayered structure that includes different materials in order to enhance efficiency and stability of the organic light emitting device, and for example, the organic material layer may be formed of a hole injection layer, a hole transport layer, a light emitting layer, an electron transport layer, an electron injection layer, and the like. In the structure of the organic light emitting device, if a voltage is applied between two electrodes, the holes are injected from an anode into the organic material layer and the electrons are injected from the cathode into the organic material layer, and when the injected holes and the electrons meet each other, an exciton is formed, and light is emitted when the exciton falls to a ground state.

There is a continuing need for the development of new materials for the organic materials used in such organic light emitting devices.

PRIOR ART LITERATURE

Patent Literature (Patent Literature 0001) Korean Patent Laid-open Publication No. 10-2013-073537

DETAILED DESCRIPTION OF THE INVENTION

Technical Problem

It is an object of the present disclosure to provide a novel heterocyclic compound and an organic light emitting device including the same.

Technical Solution

In order to achieve the above object, the present disclosure provides a compound represented by the following Formula 1.

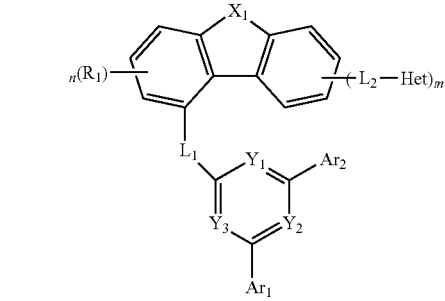

[Formula 1]

In Formula 1 above,
$X_1$ is O or S,
$R_1$ is hydrogen or a substituted or unsubstituted $C_{1-60}$ alkyl,
$L_1$ and $L_2$ are each independently a direct bond or a substituted or unsubstituted $C_{6-60}$ arylene,
$Y_1$, $Y_2$, and $Y_3$ are each independently N or $CR_2$, provided that at least one of them is N, $R_2$ is hydrogen or a substituted or unsubstituted $C_{1-60}$ alkyl,
$Ar_1$ and $Ar_2$ are each independently a substituted or unsubstituted $C_{6-60}$ aryl or a substituted or unsubstituted $C_{5-60}$ heteroaryl containing at least one of N, O, and S, which can be combined with adjacent $Y_1$, $Y_2$, and $Y_3$ to form a ring,
each Het is independently a compound represented by the following Formula 1-1:

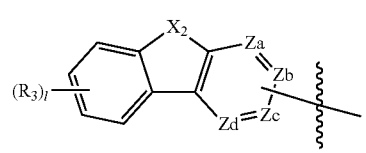

[Formula 1-1]

wherein, in Formula 1-1,
$X_2$ is O, S, or CR'R'',
R' and R'' are each independently hydrogen, or a substituted or unsubstituted $C_{1-60}$ alkyl,
Za, Zb, Zc, and Zd are each independently N or $CR'_3$ and at least two among Za, Zb, Zc, and Zd are N, $R_3$ and $R'_3$ are each independently hydrogen, a substituted or unsubstituted $C_{1-60}$ alkyl, a substituted or unsubstituted $C_{6-60}$ aryl, or a substituted or unsubstituted $C_{5-60}$ heteroaryl containing at least one of N, O, and S,
n is independently 0 or 1, and
m and l are independently 1 or 2.

The present disclosure also provides an organic light emitting device including: a first electrode; a second electrode provided at a side opposite to the first electrode; and at least one layer of the organic material layers provided between the first electrode and the second electrode, wherein the at least one layer of the organic material layers includes the compound of the present disclosure described above.

Advantageous Effects

The compound represented by Formula 1 described above can be used as a material of an organic material layer of an organic light emitting device, and can allow improvement of the efficiency, the low driving voltage, and/or the lifetime characteristic when applied to the organic light emitting device. In particular, the compound represented by Formula 1 can be used as a material for hole injection, hole transport, hole injection and transport, light emission, electron transport, or electron injection.

BRIEF DESCRIPTION OF DRAWINGS

FIG. 1 shows an example of an organic light emitting device including a substrate 1, an anode 2, a light emitting layer 3, and a cathode 4.

FIG. 2 shows an example of an organic light emitting device including a substrate 1, an anode 2, a hole injection layer 5, a hole transport layer 6, a light emitting layer 7, an electron transport layer 8, and a cathode 4.

DETAILED DESCRIPTION OF THE EMBODIMENTS

Hereinafter, the present disclosure will be described in more detail.

The present disclosure provides a compound represented by Formula 1 as follows.

A compound represented by the following Formula

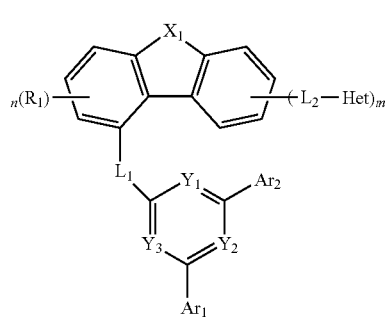

[Formula 1]

wherein, in Formula 1 above, $X_1$ is O or S, $R_1$ is hydrogen or a substituted or unsubstituted $C_{1-60}$ alkyl, $L_1$ and $L_2$ are each independently a direct bond or a substituted or unsubstituted $C_{6-60}$ arylene, $Y_1$, $Y_2$, and $Y_3$ are each independently N or $CR_2$, provided that at least one of them is N, $R_2$ is hydrogen or a substituted or unsubstituted $C_{1-60}$ alkyl, $Ar_1$ and $Ar_2$ are each independently a substituted or unsubstituted $C_{6-60}$ aryl or a substituted or unsubstituted $C_{5-60}$ heteroaryl containing at least one of N, O, and S, which can be combined with adjacent $Y_1$, $Y_2$, and $Y_3$ to form a ring, each Het is independently a compound represented by the following Formula 1-1:

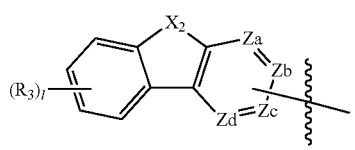

[Formula 1-1]

wherein, in Formula 1-1, $X_2$ is O, S, or CR'R'',

R' and R'' are each independently hydrogen, or a substituted or unsubstituted $C_{1-60}$ alkyl, Za, Zb, Zc, and Zd are each independently N or $CR'_3$ and at least two among Za, Zb, Zc, and Zd are N, $R_3$ and $R'_3$ are each independently hydrogen, a substituted or unsubstituted $C_{1-60}$ alkyl, a substituted or unsubstituted $C_{6-60}$ aryl, or a substituted or unsubstituted $C_{5-60}$ heteroaryl containing at least one of N, O, and S, n is independently 0 or 1, and m and l are independently 1 or 2.

In the present specification,

means a bond connected to another substituent group.

As used herein, the term "substituted or unsubstituted" means that substitution is performed by one or more substituent groups selected from the group consisting of deuterium; a halogen group; a nitrile group; a nitro group; a hydroxyl group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; or a heterocyclic group containing at least one of N, O, and S atoms, or there is no substituent group, or substitution is performed by a substituent group where two or more substituent groups of the exemplified substituent groups are linked or there is no substituent group. For example, the term "substituent group where two or more substituent groups are connected" may be a biphenyl group. That is, the biphenyl group may be an aryl group, or may be interpreted as a substituent group where two phenyl groups are connected.

In the present specification, the number of carbon atoms in a carbonyl group is not particularly limited, but is preferably 1 to 40. Specifically, the carbonyl group may be compounds having the following structures, but is not limited thereto.

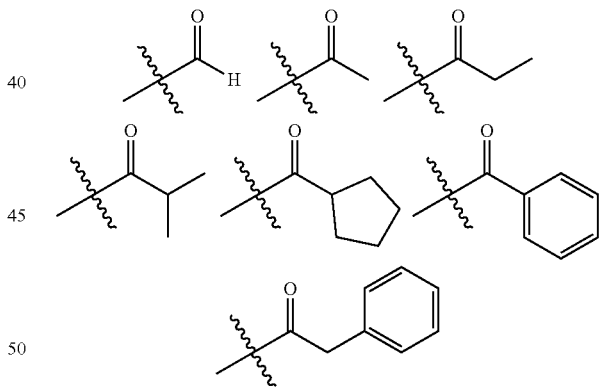

In the present specification, the ester group may have a structure in which oxygen of the ester group may be substituted by a straight-chain, branched-chain, or cyclic alkyl group having 1 to 25 carbon atoms, or an aryl group having 6 to 25 carbon atoms. Specifically, the ester group may be compounds having the following structures, but is not limited thereto.

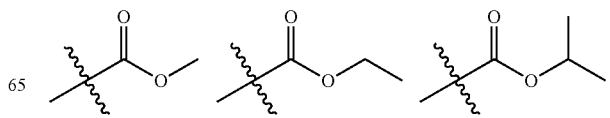

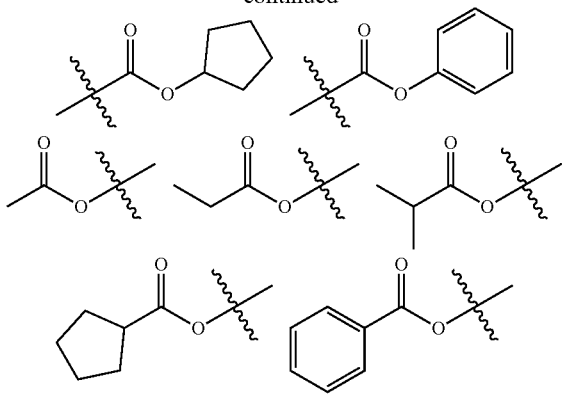

In the present specification, the number of carbon atoms in an imide group is not particularly limited, but is preferably 1 to 25. Specifically, the imide group may be compounds having the following structures, but is not limited thereto.

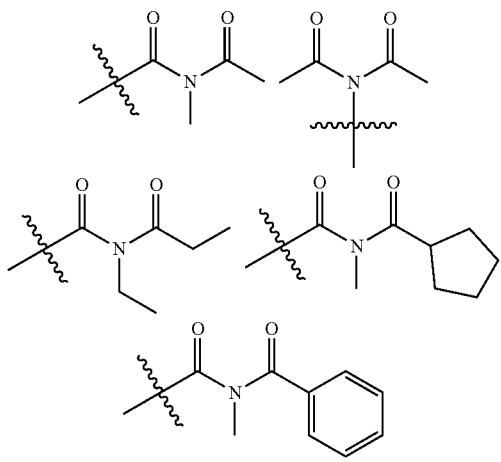

In the present specification, the silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but is not limited thereto.

In the present specification, the boron group specifically includes a trimethylboron group, a triethylboron group, a t-butyldimethylboron group, a triphenylboron group, a phenylboron group, and the like, but is not limited thereto.

In the present specification, examples of the halogen group include fluorine, chlorine, bromine, and iodine.

In the present specification, the alkyl group may be a straight chain or a branched chain, and the number of carbon atoms thereof is not particularly limited, but is preferably 1 to 40. According to one embodiment, the alkyl group has 1 to 20 carbon atoms. According to another embodiment, the alkyl group has 1 to 10 carbon atoms. According to still another embodiment, the alkyl group has 1 to 6 carbon atoms. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, the alkenyl group may be a straight chain or a branched chain, and the number of carbon atoms thereof is not particularly limited, but is preferably 2 to 40. According to one embodiment, the alkenyl group has 2 to 20 carbon atoms. According to another embodiment, the alkenyl group has 2 to 10 carbon atoms. According to still another embodiment, the alkenyl group has 2 to 6 carbon atoms. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, the cycloalkyl group is not particularly limited, but the number of carbon atoms thereof is preferably 3 to 60. According to one embodiment, the cycloalkyl group has 3 to 30 carbon atoms. According to another embodiment, the cycloalkyl group has 3 to 20 carbon atoms. According to still another embodiment, the cycloalkyl group has 3 to 6 carbon atoms. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the aryl group is not particularly limited, but preferably has 6 to 60 carbon atoms, and may be a monocyclic aryl group or a polycyclic aryl group. According to one embodiment, the aryl group has 6 to 30 carbon atoms. According to another embodiment, the aryl group has 6 to 20 carbon atoms. The aryl group may be a phenyl group, a biphenyl group, a terphenyl group, or the like as the monocyclic aryl group, but is not limited thereto. Examples of the polycyclic aryl group include a naphthyl group, an anthracenyl group, a phenanthryl group, a pyrenyl group, a perylenyl group, a chrycenyl group, a fluorenyl group, and the like, but are not limited thereto.

In the present specification, a fluorenyl group may be substituted, and two substituent groups may be combined with each other to form a spiro structure. In the case where the fluorenyl group is substituted,

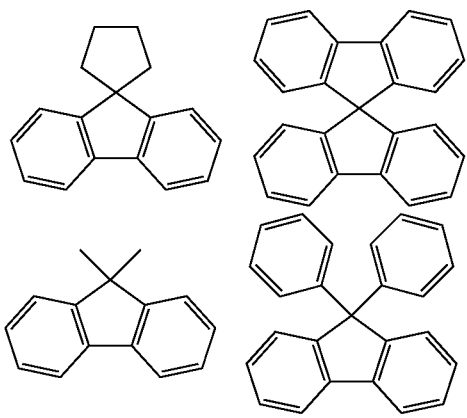

and the like can be formed. However, the structure is not limited thereto.

In the present specification, the heterocyclic group is a heterocyclic group containing at least one of O, N, Si, and S as a heteroatom, and the number of carbon atoms thereof is not particularly limited, but is preferably 2 to 60. Examples of the heterocyclic group include a thiophene group, a furan group, a pyrrole group, an imidazole group, a thiazole group, an oxazole group, an oxadiazole group, a pyridyl group, a bipyridyl group, a pyrimidyl group, a triazine group, a triazole group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, the aryl group in the aralkyl group, the aralkenyl group, the alkylaryl group, and the arylamine group is the same as the aforementioned examples of the aryl group. In the present specification, the alkyl group in the aralkyl group, the alkylaryl group, and the alkylamine group is the same as the aforementioned examples of the alkyl group. In the present specification, the heteroaryl in the heteroarylamine can be applied to the aforementioned description of the heterocyclic group. In the present specification, the alkenyl group in the aralkenyl group is the same as the aforementioned examples of the alkenyl group. In the present specification, the aforementioned description of the aryl group can be applied except that the arylene is a divalent group. In the present specification, the aforementioned description of the heterocyclic group can be applied except that the heteroarylene is a divalent group. In the present specification, the aforementioned description of the aryl group or cycloalkyl group can be applied except that the hydrocarbon ring is not a monovalent group but is formed by combining two substituent groups. In the present specification, the aforementioned description of the heterocyclic group can be applied, except that the heterocycle is not a monovalent group but is formed by combining two substituent groups.

Preferably, the compound represented by Formula 1 may be any one selected from the compounds represented by the following Formulas 2 to 6.

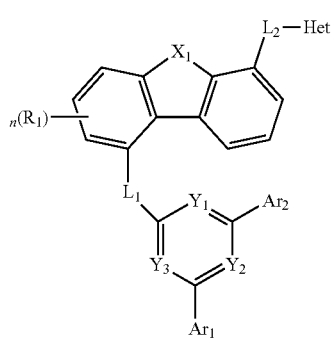

[Formula 2]

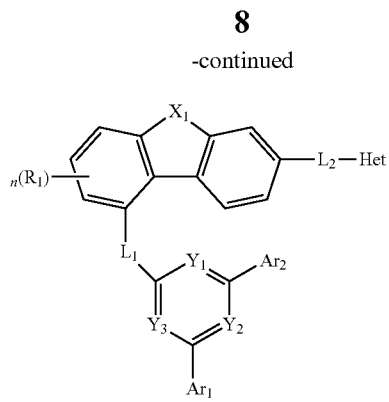

[Formula 3]

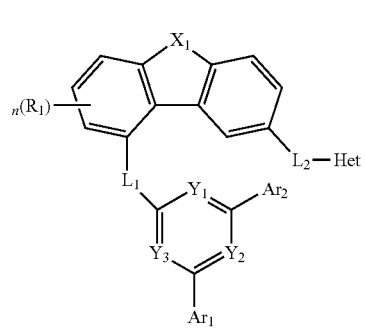

[Formula 4]

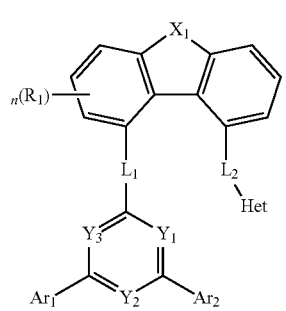

[Formula 5]

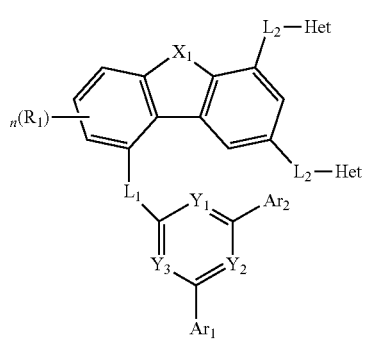

[Formula 6]

In Formulas 2 to 6 above, $X_1$, $L_1$, $L_2$, Het, $Y_1$, $Y_2$, $Y_3$, $R_1$, $Ar_1$, $Ar_2$, and n are as defined in above.

Further, more preferably, the compound of Formula 1 may be a compound of Formulas 2, 4, and 6.

Further, preferably, the compound of Formula 1 may be any one selected from compounds represented by the following Formulas 7 to 11.

[Formula 7]

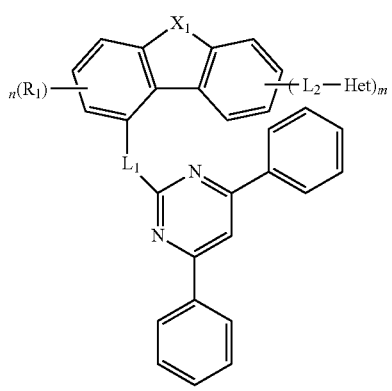

[Formula 8]

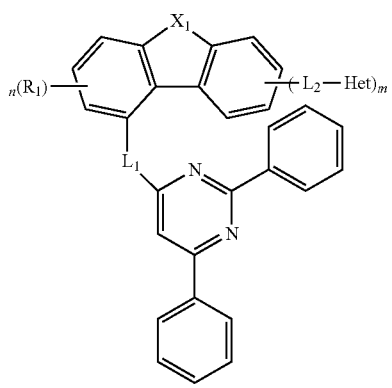

[Formula 9]

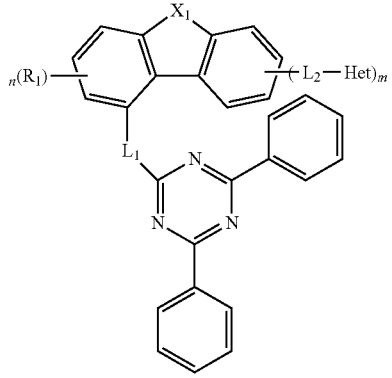

[Formula 10]

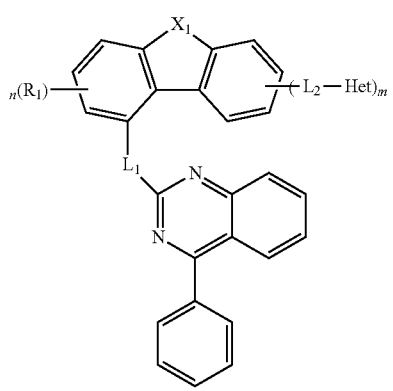

-continued

[Formula 11]

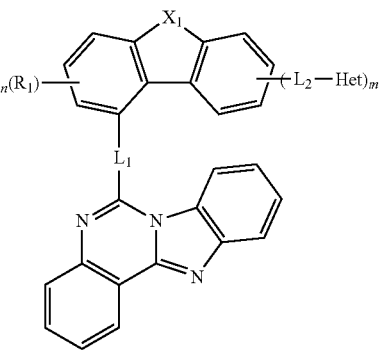

In Formulas 7 to 11 above, $X_1$, $L_1$, $L_2$, Het, $R_1$, n, and m are as defined above.

Preferably, in Formula 1, $R_1$ may be hydrogen or a substituted or unsubstituted $C_{1-10}$ alkyl, and more preferably hydrogen.

Preferably, in Formula 1, $L_1$ and $L_2$ are each independently a direct bond or

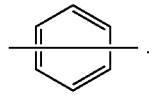

Preferably, in Formula 1, $Ar_1$ and $Ar_2$ can be combined with adjacent $Y_1$, $Y_2$, and $Y_3$ to form a ring, or may each independently be any one selected from the group consisting of the following formulas.

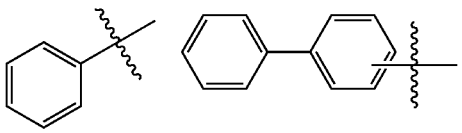

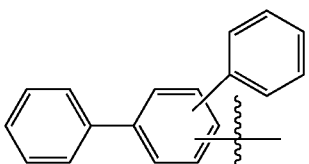

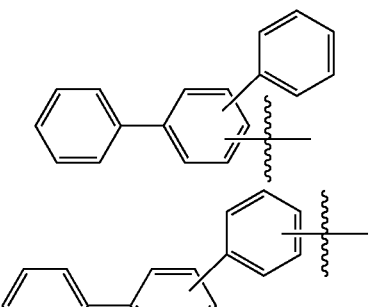

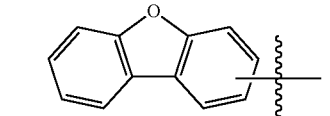

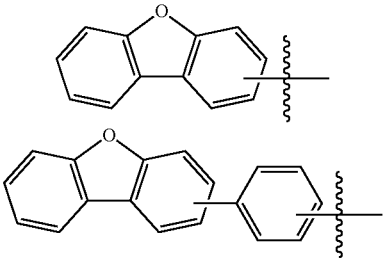

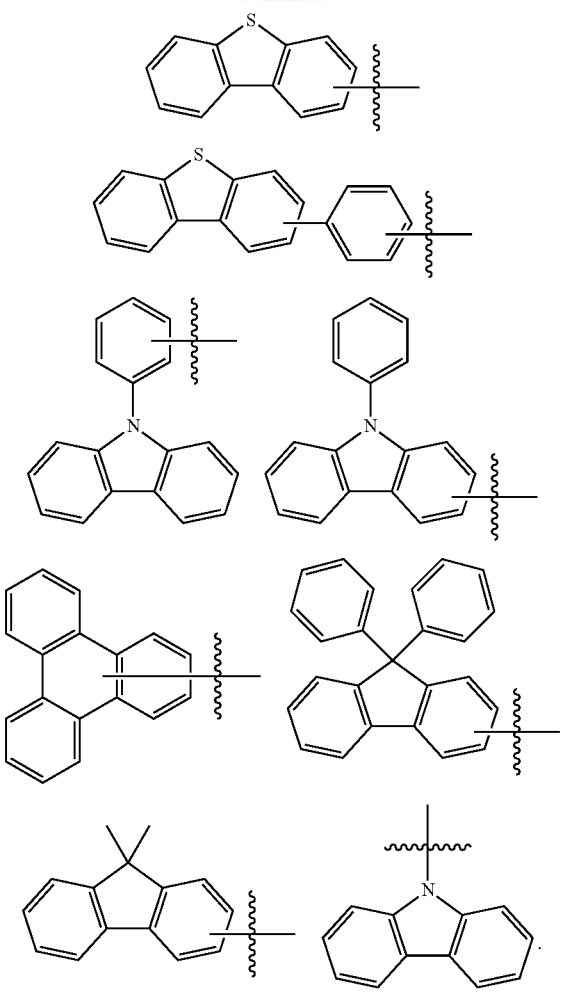
Preferably, Formula 1-1 of Het in Formula 1 may be any one selected from compounds represented by the following Formulas 1-1-1 to 1-1-4.
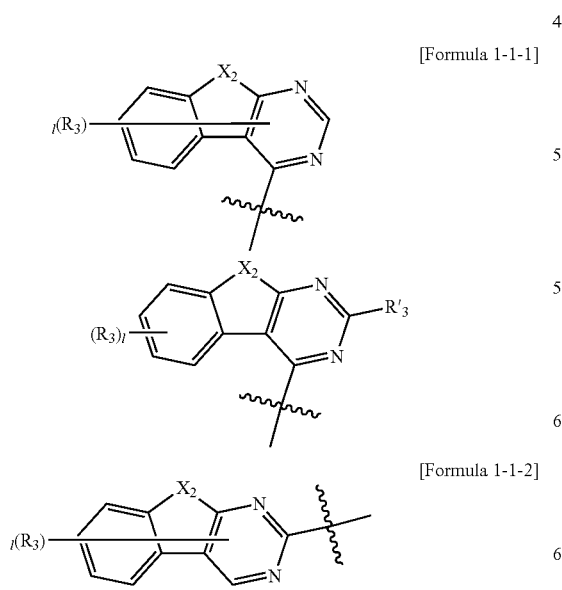
[Formula 1-1-1]
[Formula 1-1-2]
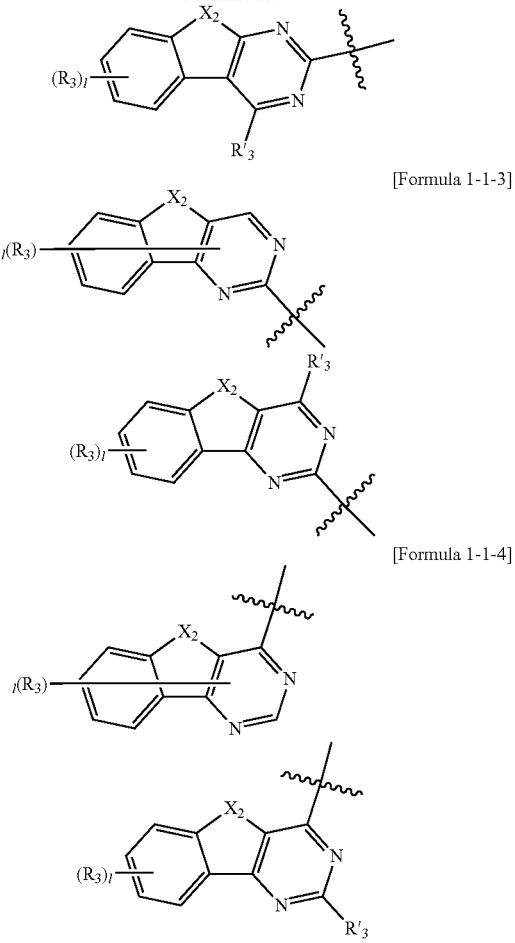
[Formula 1-1-3]
[Formula 1-1-4]
In Formulas 1-1-1 to 1-1-4 above,
$X_2$, $R'_1$, $R_3$, and l are as defined above.
Preferably, the compound represented by Formula 1-1 may be any one selected from the following formulas:
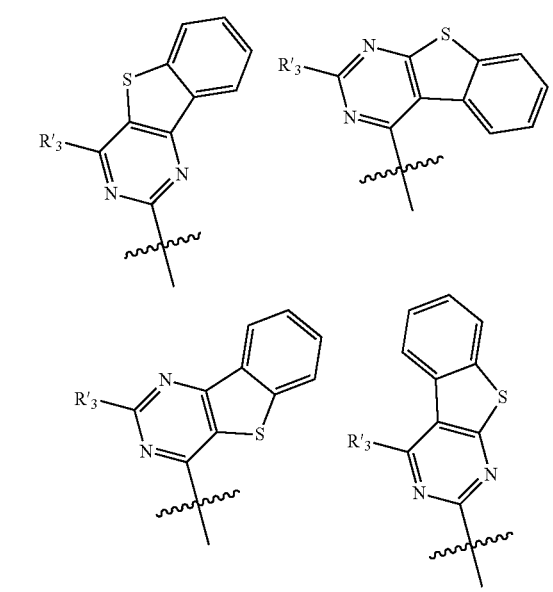

-continued
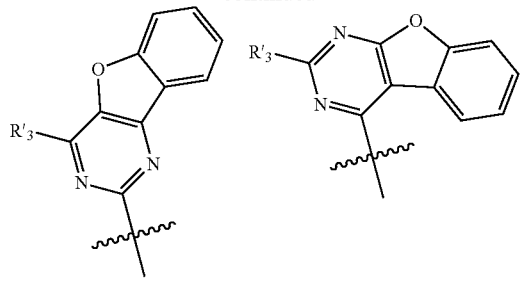
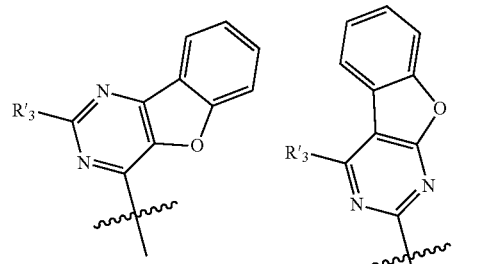
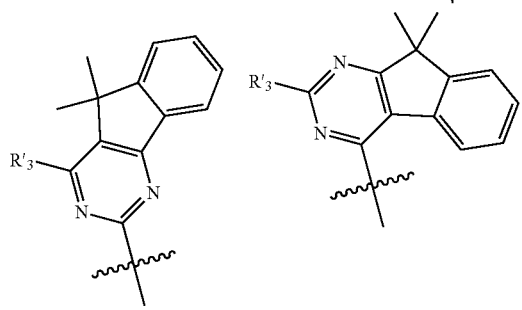

wherein
R'$_3$ and l are as defined above.
Preferably, R$_3$ may be hydrogen or any one selected from the group consisting of the following formulas.
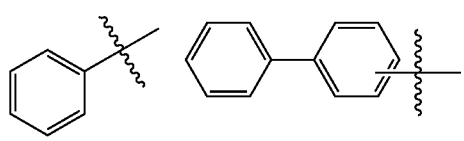
-continued
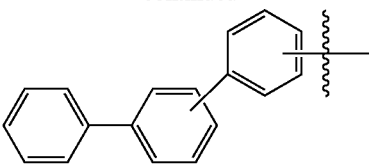
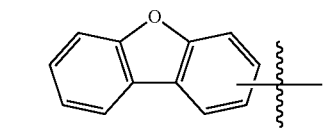
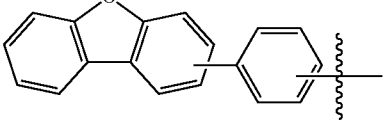
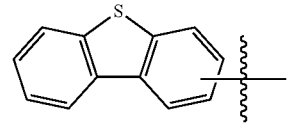
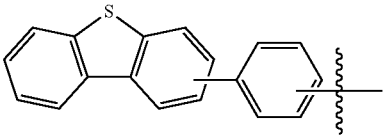
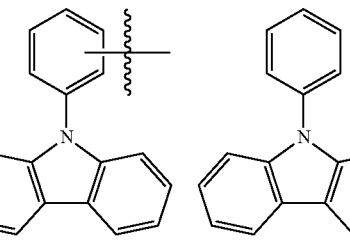
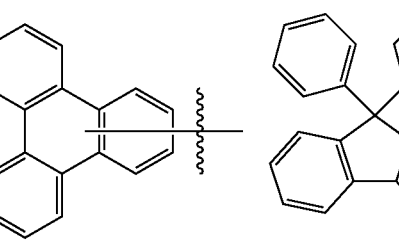
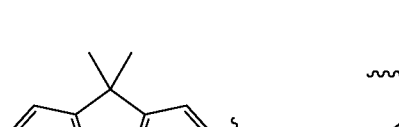
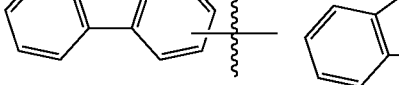
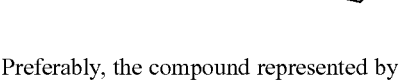
Preferably, the compound represented by Formula 1 may be any one selected from the group consisting of the following formulas.

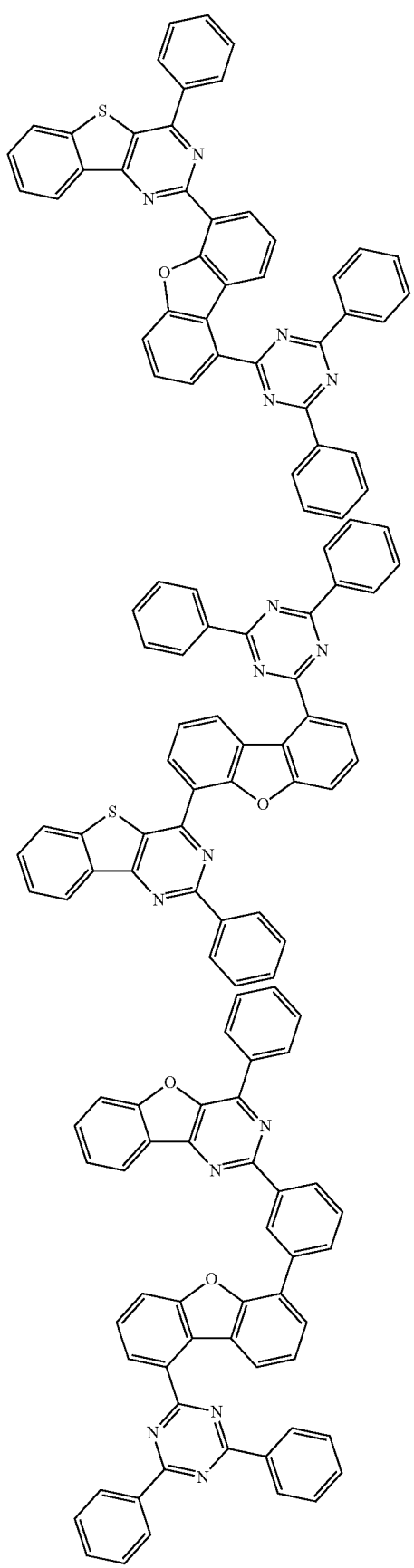
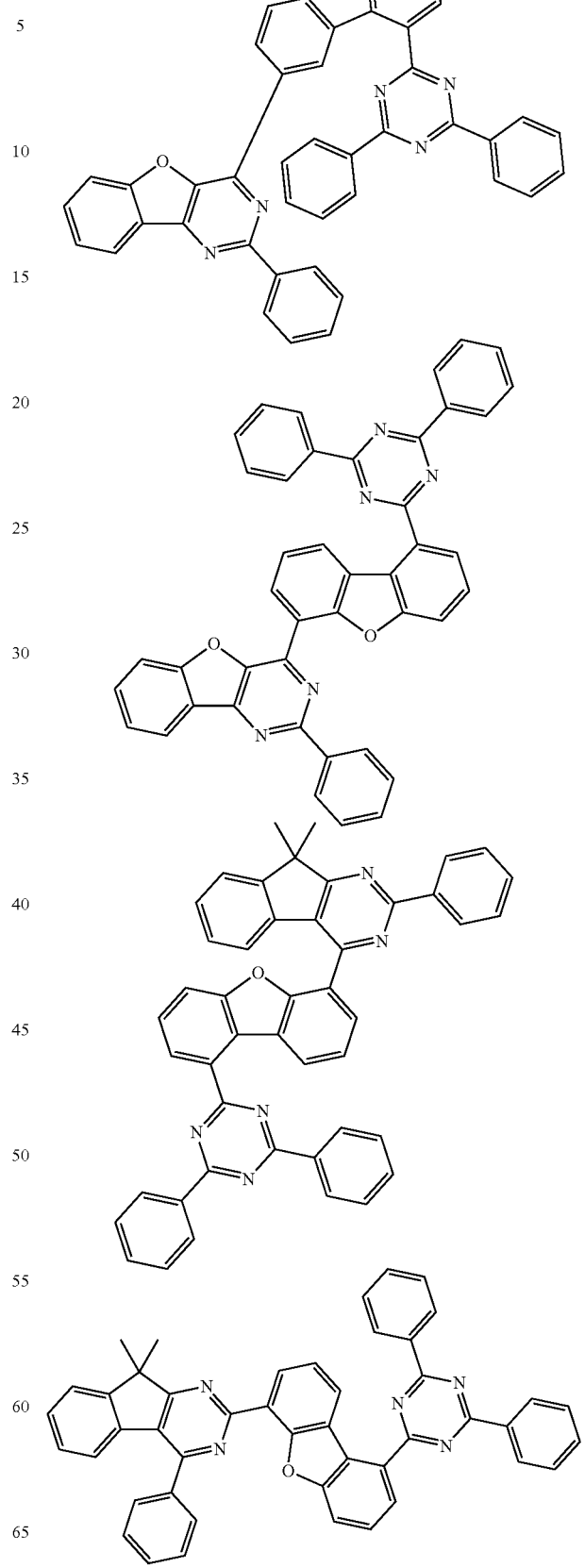

-continued
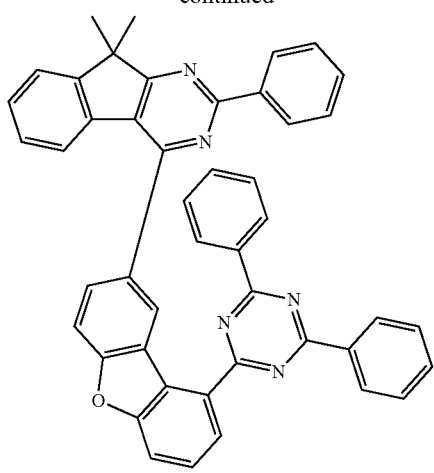
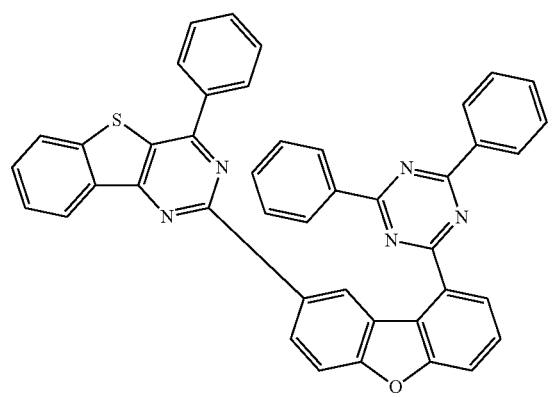
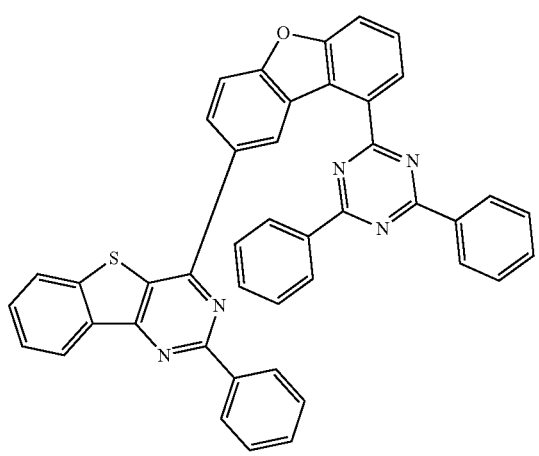
-continued
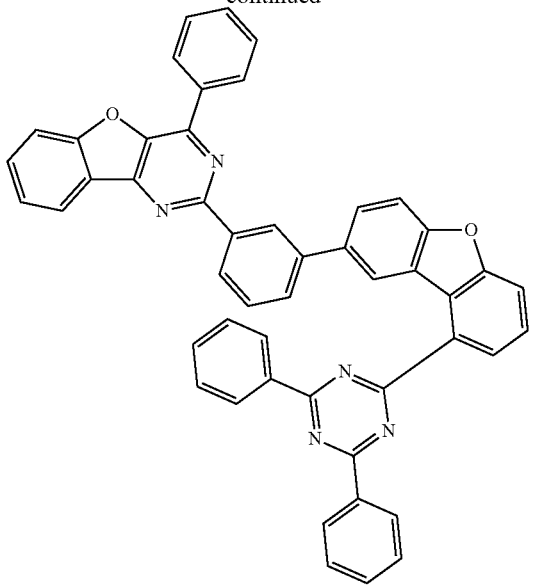
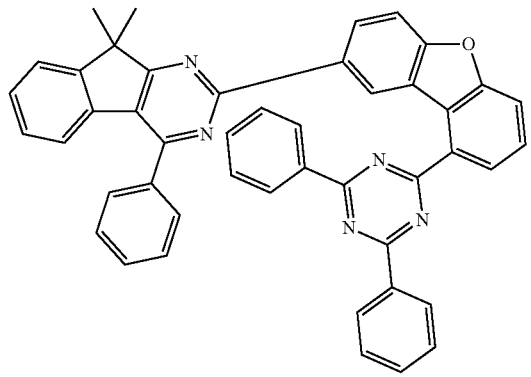
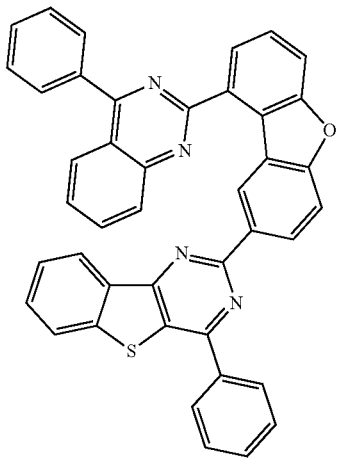

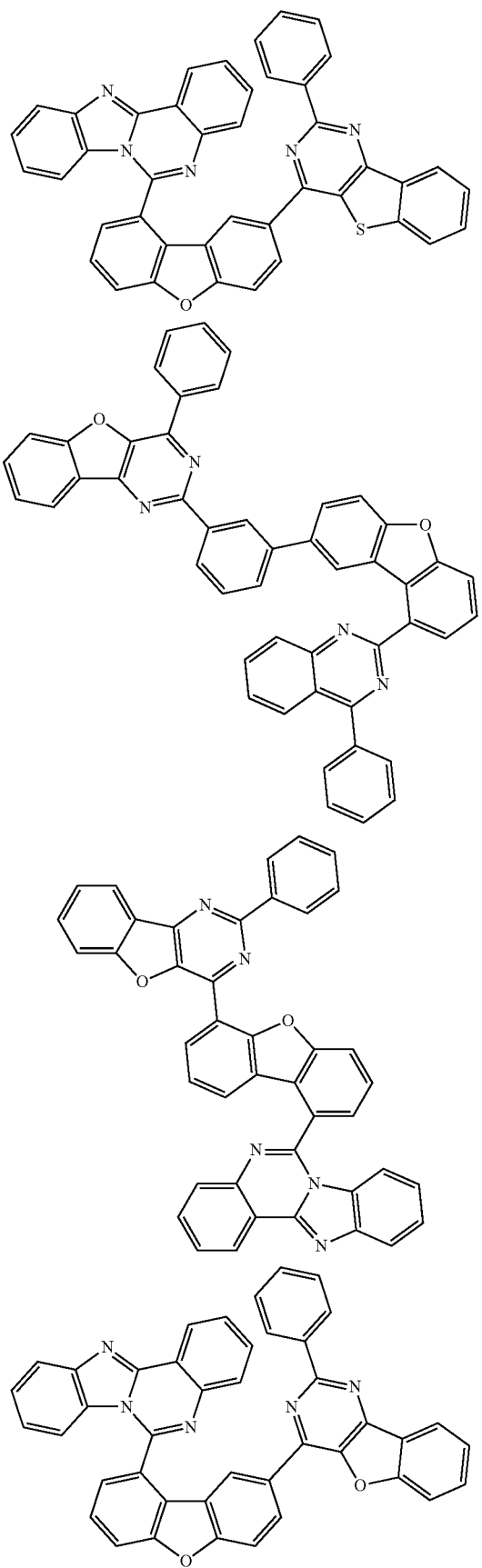
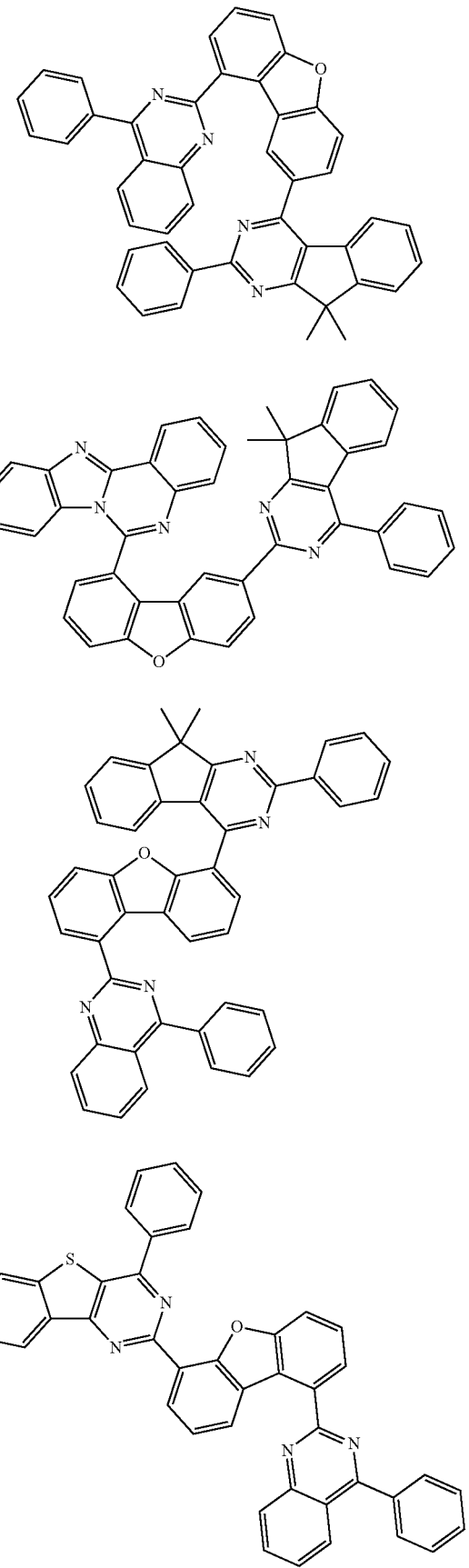

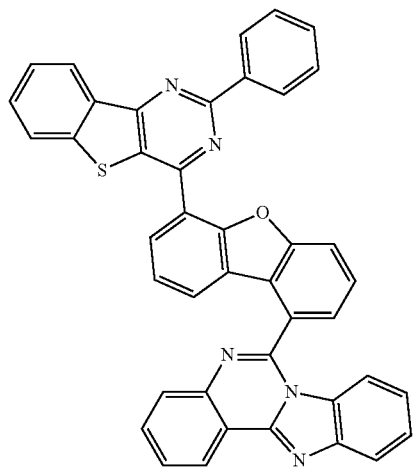
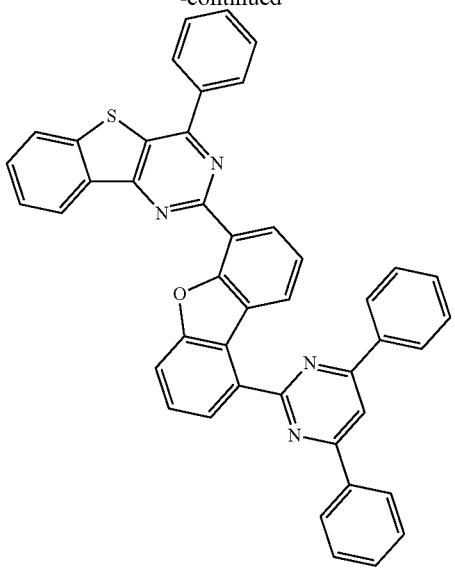
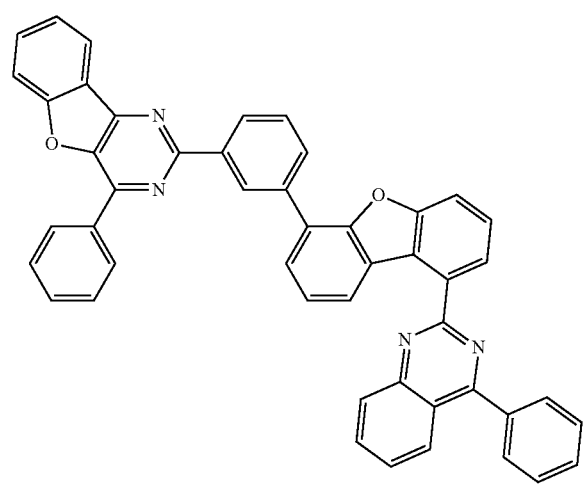
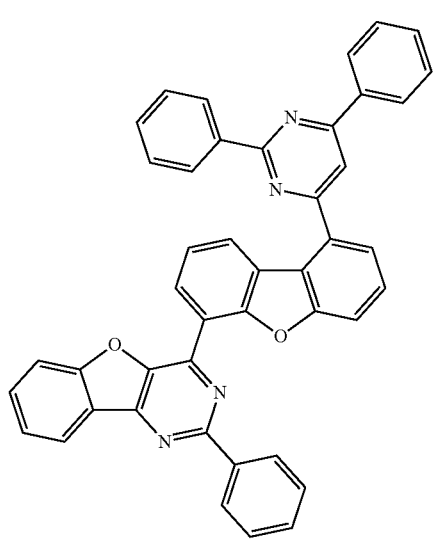
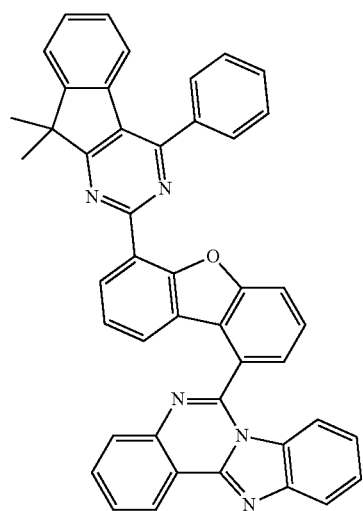
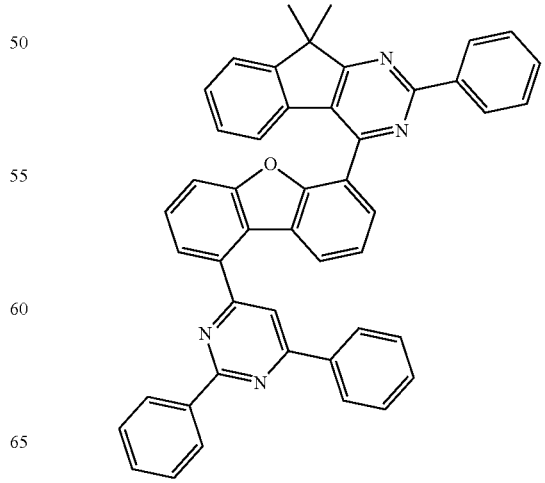

-continued
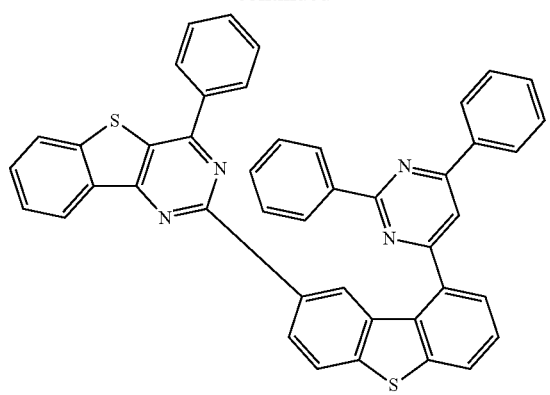
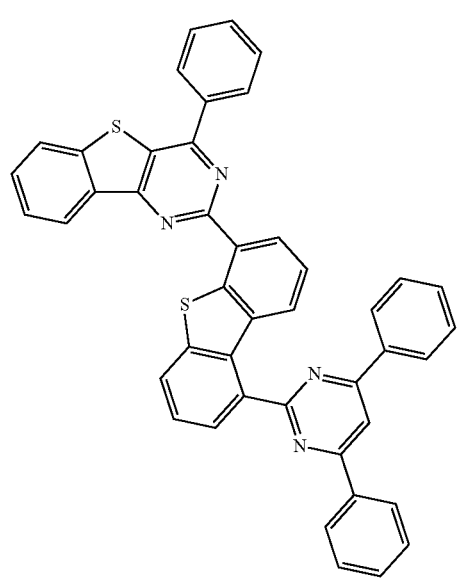
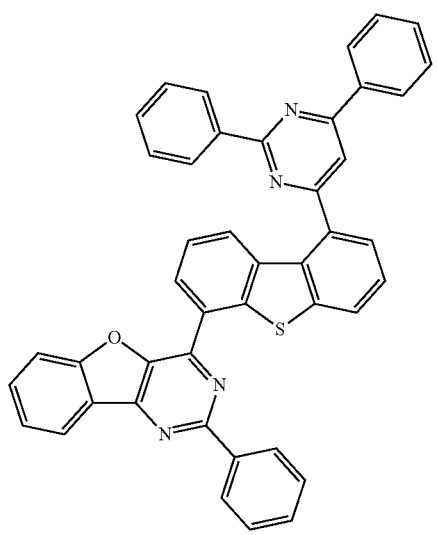
-continued
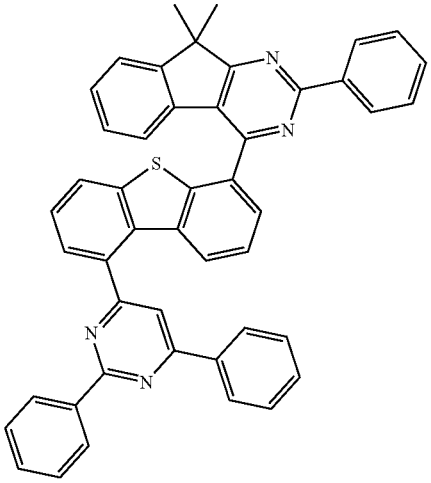
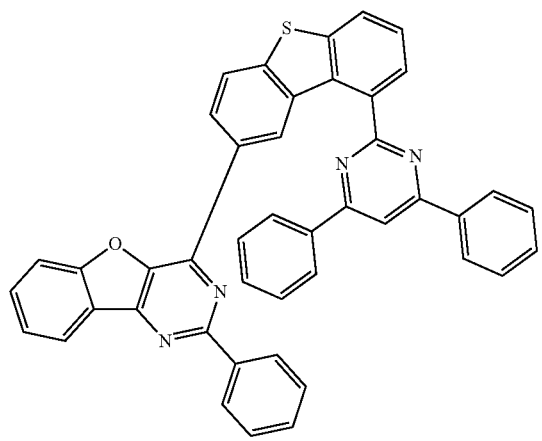
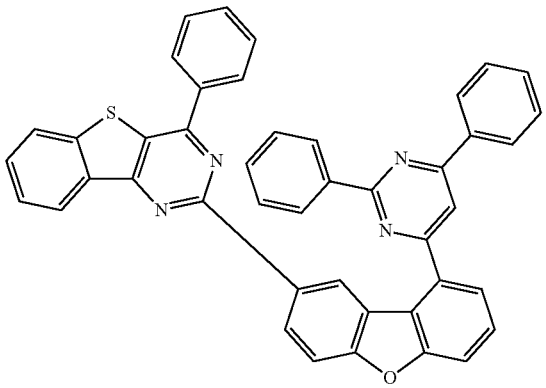

-continued
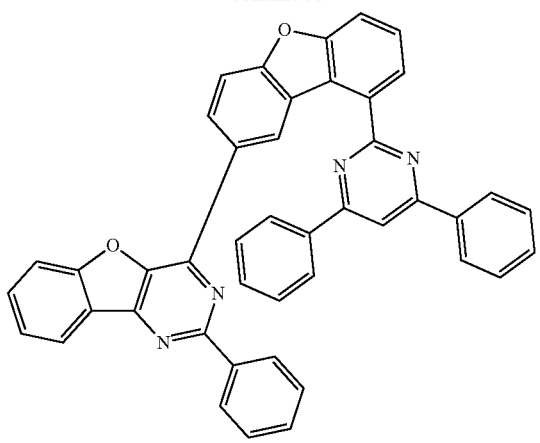
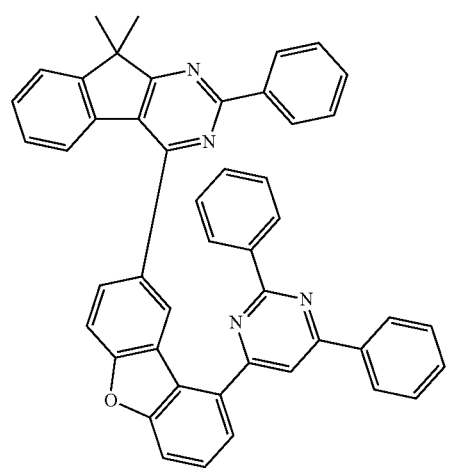
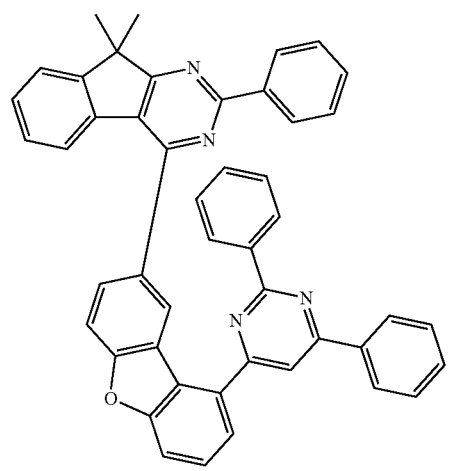
-continued
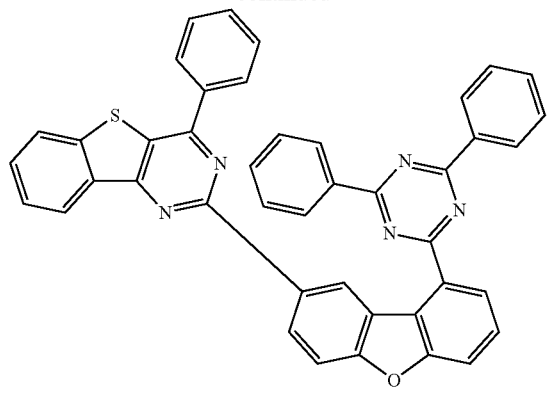
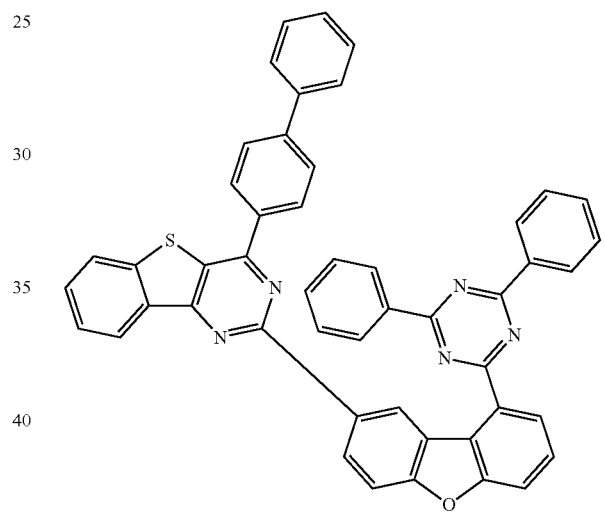
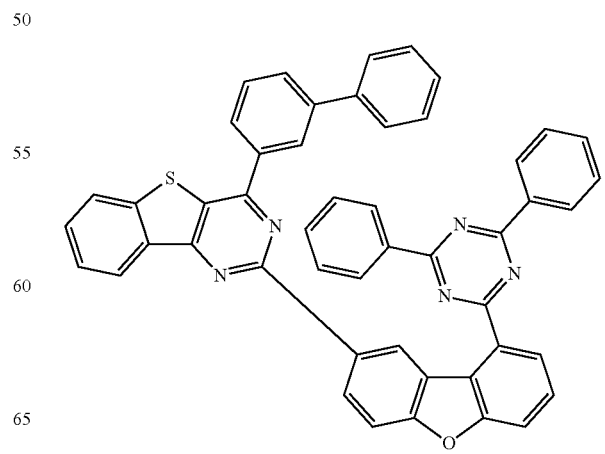

27
-continued

28
-continued

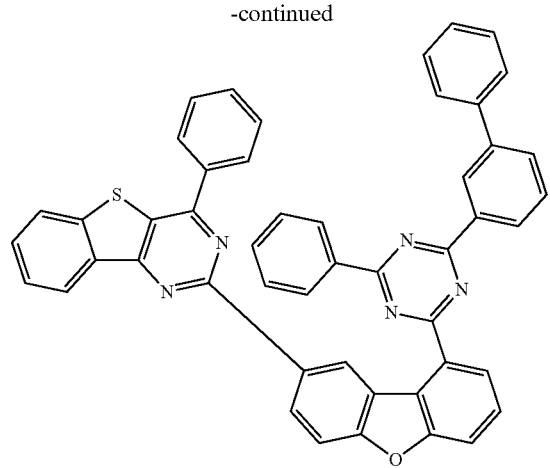
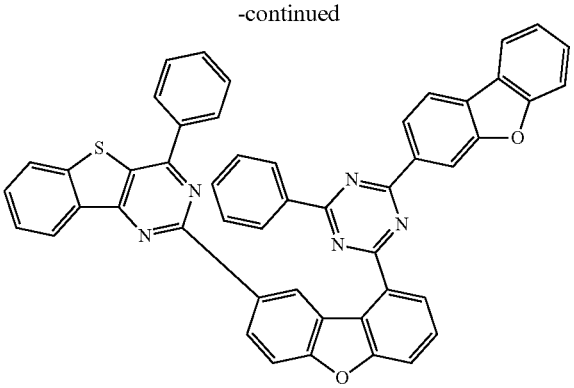
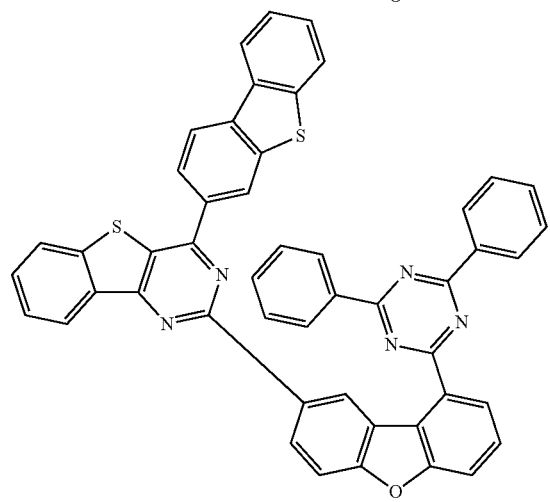
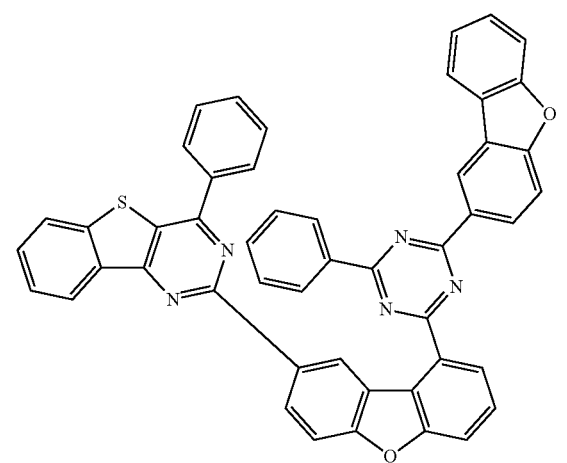
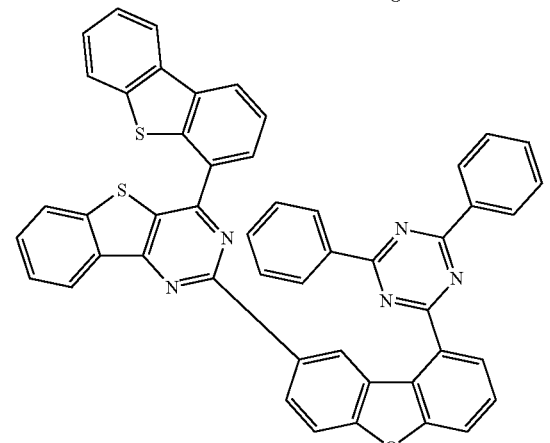
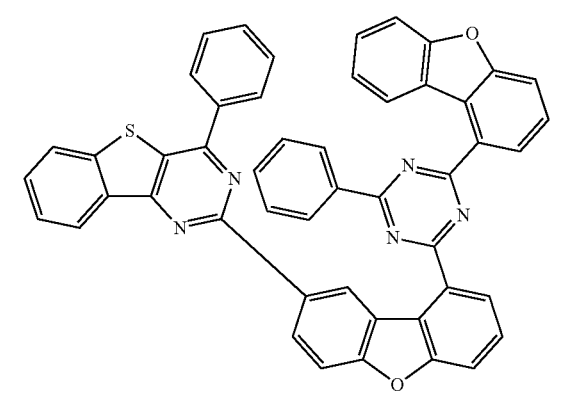
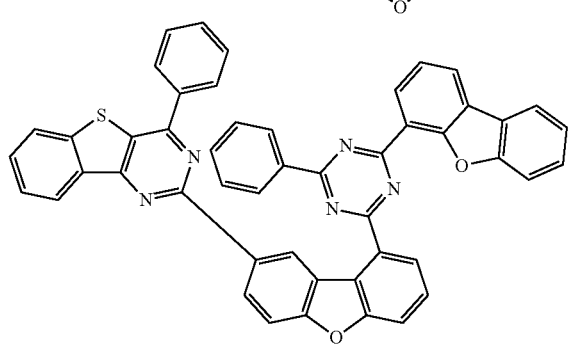
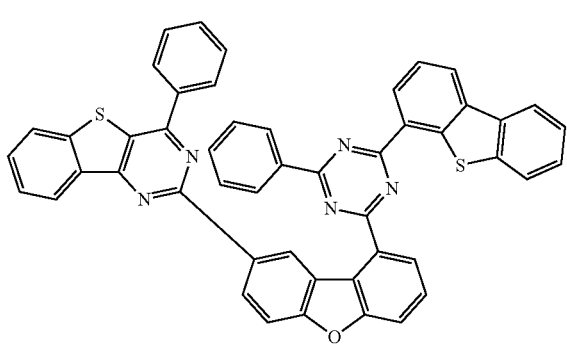

31
-continued
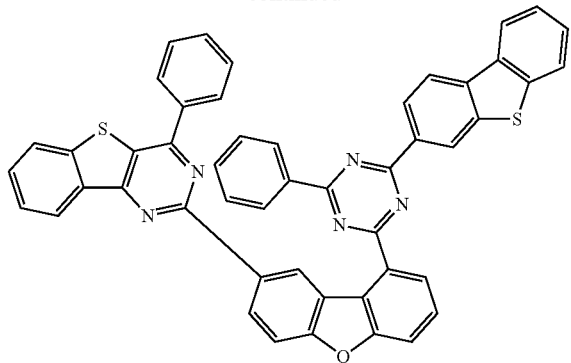
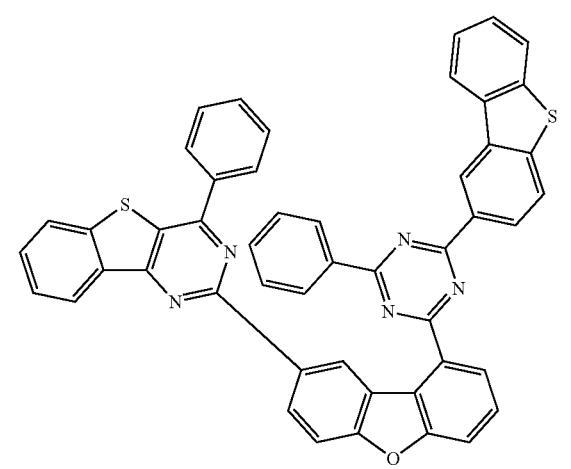
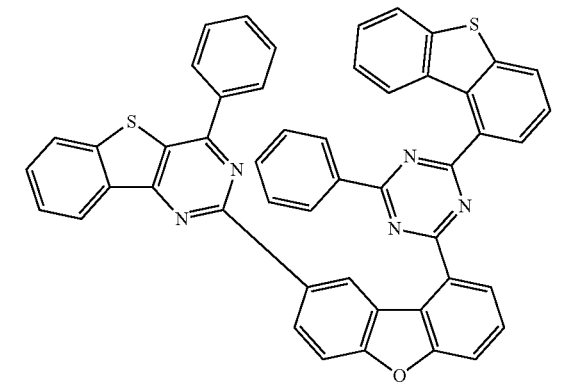
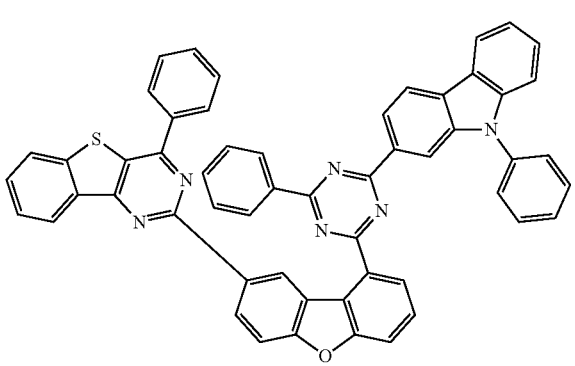
32
-continued
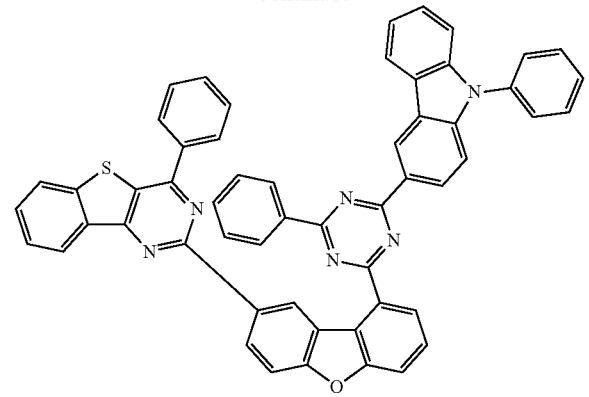
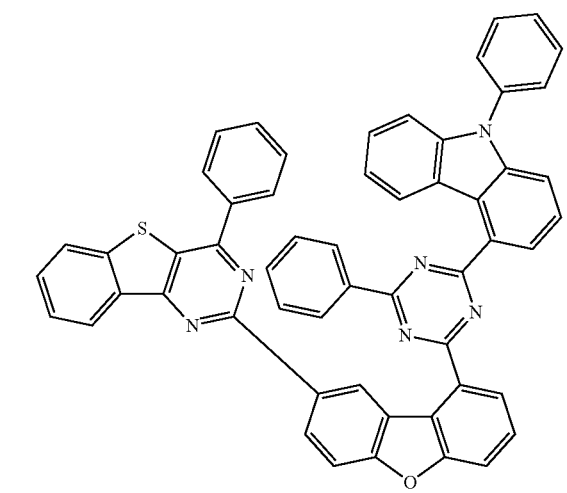
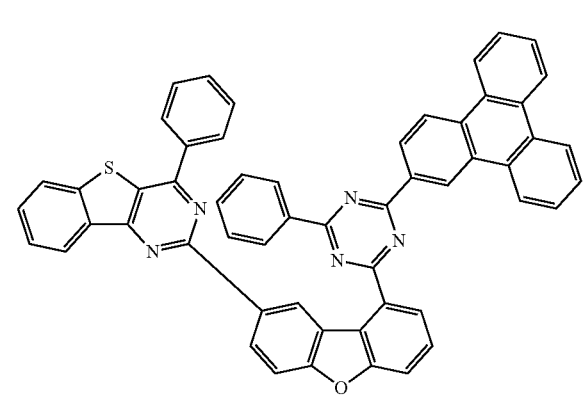
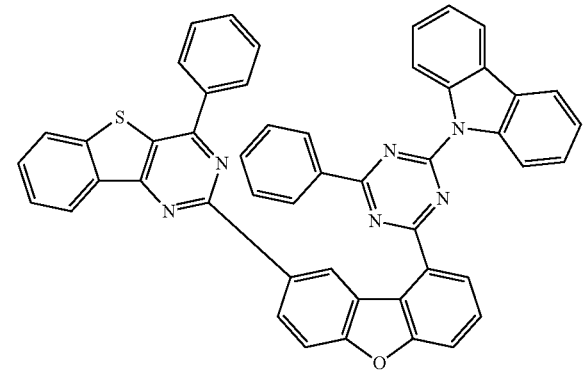

33
-continued
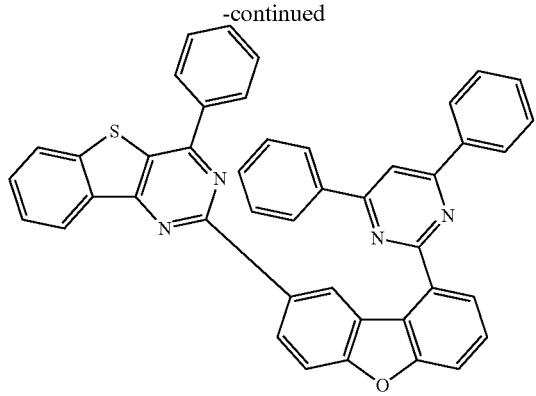
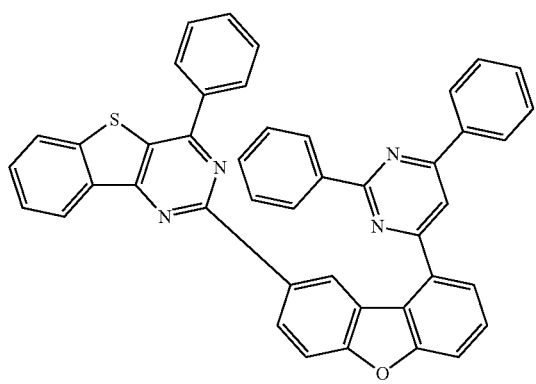
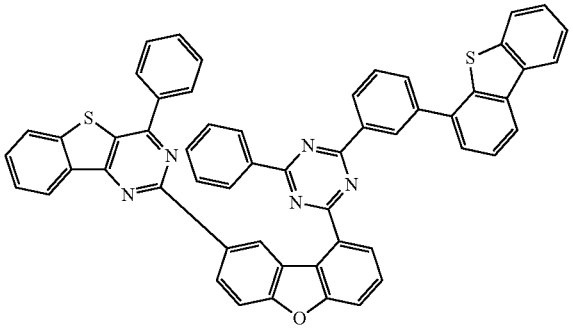
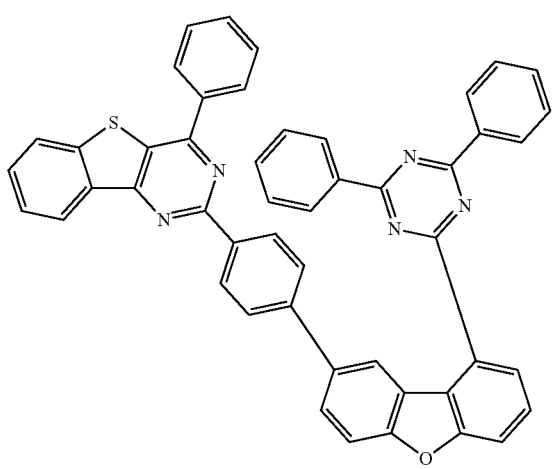
34
-continued
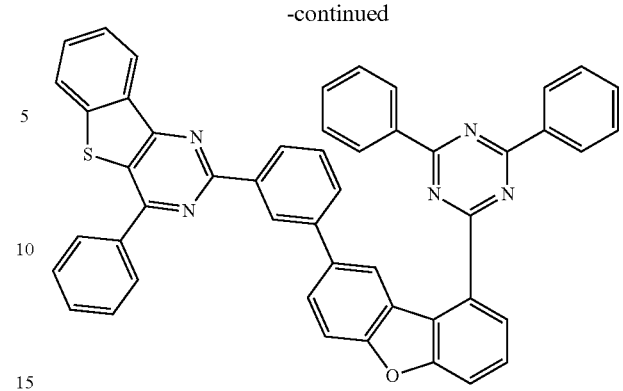
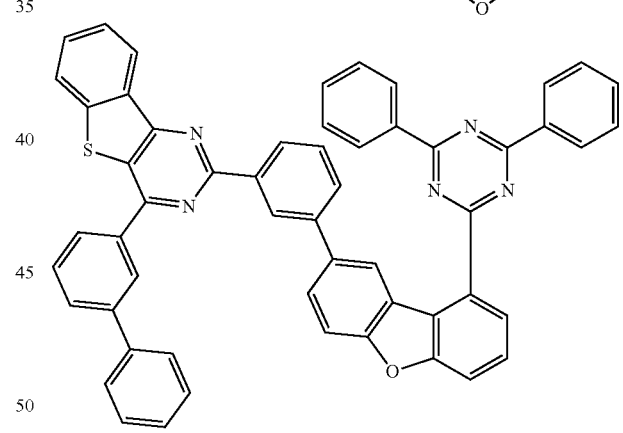
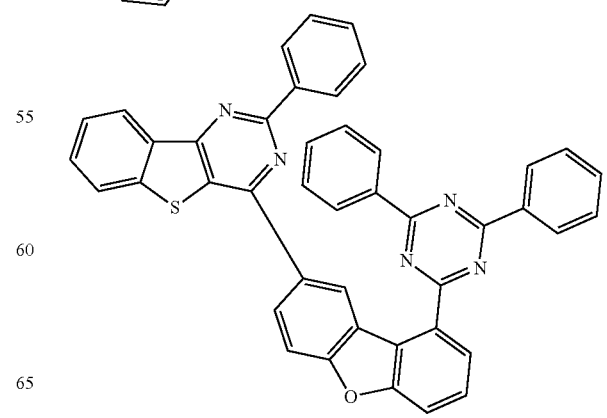

35
-continued
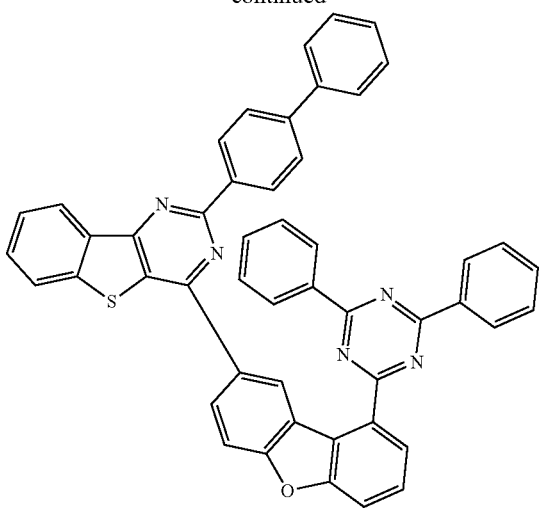
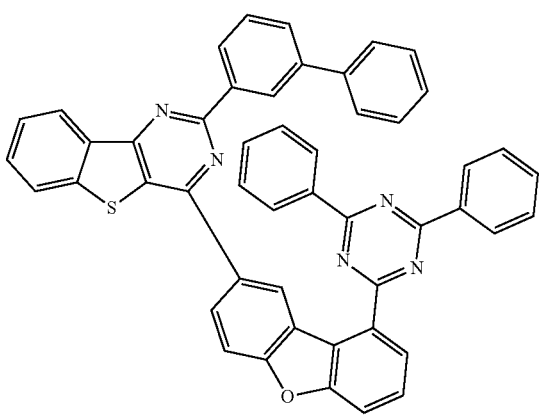
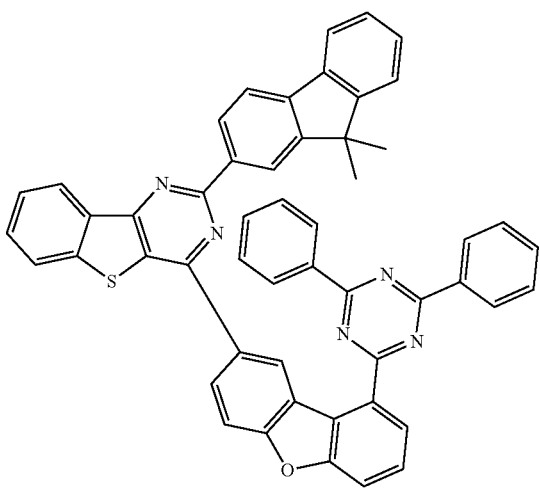
36
-continued
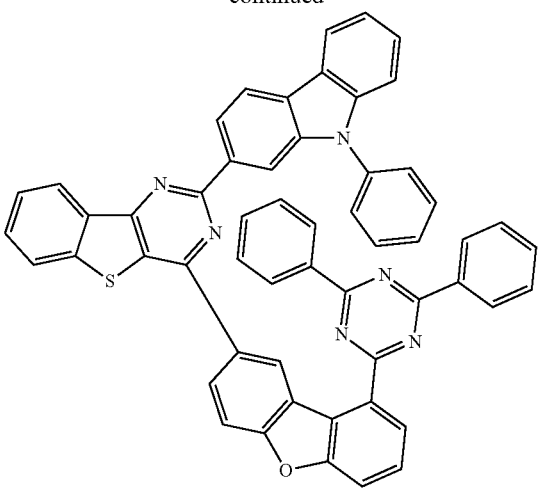
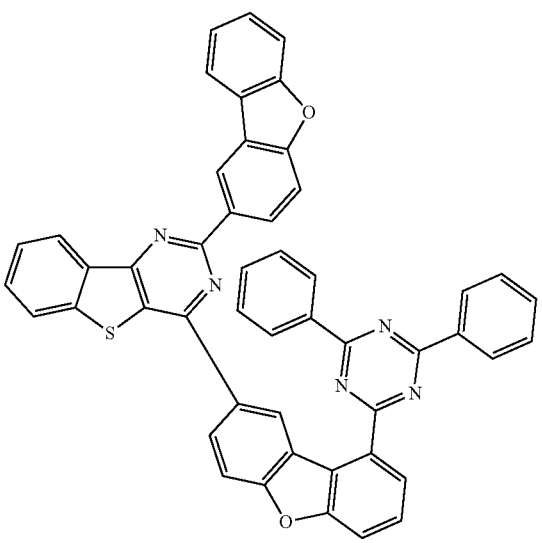
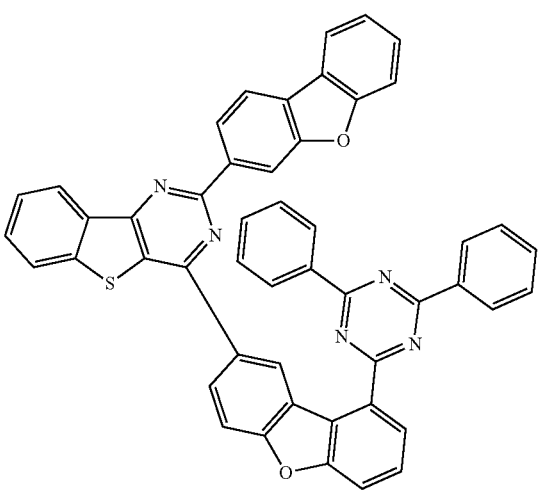

-continued
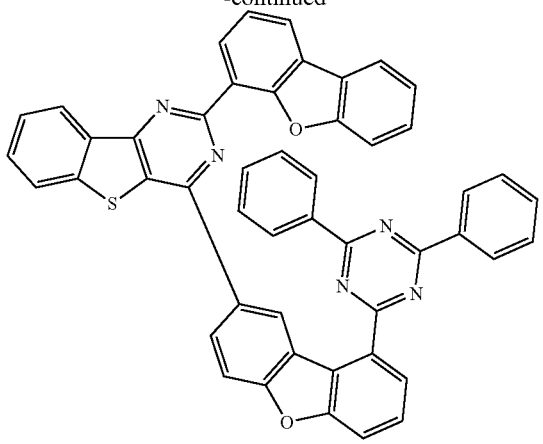
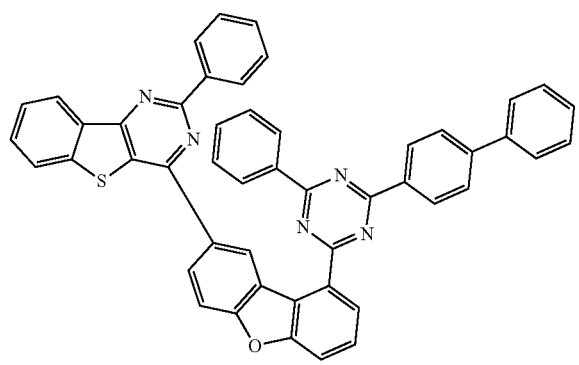
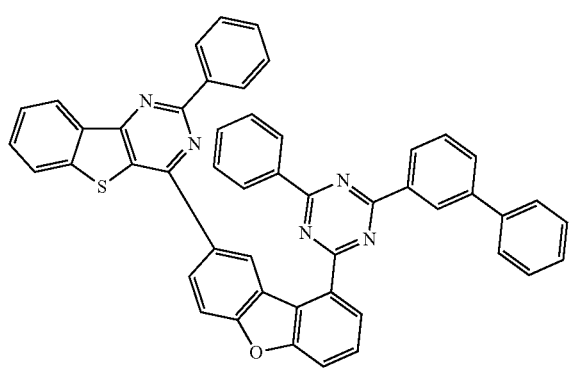
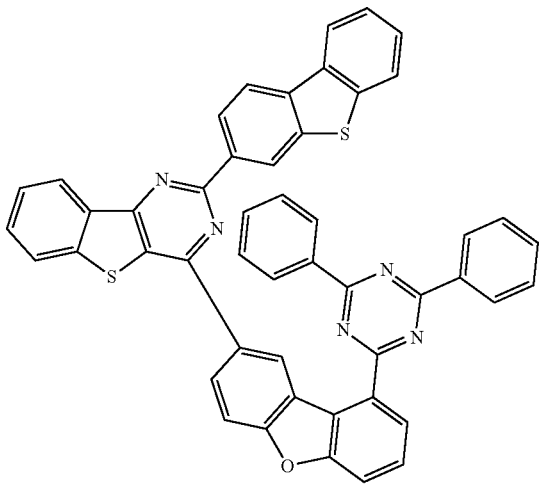
-continued
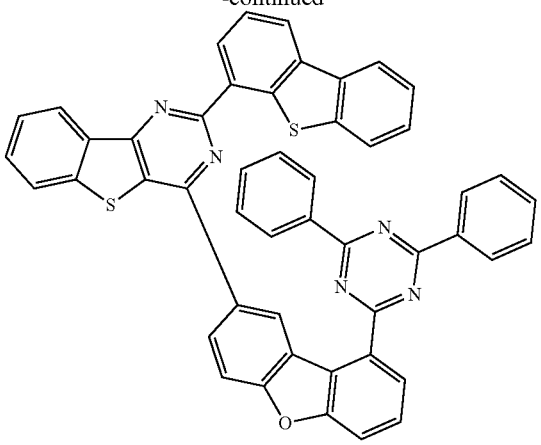
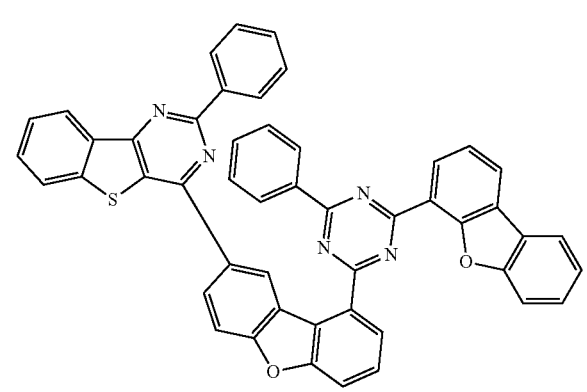
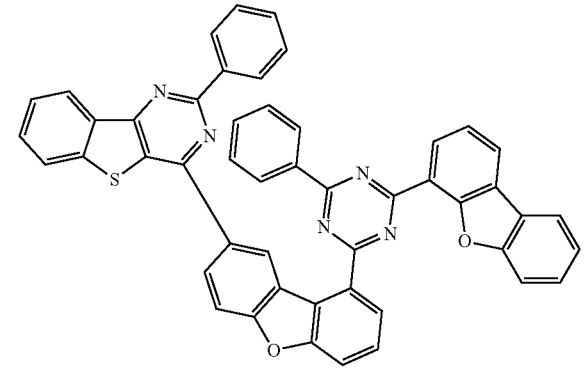
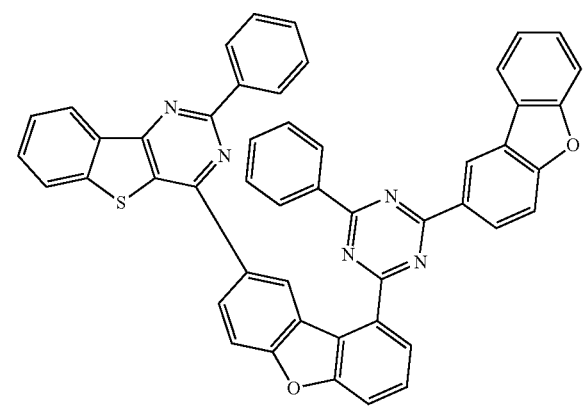

-continued
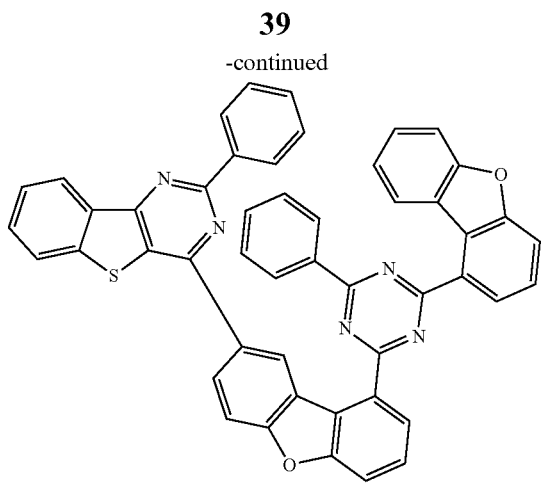
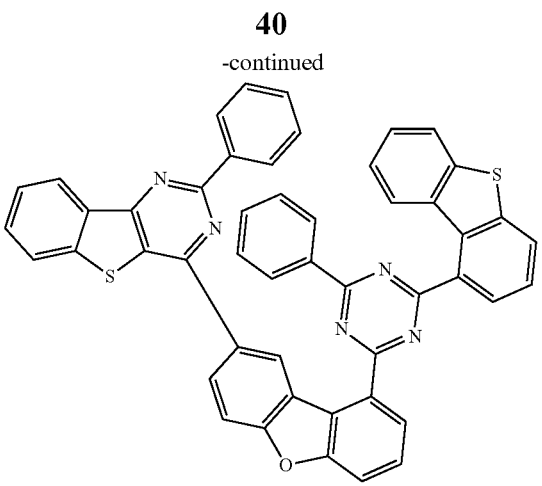
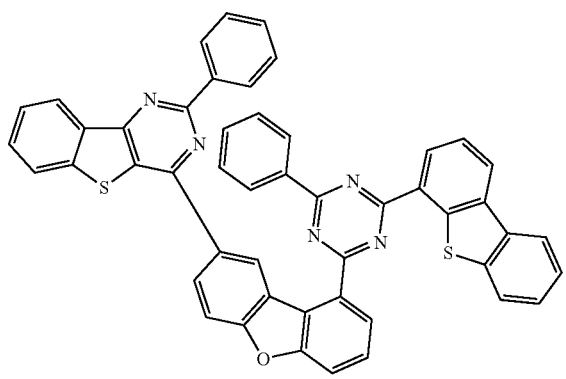
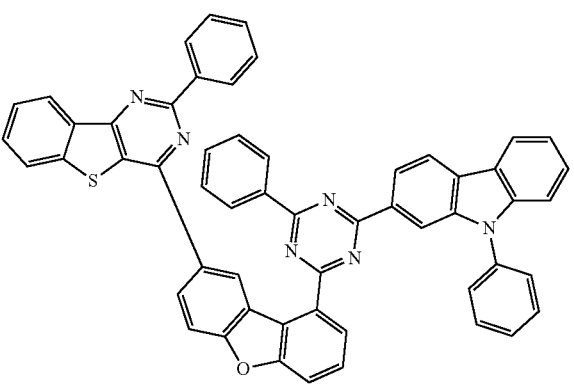
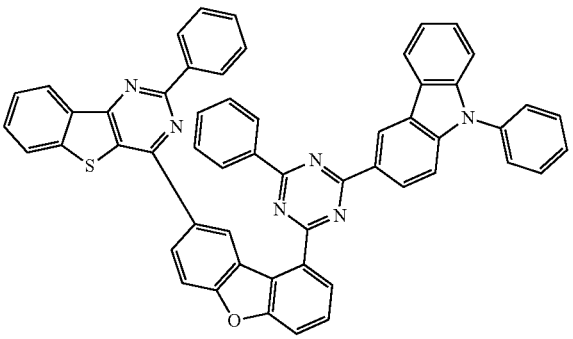
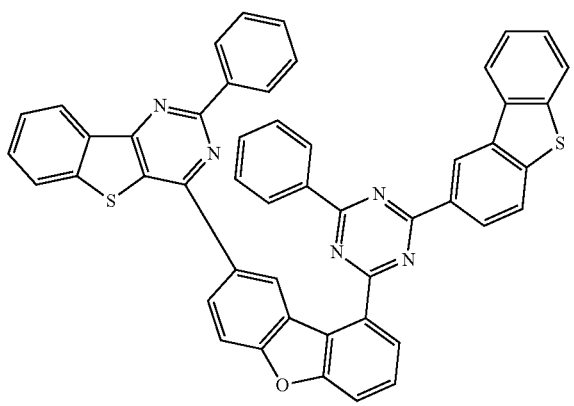
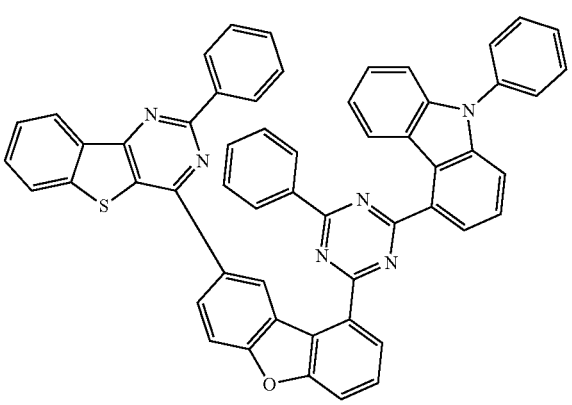

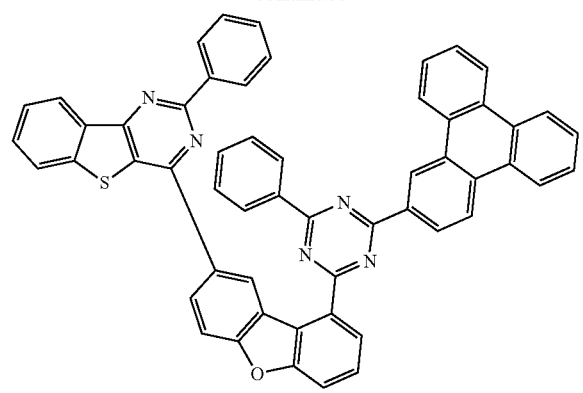
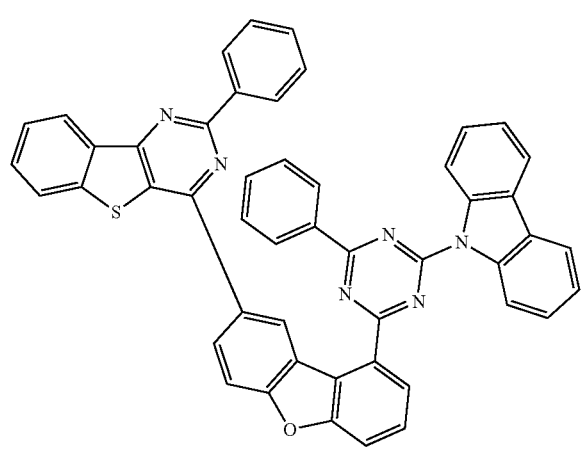
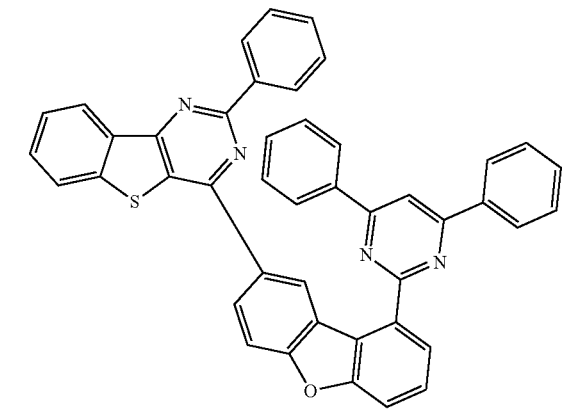
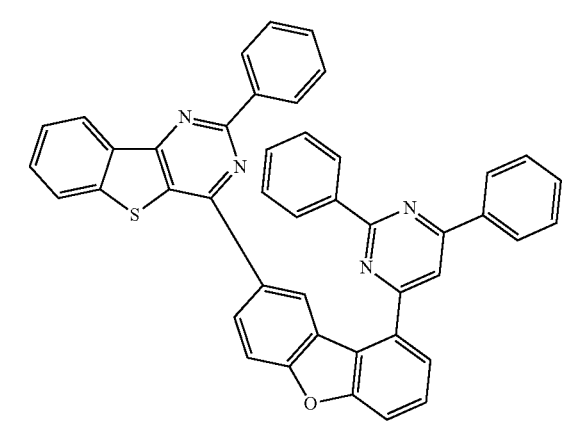
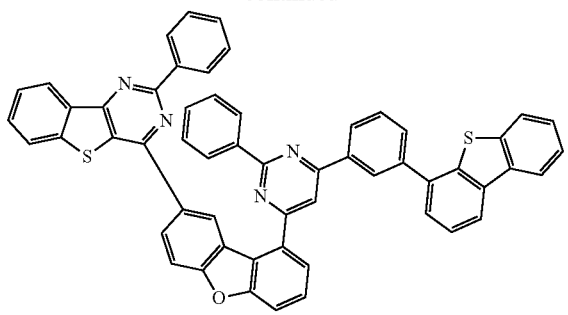
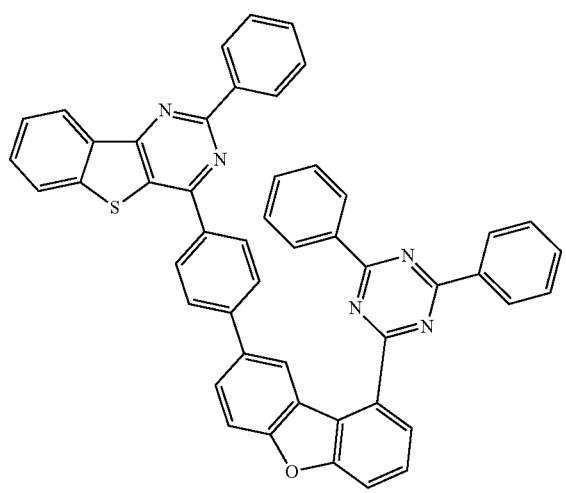
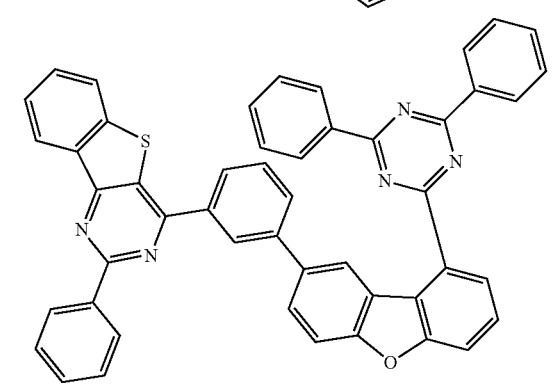
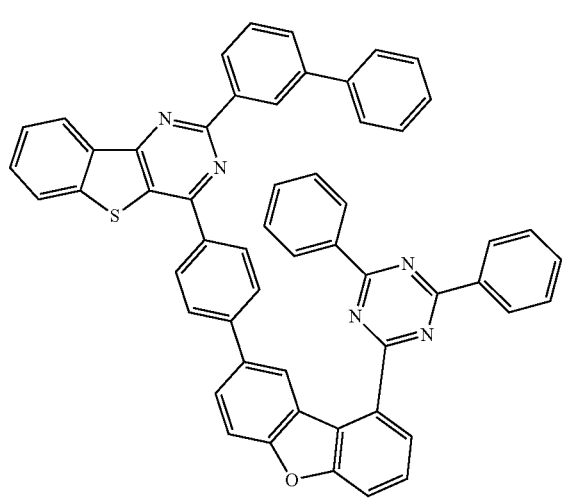

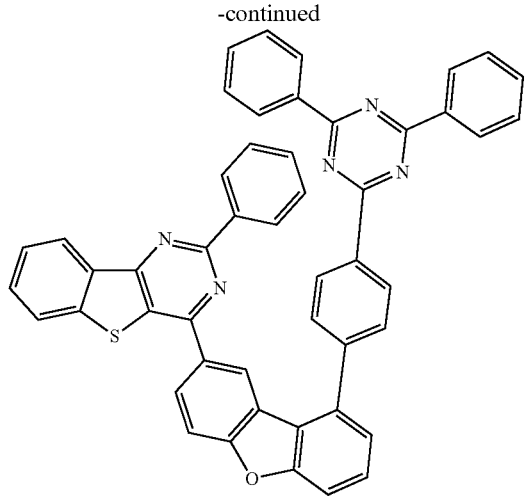
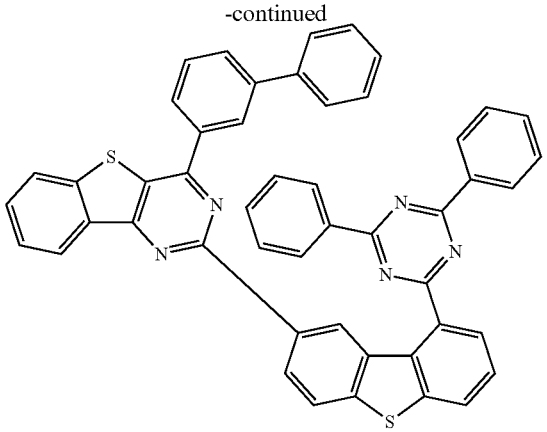
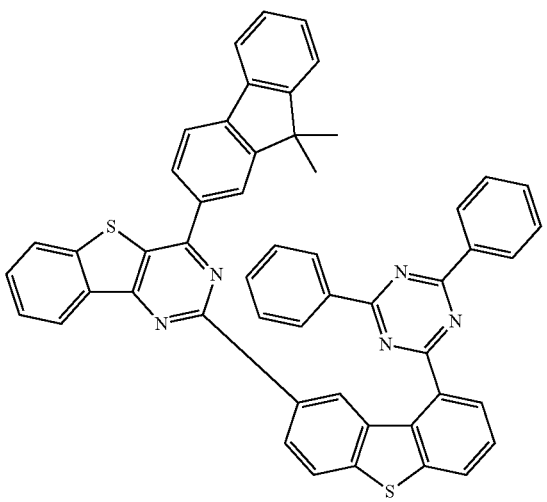
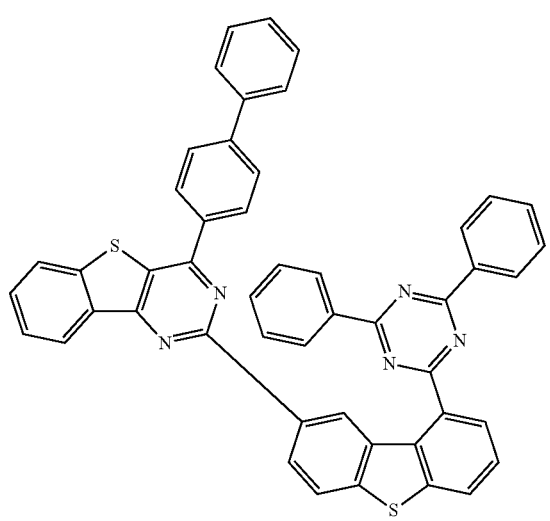
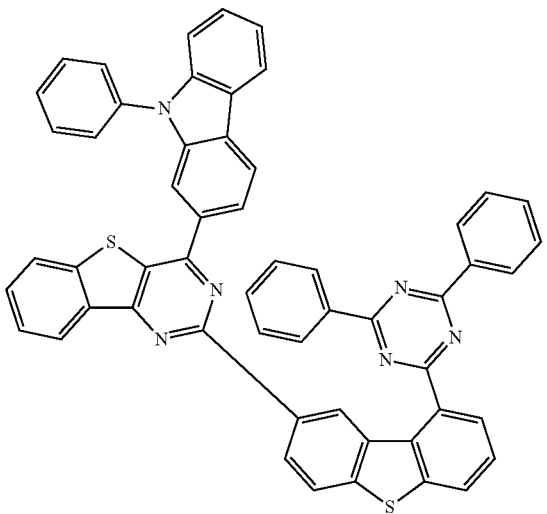

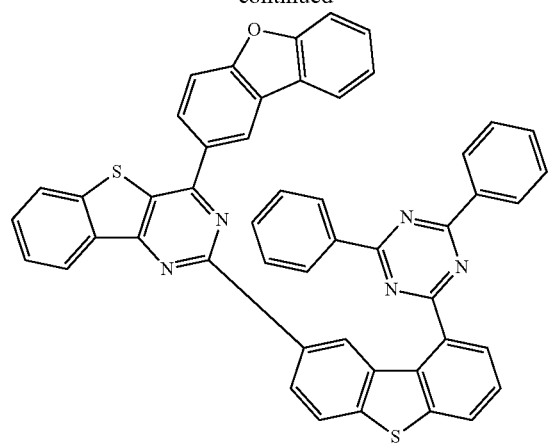
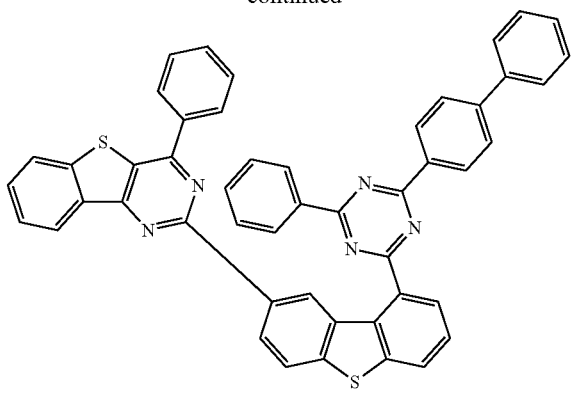
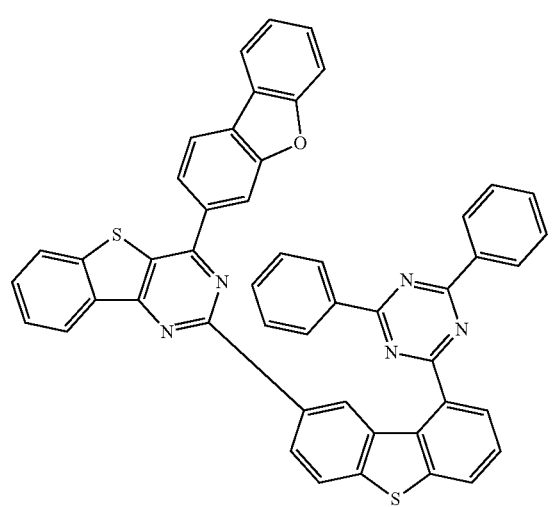
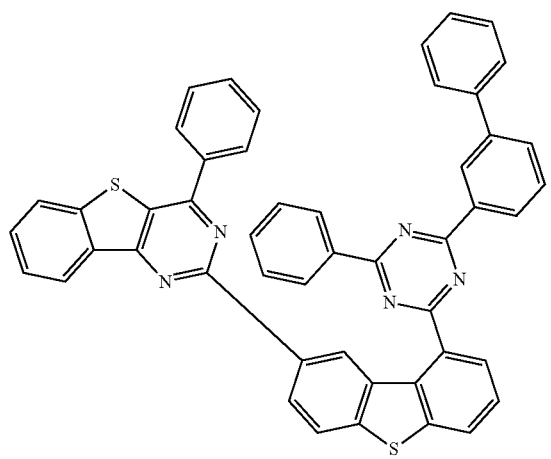
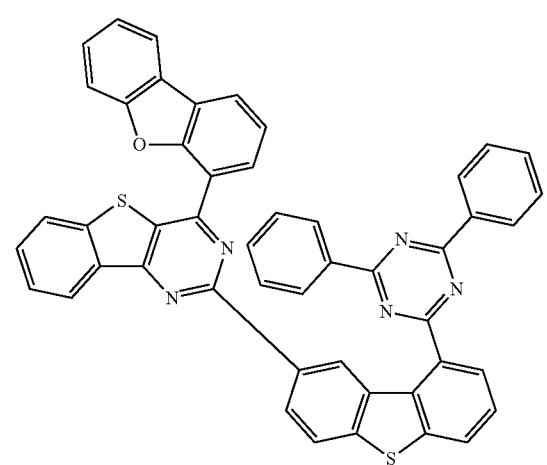
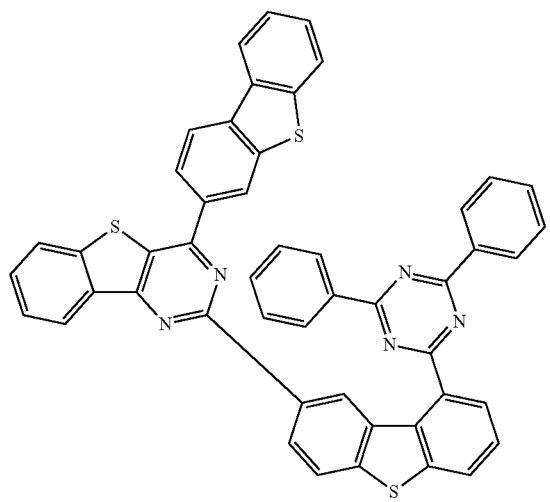

47
-continued
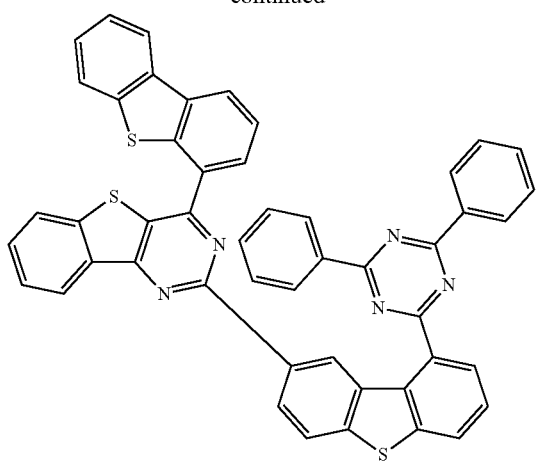
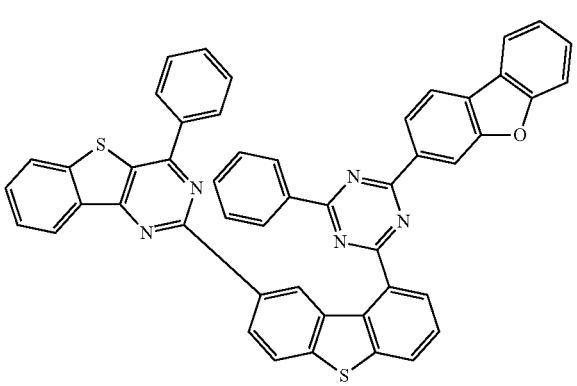
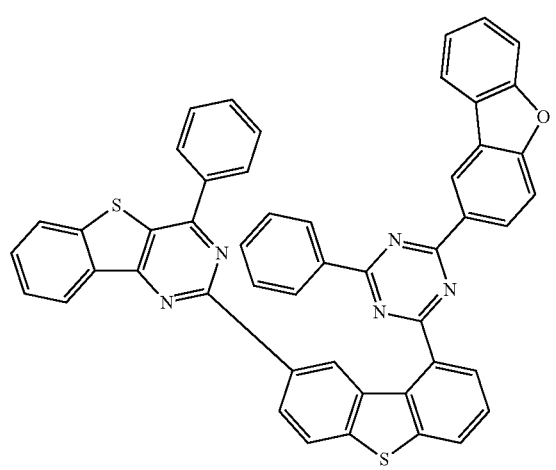
48
-continued
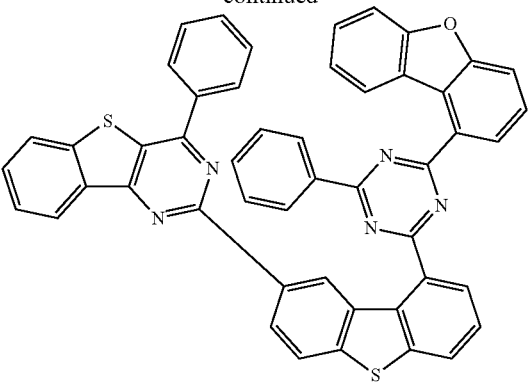
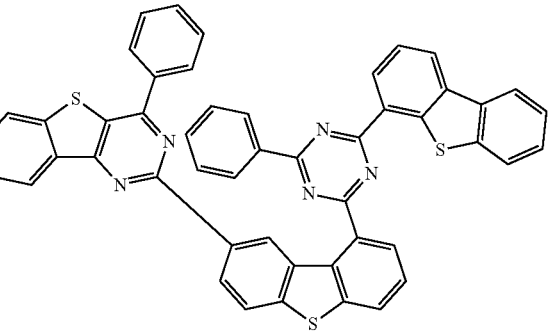
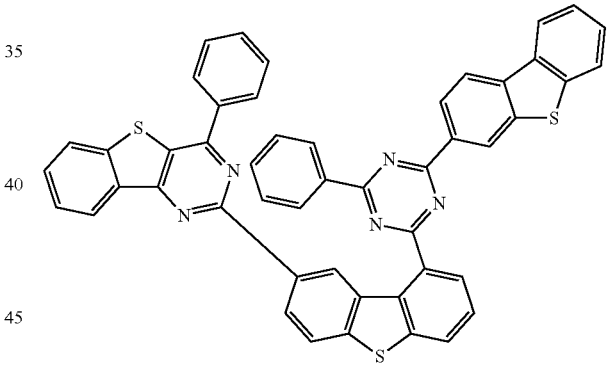
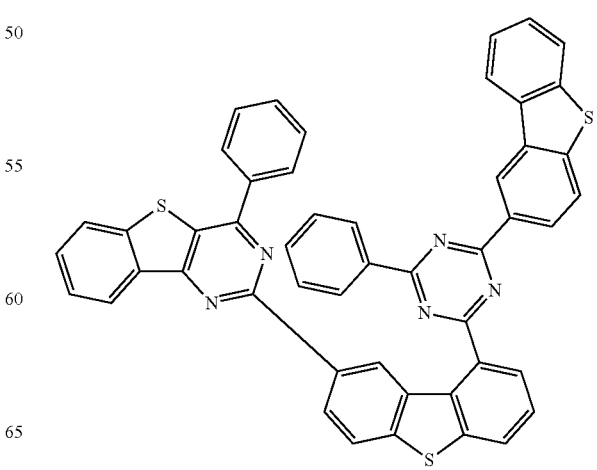

49
-continued
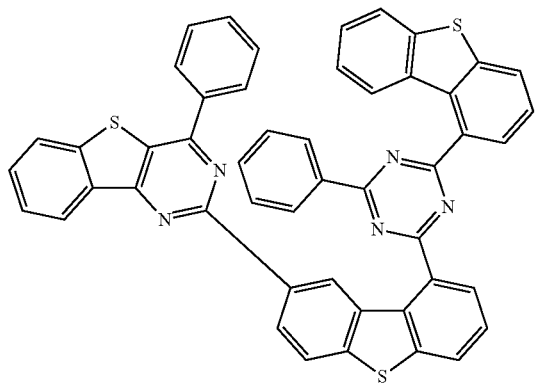
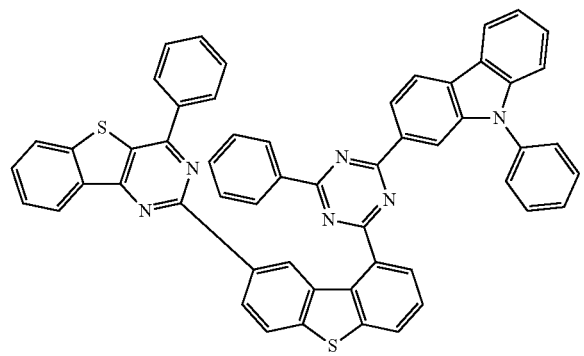
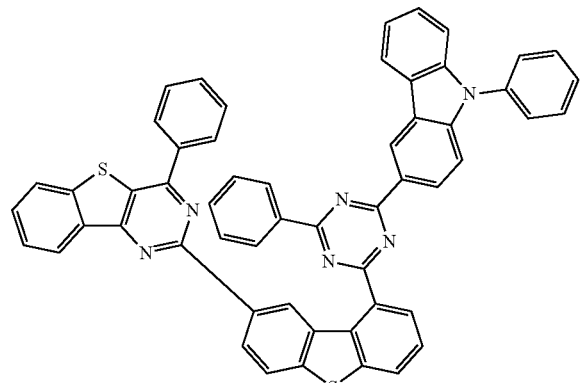
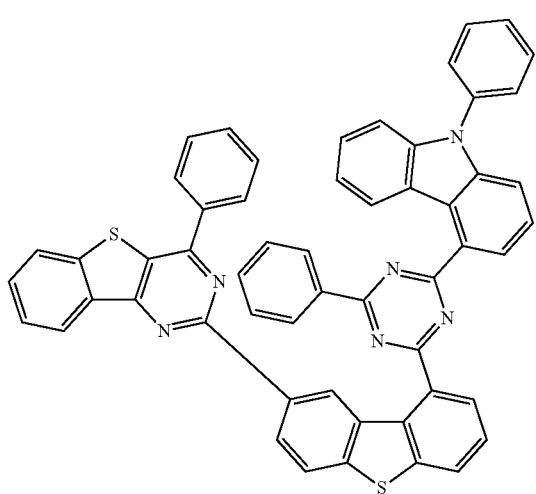
50
-continued
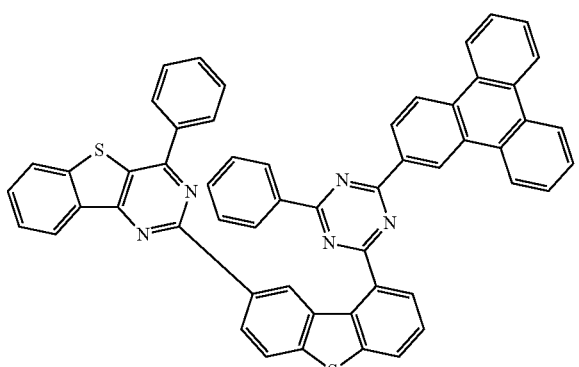
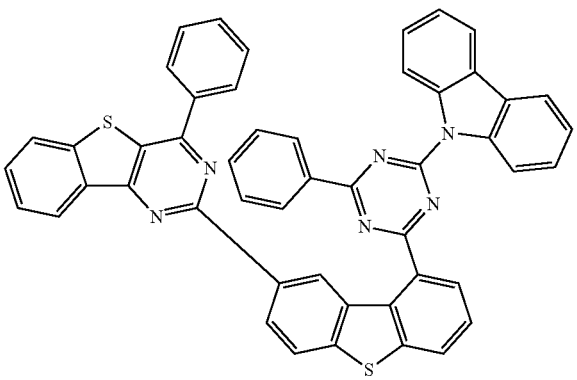
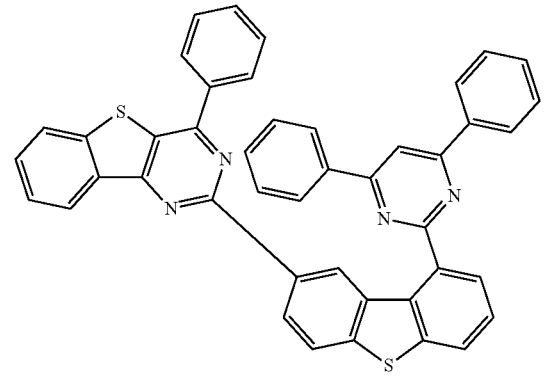
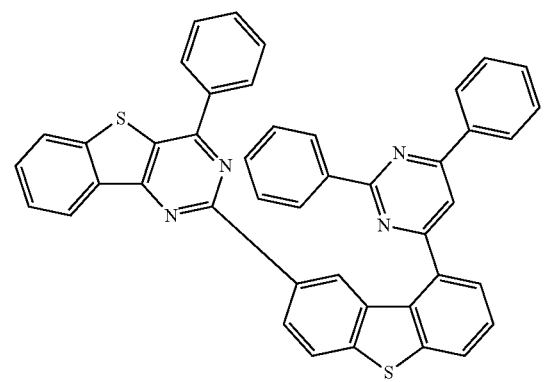

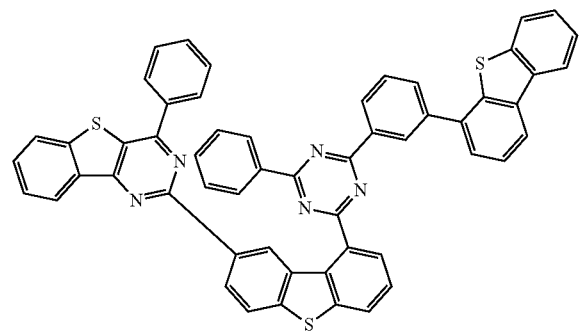
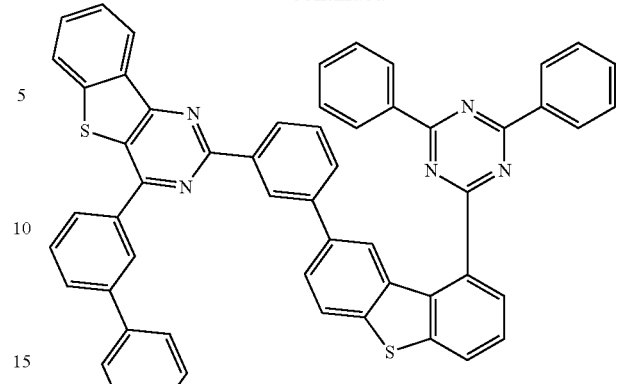
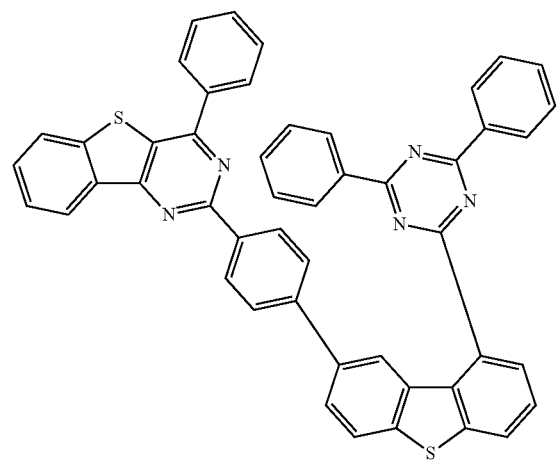
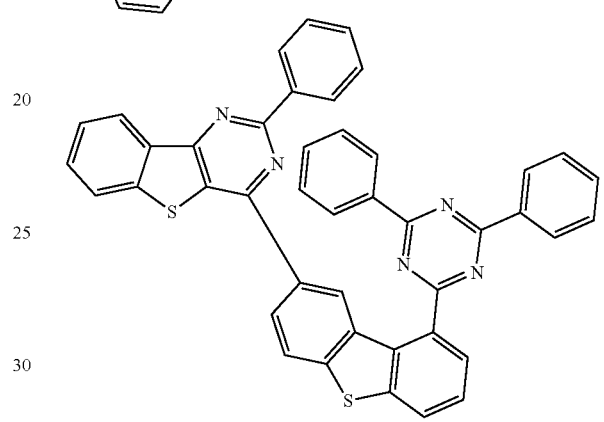
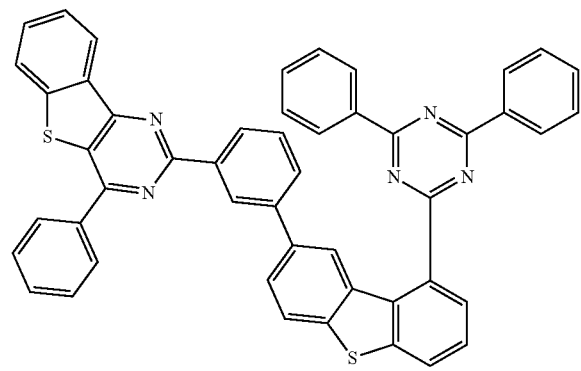
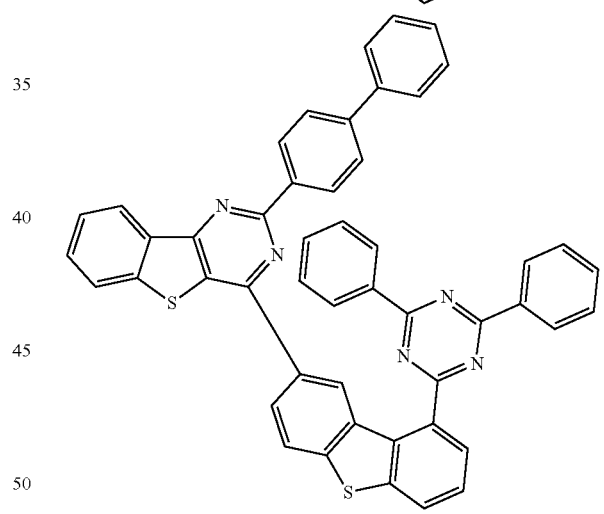
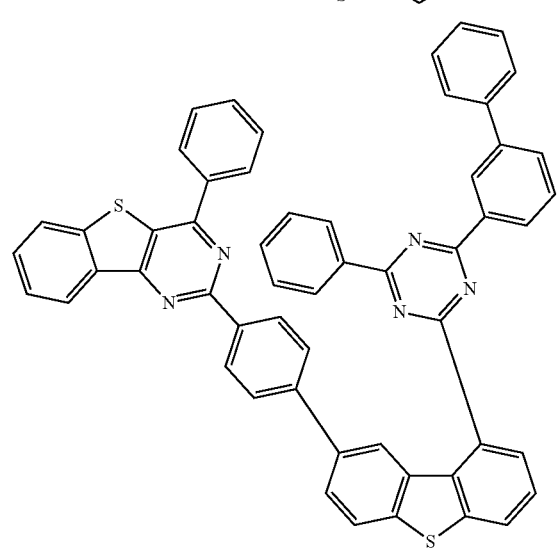
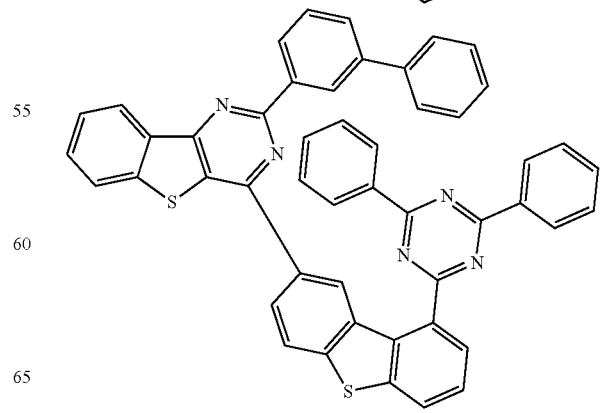

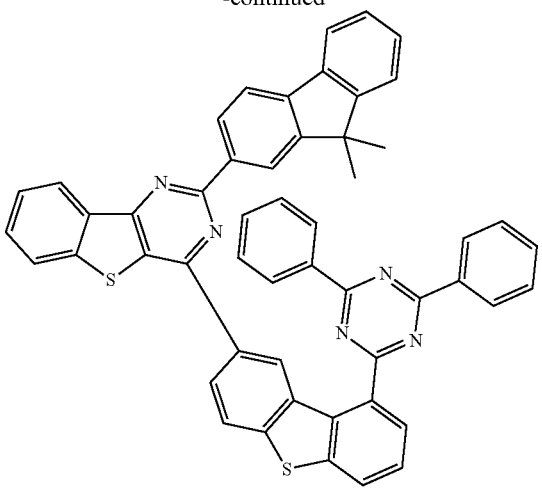
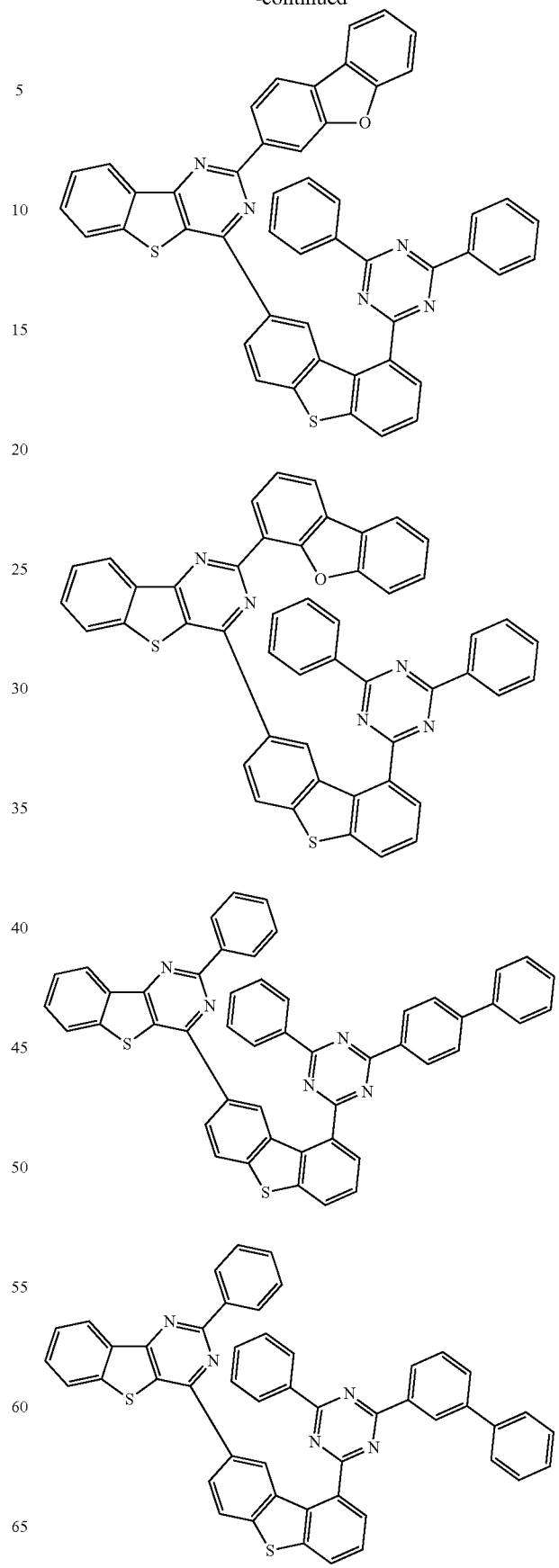

55
-continued
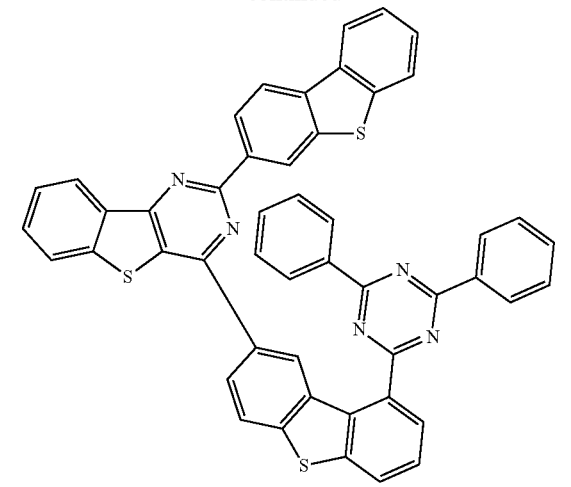
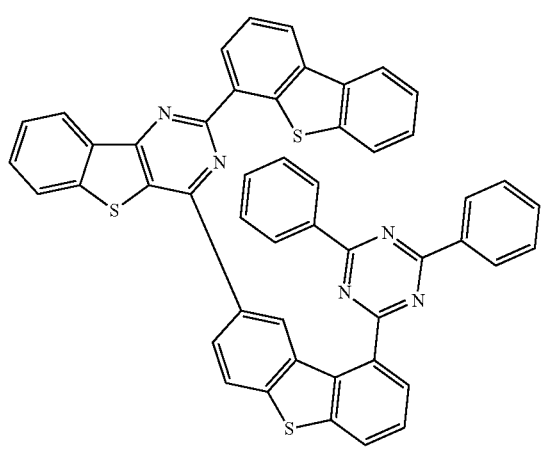
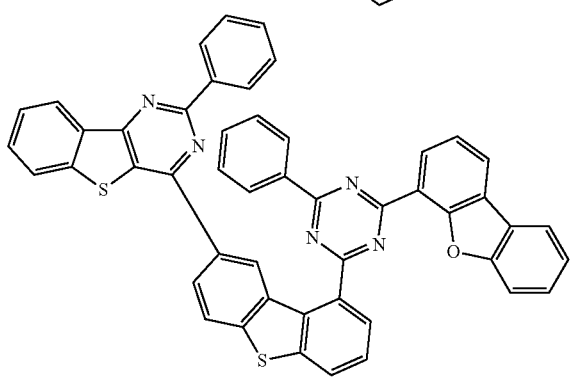
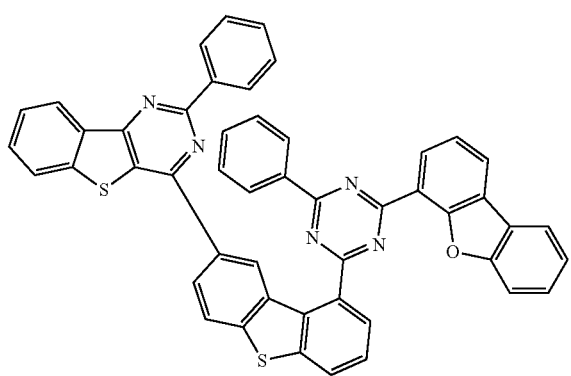
56
-continued
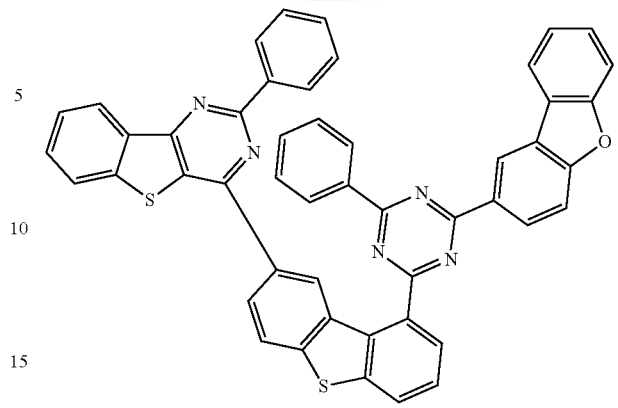
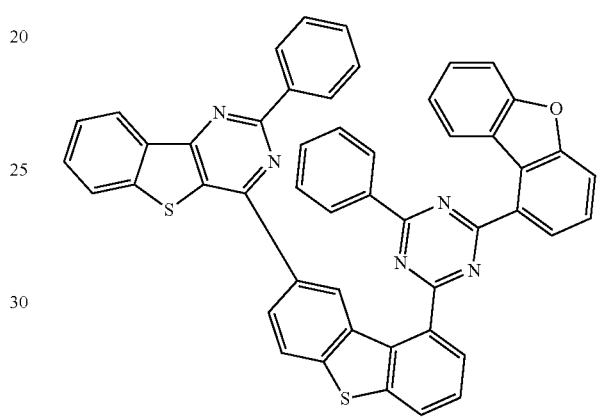
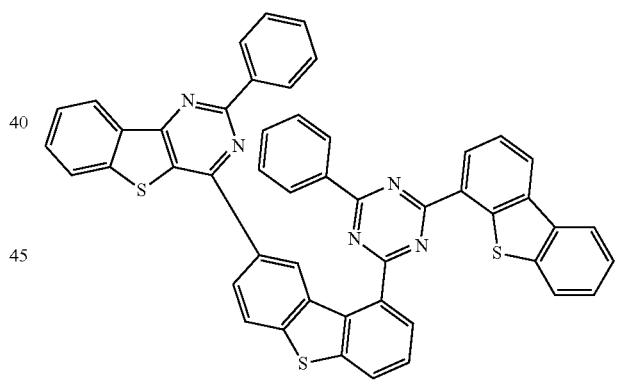
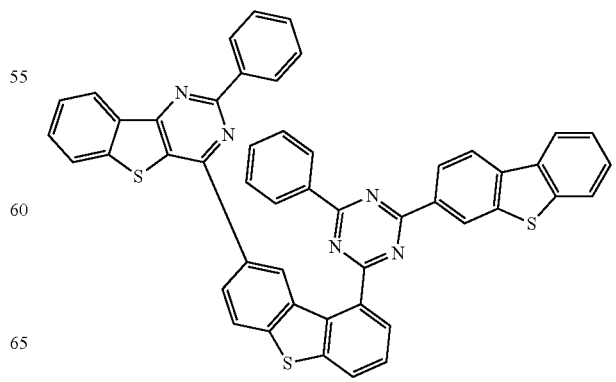

57
-continued
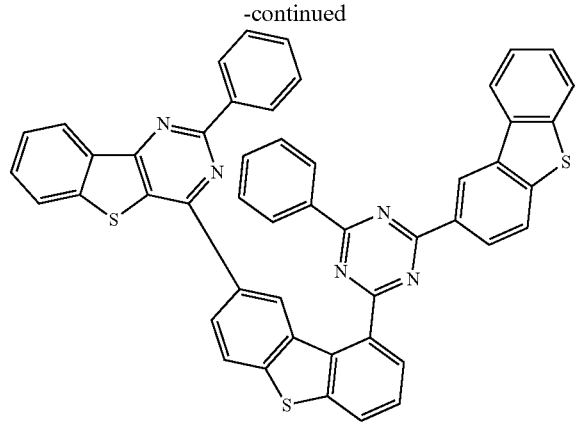
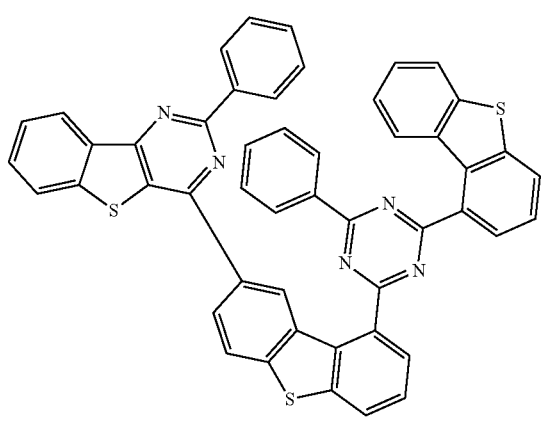
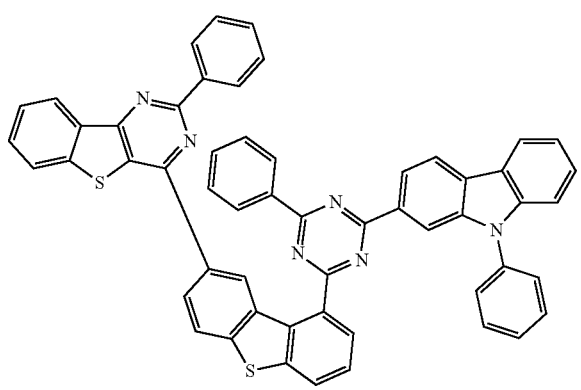
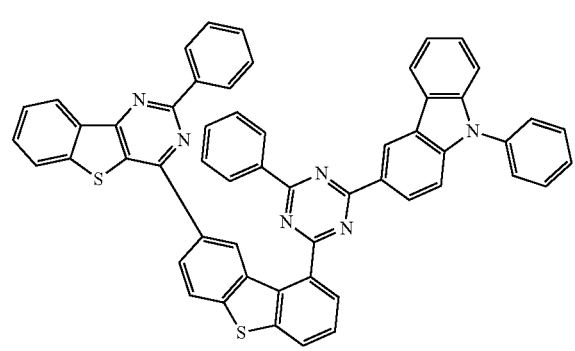
58
-continued
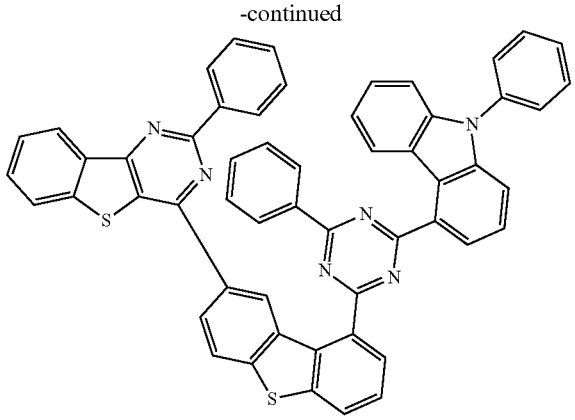
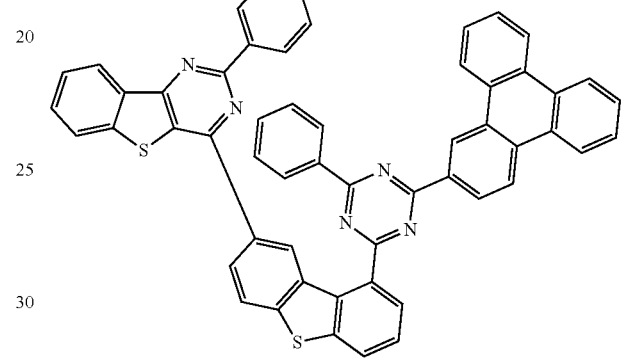
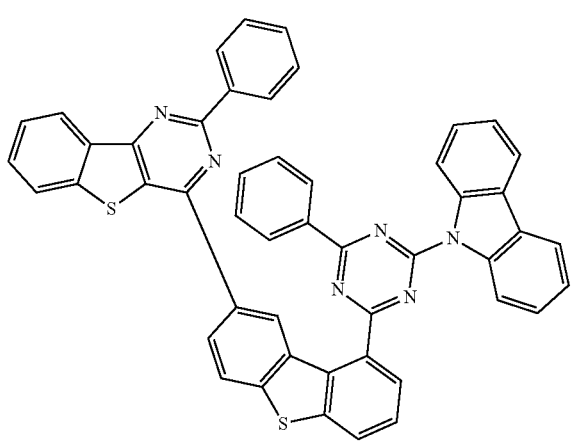
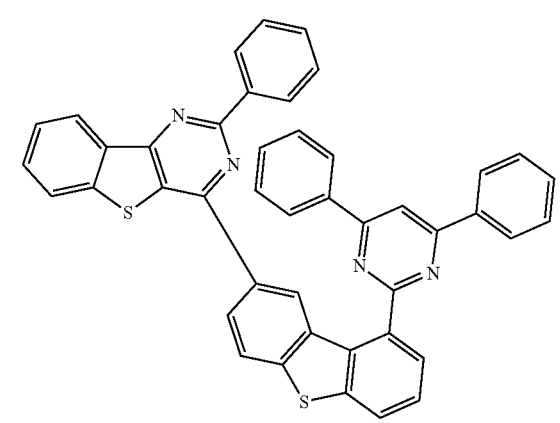

-continued
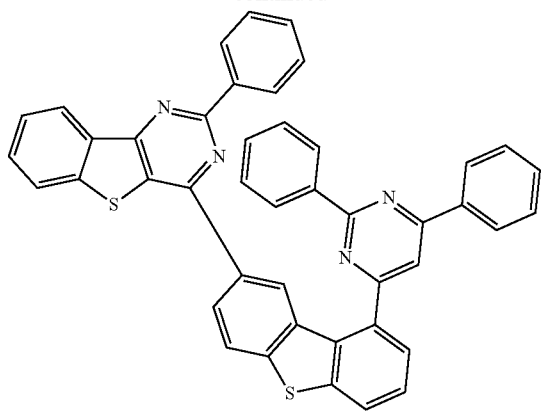
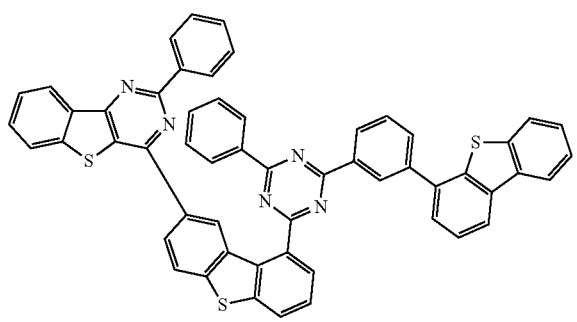
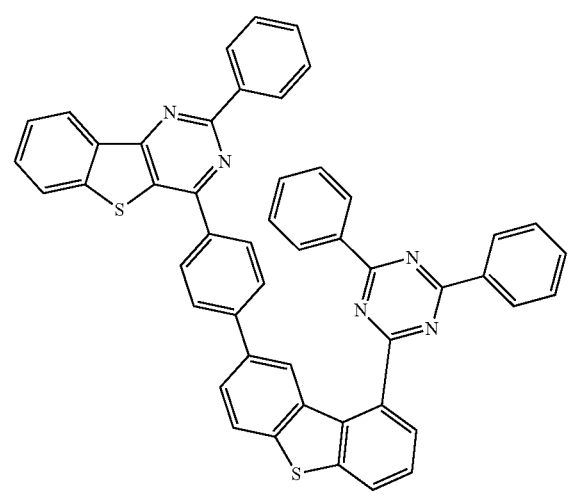
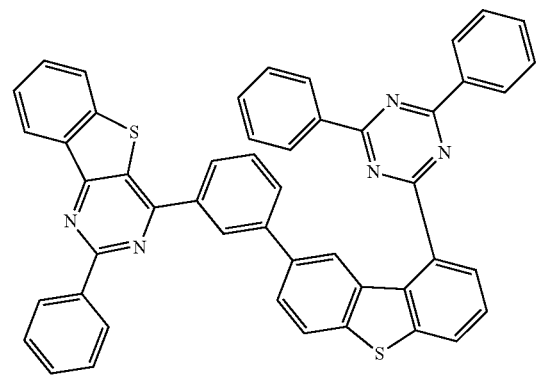
-continued
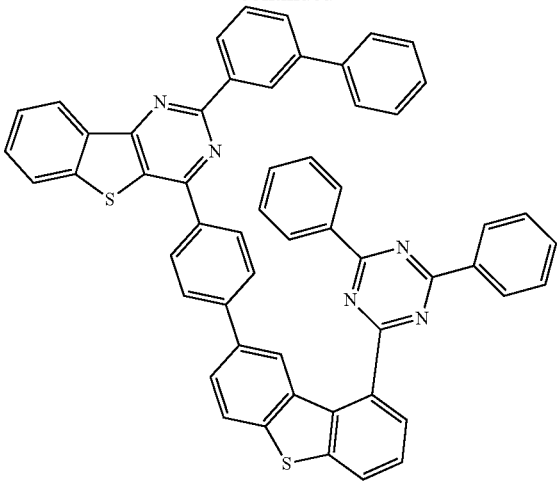
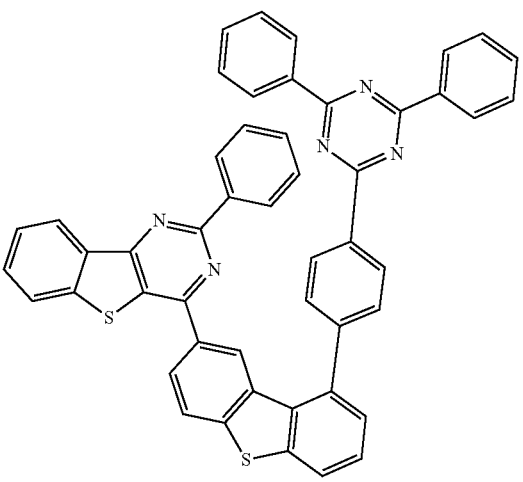
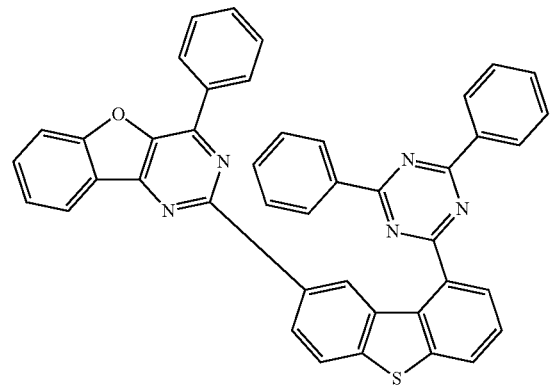

61
-continued
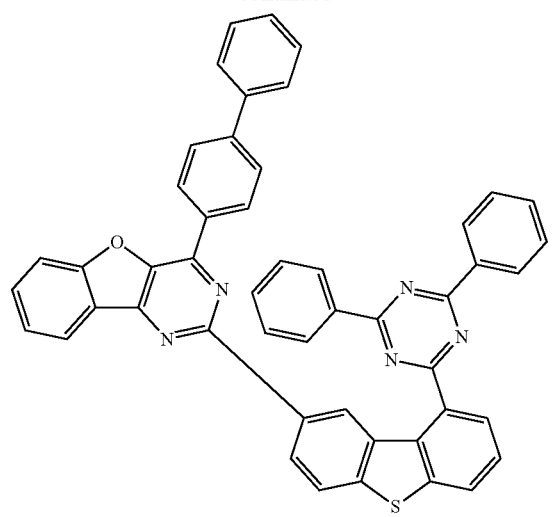
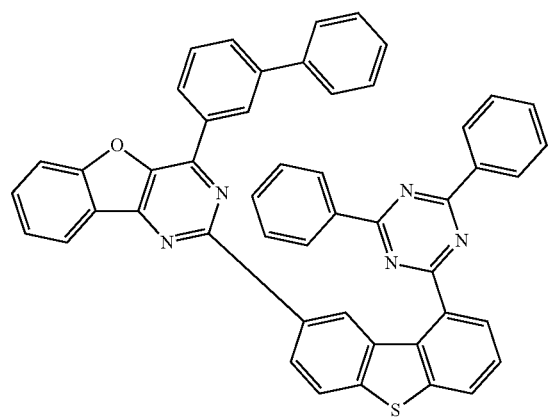
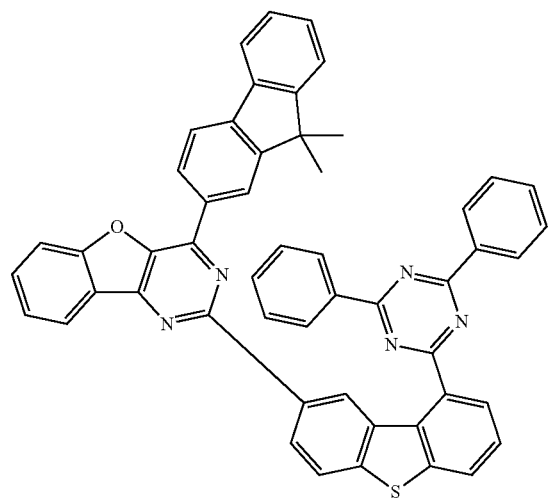
62
-continued
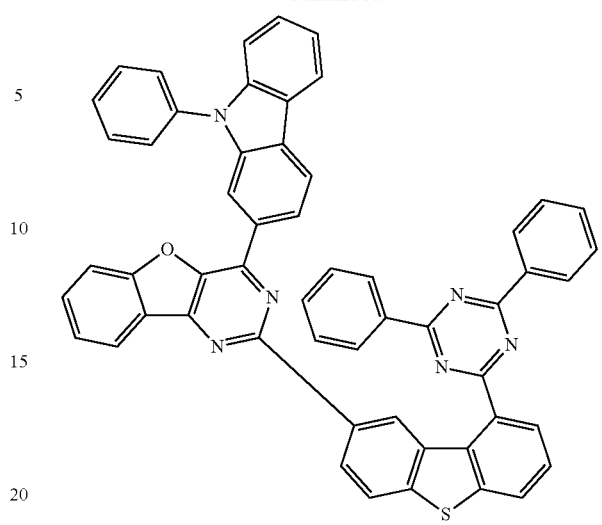
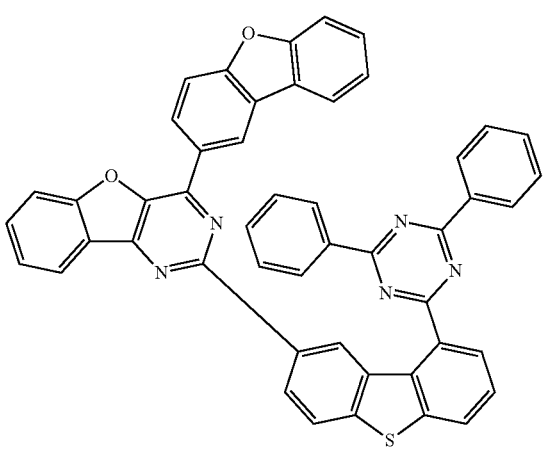
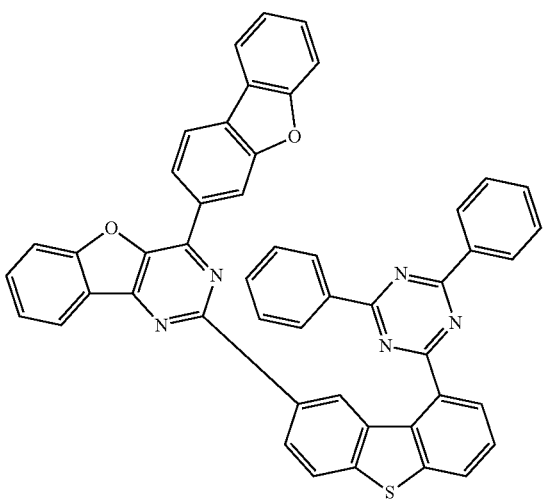

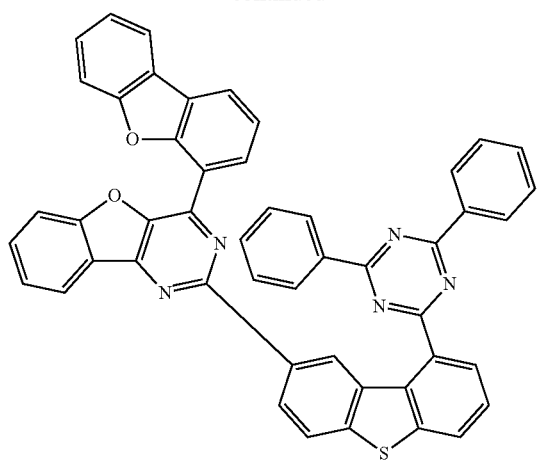
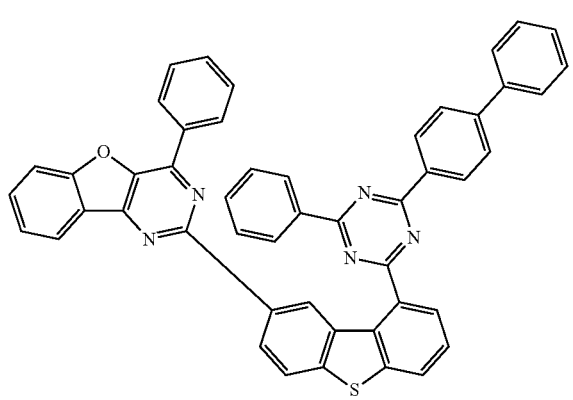
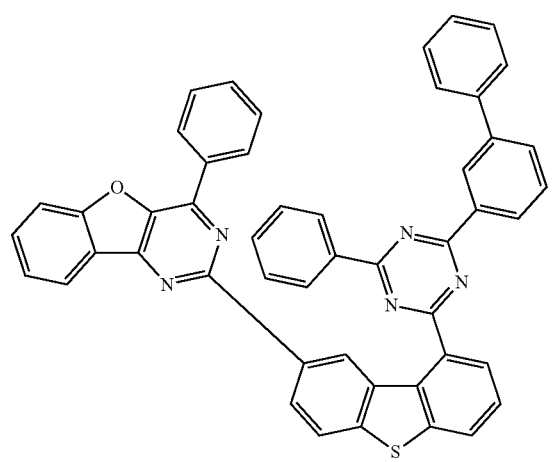
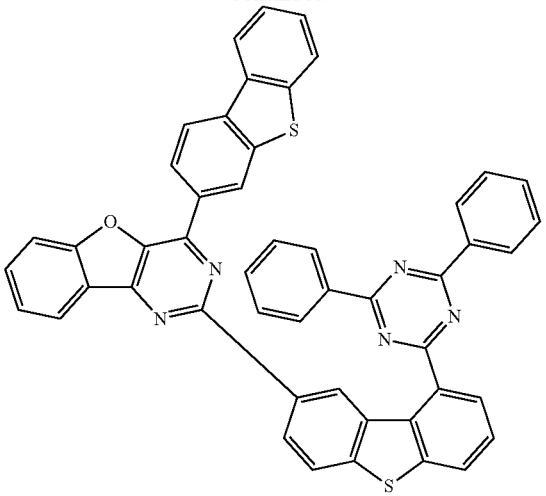
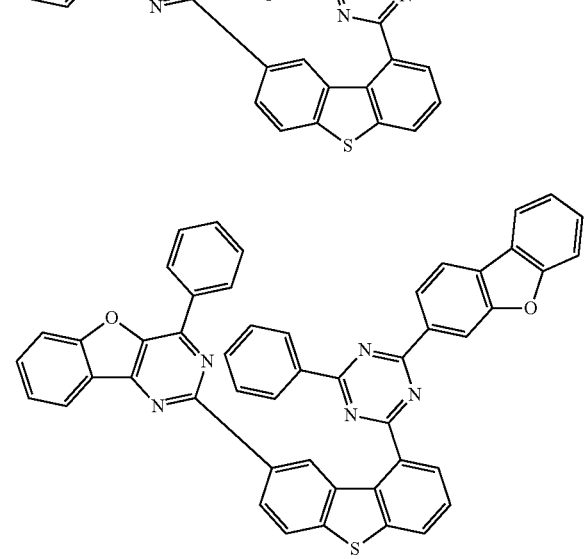

-continued
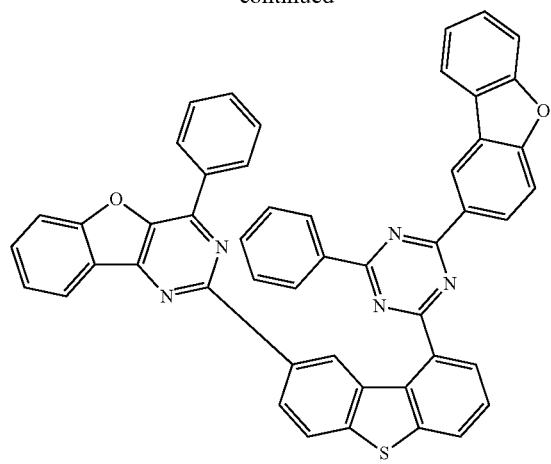
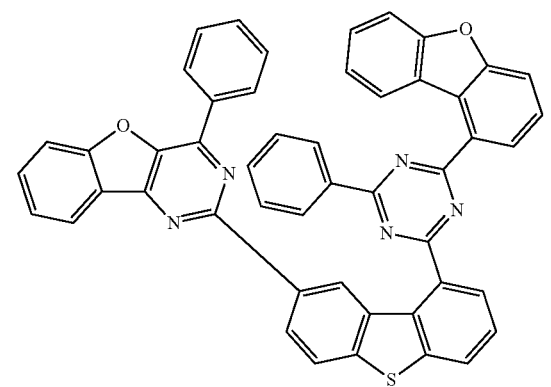
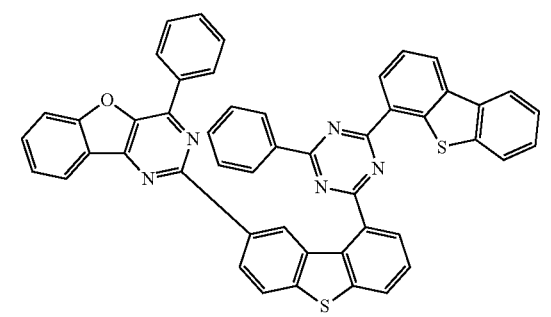
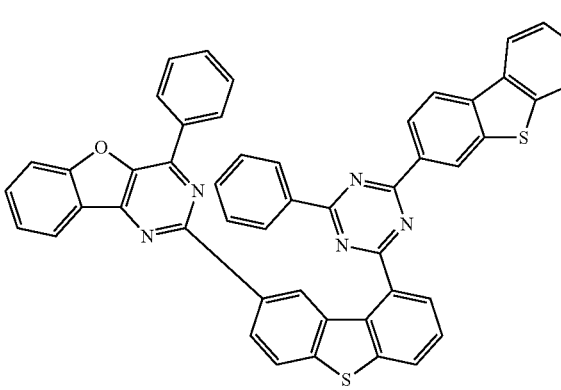
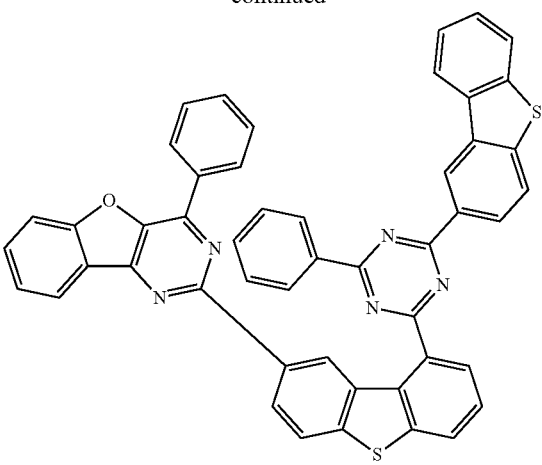
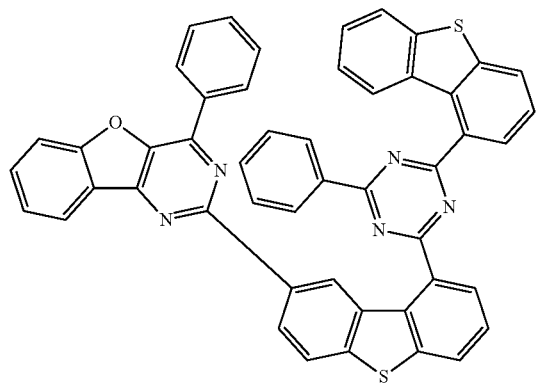
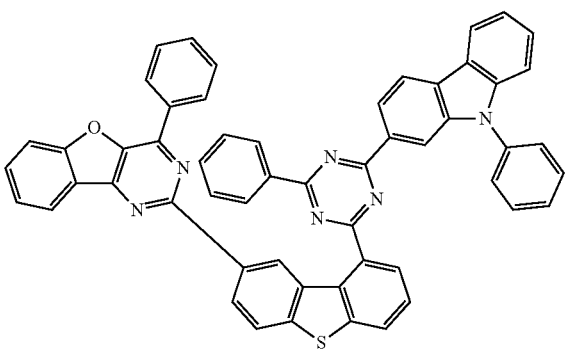
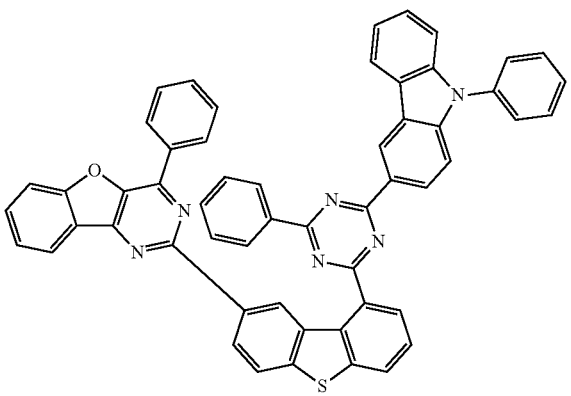

67
-continued
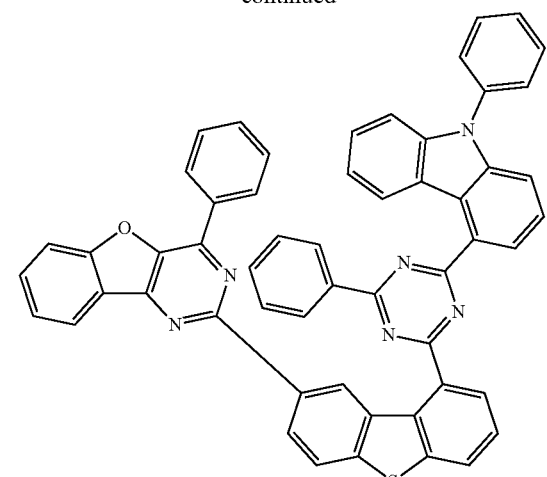
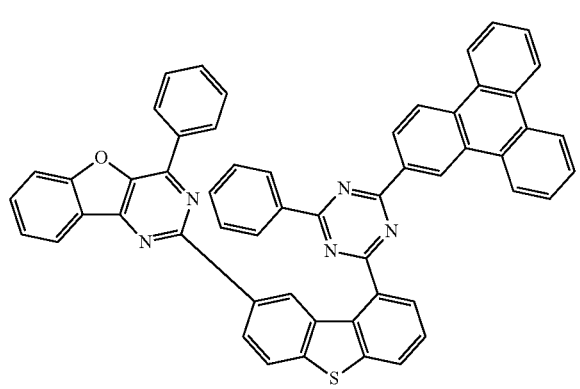
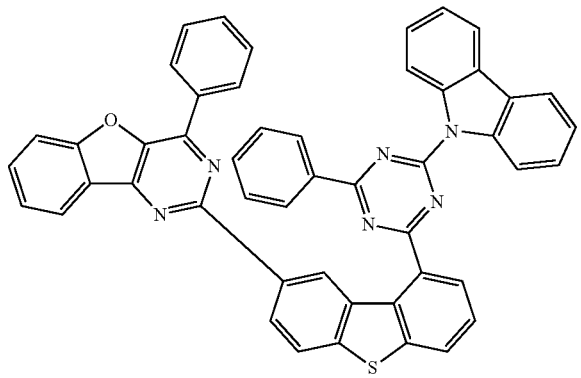
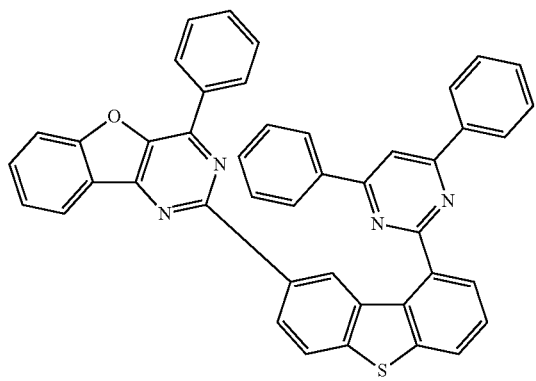
68
-continued
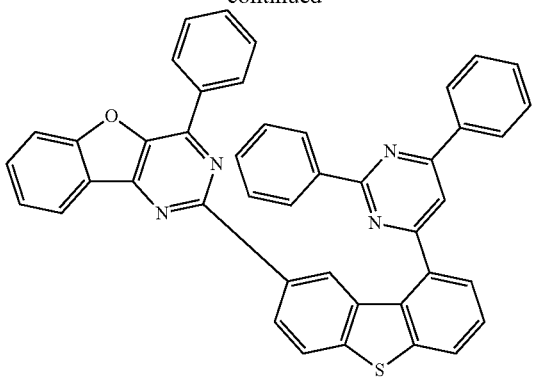
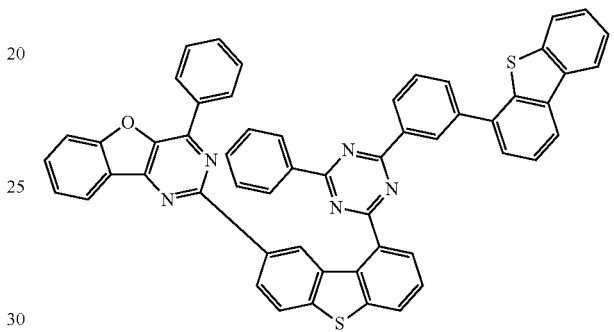
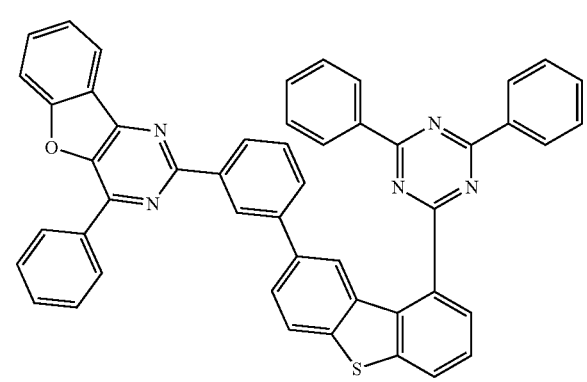

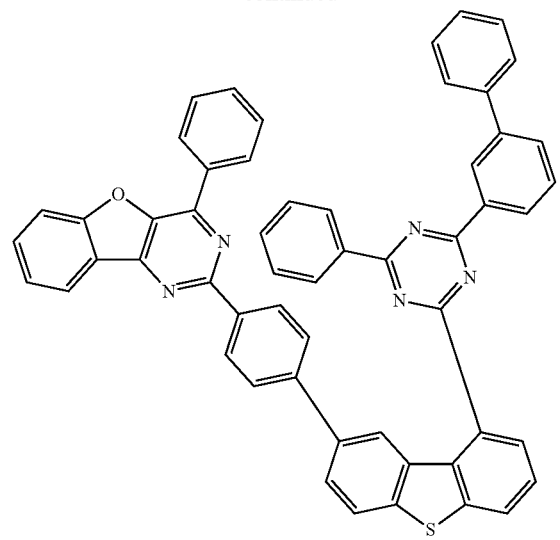
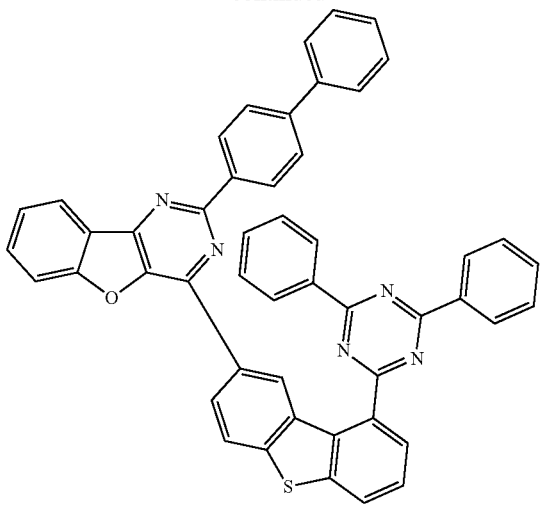
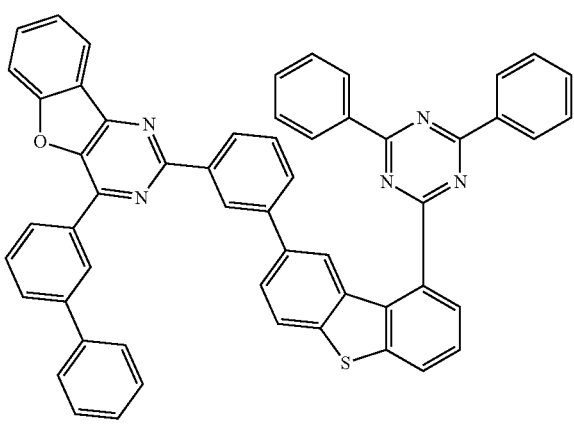
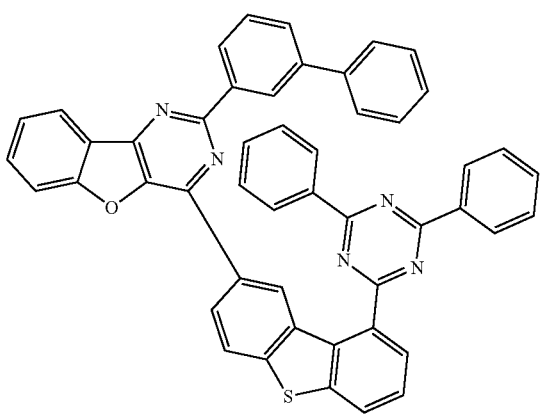
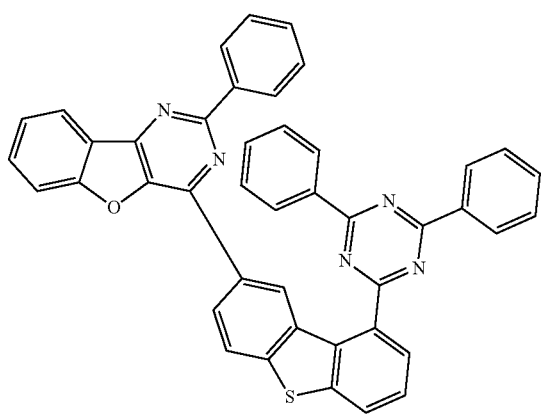
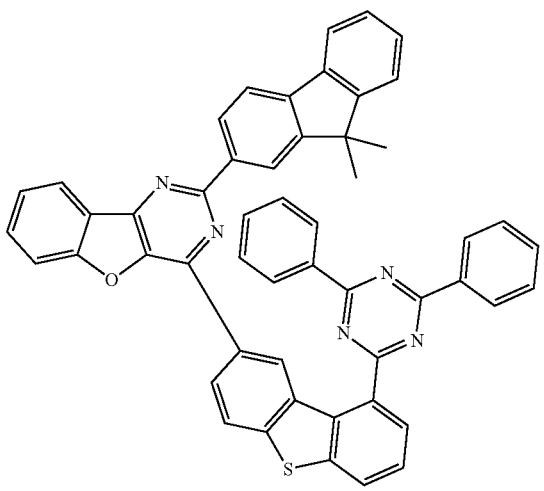

71
-continued
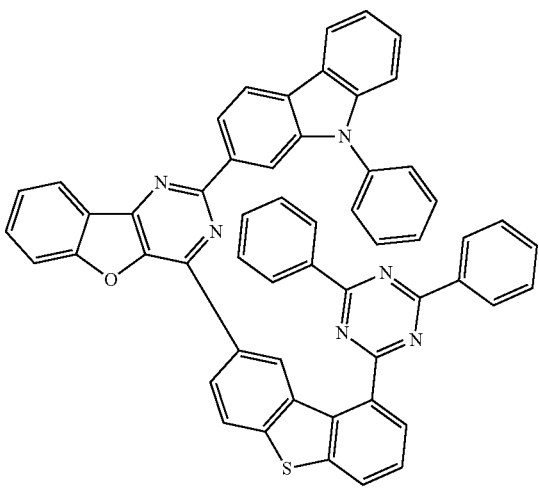
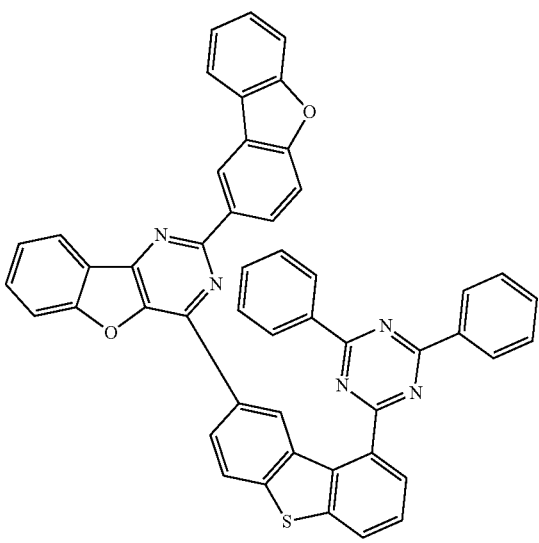
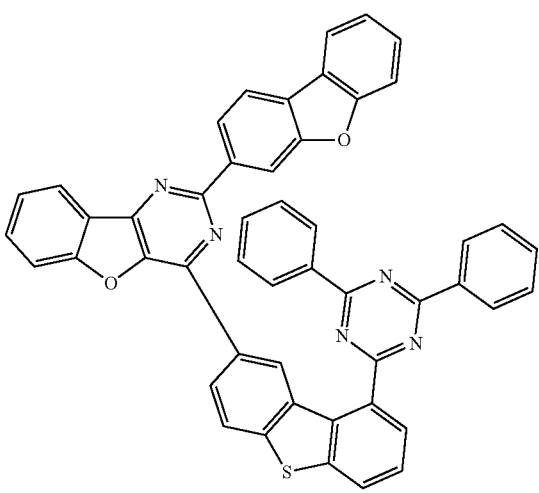
72
-continued
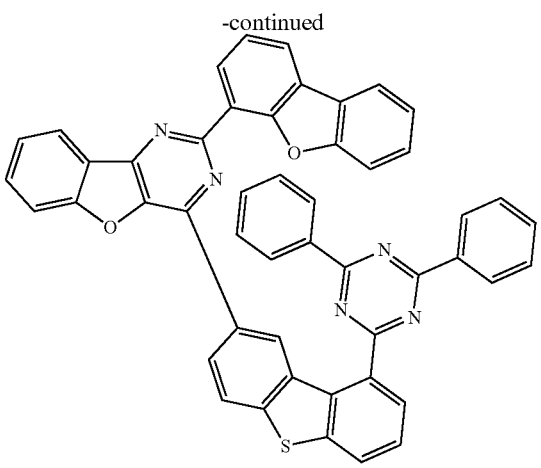
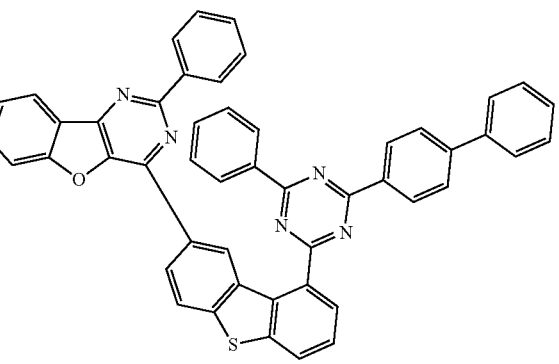
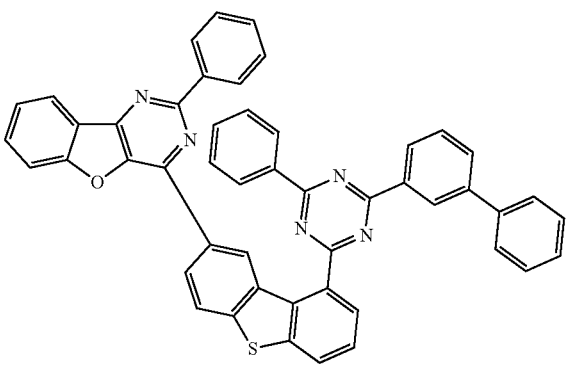
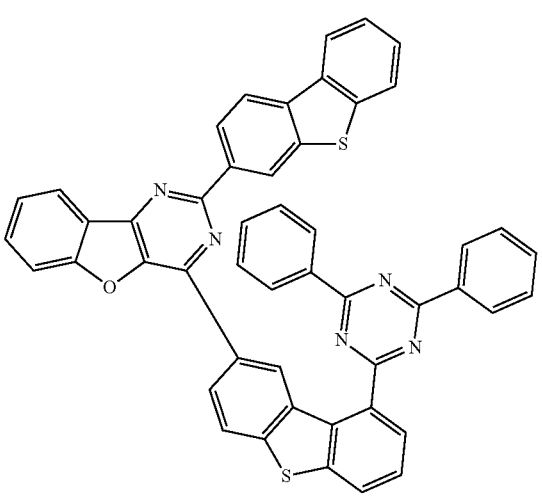

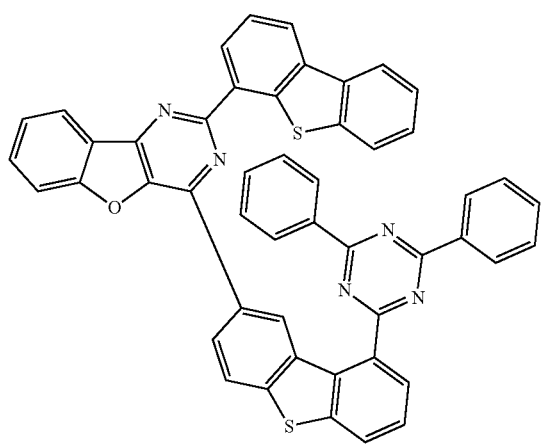
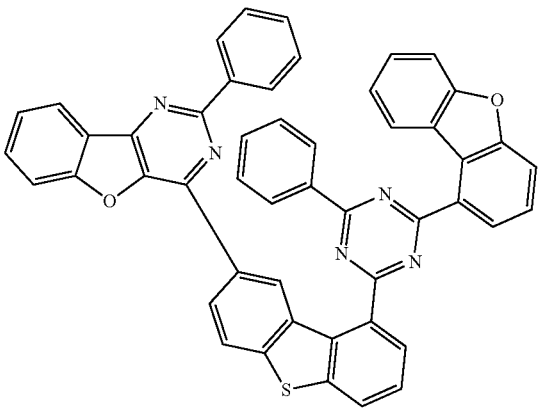
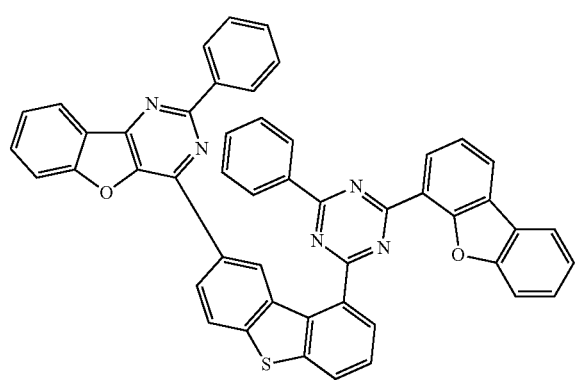
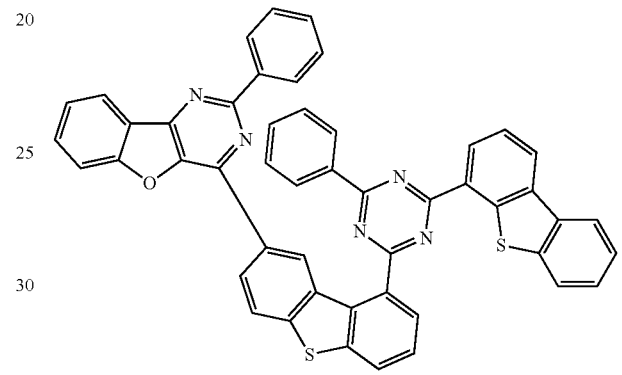
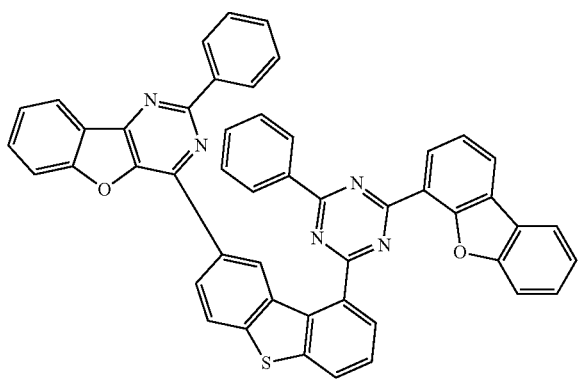
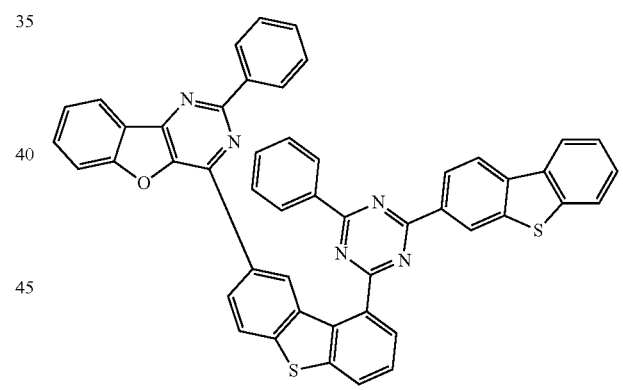
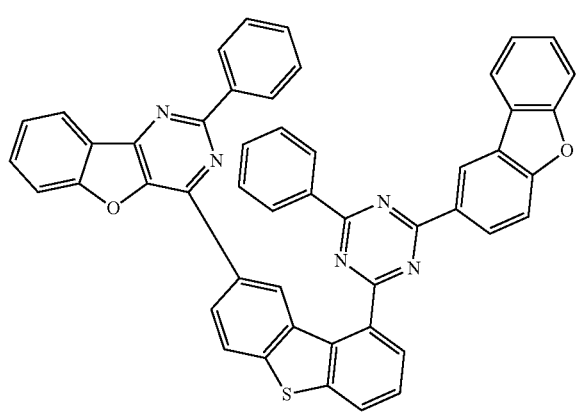
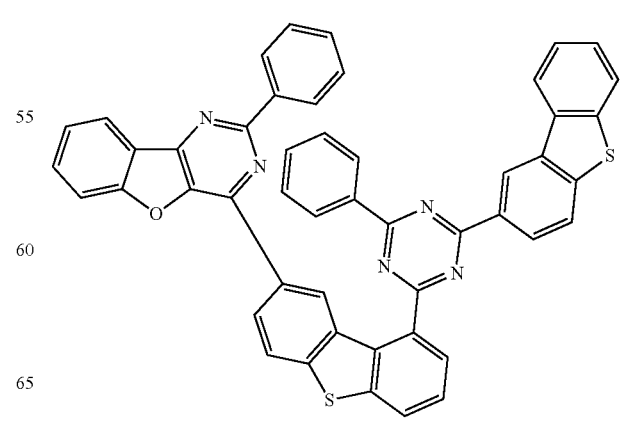

-continued
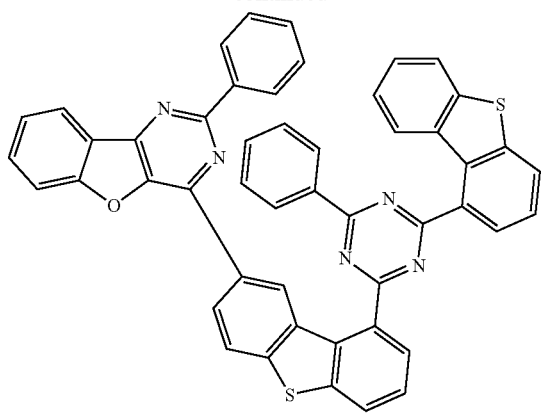
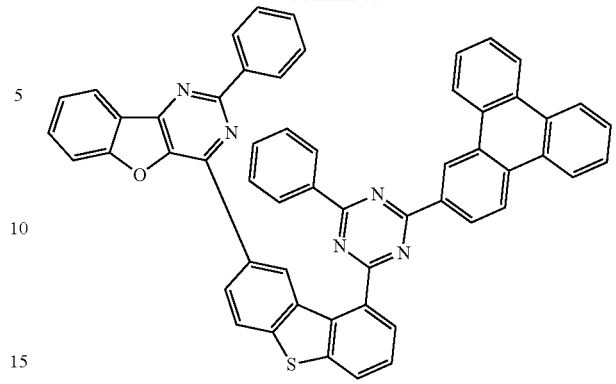
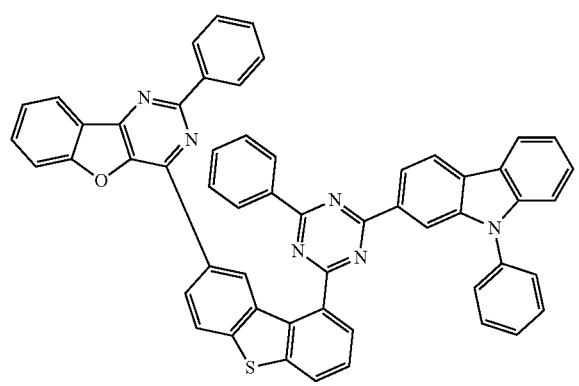
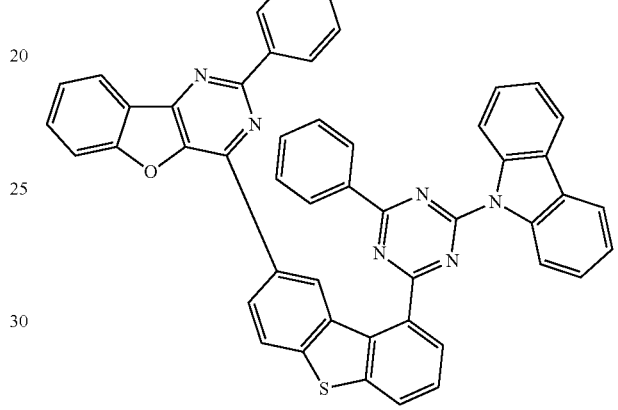
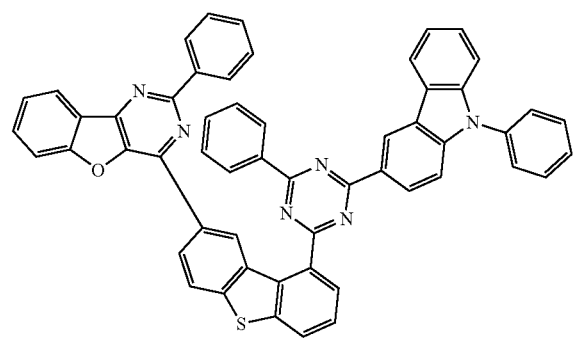
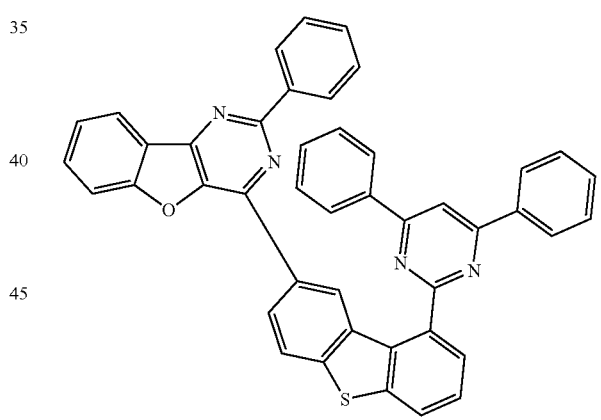
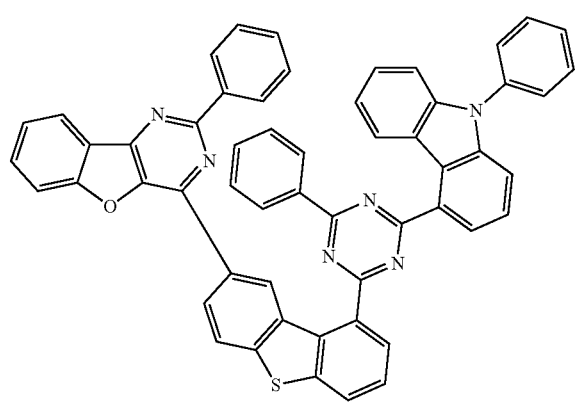
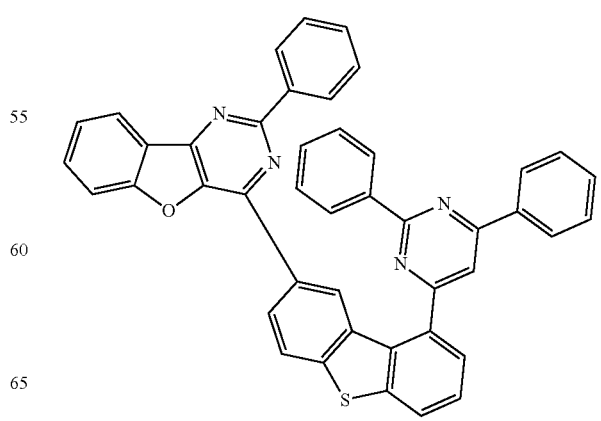

77
-continued
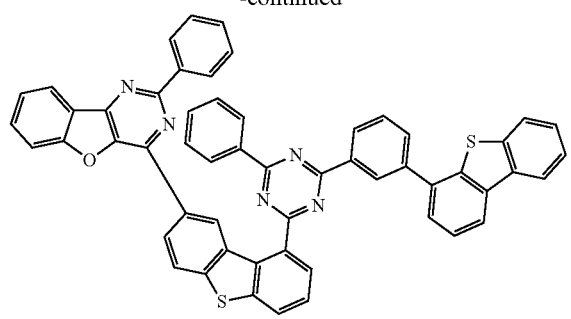
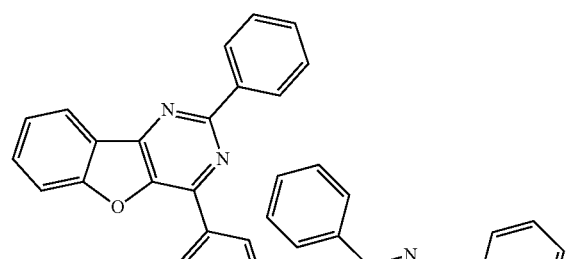
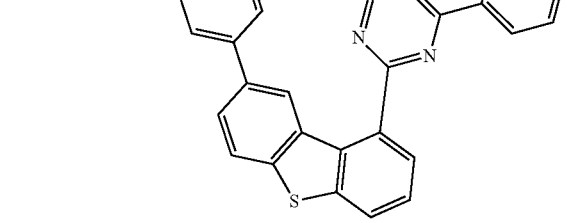
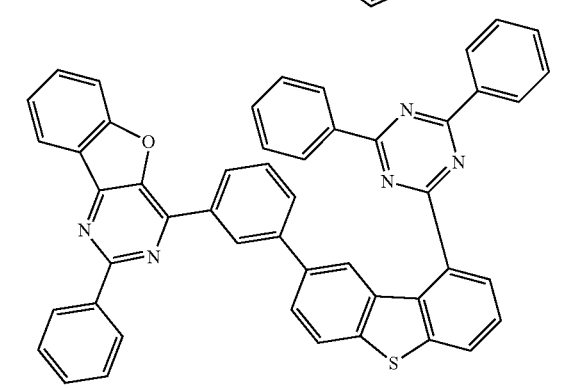
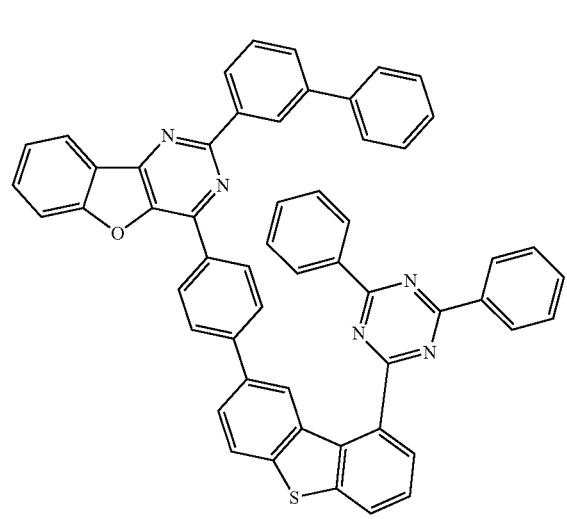
78
-continued
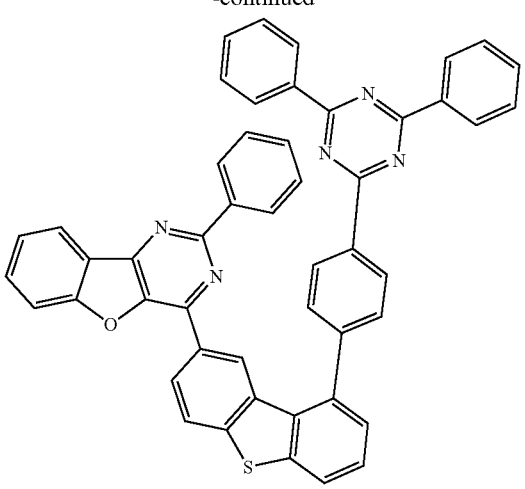

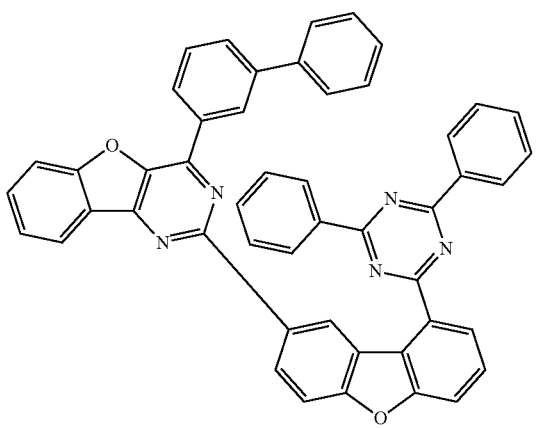
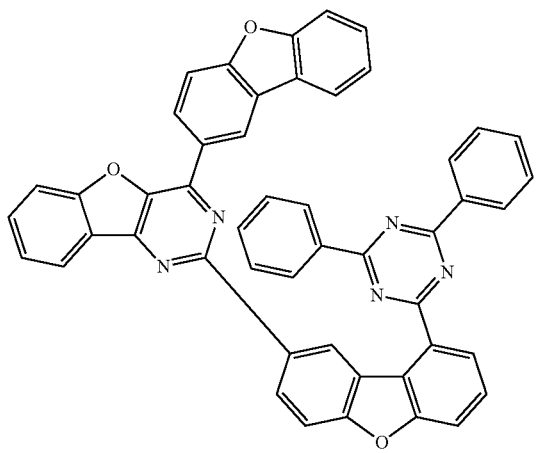
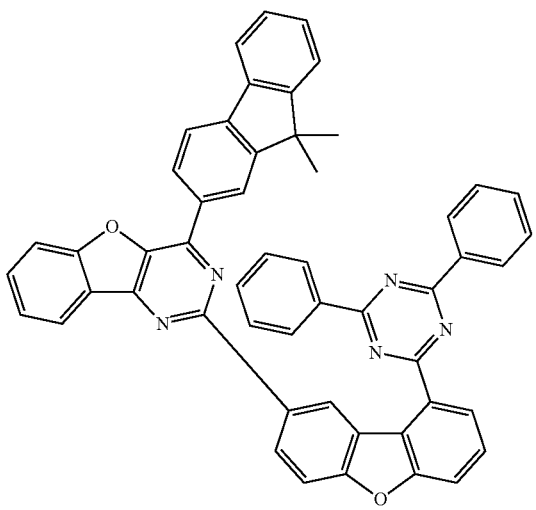
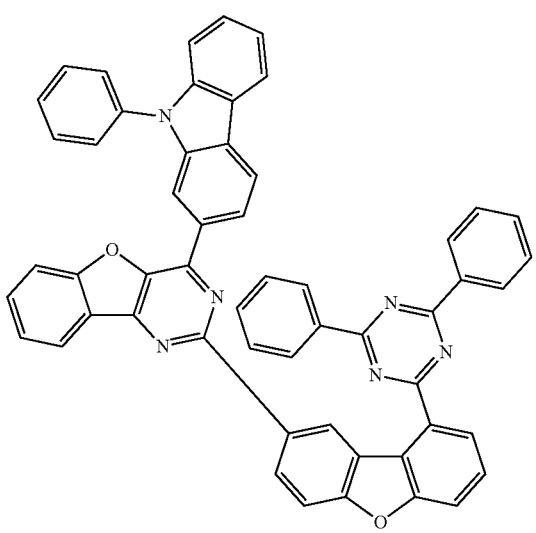
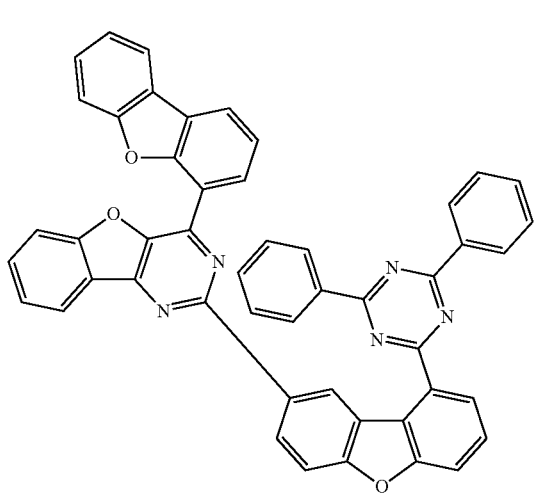

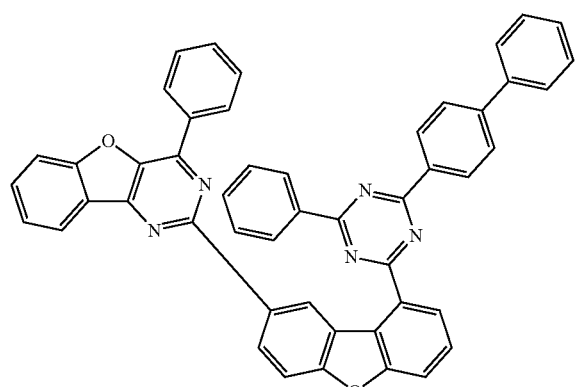
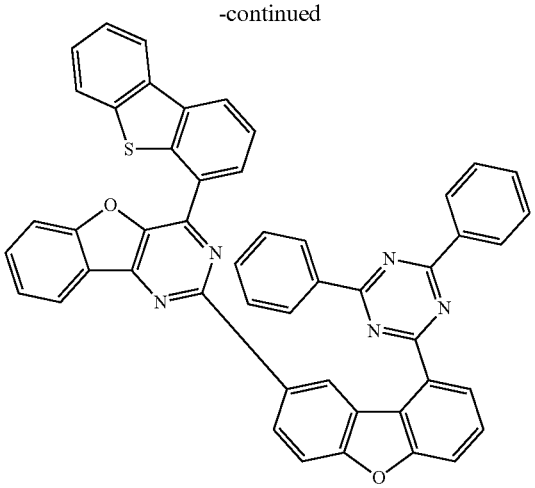
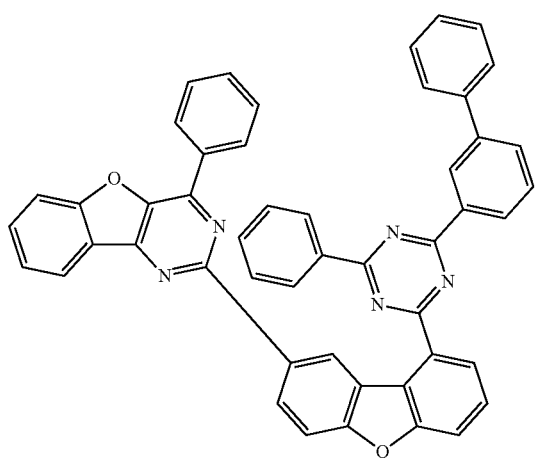
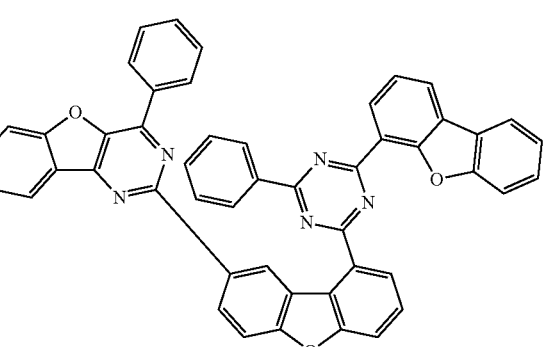
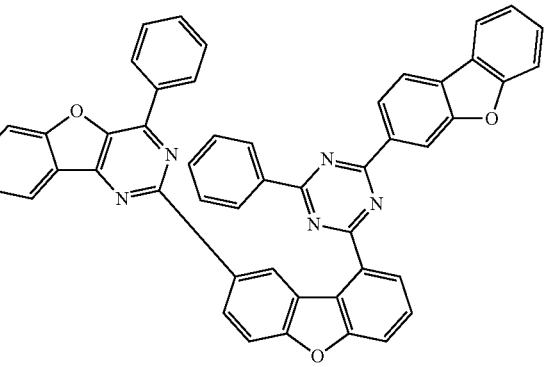
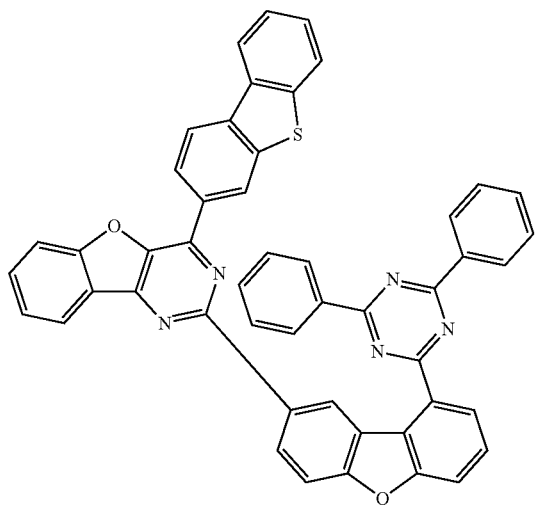
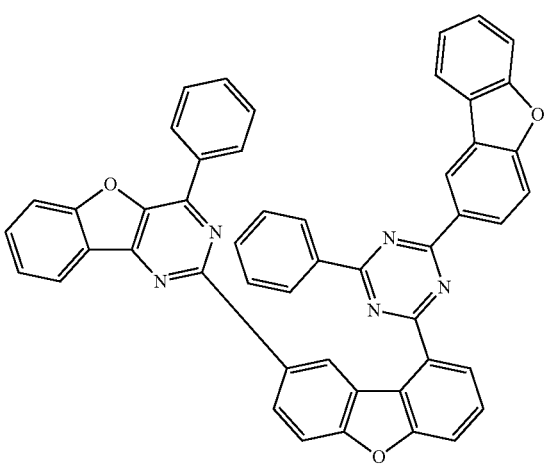

83
-continued
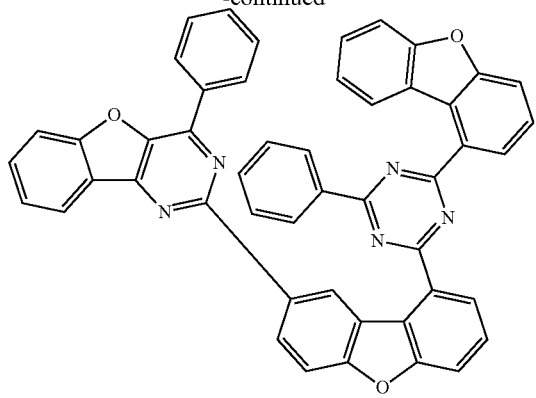
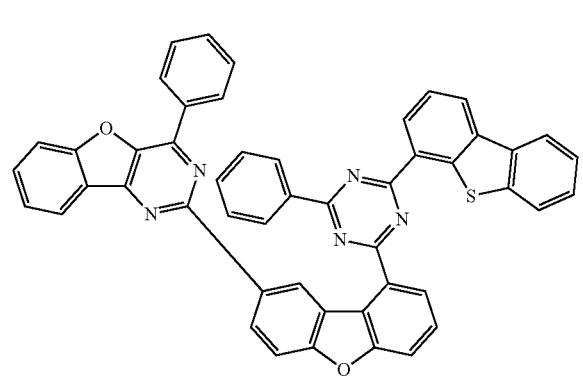
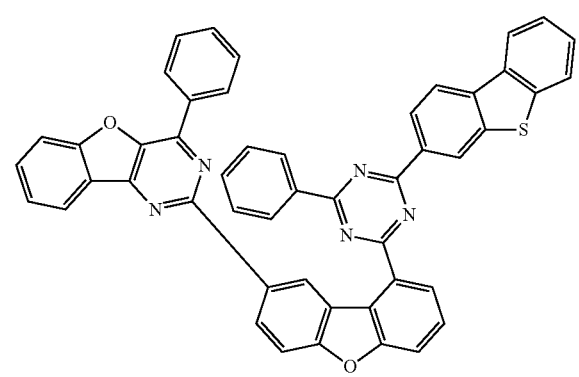
84
-continued
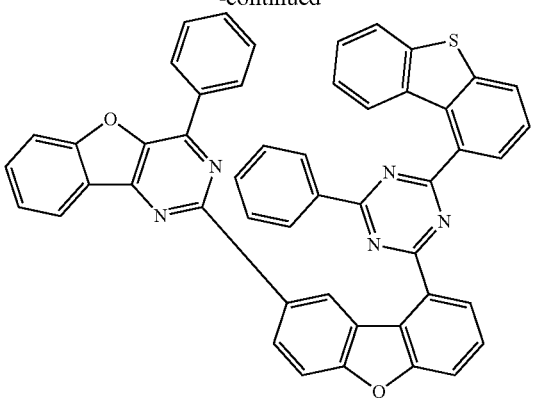
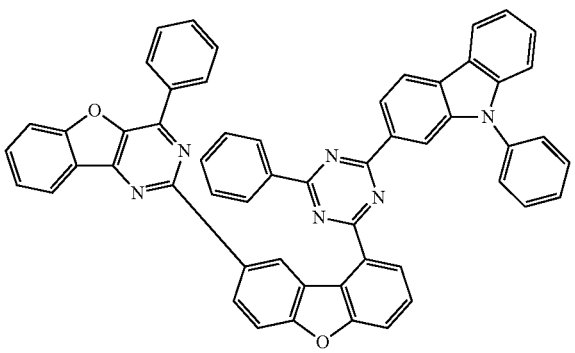
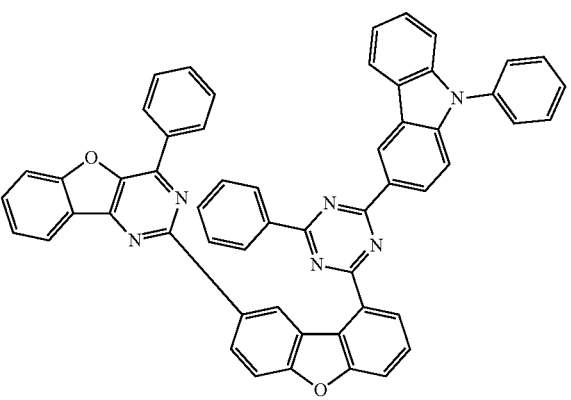
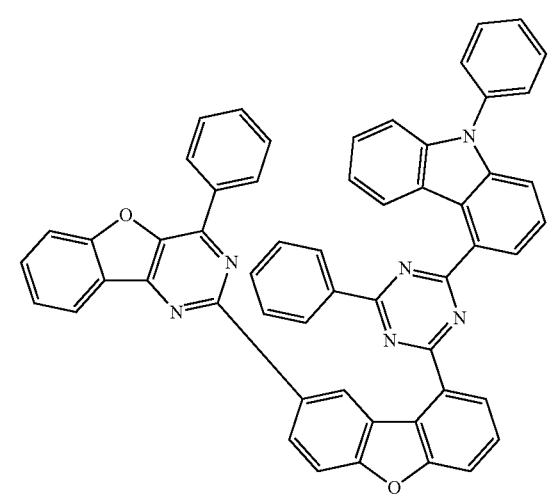

85
-continued
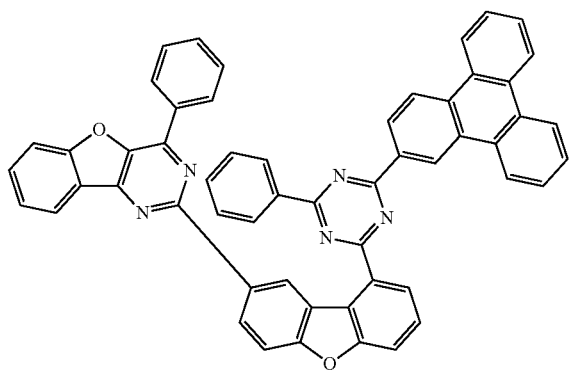
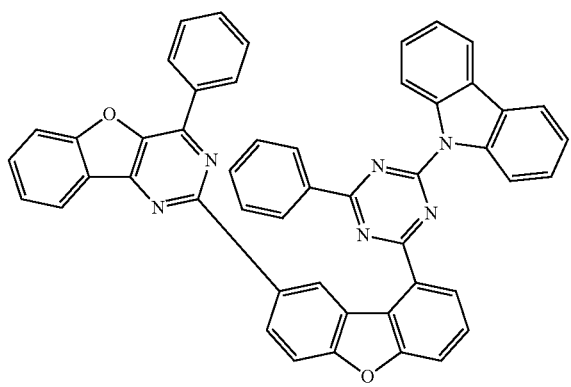
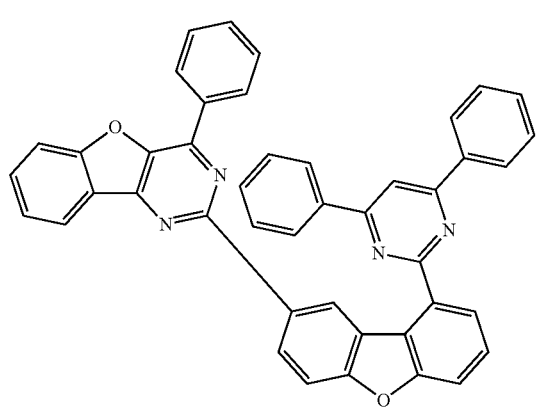
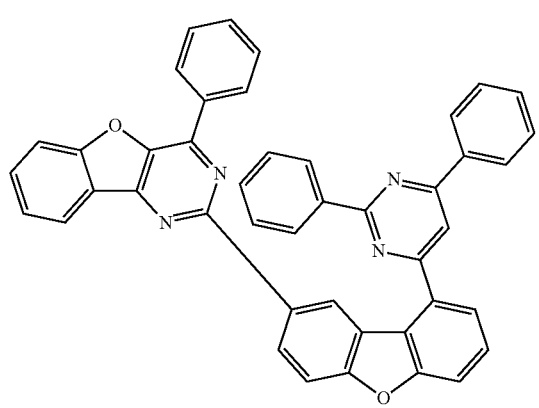
86
-continued
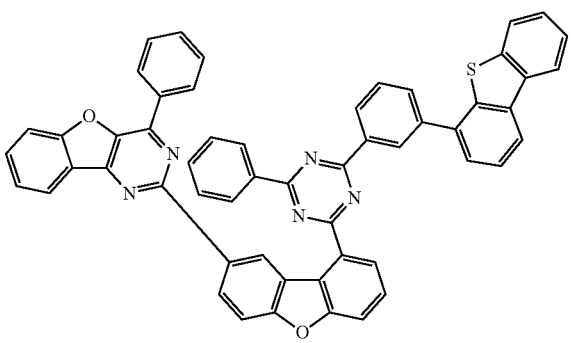
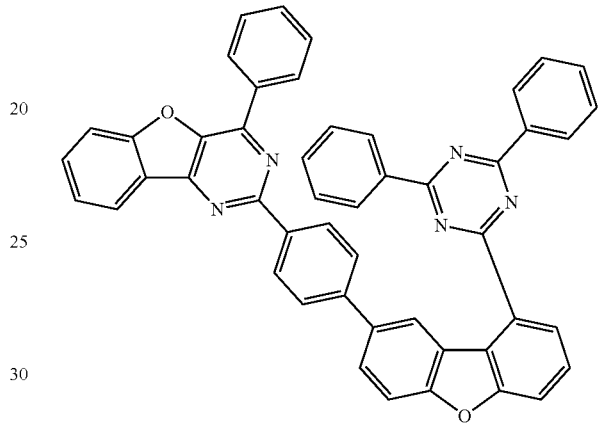
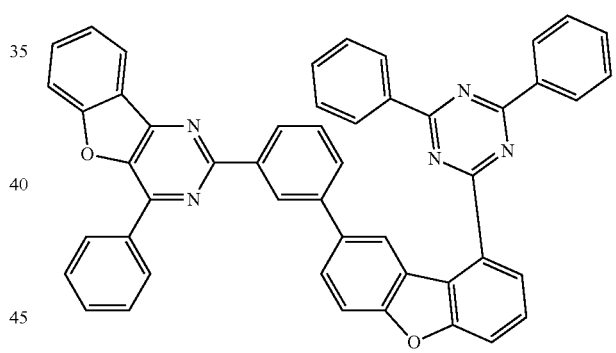
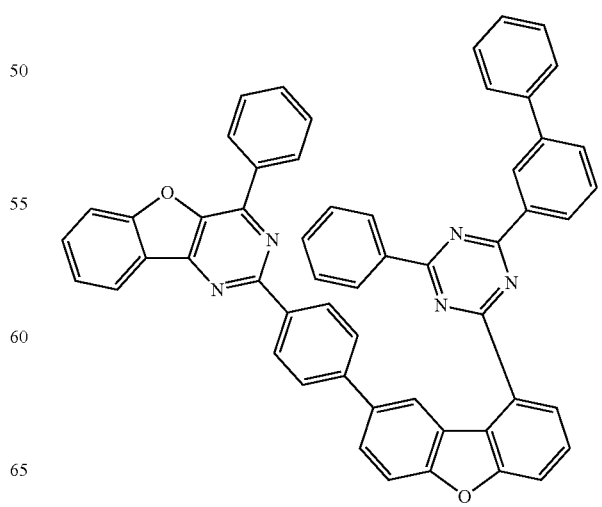

87
-continued
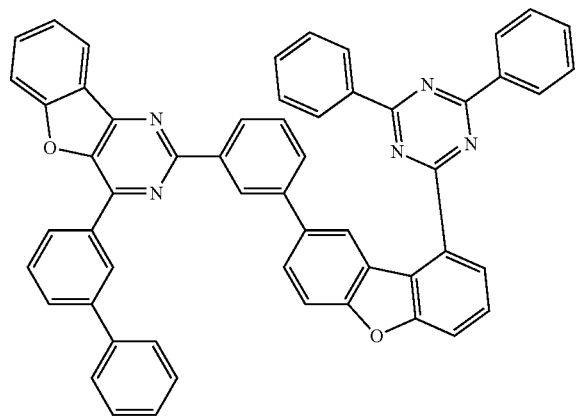
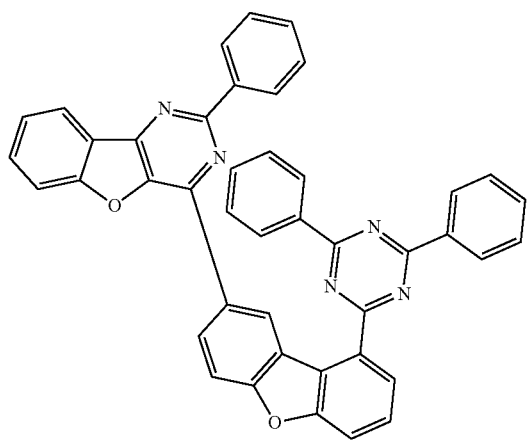
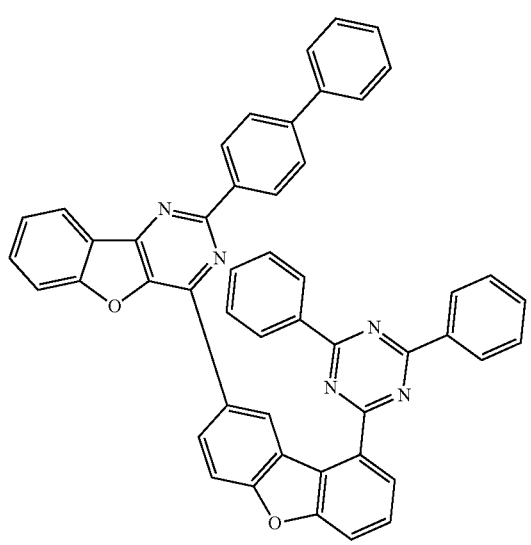
88
-continued
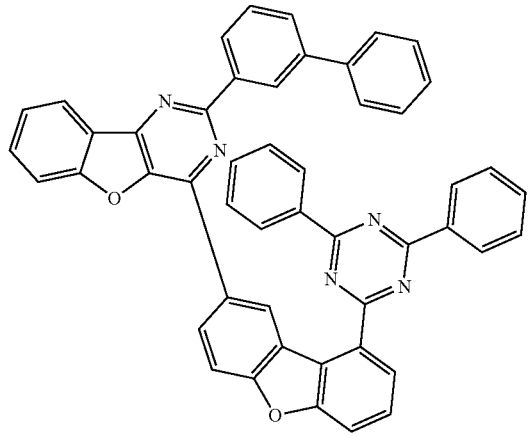
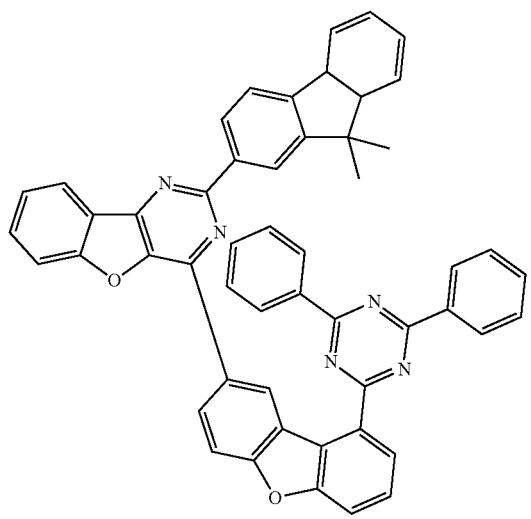
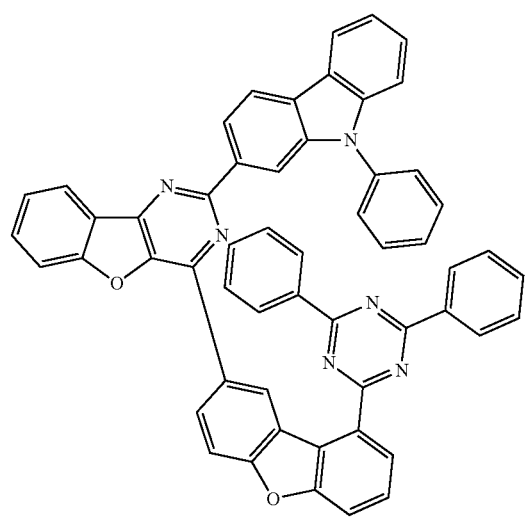

-continued
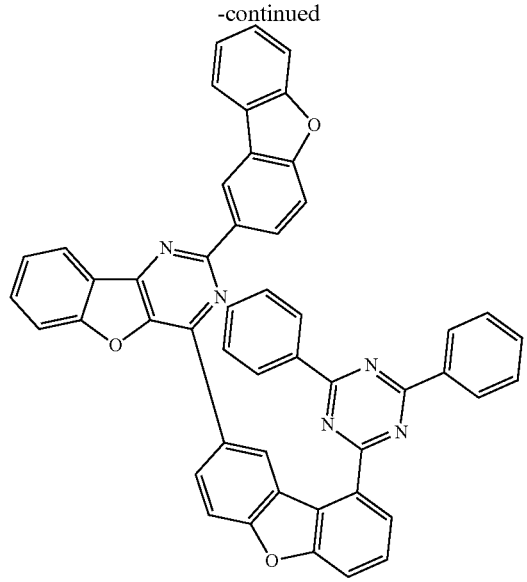
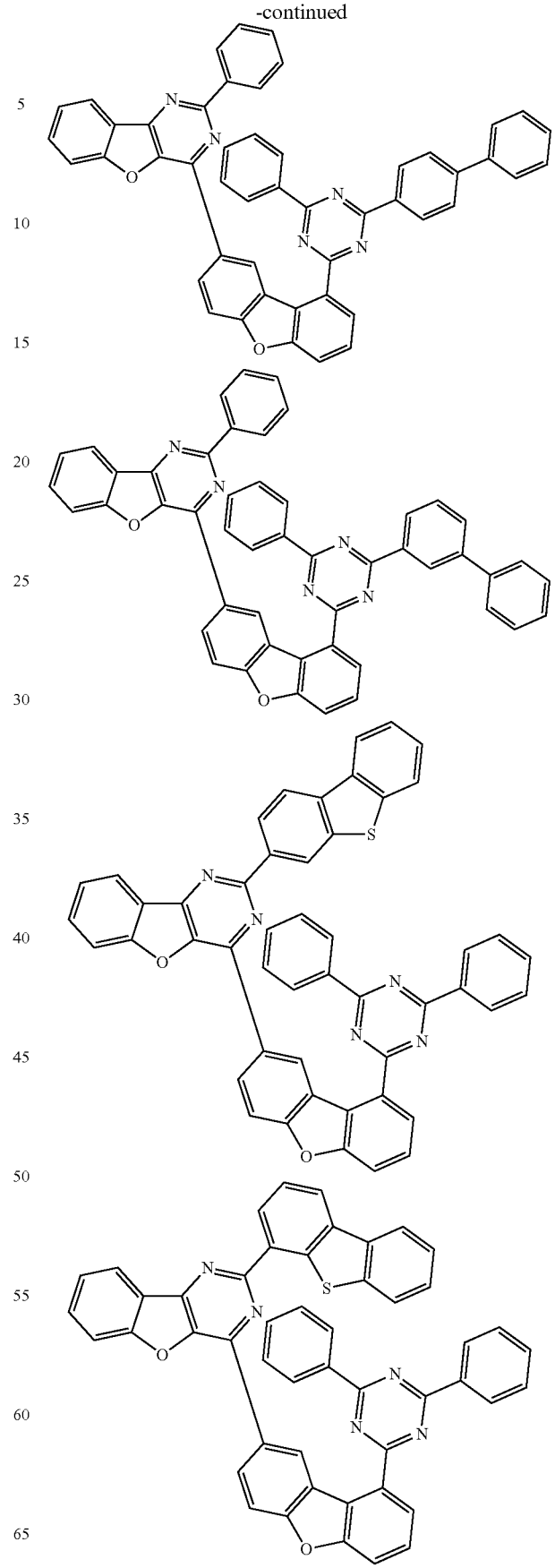

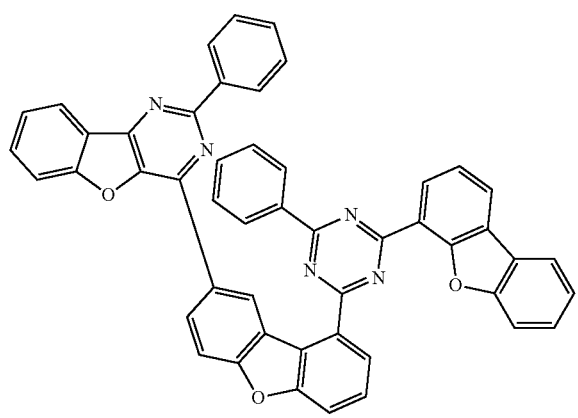
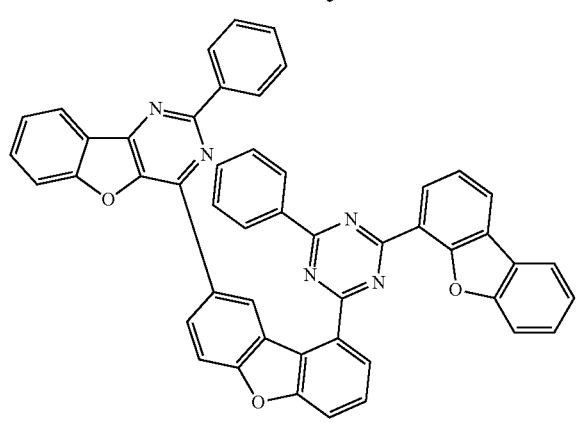
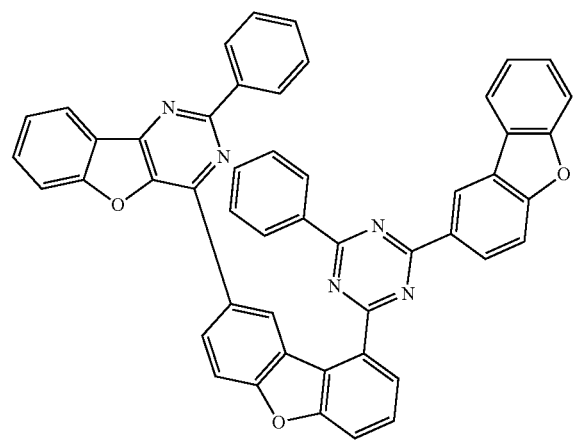
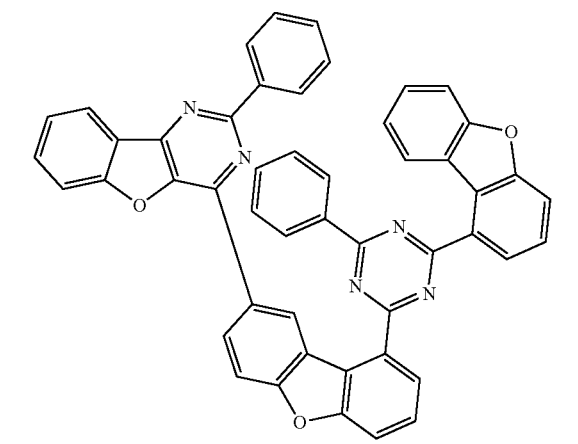
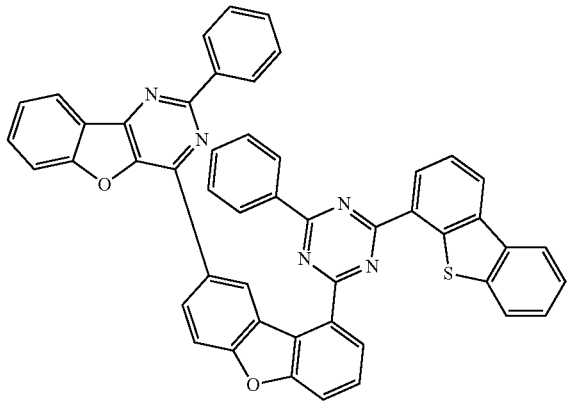
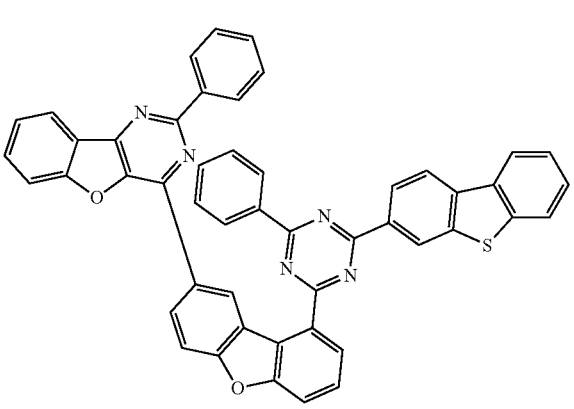
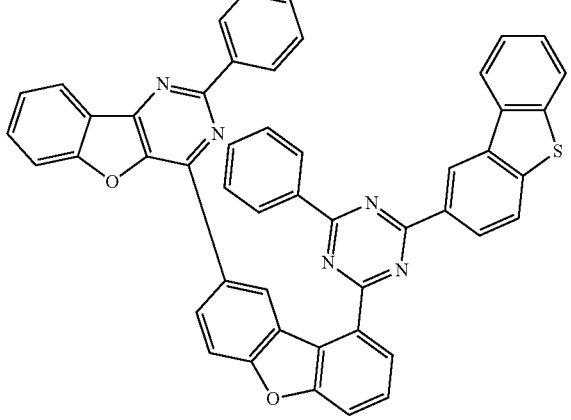
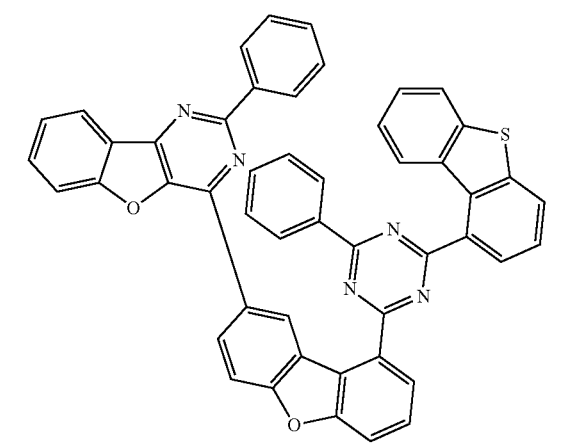

93
-continued
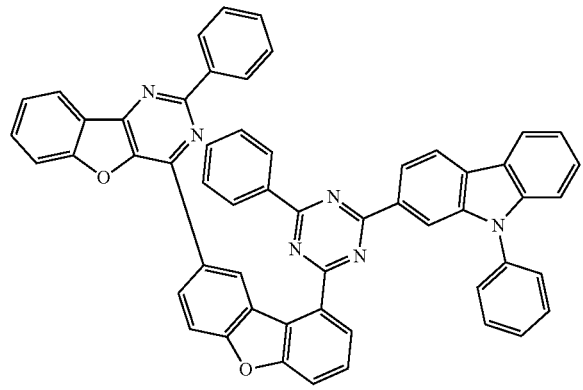
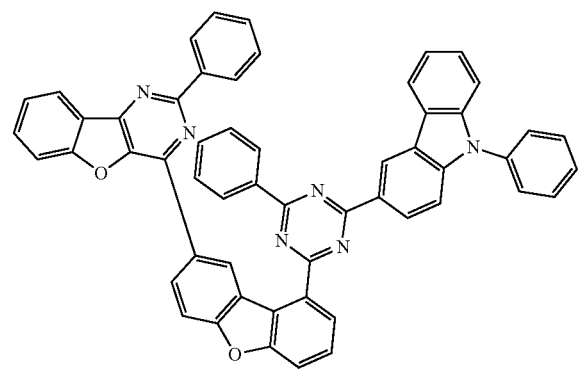
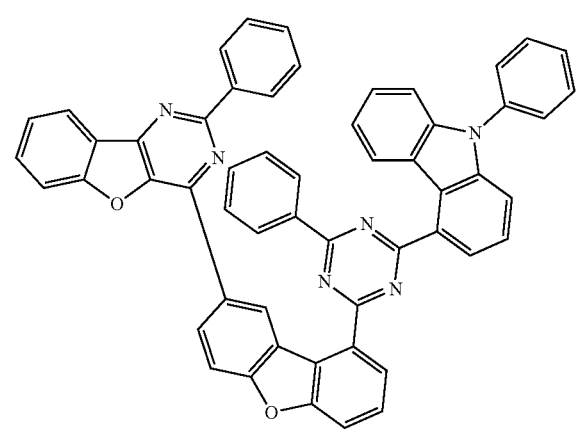
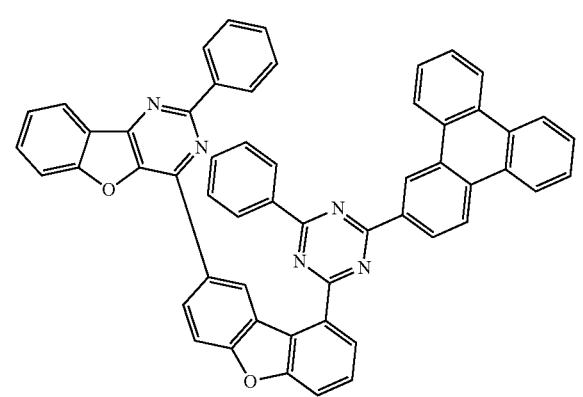
94
-continued
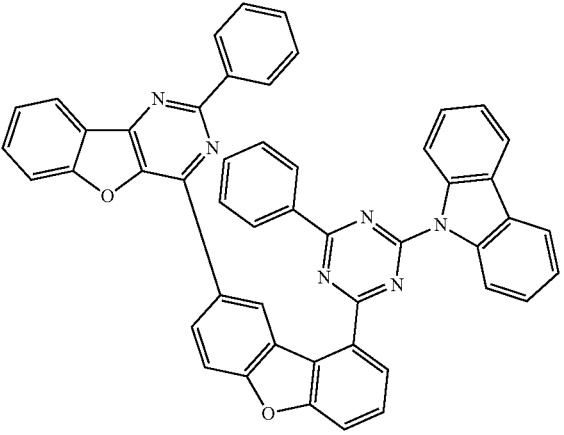
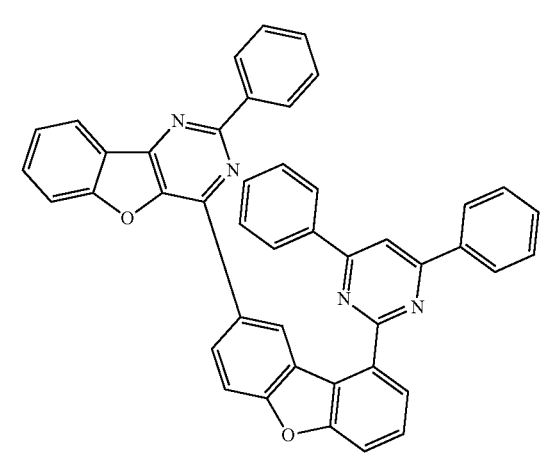
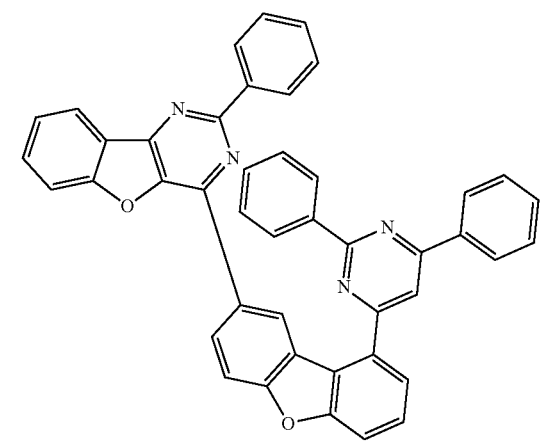
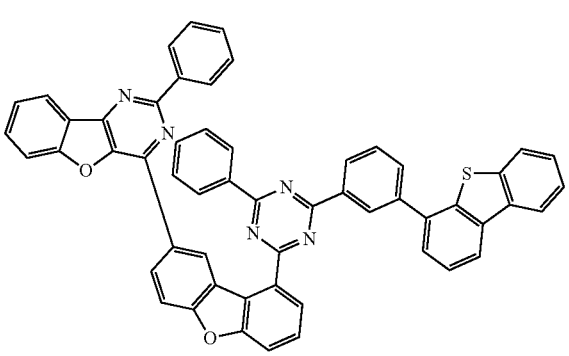

95
-continued
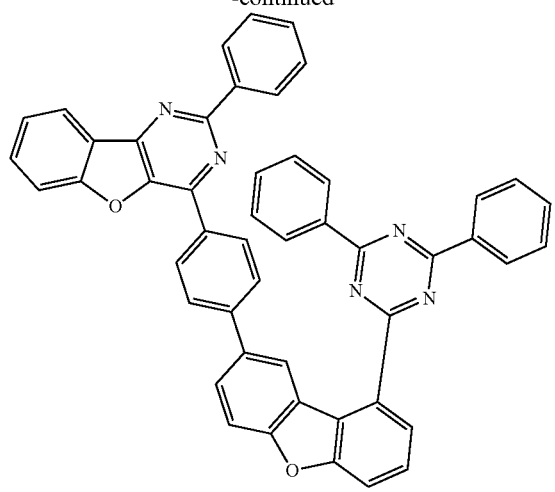
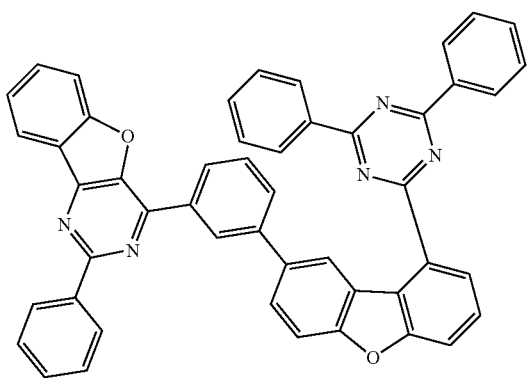
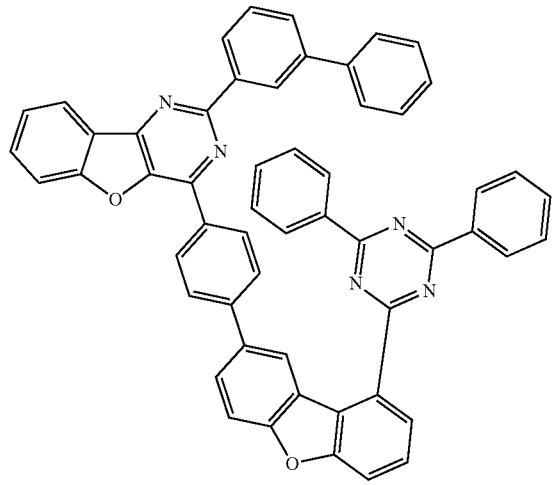
96
-continued
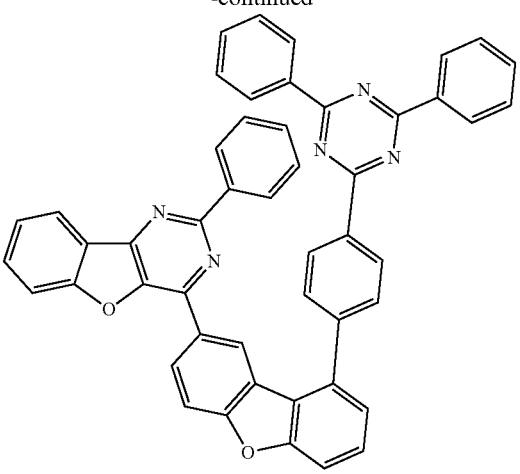
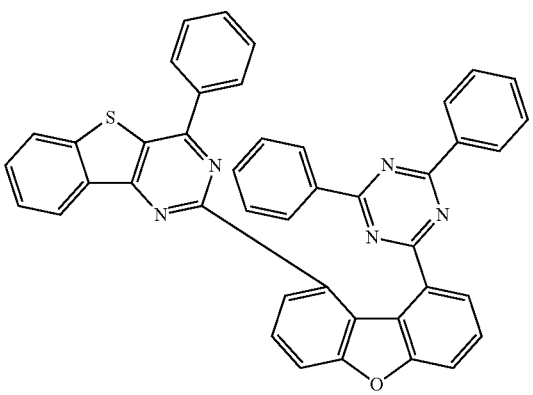
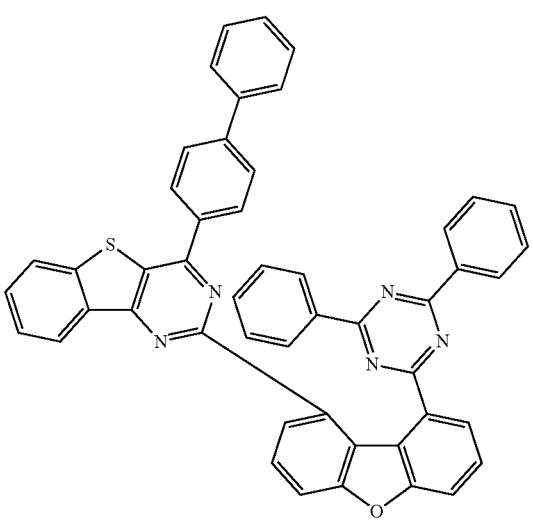

97
-continued
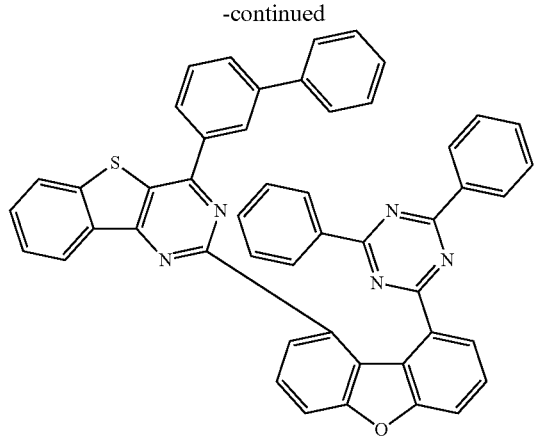
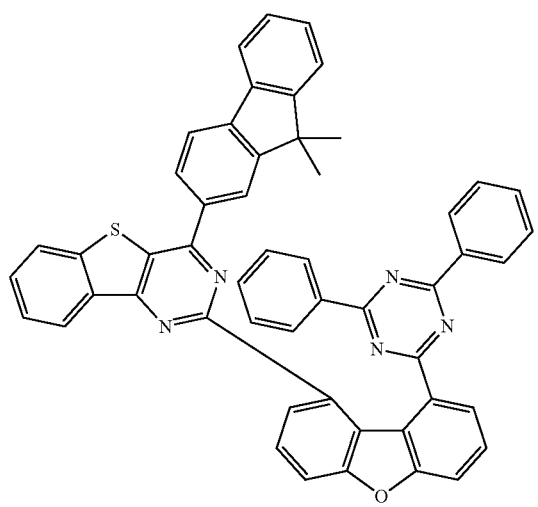
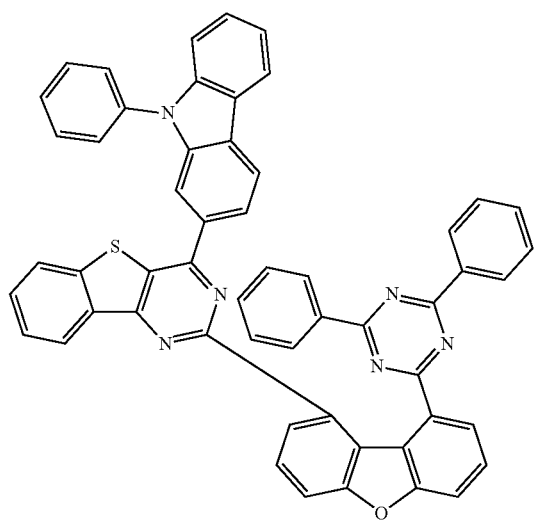
98
-continued
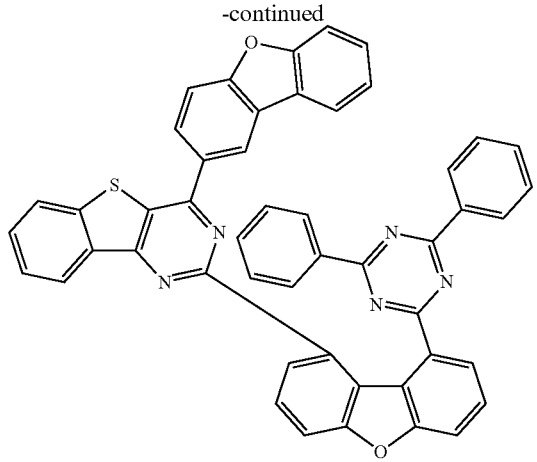
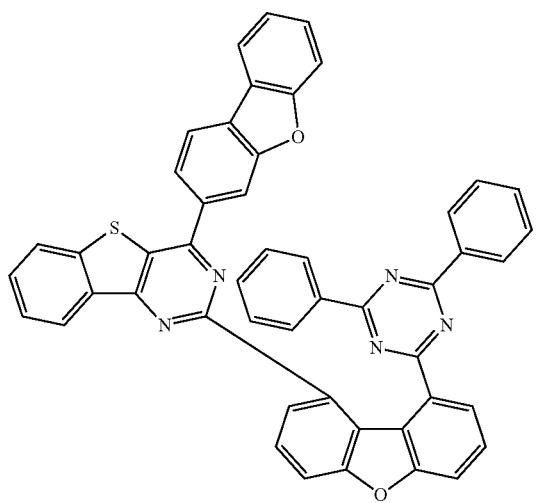
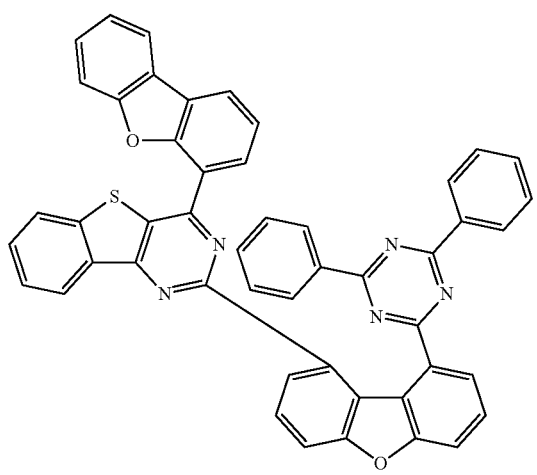

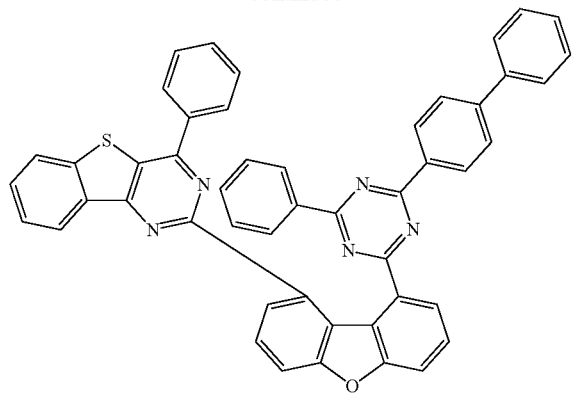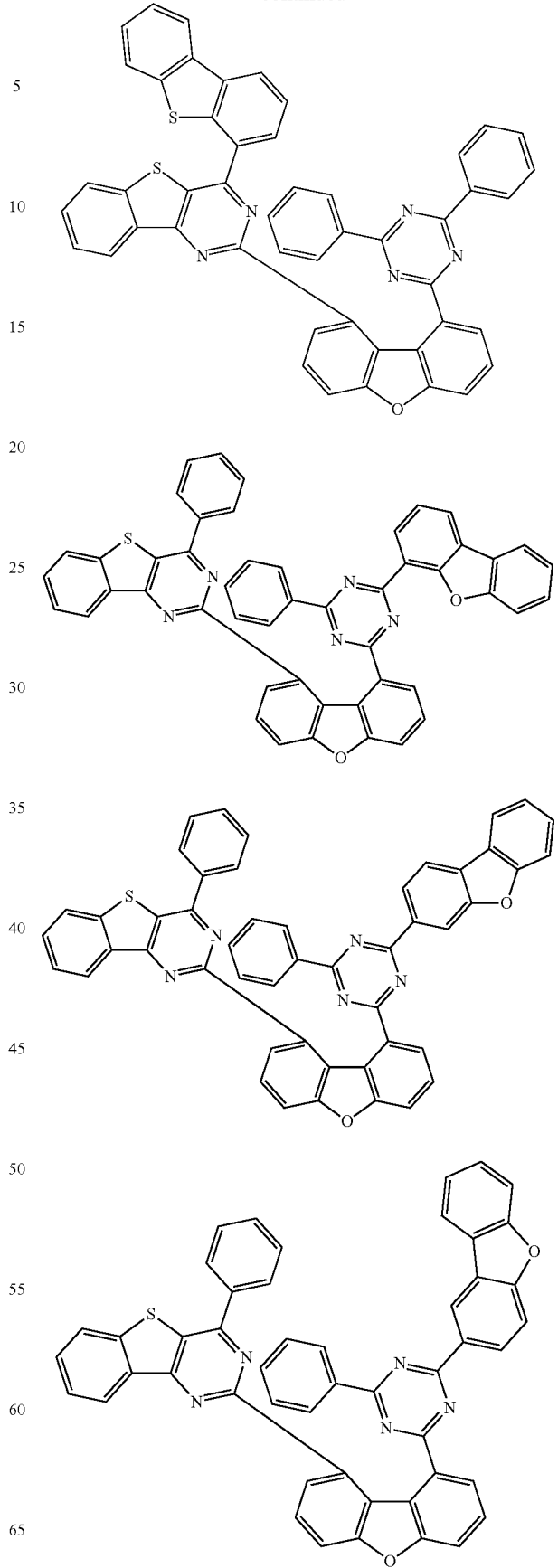

101
-continued
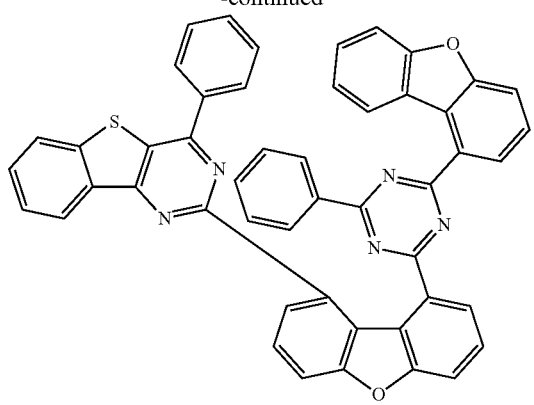
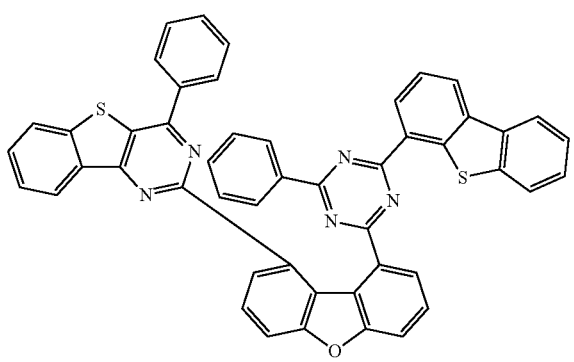
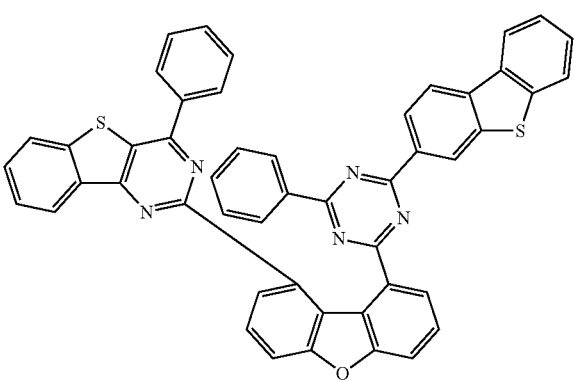
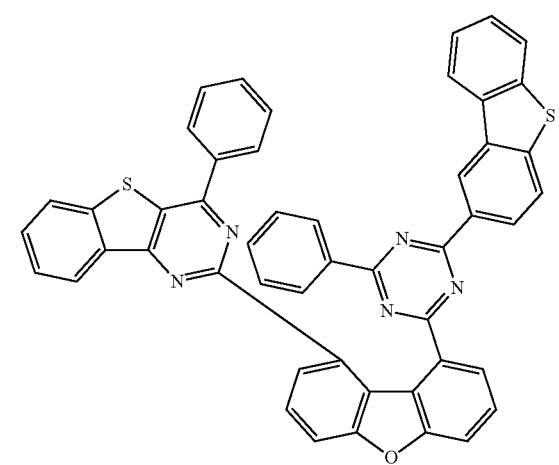
102
-continued
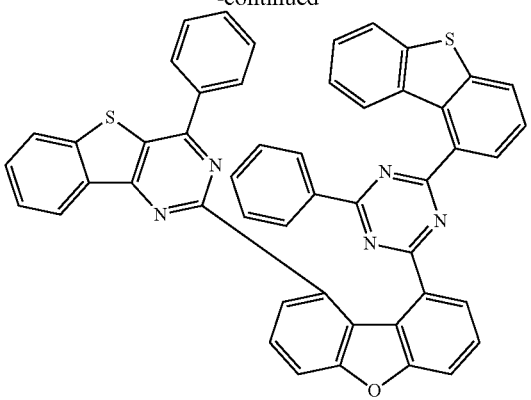
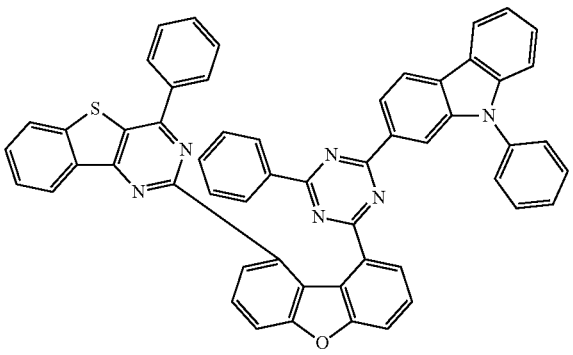
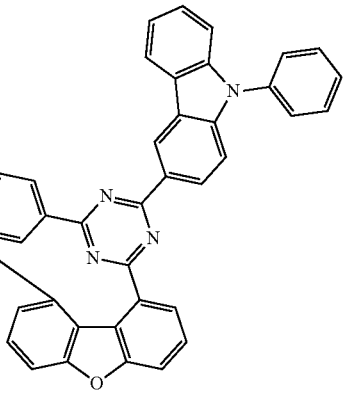
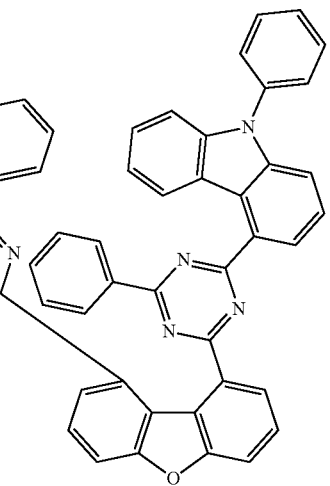

103
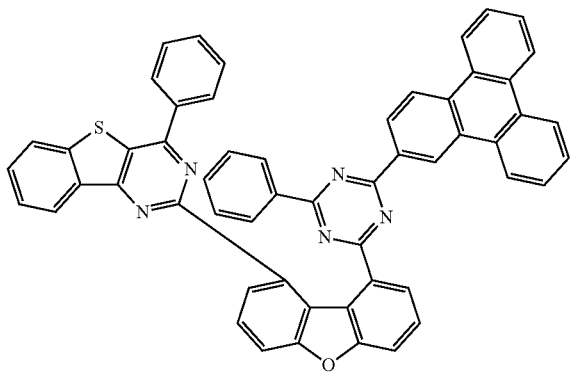
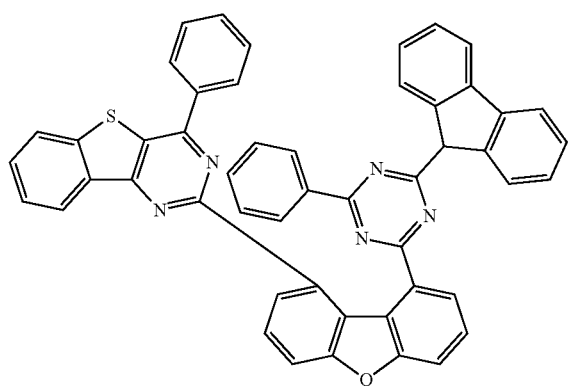
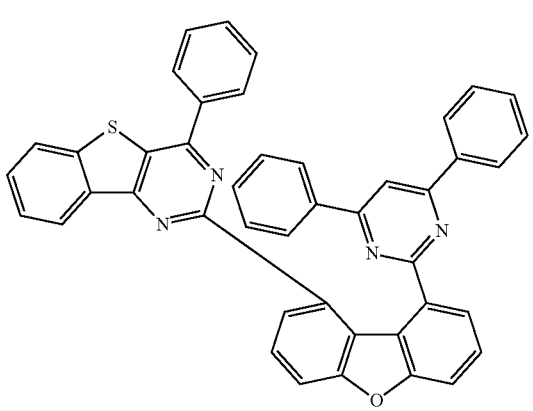
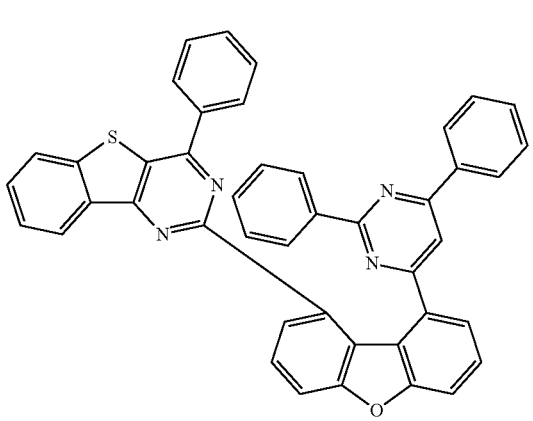
104
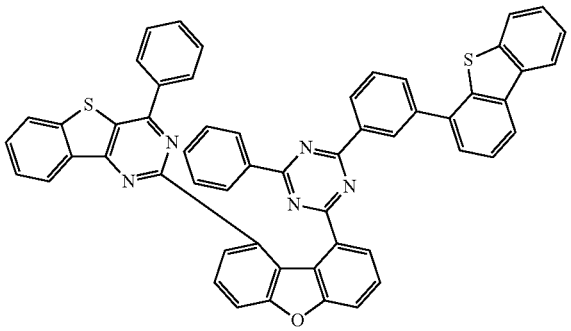
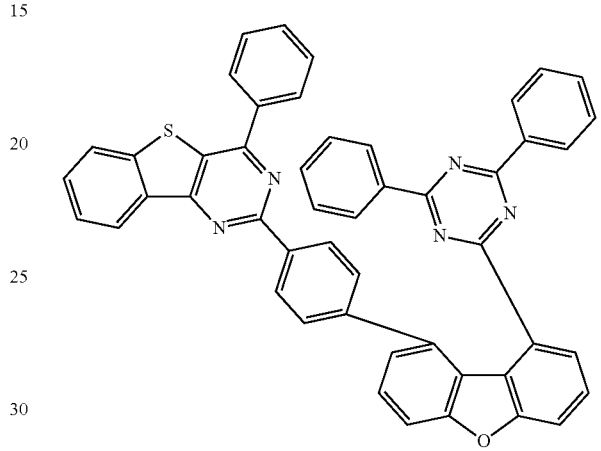
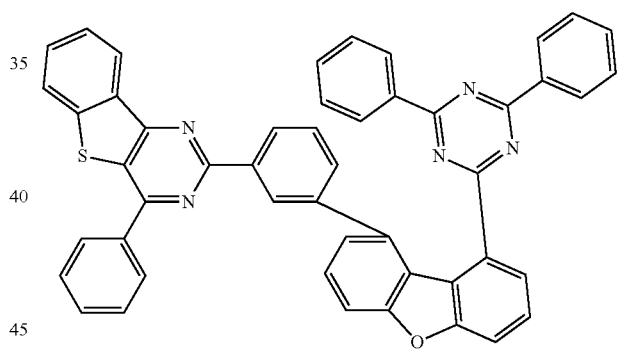
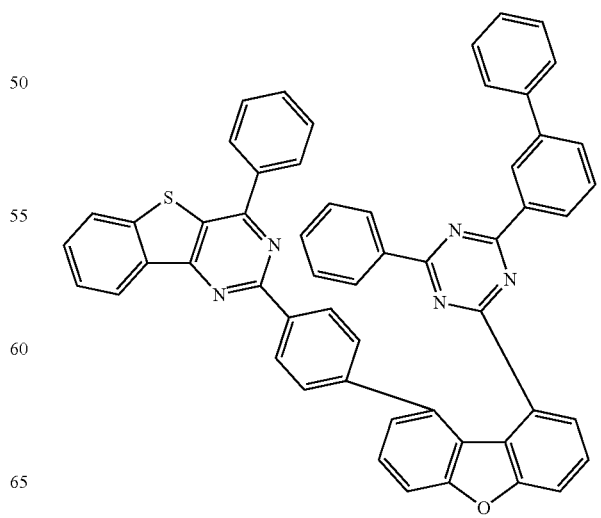

105
-continued
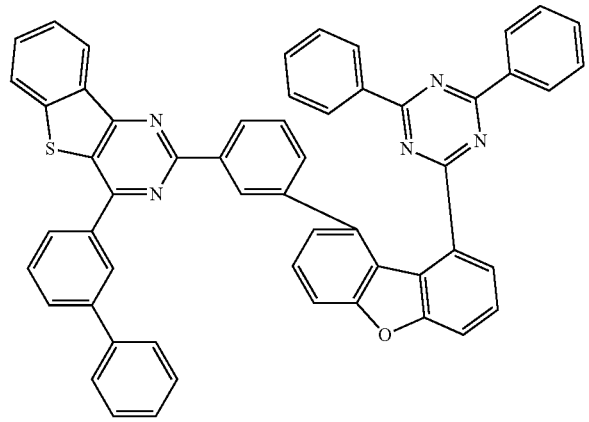
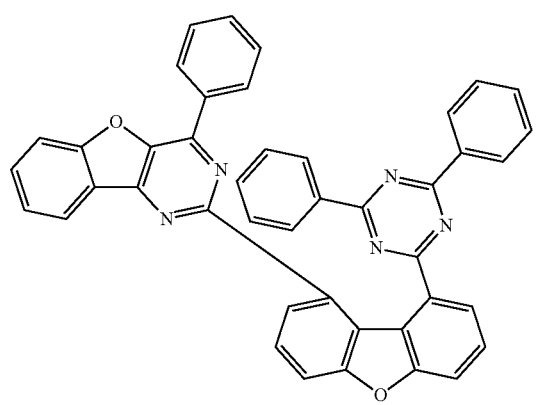
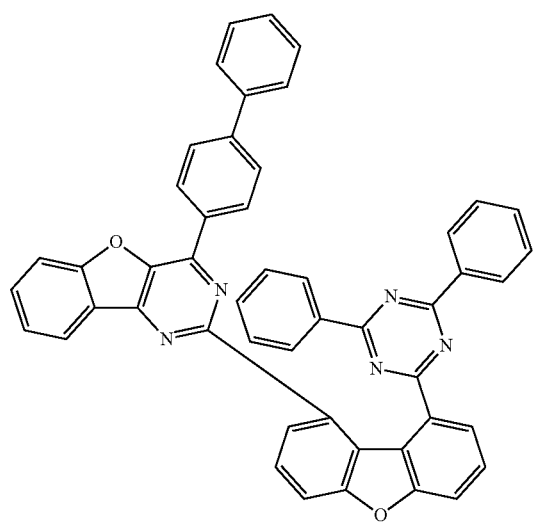
106
-continued
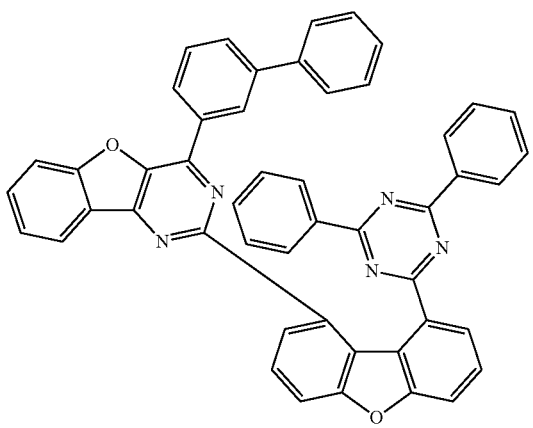
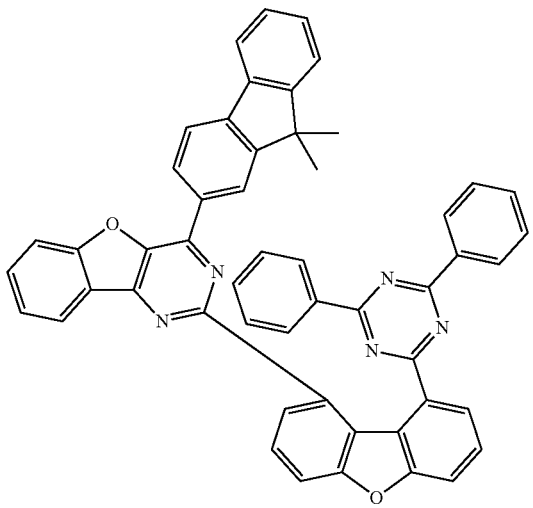
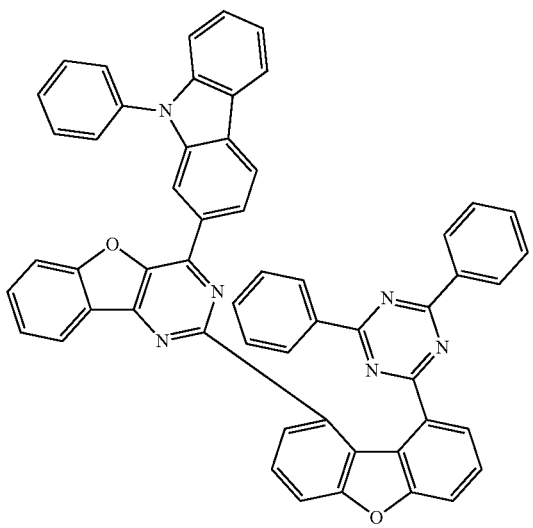

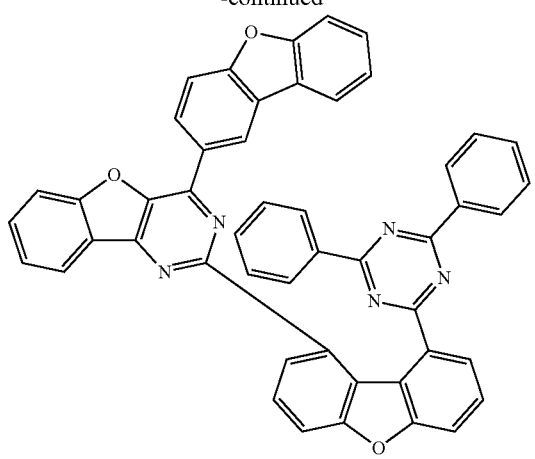
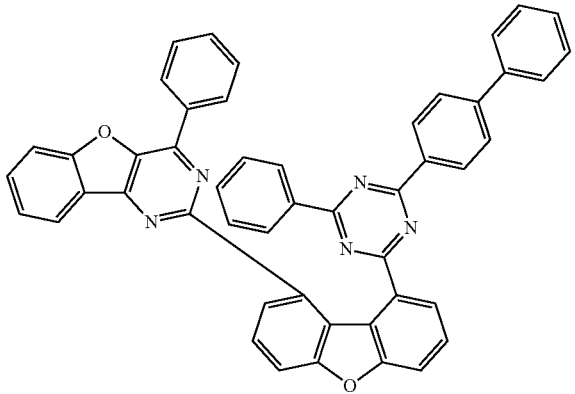
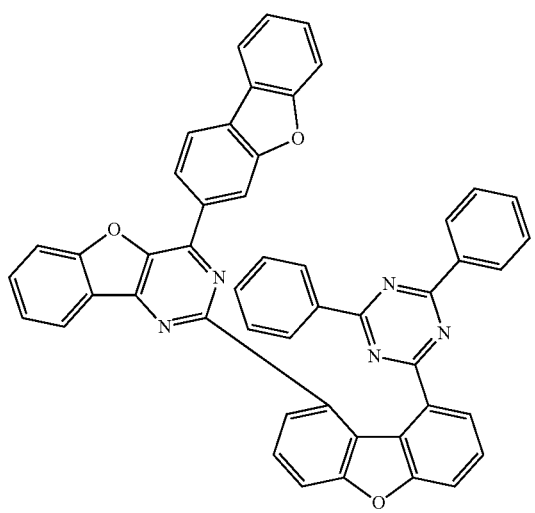
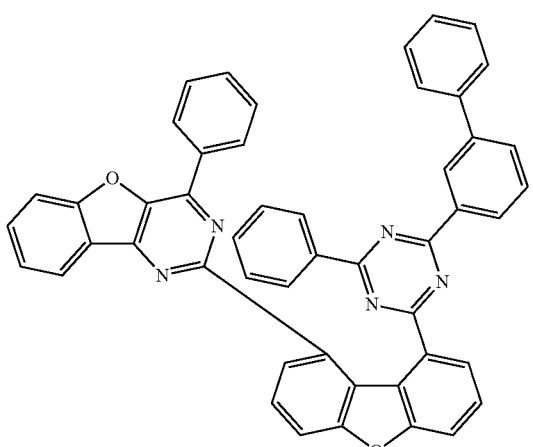
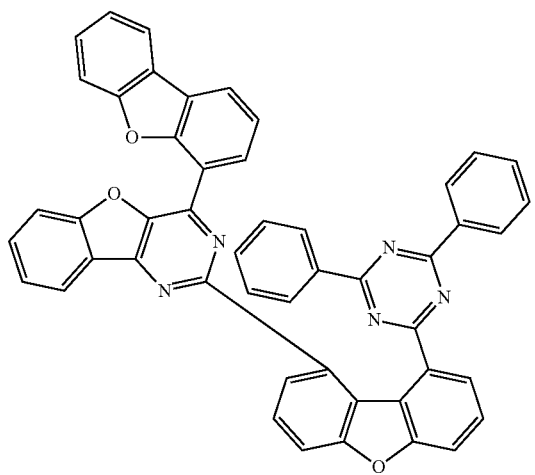
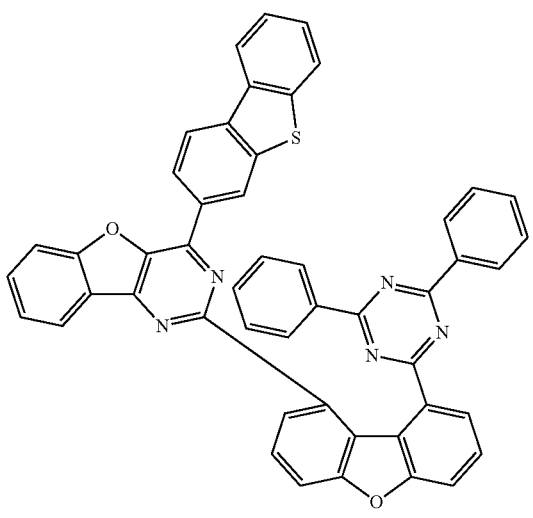

109
-continued
110
-continued
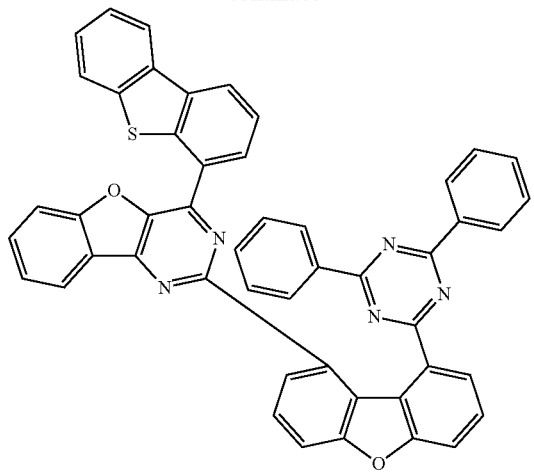
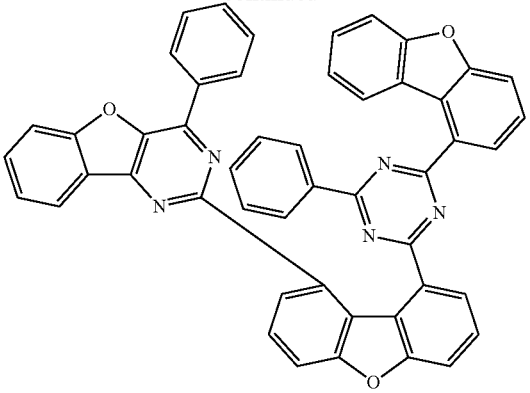
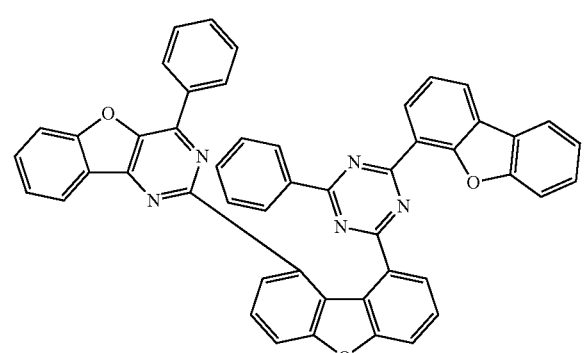
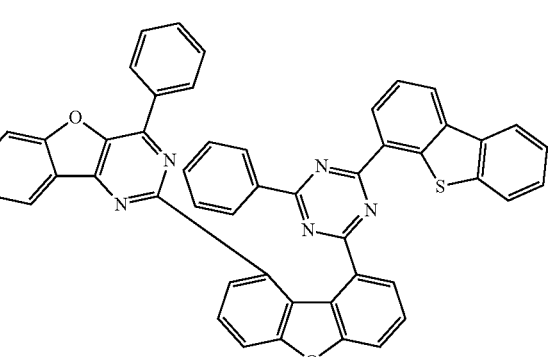
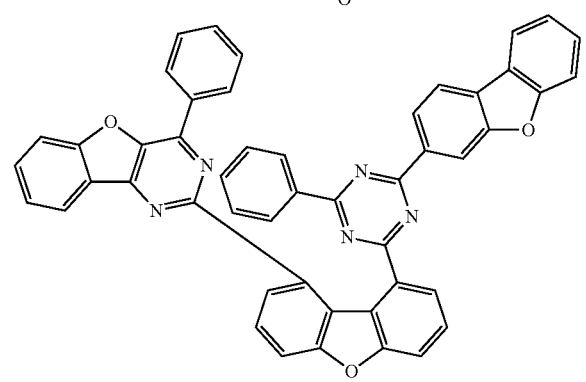
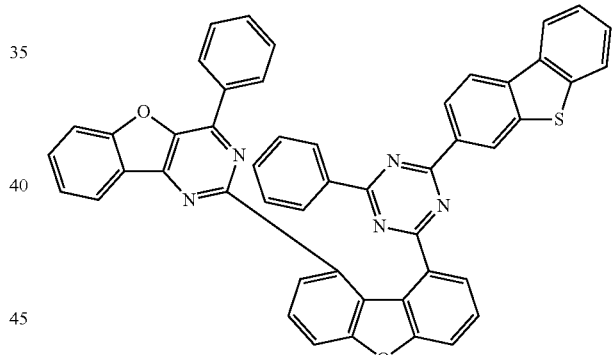
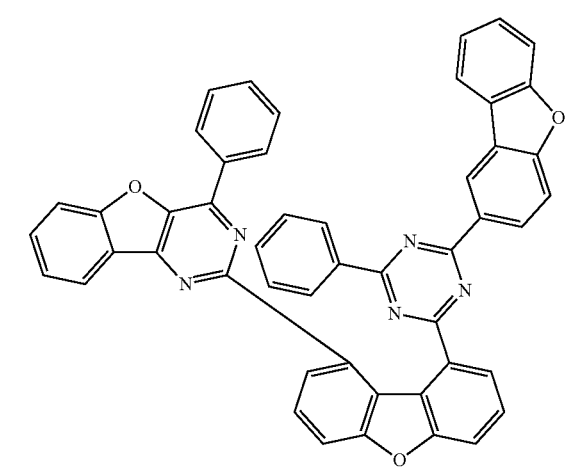
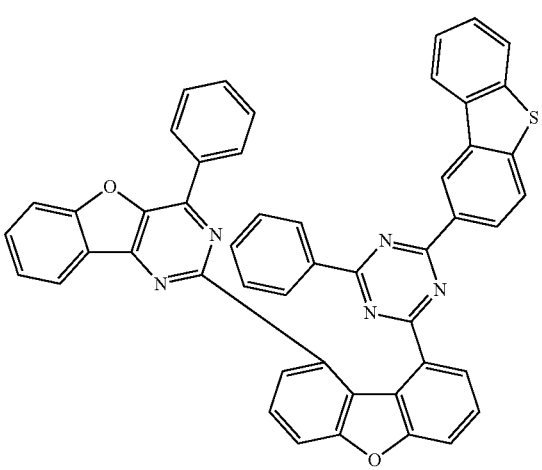

111
-continued
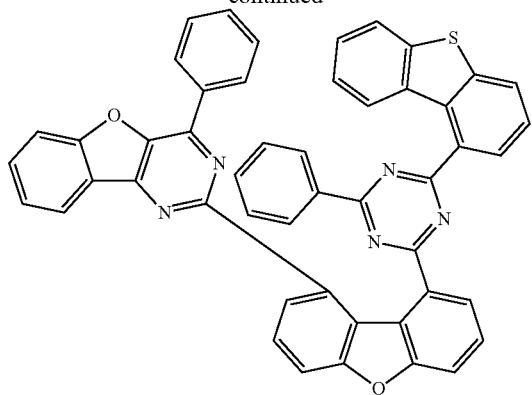
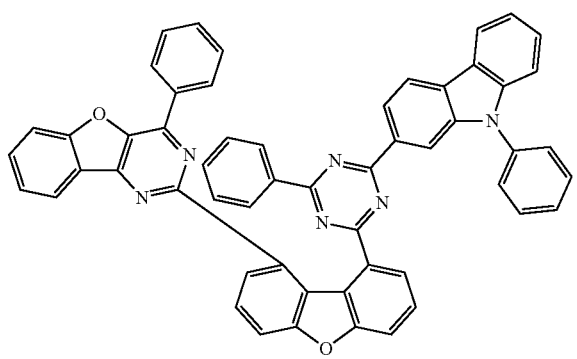
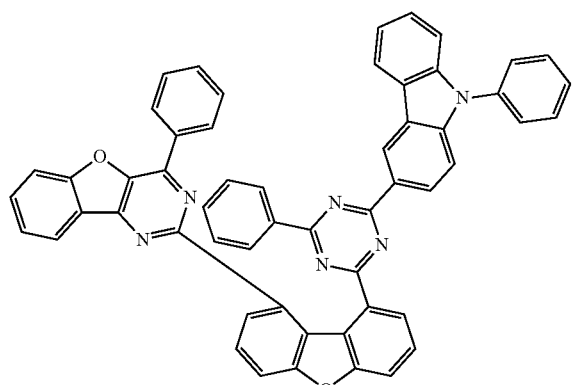
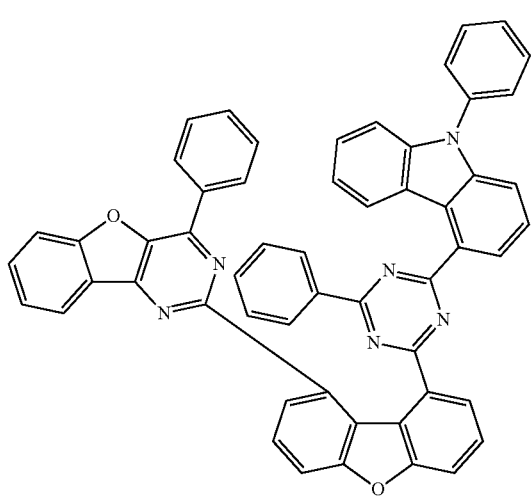
112
-continued
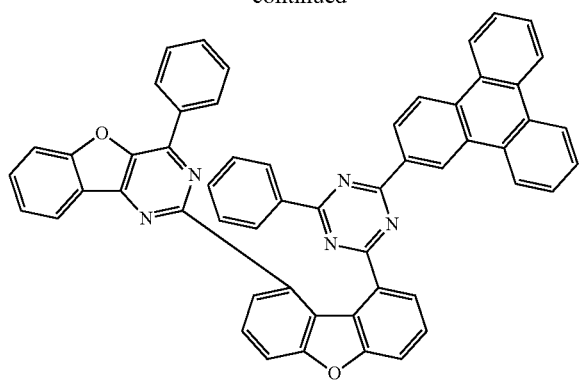
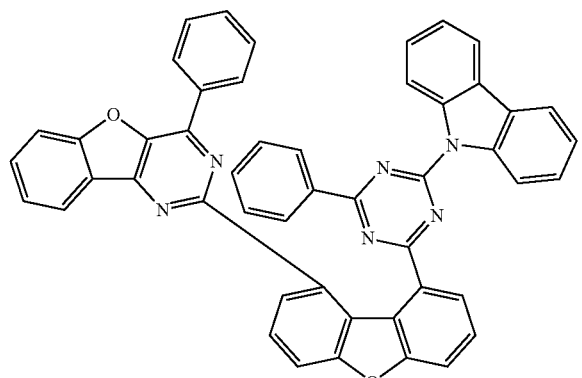
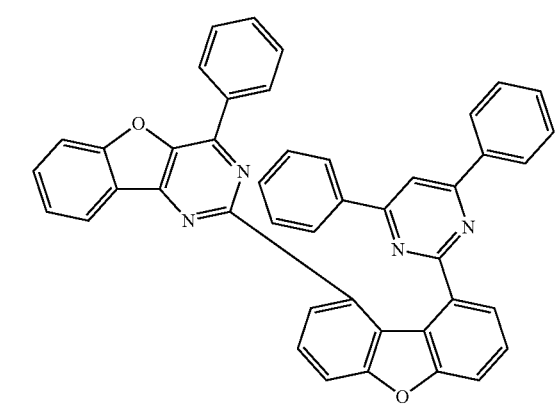
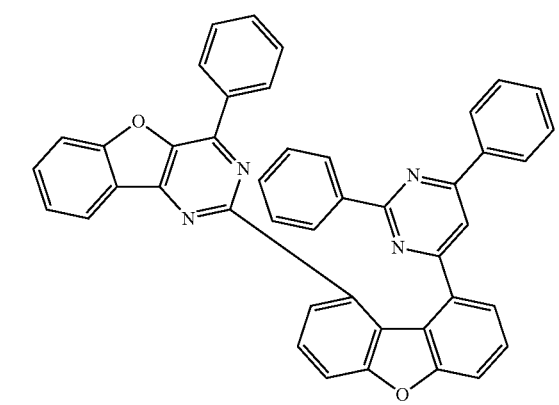

113
-continued
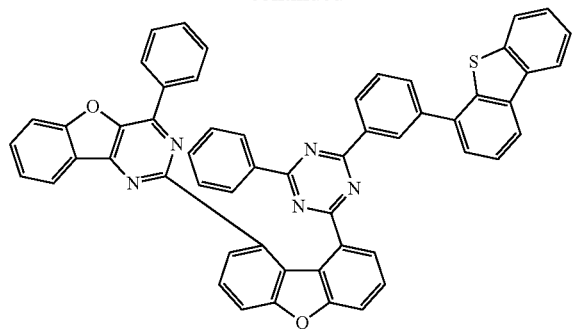
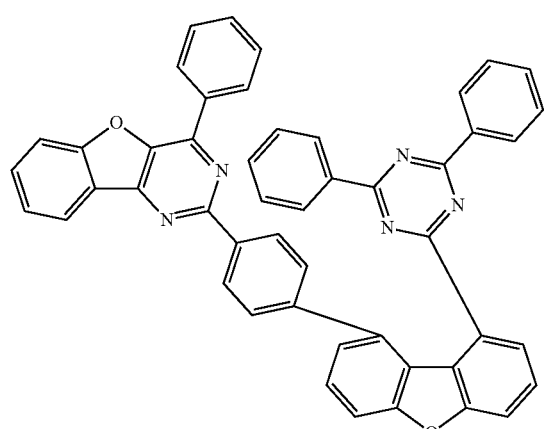
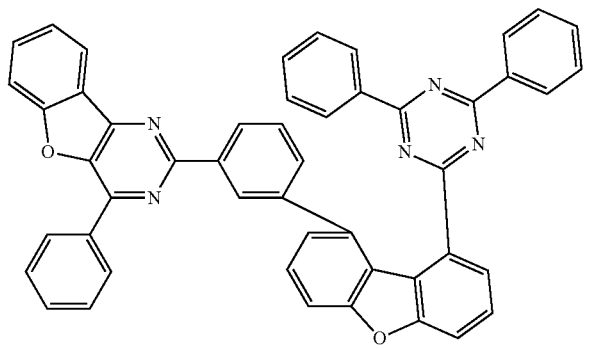
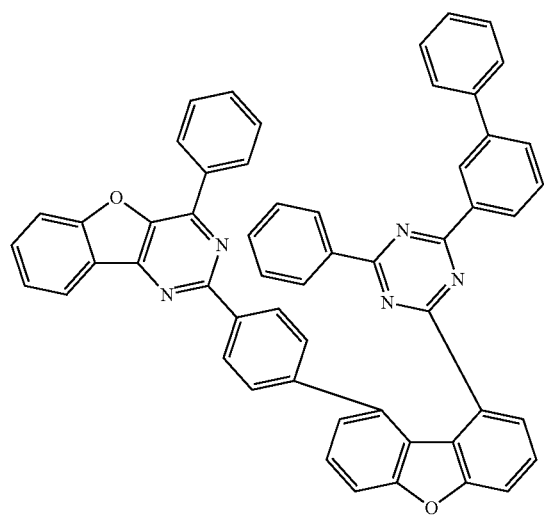
114
-continued
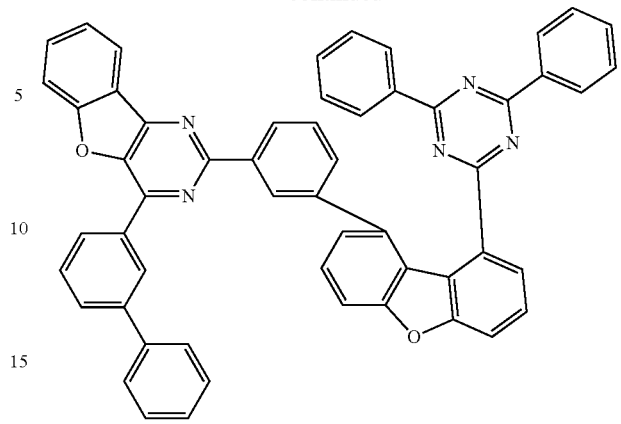
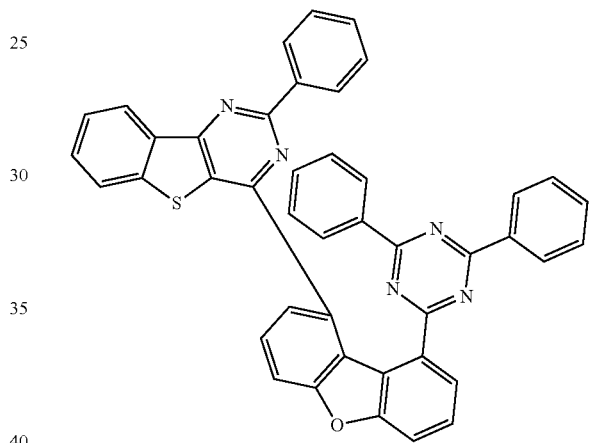
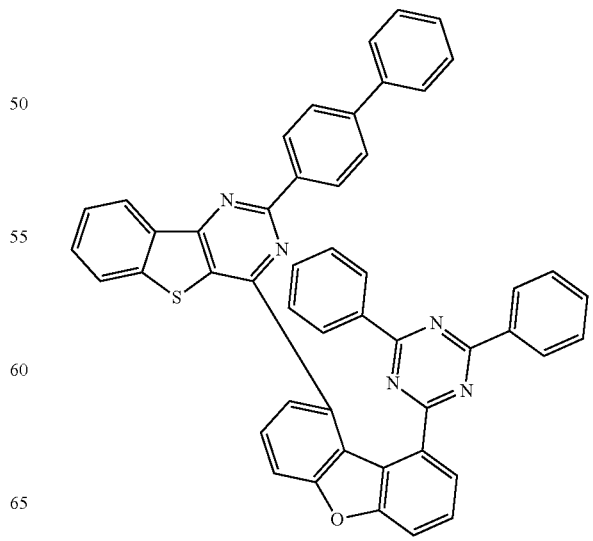

115
-continued
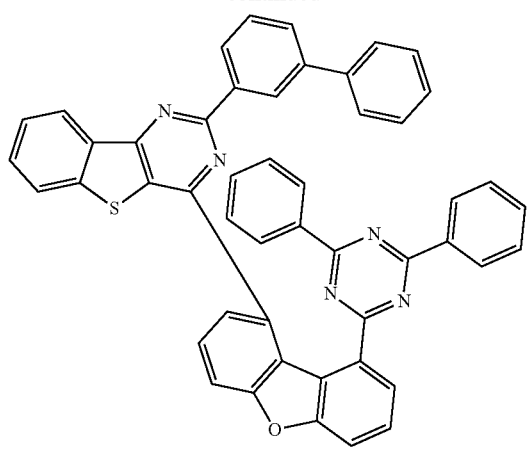
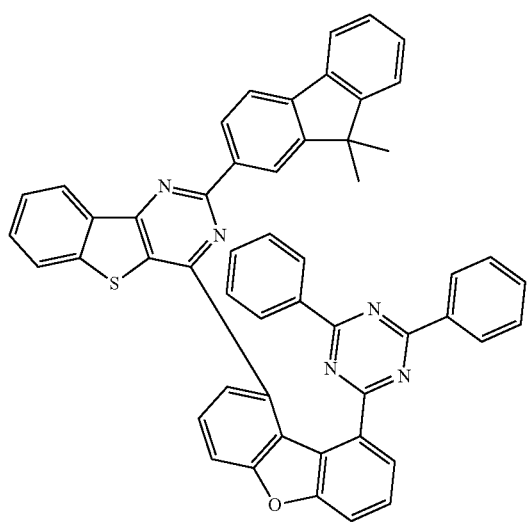
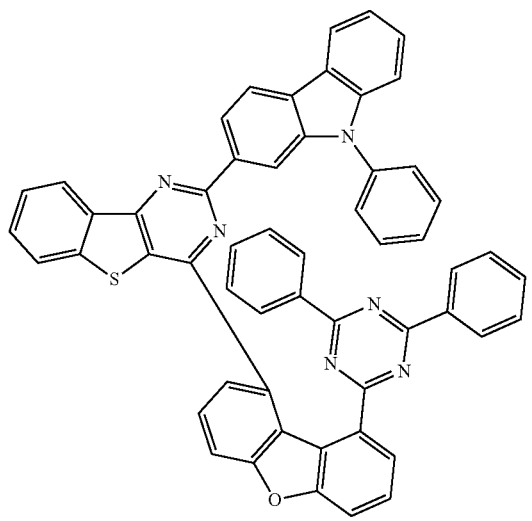
116
-continued
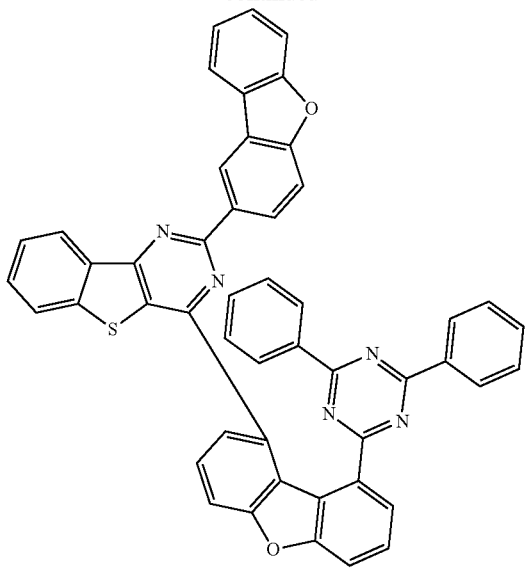
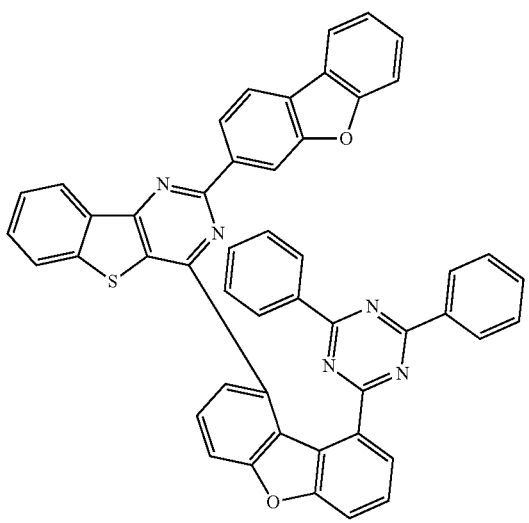
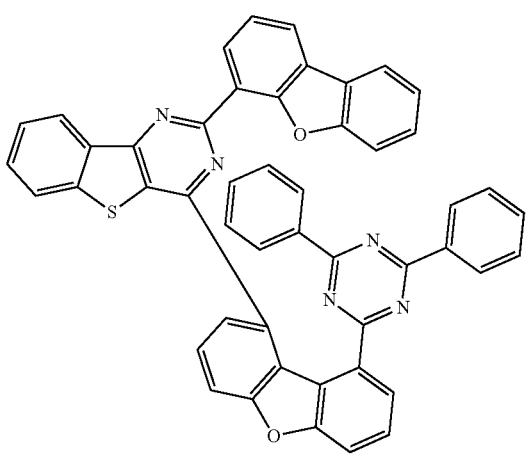

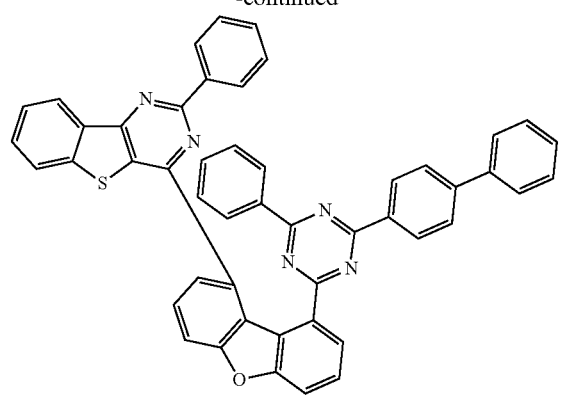
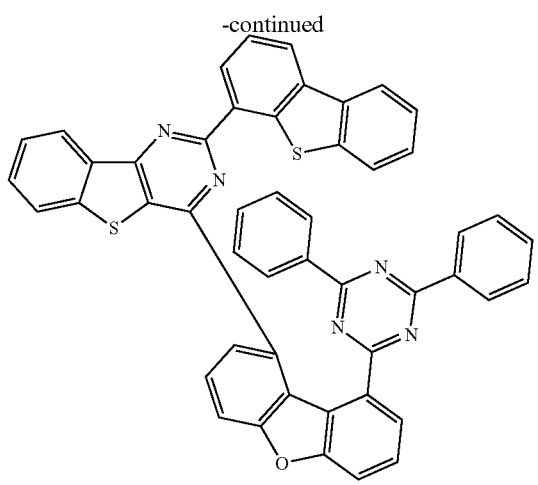
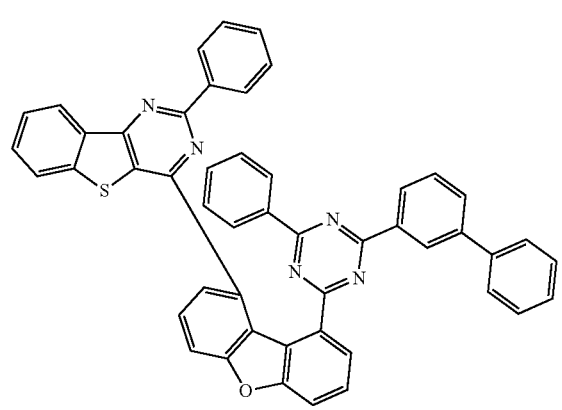
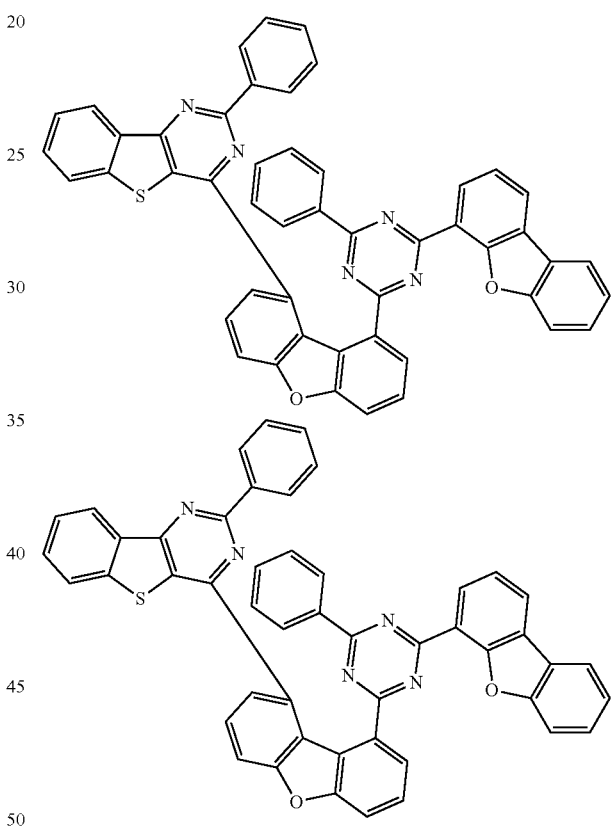
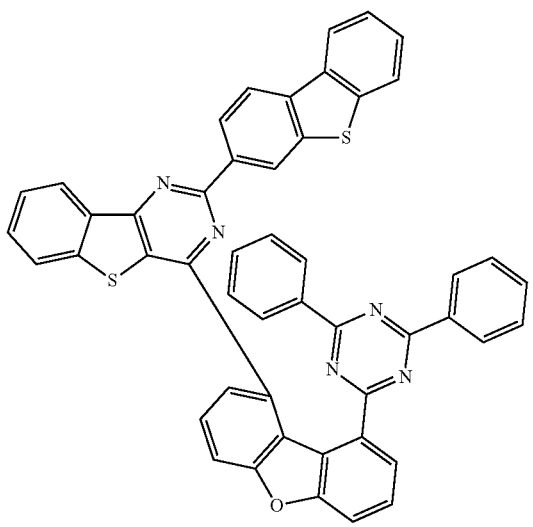
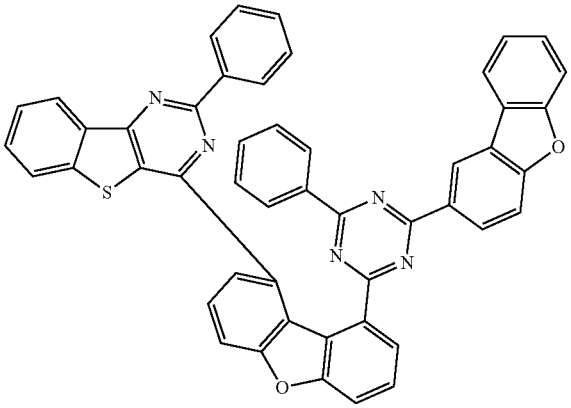

119
-continued
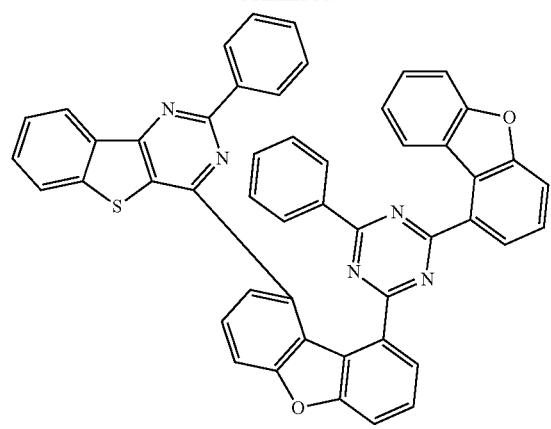
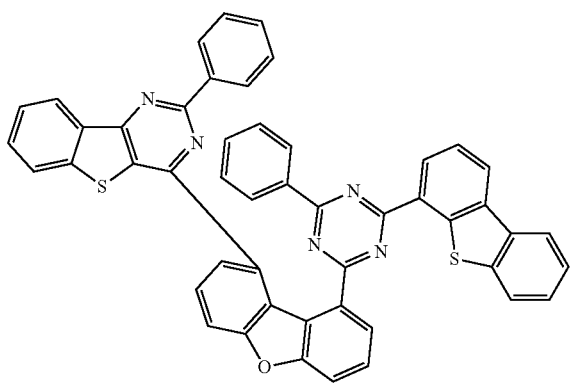
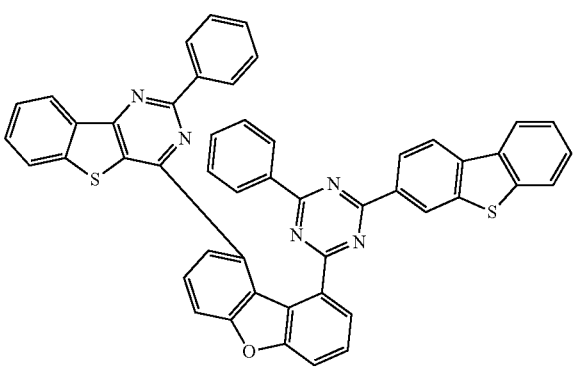
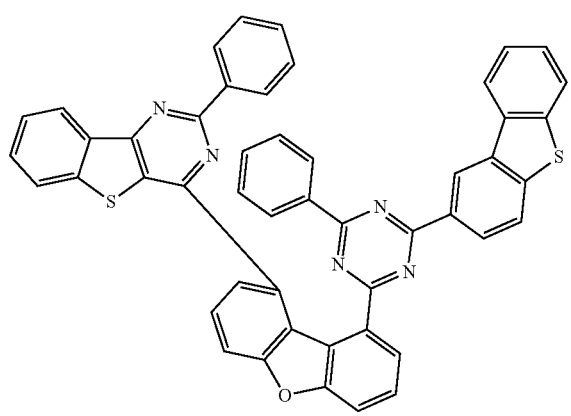
120
-continued
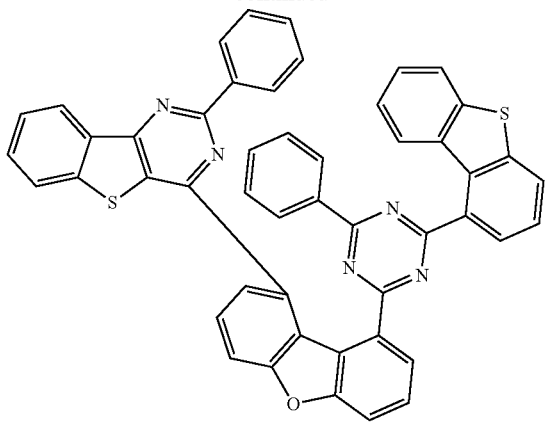
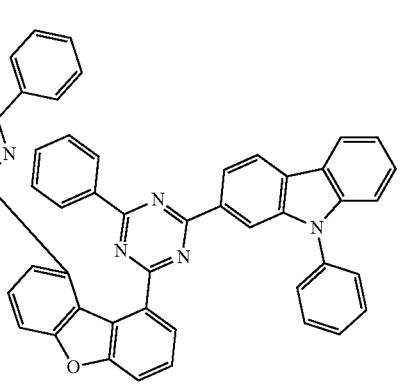
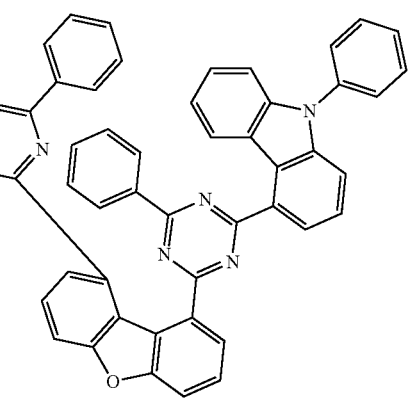

121
-continued
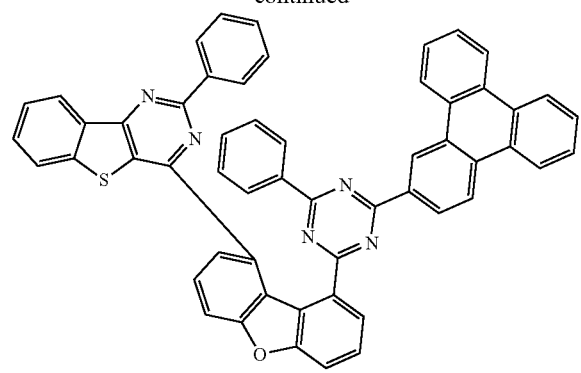
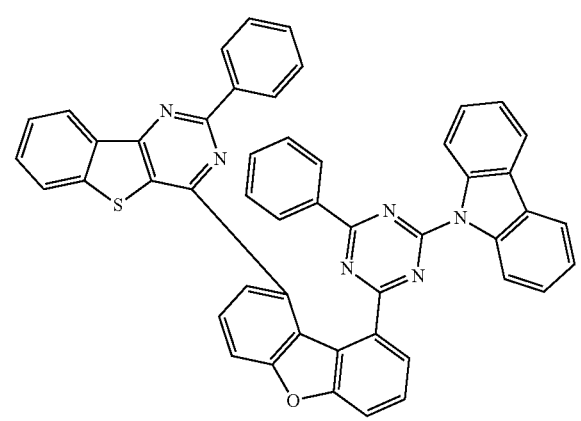
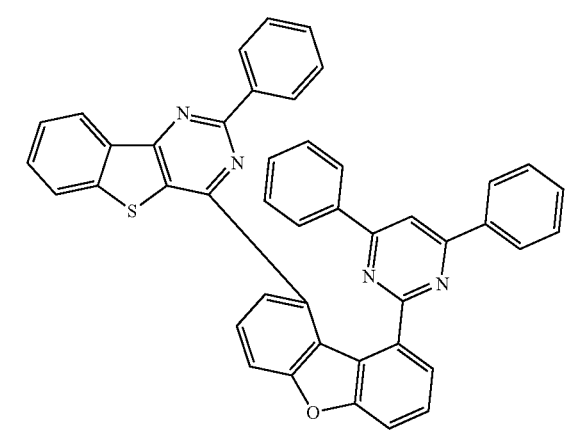
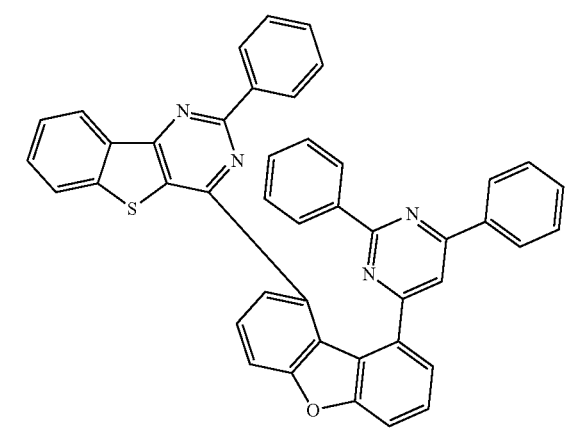
122
-continued
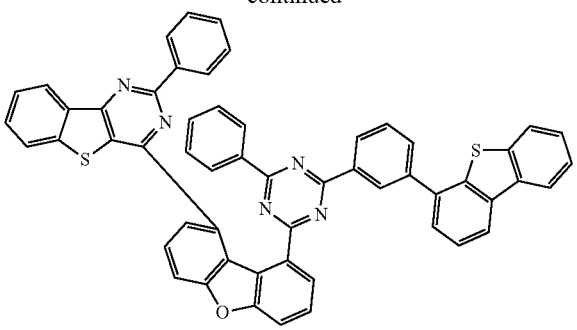
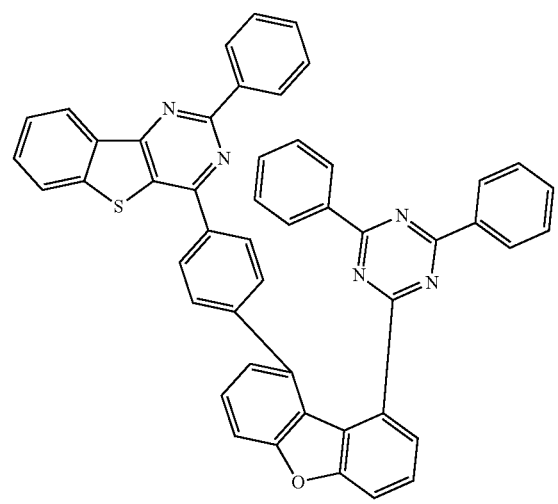
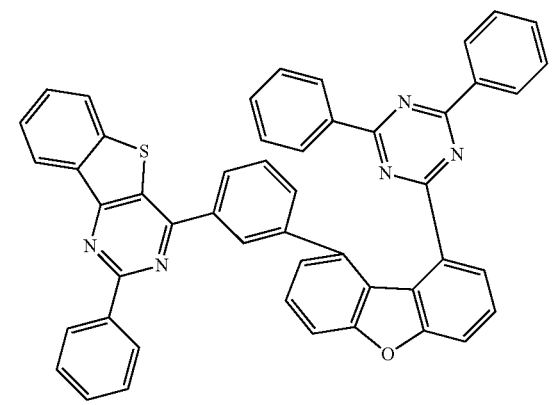
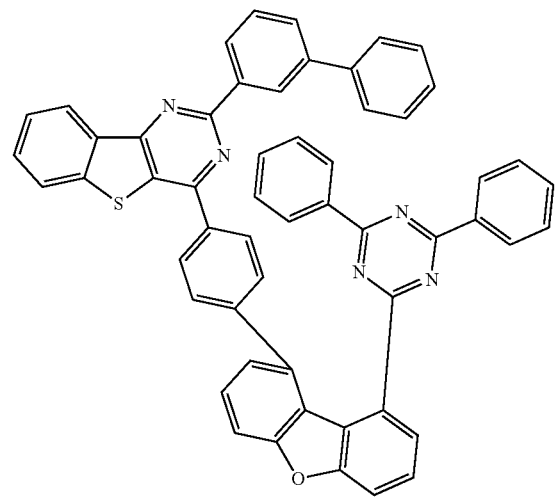

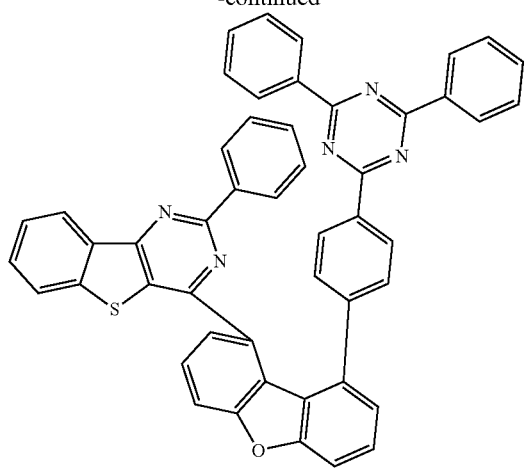
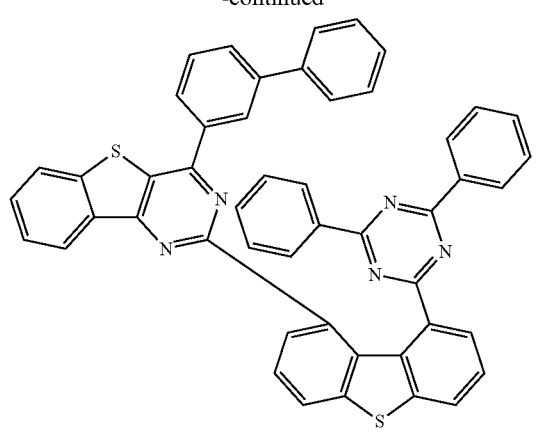
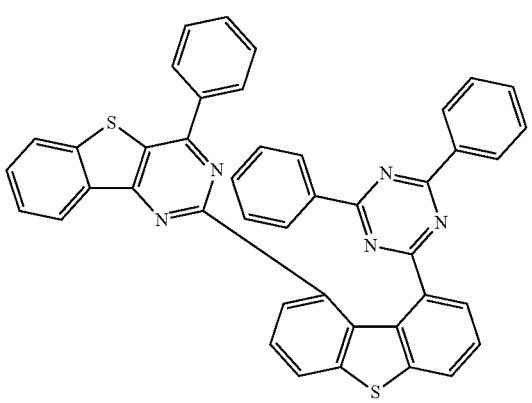
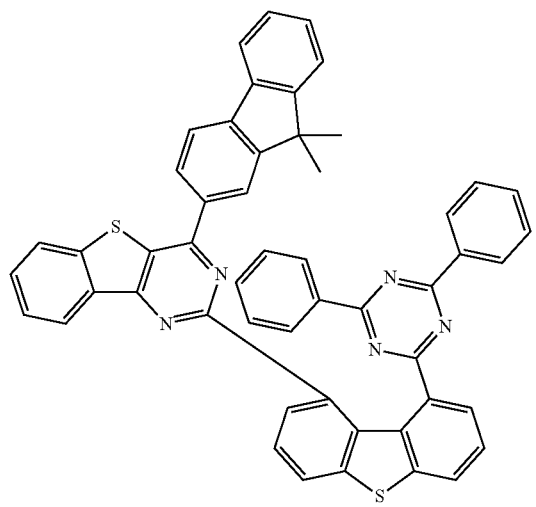
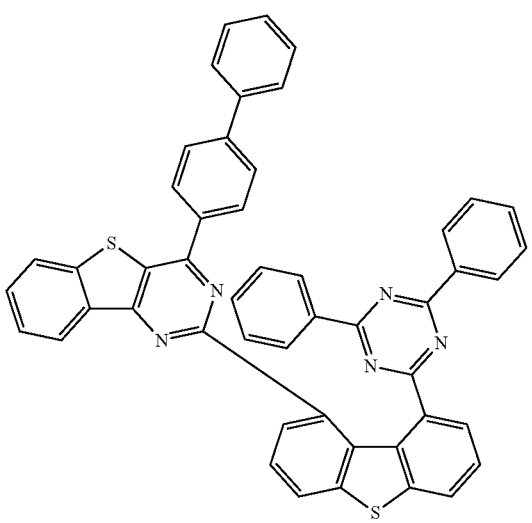
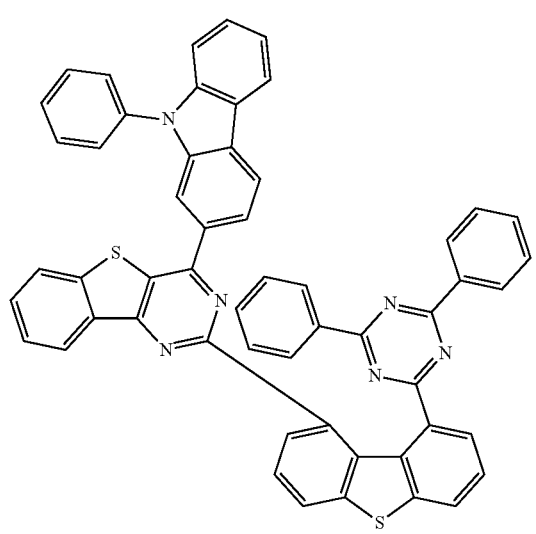

125
-continued
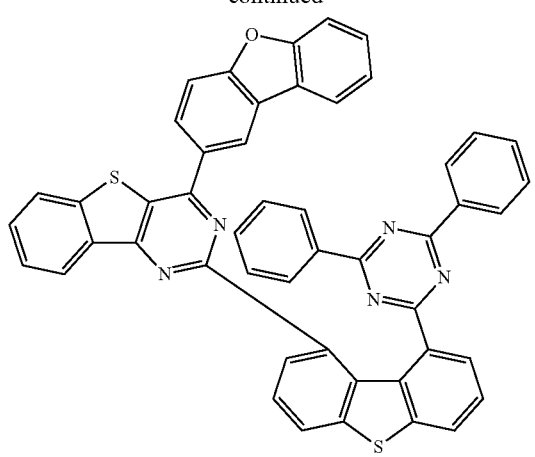
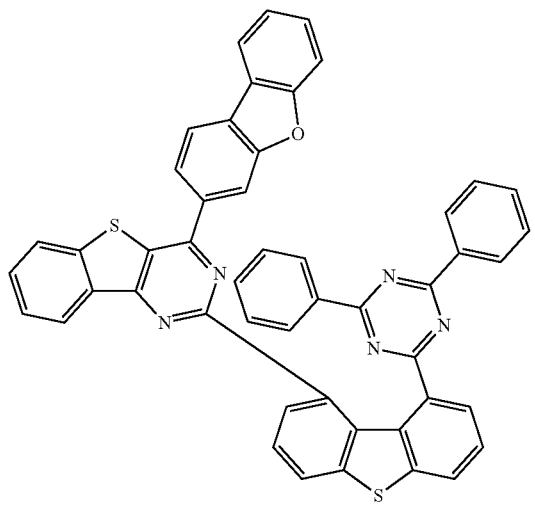
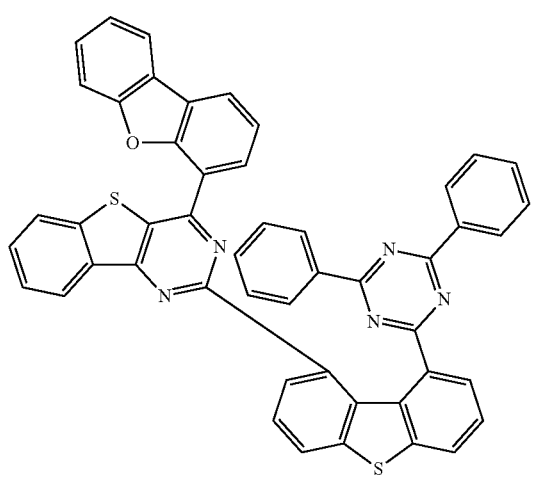
126
-continued
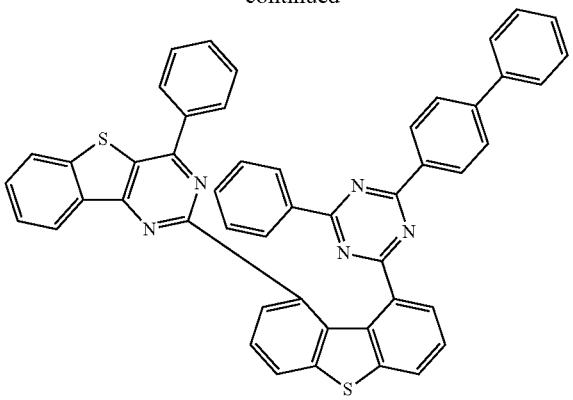
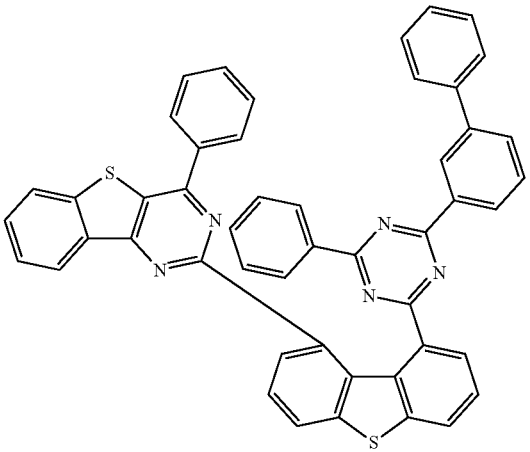
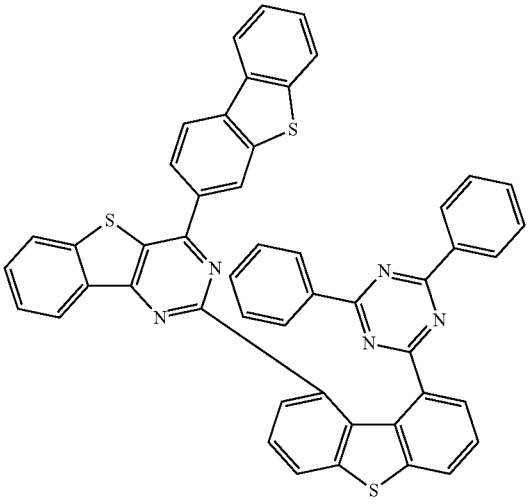

127
-continued
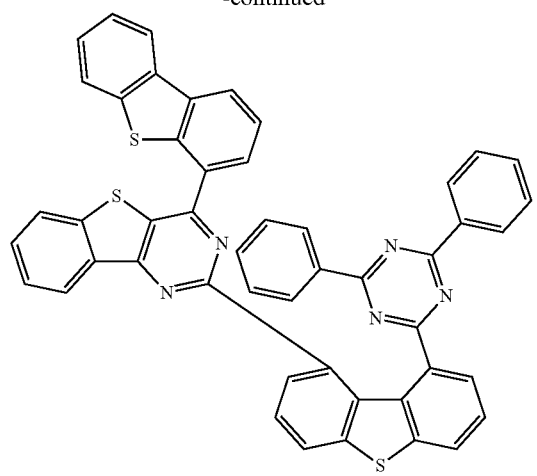
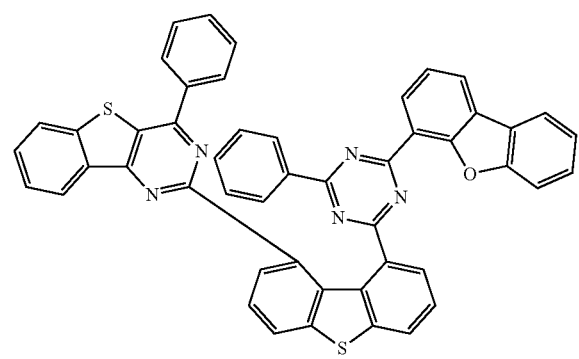
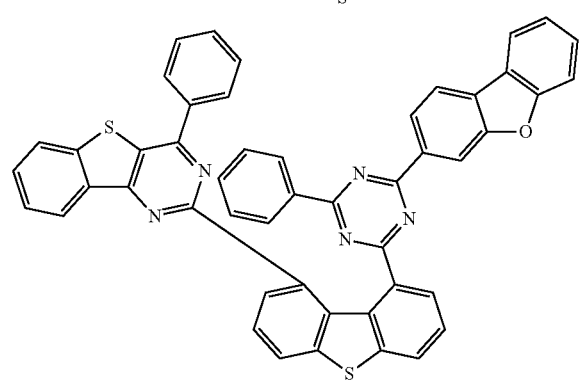
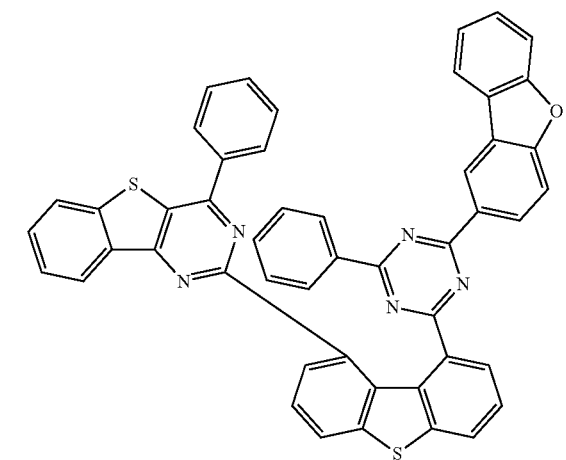
128
-continued
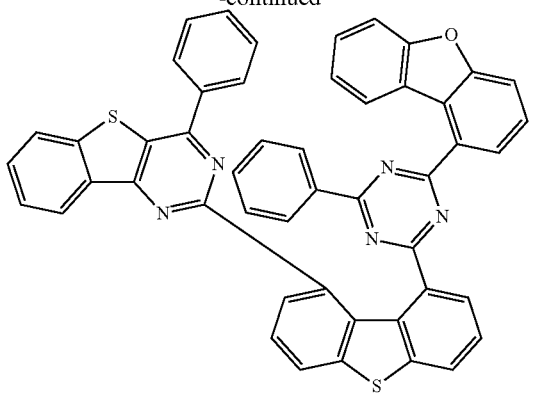
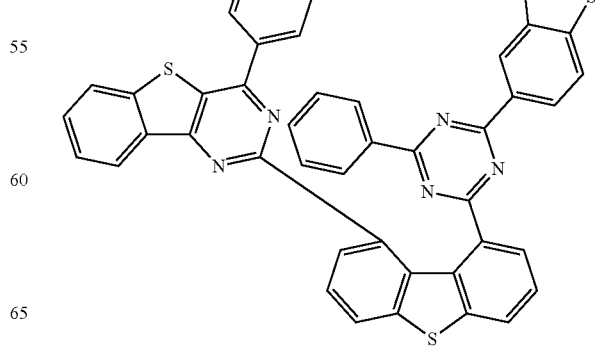

129
-continued
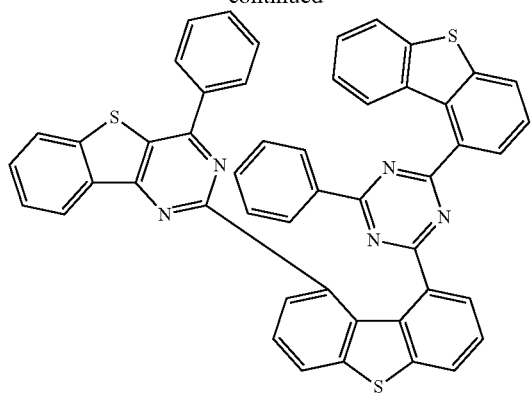
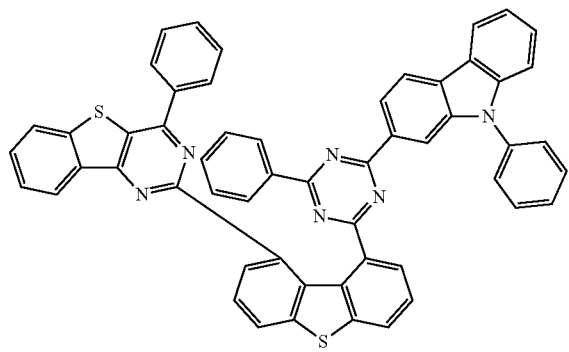
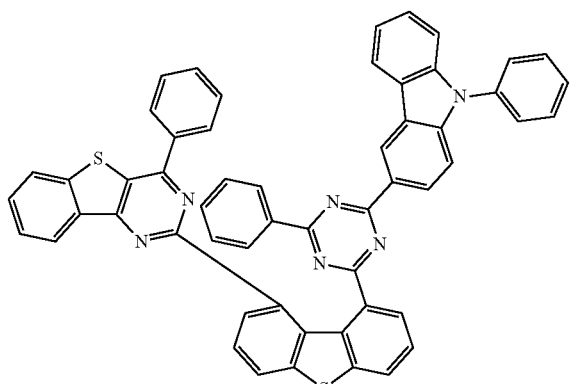
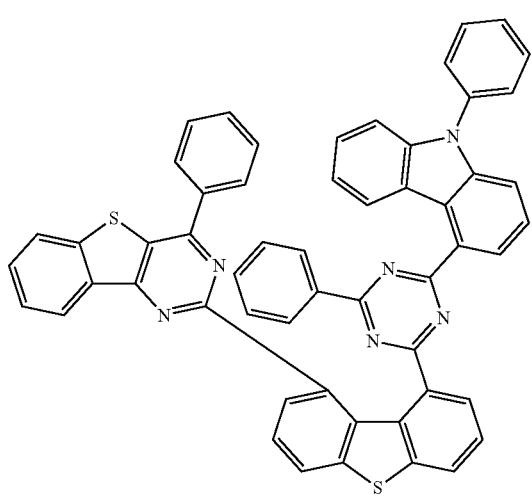
130
-continued
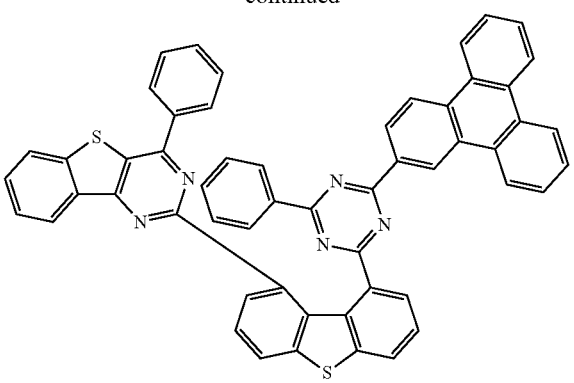
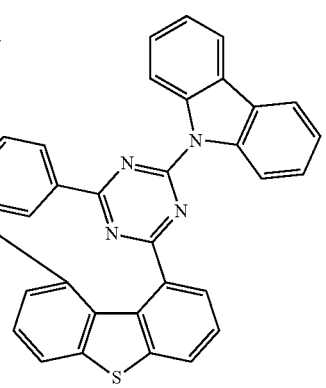
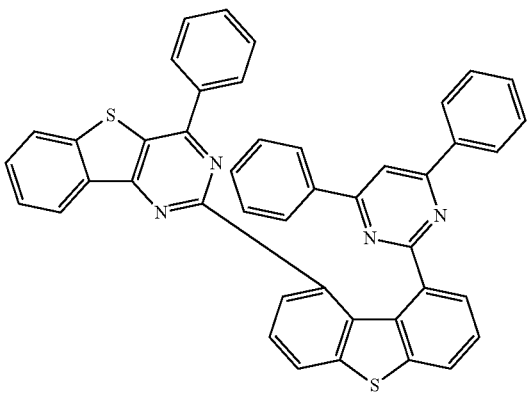
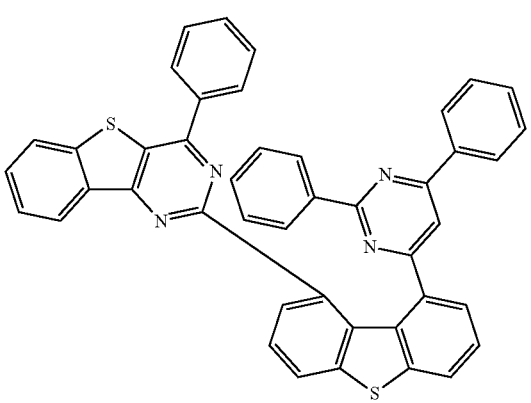

131
-continued
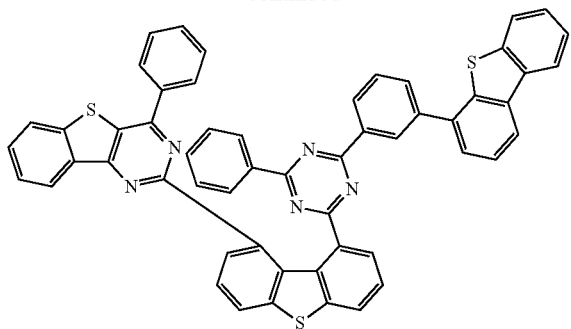
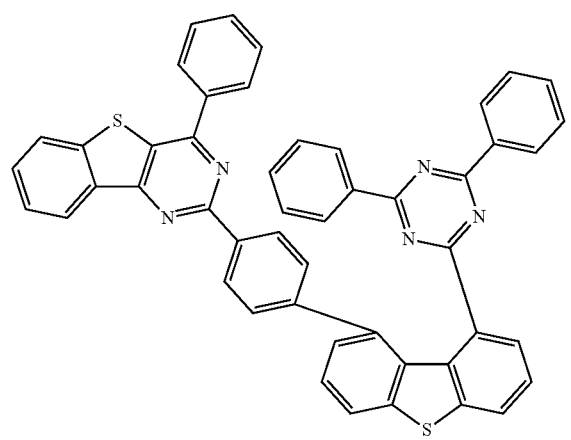
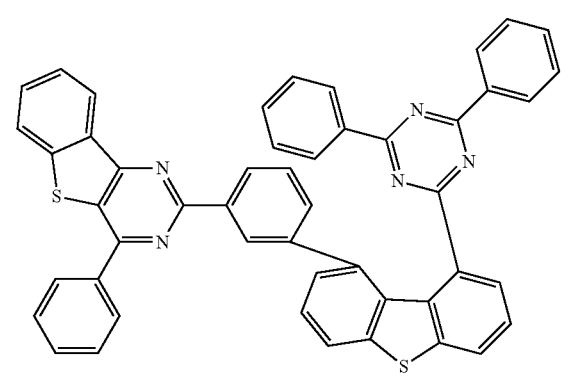
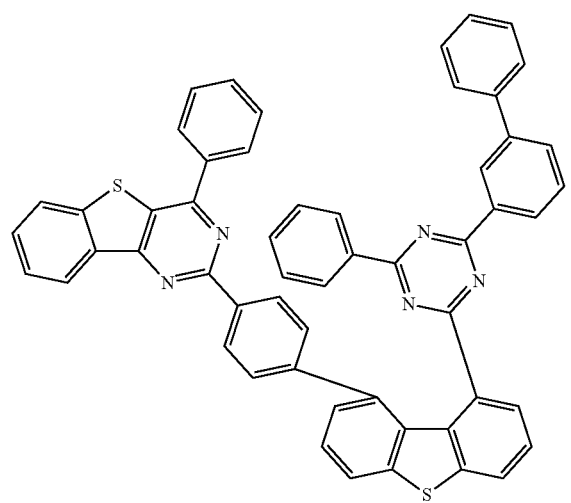
132
-continued
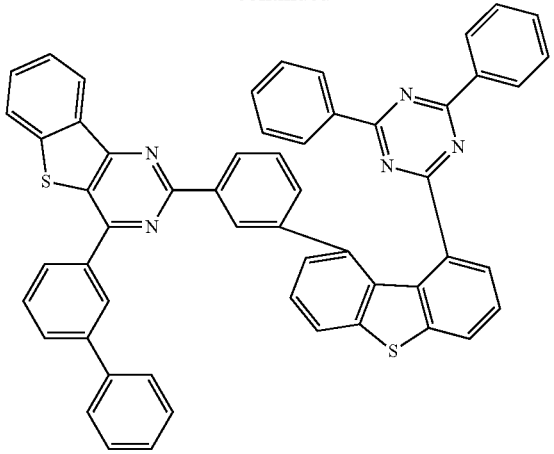
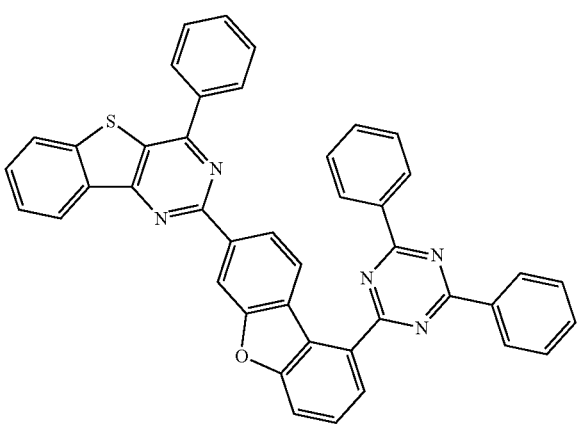
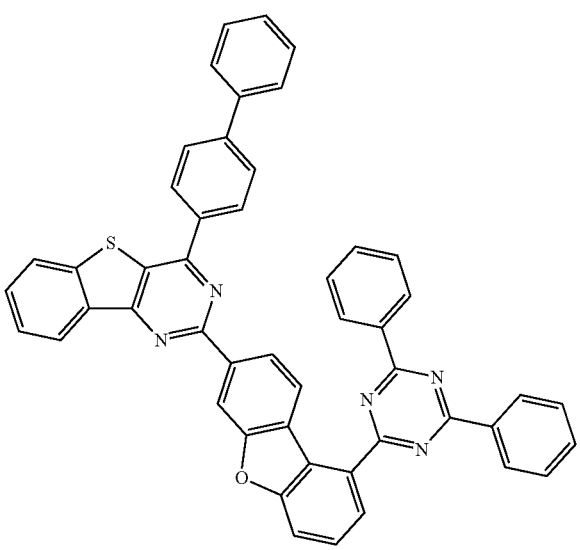

133
-continued
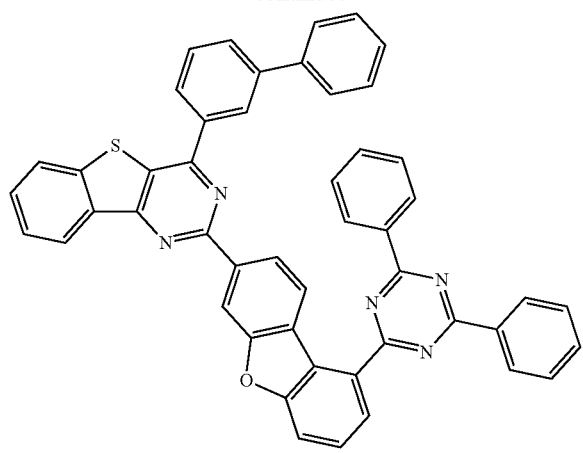
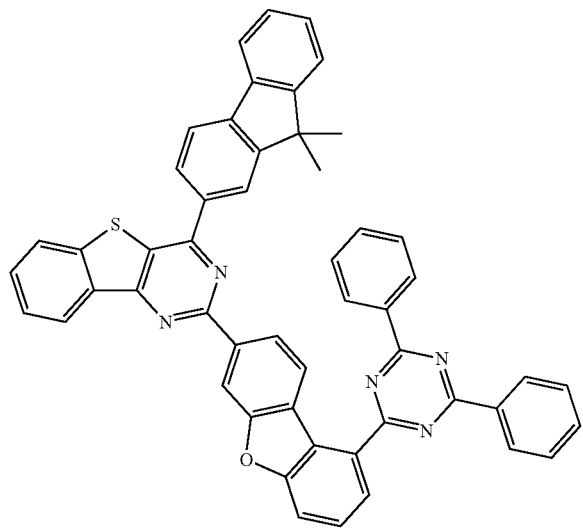
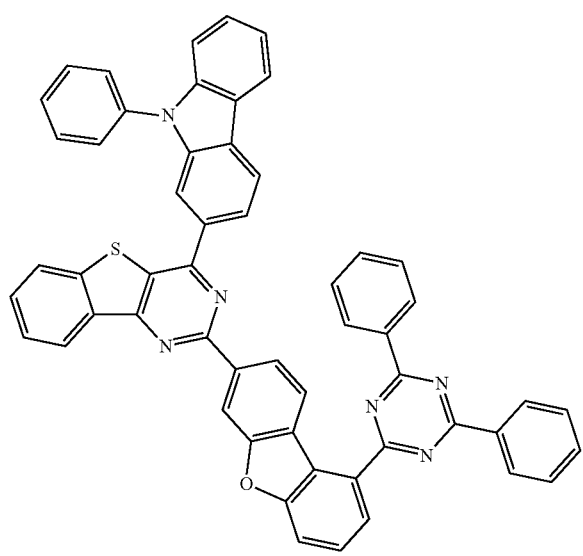
134
-continued
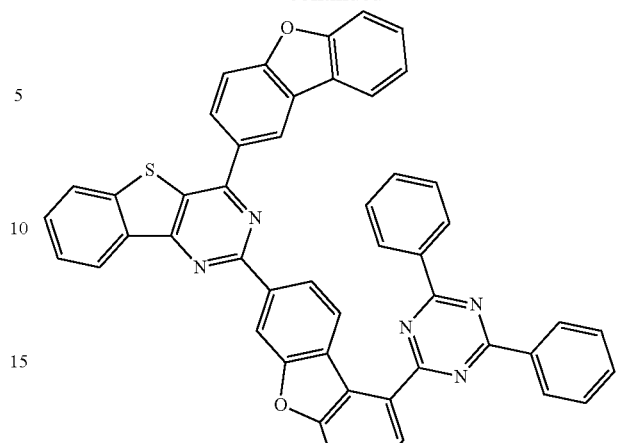
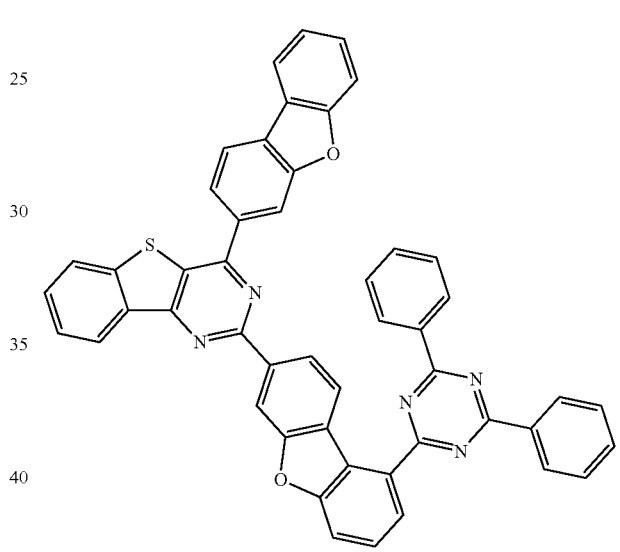
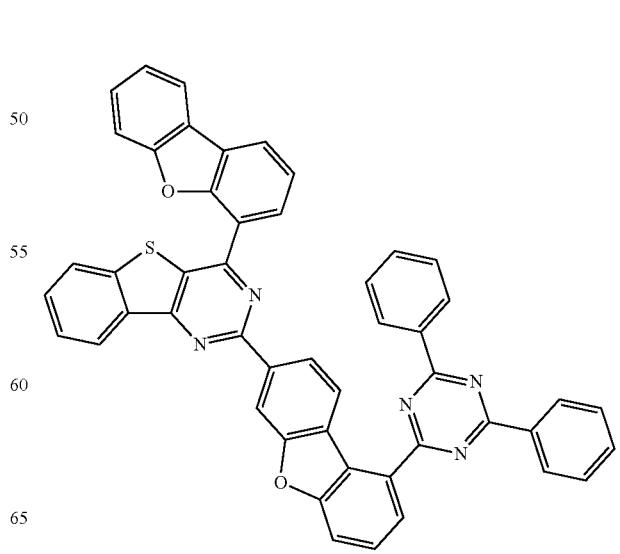

135
-continued
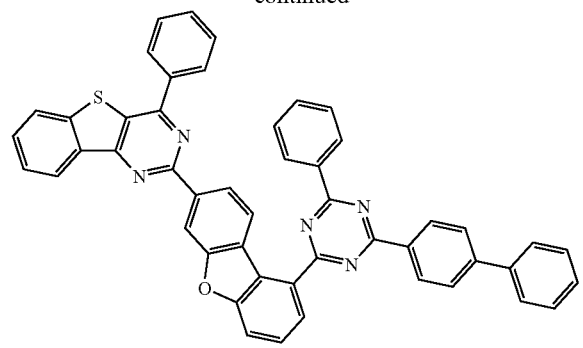

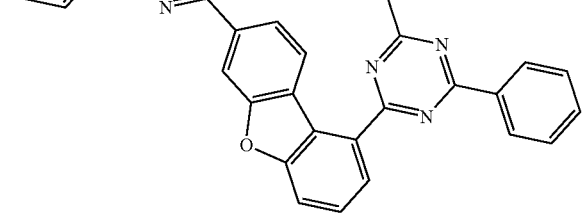
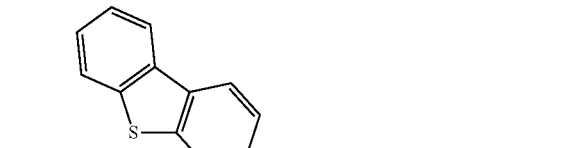
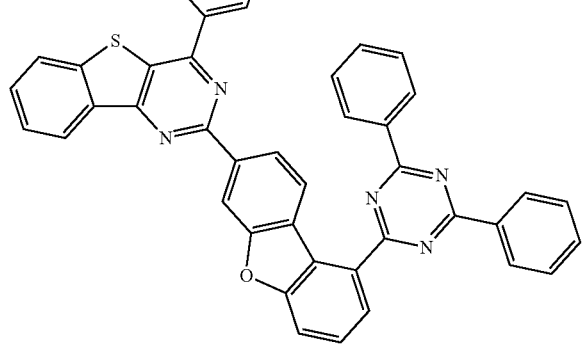
136
-continued
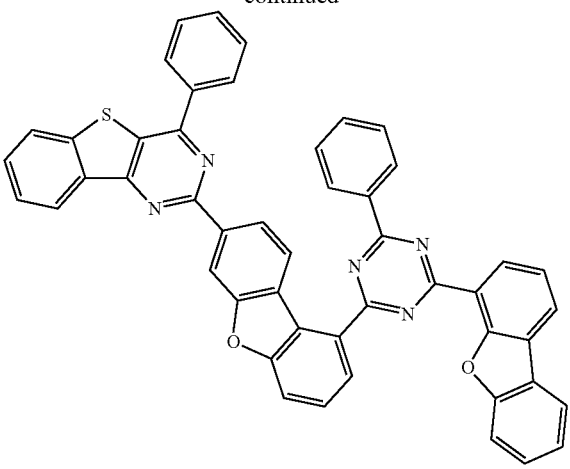
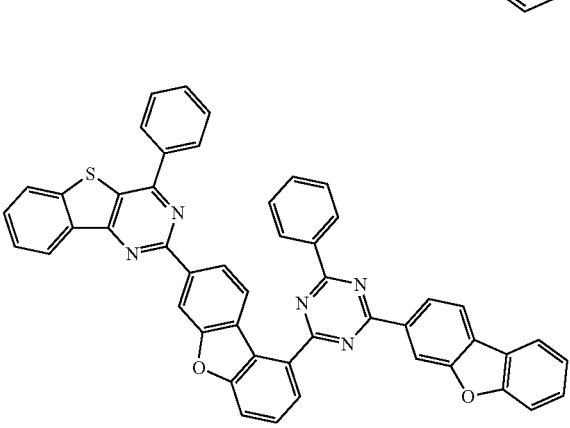
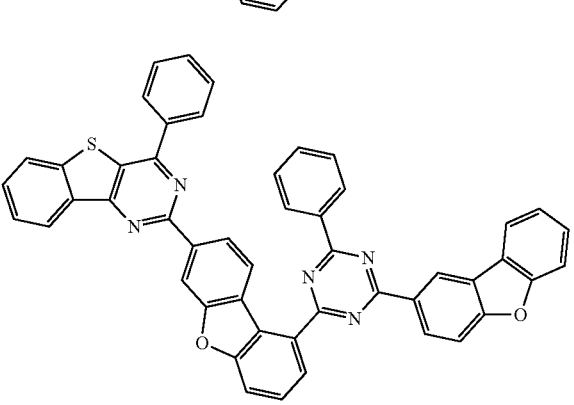
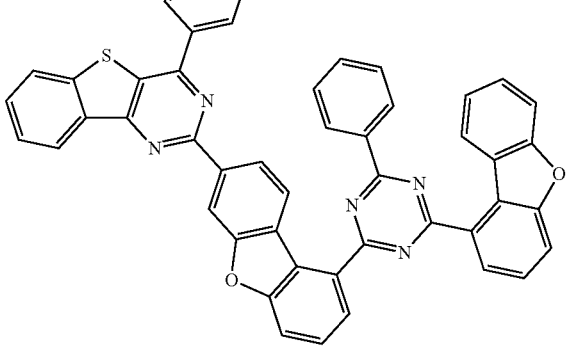

137
-continued
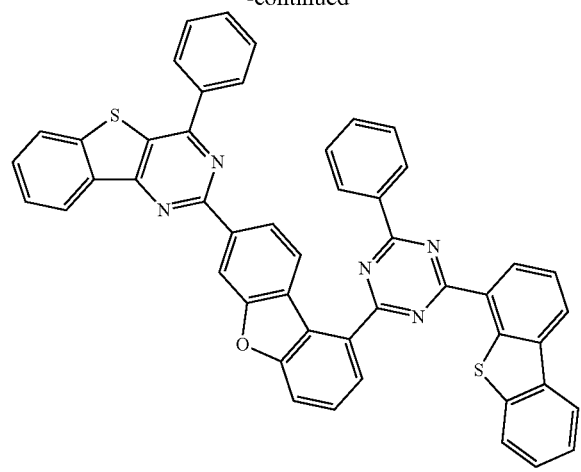
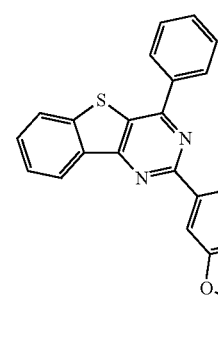
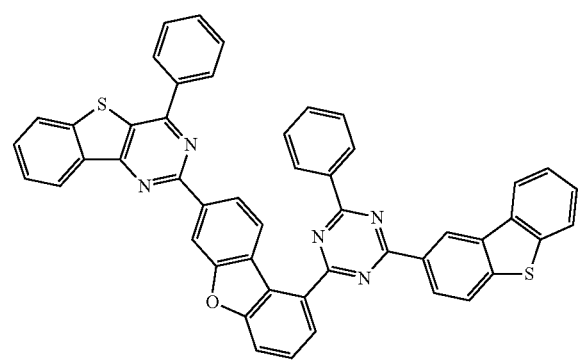
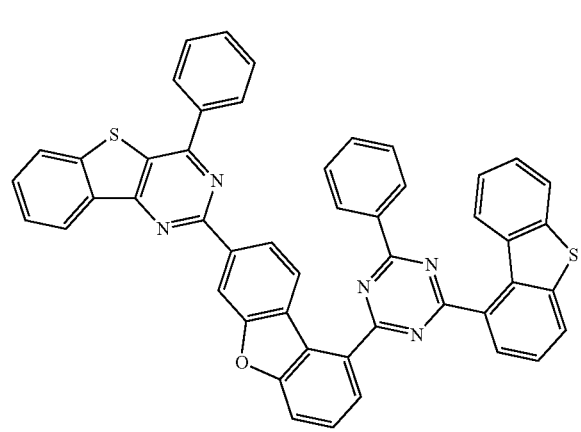
138
-continued
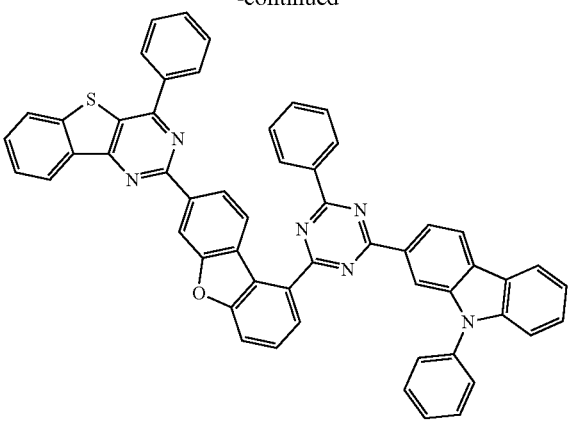
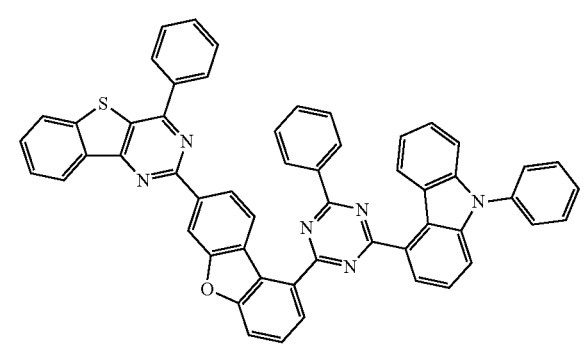
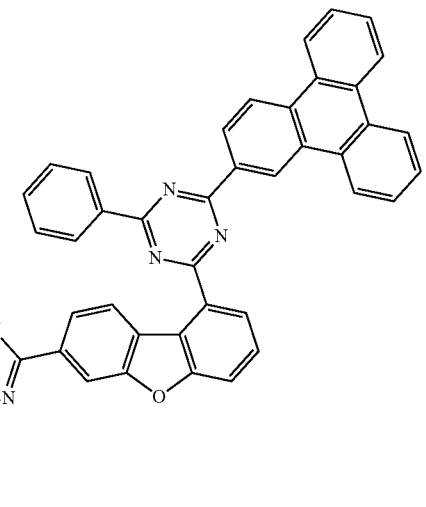

-continued
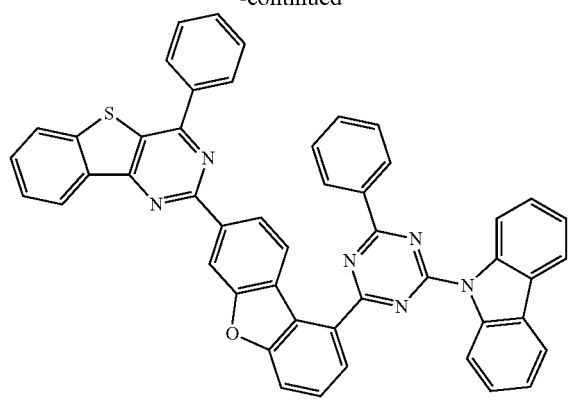
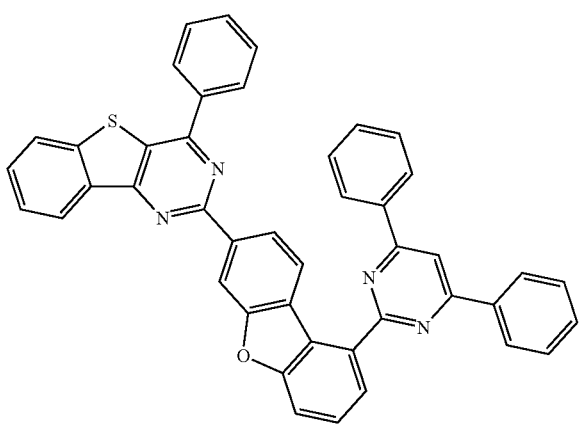
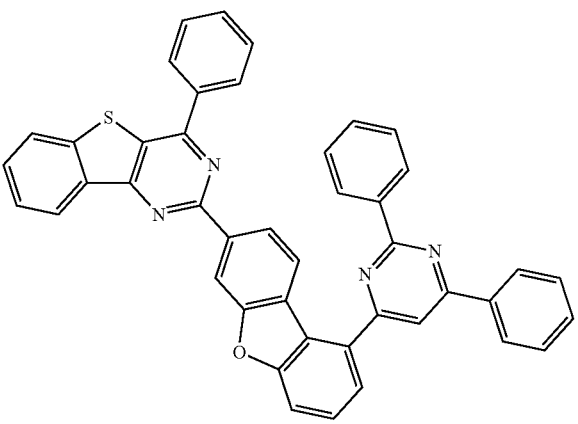
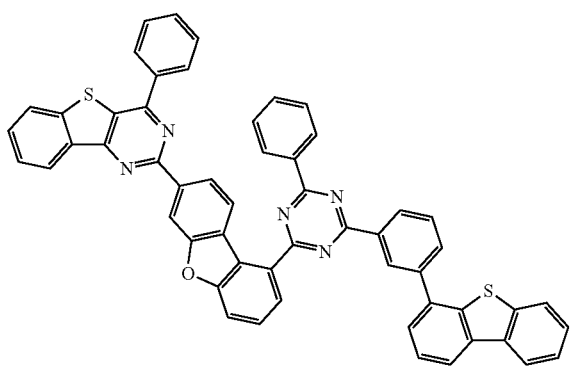
-continued
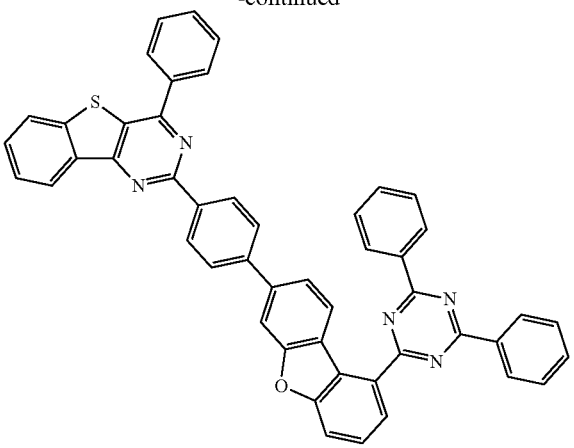
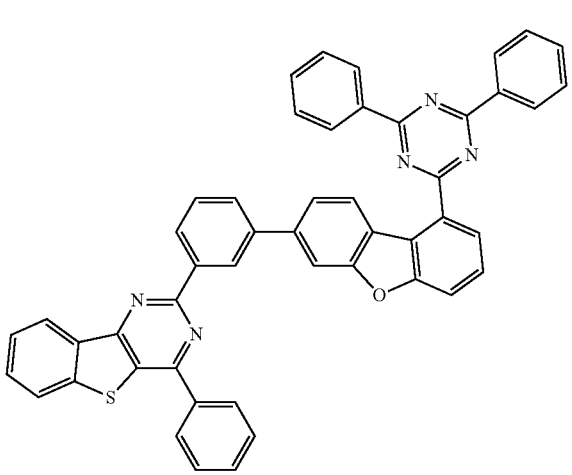
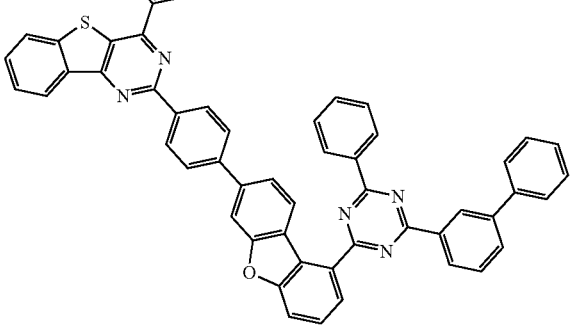
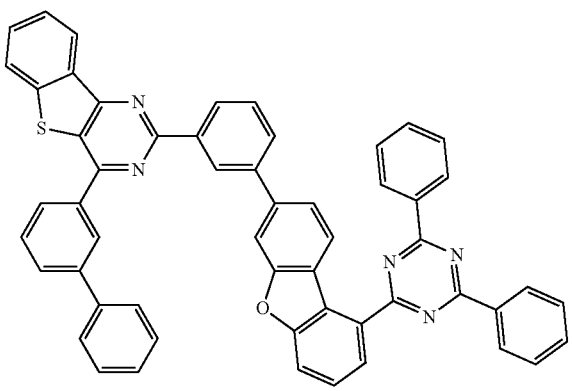

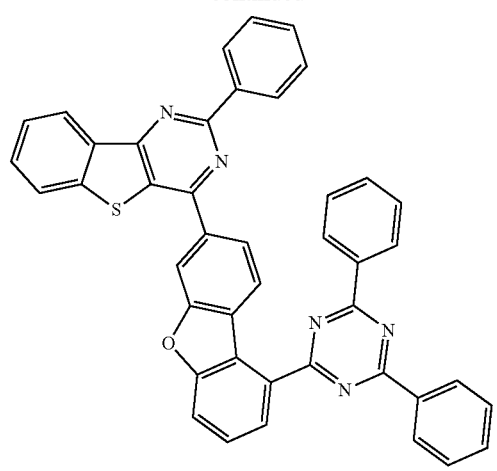
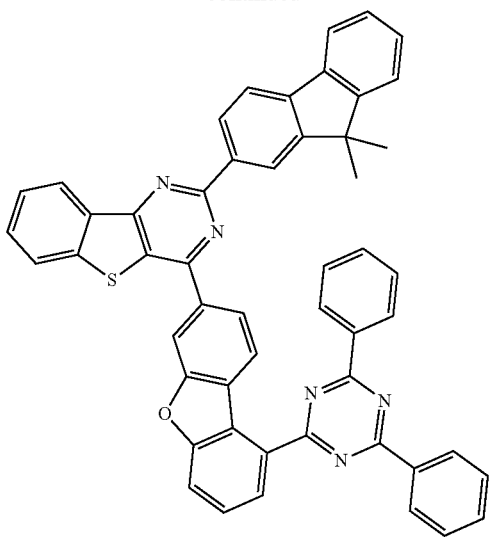 [SMILES: c1ccc(-c2nc(-c3ccccc3)nc(-c3cccc4sc5cc(-c6nc(-c7ccc8c(c7)oc7ccccc78)nc7c6oc6ccccc67)ccc5c34)n2)cc1]
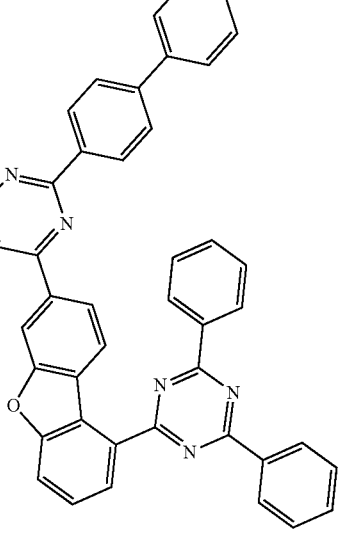
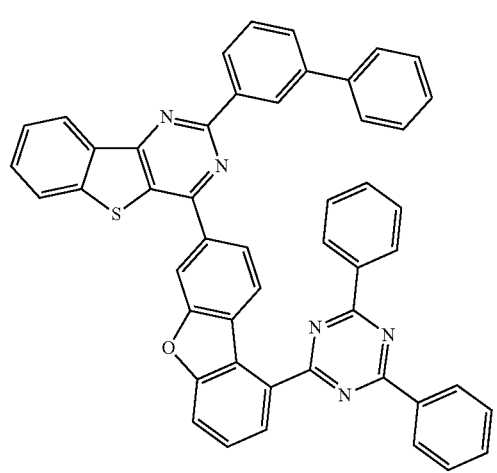
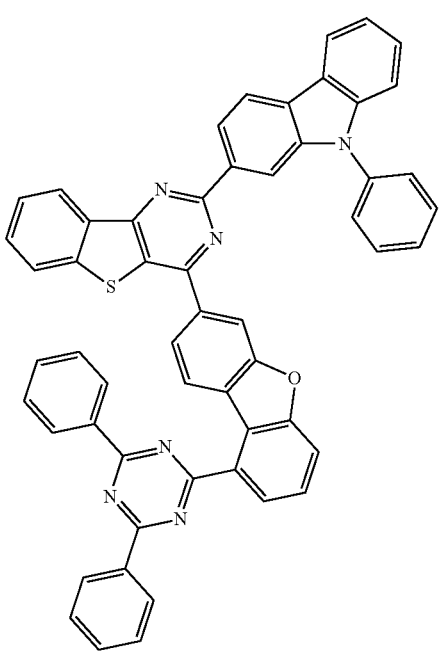

143
-continued
144
-continued
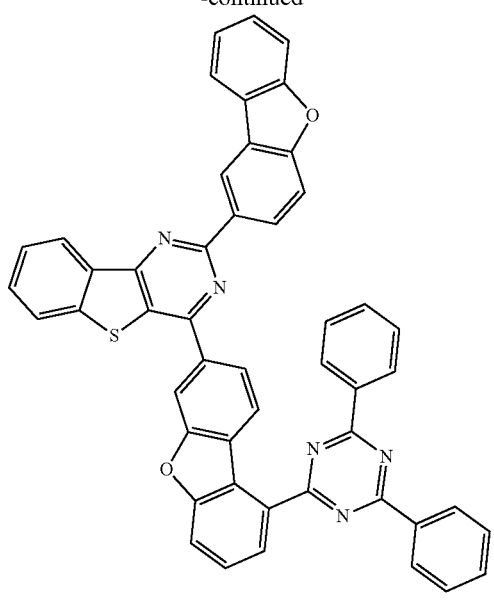
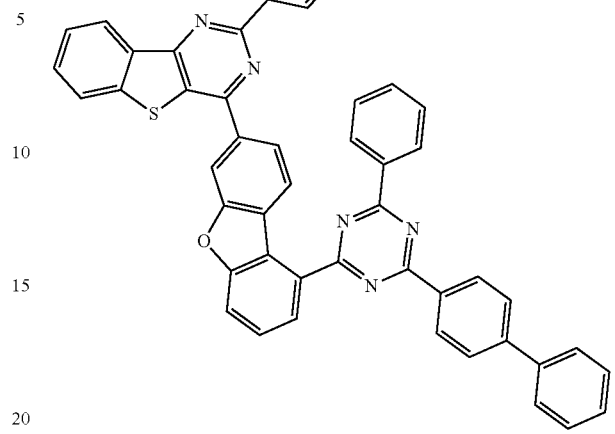
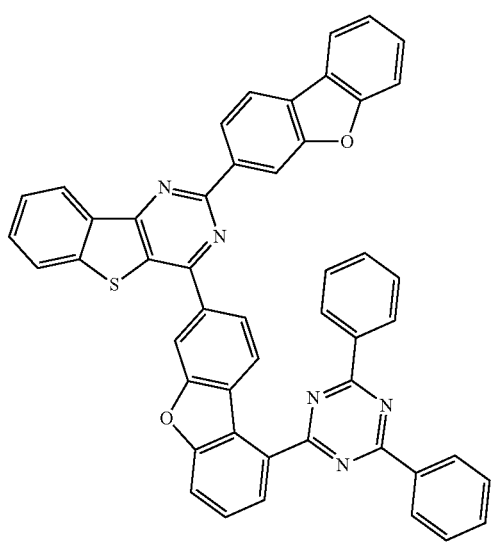
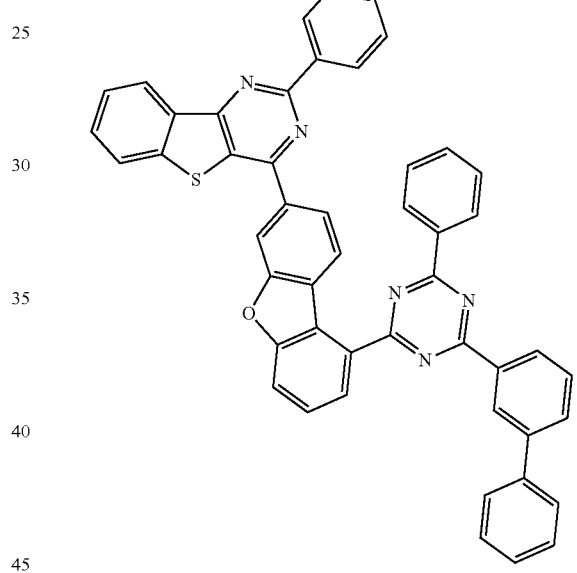
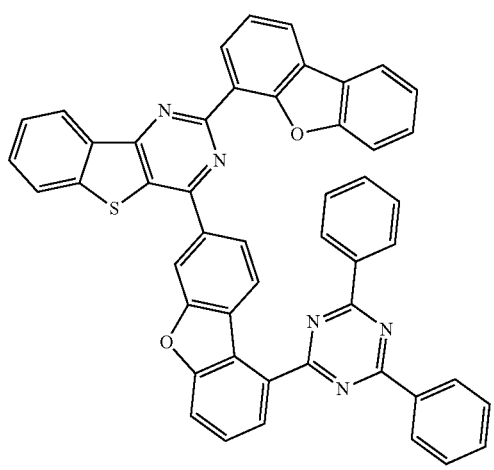
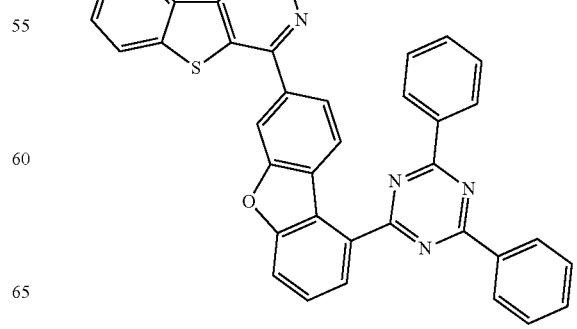

145
-continued
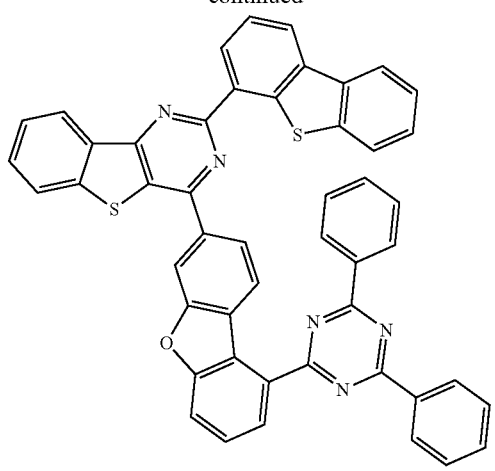
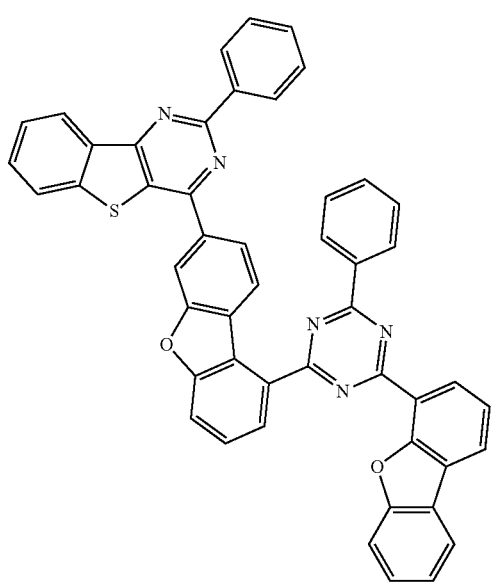
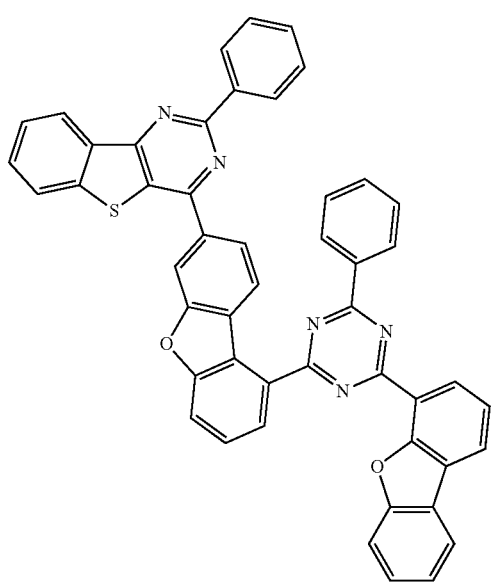
146
-continued
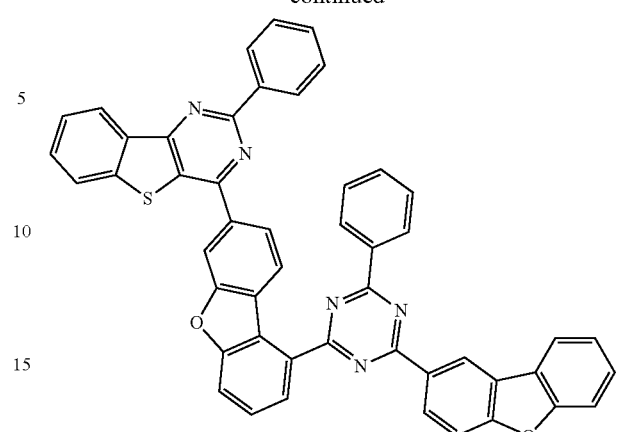
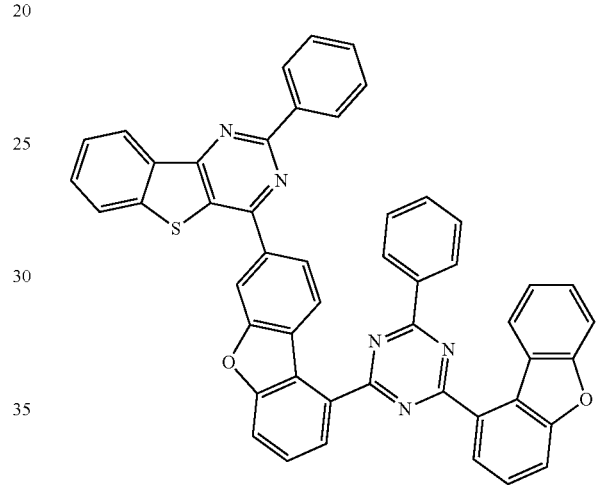
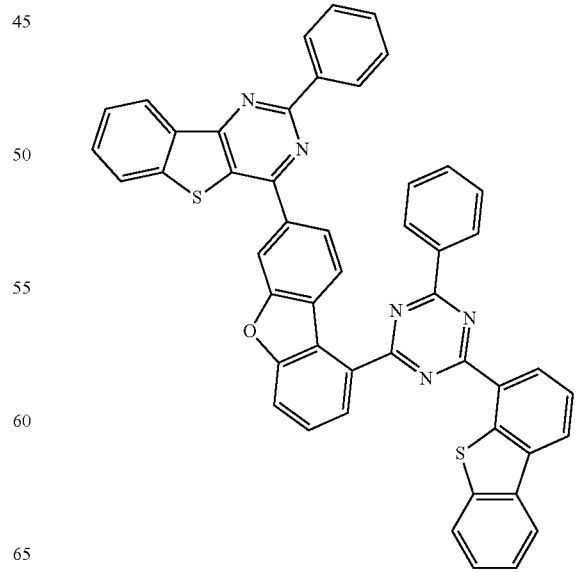

147
-continued
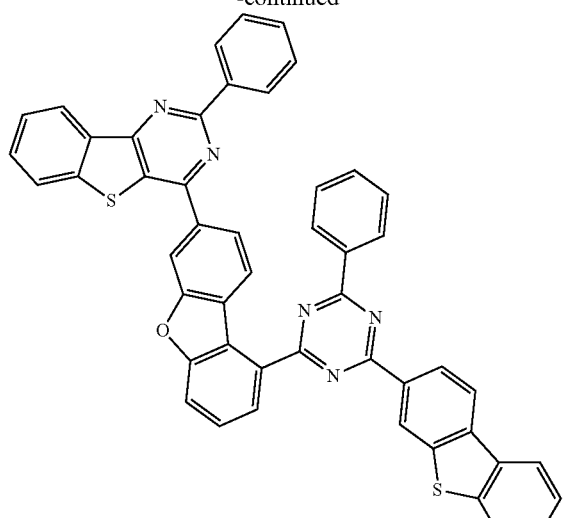
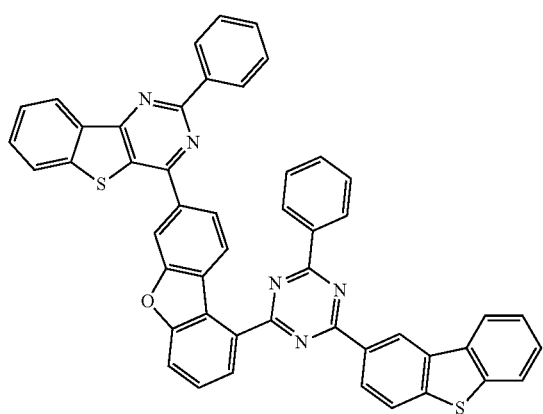
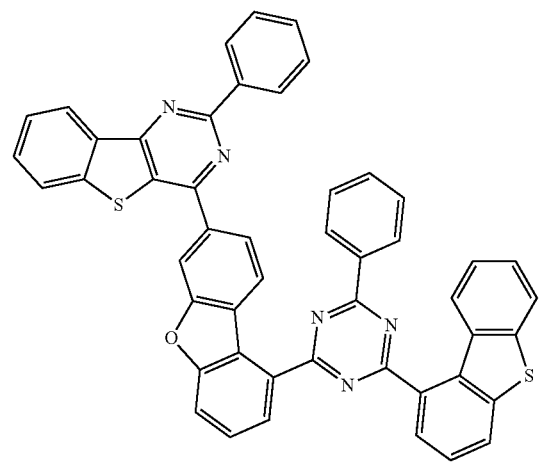
148
-continued
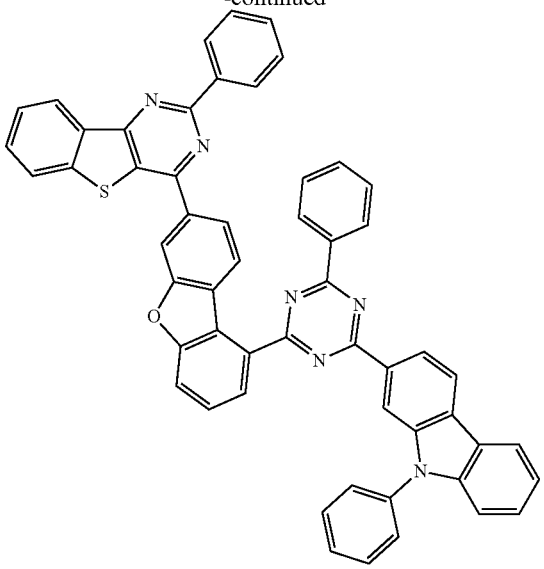
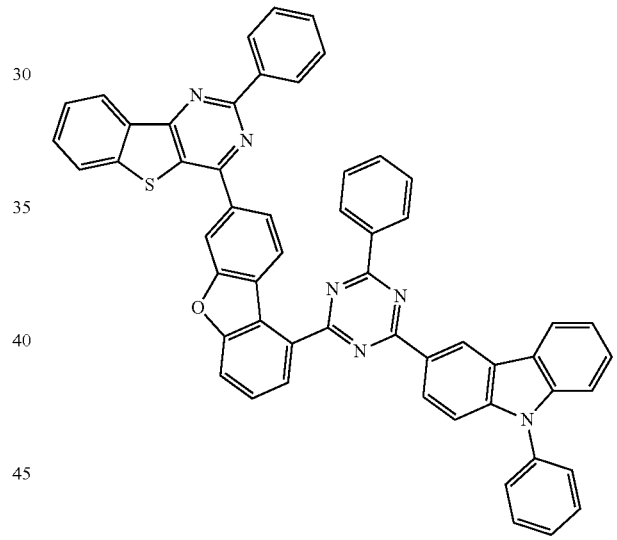
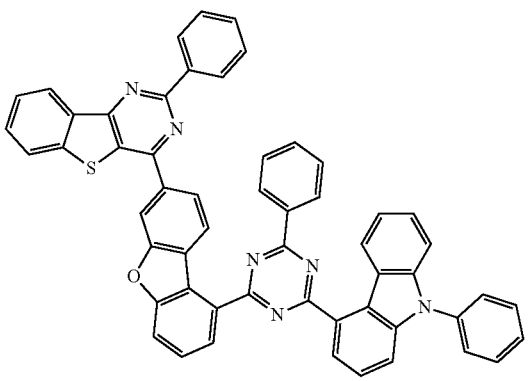

149
-continued
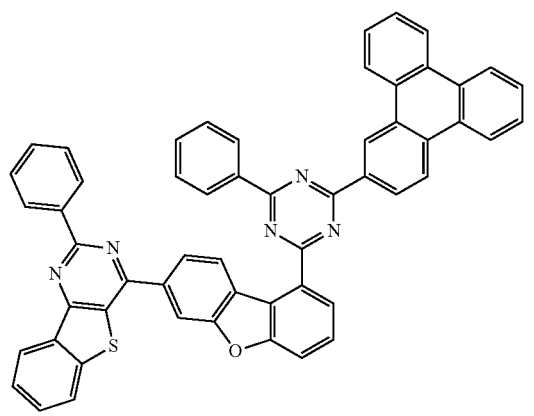
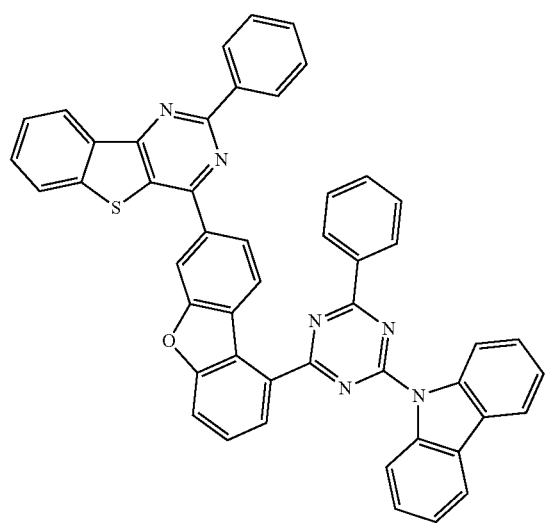
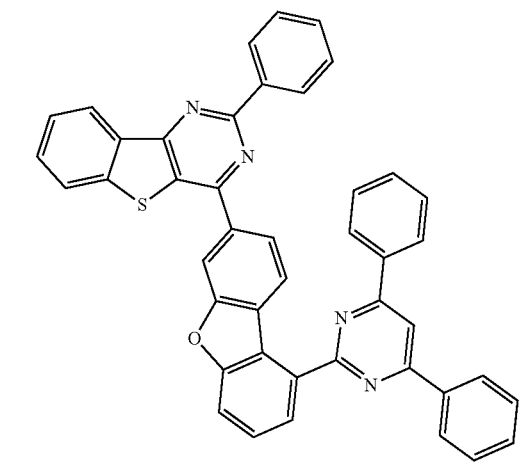
150
-continued
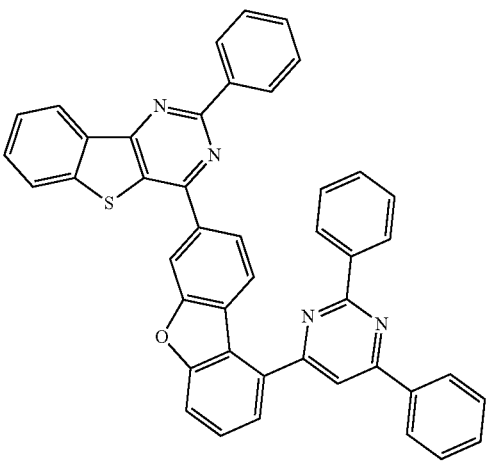
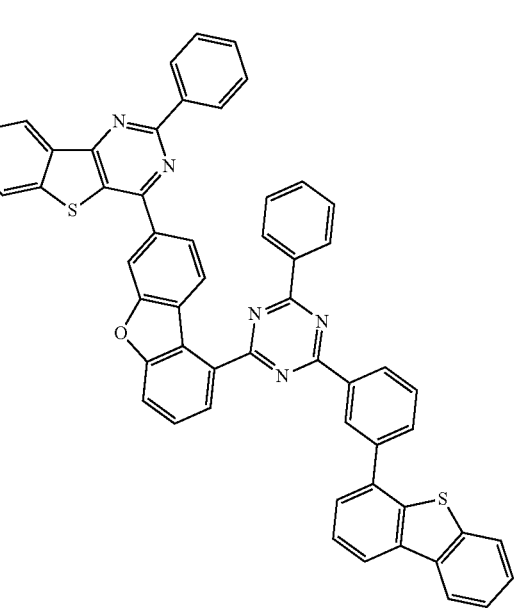
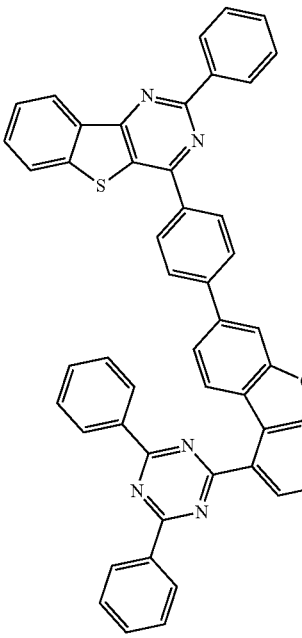

151
-continued
152
-continued
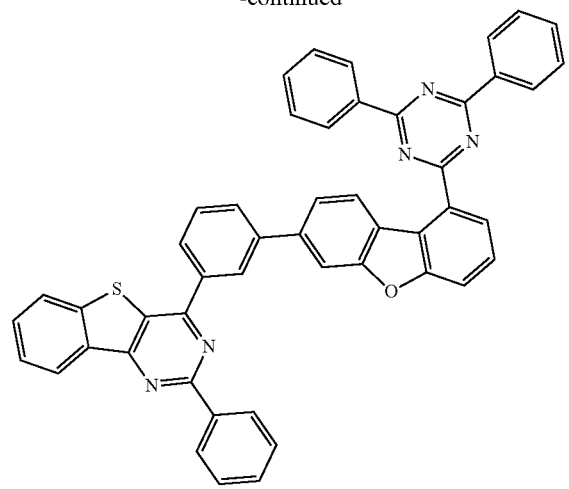
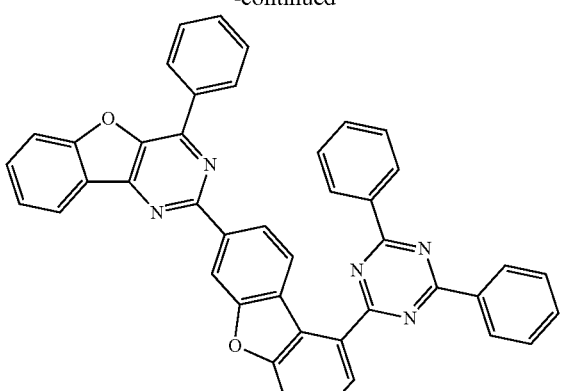
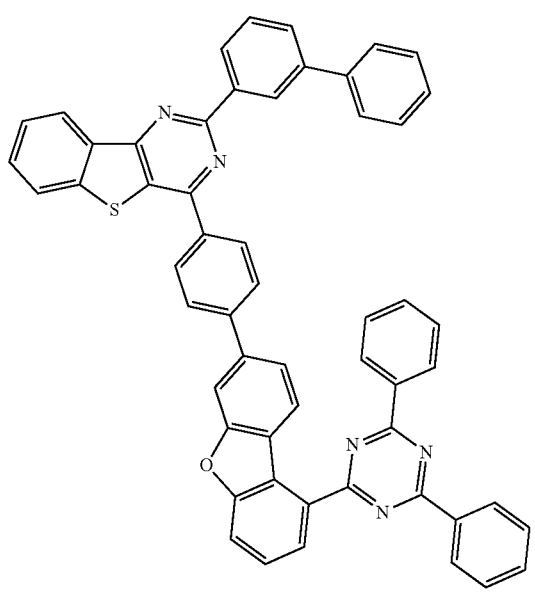
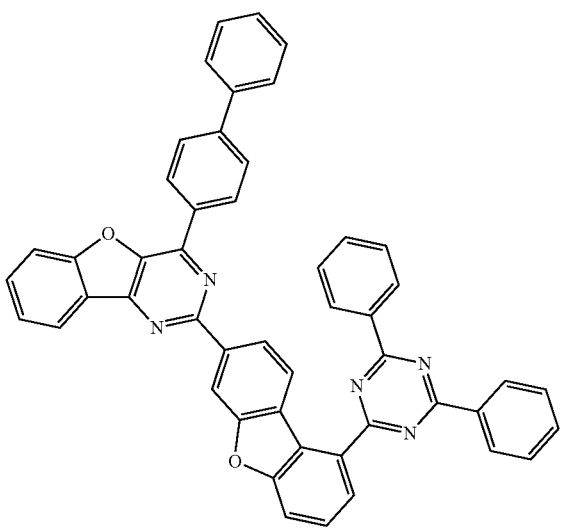
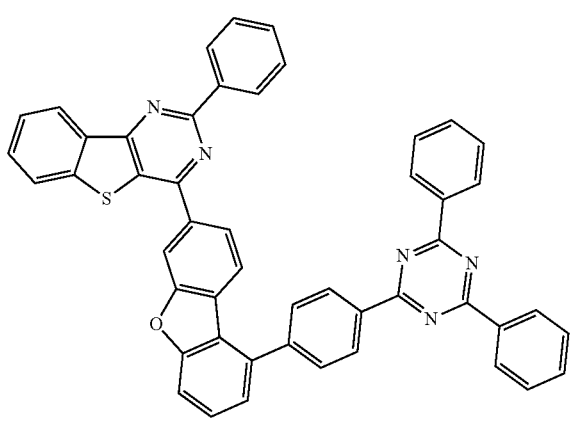
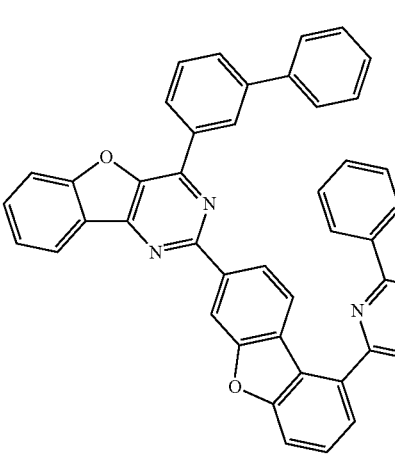

153
-continued
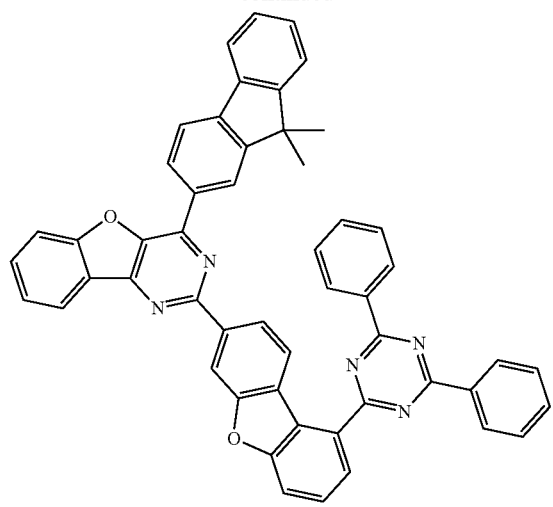
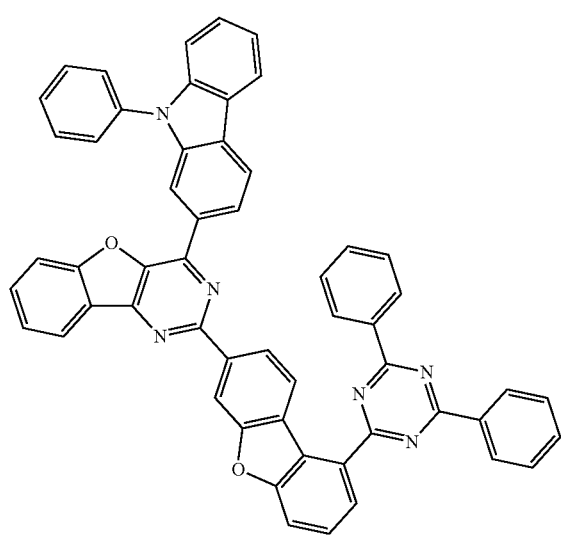
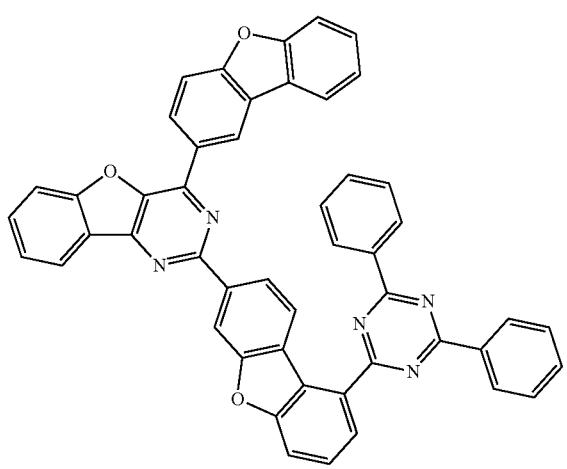
154
-continued
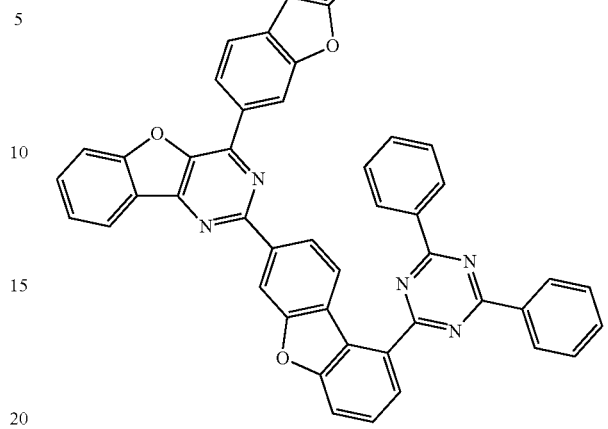
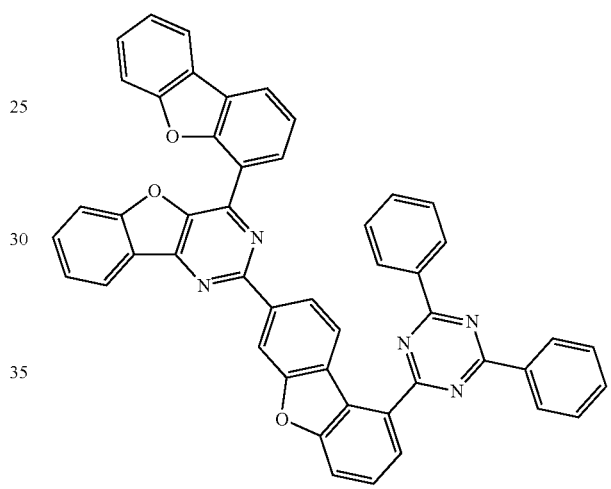
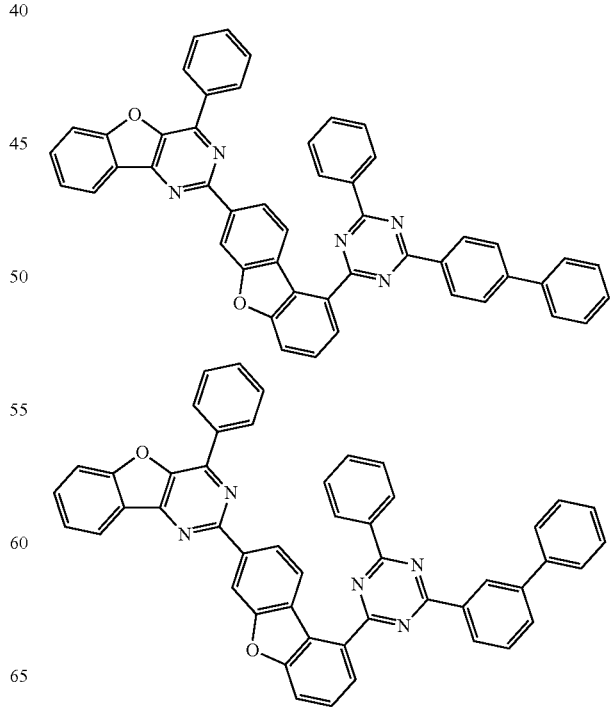

155
-continued
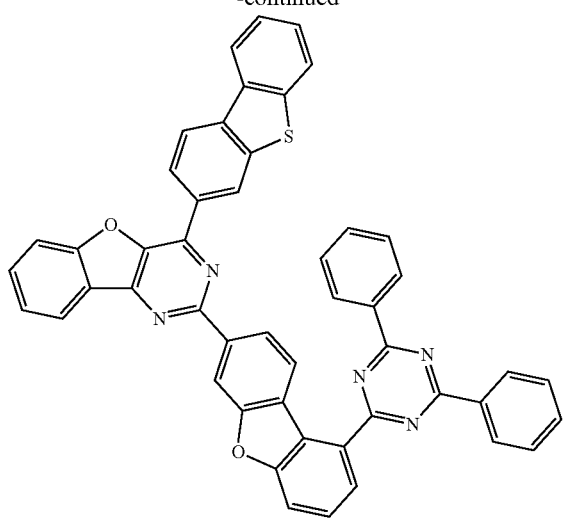
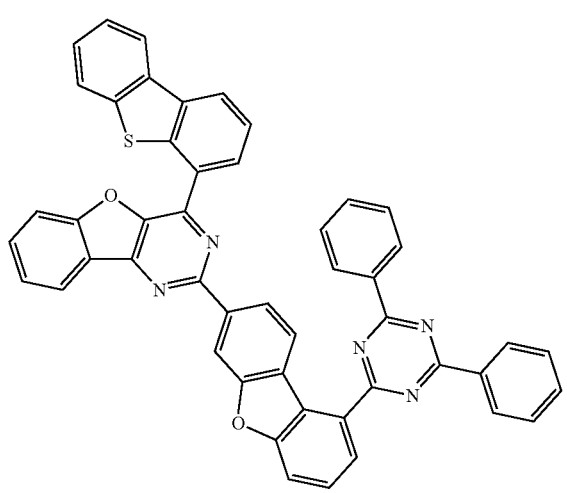
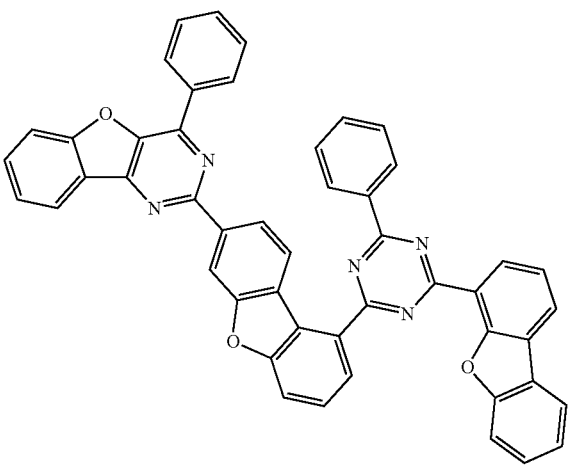
156
-continued
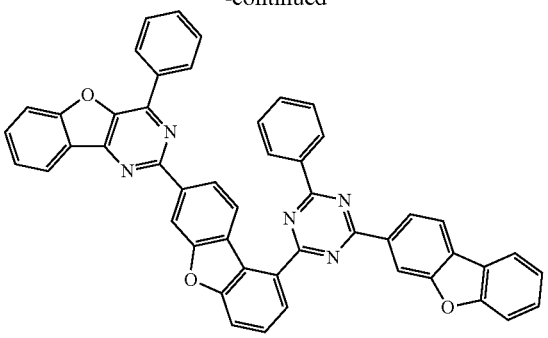
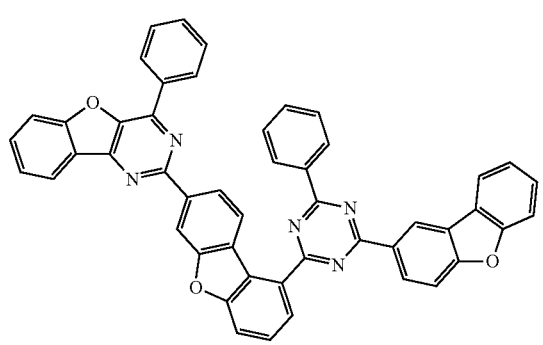
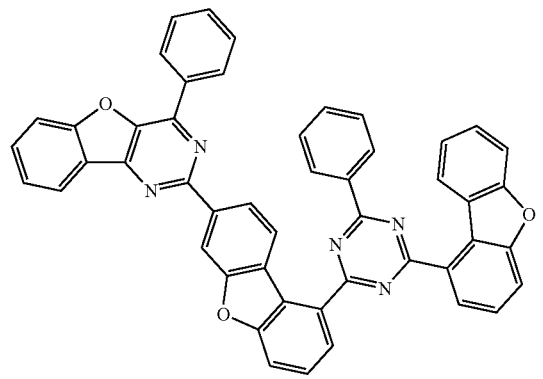
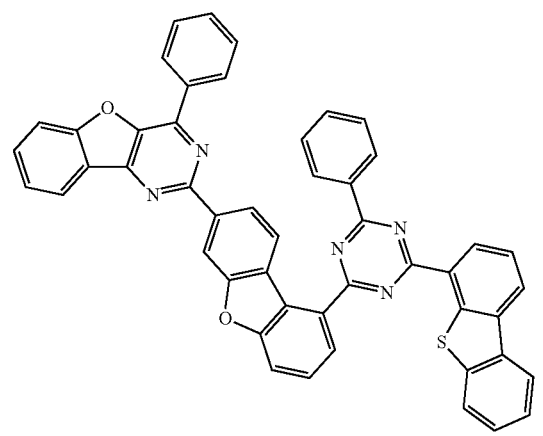

157
-continued
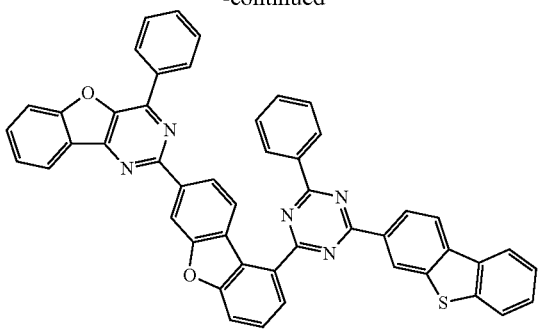
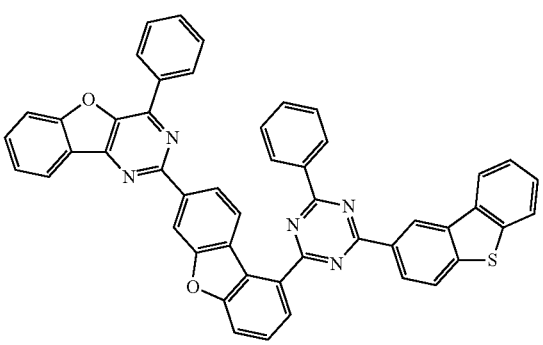
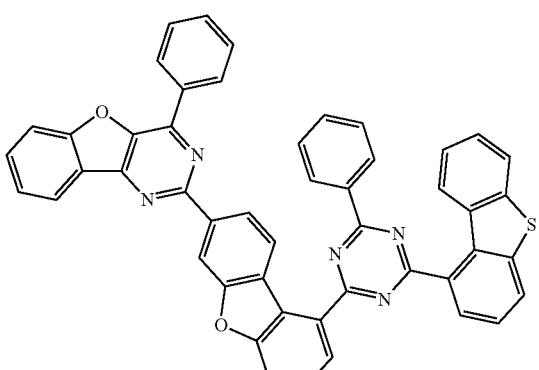
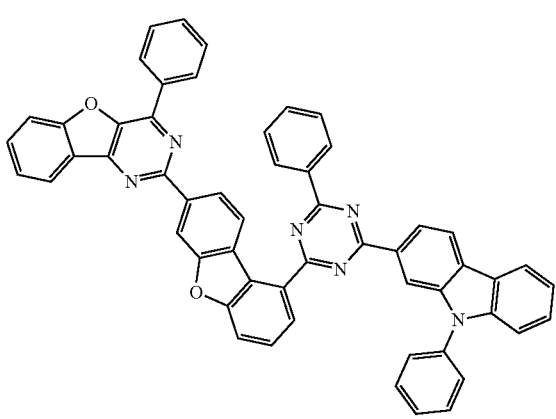
158
-continued
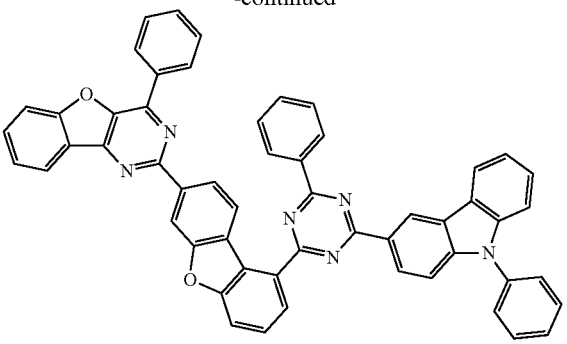
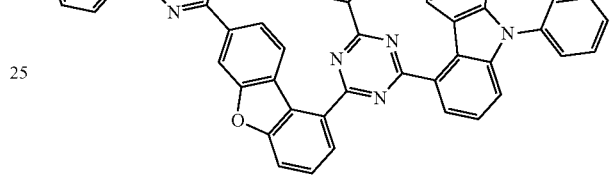
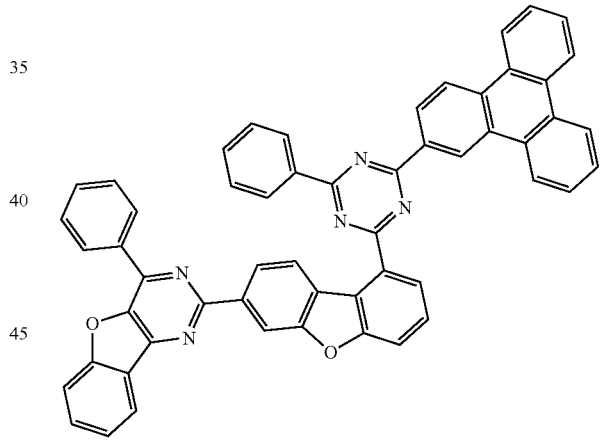
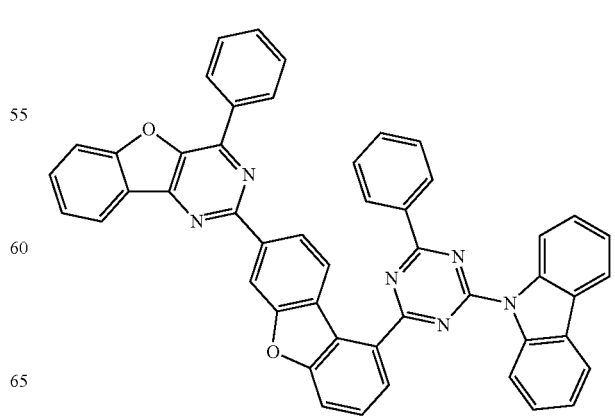

159
-continued
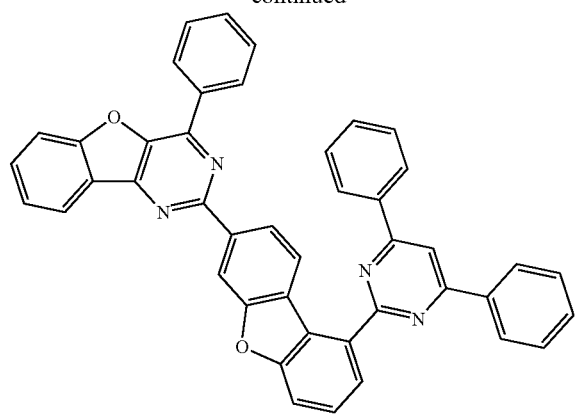
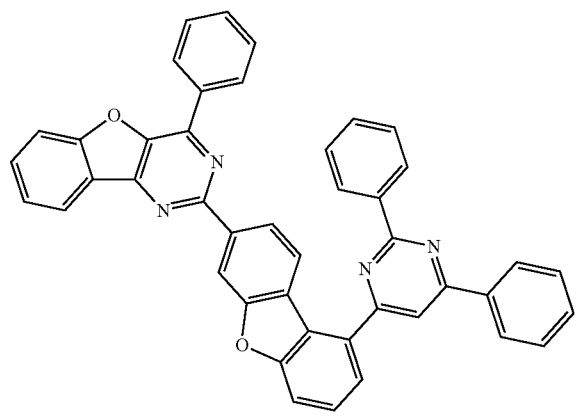
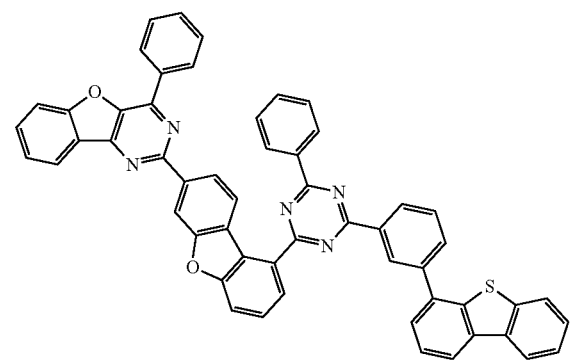
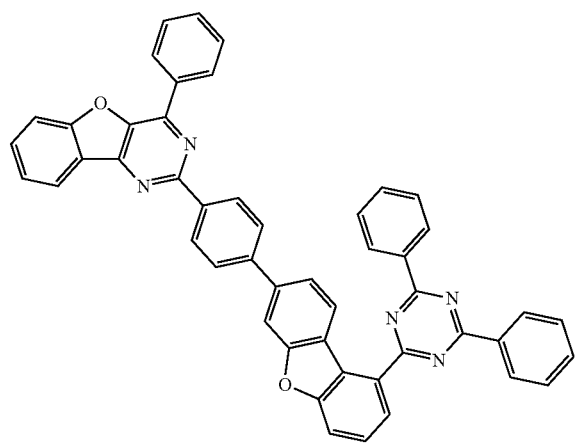
160
-continued
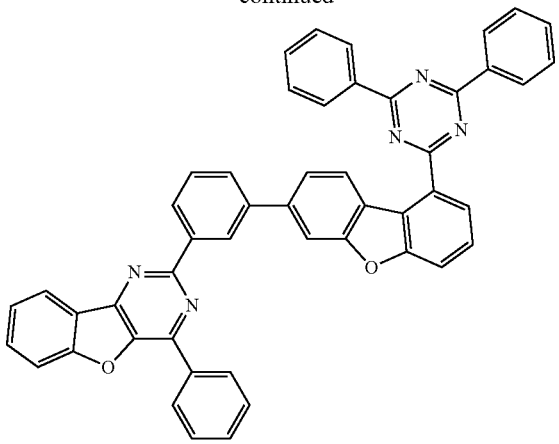
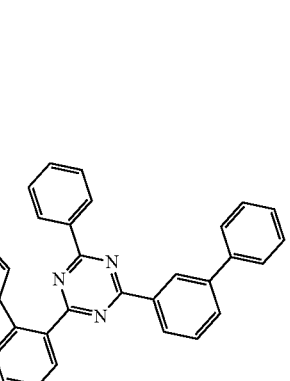
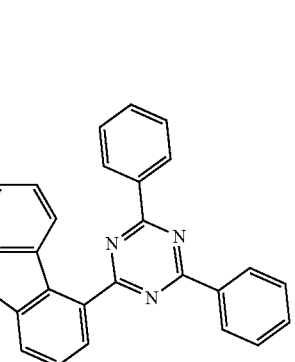
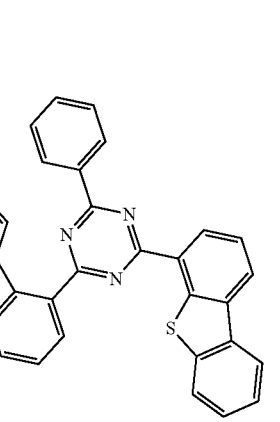

161
-continued
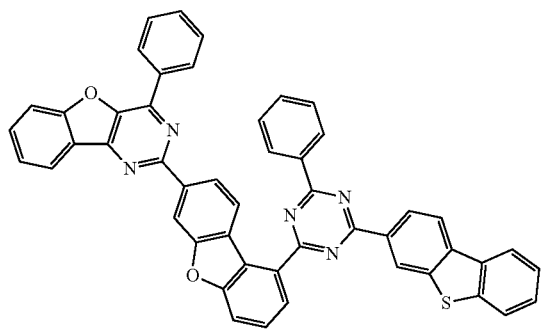
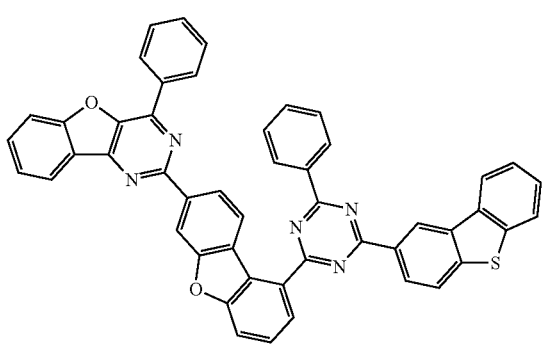
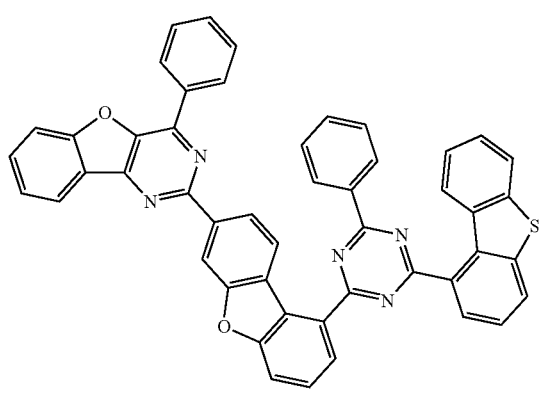
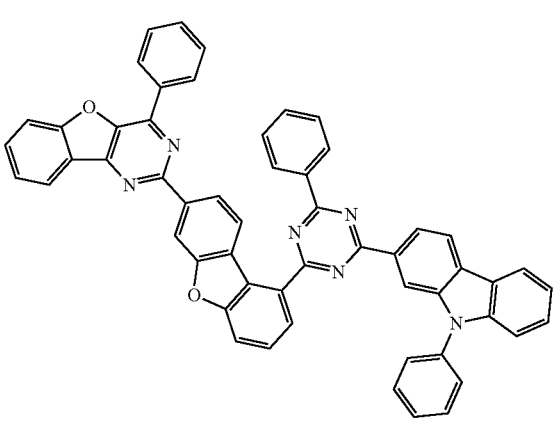
162
-continued
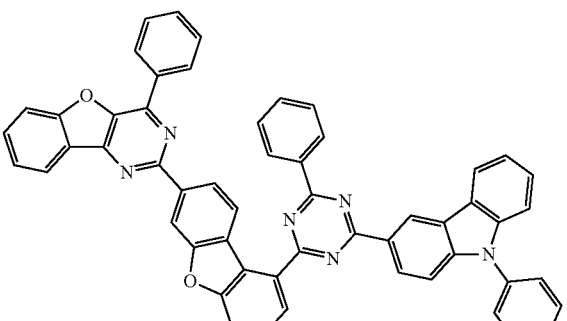
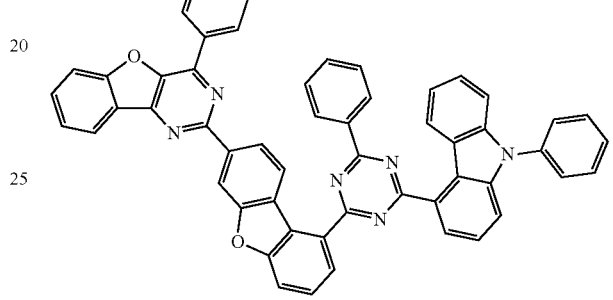
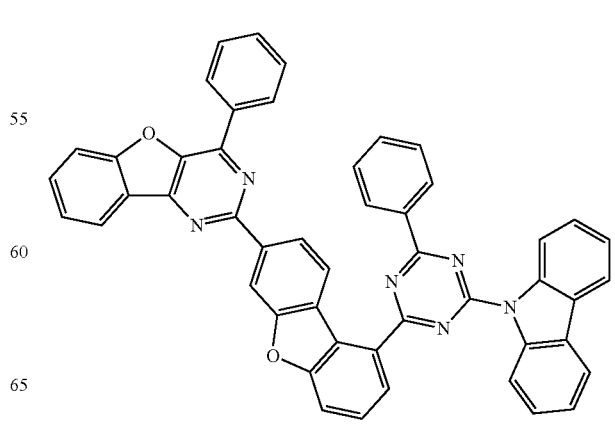

163
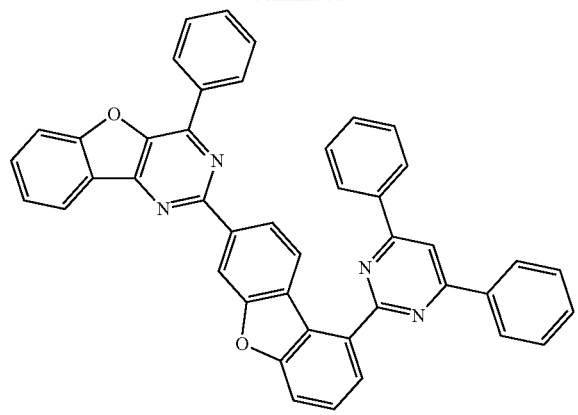
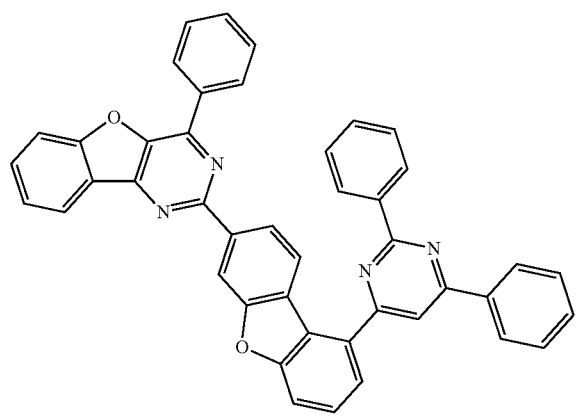
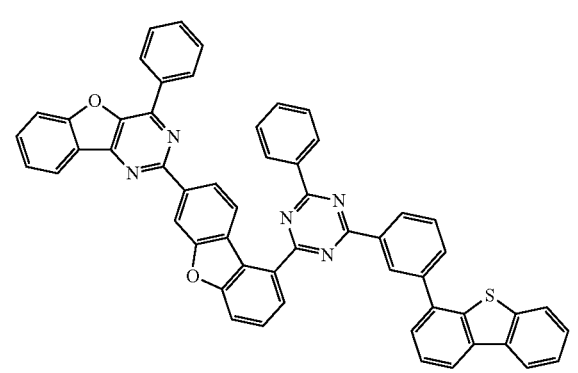
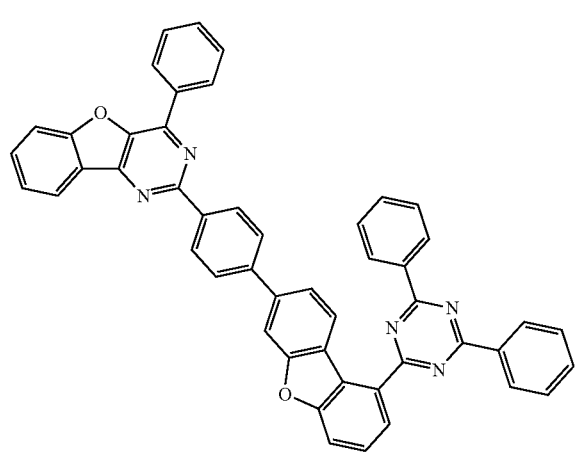
164
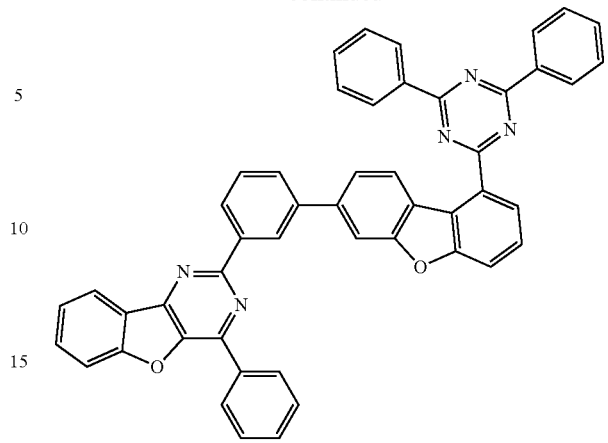
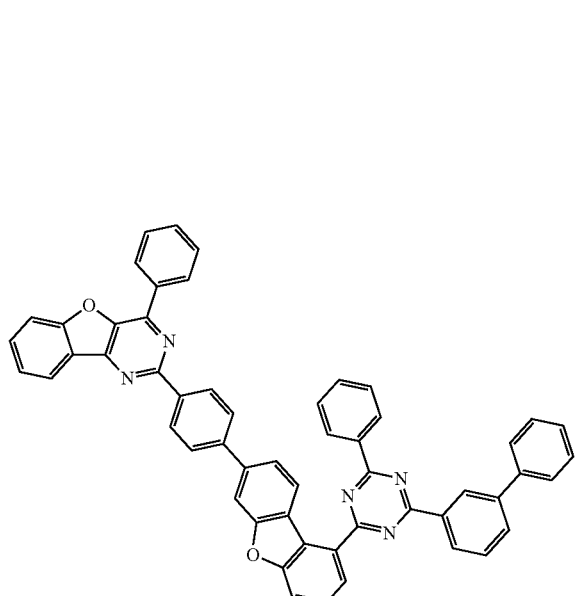
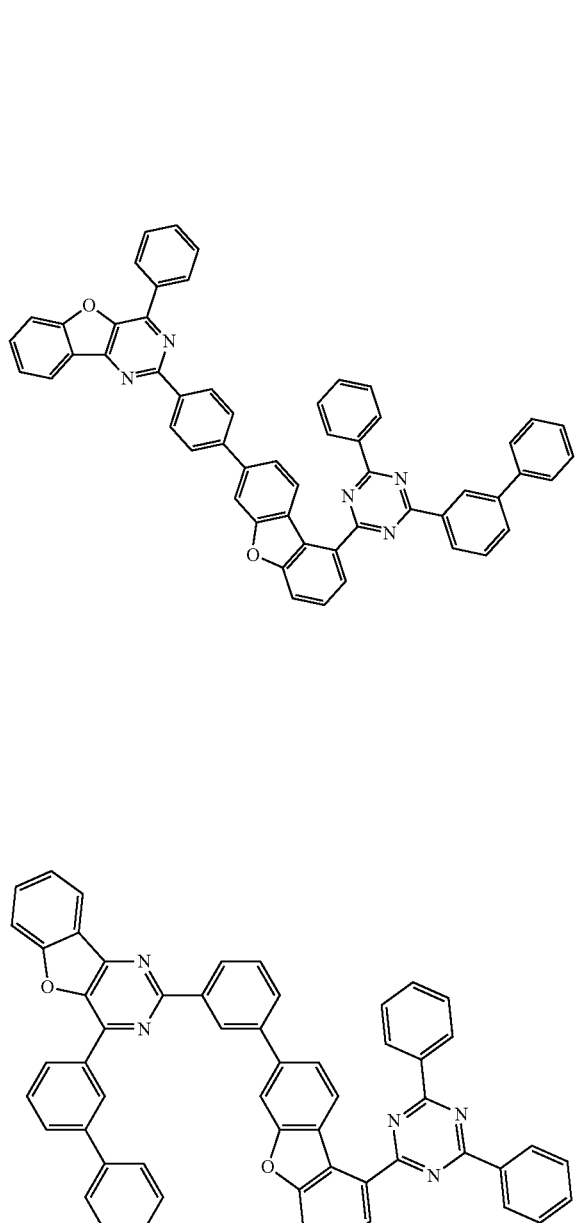

-continued
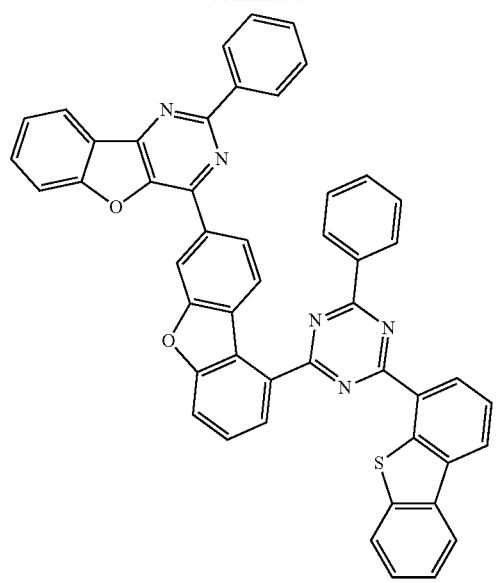
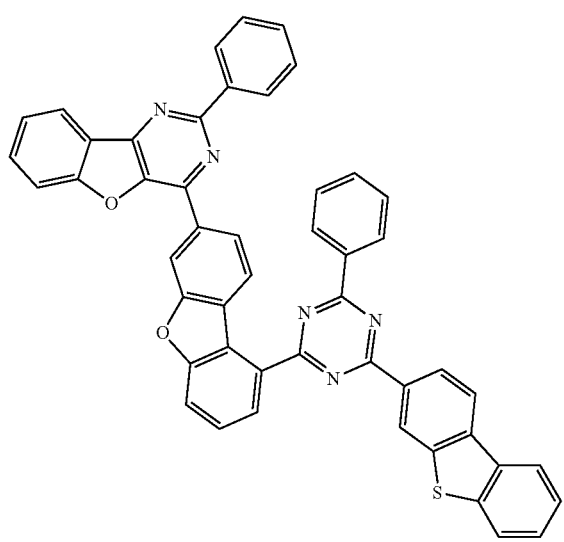
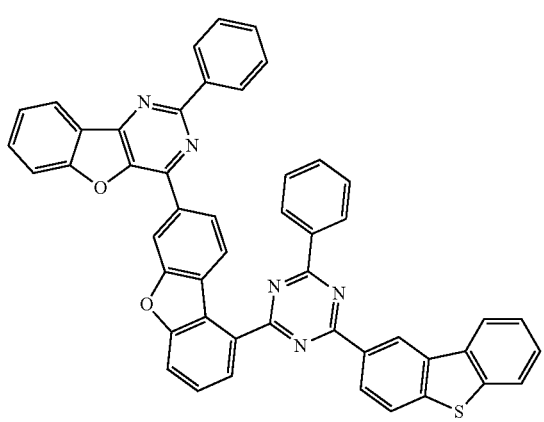
-continued
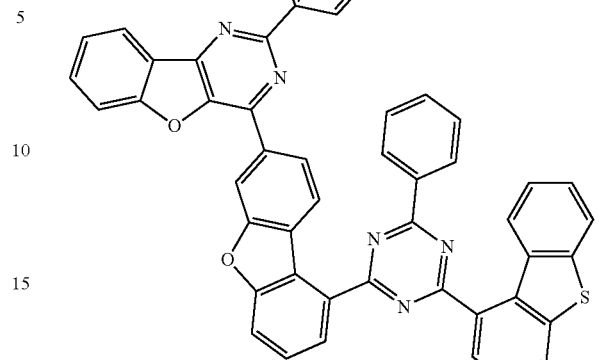
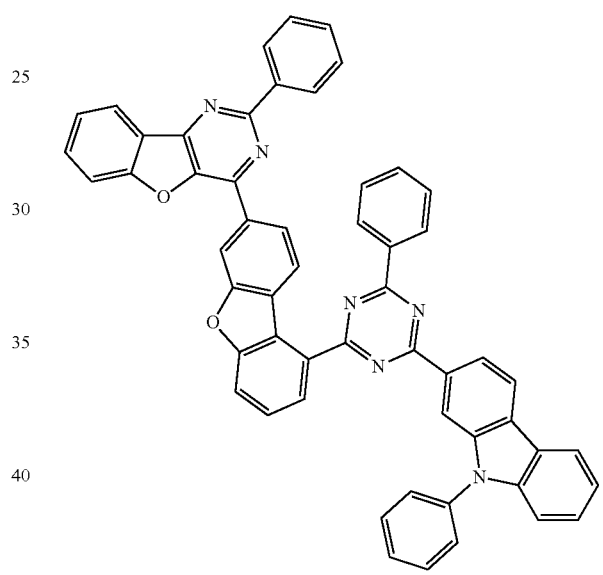
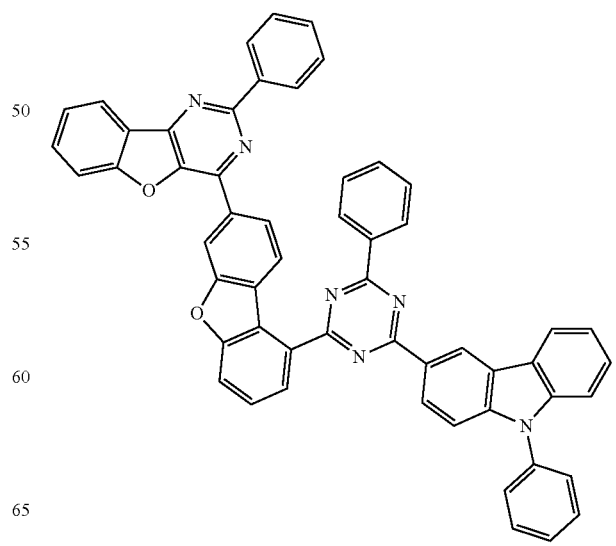

-continued
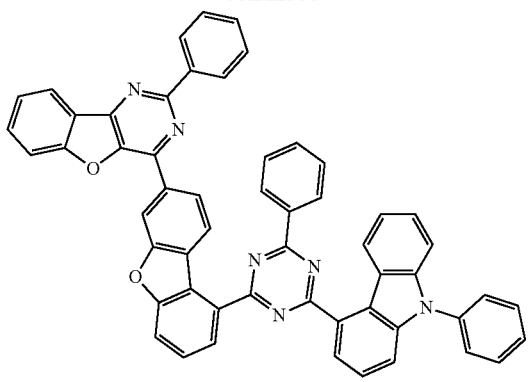
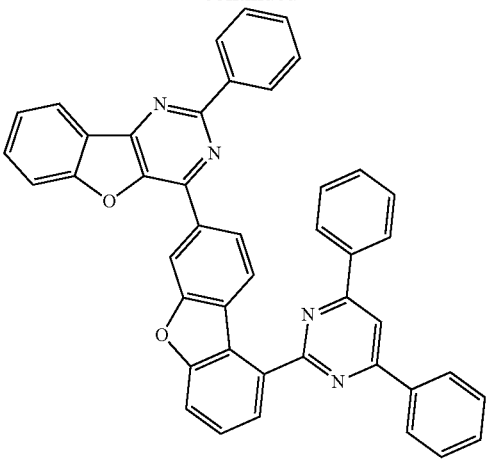
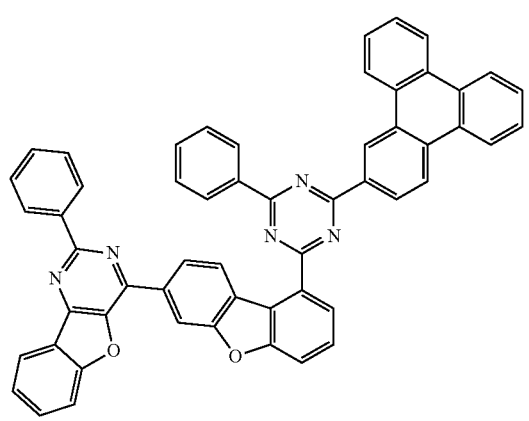
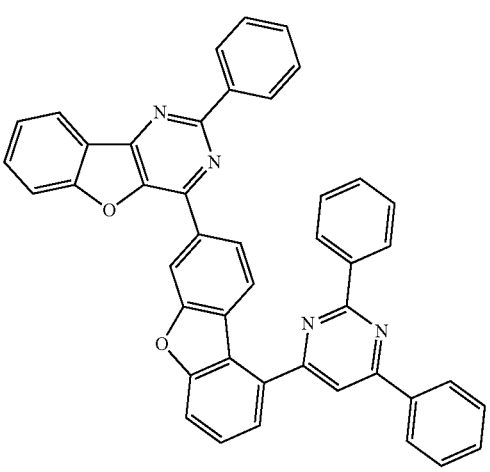
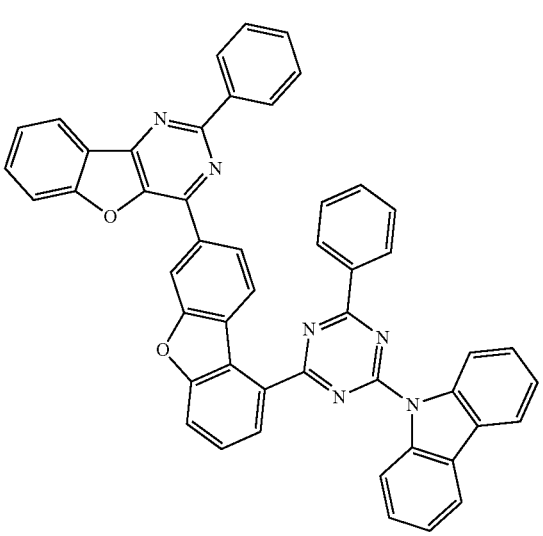
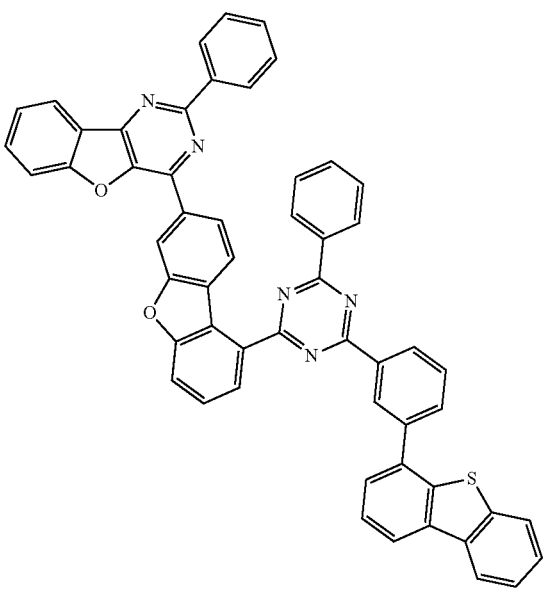

169
-continued
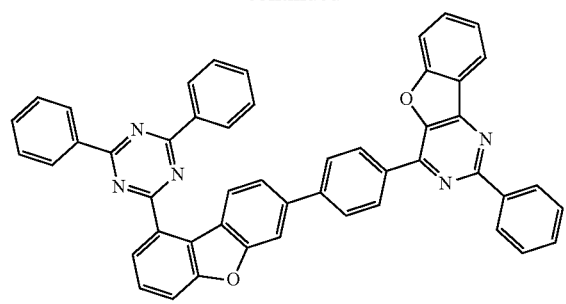
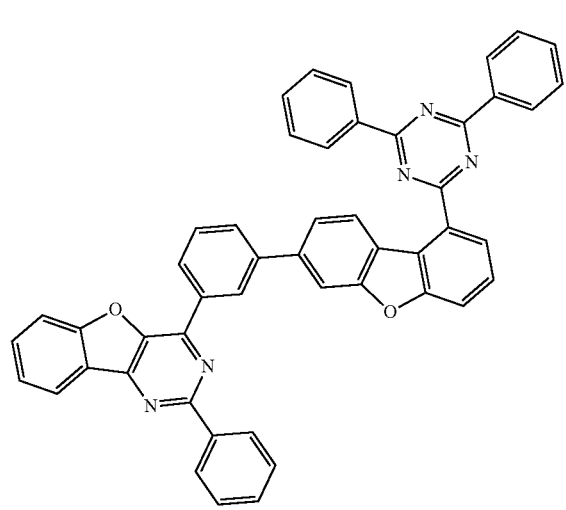
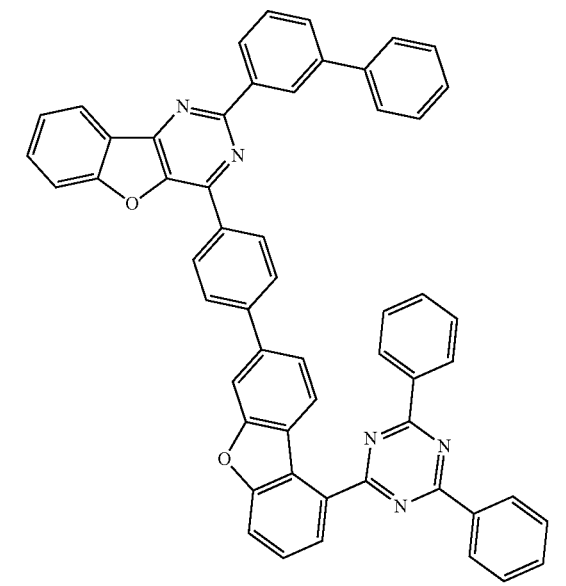
170
-continued
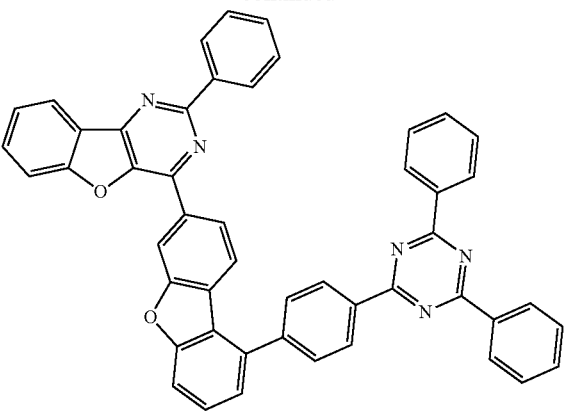
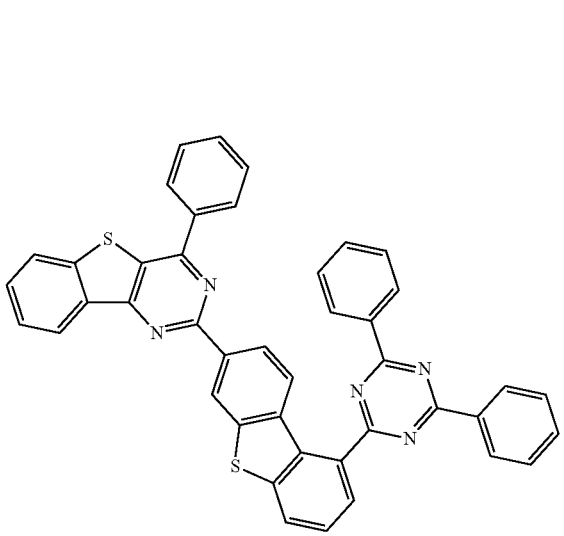
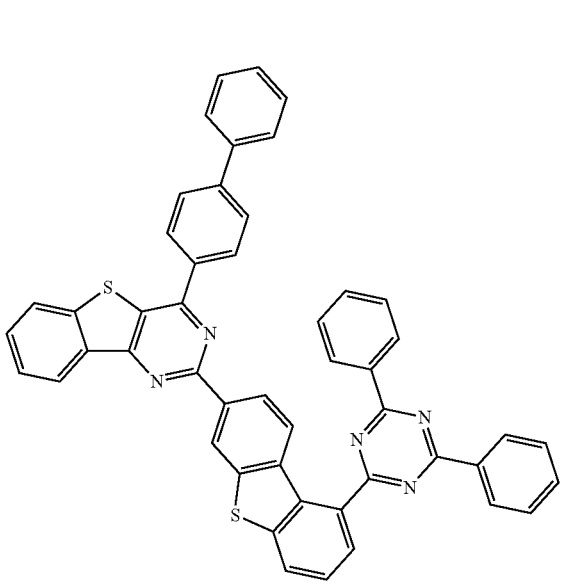

171
-continued
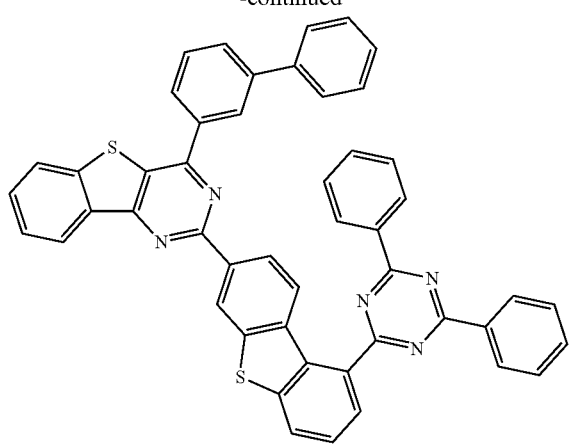
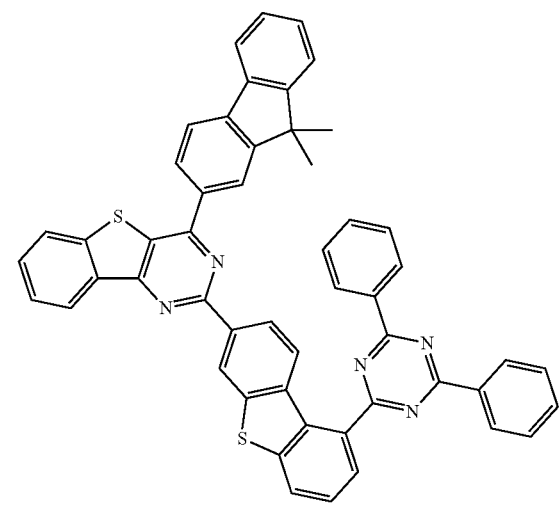
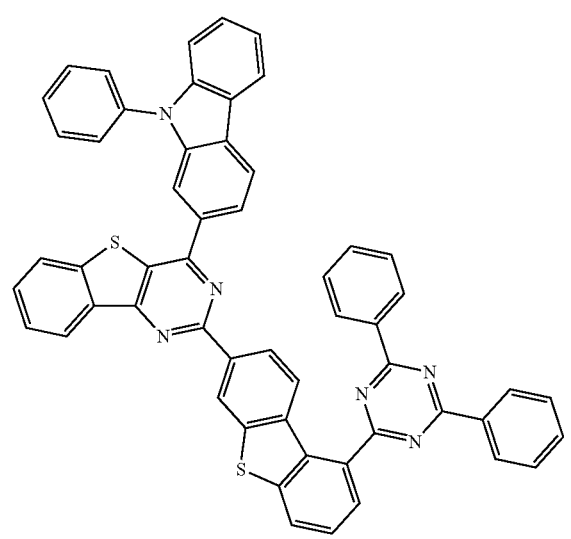
172
-continued
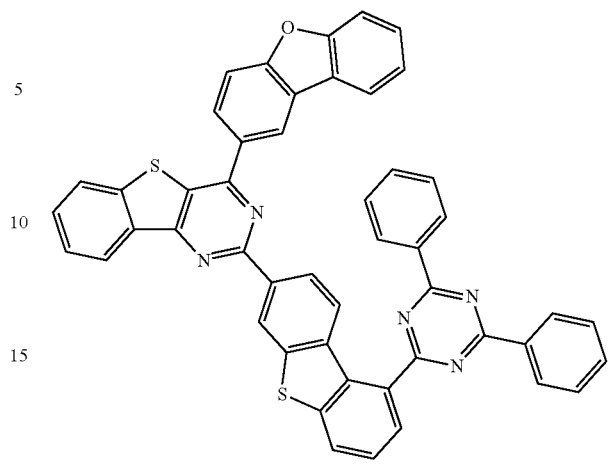

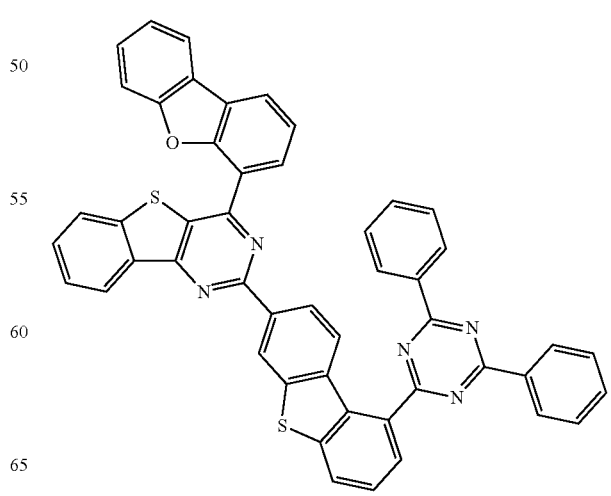

173
-continued
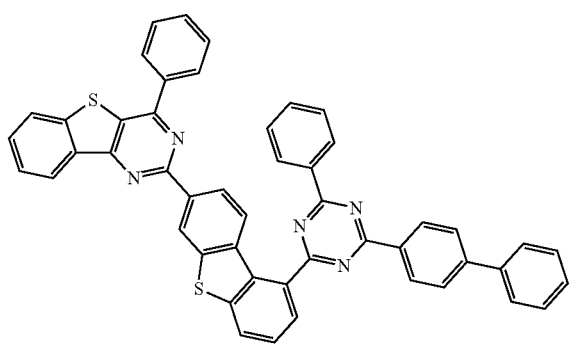
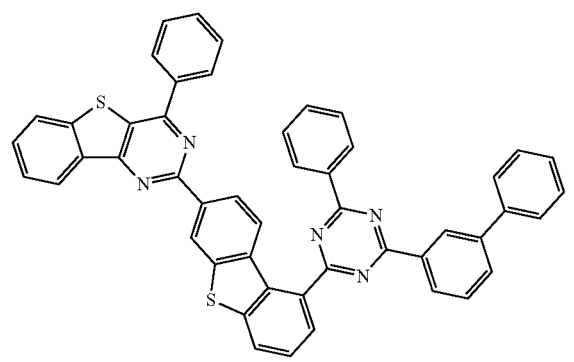
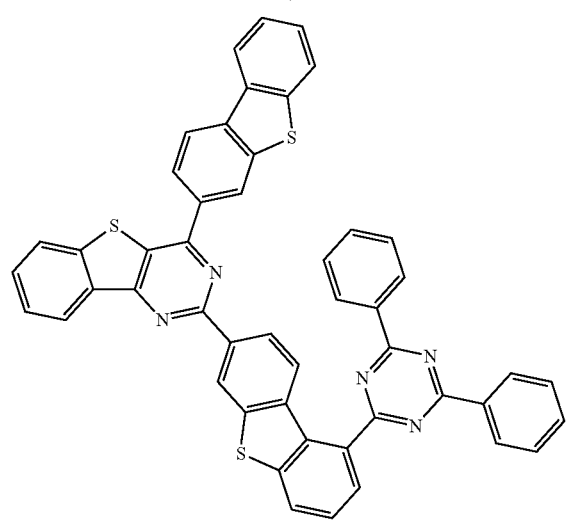
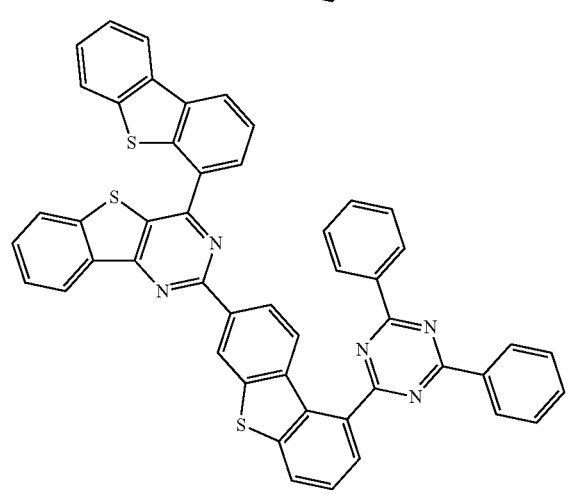
174
-continued
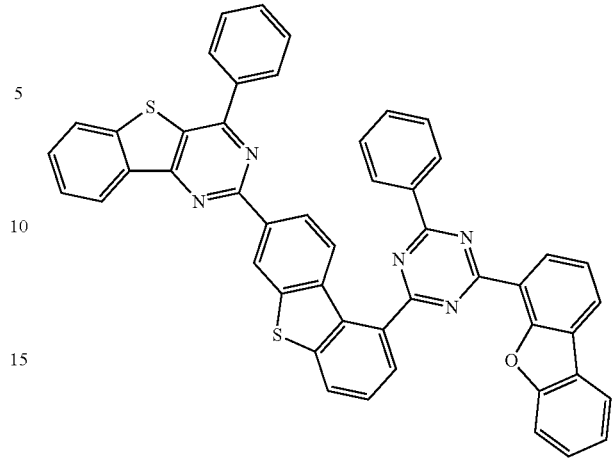
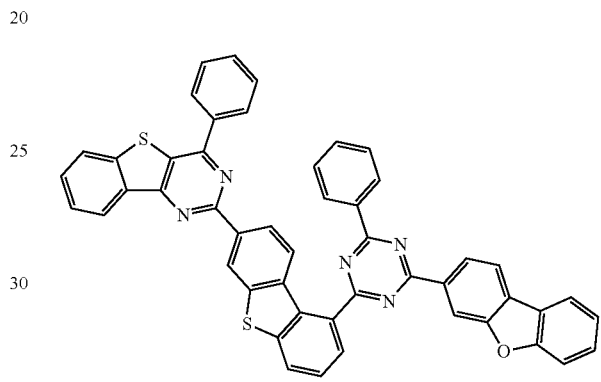
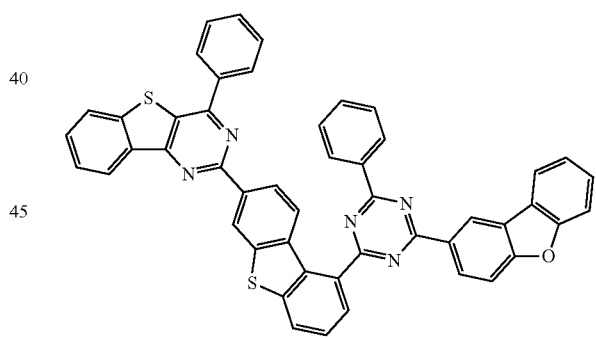
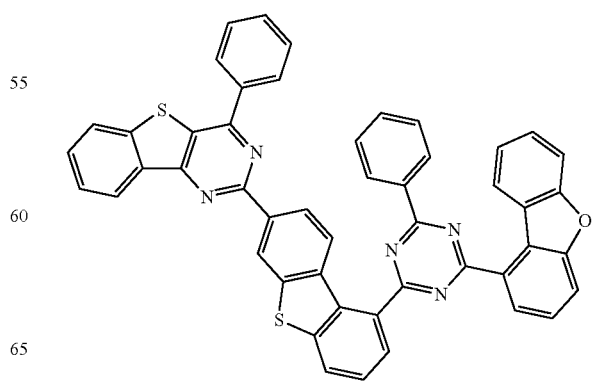

175
-continued
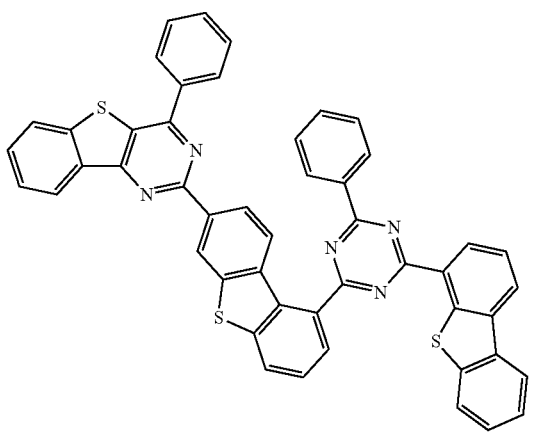
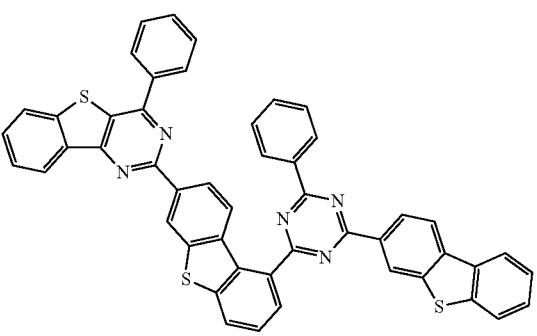
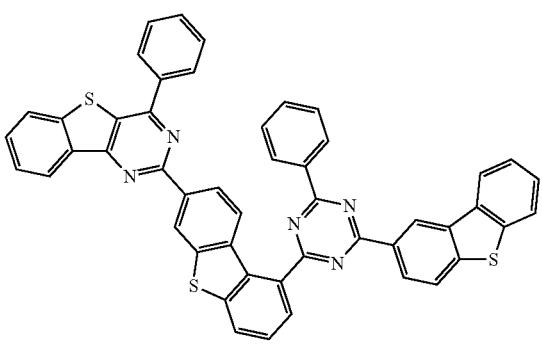
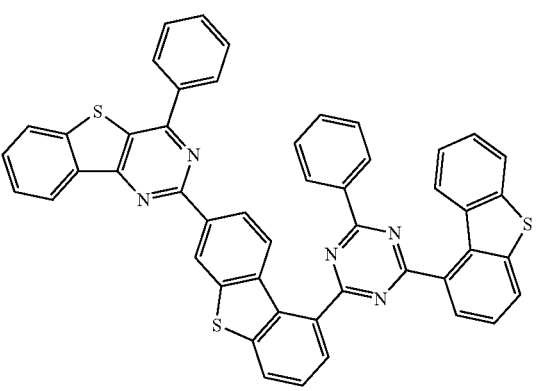
176
-continued
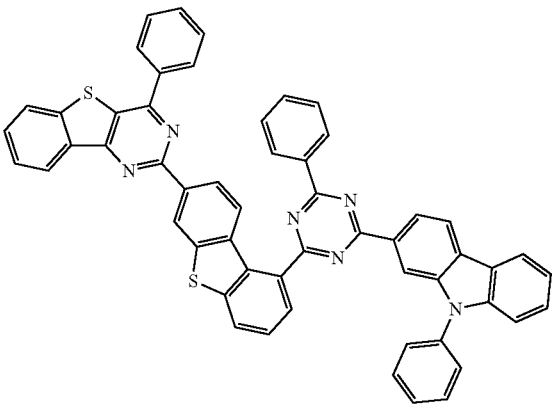
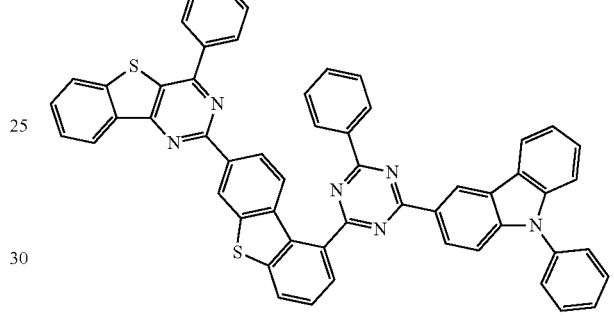
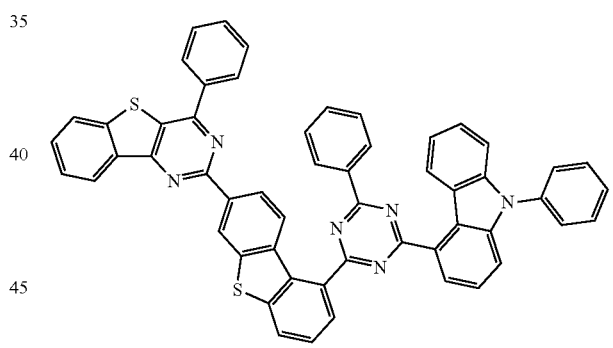
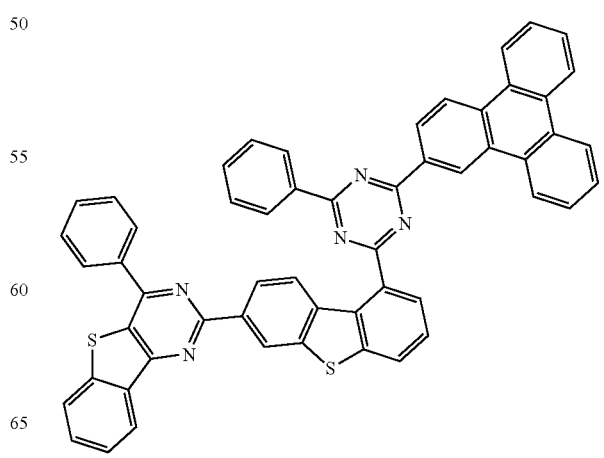

177
-continued
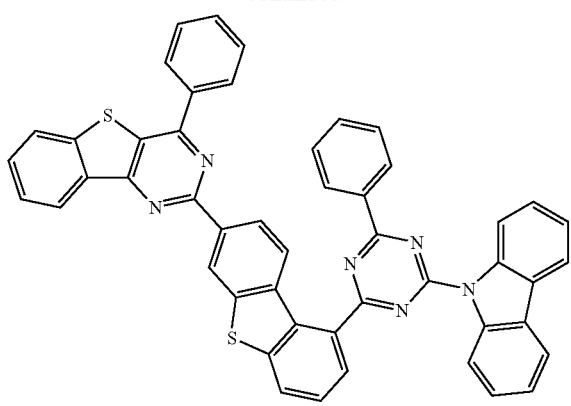
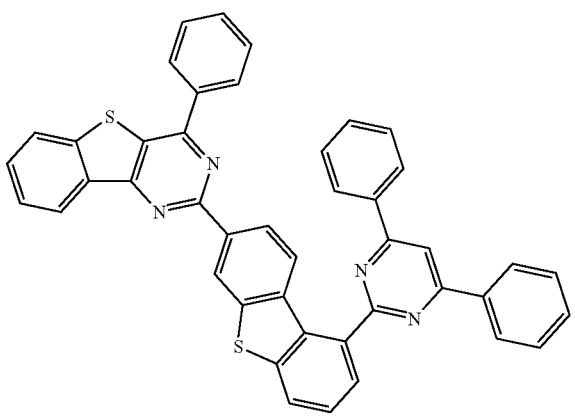
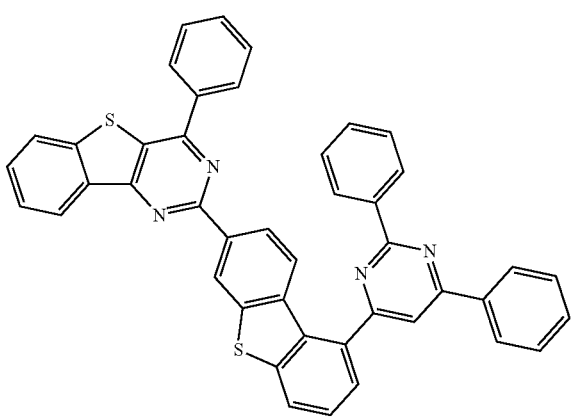
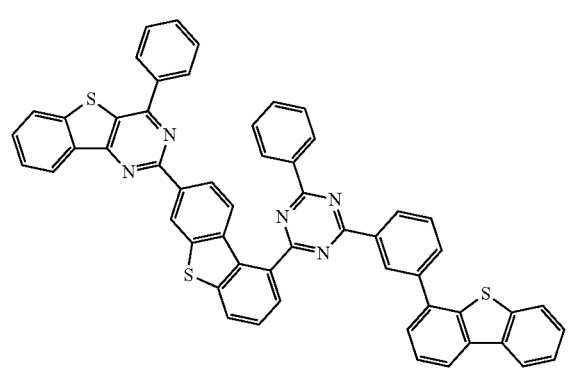
178
-continued
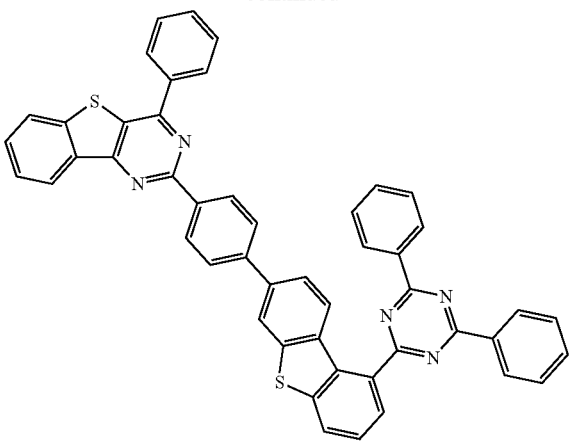
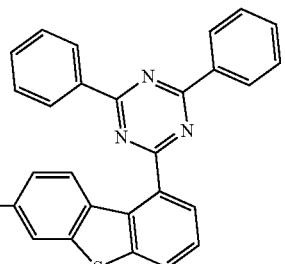
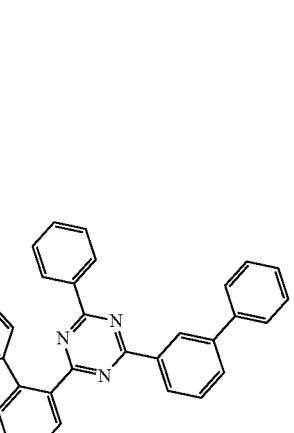
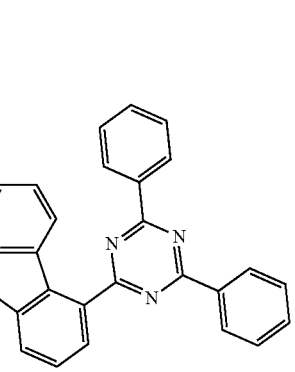

179
-continued
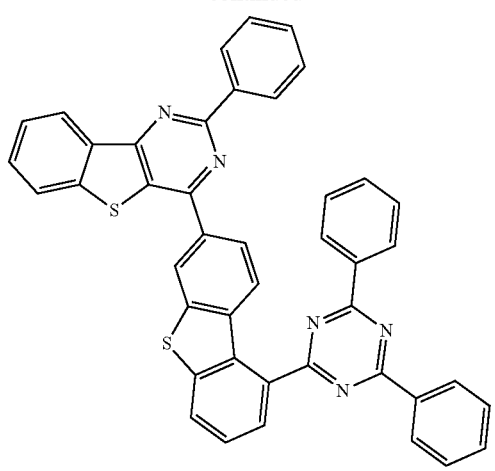
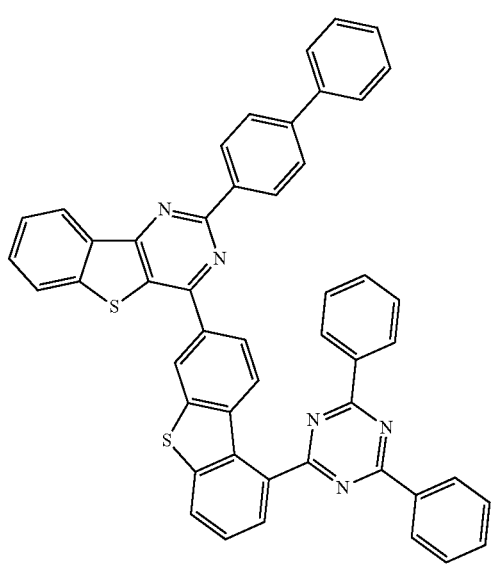
180
-continued
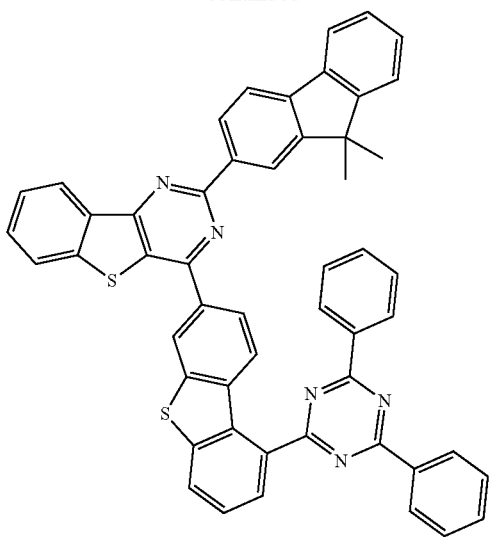
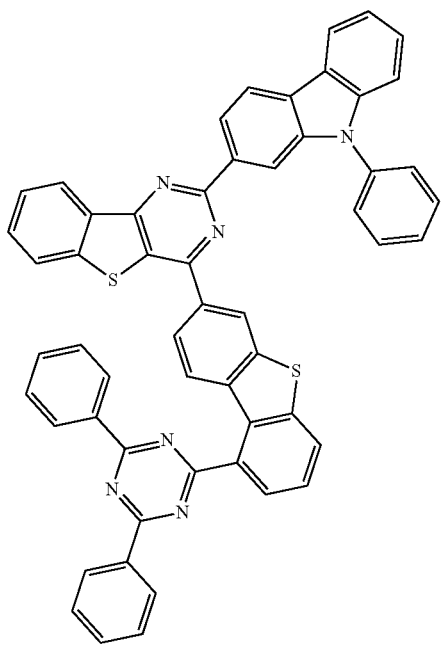

181
-continued
182
-continued
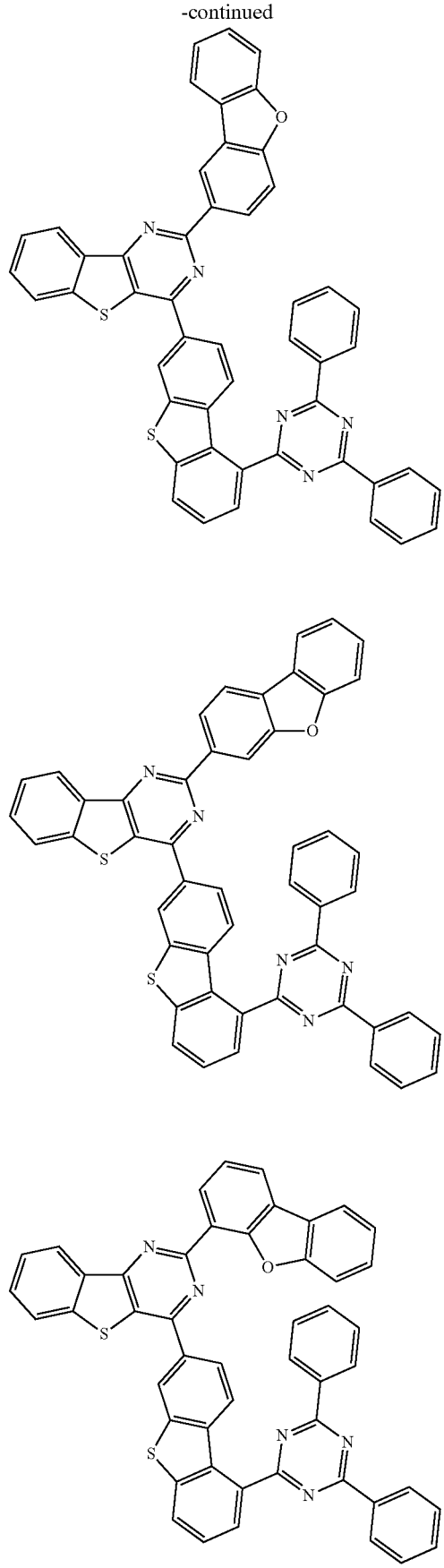
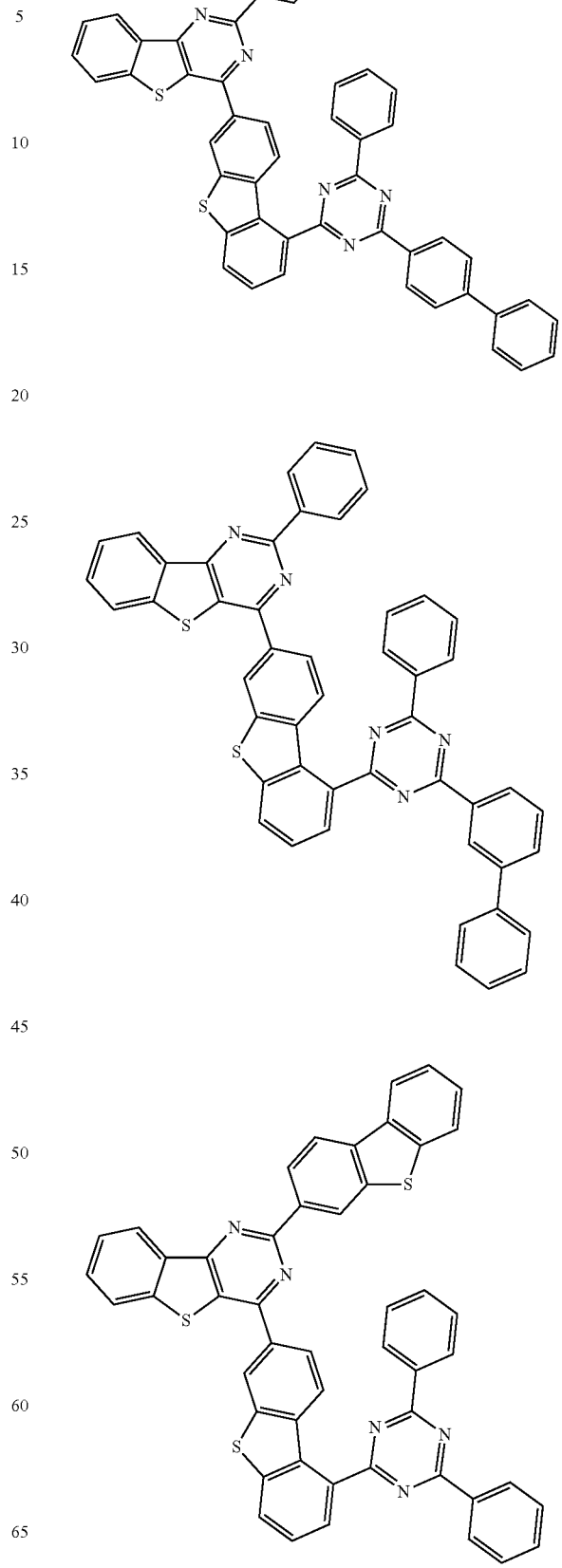

-continued
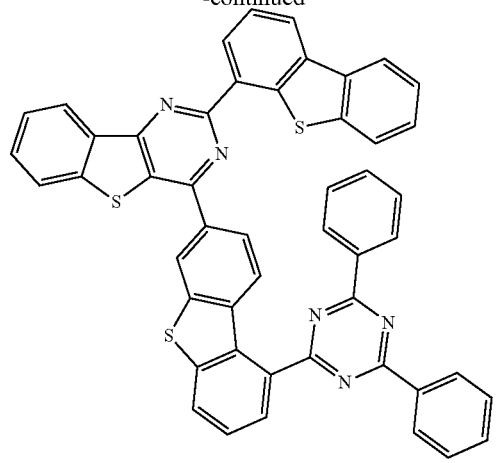
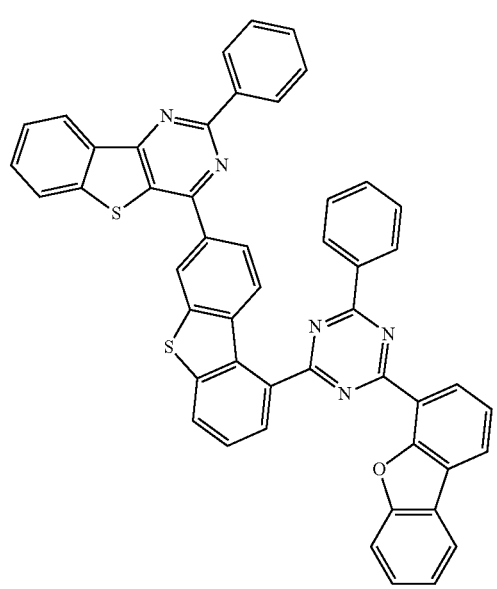
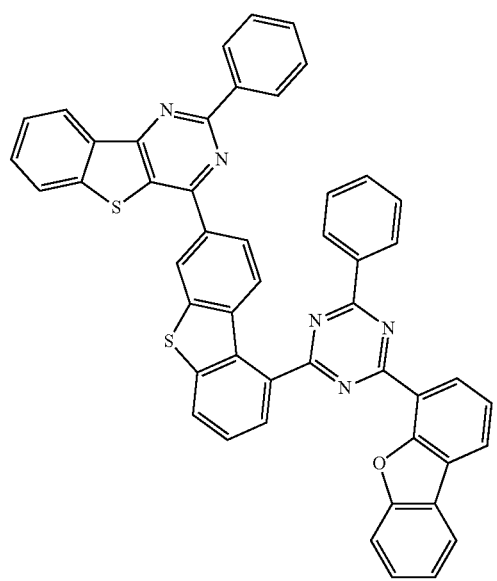
-continued
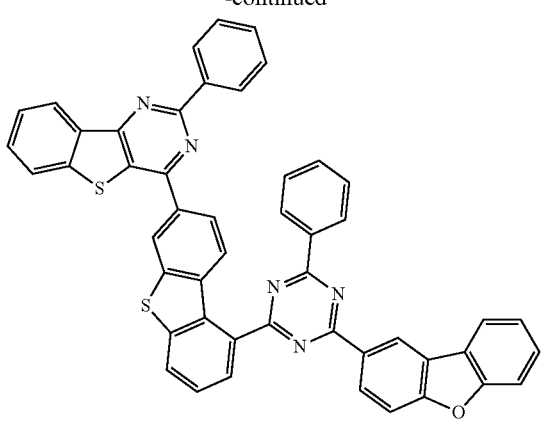
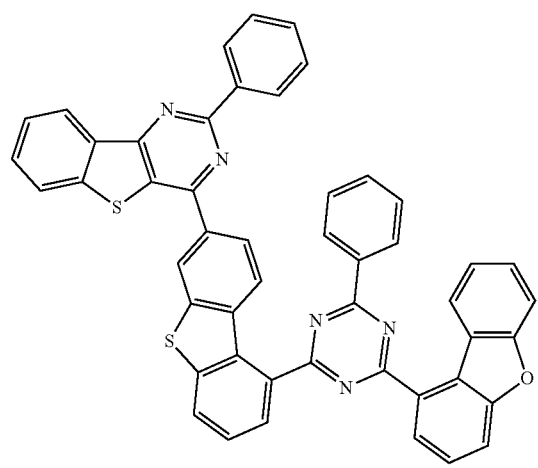
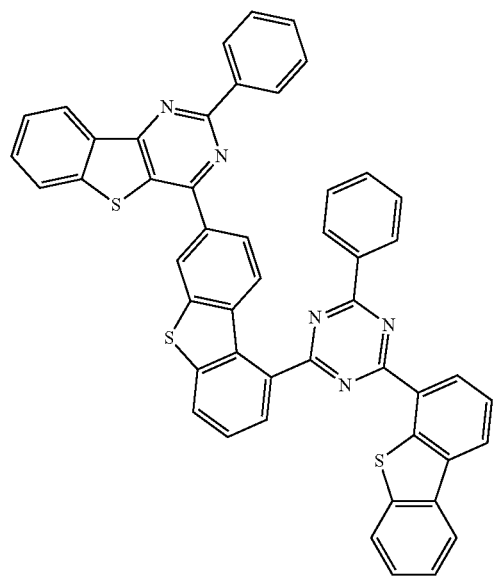

185
-continued
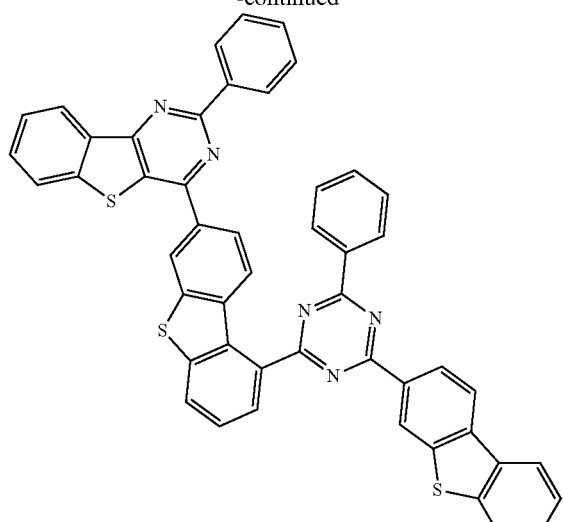
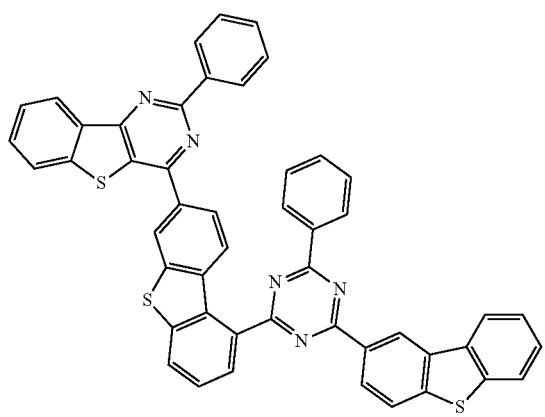
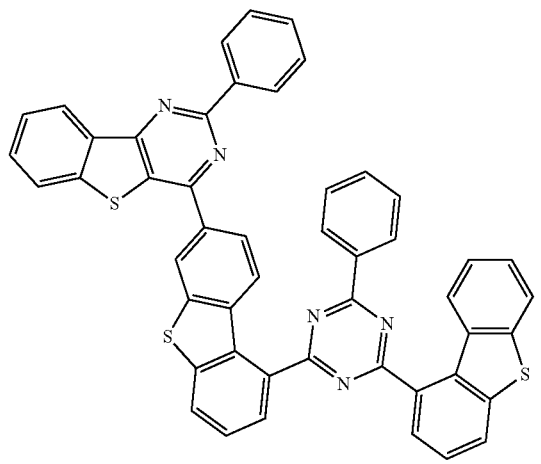
186
-continued
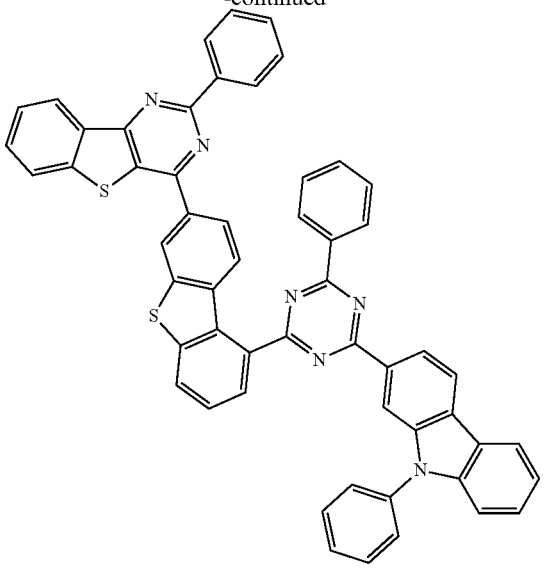
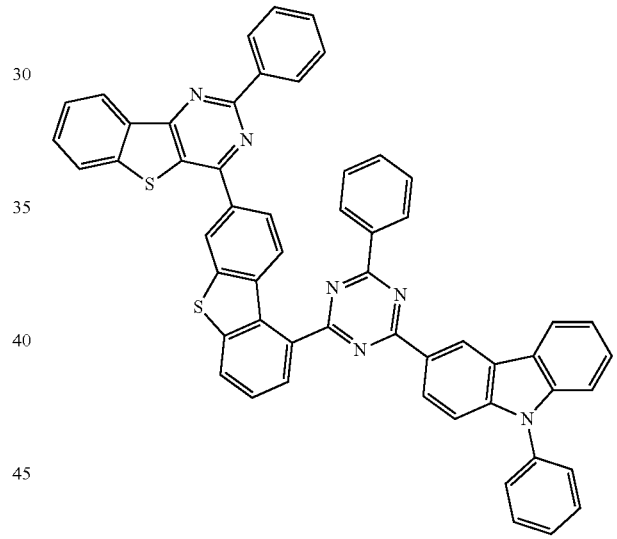
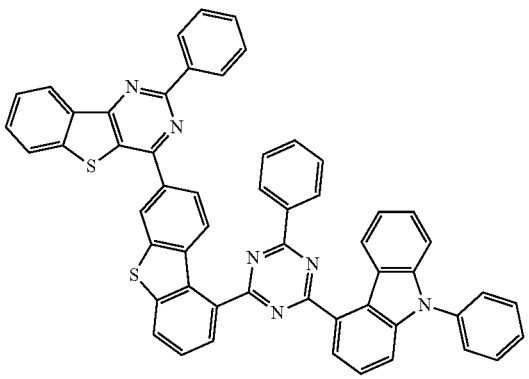

187
-continued
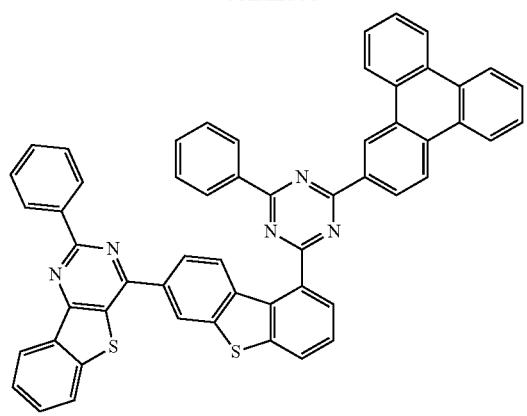
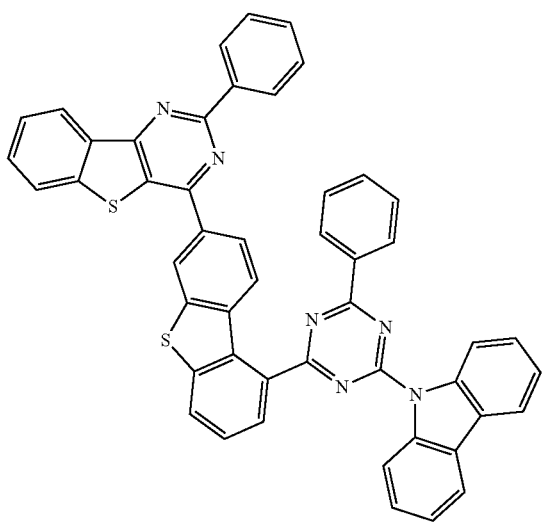
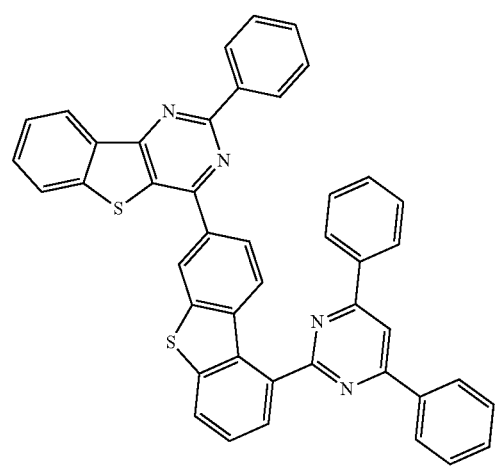
188
-continued
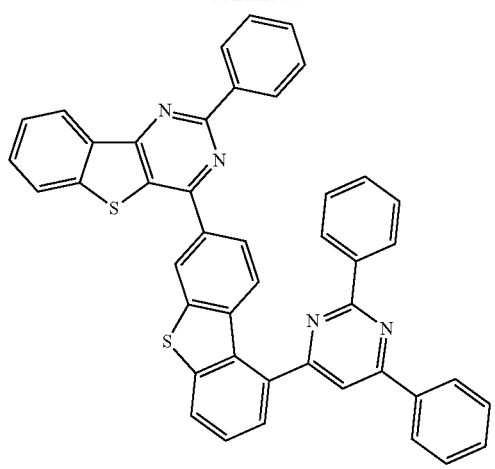
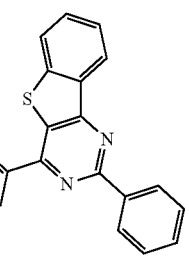

189
-continued
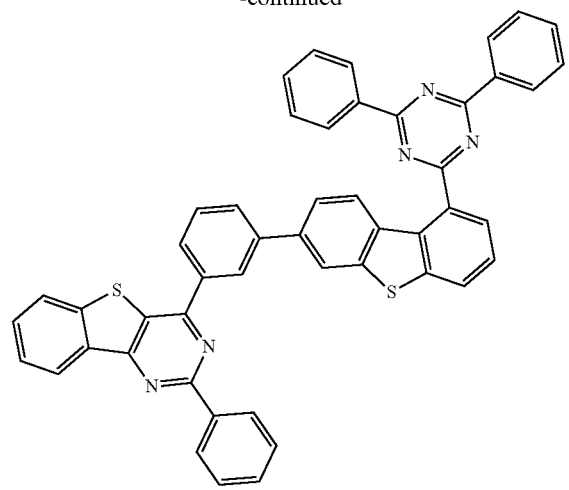
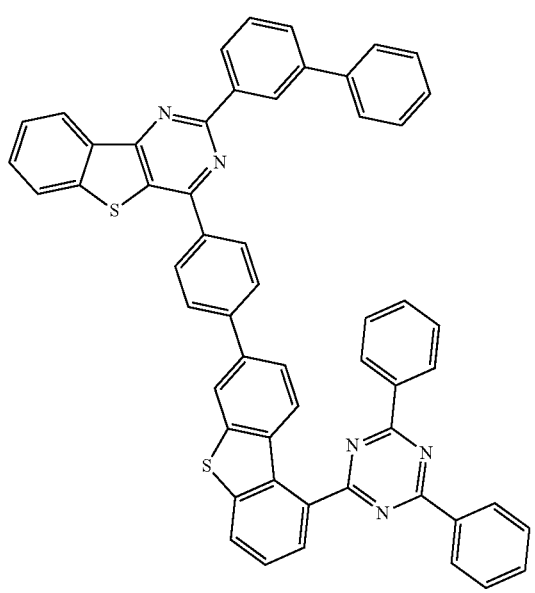
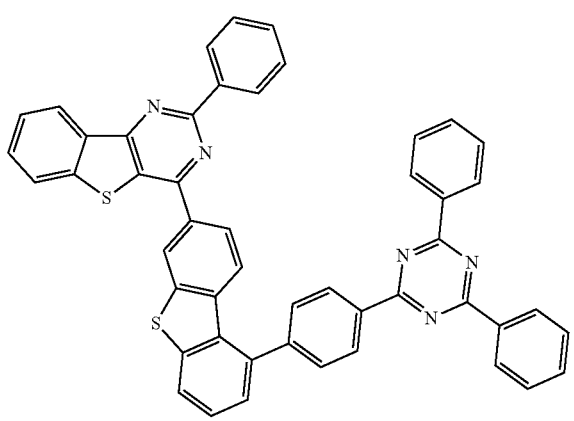
190
-continued
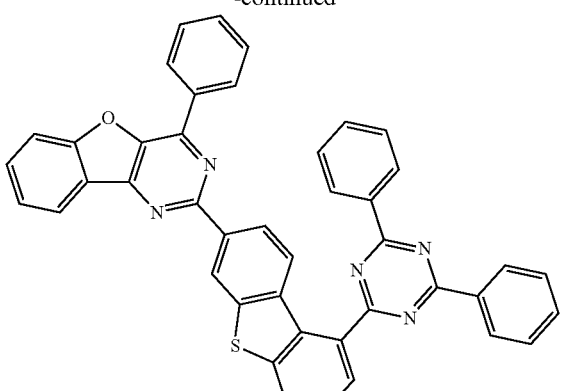
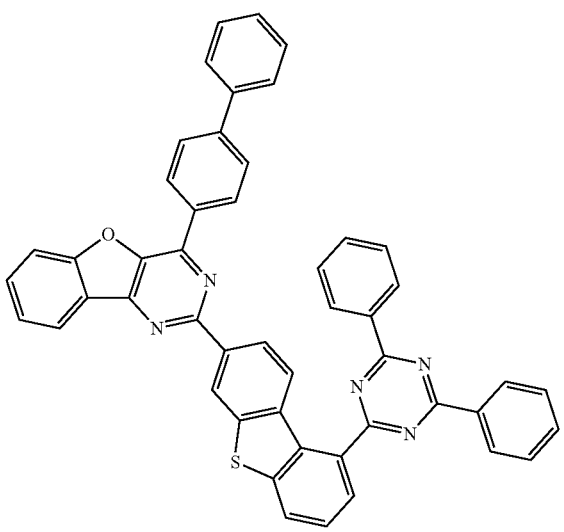
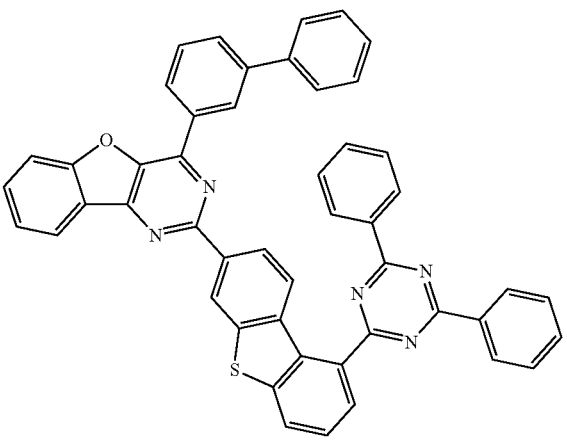

191
-continued
192
-continued
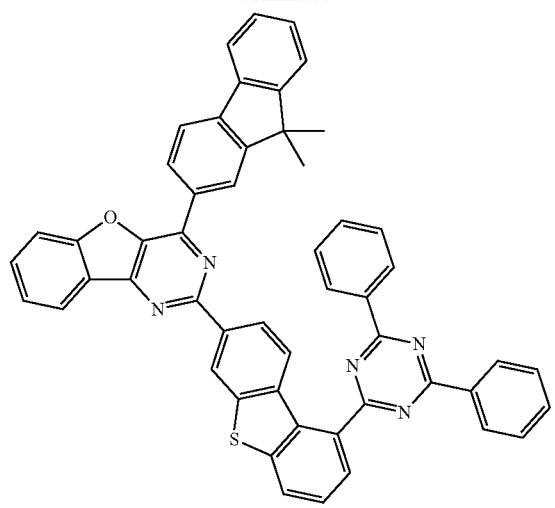
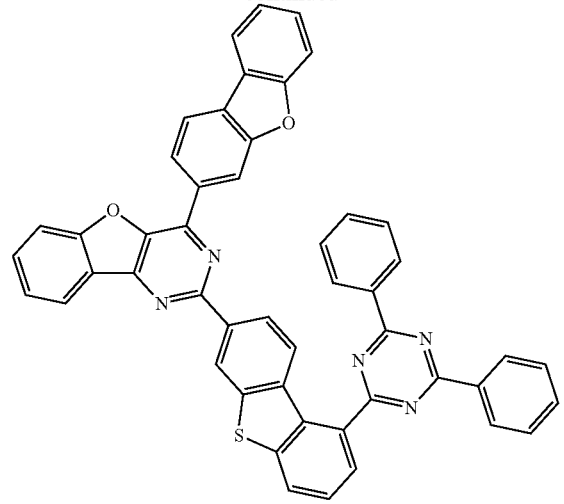
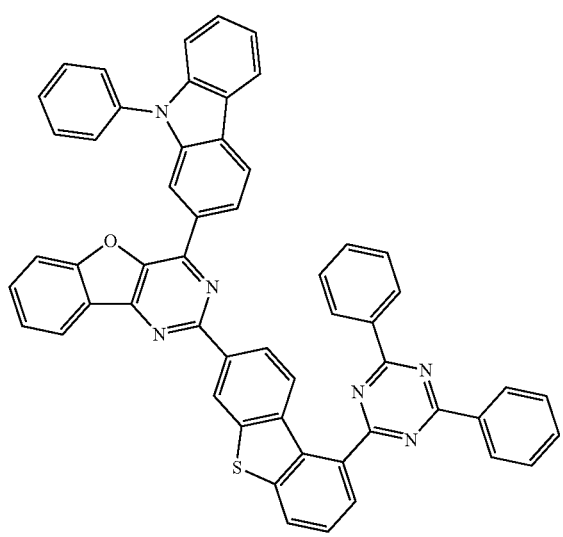
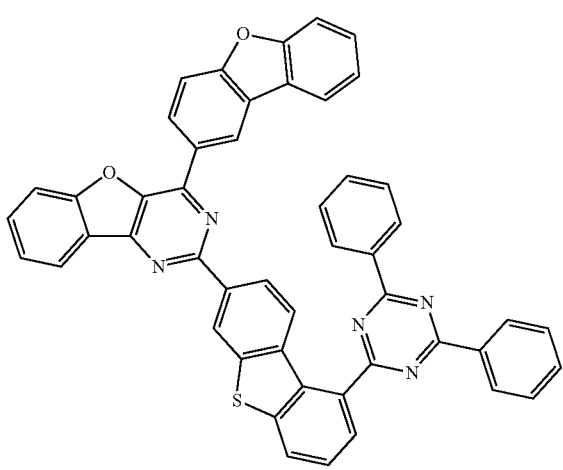
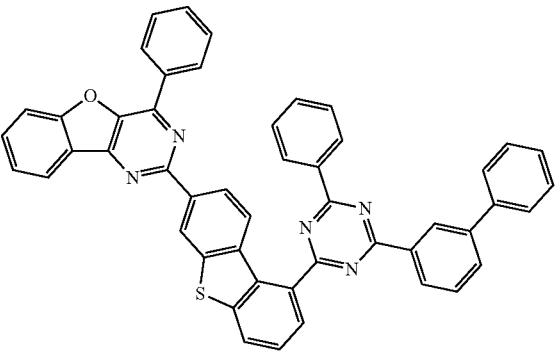

193
-continued
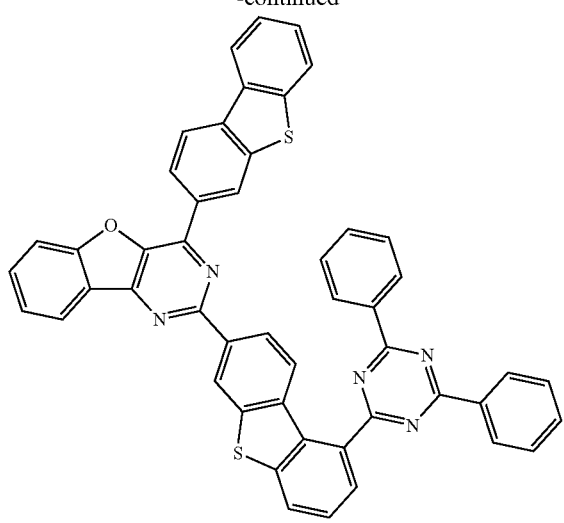
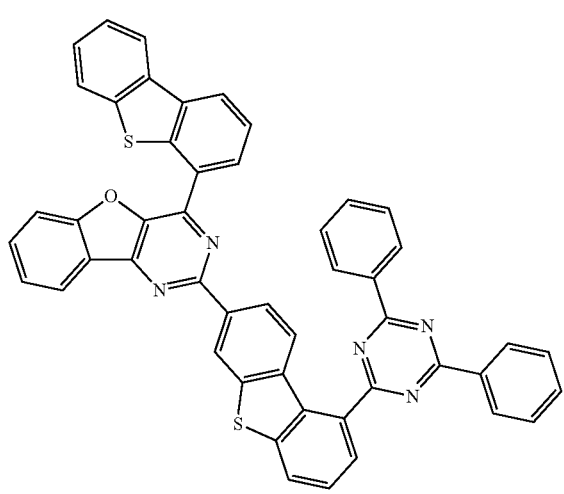
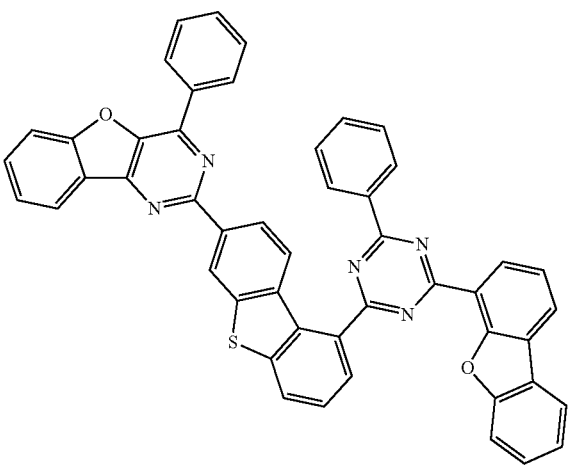
194
-continued
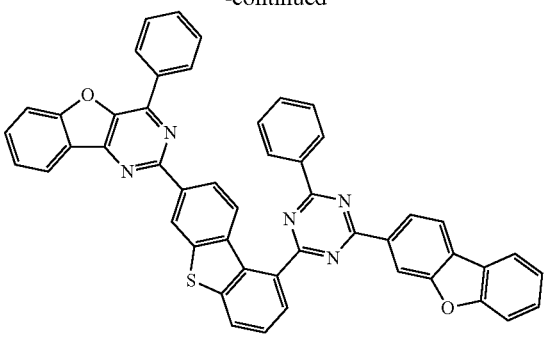
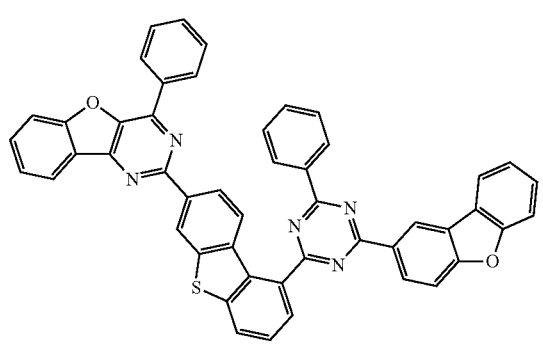
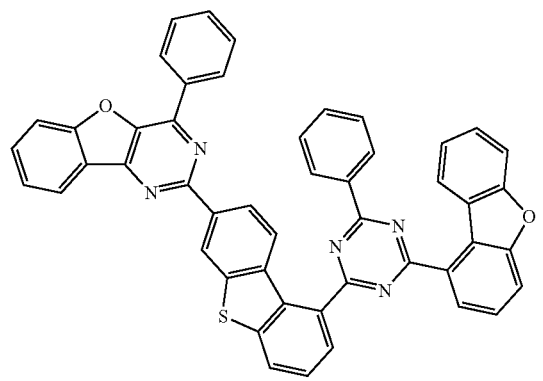
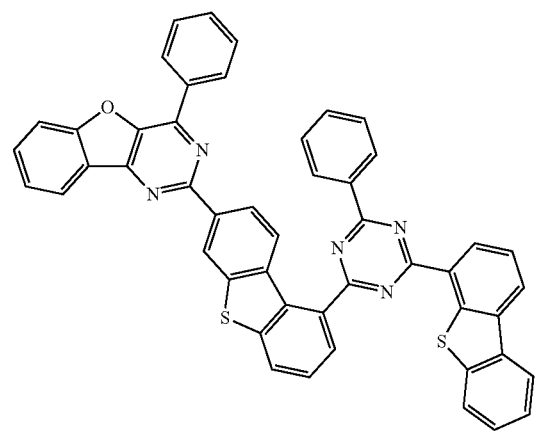

195
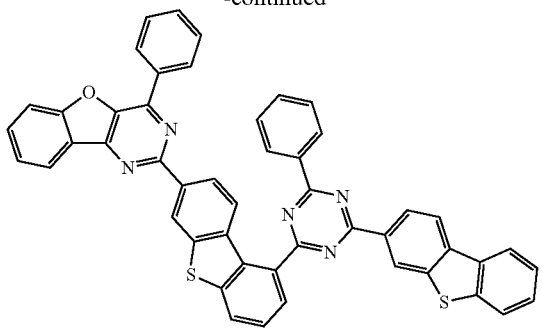
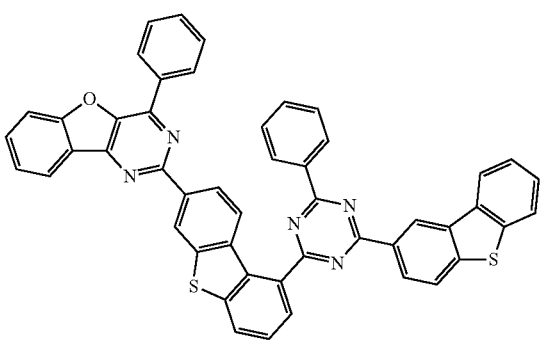
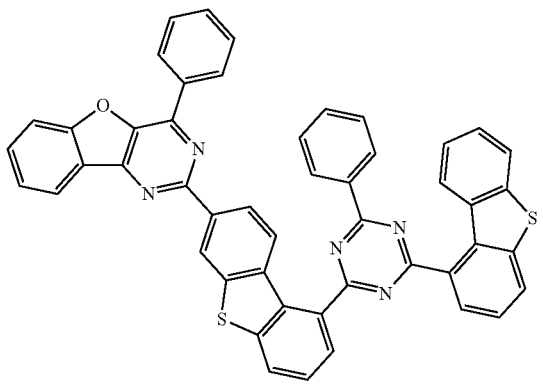
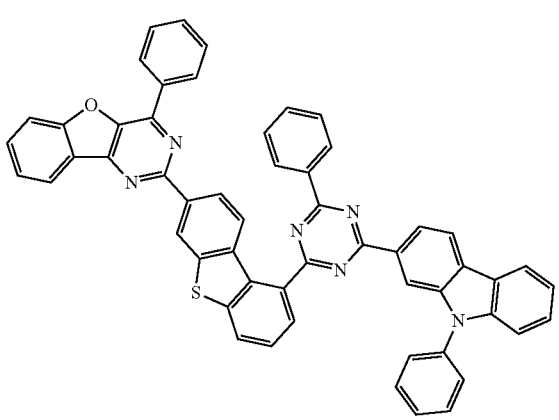
196
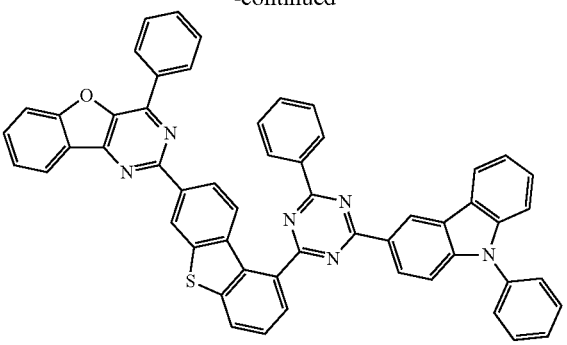
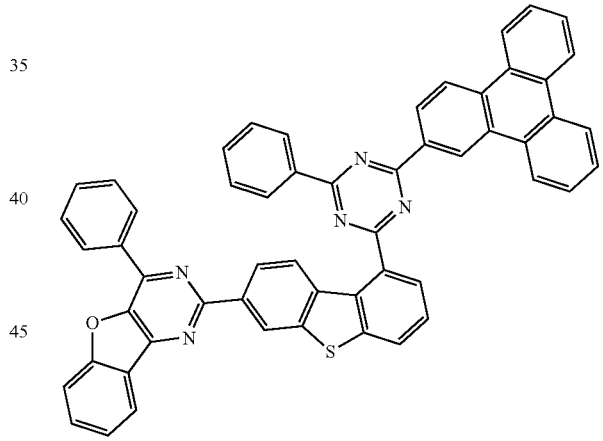
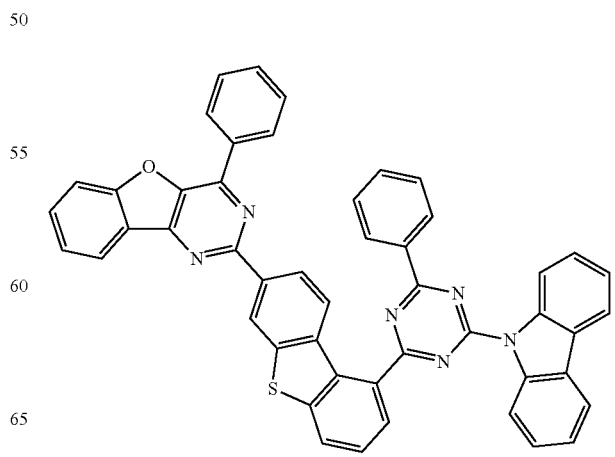

197
-continued
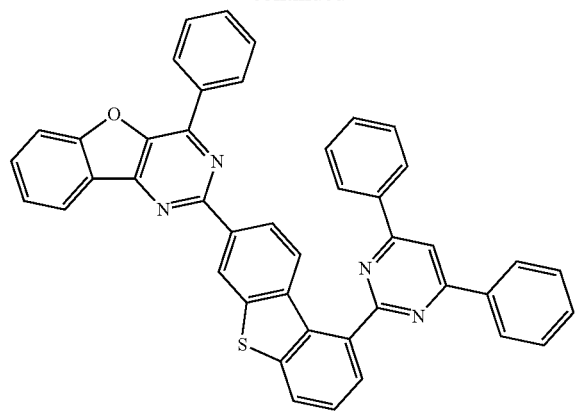
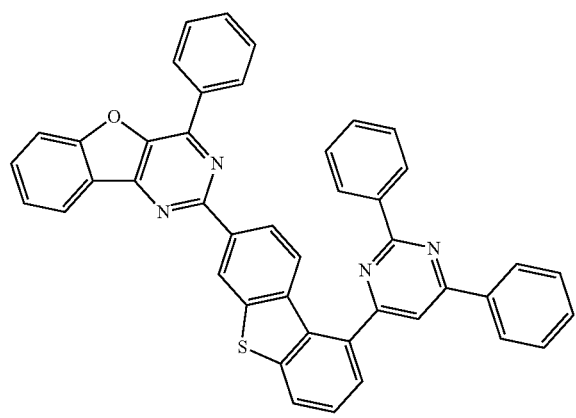
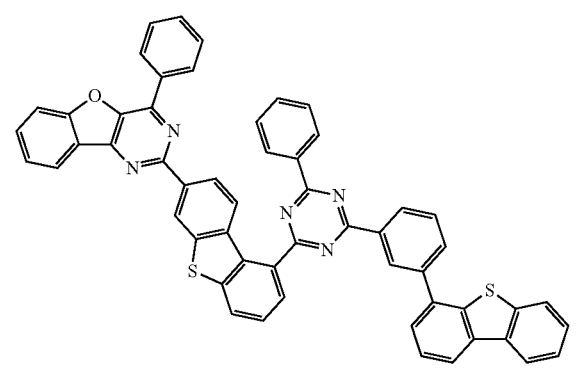
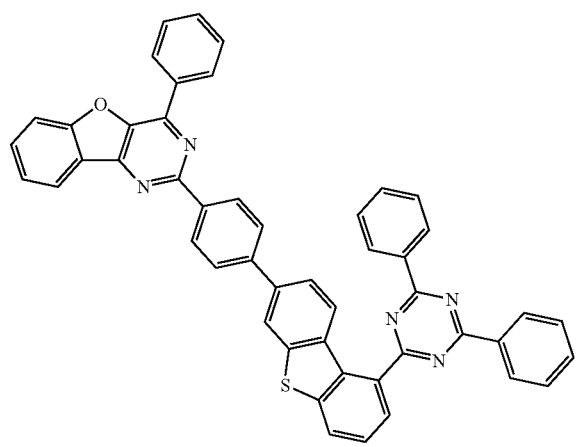
198
-continued
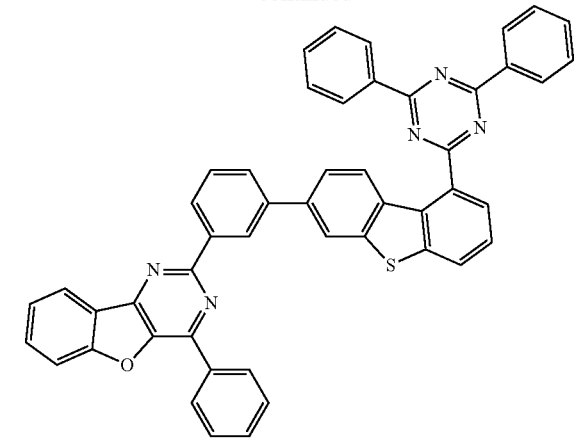
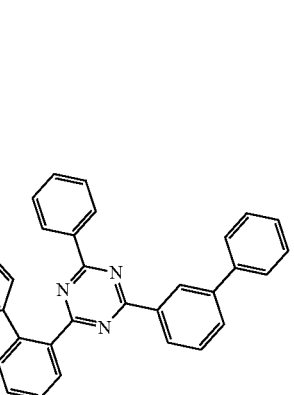
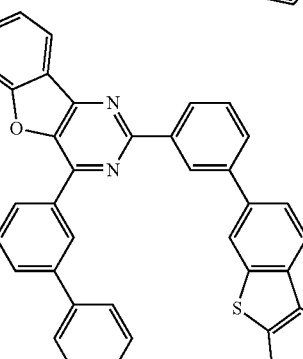
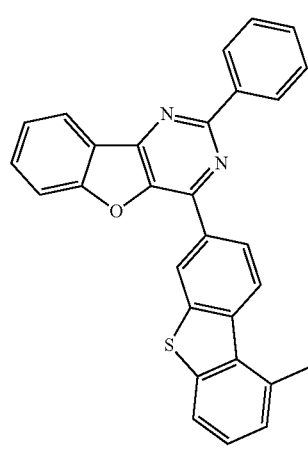

199
-continued
200
-continued
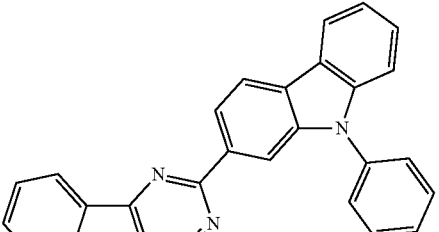
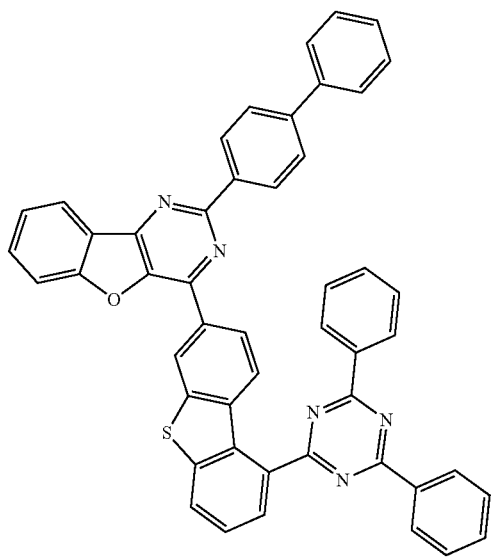
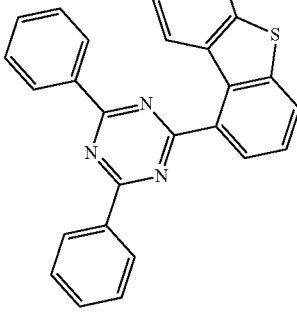

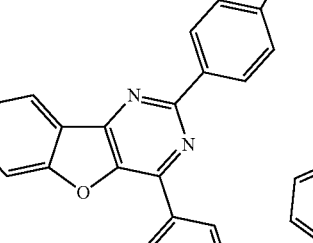
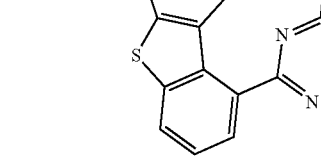

201
-continued
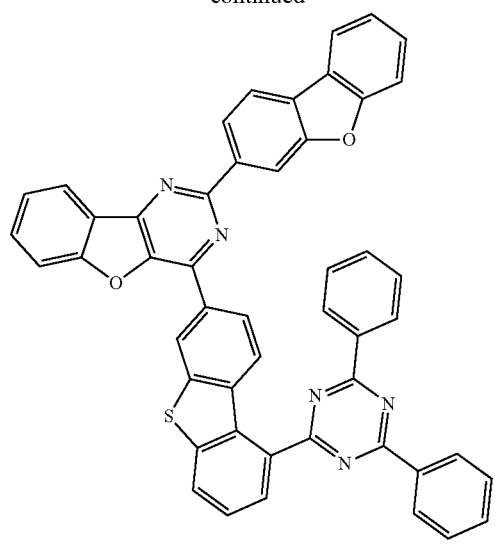
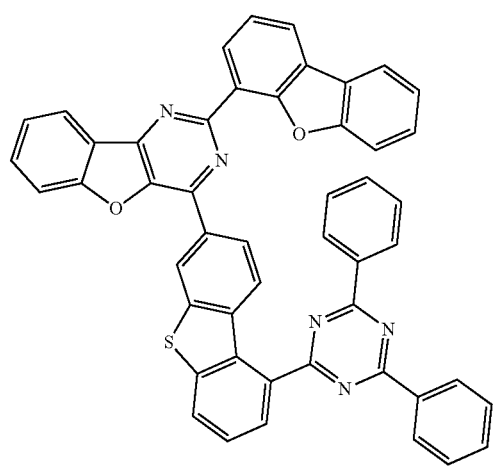
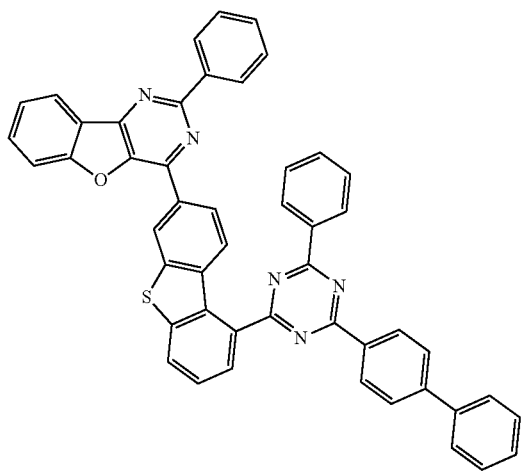
202
-continued
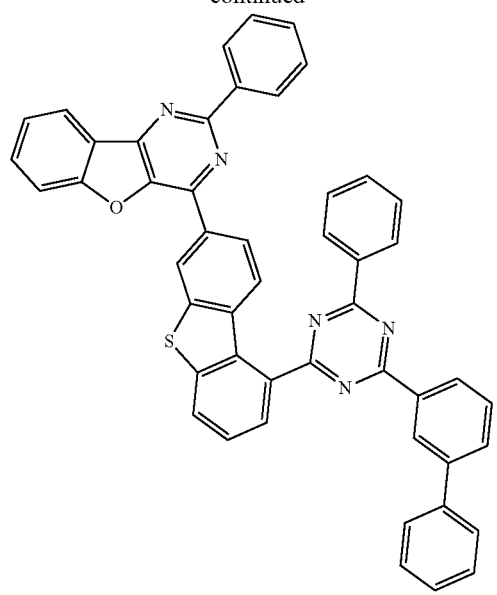
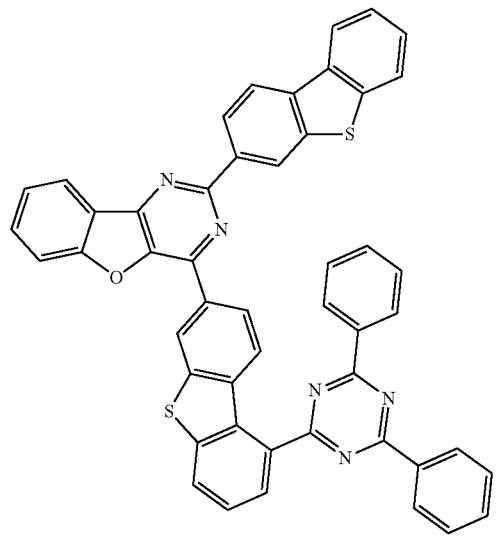
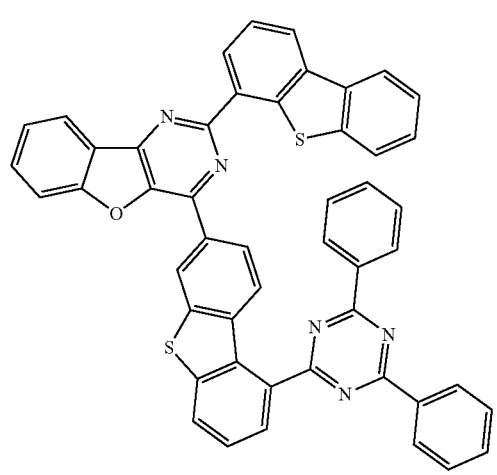

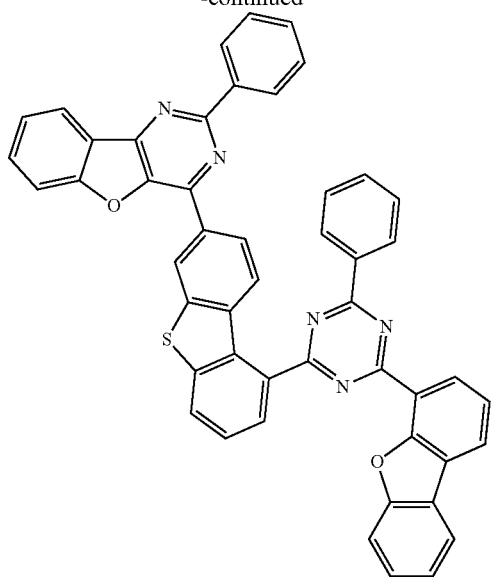
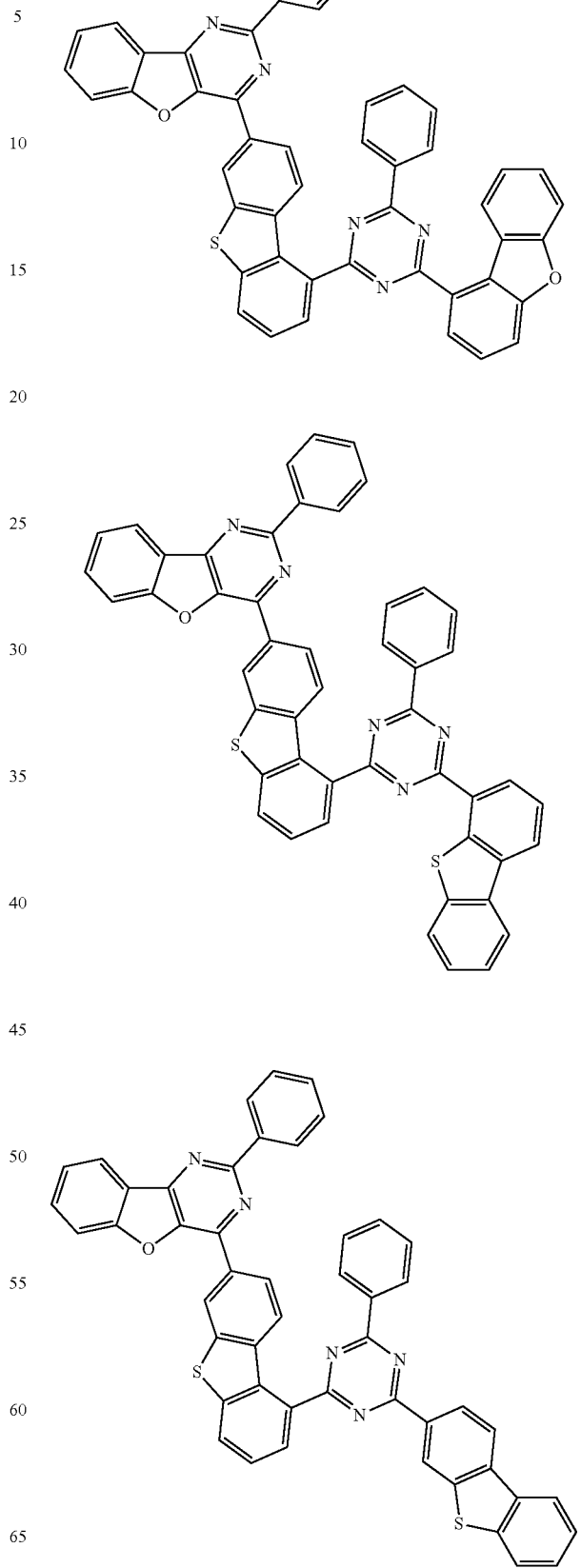

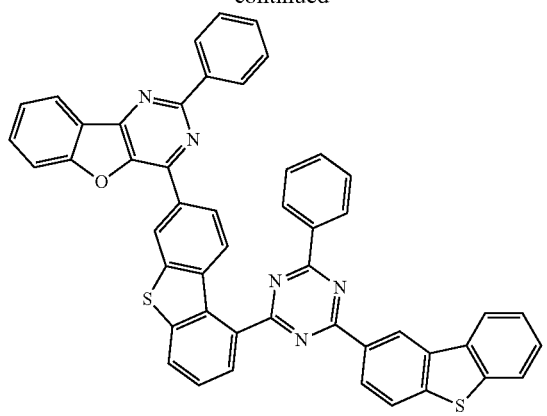
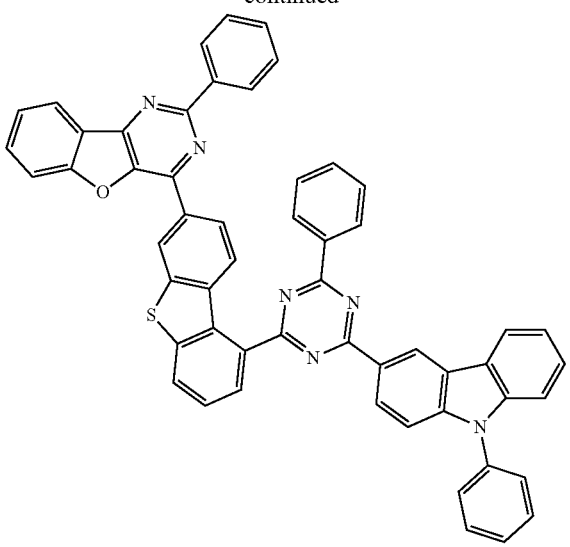
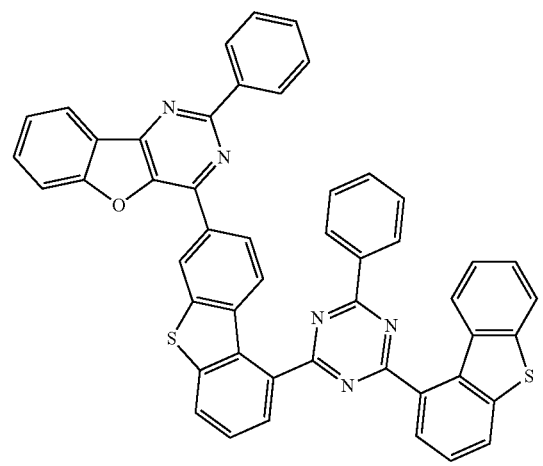
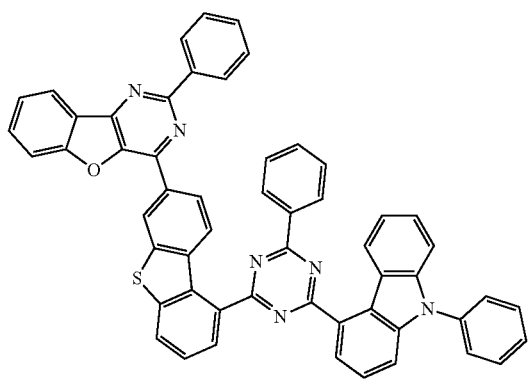
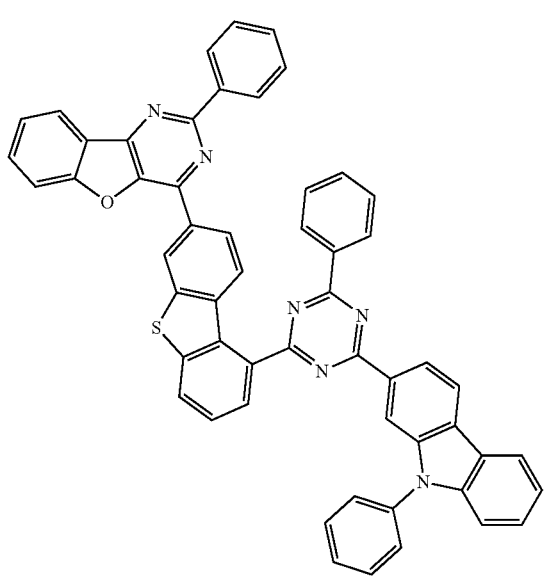
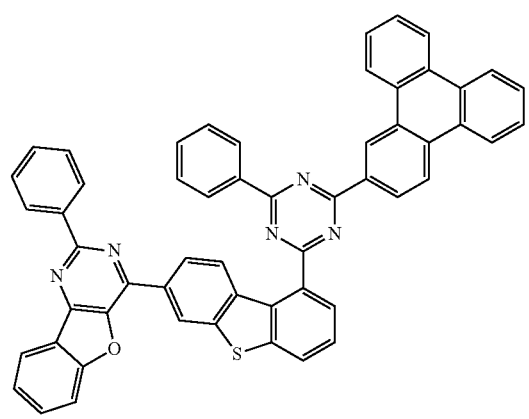

207
-continued
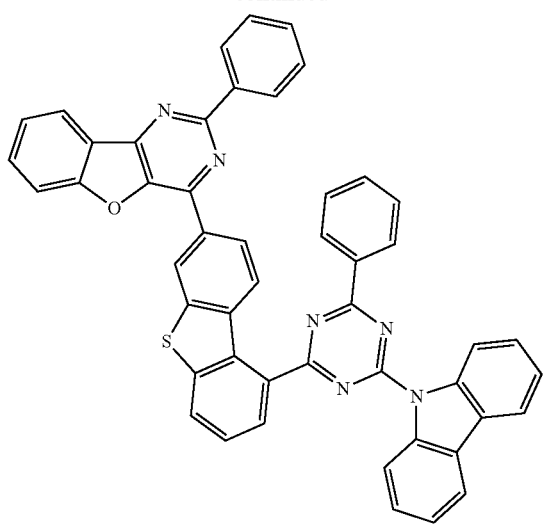
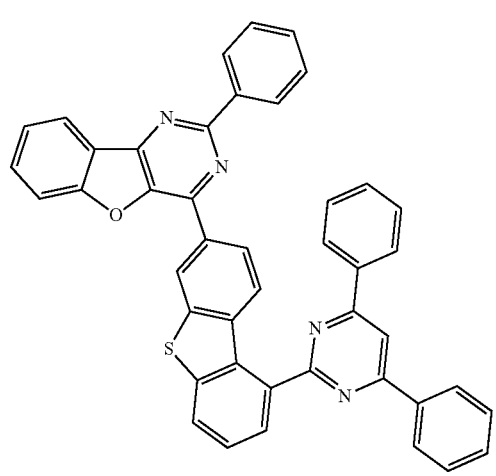
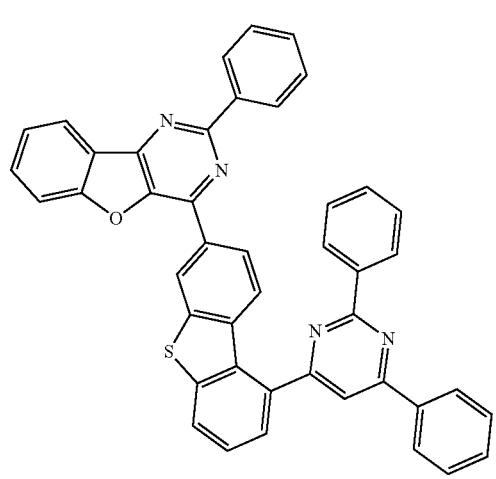
208
-continued
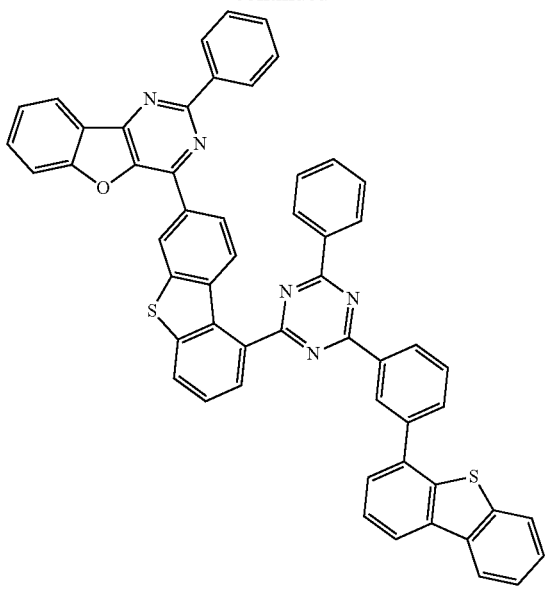
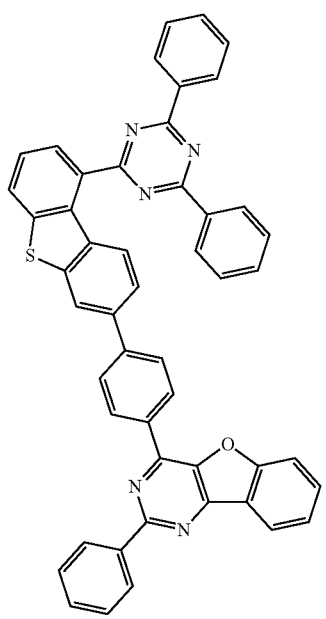
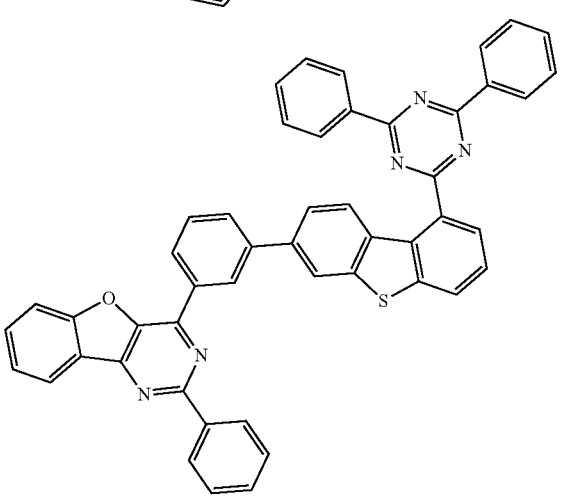

209
-continued
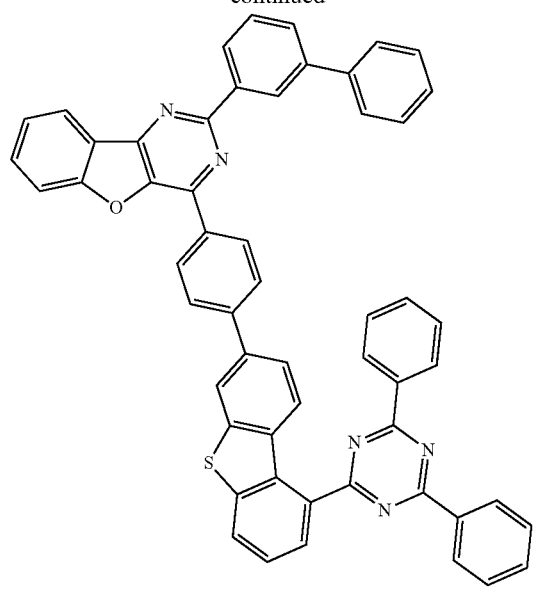
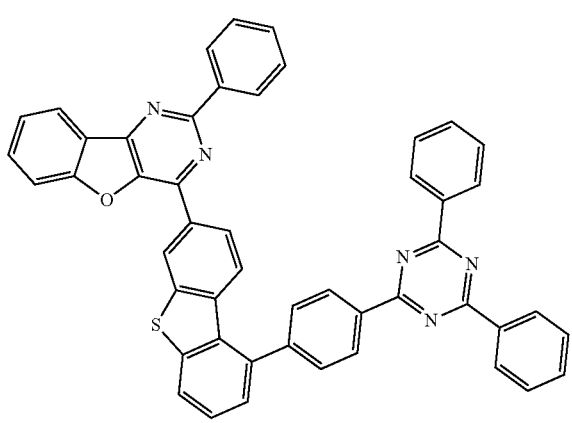
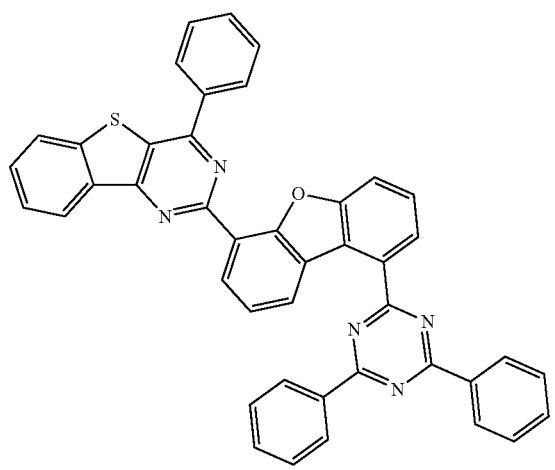
210
-continued
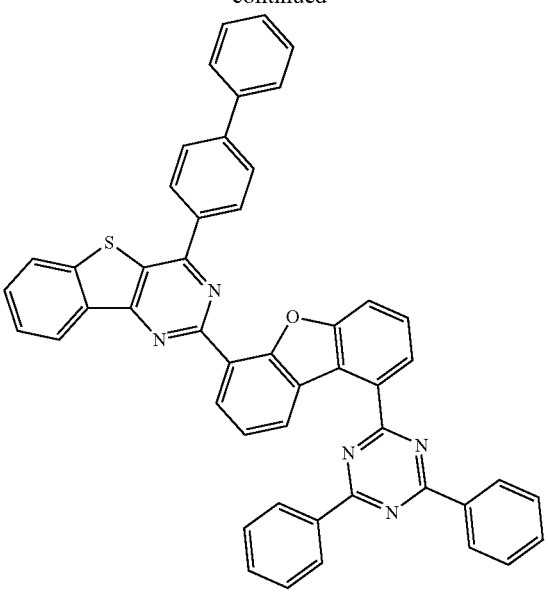
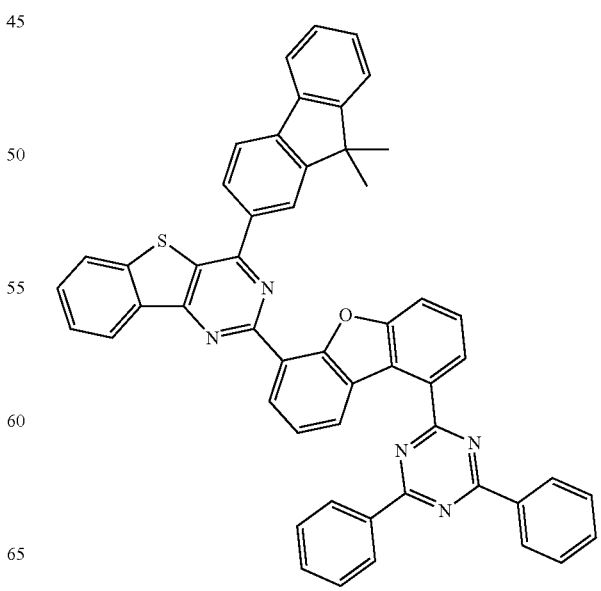

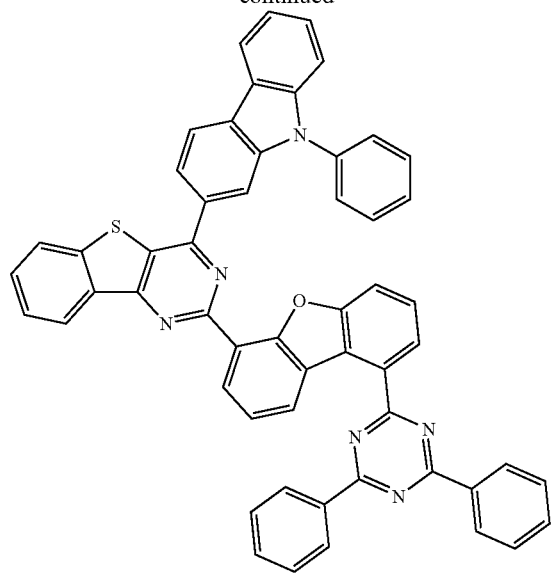
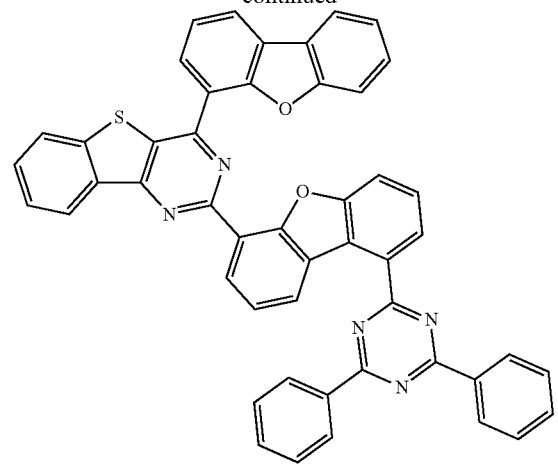
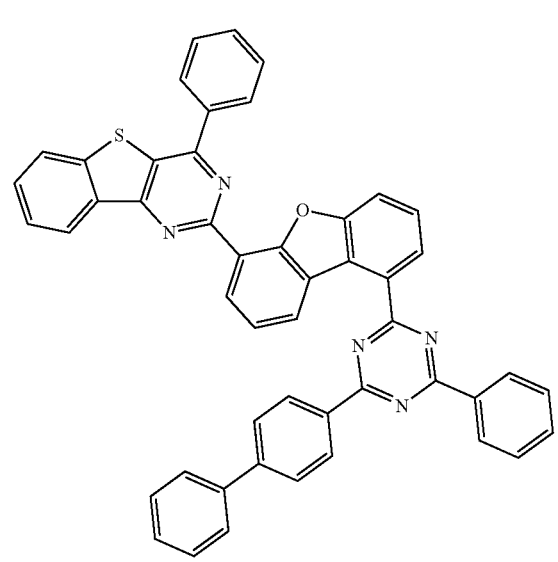

213
-continued
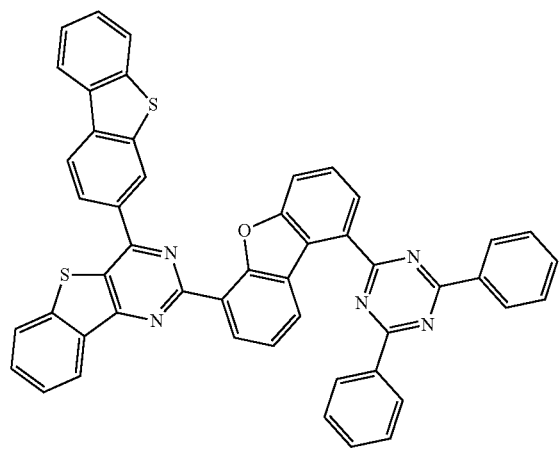
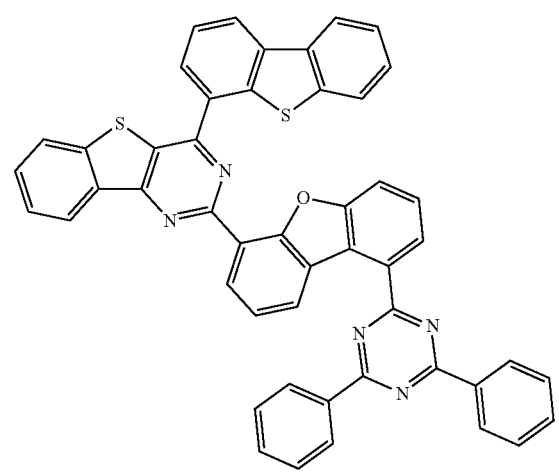
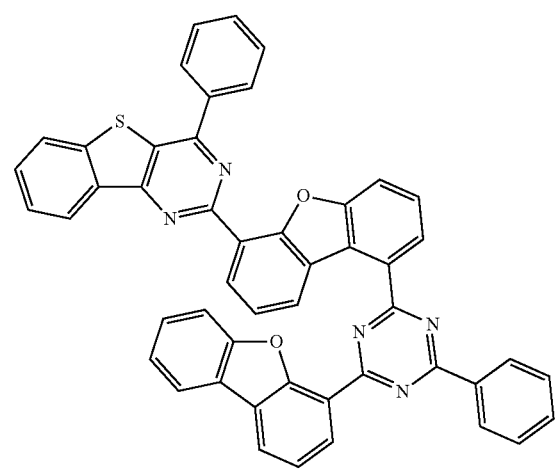
214
-continued
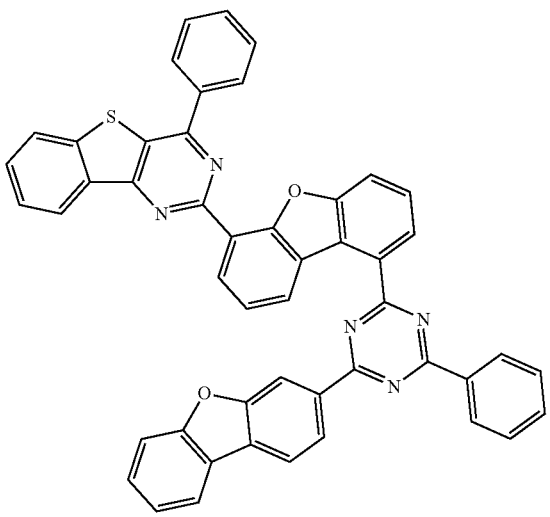
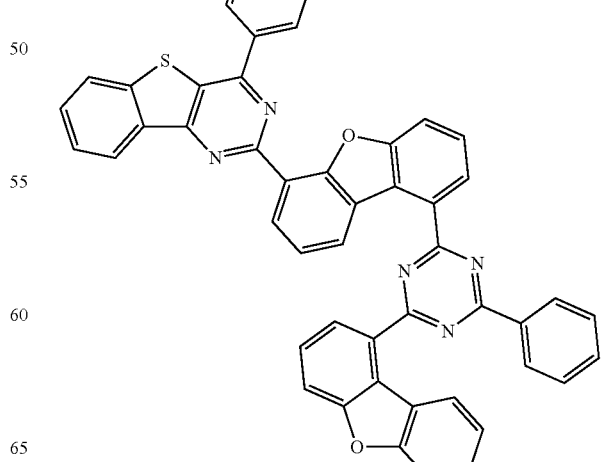

215
-continued
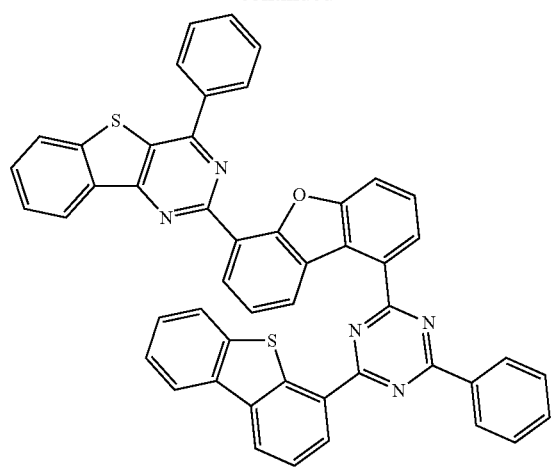
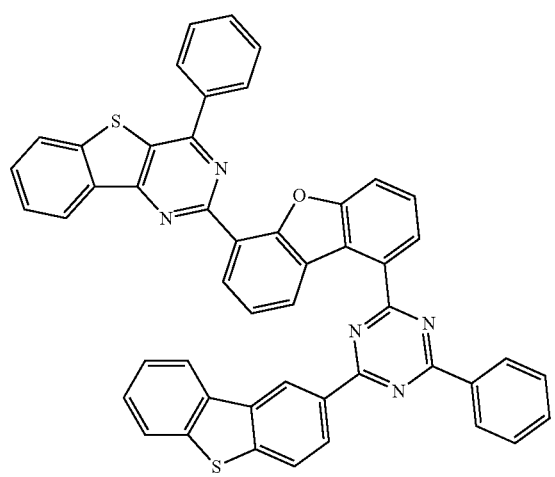
216
-continued
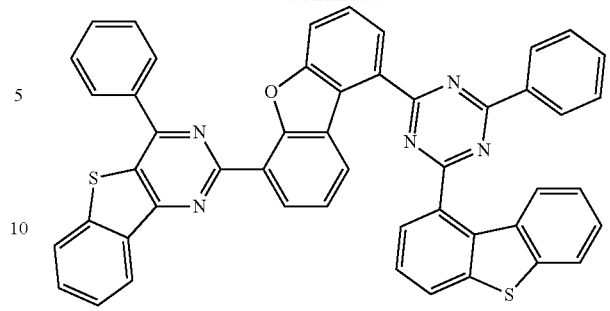
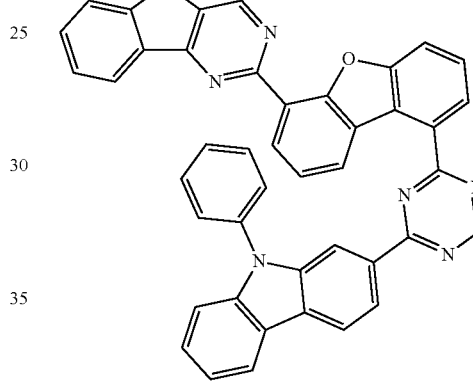
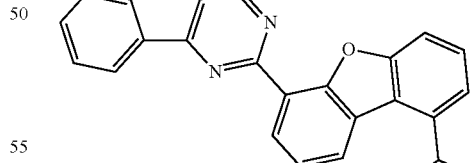

217
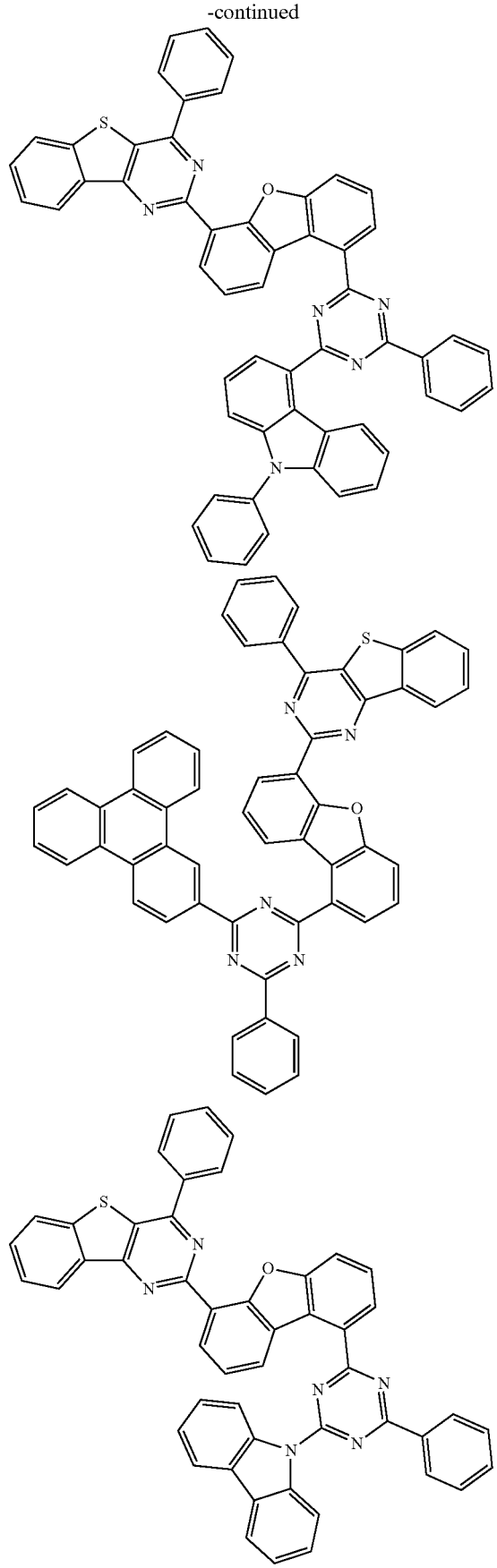
218
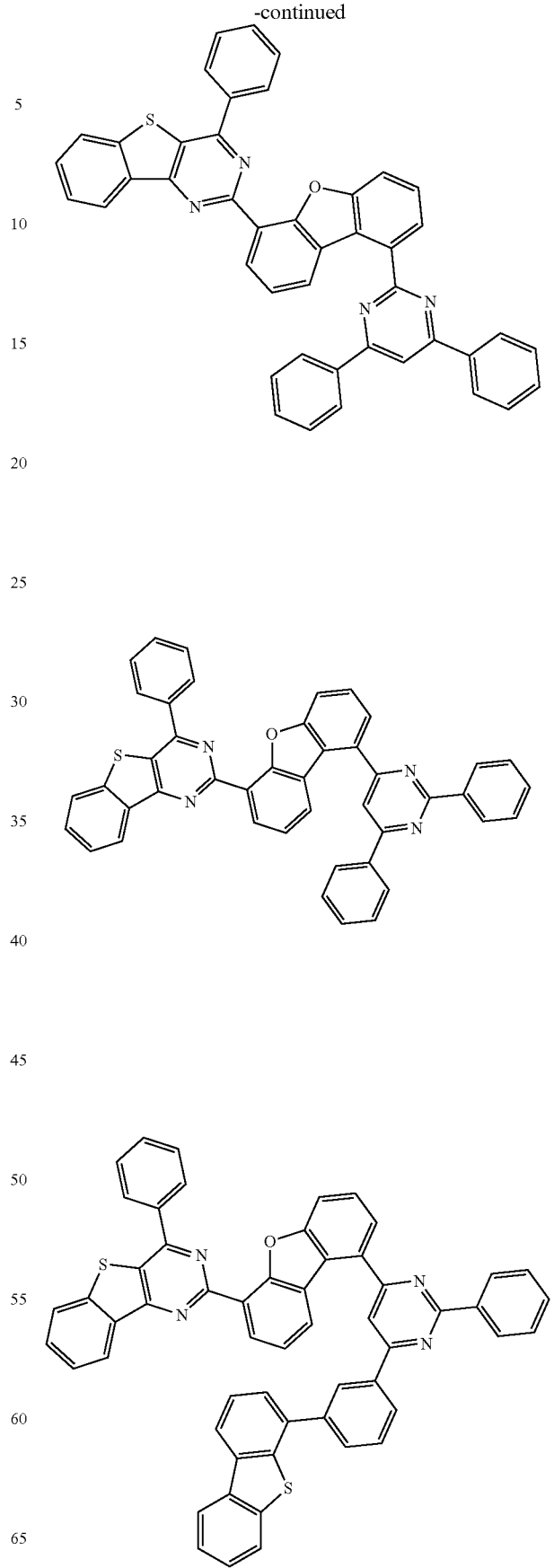

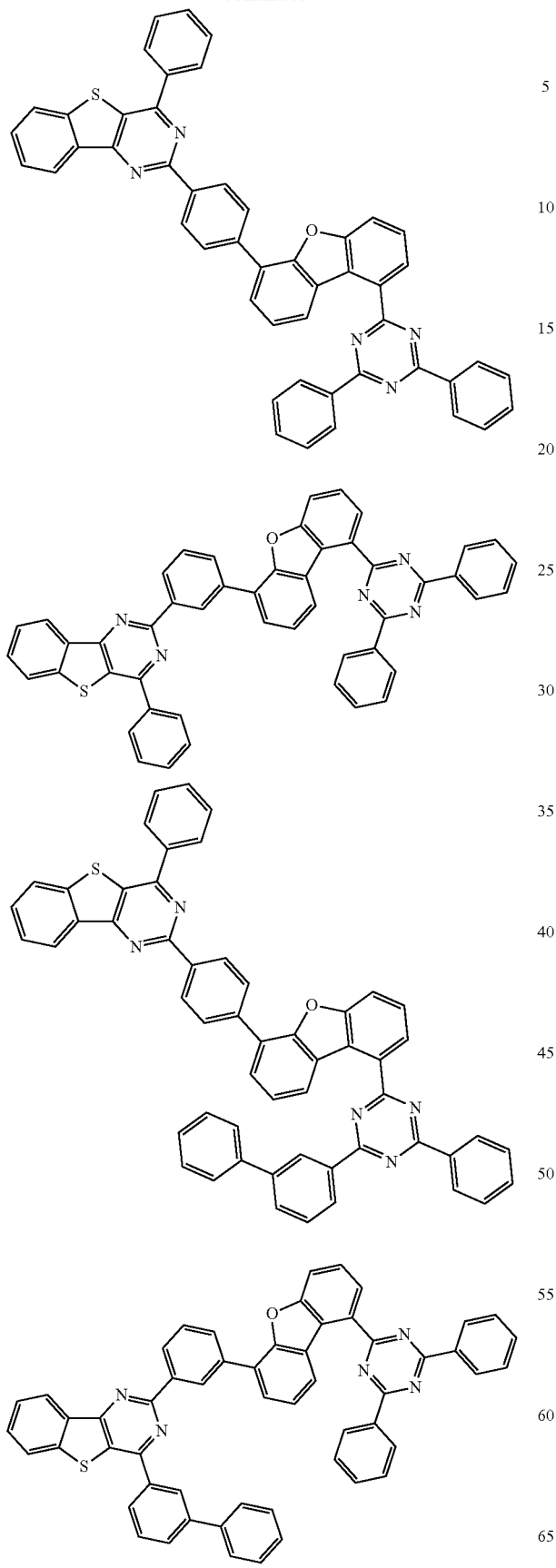
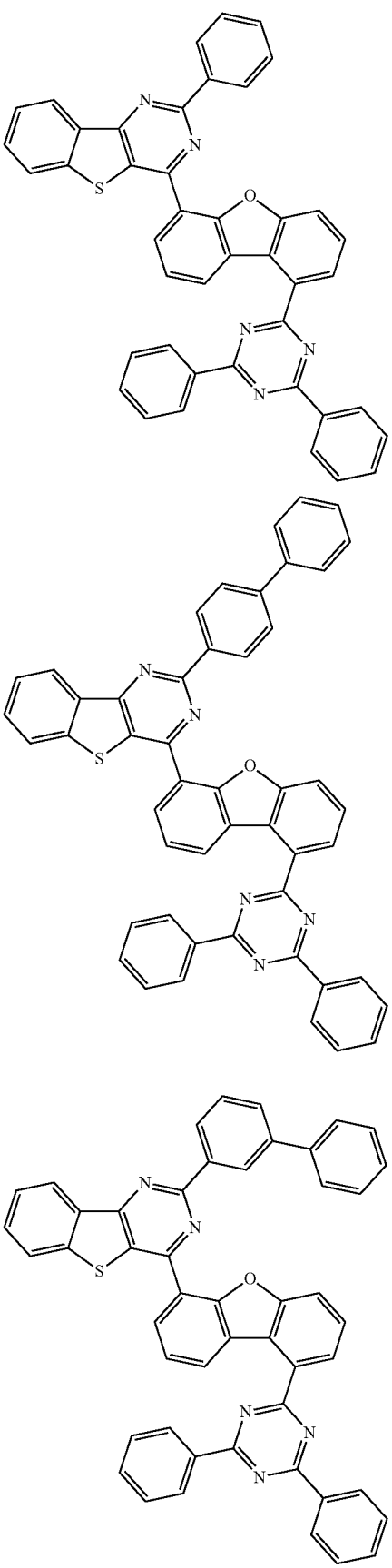

221
-continued
222
-continued
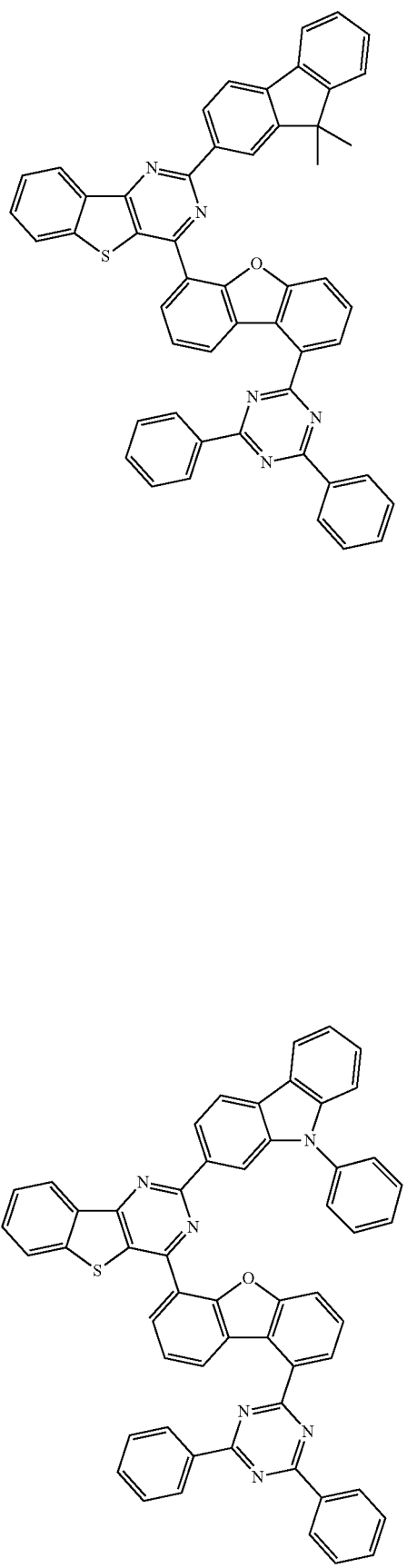
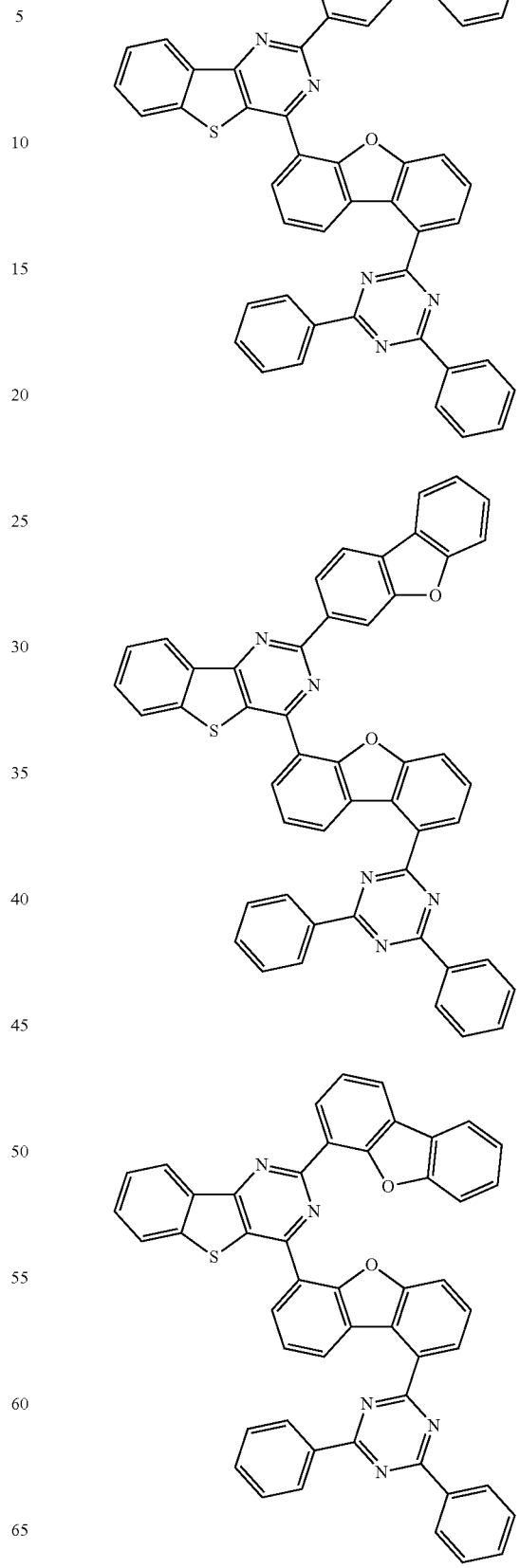

223
-continued
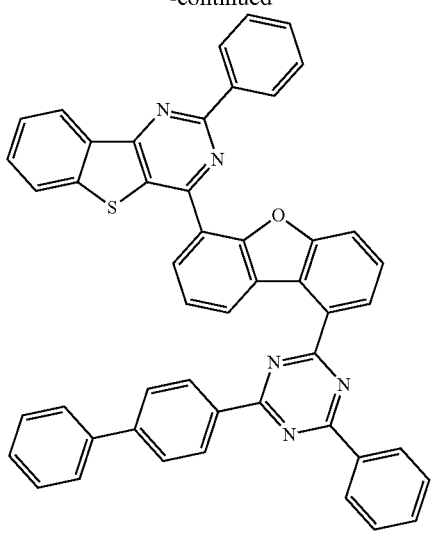
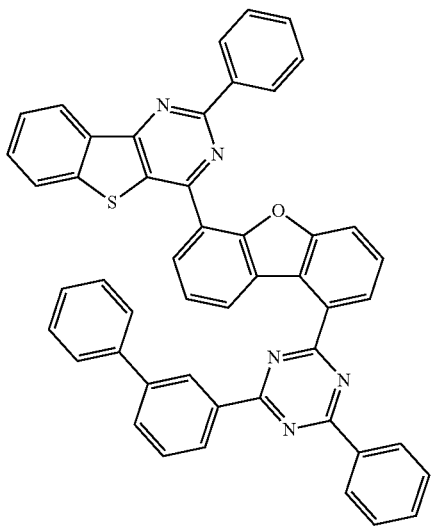
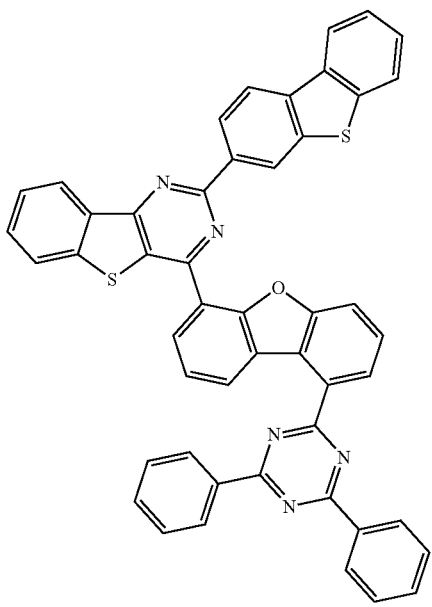
224
-continued
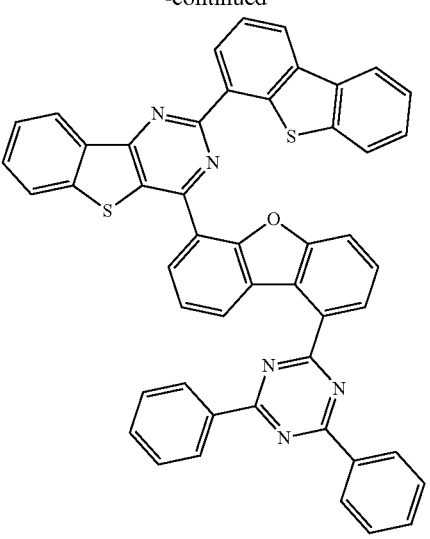
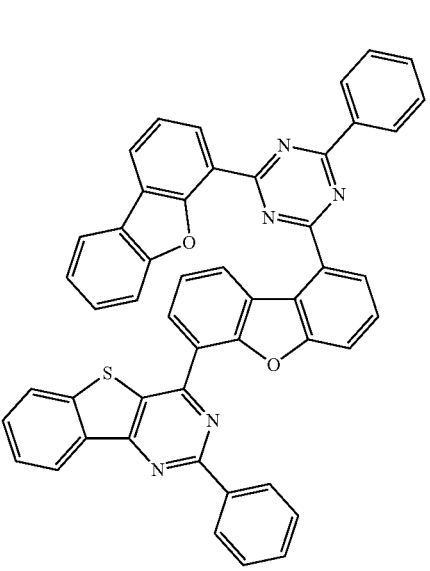
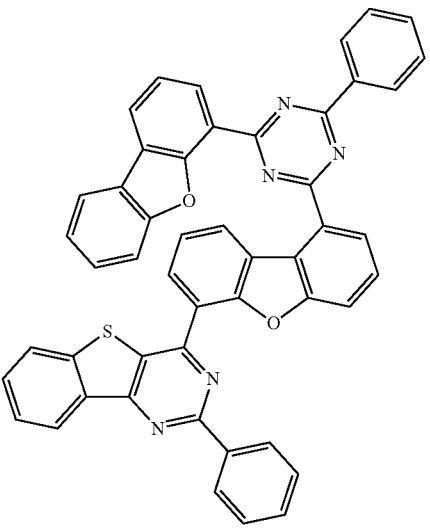

225
-continued
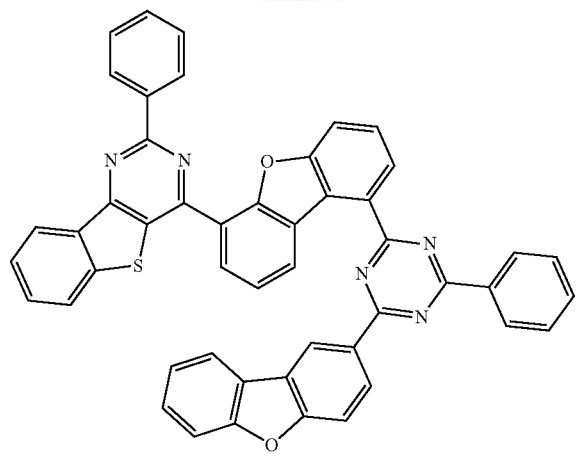
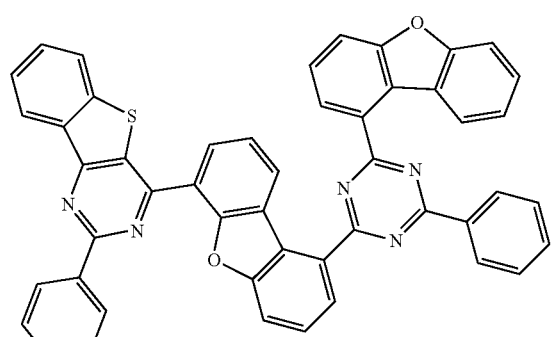
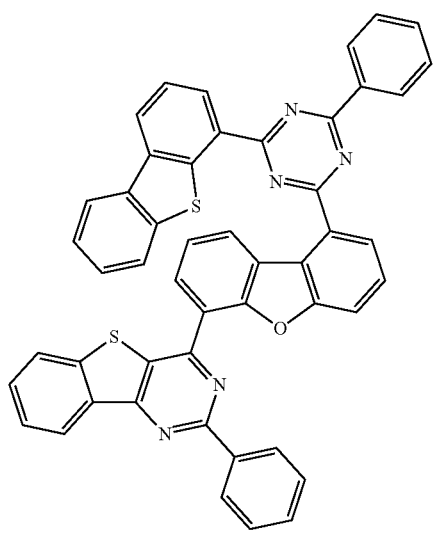
226
-continued
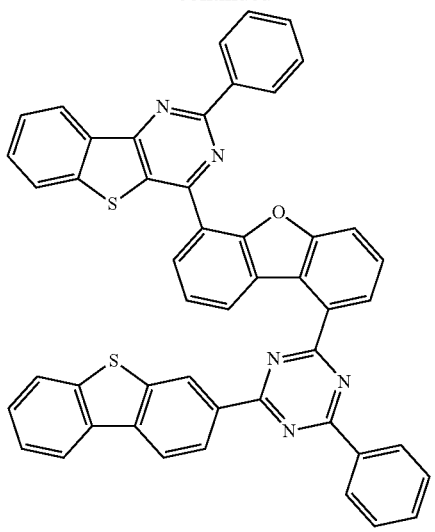
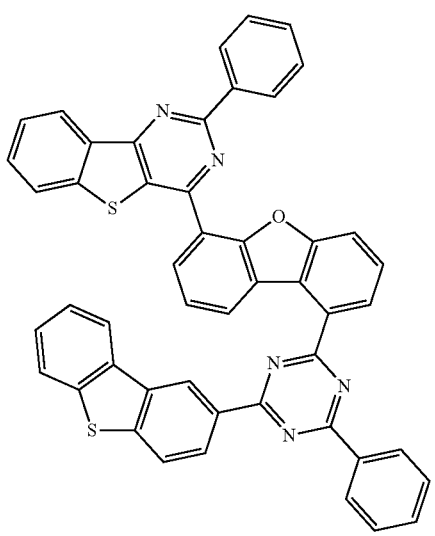
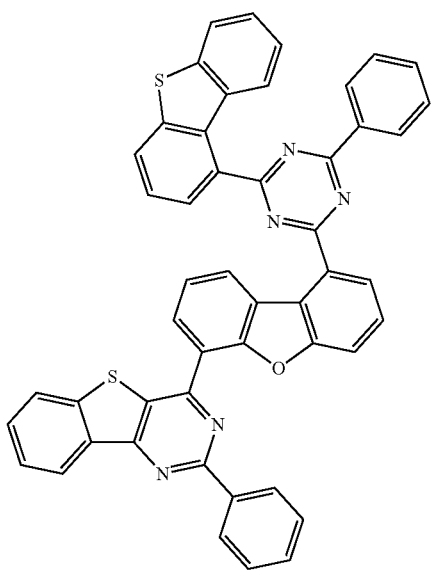

-continued
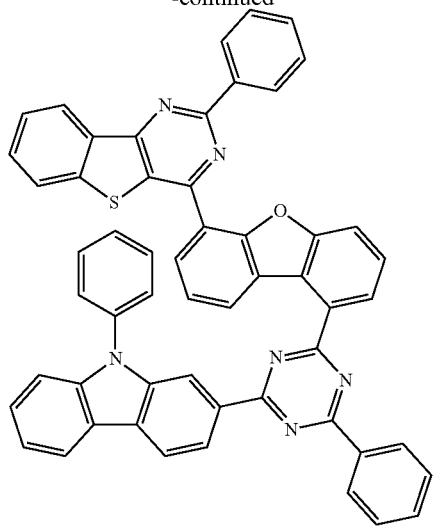
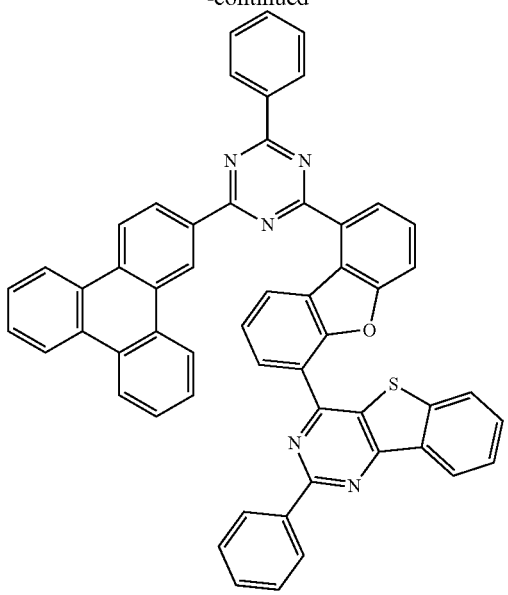
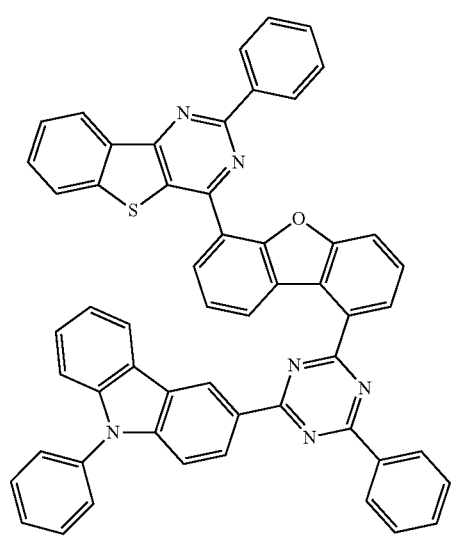
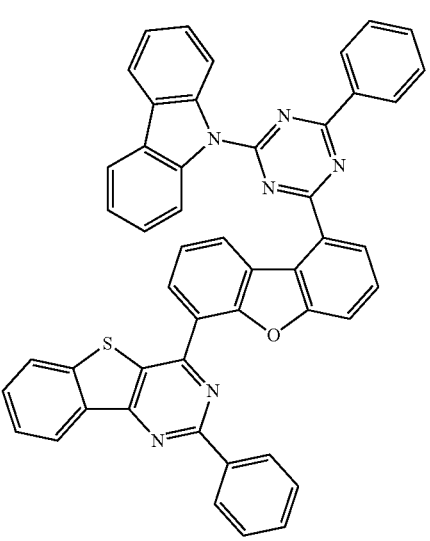
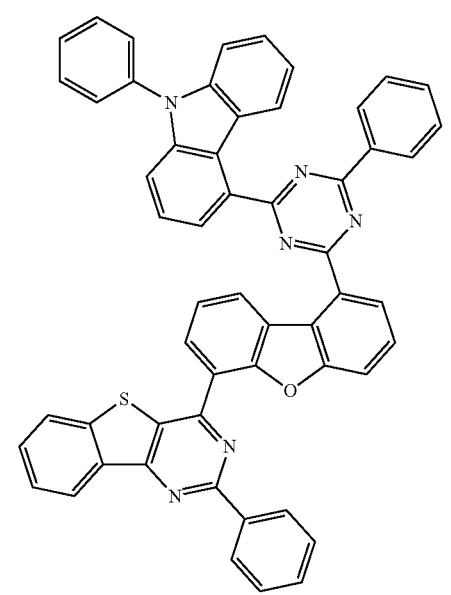
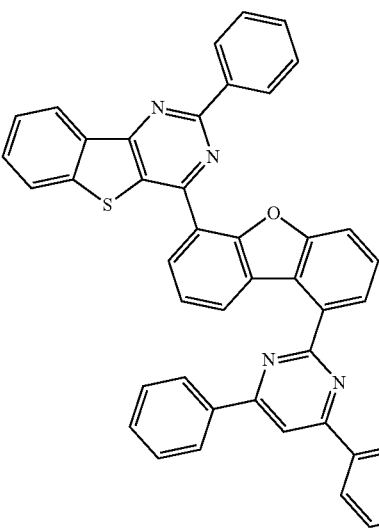

229
-continued
230
-continued
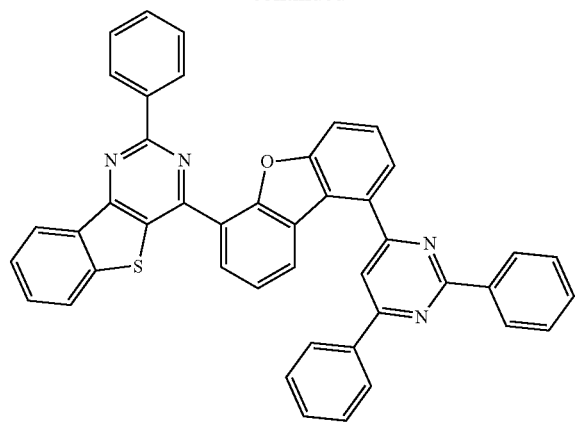
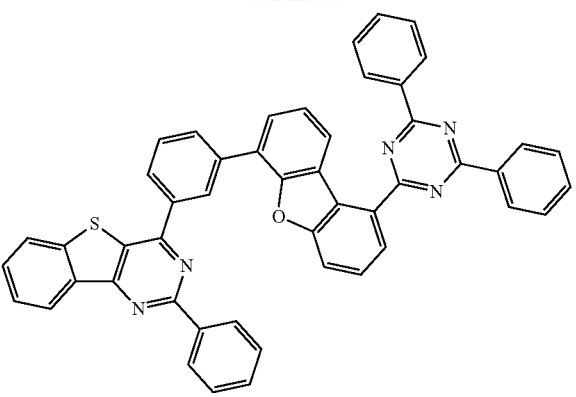
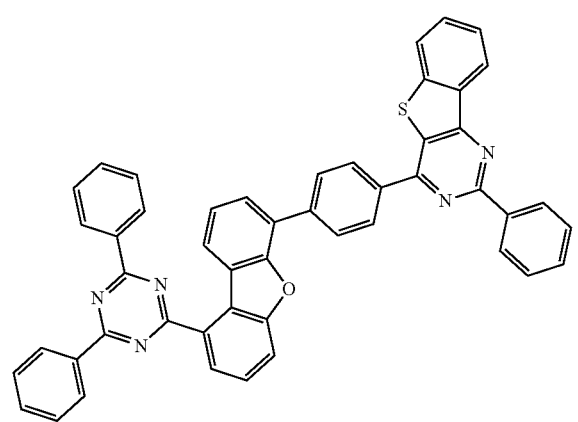
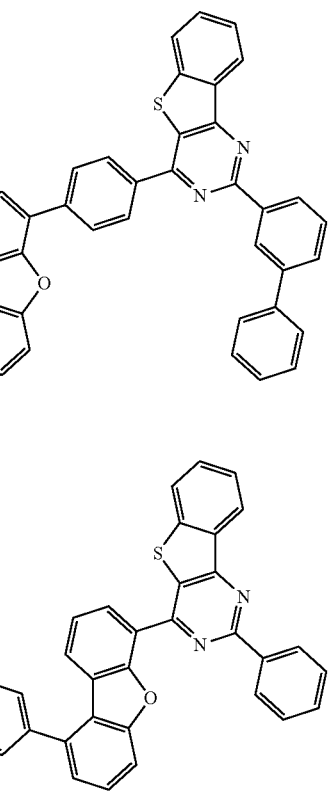

231
-continued
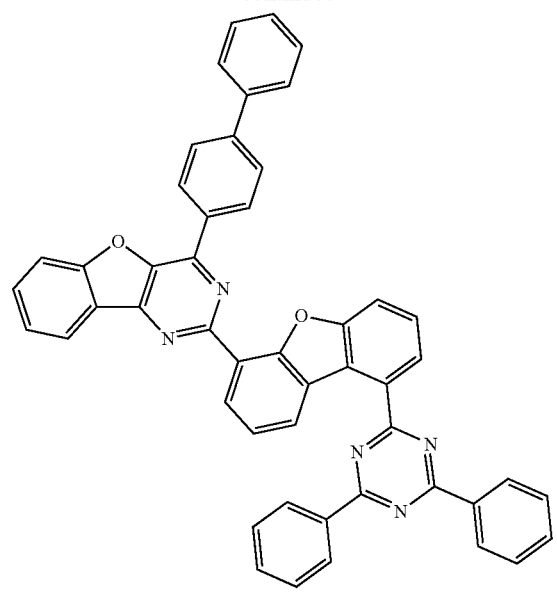
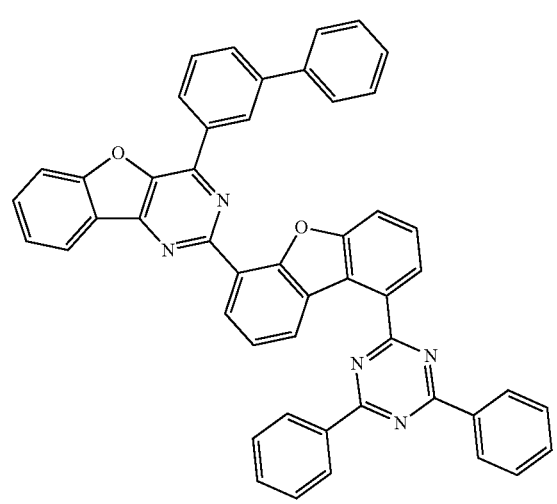
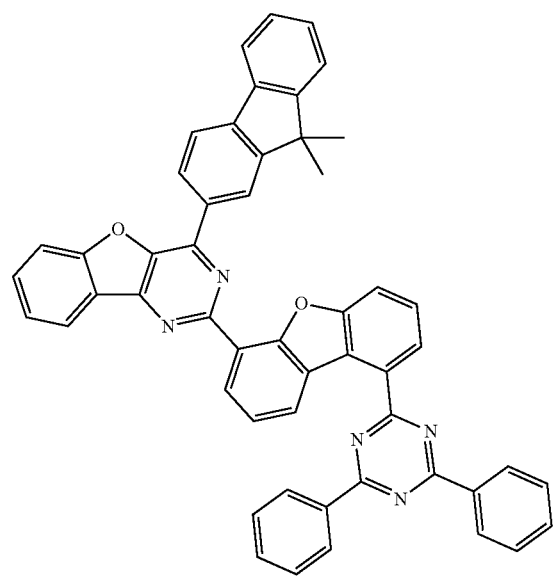
232
-continued
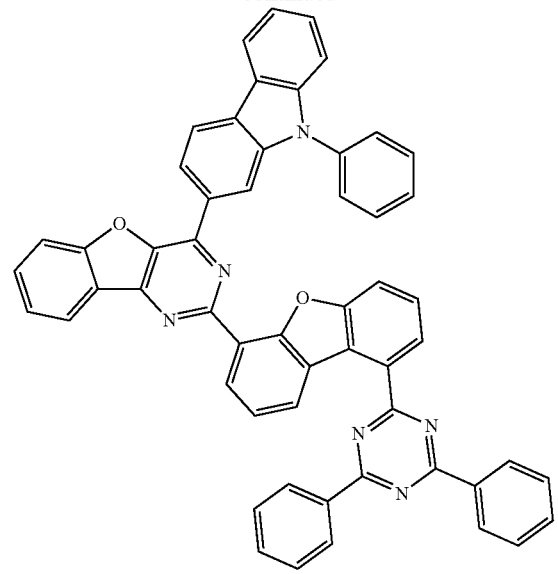
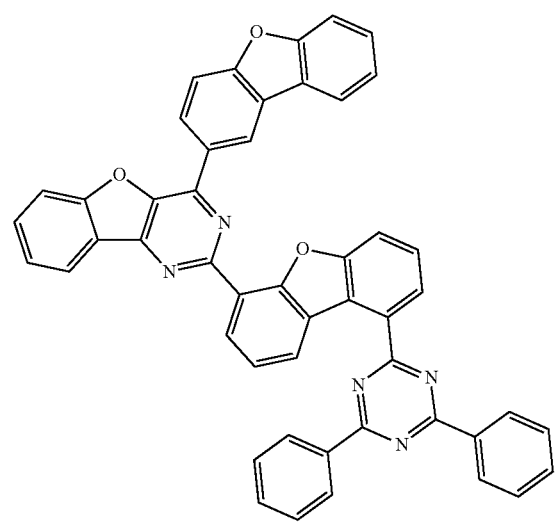
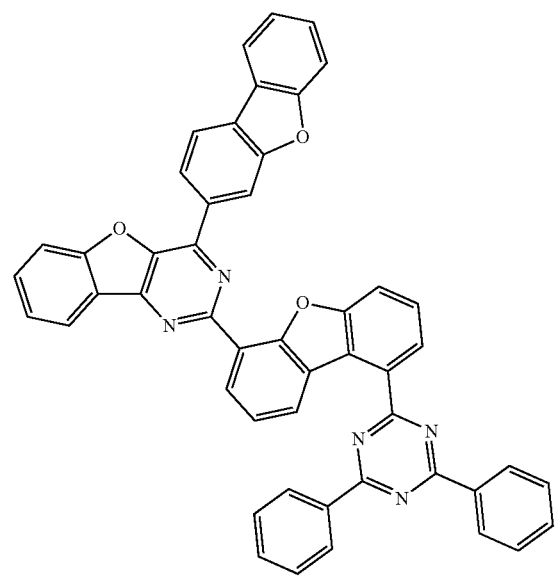

233
-continued
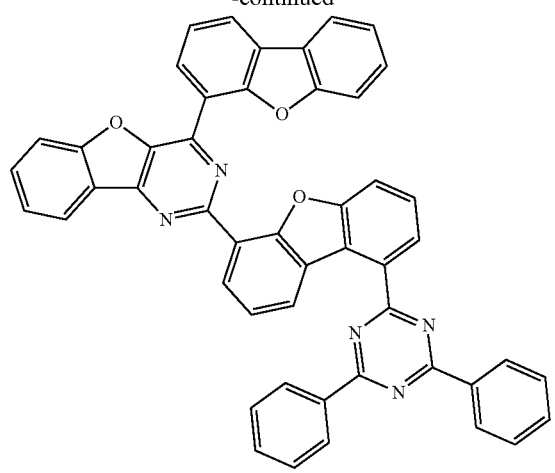
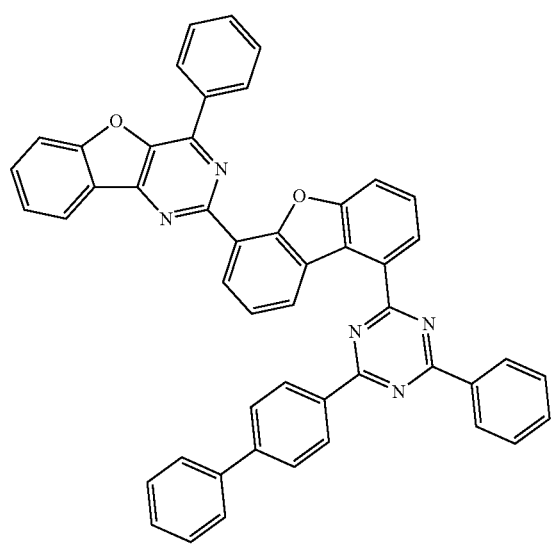
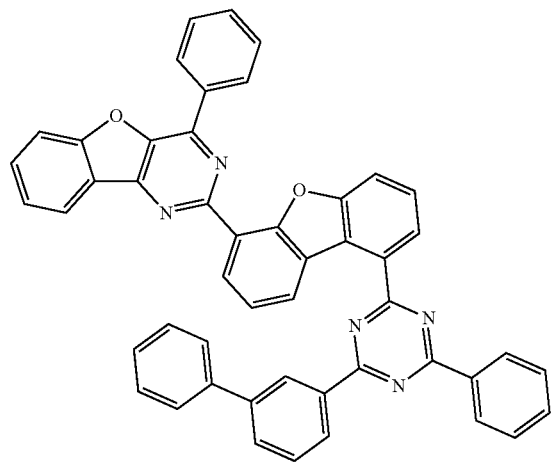
234
-continued
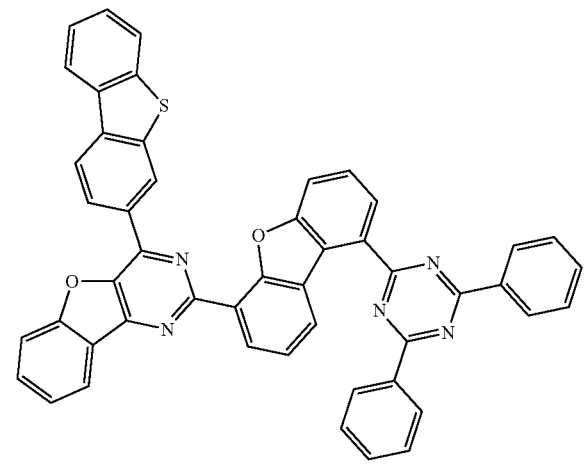
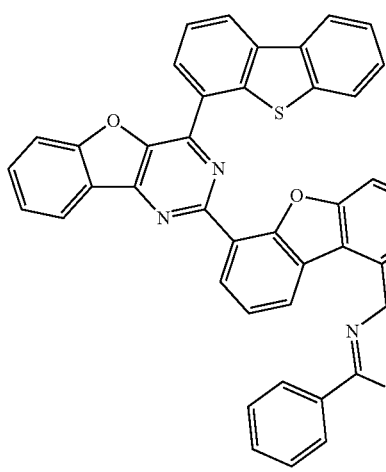
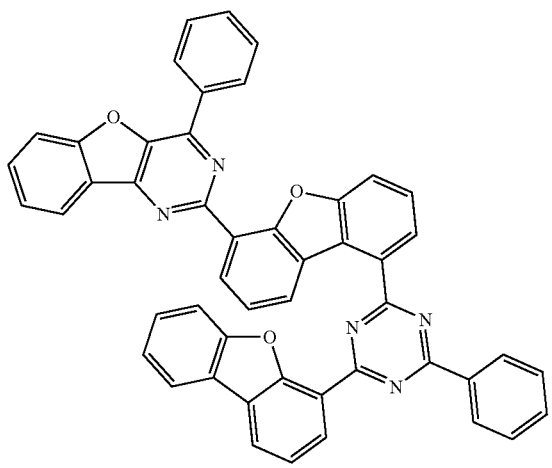

235
-continued
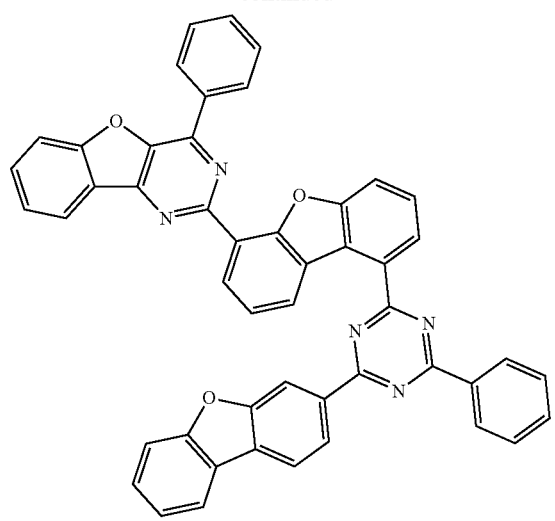 [SMILES: c1ccc(-c2nc(-c3ccc4c(c3)sc3ccccc34)nc(-c3cccc4oc5c(-c6nc(-c7ccccc7)c7sc8ccccc8c7n6)cccc5c34)n2)cc1]
236
-continued
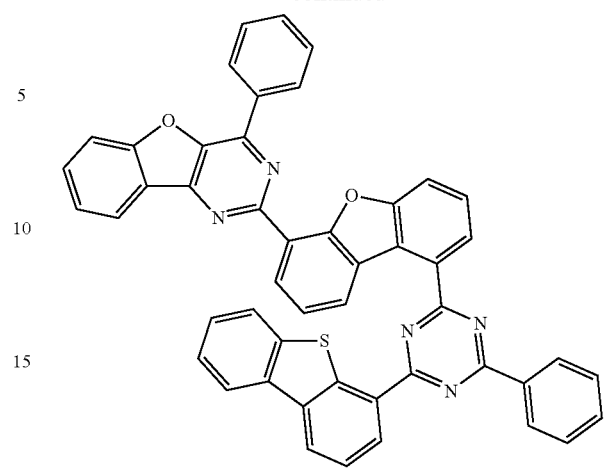
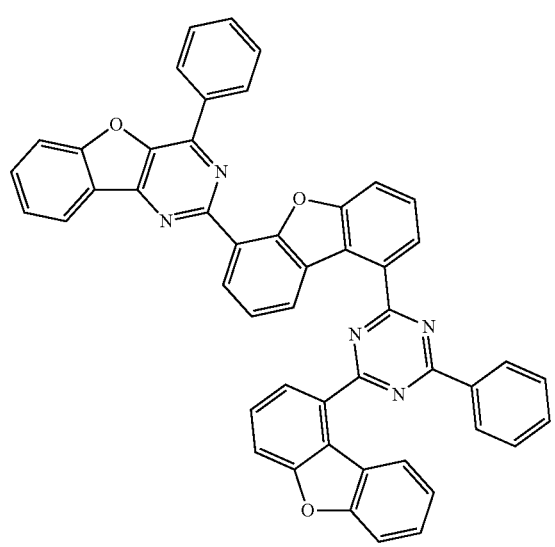
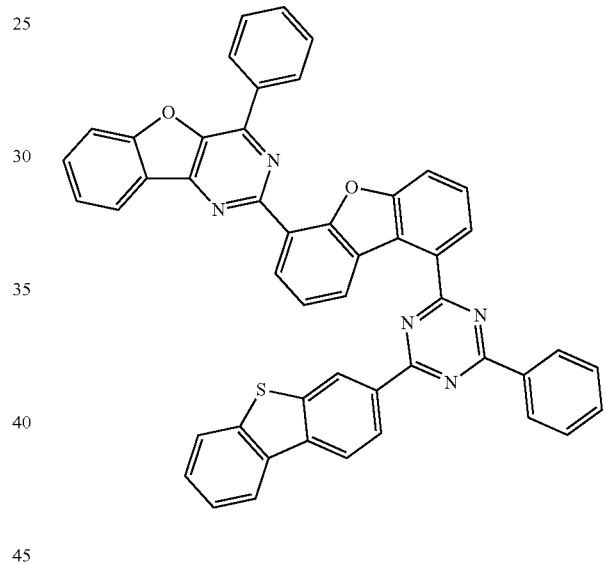

237
-continued
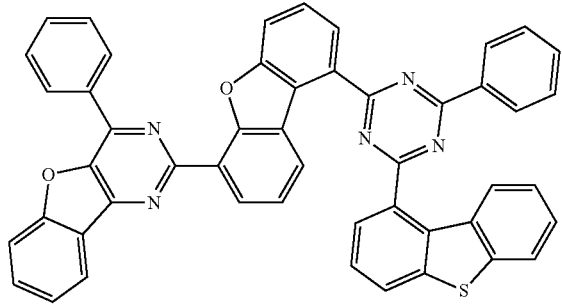
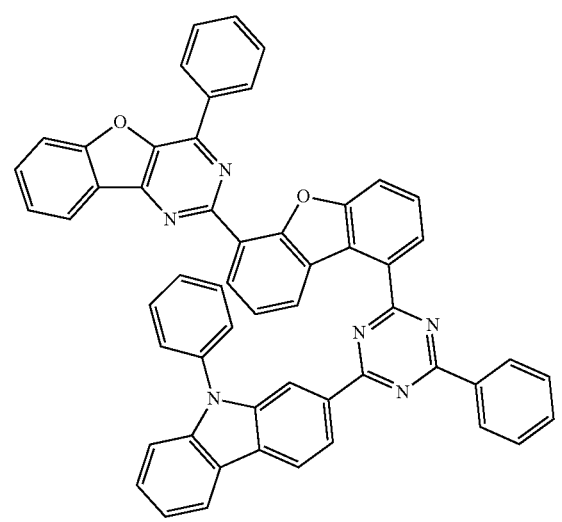
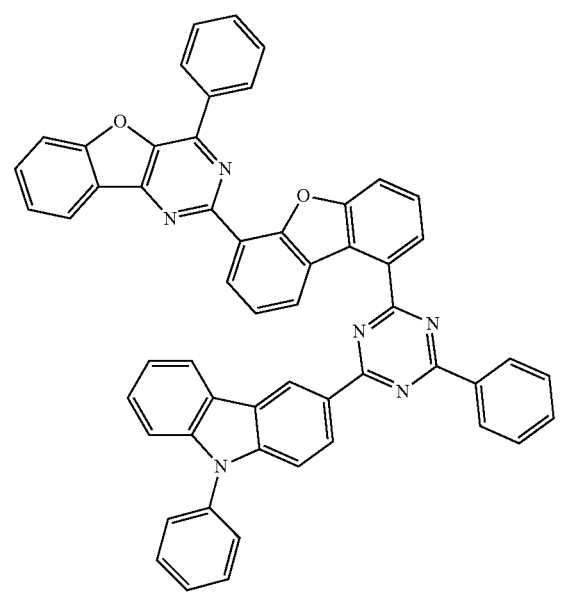
238
-continued
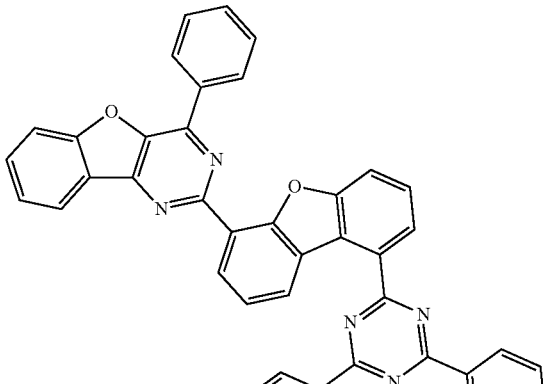
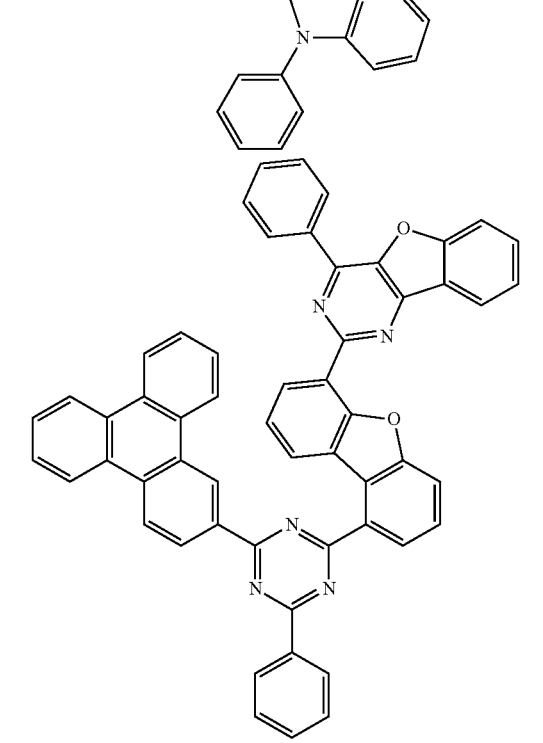
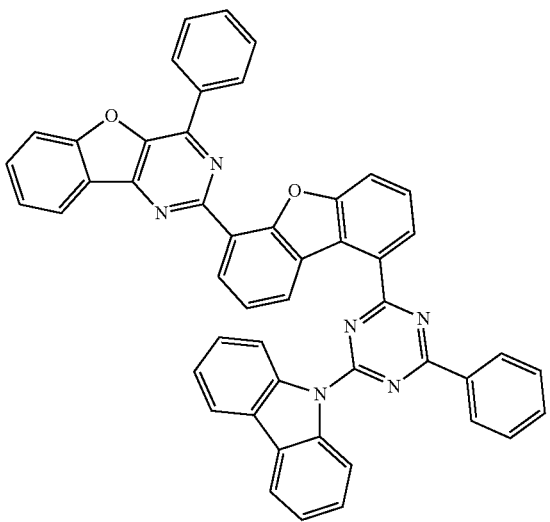

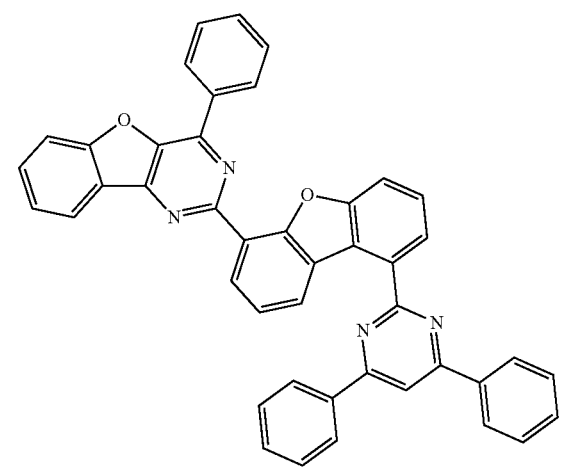
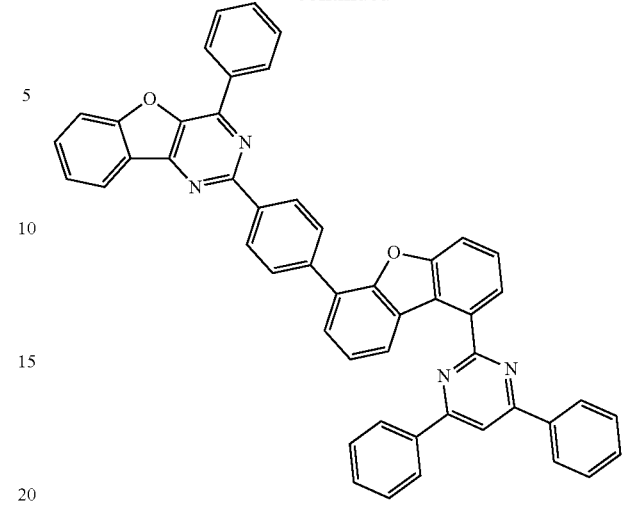
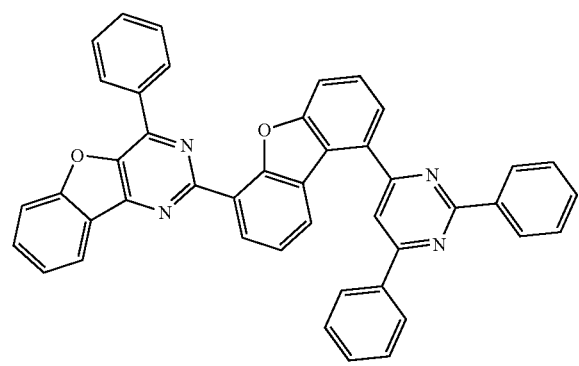
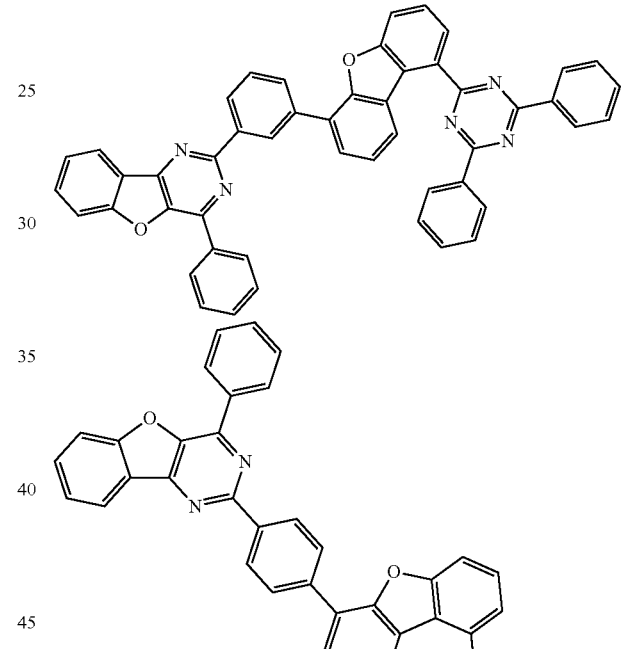
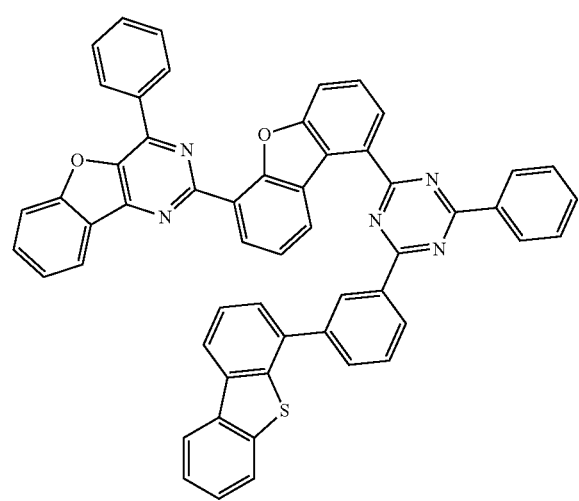
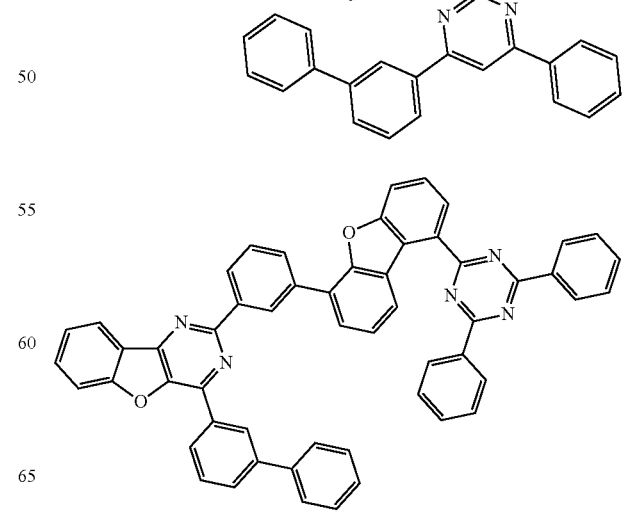

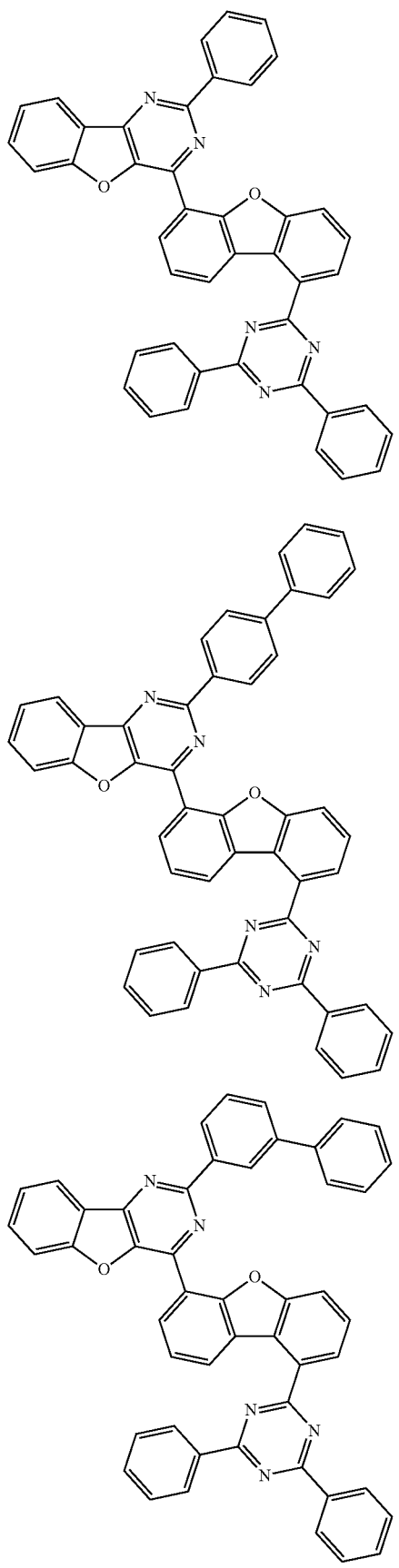
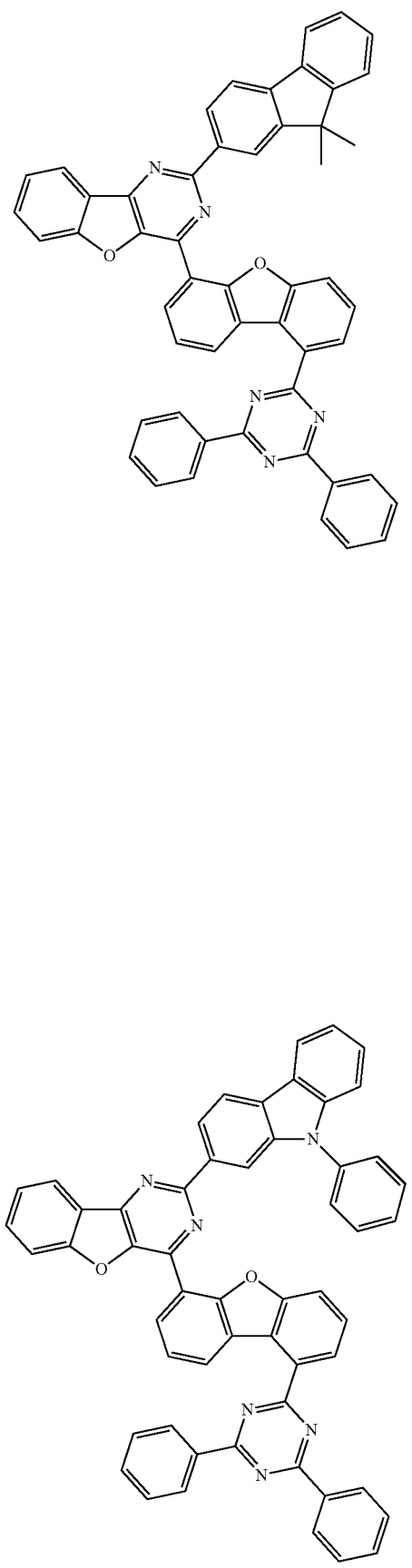

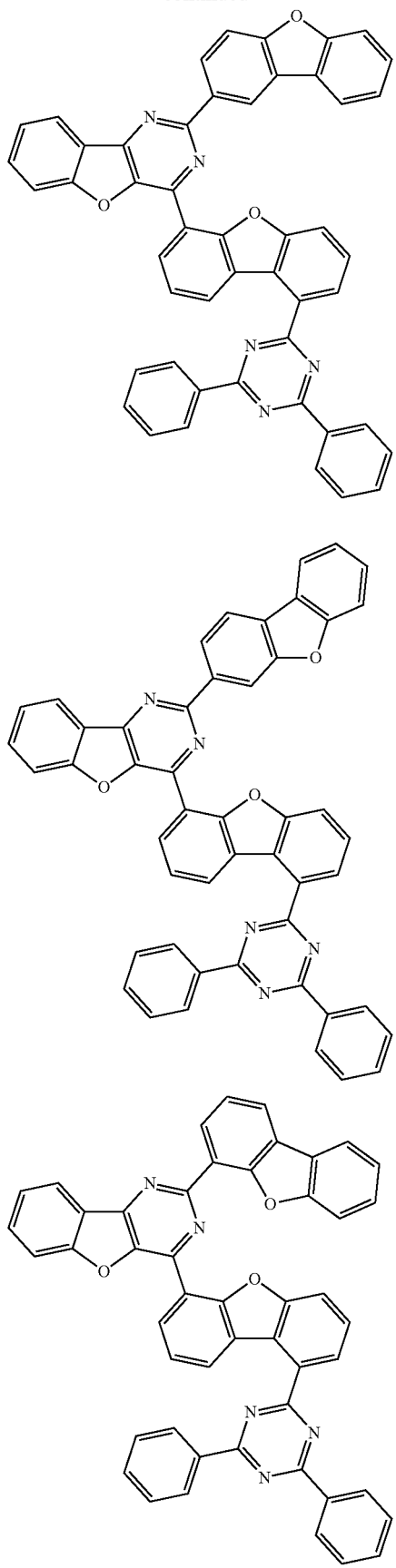
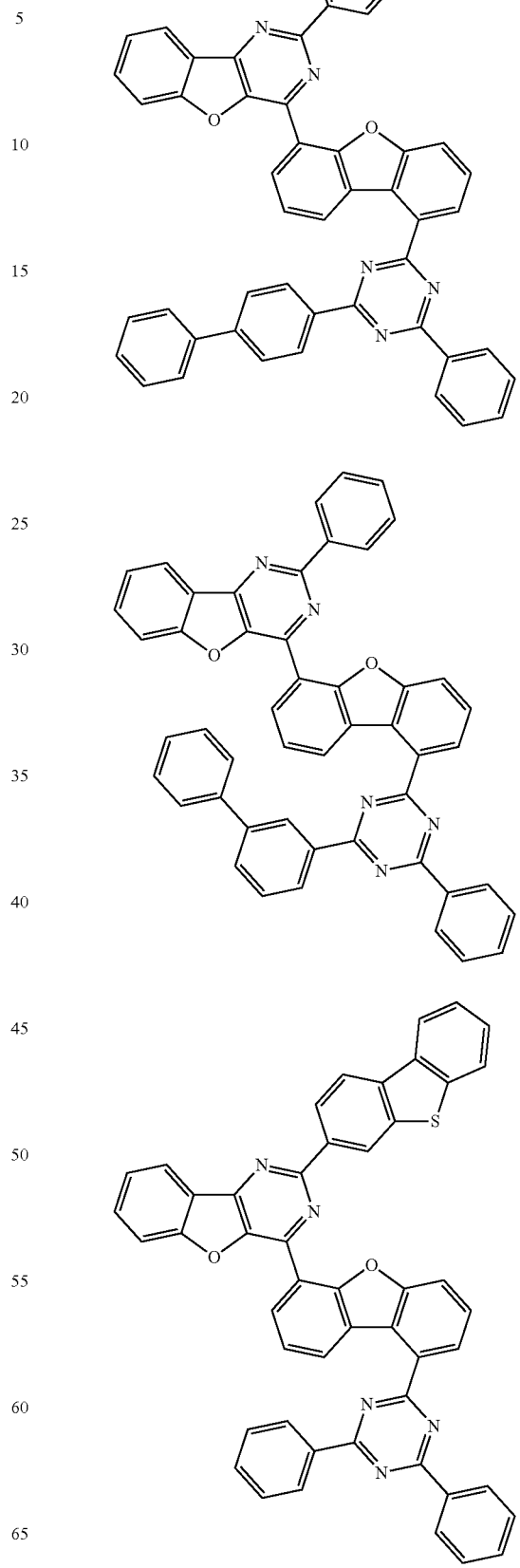

-continued
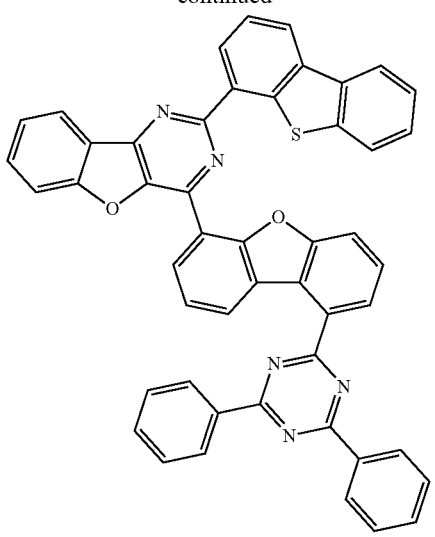
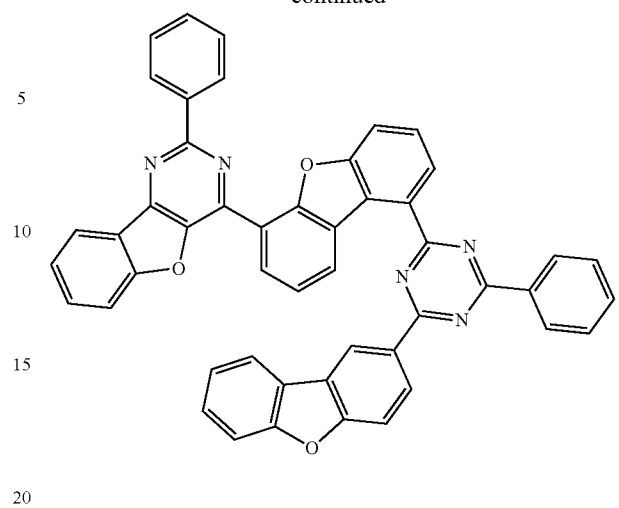
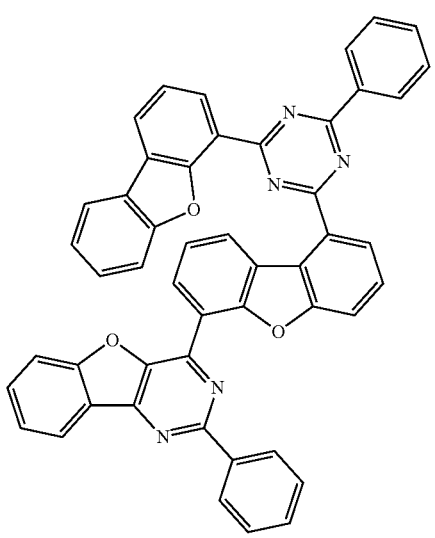
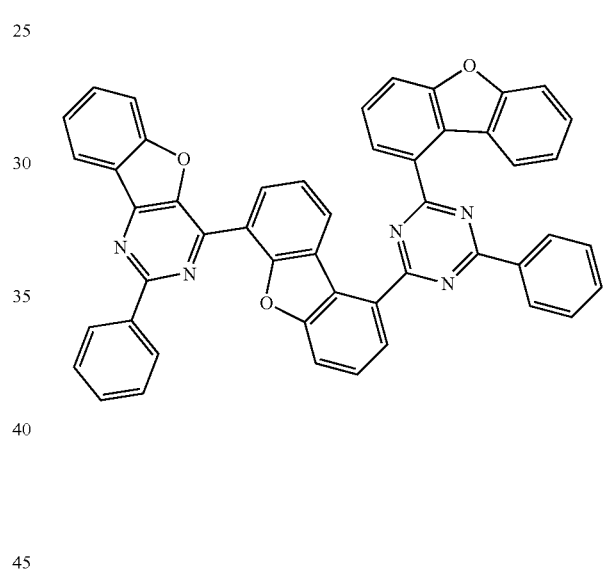
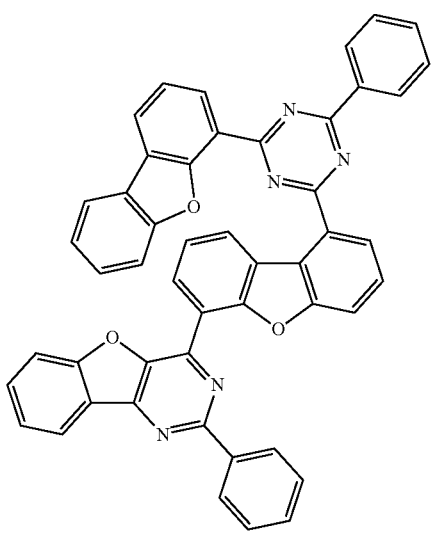
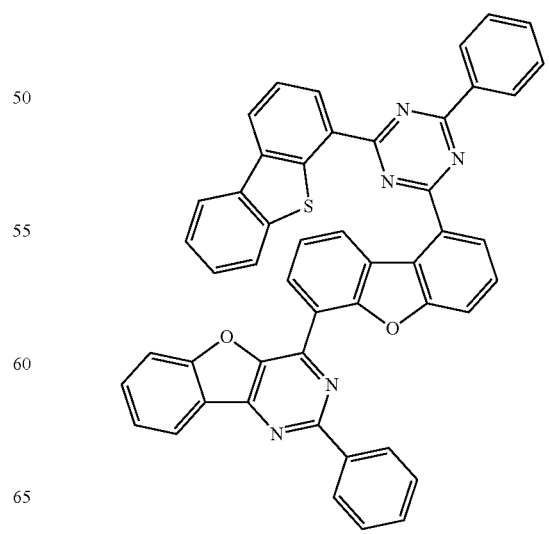

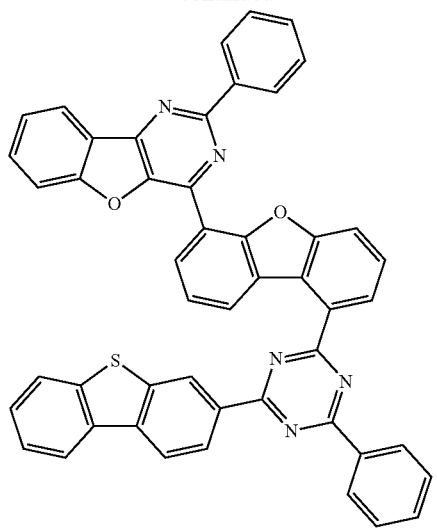
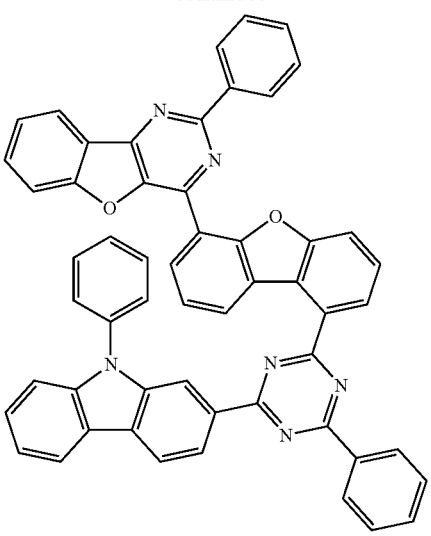
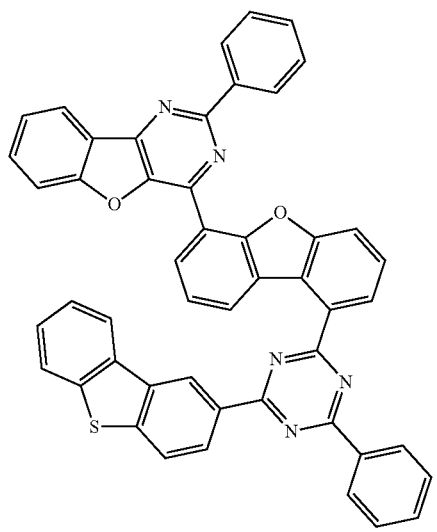
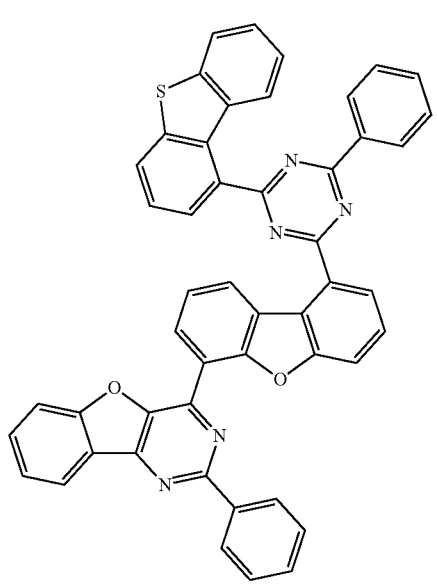
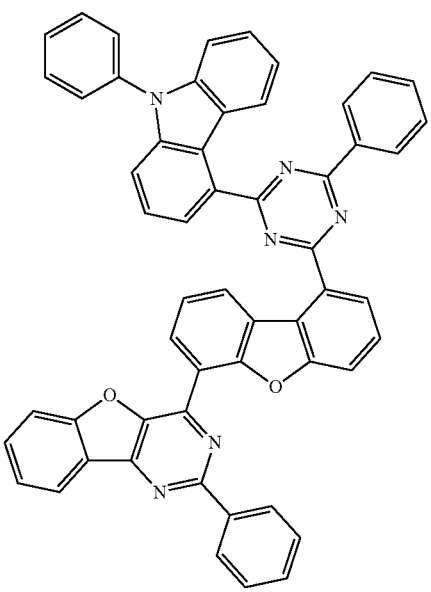

249
-continued
250
-continued
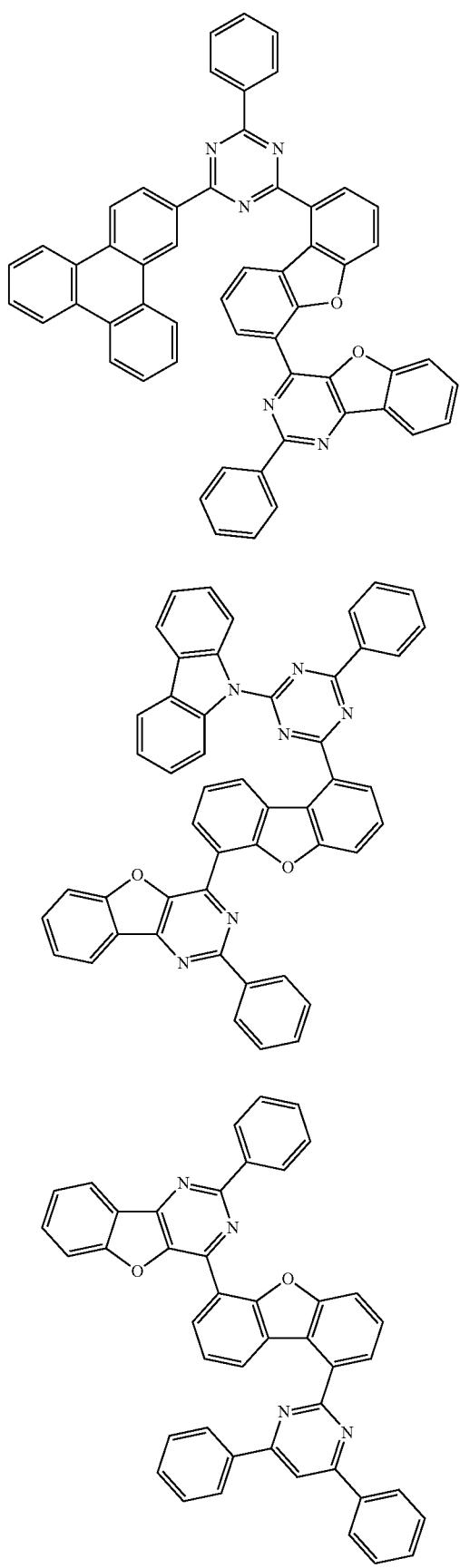
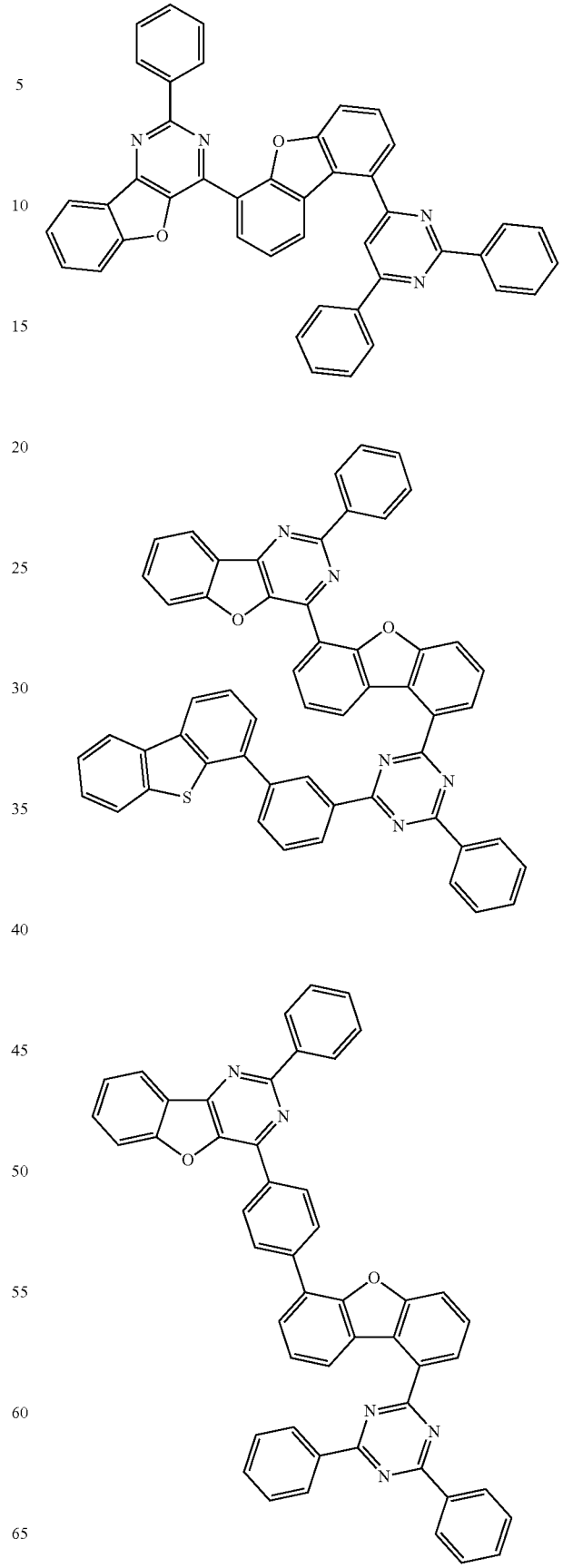

251
-continued
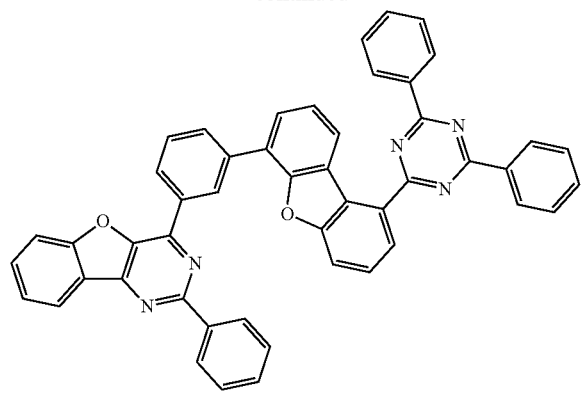
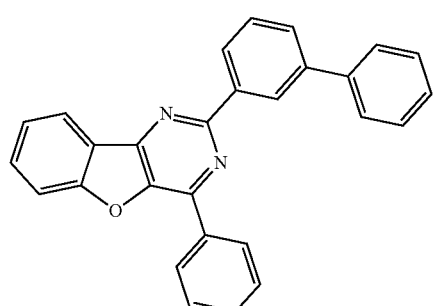
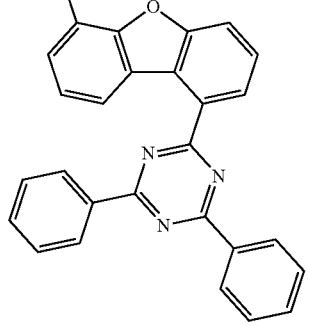
252
-continued
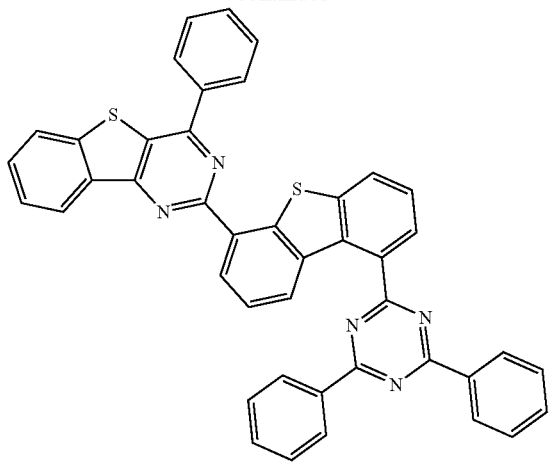
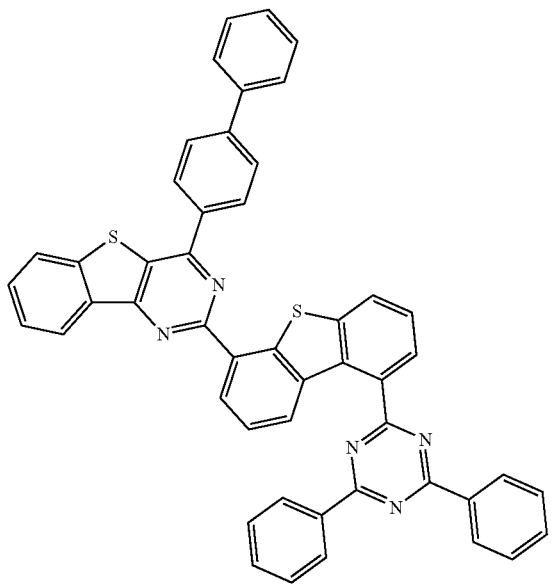
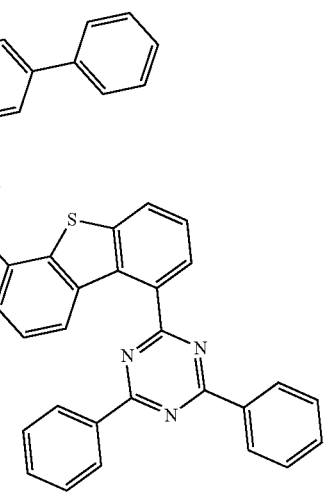
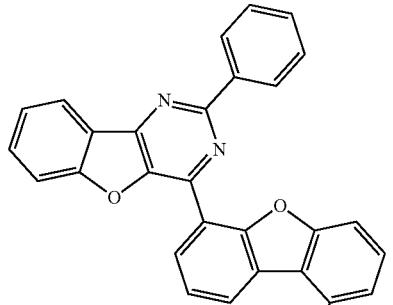
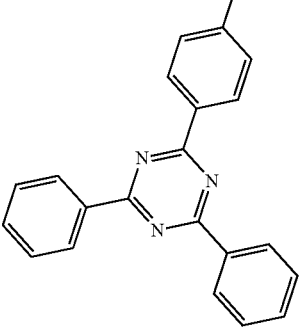

253
-continued
254
-continued
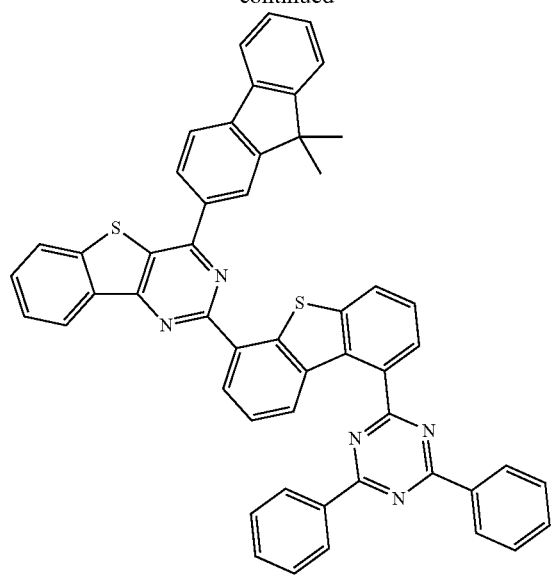
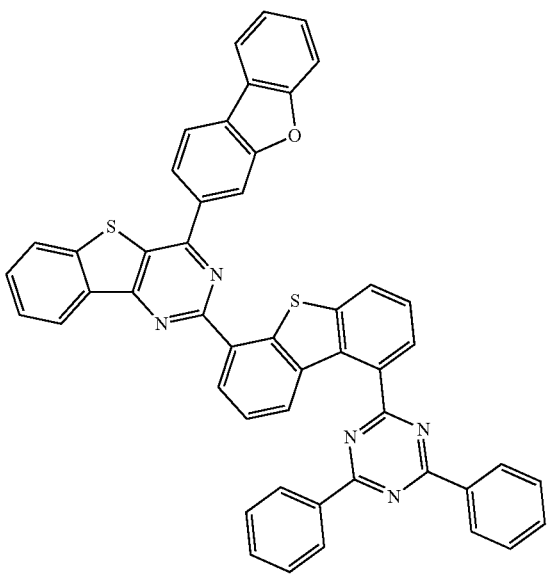

255
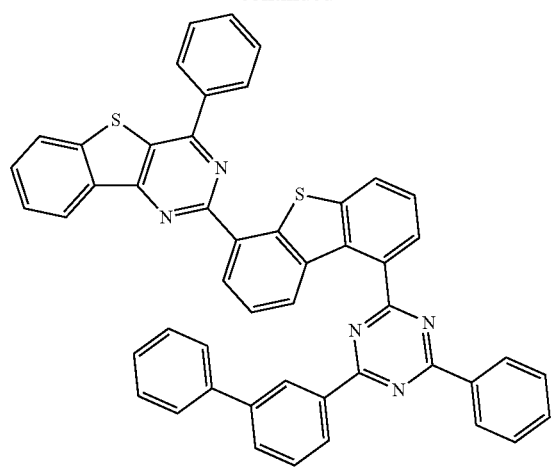
256
-continued
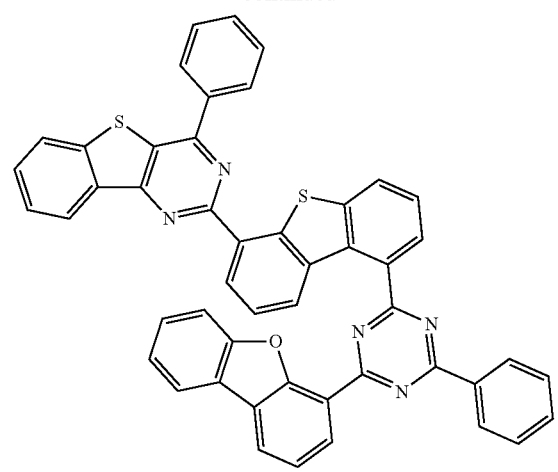
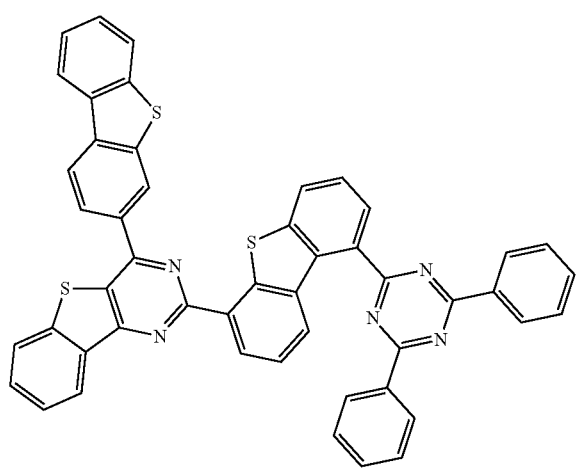
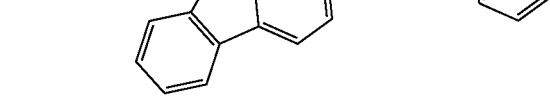
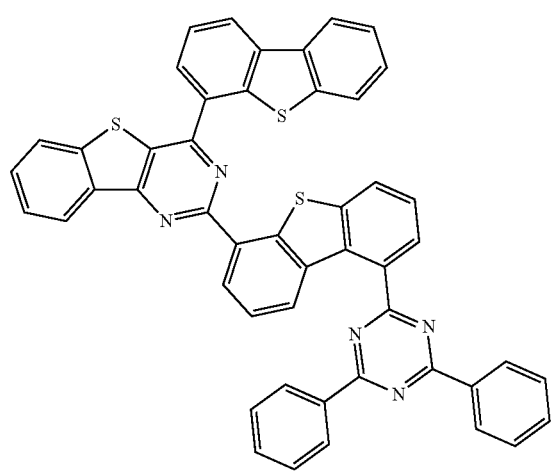
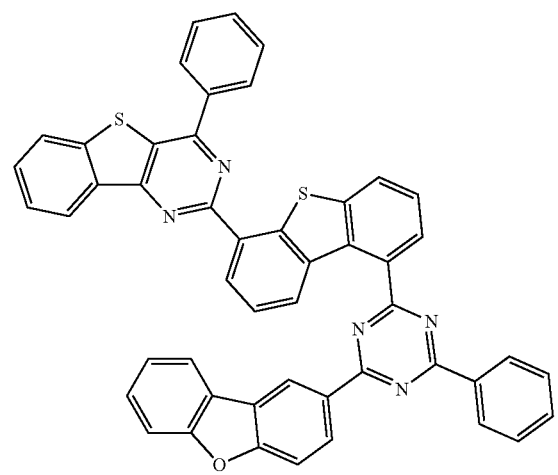

257
-continued
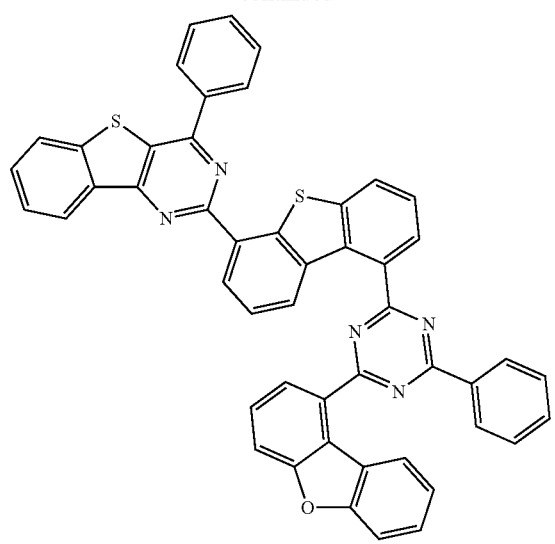
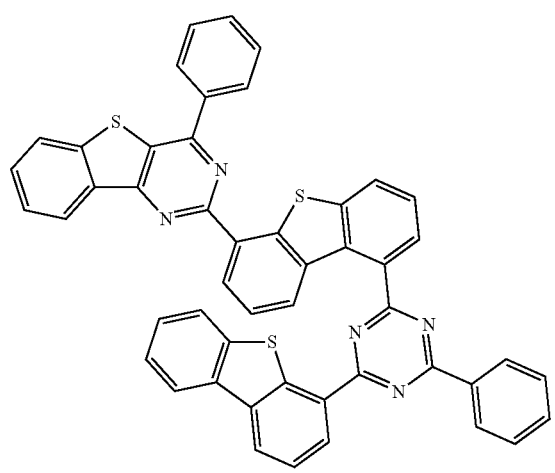
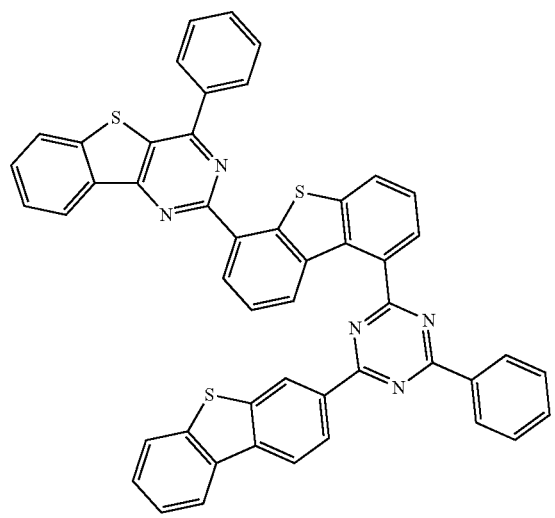
258
-continued
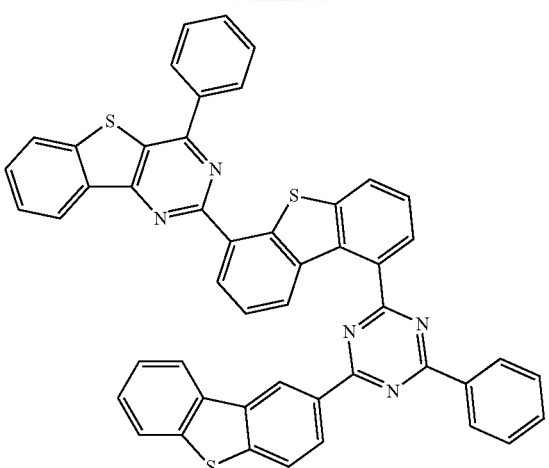
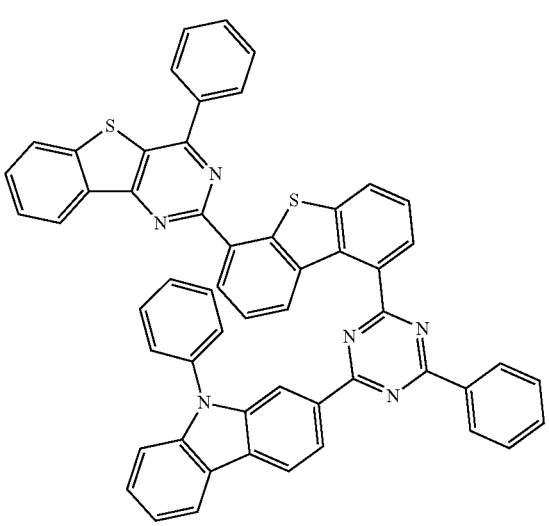

259
-continued
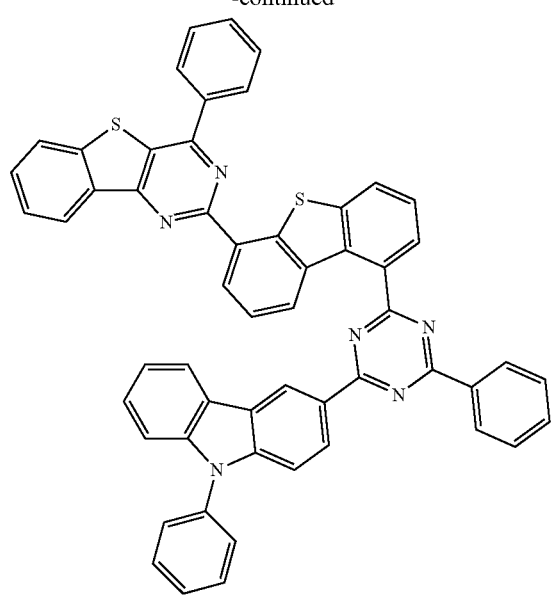
260
-continued
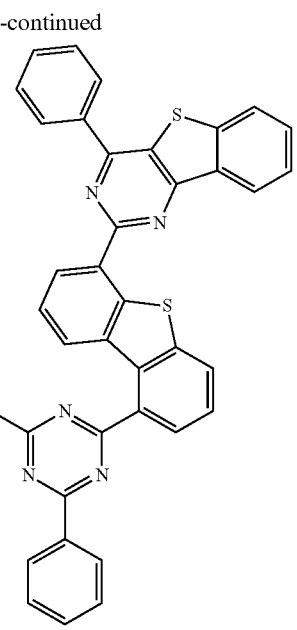
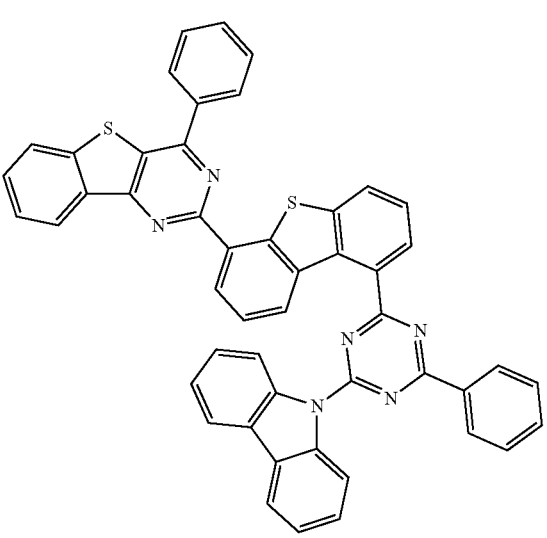
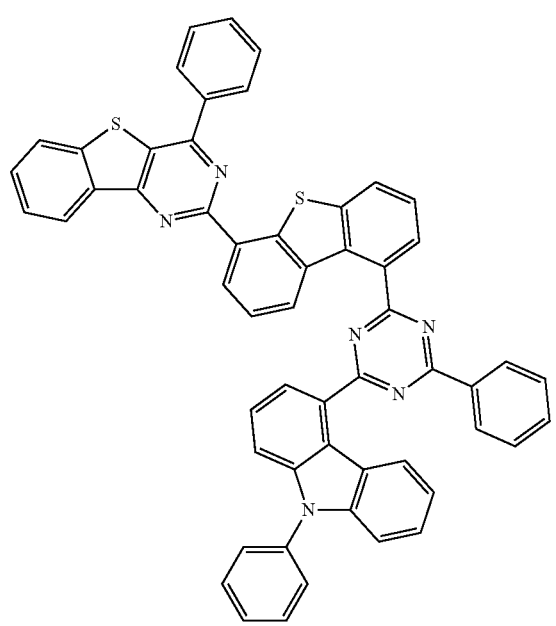

-continued
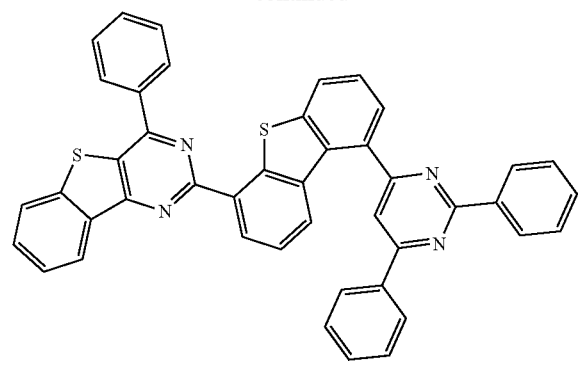
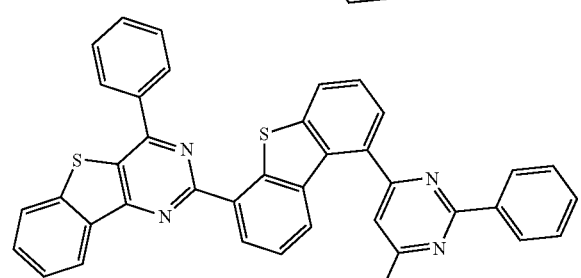
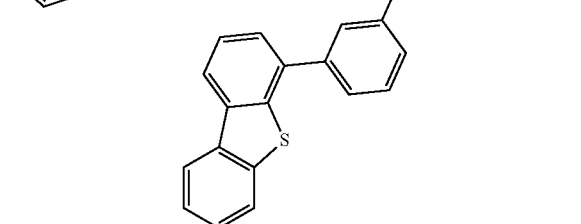
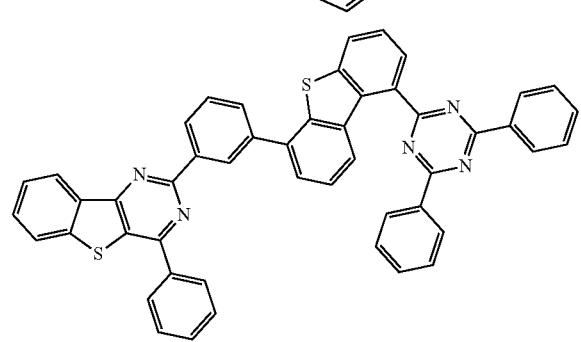
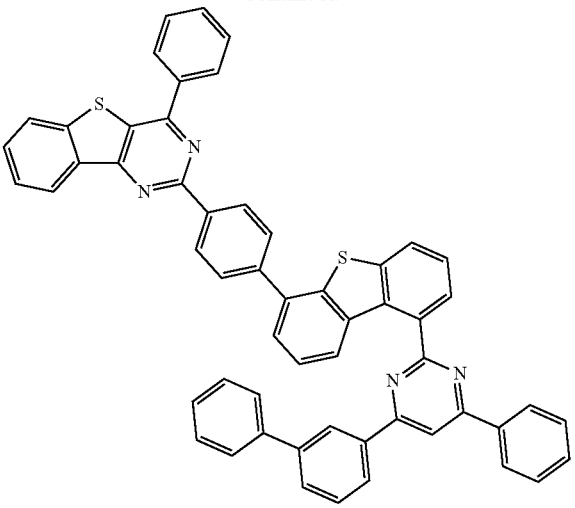
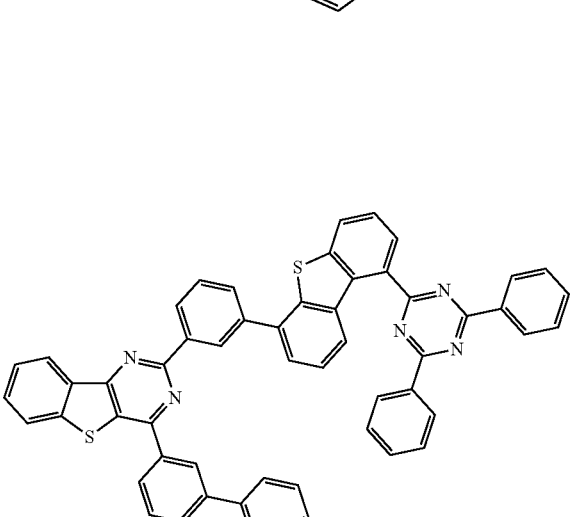
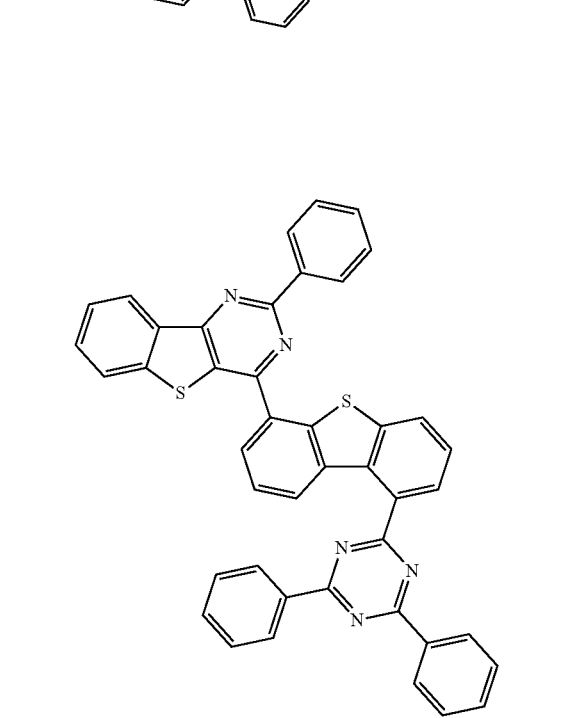

263
-continued
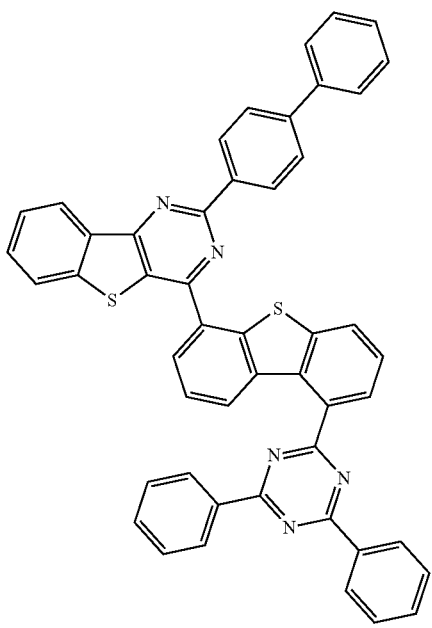
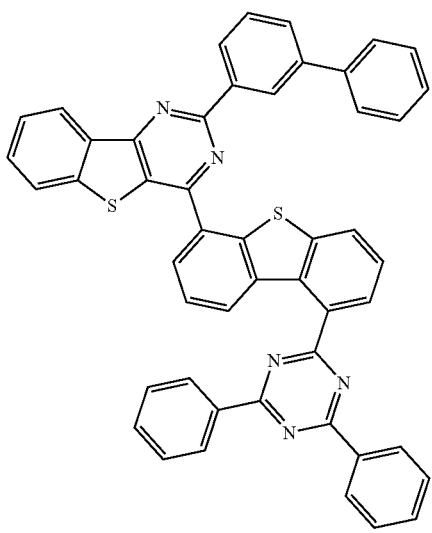
264
-continued
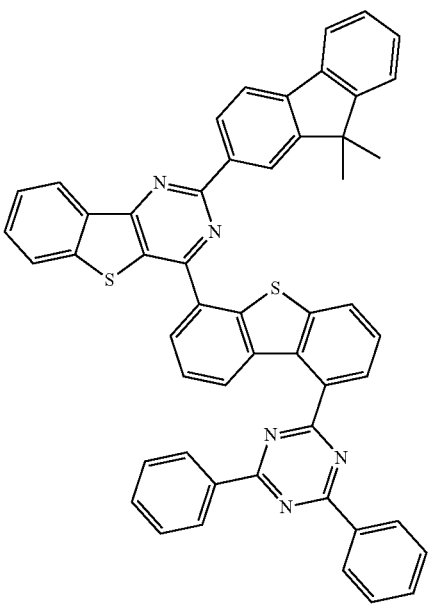
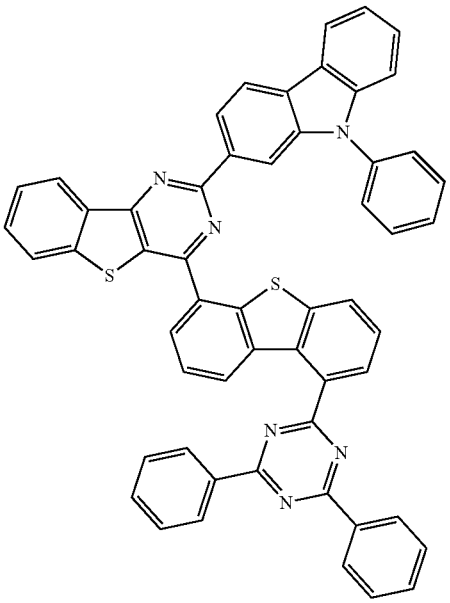

265
-continued
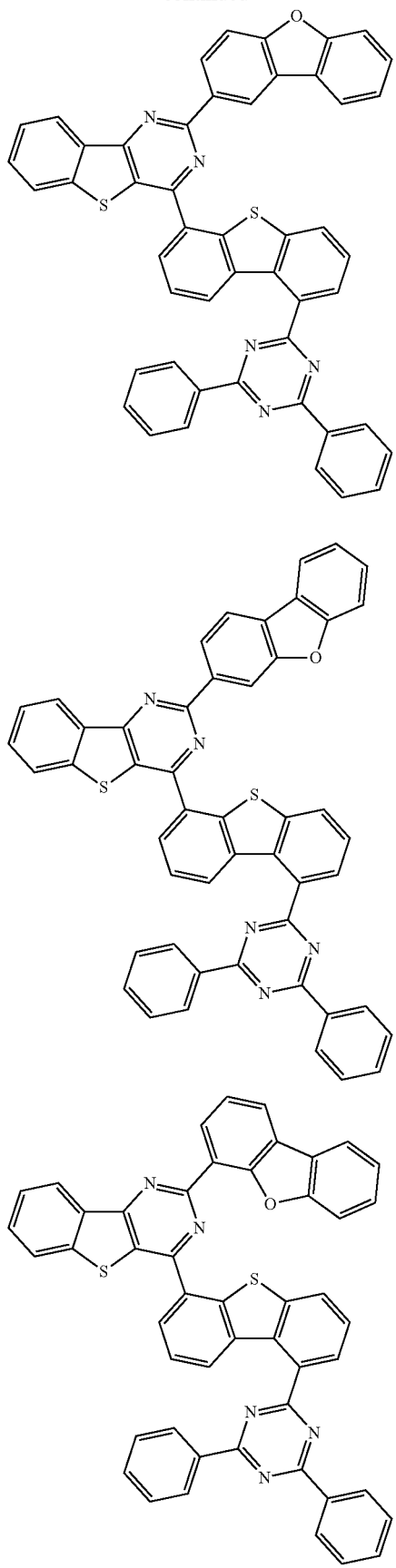
266
-continued
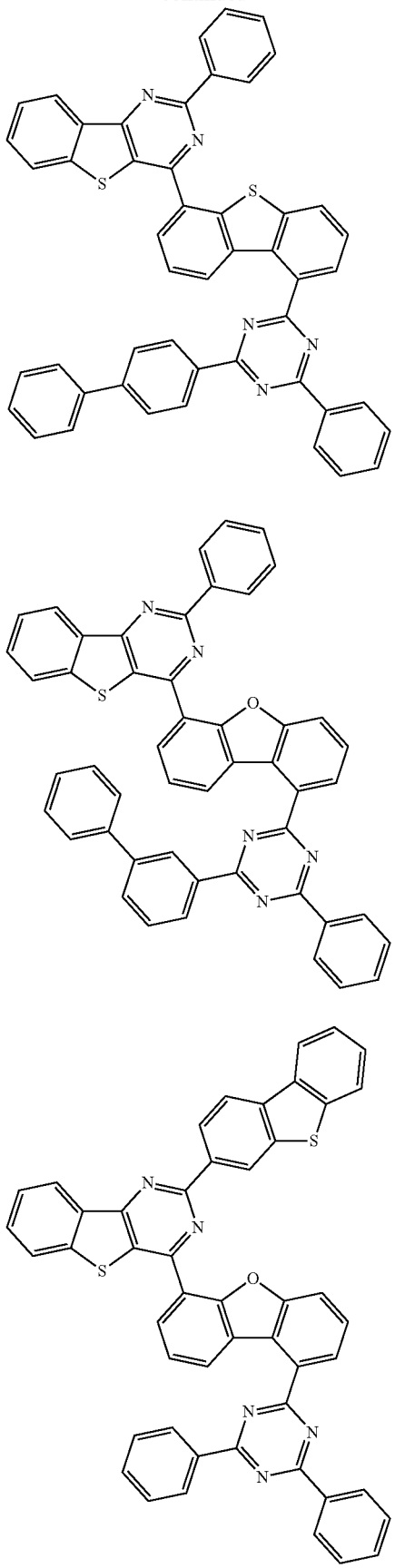

267
-continued
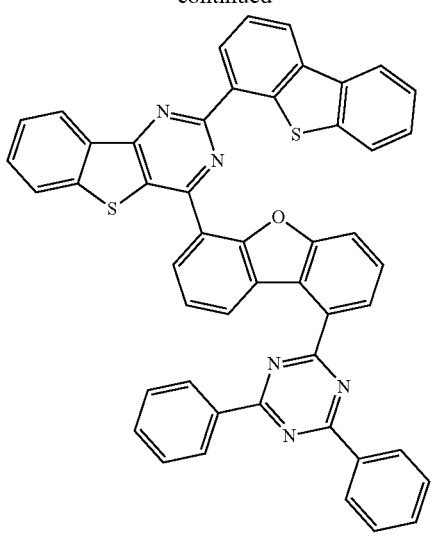
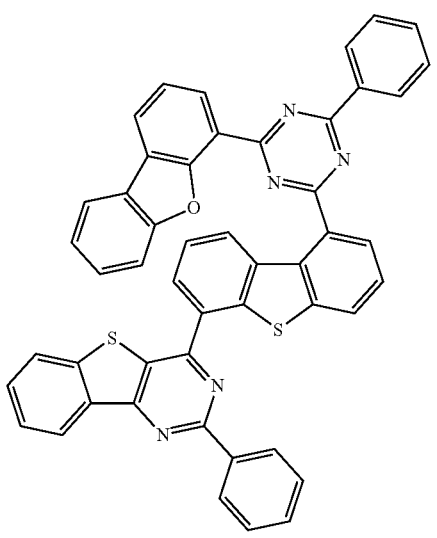
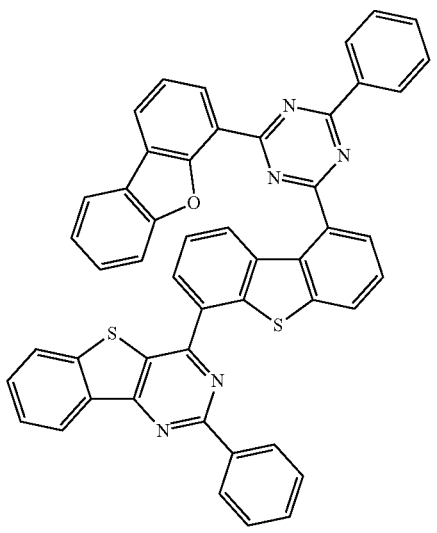
268
-continued
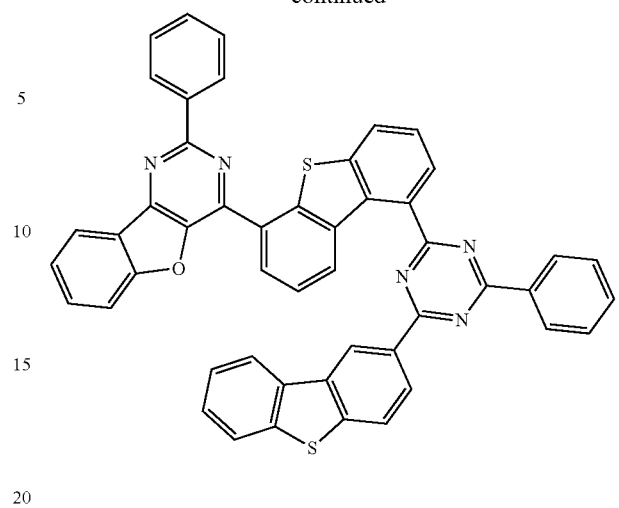
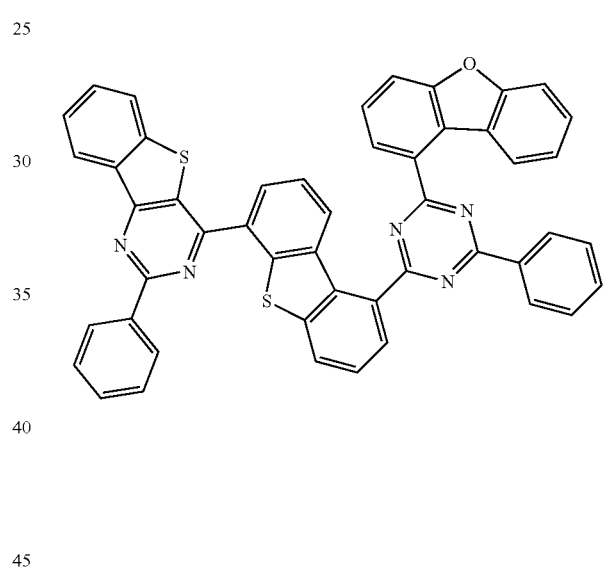
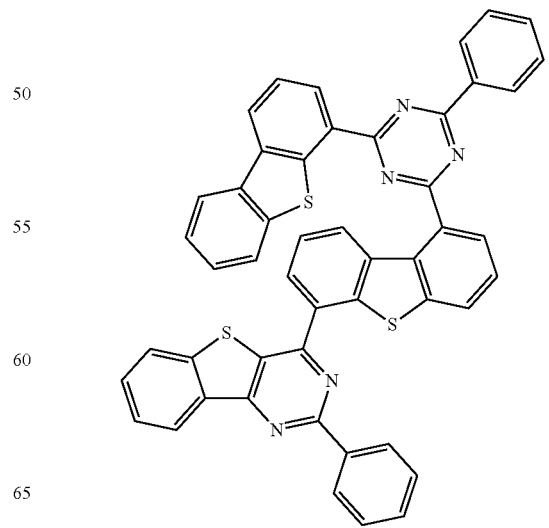

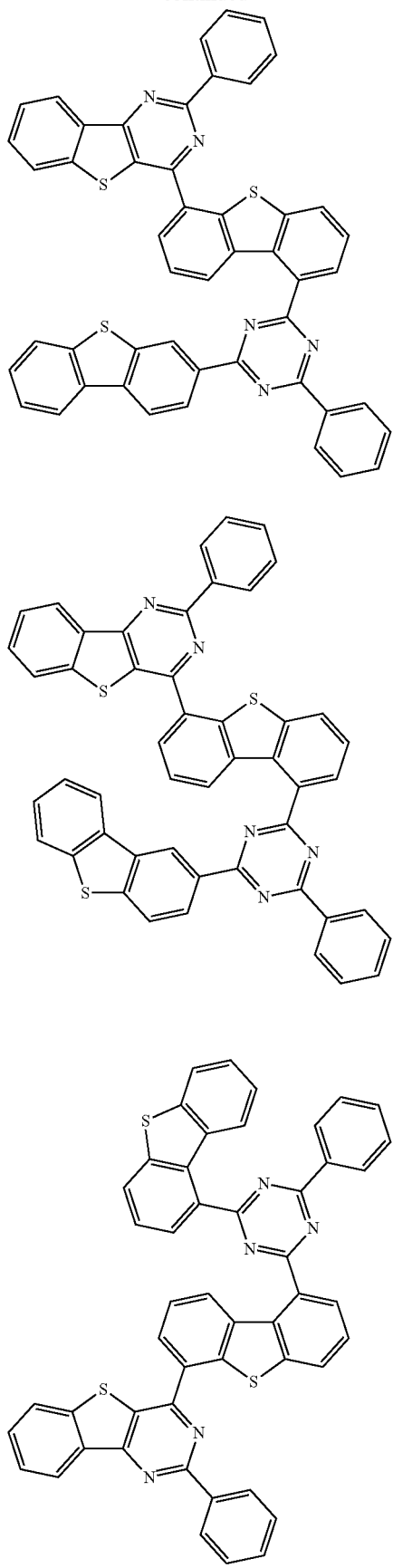
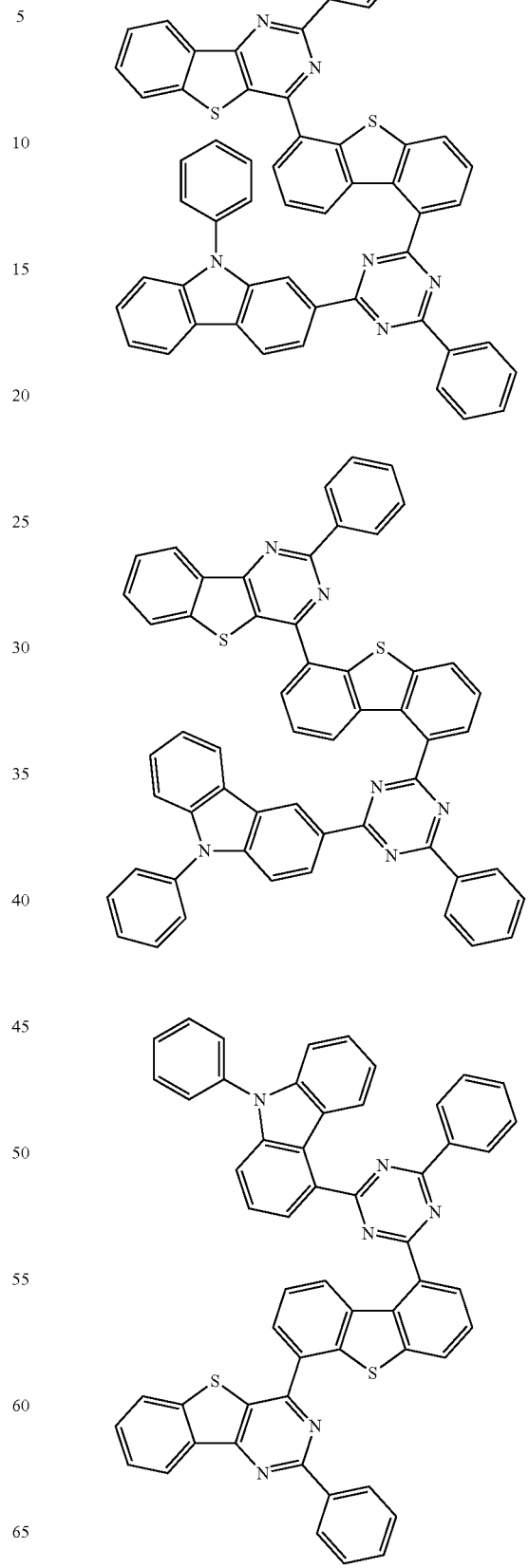

271
-continued
272
-continued
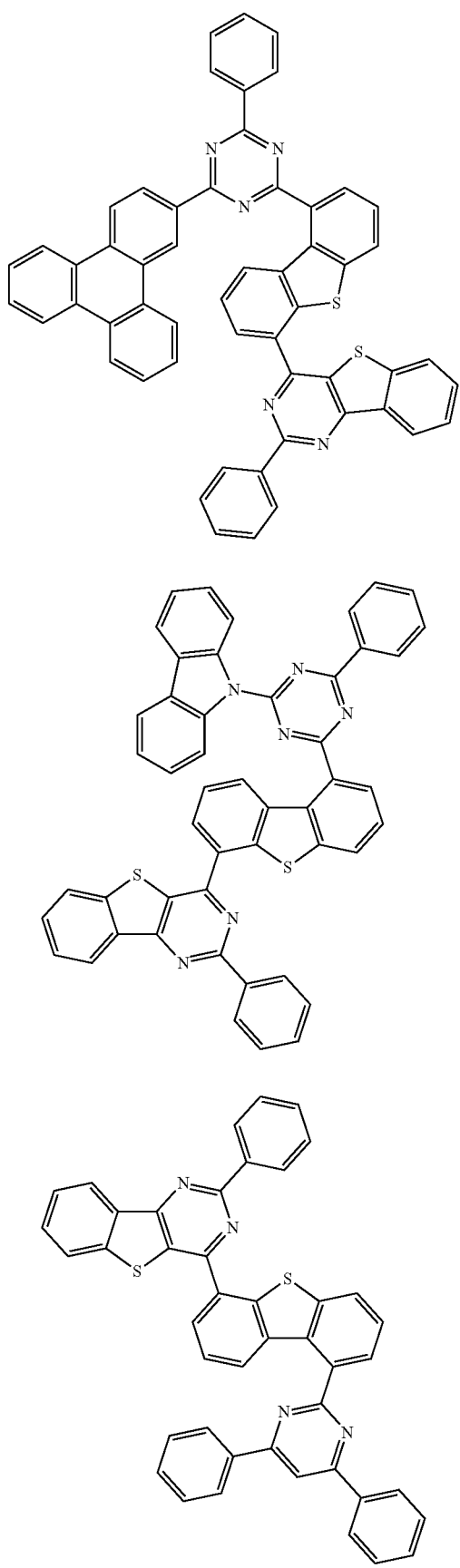
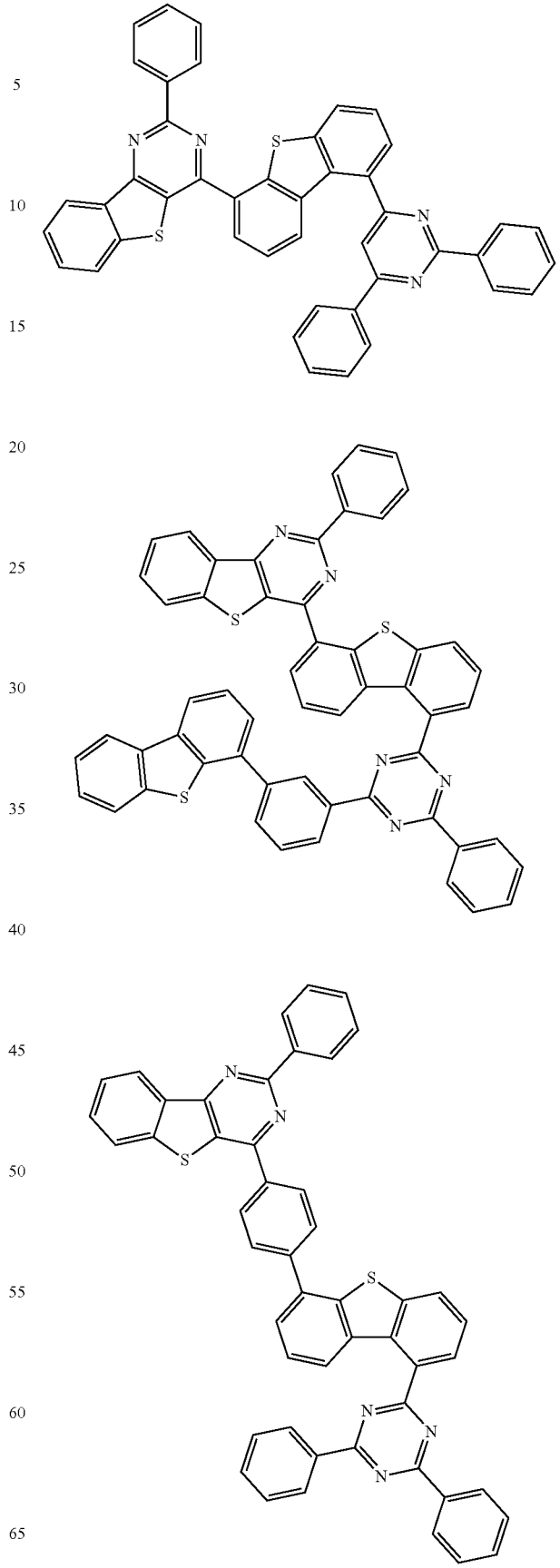

-continued
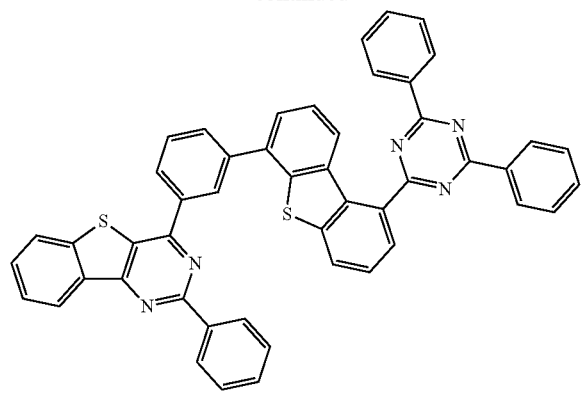
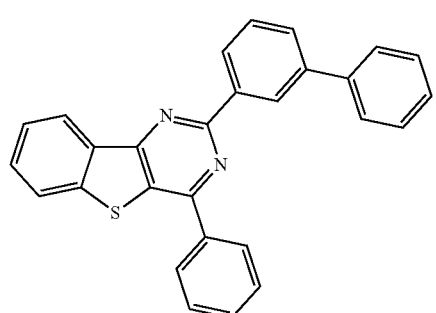
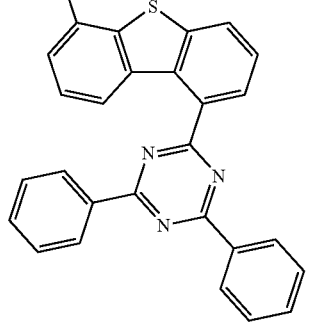
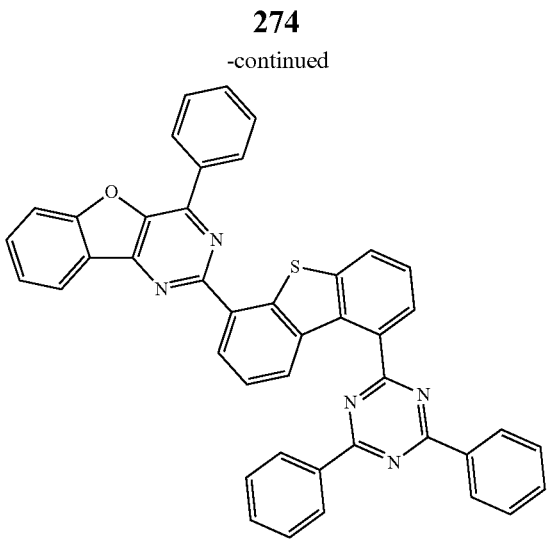
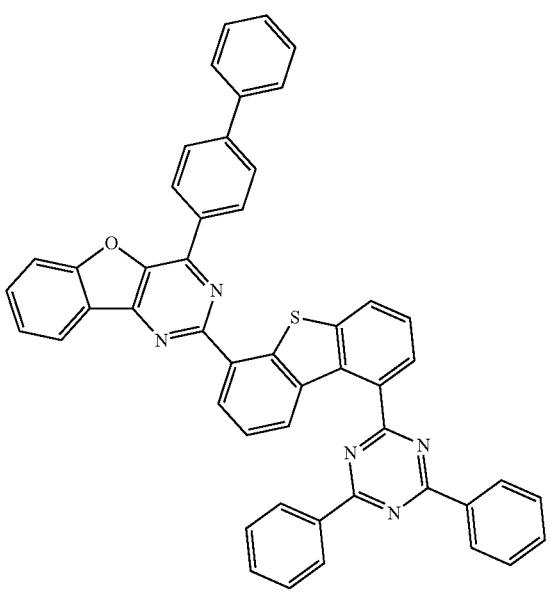
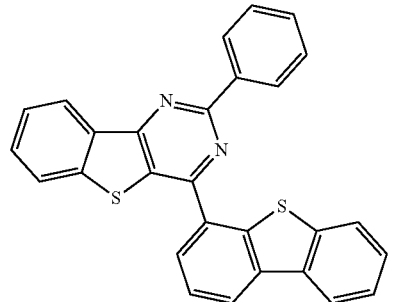
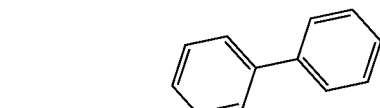
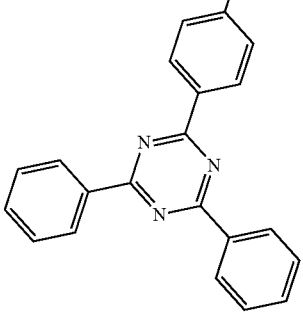
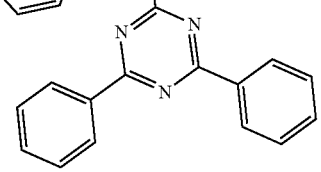

275
-continued

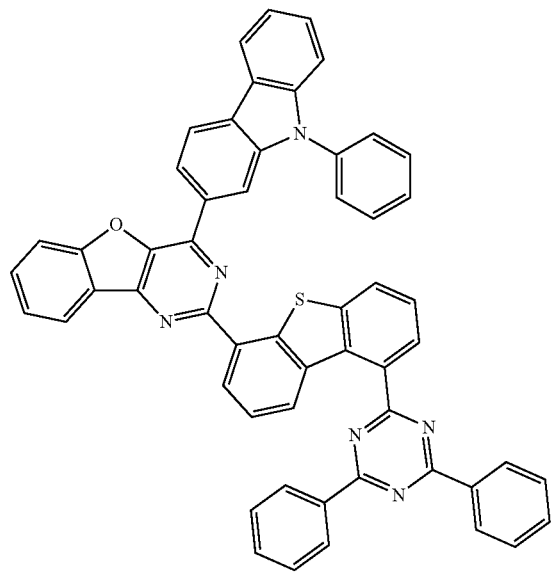
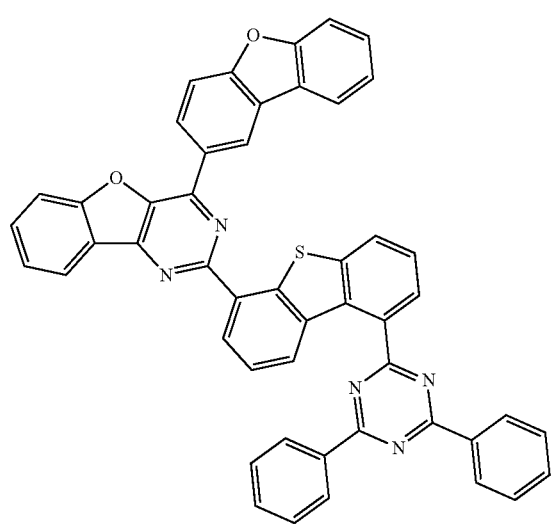
276
-continued

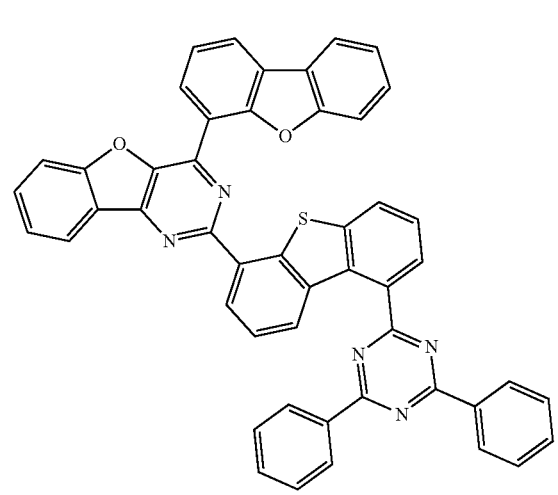
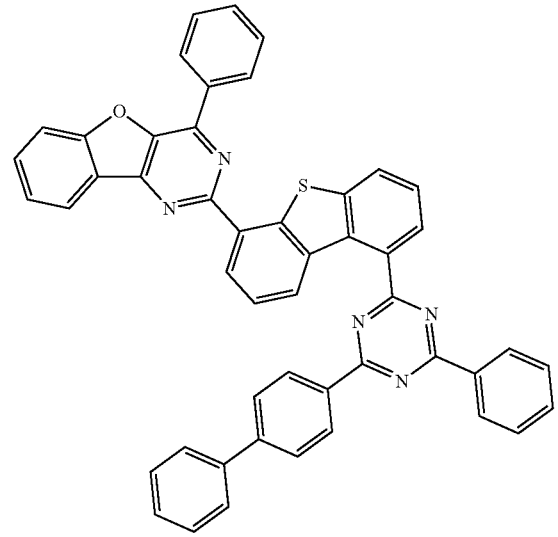

277
-continued
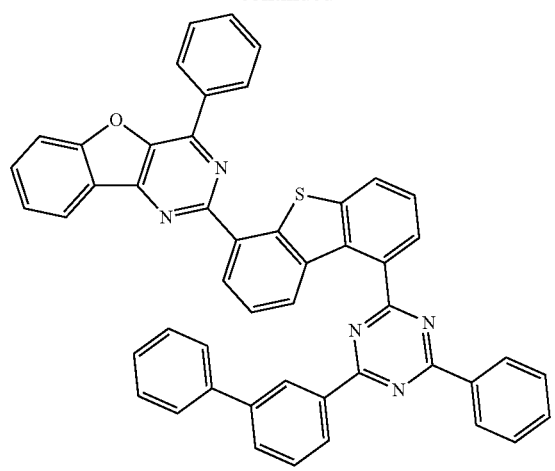
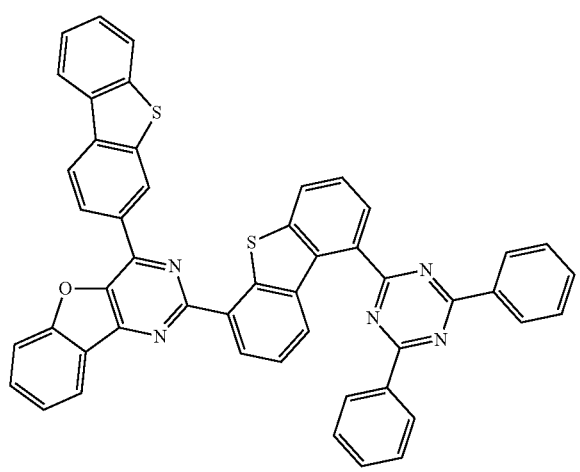
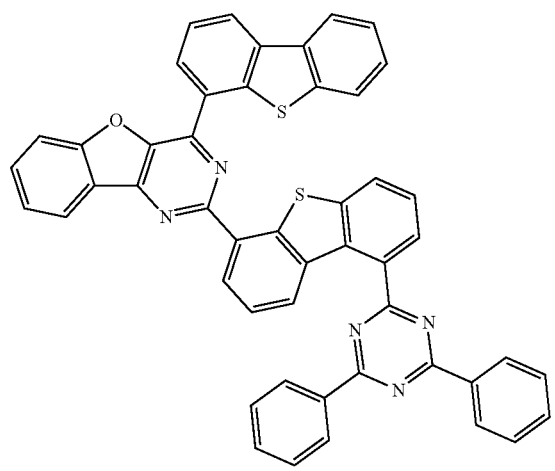
278
-continued
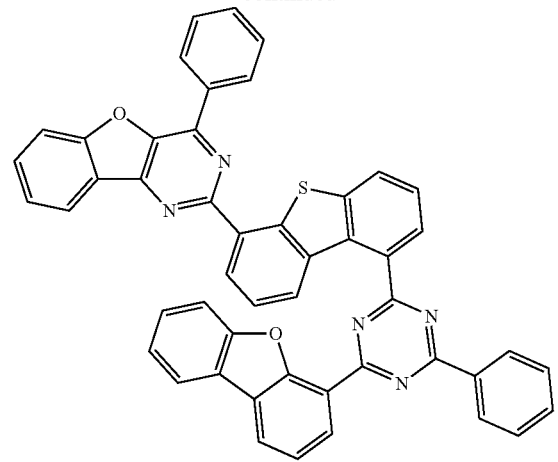
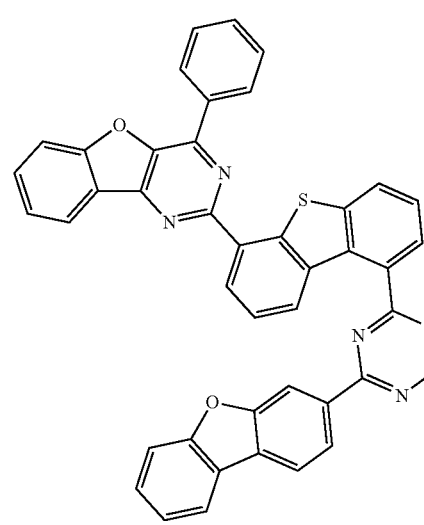
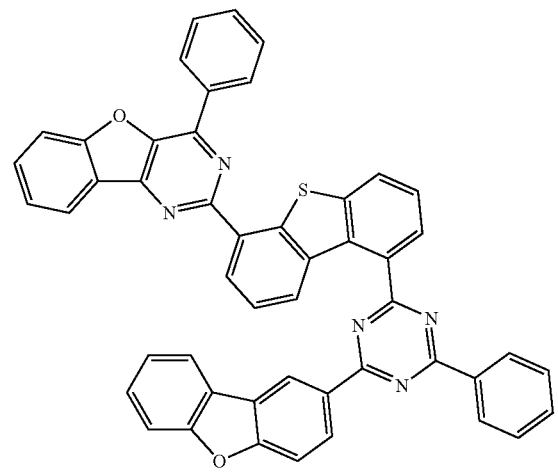

279
-continued
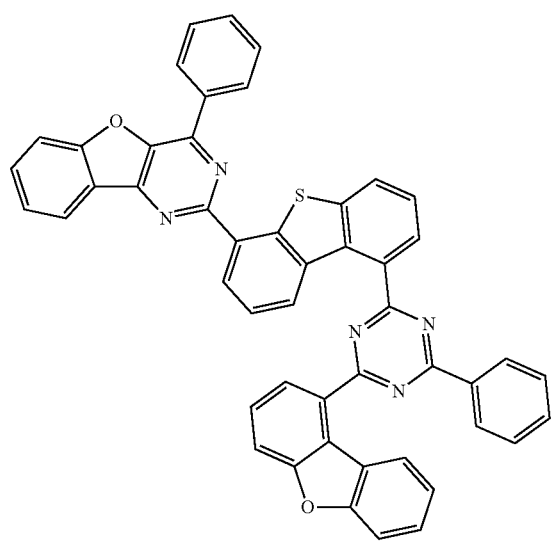
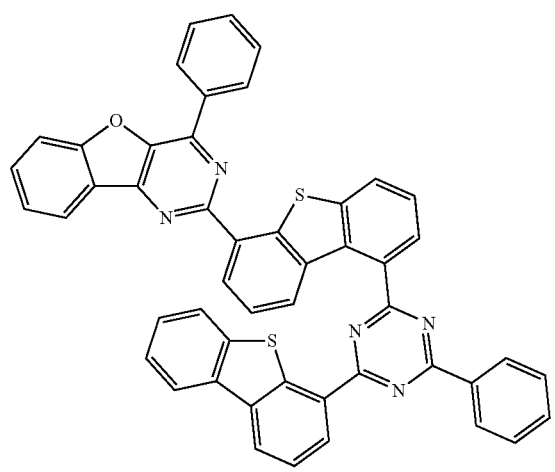
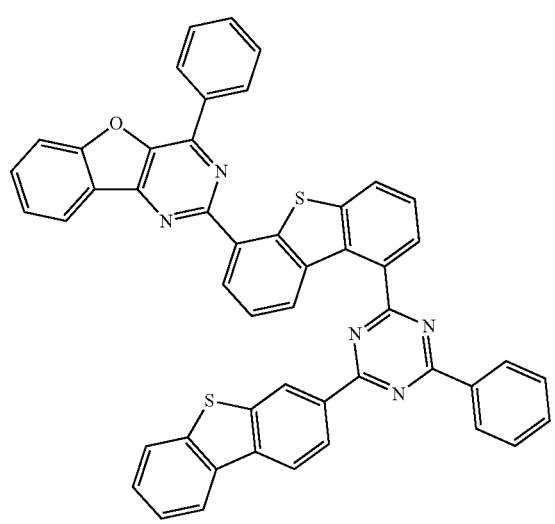
280
-continued
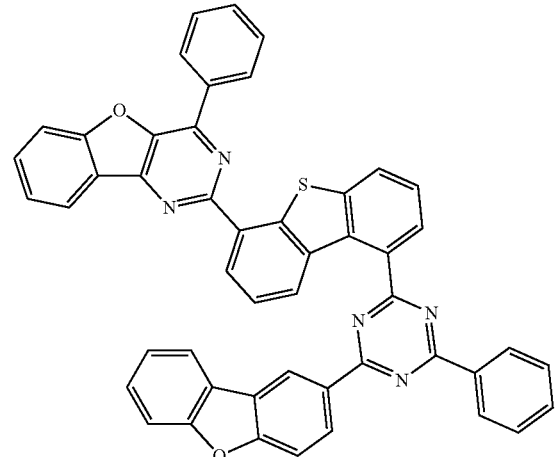
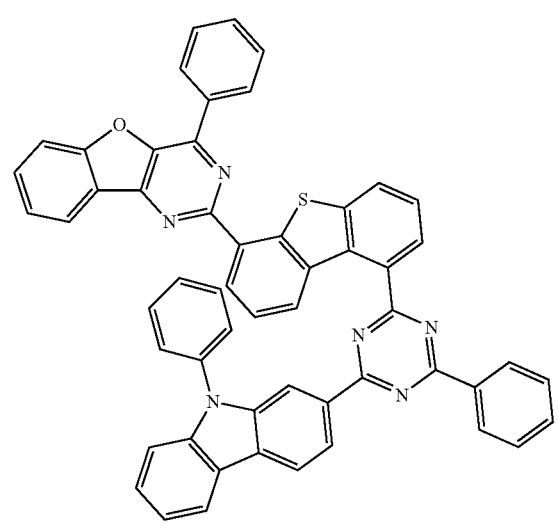

281
-continued
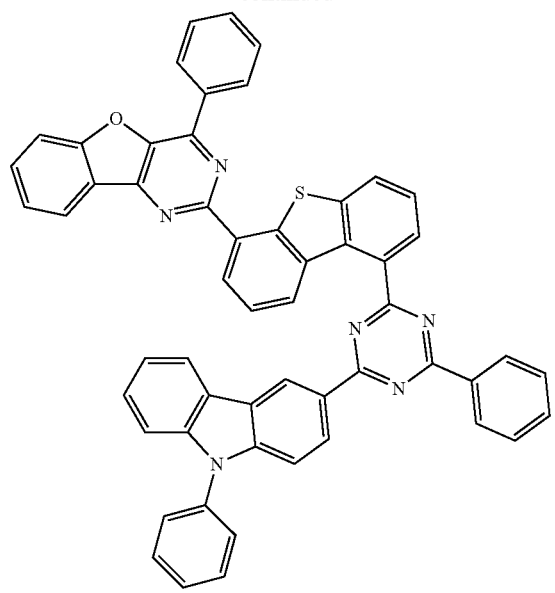
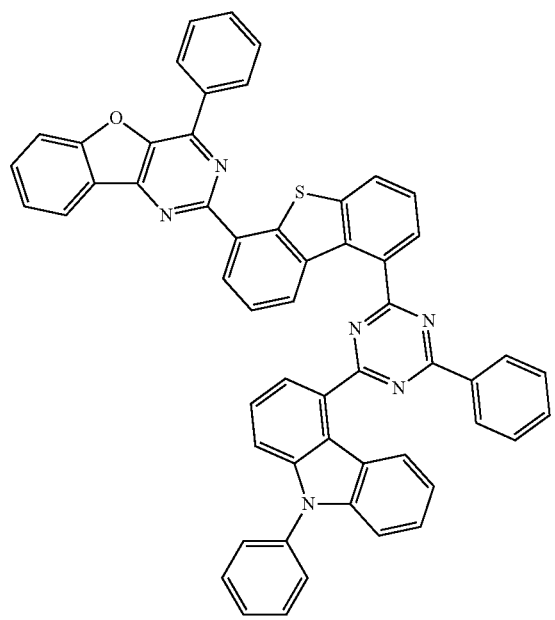
282
-continued
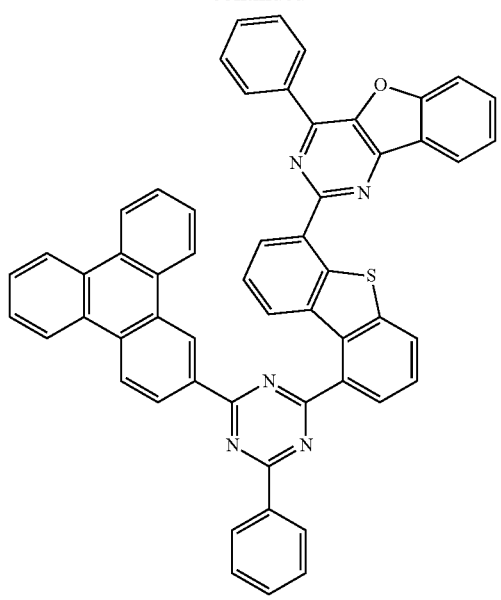
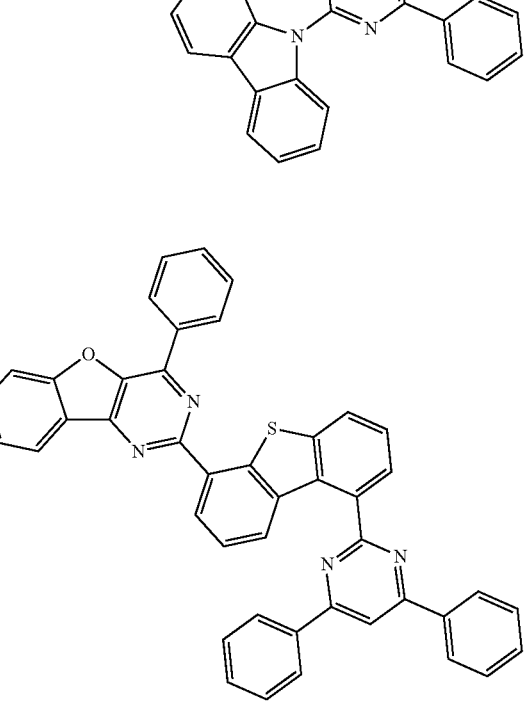

-continued
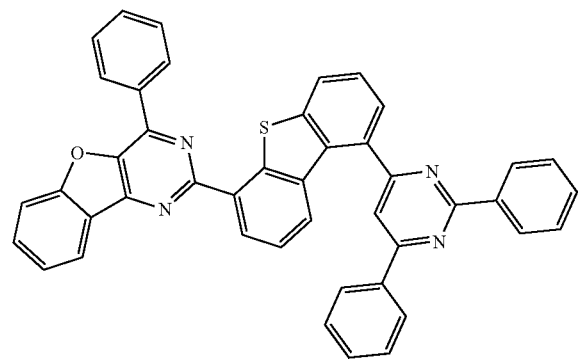
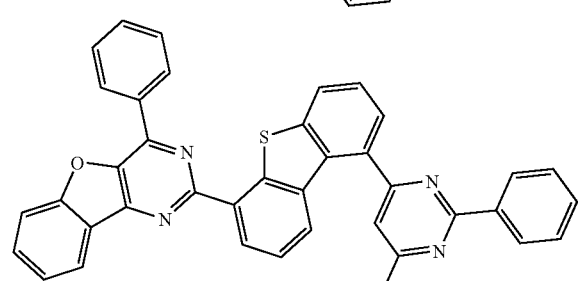
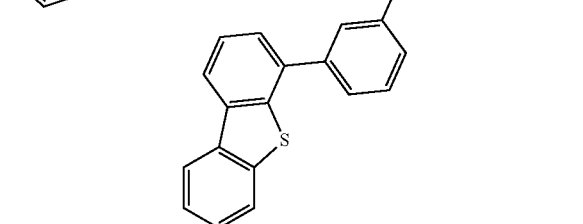
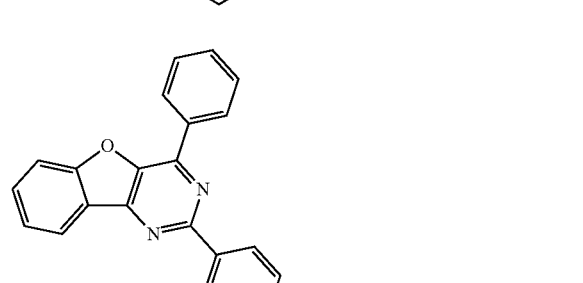
-continued
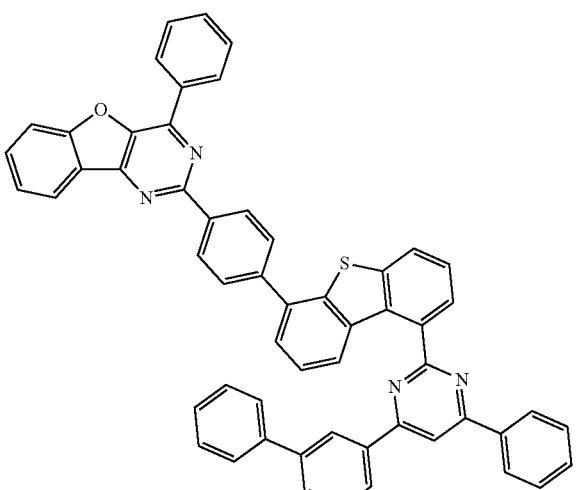
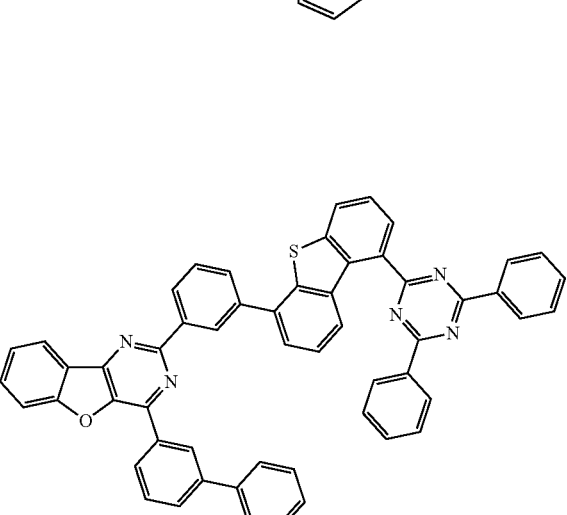
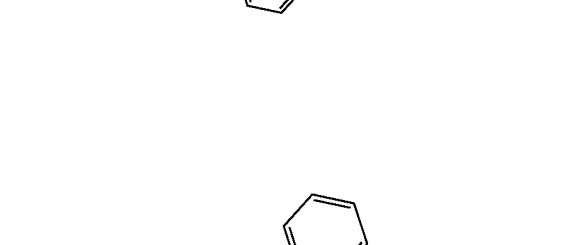

285
-continued
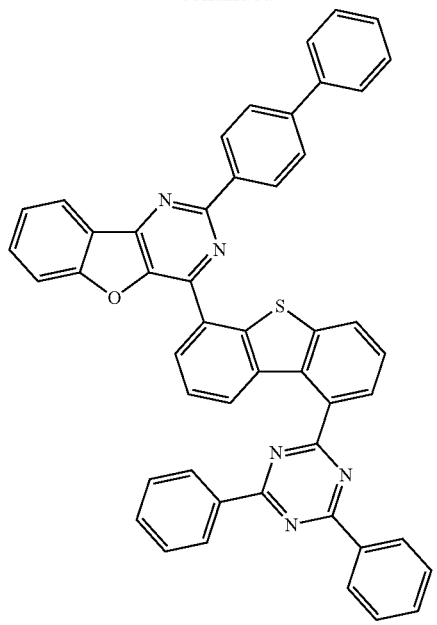
286
-continued
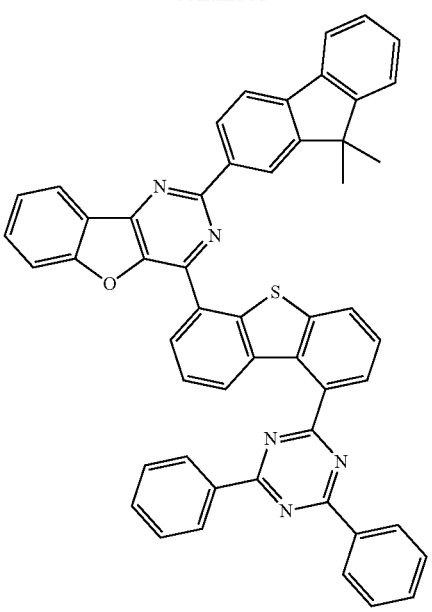
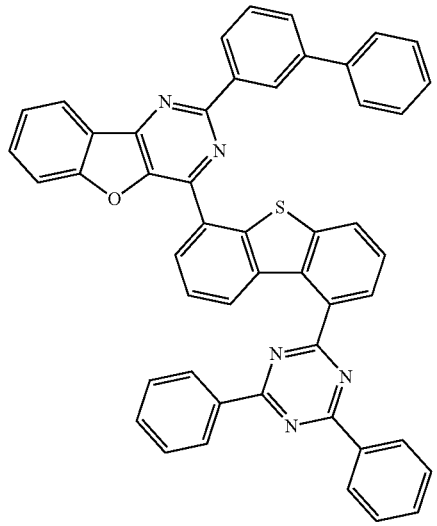
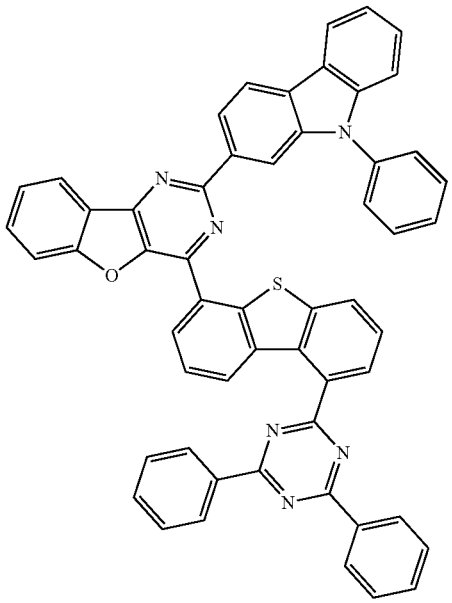

287
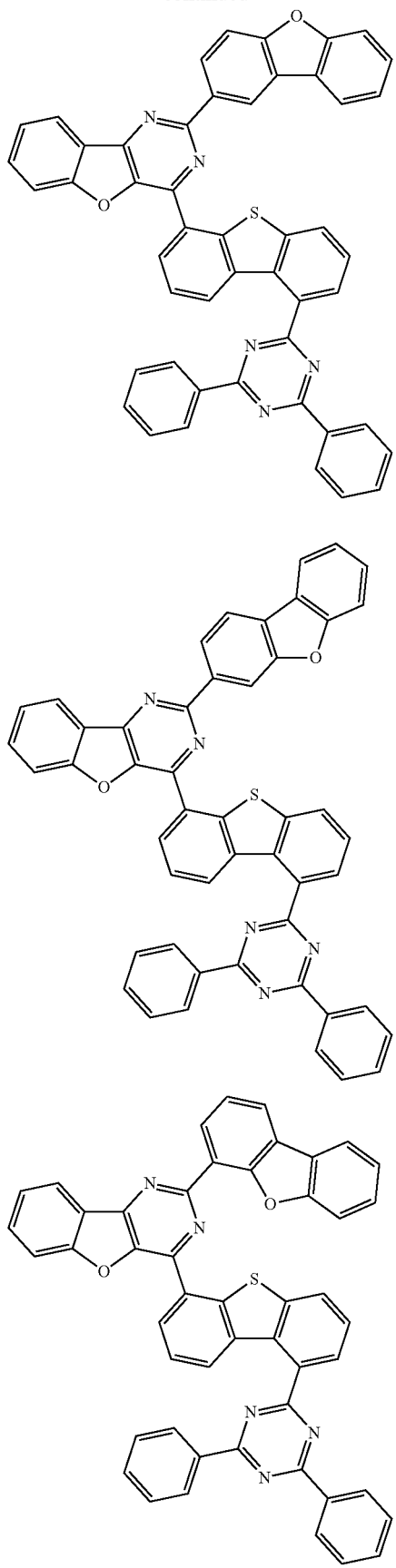
288
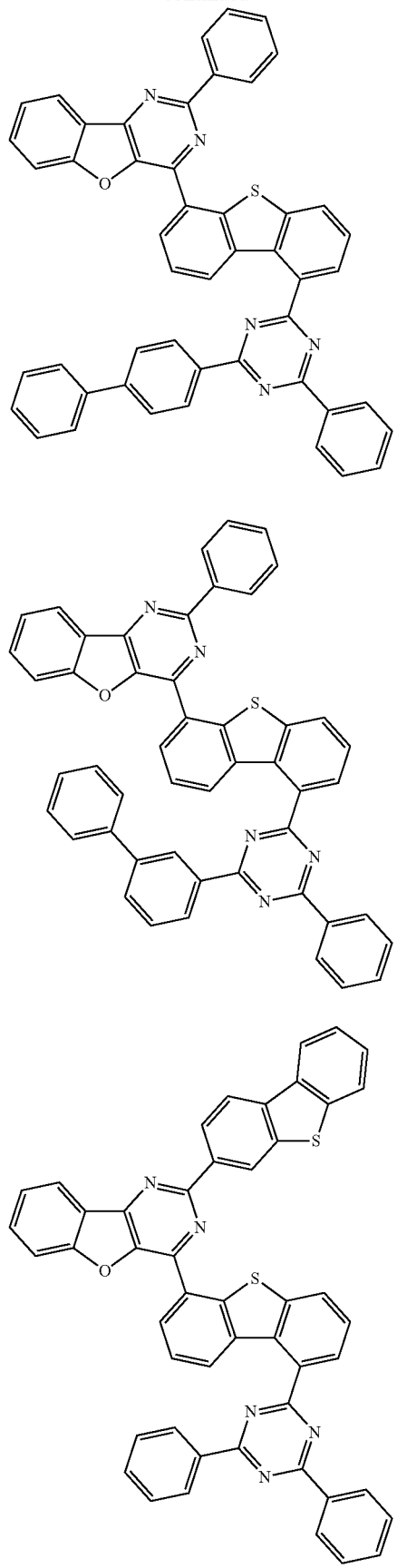

289
-continued
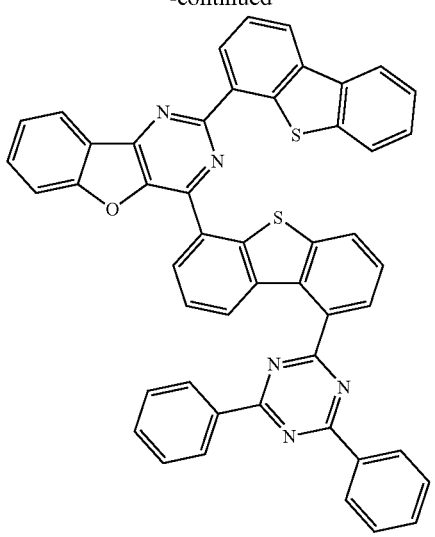
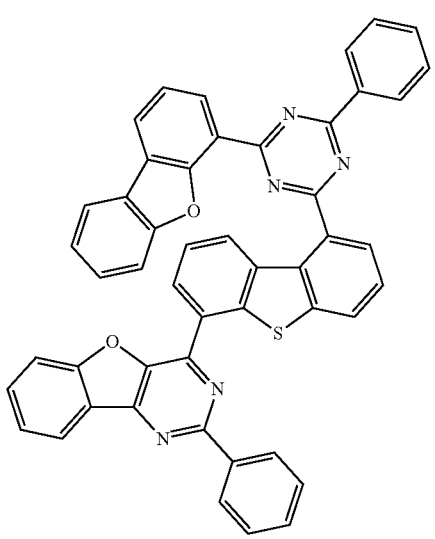
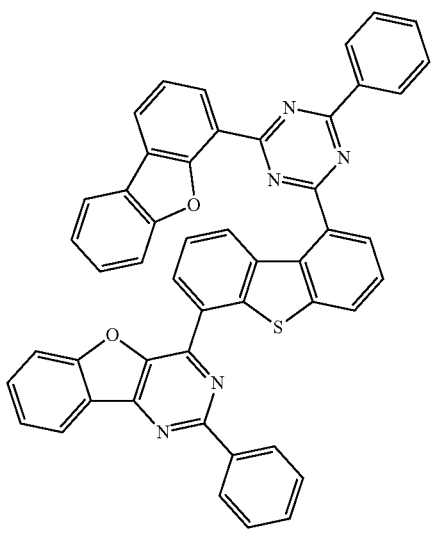
290
-continued
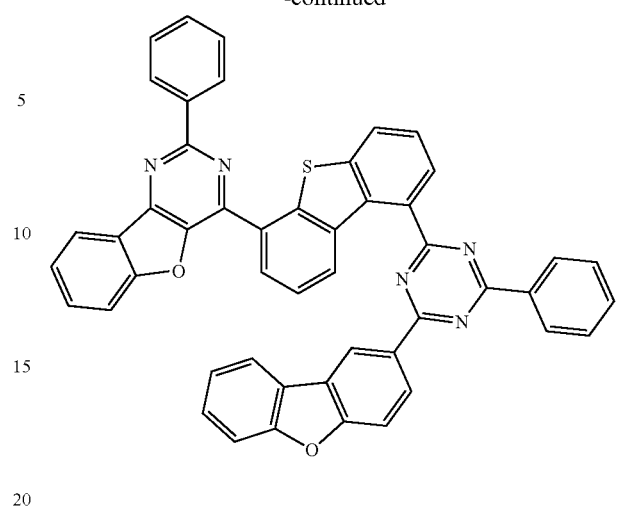
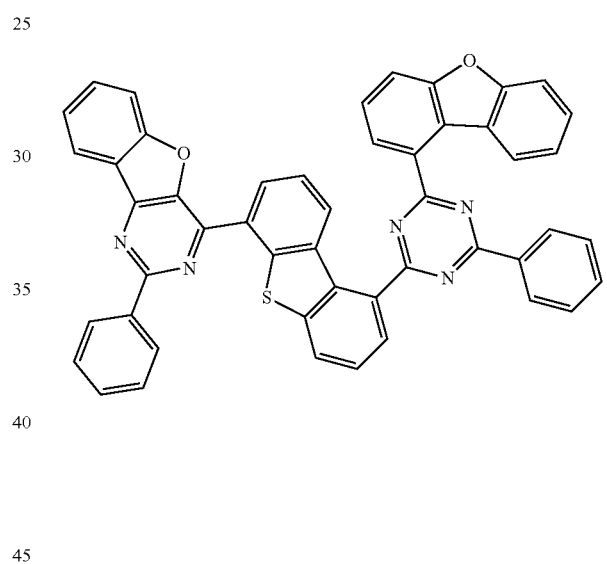
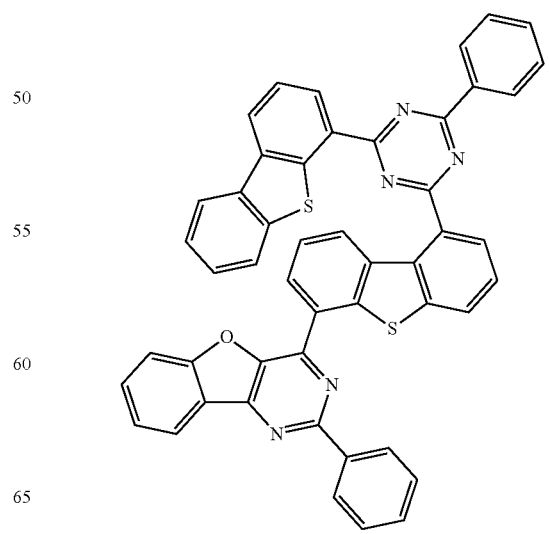

-continued
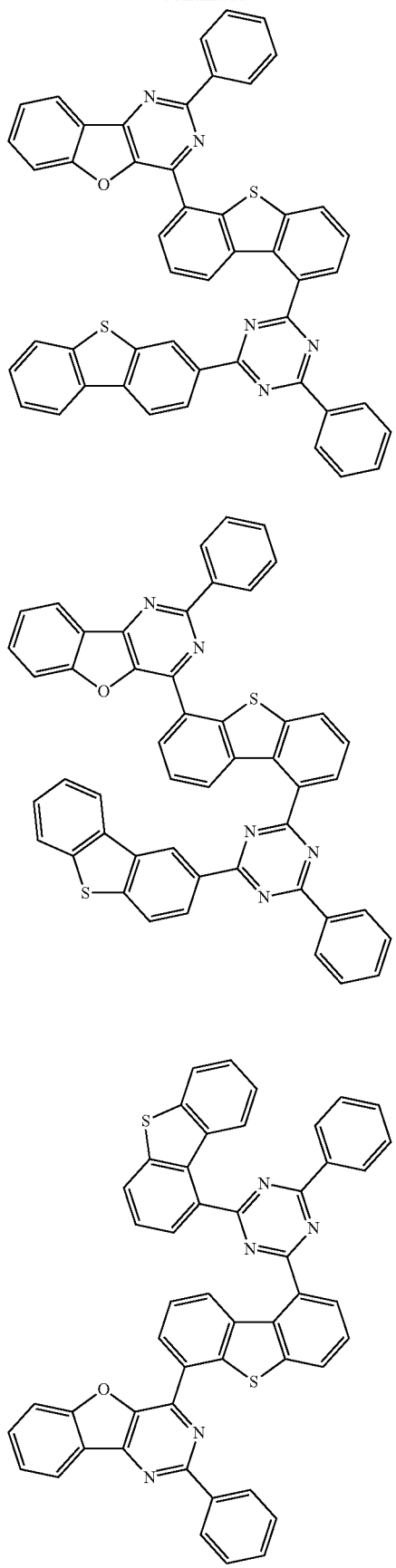
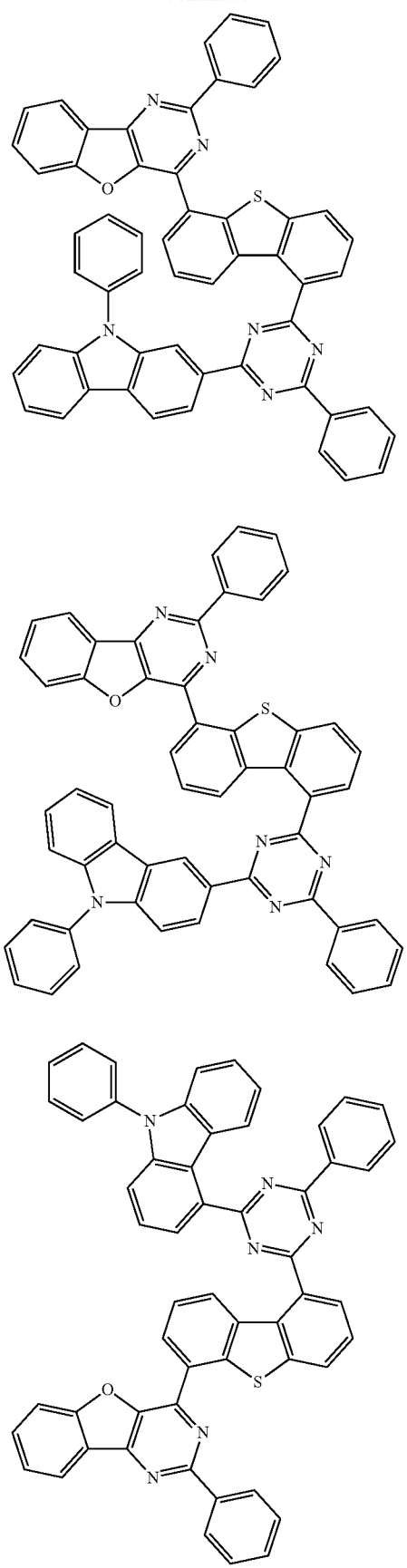

293
-continued
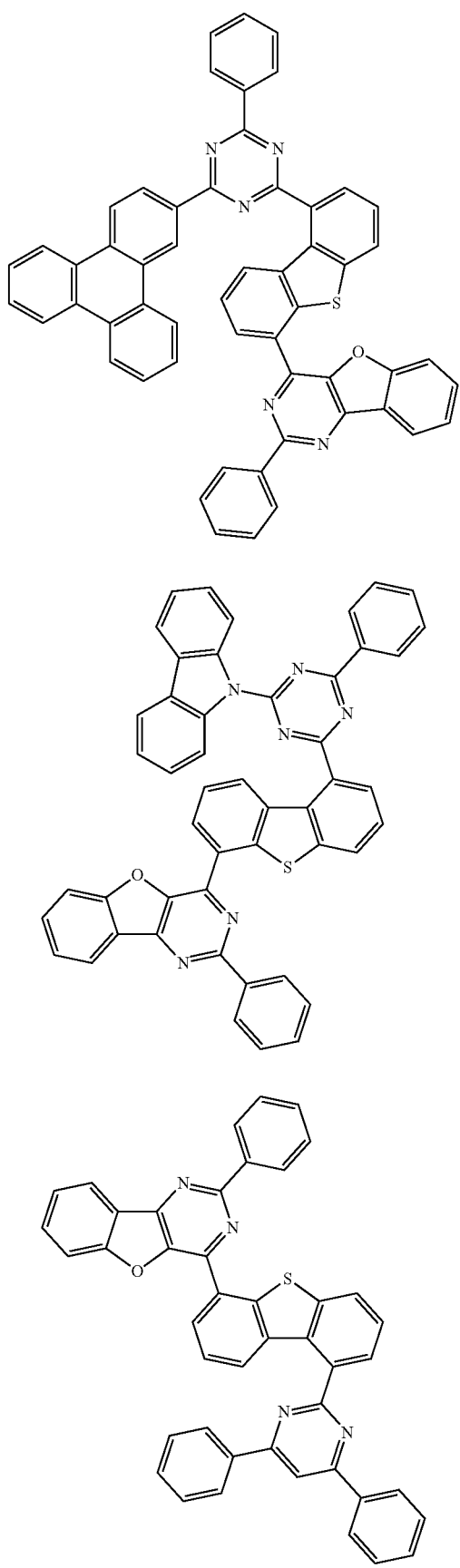
294
-continued
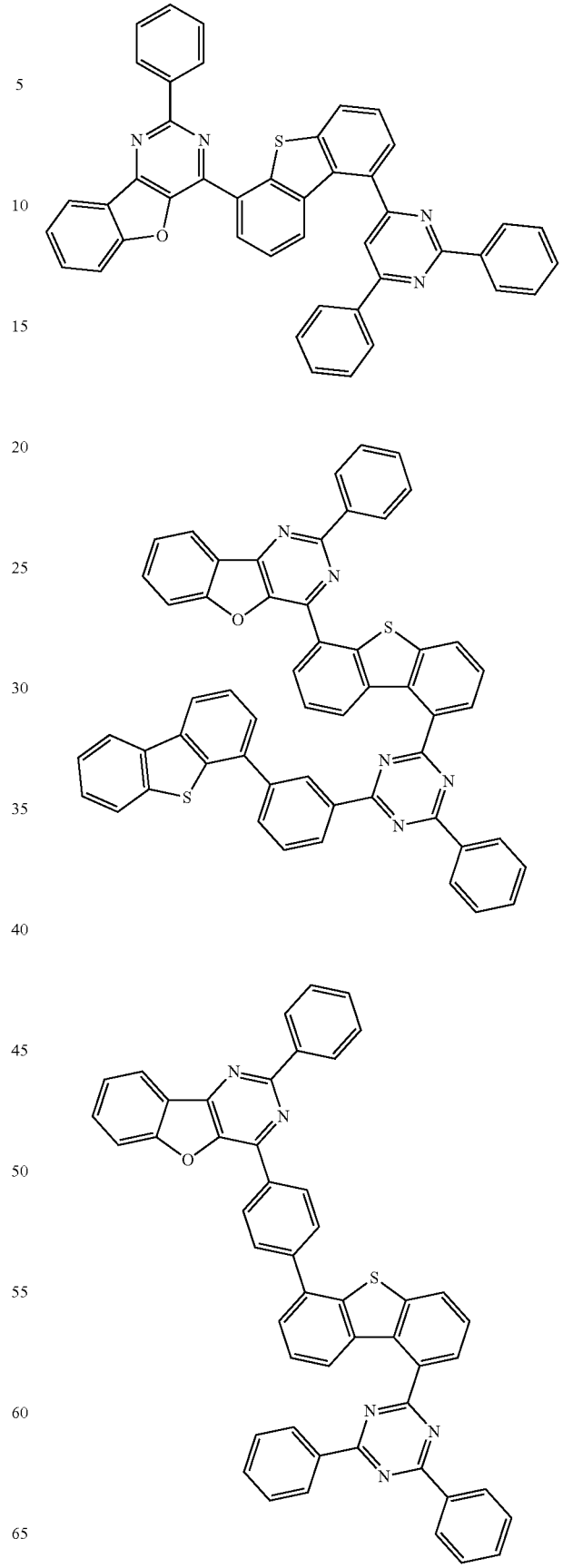

-continued

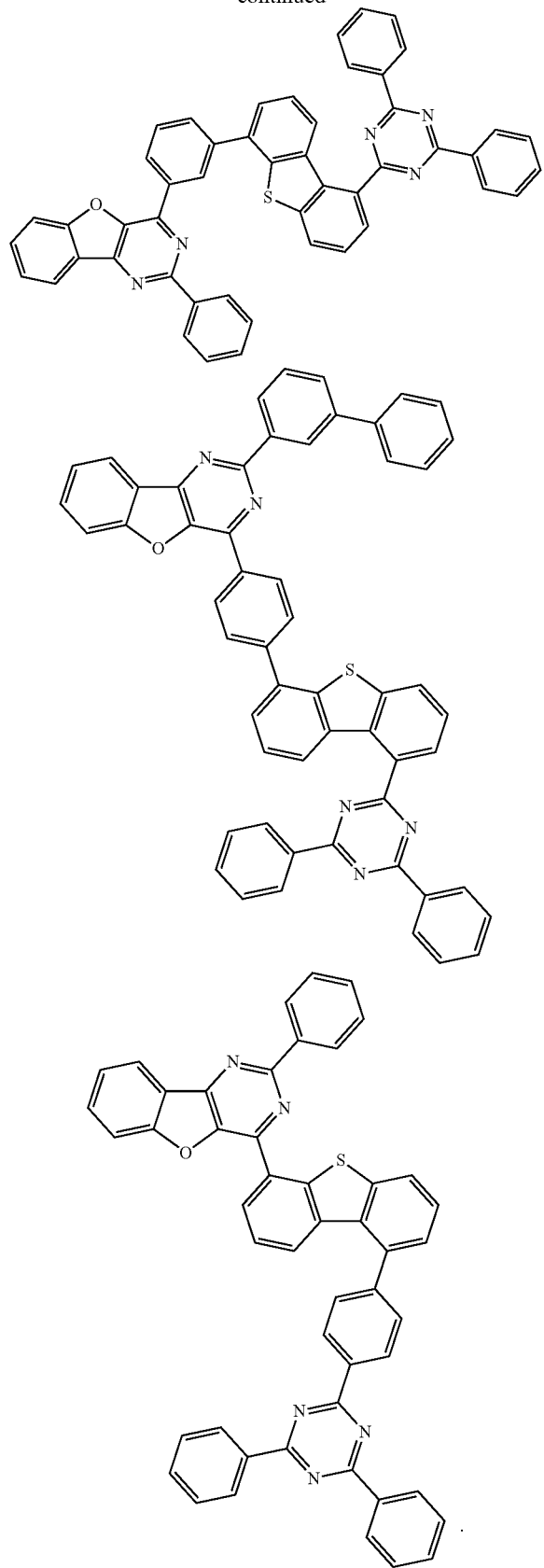

Since the compound represented by Formula 1 has a structure that simultaneously has a substituent such as triazine (pyridine, pyrimidine) substituted at the 1-position of the dibenzofuran (dibenzothiophene) core and the above-described substituent Het, it is possible to exhibit excellent heat resistance and suppress crystallization during the operation of the device. Therefore, the organic light emitting device using the same can have high efficiency, a low driving voltage, high luminance, a long lifetime, and the like.

The compound represented by Formula 1 may be prepared according to the preparation method as shown in Reaction Scheme 1 below.

[Reaction Scheme 1]

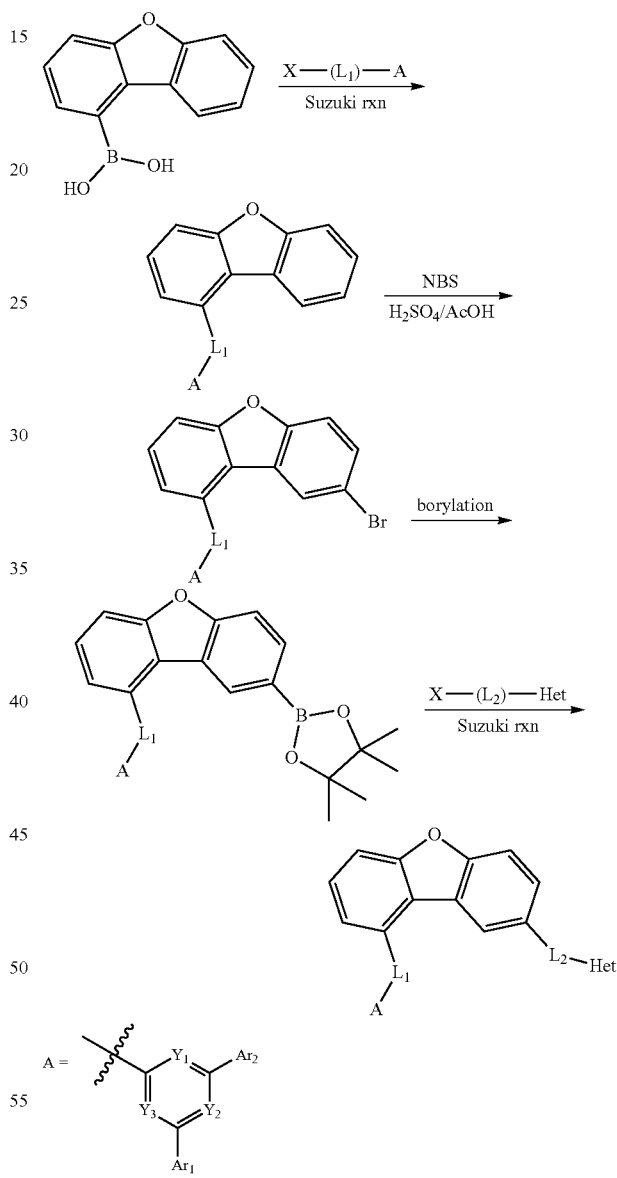

In Reaction Scheme 1, $L_1$, $L_2$, $Y_1$, $Y_2$, $Y_3$, $Ar_1$, $Ar_2$, and Het are as defined above. The type of the reactive group and the catalyst used in the above reaction scheme can be appropriately changed.

In addition, the present disclosure provides an organic light emitting device including the compound represented by Formula 1. In one example, the present disclosure provides an organic light emitting device including: a first electrode;

a second electrode provided at a side opposite to the first electrode; and at least one layer of organic material layers provided between the first electrode and the second electrode, wherein the at least one layer of the organic material layers includes a compound represented by Formula 1.

The organic material layer of the organic light emitting device of the present disclosure may have a single layer structure, or it may have a multilayered structure in which two or more organic material layers are stacked. For example, the organic light emitting device of the present disclosure may have a structure including a hole injection layer, a hole transport layer, a light emitting layer, an electron transport layer, an electron injection layer, and the like as the organic material layer. However, the structure of the organic light emitting device is not limited thereto, and it may include a smaller number of organic layers.

The organic material layer may include a hole injection layer, a hole transport layer, or a layer simultaneously performing hole injection and transport, wherein the hole injection layer, the hole transport layer, and the layer simultaneously performing hole injection and transport include a compound represented by Formula 1.

The organic material layer may include a light emitting layer, wherein the light emitting layer includes a compound represented by Formula 1.

The organic material layer may include an electron transport layer or an electron injection layer, wherein the electron transport layer or the electron injection layer includes a compound represented by Formula 1.

The electron transport layer, the electron injection layer, and the layer simultaneously performing electron injection and electron transport include a compound represented by Formula 1. In particular, the compound represented by Formula 1 according to one embodiment of the present invention has excellent thermal stability, a deep HOMO level of 6.0 eV or more, and high triplet energy (ET) and hole stability. Further, when the compound represented by Formula 1 is used for an organic material layer capable of simultaneously performing electron injection and electron transport, the n-type dopant used in the art can be mixed and used.

The organic material layer may include a light emitting layer and an electron transport layer, wherein the electron transport layer may include a compound represented by Formula 1.

The organic light emitting device according to the present disclosure may be a normal type of organic light emitting device in which an anode, at least one organic material layer, and a cathode are sequentially stacked on a substrate. The organic light emitting device according to the present disclosure may be an inverted type of organic light emitting device in which a cathode, at least one organic material layer, and an anode are sequentially stacked on a substrate. For example, the structure of an organic light emitting device according to an embodiment of the present invention is illustrated in FIGS. 1 and 2.

FIG. 1 shows an example of an organic light emitting device including a substrate 1, an anode 2, a light emitting layer 3, and a cathode 4. In such a structure, the compound represented by Formula 1 may be included in the light emitting layer.

FIG. 2 shows an example of an organic light emitting device including a substrate 1, an anode 2, a hole injection layer 5, a hole transport layer 6, a light emitting layer 7, an electron transport layer 8, and a cathode 4. In such a structure, the compound represented by Formula 1 may be included in at least one layer of the hole injection layer, the hole transport layer, the light emitting layer, and the electron transport layer.

The organic light emitting device according to the present disclosure may be manufactured by materials and methods known in the art, except that at least one layer of the organic material layers includes the compound represented by Formula 1. In addition, when the organic light emitting device includes a plurality of organic material layers, the organic material layers may be formed of the same material or different materials.

For example, the organic light emitting device according to the present disclosure can be manufactured by sequentially stacking a first electrode, an organic material layer, and a second electrode on a substrate. In this case, the organic light emitting device may be manufactured by depositing a metal, metal oxides having conductivity, or an alloy thereof on the substrate by using a PVD (physical vapor deposition) method such as a sputtering method or an e-beam evaporation method to form the anode, forming an organic material layer including the hole injection layer, the hole transport layer, the light emitting layer, and the electron transport layer thereon, and then depositing a material that can be used as the cathode thereon. In addition to such a method, the organic light emitting device may be manufactured by sequentially depositing a cathode material, an organic material layer, and an anode material on a substrate.

In addition, the compound represented by Formula 1 may be formed into an organic layer by a solution coating method as well as a vacuum deposition method at the time of manufacturing an organic light emitting element. Herein, the solution coating method means spin coating, dip coating, doctor blading, inkjet printing, screen printing, a spray method, roll coating, or the like, but is not limited thereto.

In addition to such a method, the organic light emitting device may be manufactured by sequentially depositing a cathode material, an organic material layer, and an anode material on a substrate (International Publication WO 2003/012890). However, the manufacturing method is not limited thereto.

For example, the first electrode is an anode and the second electrode is a cathode, or the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or SnO$_2$:Sb; conductive polymers such as poly(3-methylthiophene), poly[3,4-(ethylene-1,2-dioxy)thiophene](PEDOT), polypyrrole, and polyaniline; and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or LiO$_2$/Al; and the like, but are not limited thereto.

The hole injection layer is a layer for injecting holes from the electrode, and the hole injection material is preferably a compound which has an ability to transport the holes, a hole injecting effect in the anode, and an excellent hole injecting effect to the light emitting layer or the light emitting material, prevents movement of an exciton generated in the light emitting layer to the electron injection layer or the electron injection material, and has an excellent thin film forming ability. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline, and a polythiophene-based conductive polymer, and the like, but are not limited thereto.

The hole transport layer is a layer that receives holes from a hole injection layer and transports the holes to the light emitting layer. The hole transport material is suitably a material having large mobility to the holes, which may receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The light emitting material is a material capable of emitting light in the visible light region by combining holes and electrons respectively transported from the hole transport layer and the electron transport layer, and having good quantum efficiency for fluorescence or phosphorescence. Specific examples include an 8-hydroxy-quinoline aluminum (Alq$_3$) complex; carbazole-based compounds; dimerized styryl compounds; BAlq; 10-hydroxybenzoquinoline-metal compounds; benzoxazole, benzothiazole and benzimidazole-based compounds; poly(p-phenylenevinylene)(PPV)-based polymers; spiro compounds; and polyfluorene, rubrene, and the like, but are not limited thereto.

The light emitting layer may include a host material and a dopant material, and the compound of the present disclosure may be included as a host material in the light emitting layer. The host material may be a fused aromatic ring derivative, a heterocycle-containing compound, or the like. Specific examples of the fused aromatic ring derivatives include anthracene derivatives, pyrene derivatives, naphthalene derivatives, pentacene derivatives, phenanthrene compounds, and fluoranthene compounds. Examples of heterocyclic compounds include carbazole derivatives, dibenzofuran derivatives, ladder-type furan compounds, pyrimidine derivatives, and the like, but are not limited thereto.

Examples of the dopant material include an aromatic amine derivative, a styrylamine compound, a boron complex, a fluoranthene compound, a metal complex, and the like. Specific examples of the aromatic amine derivatives include substituted or unsubstituted fused aromatic ring derivatives having an arylamino group, examples thereof include pyrene, anthracene, chrysene, and periflanthene having the arylamino group, and the like, the styrylamine compound is a compound where at least one arylvinyl group is substituted in a substituted or unsubstituted arylamine, in which one or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transport layer is a layer receiving the electrons from the electron injection layer and transporting the electrons to the light emitting layer, and the electron transport material is a material that can receive the electrons well from the cathode and transport the electrons to the light emitting layer, wherein a material having large mobility to the electrons is suitable. Specific examples thereof include an 8-hydroxyquinoline Al complex; a complex including Alq$_3$; an organic radical compound; a hydroxyflavone-metal complex; and the like, but are not limited thereto. The electron transport layer may be used together with a predetermined desired cathode material as used according to the prior art. Particularly, an example of an appropriate cathode material is a general material having the low work function and followed by an aluminum layer or a silver layer. Specific examples thereof include cesium, barium, calcium, ytterbium, and samarium, and each case is followed by the aluminum layer or the silver layer.

The electron injection layer is a layer injecting the electrons from the electrode, and a compound which has an ability of transporting the electrons, an electron injecting effect from the cathode, and an excellent electron injecting effect to the light emitting layer or the light emitting material, prevents movement of an exciton generated in the light emitting layer to the hole injection layer, and has an excellent thin film forming ability is preferable. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone, and the like, and a derivative thereof, a metal complex compound, a nitrogen-containing 5-membered cycle derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato) (o-cresolato)gallium, bis(2-methyl-8-quinolinato) (1-naphtholato)aluminum, bis(2-methyl-8-quinolinato) (2-naphtholato)gallium, and the like, but are not limited thereto.

The organic light emitting device according to the present disclosure may be a front side emission type, a back side emission type, or a double side emission type according to the material used.

In addition, the compound represented by Formula 1 may be included in an organic solar cell or an organic transistor in addition to an organic light emitting device.

The preparation of the compound represented by Formula 1 and the organic light emitting device including the same will be described in detail in the following examples. However, these examples are presented for illustrative purposes only, and the scope of the present invention is not limited thereto.

Preparation Example 1

Preparation Example 1-1: Synthesis of Intermediate Compound A-4

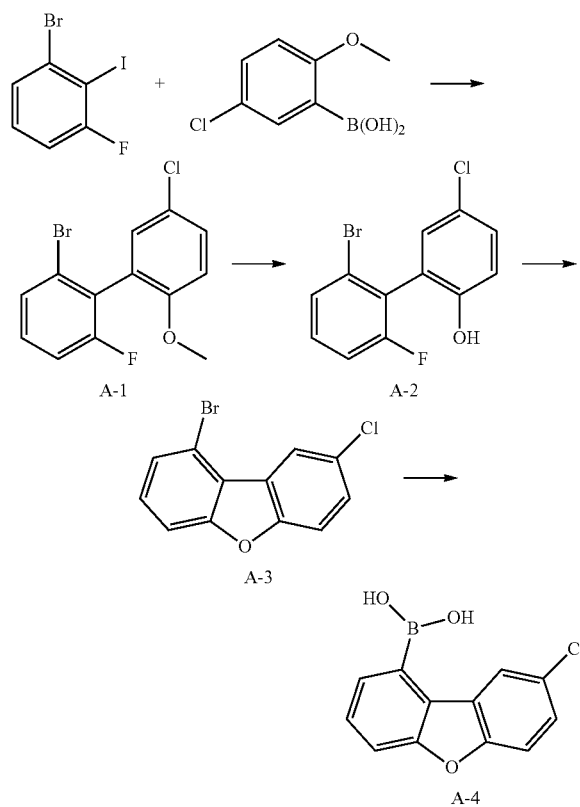

1) Preparation of Compound A-1

1-bromo-3-fluoro-2-iodobenzene (75 g, 249.3 mmol), and (5-chloro-2-methoxyphenyl)boronic acid (51.1 g, 249.3 mmol) were dissolved in 550 mL of tetrahydrofuran. A 2 M sodium carbonate ($Na_2CO_3$) solution (350 mL) and tetrakis(triphenylphosphine)palladium(0) (2.88 g, 2.49 mmol) were added thereto and refluxed for 11 hours. After the reaction was completed, the reaction mixture was cooled to room temperature. The aqueous layer was separated and removed, dried over anhydrous magnesium sulfate, and concentrated under reduced pressure. The resulting mixture was recrystallized using chloroform and ethanol to obtain Compound A-1 (63.2 g, yield 80%; MS:[M+H]$^+$=314).

2) Preparation of Compound A-2

Compound A-1 (63.2 g, 200.3 mmol) was dissolved in 750 mL of dichloromethane and then cooled to 0° C. Boron tribromide (20.0 mL, 210.3 mmol) was slowly added dropwise and then stirred for 12 hours. After the reaction was completed, the reaction mixture was washed three times with water, dried over magnesium sulfate, and filtered. The filtrate was distilled under reduced pressure and purified by column chromatography to obtain Compound A-2 (57.9 g, yield 96%; MS:[M+H]$^+$=300).

3) Preparation of Compound A-3

Compound A-2 (57.9 g, 192.0 mmol) and calcium carbonate (79.6 g, 576.0 mol) were dissolved in 350 mL of N-methyl-2-pyrrolidone and then heated and stirred for 2 hours. After lowering the temperature to room temperature, the reaction mixture was subjected to reverse precipitation in water and filtered. The mixture was completely dissolved in dichloromethane, washed with water, dried over anhydrous magnesium sulfate, concentrated under reduced pressure, recrystallized using ethanol, and dried to obtain Compound A-3 (42.1 g, yield 78%; MS: [M+H]$^+$=280).

4) Preparation of Compound A-4

After Compound A-3 (42.1 g, 149.5 mmol) was dissolved in tetrahydrofuran (330 mL), the temperature was lowered to −78° C. and 2.5 M tert-butyllithium (t-BuLi) (60.4 mL, 151.0 mmol) was added slowly. The mixture was stirred at the same temperature for 1 hour, and then triisopropylborate (51.8 mL, 224.3 mmol) was added thereto, and stirred for 3 hours while gradually raising the temperature to room temperature. To the reaction mixture was added a 2N aqueous hydrochloric acid solution (300 mL) and the mixture was stirred at room temperature for 1.5 hours. The resulting precipitate was filtered, washed with water and ethyl ether, and then vacuum dried to obtain Compound A-4 (34.3 g, yield 93%; MS: [M+H]$^+$=247).

Preparation Example 1-2: Synthesis of Intermediate Compound B-5

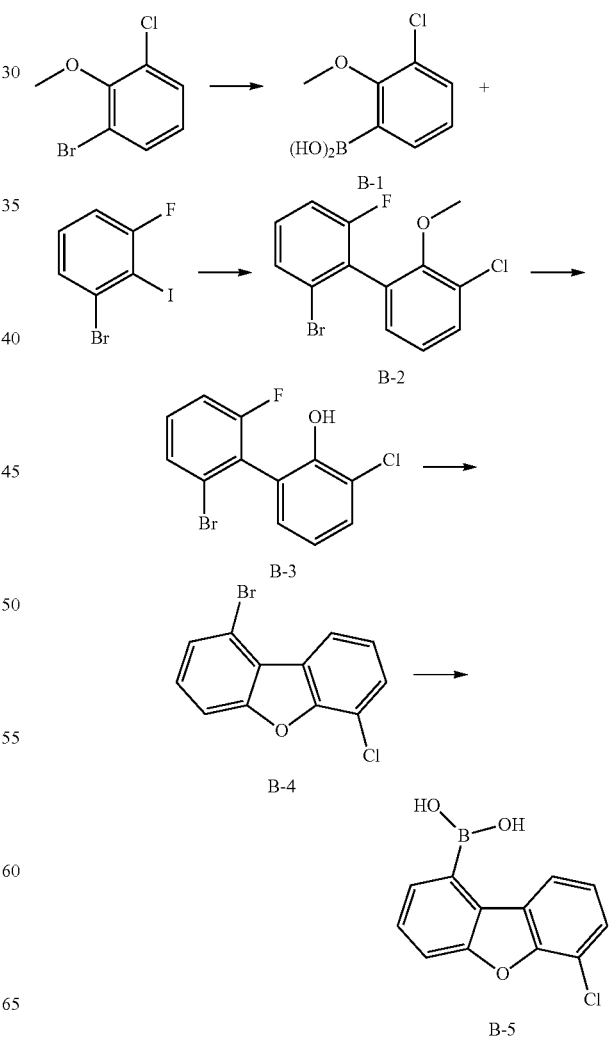

1) Preparation of Compound B-1

After 1-bromo-3-fluoro-2-methoxybenzene (100.0 g, 451.5 mmol) was dissolved in tetrahydrofuran (1000 mL), the temperature was lowered to −78° C. and 2.5 M tert-butyl lithium (t-BuLi) (182.4 mL, 456.0 mmol) was slowly added dropwise. The mixture was stirred at the same temperature for 1 hour, and triisopropylborate (B(OiPr)$_3$) (156.3 mL, 677.3 mmol) was added thereto and stirred for 3 hours while gradually raising the temperature to room temperature. A 2N aqueous hydrochloric acid solution (150 mL) was added to the reaction mixture and the mixture was stirred at room temperature for 1.5 hours. The resulting precipitate was filtered, washed sequentially with water and ethyl ether, and then vacuum dried. After drying, it was recrystallized with chloroform and ethyl acetate and dried to produce Compound B-1 (84.2 g, yield 90%; MS: [M+H]$^+$=230).

2) Preparation of Compound B-2

Compound B-2 (74.6 g, yield 52%; MS:[M+H]$^+$=314) was prepared in the same manner as in the preparation of Compound A-1 of preparation Example 1, except that Compound B-1 (84.2 g, 451.7 mmol) was used instead of (5-chloro-2-methoxyphenyl) boronic acid.

3) preparation of Compound B-3

Compound B-3 (60.3 g, yield 85%; MS:[M+H]$^+$=300) was prepared in the same manner as in the preparation of Compound A-2, except that Compound B-2 (74.6 g, 236.4 mmol) was used instead of Compound A-1.

4) Preparation of Compound B-4

Compound B-4 (48.1 g, yield 85%; MS:[M+H]+=280) was prepared in the same manner as in the preparation of Compound A-3, except that Compound B-3 (60.3 g, 199.9 mmol) was used instead of Compound A-2.

5) Preparation of Compound B-5

Compound B-5 (40.1 g, yield 95%; MS:[M+H]$^+$=247) was prepared in the same manner as in the preparation of Compound A-4, except that Compound B-3 (48.1 g, 170.9 mmol) was used instead of Compound A-3.

Preparation Example 1-3: Synthesis of Intermediate Compound C-4

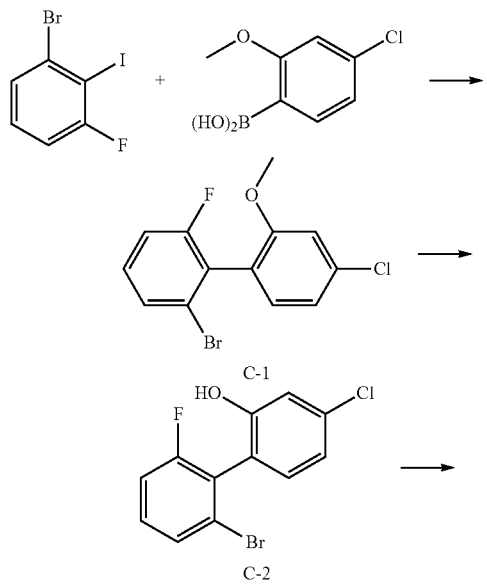

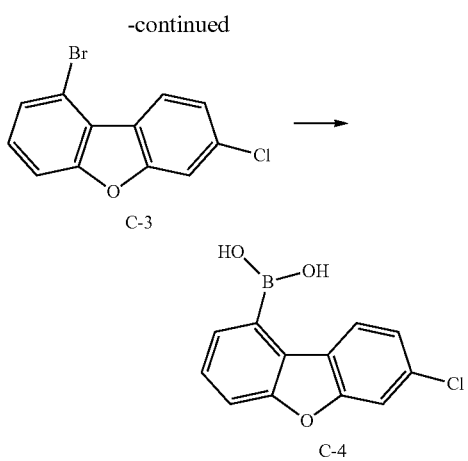

1) Preparation of Compound C-1

Compound C-1 (60.1 g, yield 76%; MS:[M+H]$^+$=314) was prepared in the same manner as in the preparation of Compound A-1 of preparation Example 1, except that (4-chloro-2-methoxyphenyl)boronic acid (51.1 g, 249.3 mmol) was used instead of (5-chloro-2-methoxyphenyl) boronic acid.

2) Preparation of Compound C-2

Compound C-2 (54.0 g, yield 94%; MS:[M+H]$^+$=300) was prepared in the same manner as in the preparation of Compound A-2, except that Compound C-1 (60.1 g, 190.4 mmol) was used instead of Compound A-1.

3) Preparation of Compound C-3

Compound C-3 (42.2 g, yield 83%; MS:[M+H]$^+$=280) was prepared in the same manner as in the preparation of Compound A-3, except that Compound C-2 (54.0 g, 179.1 mmol) was used instead of Compound A-2.

4) Preparation of Compound C-4

Compound C-4 (34.1 g, yield 92%; MS:[M+H]$^+$=247) was prepared in the same manner as in the preparation of Compound A-4, except that Compound C-3 (42.2 g, 170.9 mmol) was used instead of Compound A-3.

Preparation Example 1-4: Synthesis of Intermediate Compound D-4

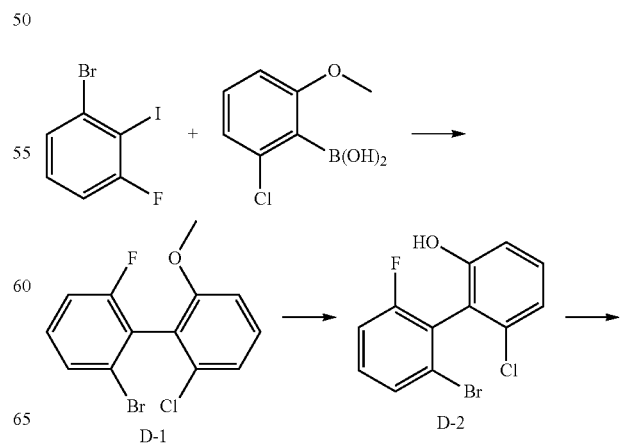

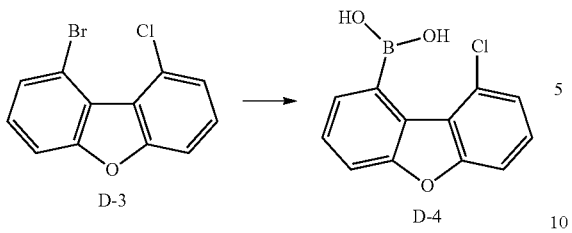

1) Preparation of Compound D-1

Compound D-1 (63.5 g, yield 81%; MS:[M+H]⁺=314) was prepared in the same manner as in the preparation of Compound A-1 of Preparation Example 1, except that (2-chloro-6-methoxyphenyl)boronic acid (51.1 g, 249.3 mmol) was used instead of (5-chloro-2-methoxyphenyl) boronic acid.

2) Preparation of Compound D-2

Compound D-2 (55.1 g, yield 91%; MS:[M+H]⁺=300) was prepared in the same manner as in the preparation of Compound A-2, except that Compound D-1 (63.5 g, 201.2 mmol) was used instead of Compound A-1.

3) Preparation of Compound D-3

Compound D-3 (42.0 g, yield 82%; MS:[M+H]⁺=280) was prepared in the same manner as in the preparation of Compound A-3, except that Compound D-2 (55.1 g, 182.7 mmol) was used instead of Compound A-2.

4) Preparation of Compound D-4

Compound D-4 (35.7 g, yield 85%; MS:[M+H]⁺=247) was prepared in the same manner as in the preparation of Compound A-4, except that Compound D-3 (42.0 g, 149.2 mmol) was used instead of Compound A-3.

Preparation Example 2

Preparation Example 2-1: Synthesis of Intermediate Compound A-6

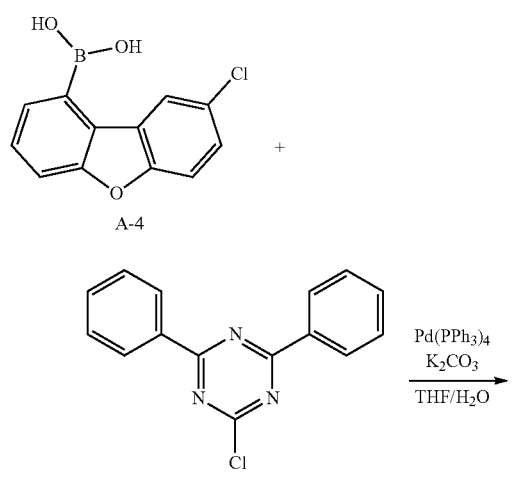

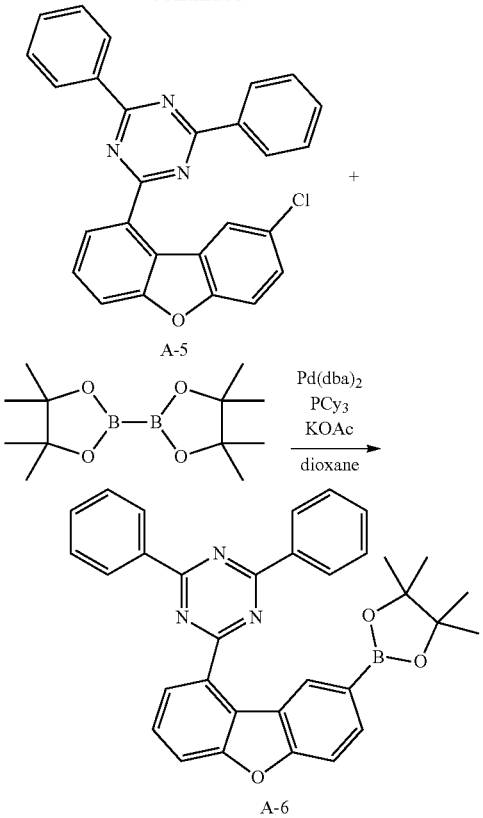

1) Preparation of Compound A-5

Compound A-4 (20.0 g, 61 mmol) and 2-chloro-4,6-diphenyltriazine (16.3 g, 61 mmol) were dissolved in 200 mL of tetrahydrofuran in a 500 mL round bottom flask under a nitrogen atmosphere. Then, a 1.5 M potassium carbonate aqueous solution (100 mL) was added and tetrakis(triphenylphosphine)palladium (0.93 g, 1.8 mmol) were added thereto, and then stirred while heating for 7 hours. The temperature of the mixture was lowered to room temperature, the aqueous layer was separated and removed, dried over anhydrous magnesium sulfate, and concentrated under reduced pressure. The resulting material was recrystallized using a mixed solution of tetrahydrofuran and ethyl acetate, and dried to produce Compound A-5 (20.5 g, yield 78%, MS:[M+H]⁺=434).

2) Preparation of Compound A-6

Under a nitrogen atmosphere, Formula A-5 (20.5 g, 47 mmol), bis(pinacolato)diboron (13.2 g, 52 mmol), and potassium acetate (16.2 g, 165 mmol) were mixed and added to 250 ml of dioxane and heated while stirring.

Bis(dibenzylidineacetone)palladium (0.81 g, 1 mmol) and tricyclohexylphosphine (0.8 g, 2 mmol) were added thereto under reflux and stirred while heating for 13 hours. After the reaction was completed, the reaction solution was cooled to room temperature and then filtered. The filtrate was poured into water, extracted with chloroform, and the organic layer was dried over anhydrous magnesium sulfate. The resulting material was distilled under reduced pressure and recrystallized from ethyl acetate to produce Formula A-6 (20.7 g, 83%).

Preparation Example 2-2: Synthesis of Intermediate Compound A-8

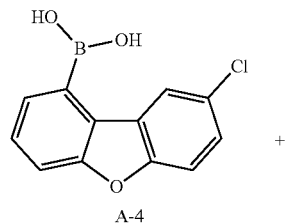

A-4

+

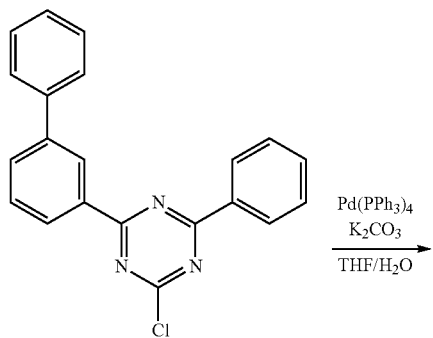

Pd(PPh₃)₄
K₂CO₃
─────→
THF/H₂O

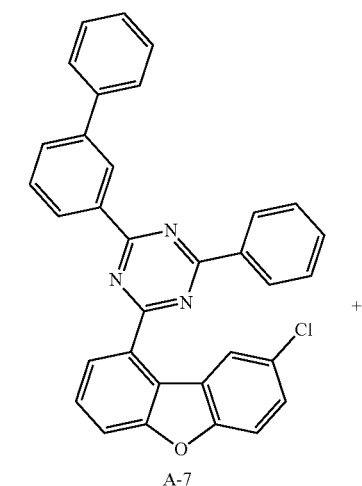

A-7

+

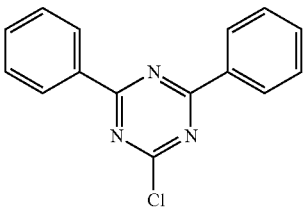

Pd(dba)₂
PCy₃
KOAc
─────→
dioxane

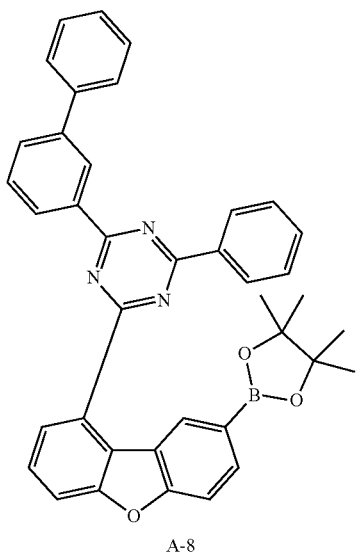

A-8

1) Preparation of Compound A-7

Compound A-7 (14.2 g, yield 68%, MS:[M+H]⁺=510) was prepared in the same manner as in the preparation of Compound A-5, except that 2-([1,1'-biphenyl]-3-yl)-4-chloro-6-phenyl-1,3,5-triazine was used instead of 2-chloro-4,6-diphenyltriazine.

2) Preparation of Compound A-8

Compound A-8 (13.9 g, yield 82%, MS:[M+H]⁺=602) was prepared in the same manner as in the preparation of Compound A-6, except that Compound A-7 was used instead of Compound A-5.

Preparation Example 3-1: Synthesis of Intermediate Compound B-7

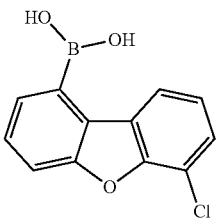

B-5

+

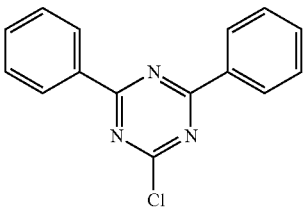

Pd(PPh₃)₄
K₂CO₃
─────→
THF/H₂O

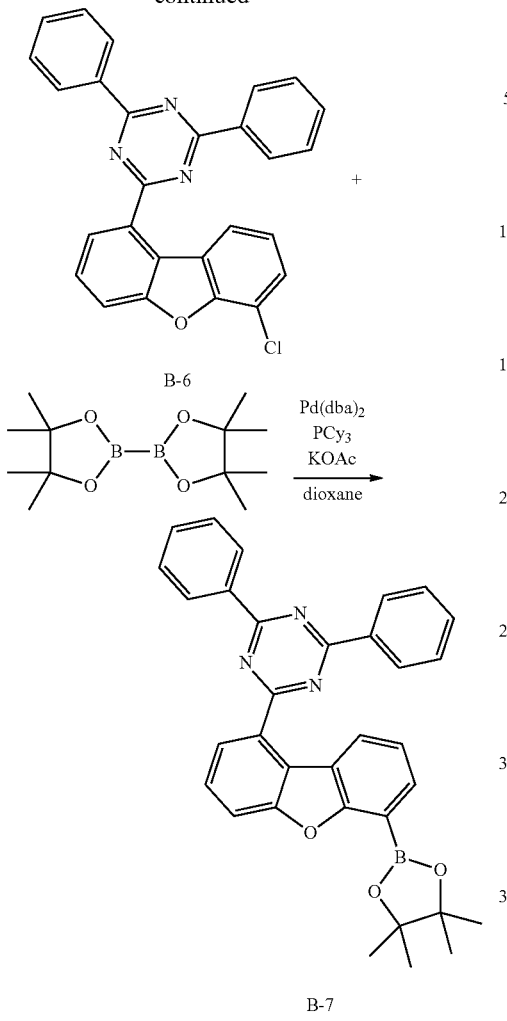

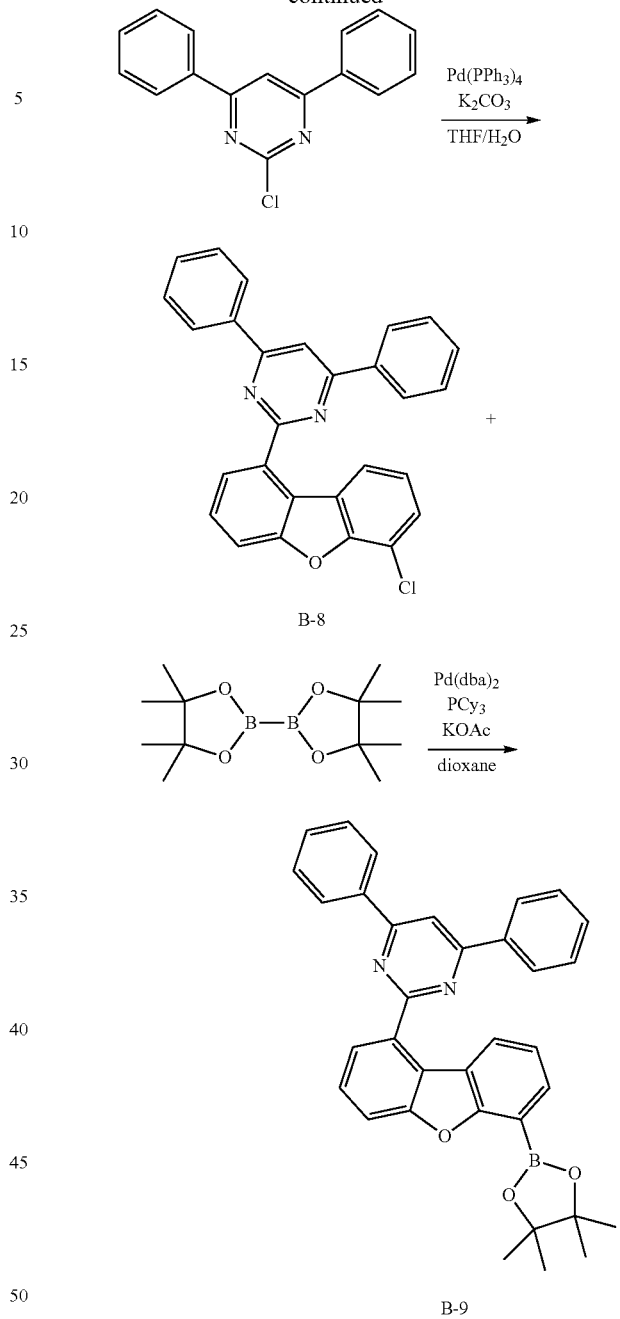

1) Preparation of Compound B-6

Compound B-6 (14.2 g, yield 82%, MS:[M+H]⁺=434) was prepared in the same manner as in the preparation of Compound A-5, except that Compound B-5 was used instead of Compound A-4.

2) Preparation of Compound B-7

Compound B-7 (15.0 g, yield 82%, MS:[M+H]⁺=526) was prepared in the same manner as in the preparation of Compound A-6, except that Compound B-6 was used instead of Compound A-5.

Preparation Example 3-2: Synthesis of Intermediate Compound B-9

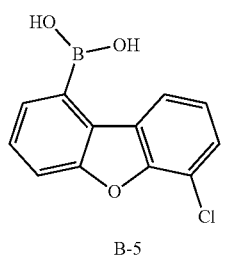

1) Preparation of Compound B-8

Compound B-8 (13.4 g, yield 76%, MS:[M+H]⁺=433) was prepared in the same manner as in the preparation of Compound A-5, except that Compound B-5 and 2-chloro-4,6-diphenylpyrimidine were used instead of Compound A-4 and 2-chloro-4,6-diphenyltriazine.

2) Preparation of Compound B-9

Compound B-9 (10.4 g, yield 64%, MS:[M+H]⁺=525) was prepared in the same manner as in the preparation of Compound A-6, except that Compound B-8 was used instead of Compound A-5.

Preparation Example 3-3: Synthesis of Intermediate Compound B-11

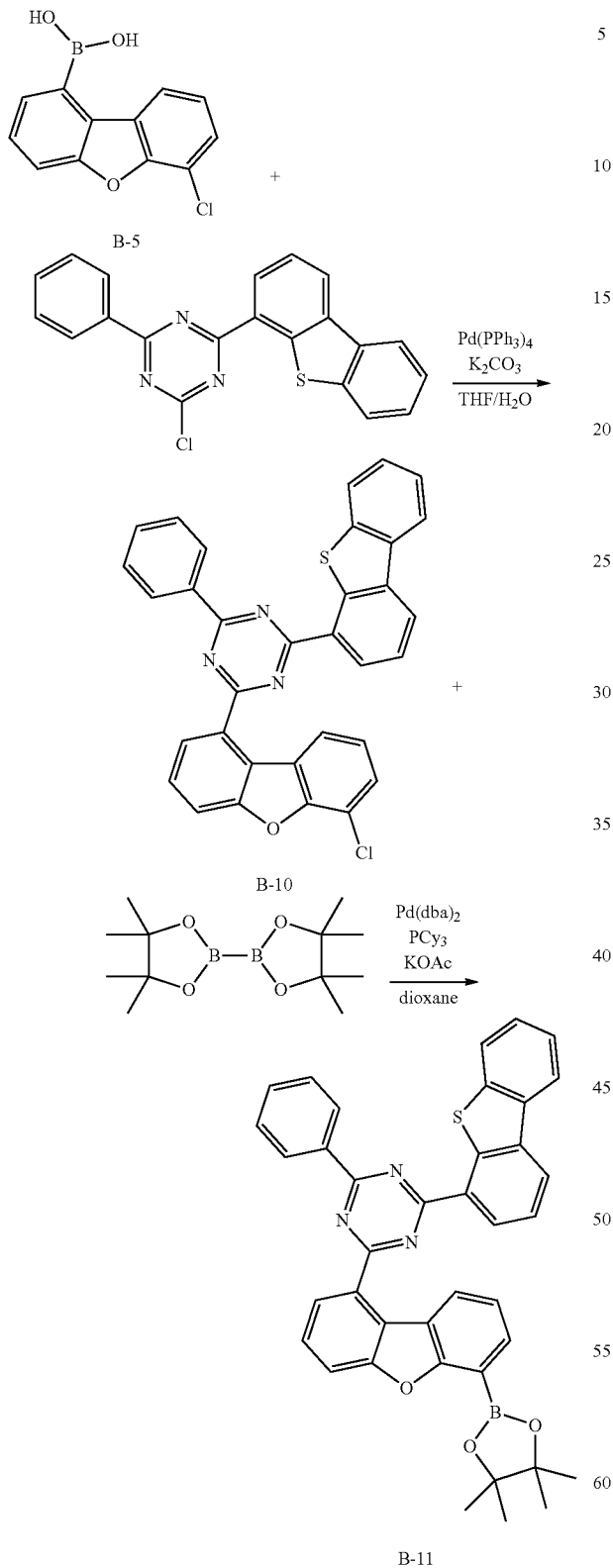

B-11

1) Preparation of Compound B-10

Compound B-10 (14.5 g, yield 66%, MS:[M+H]$^+$=541) was prepared in the same manner as in the preparation of Compound A-5, except that Compound B-5 and 2-chloro-4-(dibenzothiophen-4-yl)-6-phenyl-1,3,5-triazine were used instead of Compound A-4 and 2-chloro-4,6-diphenyltriazine.

2) Preparation of Compound B-11

Compound B-11 (10.6 g, yield 63%, MS:[M+H]$^+$=632) was prepared in the same manner as in the preparation of Compound A-6, except that Compound B-10 was used instead of Compound A-5.

Preparation Example 3-4: Synthesis of Intermediate Compound B-13

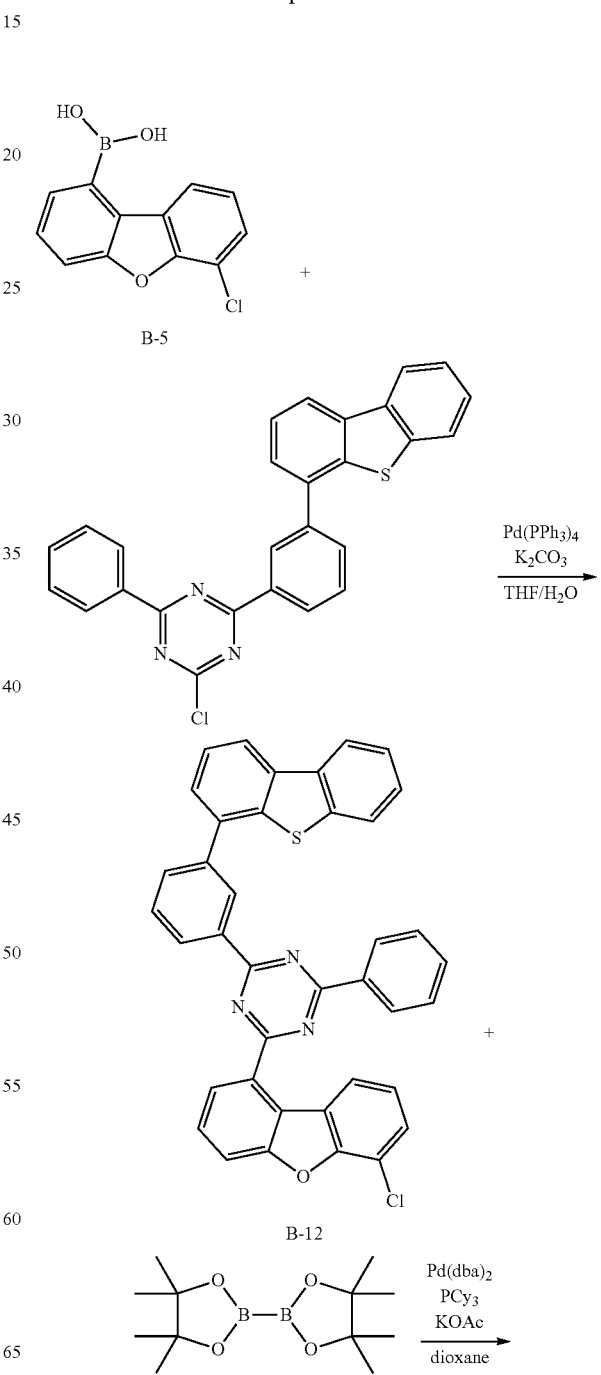

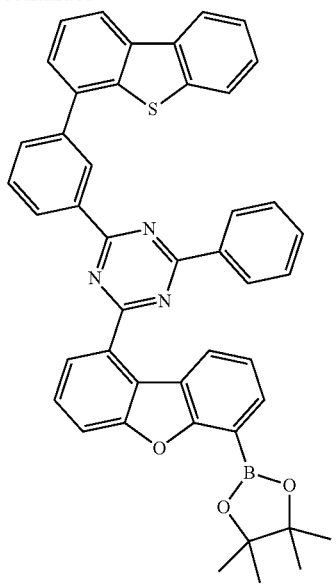

B-13

1) Preparation of Compound B-12

Compound B-12 (16.2 g, yield 65%, MS:[M+H]⁺=616) was prepared in the same manner as in the preparation of Compound A-5, except that Compound B-5 and 3-(4-chloro-6-(3-dibenzothiophen-4-yl)phenyl)-6-phenyl-1,3,5-triazine were used instead of Compound A-4 and 2-chloro-4,6-diphenyltriazine.

2) Preparation of Compound B-13

Compound B-13 (14.7 g, yield 79%, MS:[M+H]⁺=708) was prepared in the same manner as in the preparation of Compound A-6, except that Compound B-12 was used instead of Compound A-5.

Preparation Example 4-1: Synthesis of Intermediate Compound C-6

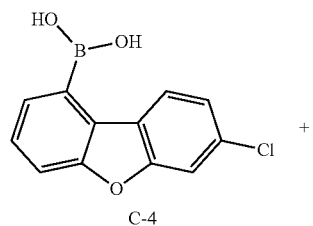

C-4

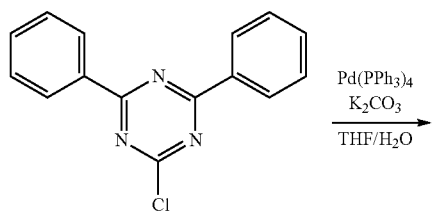

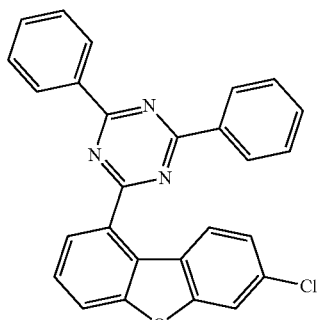

C-5

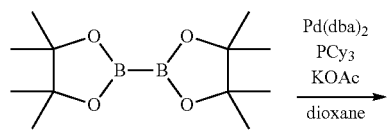

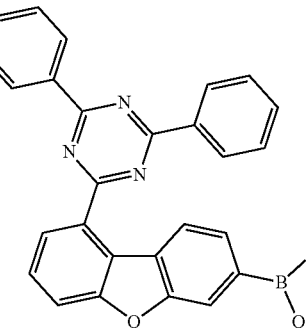

C-6

1) Preparation of Compound C-5

Compound C-5 (13.0 g, yield 77%, MS:[M+H]⁺=434) was prepared in the same manner as in the preparation of Compound A-5, except that Compound C-4 was used instead of Compound A-4.

2) Preparation of Compound C-6

Compound C-6 (12.8 g, yield 82%, MS:[M+H]⁺=526) was prepared in the same manner as in the preparation of Compound A-6, except that Compound C-5 was used instead of Compound A-5.

Preparation Example 4-2: Synthesis of Intermediate Compound C-8

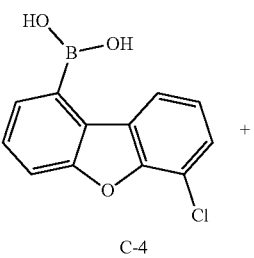

C-4

-continued

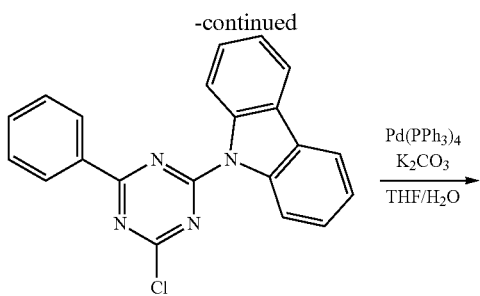

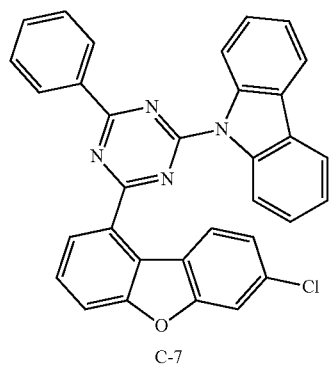

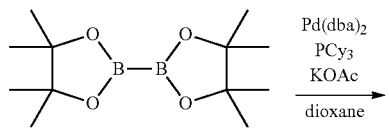

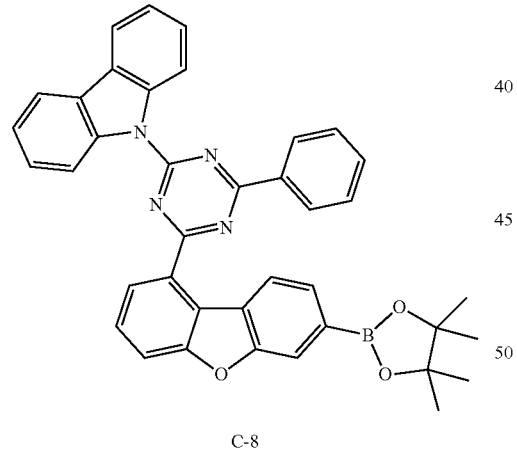

C-8

1) Preparation of Compound C-7

Compound C-7 (11.9 g, yield 56%, MS:[M+H]⁺=523) was prepared in the same manner as in the preparation of Compound A-5, except that Compound C-4 and 9-(4-chloro-6-phenyl-1,3,5-triazin-2-yl)-9H-carbazole were used instead of Compound A-4 and 2-chloro-4,6-diphenyltriazine.

2) Preparation of Compound C-8

Compound C-8 (10.8 g, yield 77%, MS:[M+H]⁺=615) was prepared in the same manner as in the preparation of Compound A-6, except that Compound C-7 was used instead of Compound A-5.

Preparation Example 4-3: Synthesis of Intermediate Compound C-10

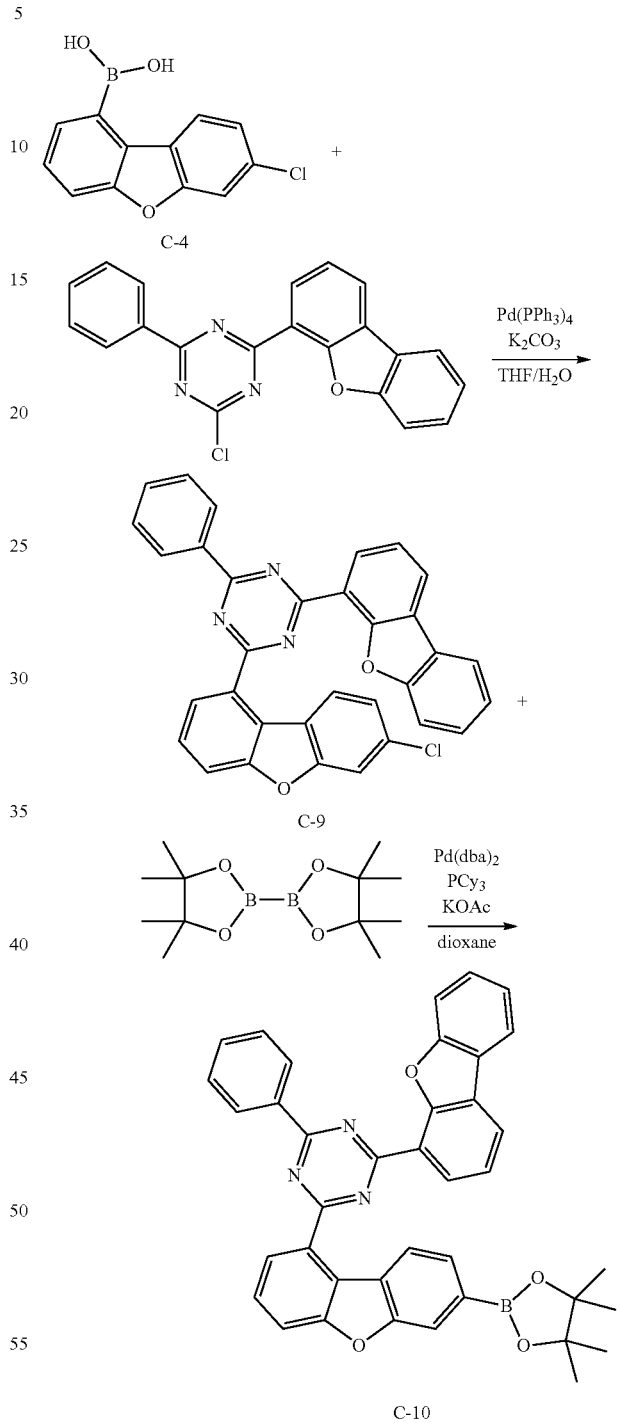

1) Preparation of Compound C-9

Compound C-9 (12.1 g, yield 56%, MS:[M+H]⁺=524) was prepared in the same manner as in the preparation of Compound A-5, except that Compound C-4 and 2-chloro-4-(dibenzofuran-4-yl)-6-phenyl-1,3,5-triazine were used instead of Compound A-4 and 2-chloro-4,6-diphenyltriazine.

2) Preparation of Compound C-10

Compound C-10 (12.5 g, yield 73%, MS:[M+H]⁺=616) was prepared in the same manner as in the preparation of Compound A-6, except that Compound C-9 was used instead of Compound A-5.

Preparation Example 4-4: Synthesis of Intermediate Compound C-12

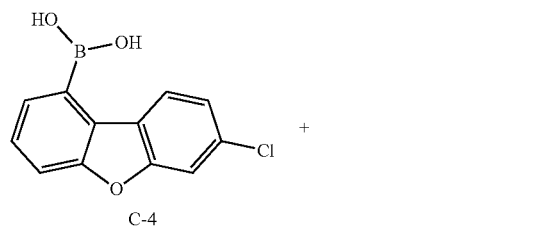

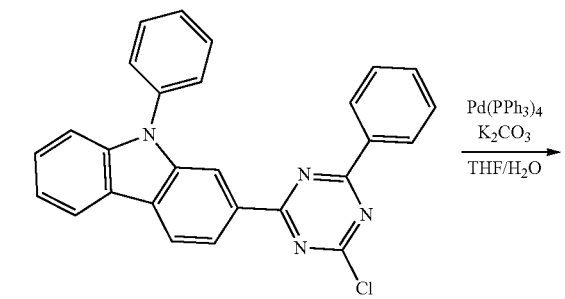

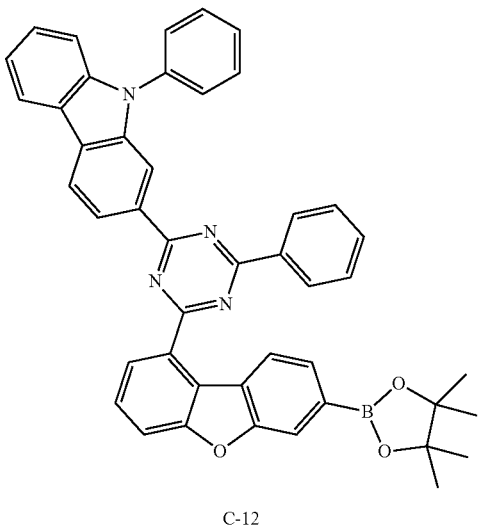

1) Preparation of Compound C-11

Compound C-11 (13.9 g, yield 57%, MS:[M+H]⁺=599) was prepared in the same manner as in the preparation of Compound A-5, except that Compound C-4 and 2-(4-chloro-6-phenyl-1,3,5-triazin-2-yl)9-phenyl-9H-carbazole were used instead of Compound A-4 and 2-chloro-4,6-diphenyl-triazine.

2) Preparation of Compound C-12

Compound C-12 (10.3 g, yield 64%, MS:[M+H]⁺=691) was prepared in the same manner as in the preparation of Compound A-6, except that Compound C-11 was used instead of Compound A-5.

Preparation Example 5-1: Synthesis of Intermediate Compound D-6

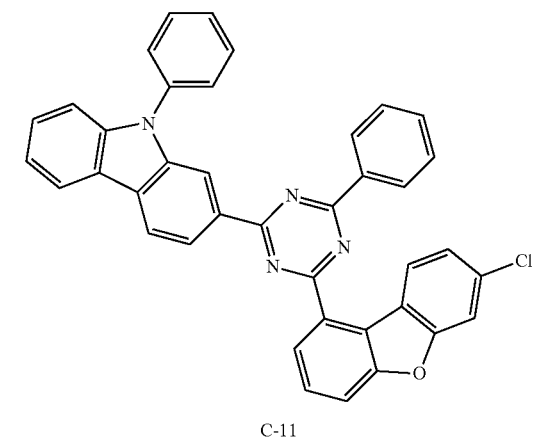

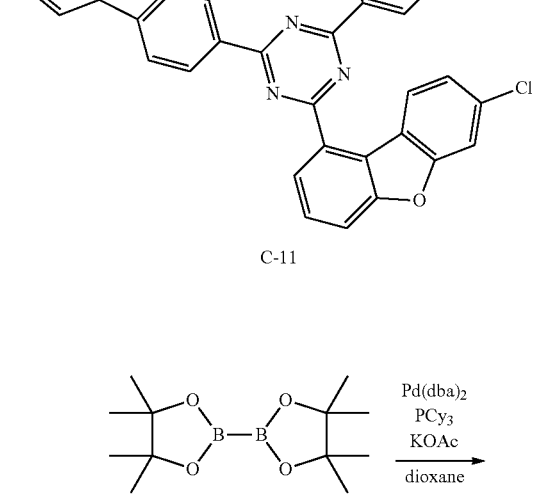

-continued

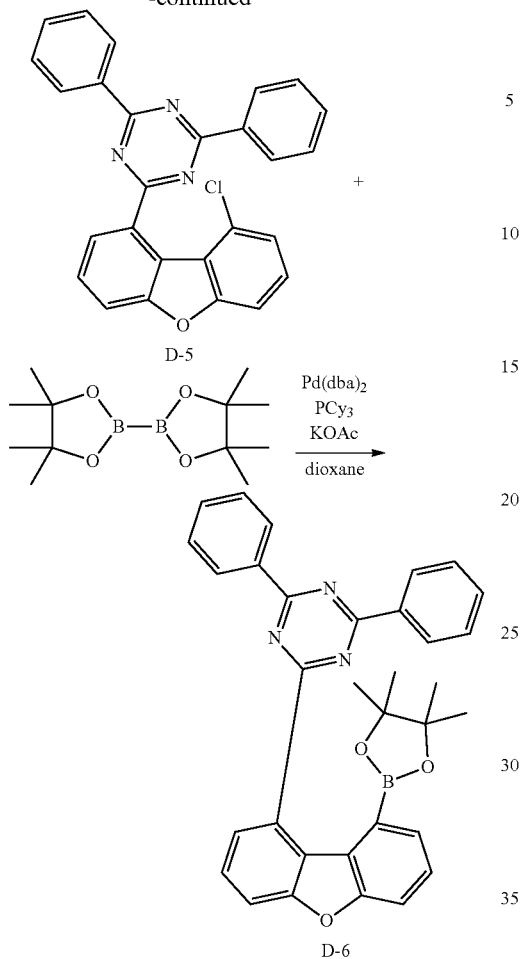

1) Preparation of Compound D-5

Compound D-5 (13.0 g, yield 74%, MS:[M+H]$^+$=434) was prepared in the same manner as in the preparation of Compound A-5, except that Compound D-4 was used instead of Compound A-4.

2) Preparation of Compound D-6

Compound D-6 (9.5 g, yield 60%, MS:[M+H]$^+$=526) was prepared in the same manner as in the preparation of Compound A-6, except that Compound D-5 was used instead of Compound A-5.

Preparation Example 6-1: Synthesis of Intermediate Compound E-1

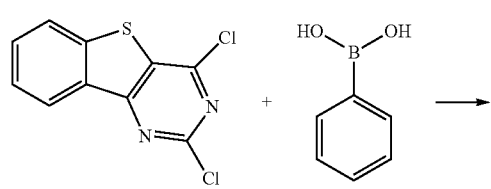

-continued

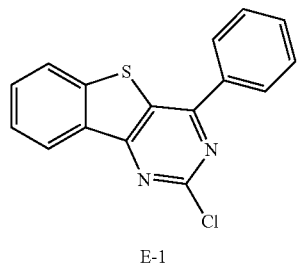

After 2,4-dichlorobenzothieno[3,2-d]pyrimidine (15 g, 57.8 mmol) and phenylboronic acid (7.9 g, 64.7 mmol) were dissolved in 250 mL of tetrahydrofuran, 1.5 M of a potassium carbonate aqueous solution (120 mL) was added and tetrakis(triphenylphosphine)palladium (1.4 g, 1.28 mmol) were added thereto, and then stirred while heating for 7 hours. The temperature of the mixture was lowered to room temperature, the aqueous layer was separated and removed, dried over anhydrous magnesium sulfate, and concentrated under reduced pressure. The resulting material was recrystallized using chloroform and ethyl acetate and dried to produce Compound E-1 (14.1 g, yield 83%, MS: [M+H]$^+$=297).

Preparation Example 6-2: Synthesis of Intermediate Compound E-2

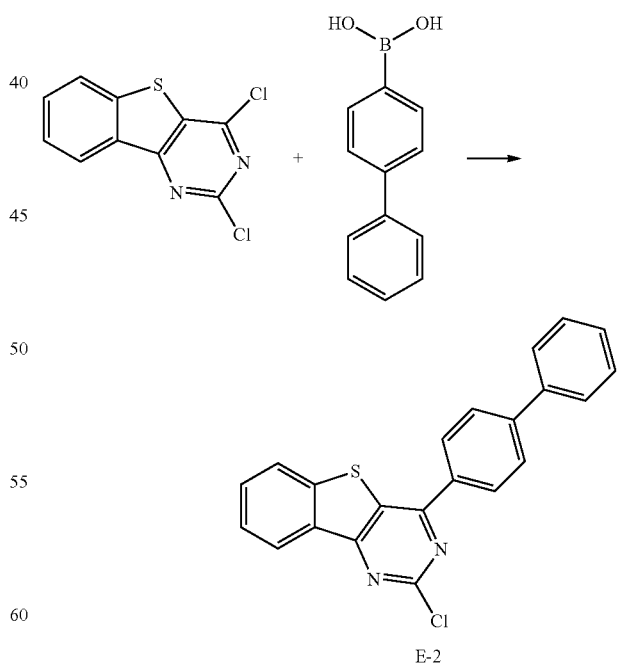

Compound E-2 was prepared in the same manner as in the preparation of Compound E-1, except that [1,1'-biphenyl]-4-ylboronic acid was used instead of phenylboronic acid.

Preparation Example 6-3: Synthesis of Intermediate Compound E-3

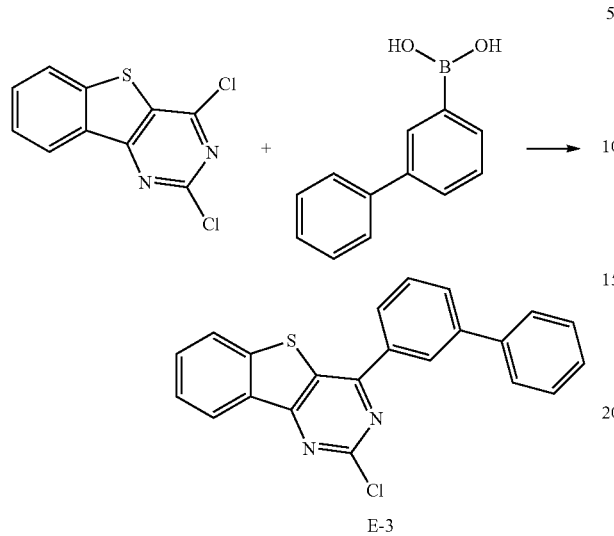

Compound E-3 was prepared in the same manner as in the preparation of Compound E-1, except that [1,1'-biphenyl]-3-ylboronic acid was used instead of phenylboronic acid.

Preparation Example 6-4: Synthesis of Intermediate Compound E-4

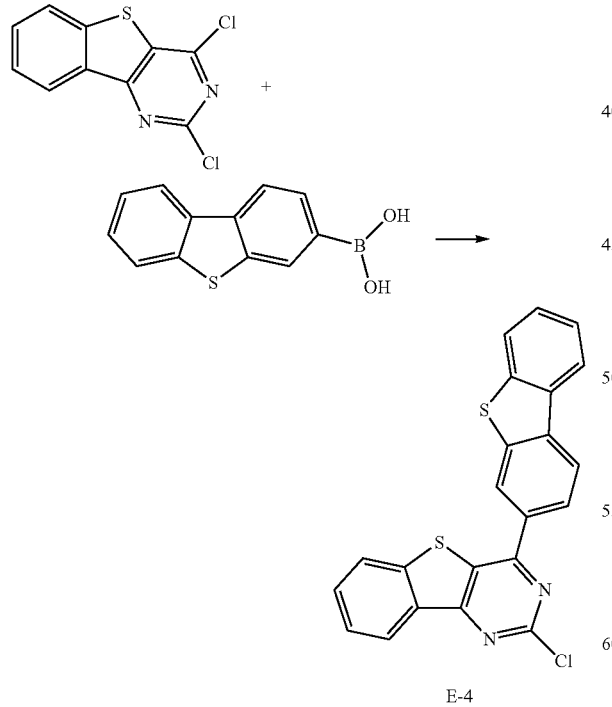

Compound E-4 was prepared in the same manner as in the preparation of Compound E-1, except that dibenzothiophen-3-yl-boronic acid was used instead of phenylboronic acid.

Preparation Example 6-5: Synthesis of Intermediate Compound E-5

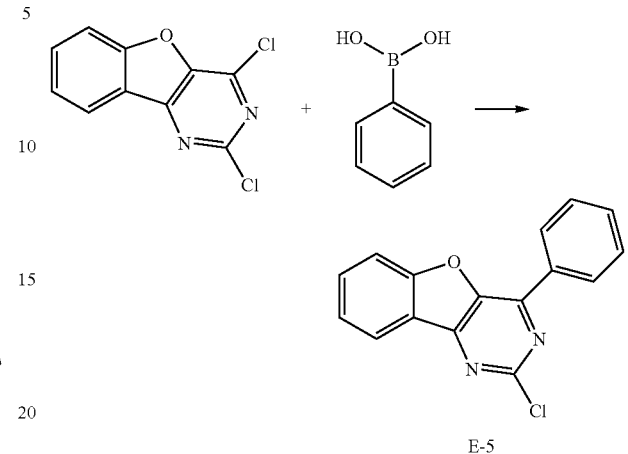

Compound E-5 was prepared in the same manner as in the preparation of Compound E-1, except that 2,4-dichlorobenzofuro[3,2-d]pyrimidine was used instead of 2,4-dichlorobenzothieno[3,2-d]pyrimidine.

Preparation Example 6-6: Synthesis of Intermediate Compound E-6

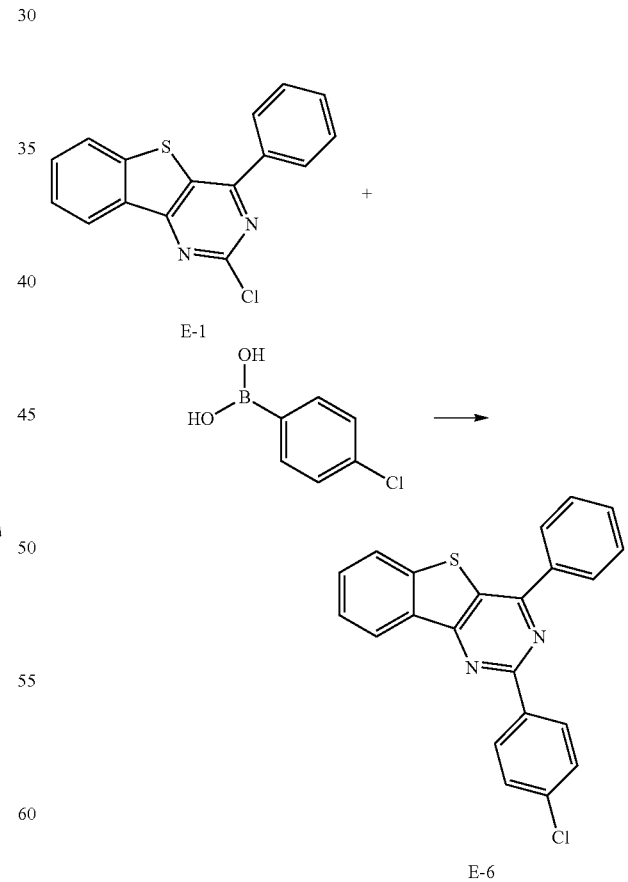

After Compound E-1 (15.0 g, 0.05 mol) and (4-chlorophenyl)boronic acid (21.4 g, 0.06 mol) were dissolved in 200 ml of dioxane, $K_3PO_4$ (21.4 g, 0.1 mol) was added, and bis(tri-t-butylphosphine)palladium (0) (0.26 g, 0.5 mmol)

was added thereto, and then stirred while heating for 13 hours. The temperature of the mixture was lowered to room temperature, the aqueous layer was separated and removed, dried over anhydrous magnesium sulfate, and concentrated under reduced pressure. The resulting material was recrystallized using ethyl acetate and dried to produce Compound E-6 (14.1 g, yield 81%: [M+H]⁺=373).

Preparation Example 6-7: Synthesis of Intermediate Compound E-7

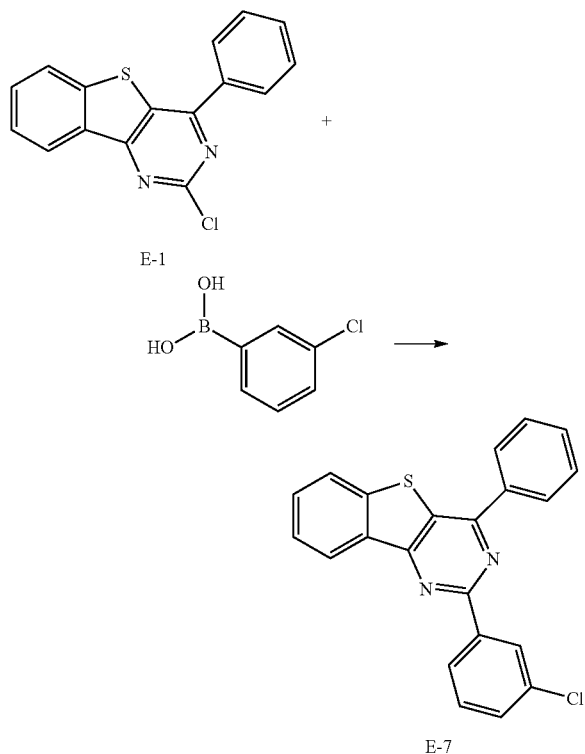

Compound E-7 was prepared in the same manner as in the preparation of Compound E-6, except that (3-chlorophenyl)boronic acid was used instead of (4-chlorophenyl)boronic acid.

EXAMPLE

Example 1: Preparation of Compound 1

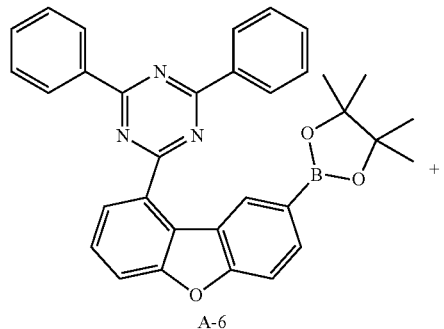

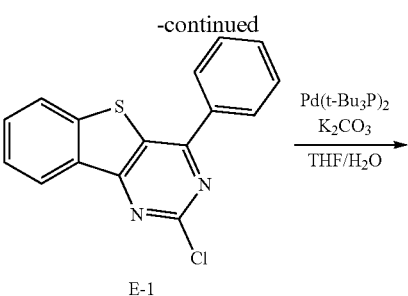

Formula A-6 (10 g, 19 mmol) and Formula E-1 (5.64 g, 19 mmol) were added to 120 ml of tetrahydrofuran under nitrogen atmosphere and stirred and refluxed. Then, potassium carbonate (7.89 g, 57 mmol) was dissolved in 50 ml of water and added thereto. After thoroughly stirring, bis(tri-t-butylphosphine)palladium(0) (0.1 g, 0.2 mmol) was added. After reaction for 9 hours, the temperature of the mixture was lowered to room temperature and filtered. The filtrate was extracted with chloroform and water, and then the organic layer was dried with magnesium sulfate. After that, the organic layer was distilled under reduced pressure, and recrystallized using a mixed solution of tetrahydrofuran and ethyl acetate. The resulting solid was filtered and dried to produce Compound 1 (7.8 g, 62%, MS: [M+H]⁺=660).

Example 2: Preparation of Compound 2

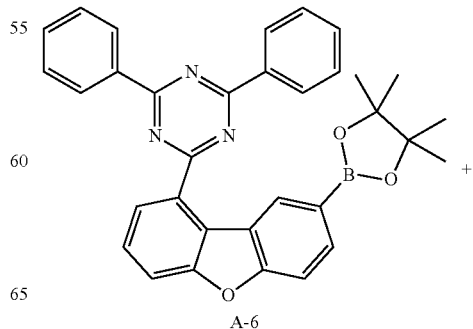

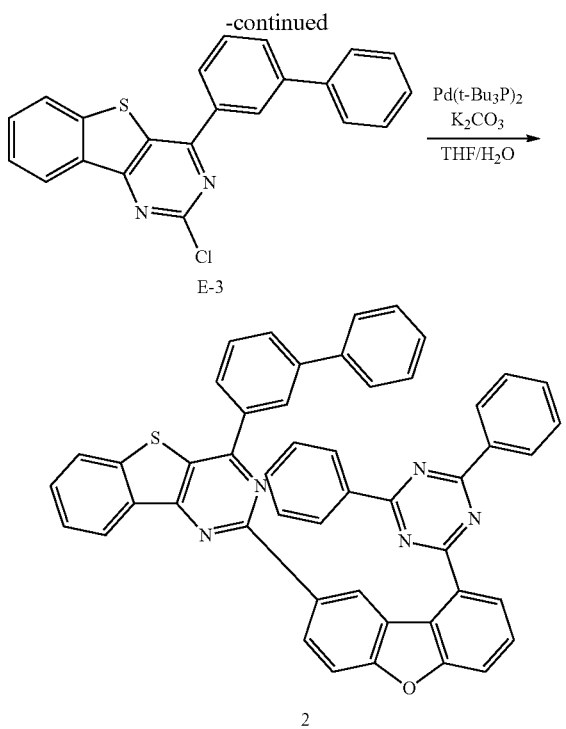

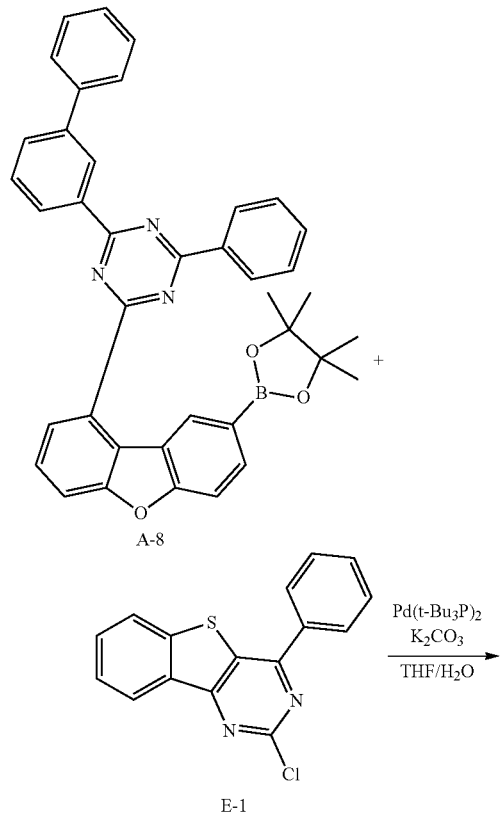

Compound 2 (8.0 g, yield 57%, MS:[M+H]$^+$=736) was prepared in the same manner as in the preparation of Compound 1 of Example 1, except that Formula E-3 was used instead of Formula E-1.

Example 3: Preparation of Compound 3

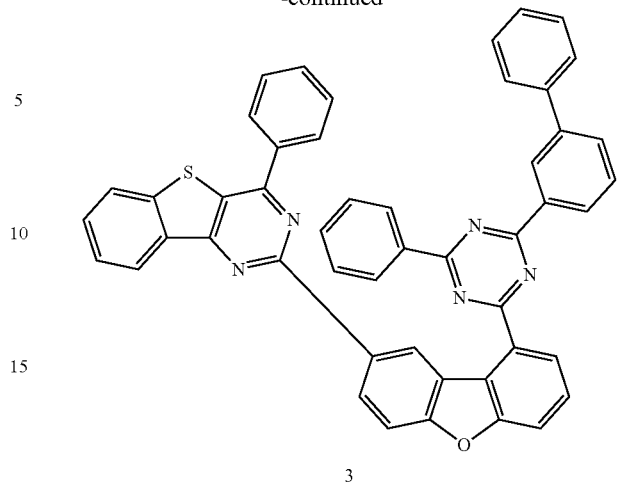

Compound 3 (7.5 g, yield 54%, MS:[M+H]$^+$=736) was prepared in the same manner as in the preparation of Compound 1 of Example 1, except that Formula A-8 was used instead of Formula A-6.

Example 4: Preparation of Compound 4

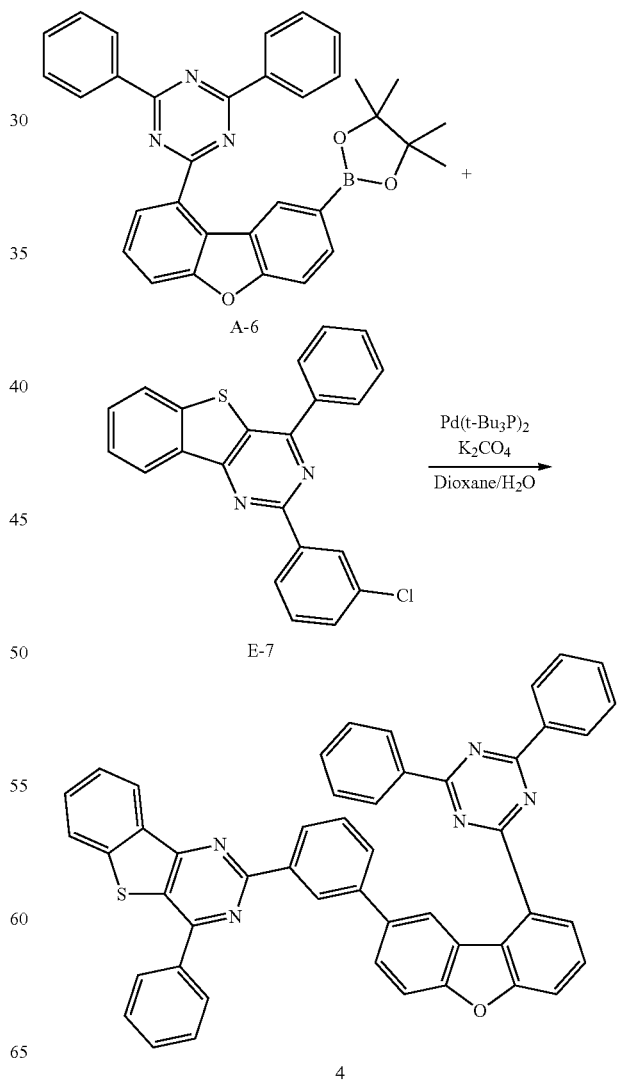

Compound 4 (7.7 g, yield 55%, MS:[M+H]⁺=736) was prepared in the same manner as in the preparation of Compound 1 of Example 1, except that Formula E-7 was used instead of Formula E-1.

Example 5: Preparation of Compound 5

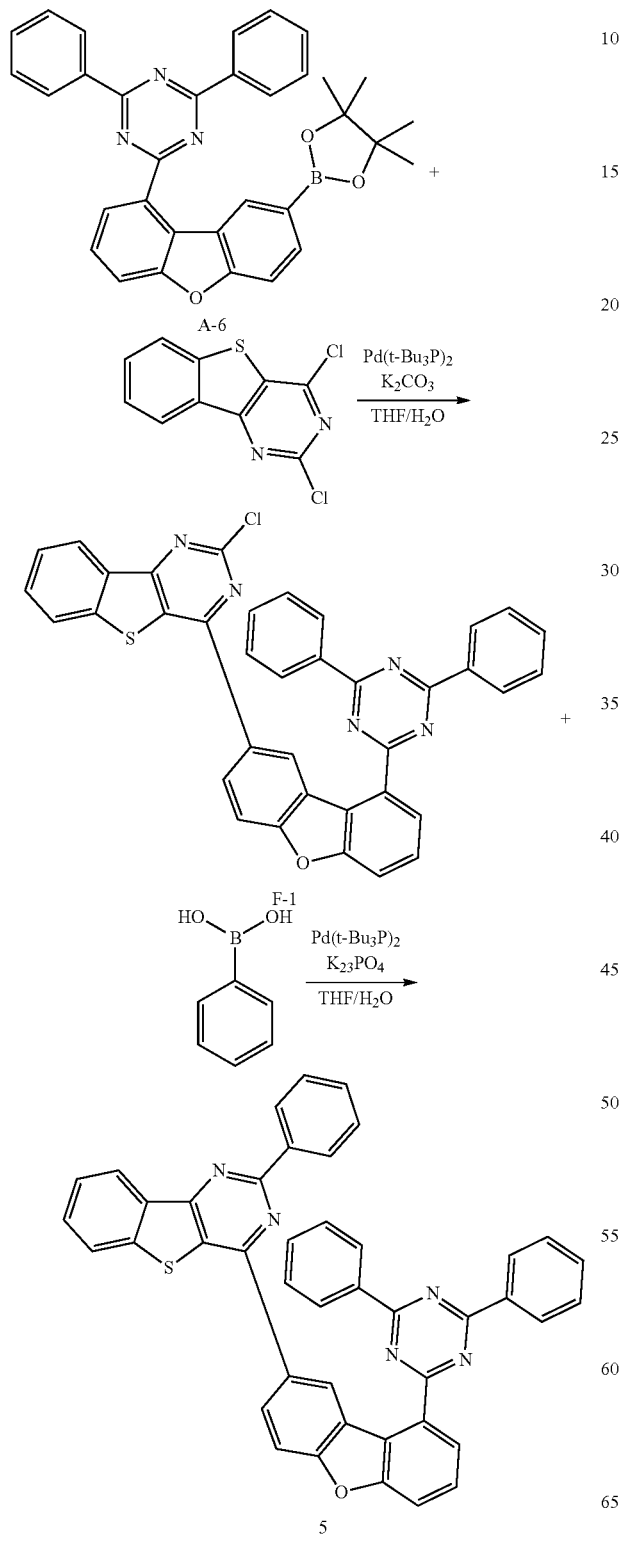

1) Preparation of Formula F-1

Compound F-1 (7.3 g, yield 62%, MS:[M+H]⁺=619) was prepared in the same manner as in the preparation of Compound 1 of Example 1, except that 2,4-dichlorobenzothieno[3,2-d]pyrimidine was used instead of Compound E-1.

2) Preparation of Formula 5

After Formula F-1 (7.3 g, 12 mmol) and phenylboronic acid (1.5 g, 13 mmol) were dissolved in 90 ml of dioxane, K₃PO₄ (7.5 g, 35 mol) was added, and bis(tri-t-butylphosphine)palladium (0) (0.06 g, 0.1 mmol) was added thereto, and then stirred while heating for 8 hours. The temperature of the mixture was lowered to room temperature and filtered. The filtrate was extracted with chloroform and water, and then the organic layer was dried with magnesium sulfate. After that, the organic layer was distilled under reduced pressure, recrystallized using a mixed solution of tetrahydrofuran and ethyl acetate, and dried to produce Compound 5 (5.8 g, yield 68%, MS: [M+H]⁺=660).

Example 6 Preparation of Compound 6

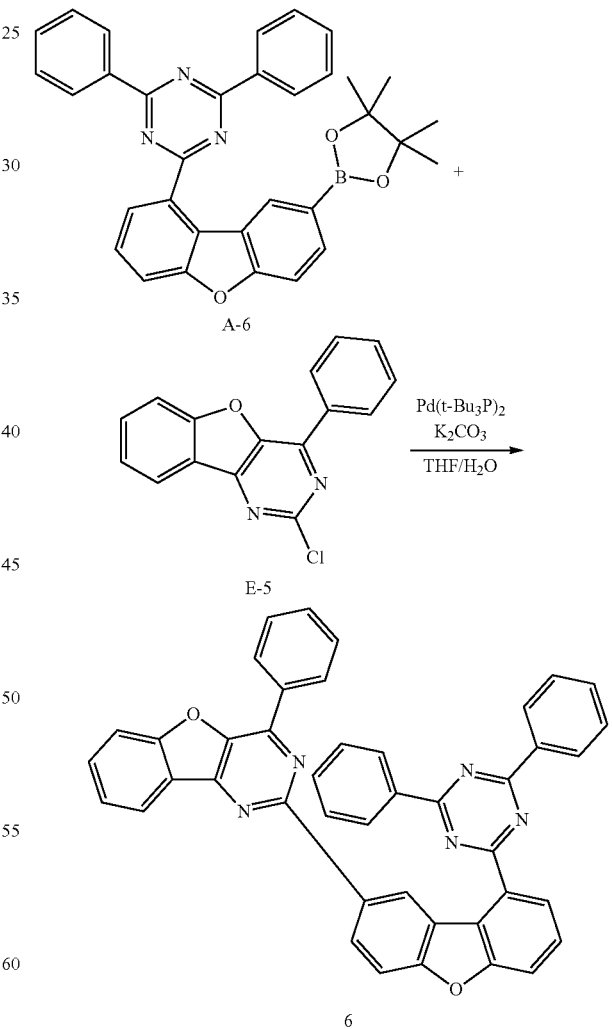

Compound 6 (6.9% g, yield 56%, MS: [H+H]⁺=644) was prepared in the same manner as in the preparation of Compound 1 of Example 1, except that Formula E-5 was used instead of Formula E-1.

Example 7 Preparation of Compound 7

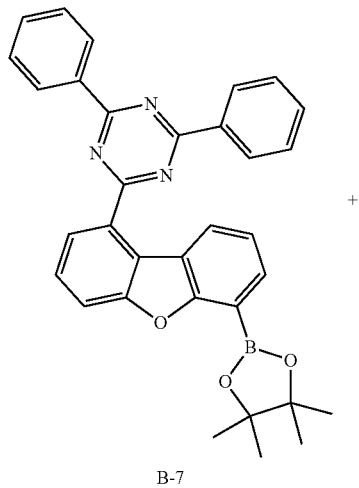

B-7

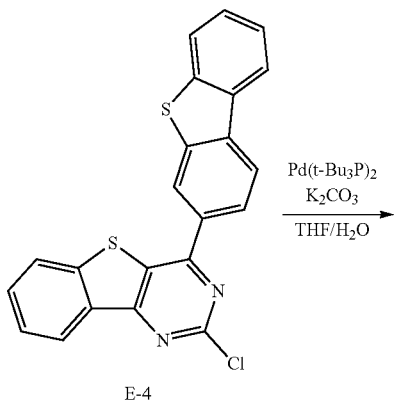

E-4

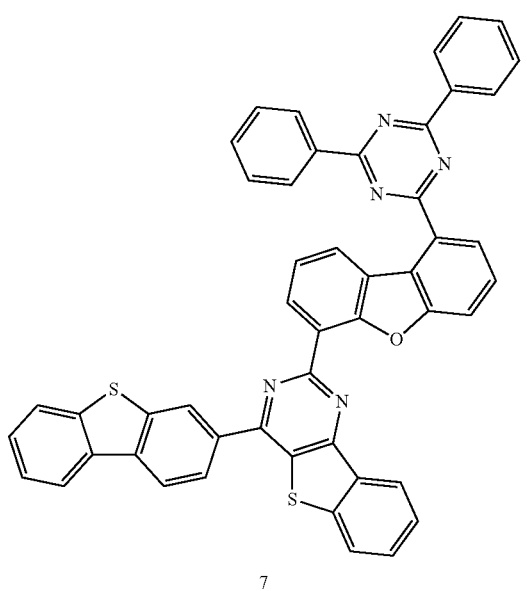

7

Compound 7 (10.6 g, yield 72%, MS:[M+H]$^+$=766) was prepared in the same manner as in the preparation of Compound 1 of Example 1, except that Formula B-7 and Formula E-4 were used instead of Formula A-6 and Formula E-1.

Example 8: Preparation of Compound 8

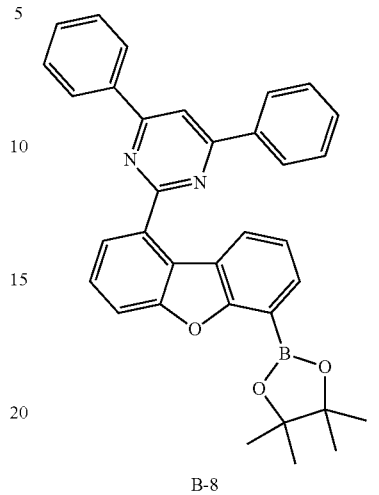

B-8

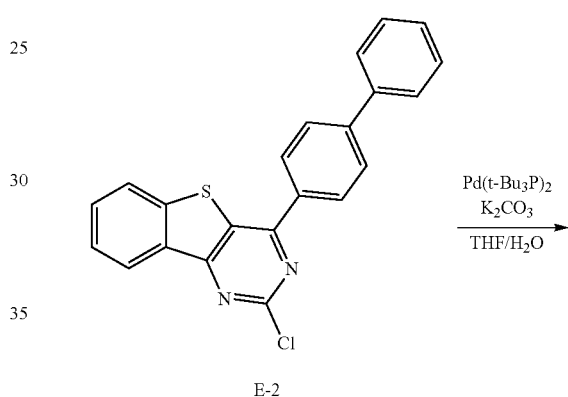

E-2

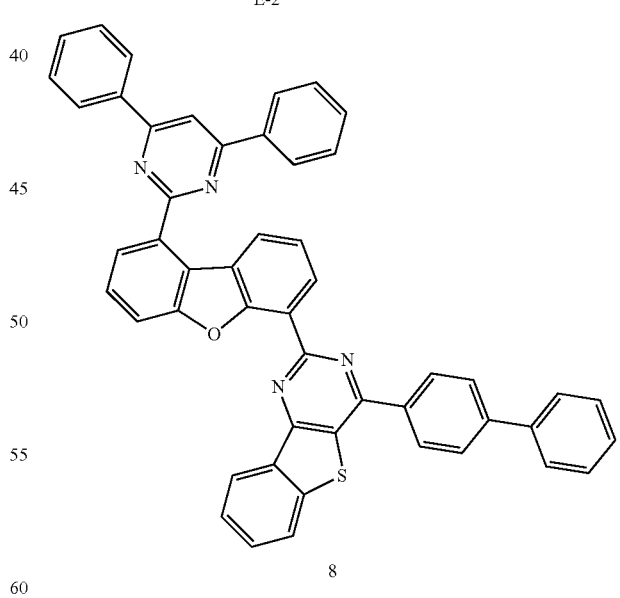

8

Compound 8 (8.4 g, yield 60%, MS:[M+H]$^+$=735) was prepared in the same manner as in the preparation of Compound 1 of Example 1, except that Formula B-8 and Formula E-2 were used instead of Formula A-6 and Formula E-1.

Example 9: Preparation of Compound 9

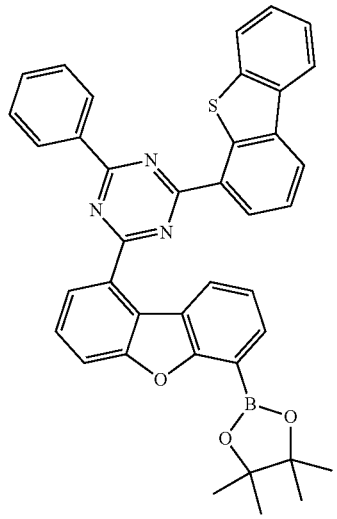

B-11

+

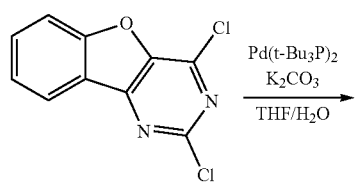

Pd(t-Bu₃P)₂
K₂CO₃
⟶
THF/H₂O

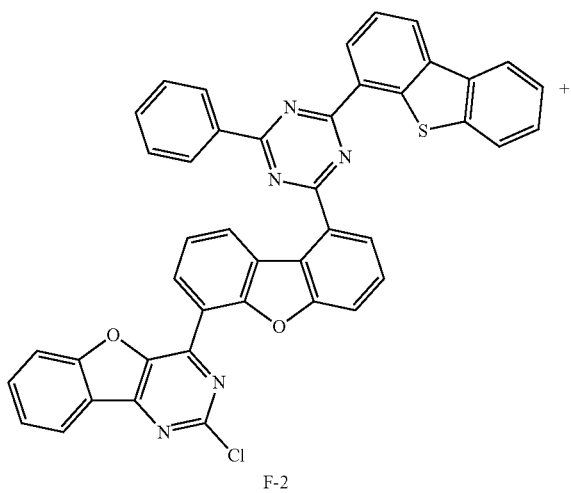

F-2

+

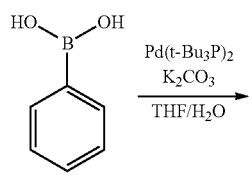

Pd(t-Bu₃P)₂
K₂CO₃
⟶
THF/H₂O

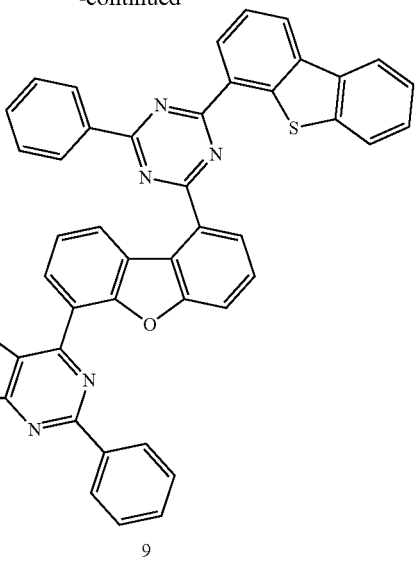

9

Formula F-2 and subsequently Compound 9 (5.1 g, yield 64%, MS:[M+H]⁺=750) was prepared in the same manner as in the preparation of Compound 5 of Example 5, except that Formula B-11 and 2,4-dichlorobenzofuro[3,2-d]pyrimidine was used instead of Formula A-6 and 2,4-dichlorobenzothieno[3,2-d]pyrimidine.

Example 10: Preparation of Compound 10

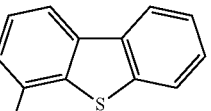

+

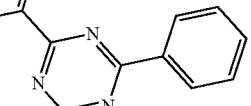

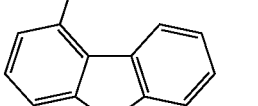

B-13

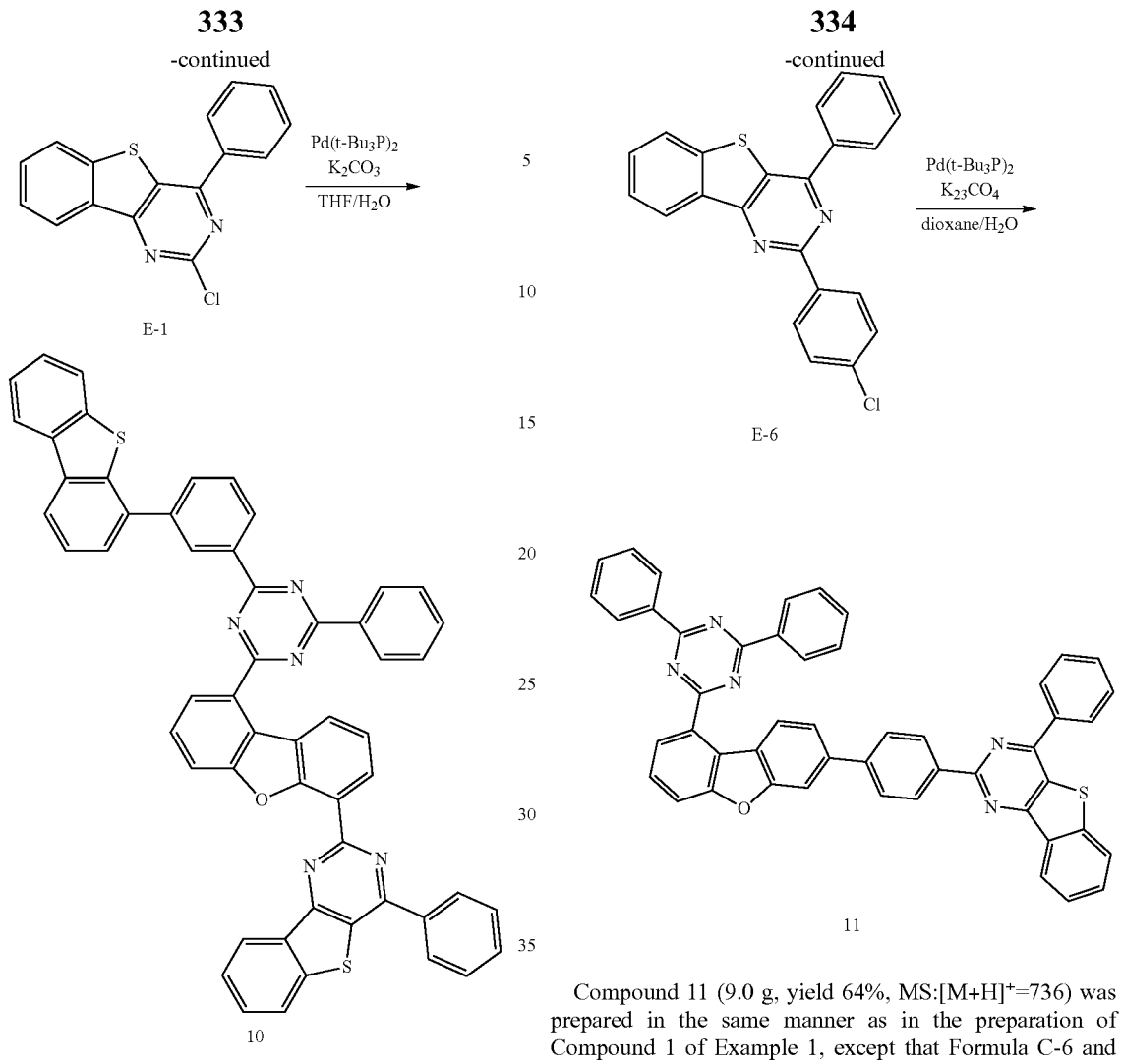

Compound 10 (8.1 g, yield 68%, MS:[M+H]$^+$=843) was prepared in the same manner as in the preparation of Compound 1 of Example 1, except that Formula B-13 and Formula E-1 were used instead of Formula A-6 and Formula E-1.

Example 11: Preparation of Compound 11

Compound 11 (9.0 g, yield 64%, MS:[M+H]$^+$=736) was prepared in the same manner as in the preparation of Compound 1 of Example 1, except that Formula C-6 and Formula E-6 were used instead of Formula A-6 and Formula E-1.

Example 12: Preparation of Compound 12

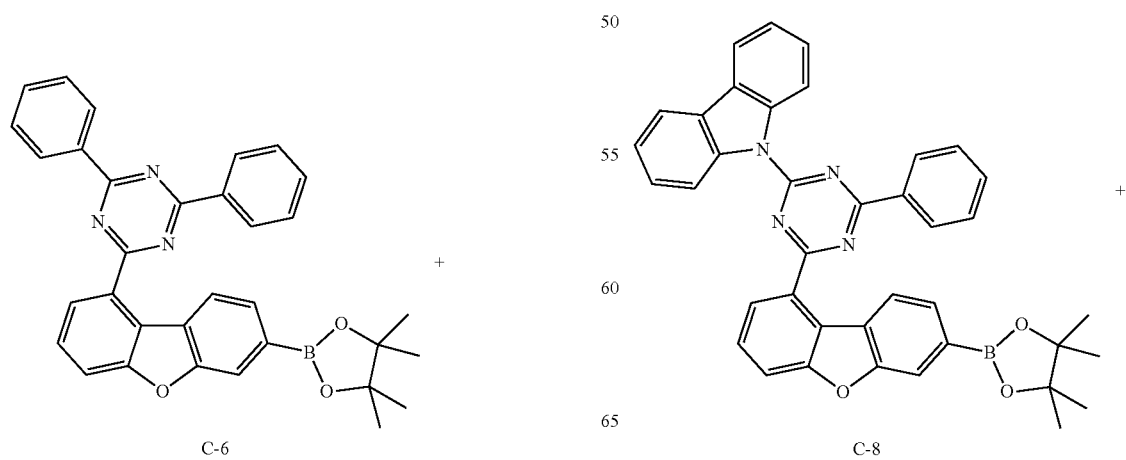

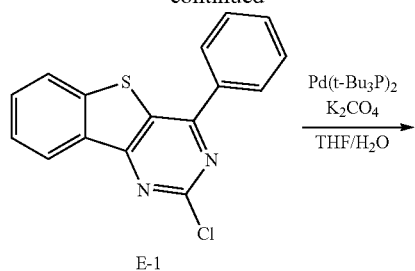

E-1

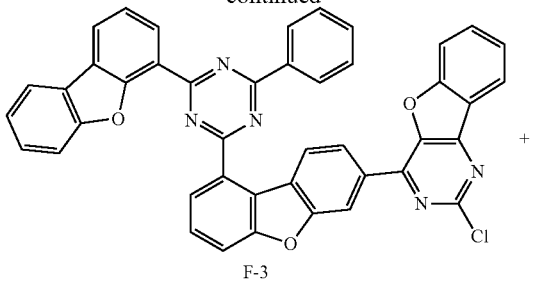

F-3

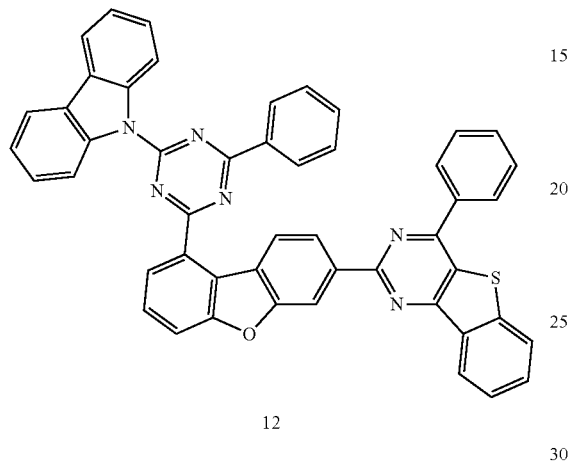

12

Compound 12 (7.8 g, yield 64%, MS:[M+H]$^+$=749) was prepared in the same manner as in the preparation of Compound 1 of Example 1, except that Formula C-8 and Formula E-1 were used instead of Formula A-6 and Formula E-1.

Example 13: Preparation of Compound 13

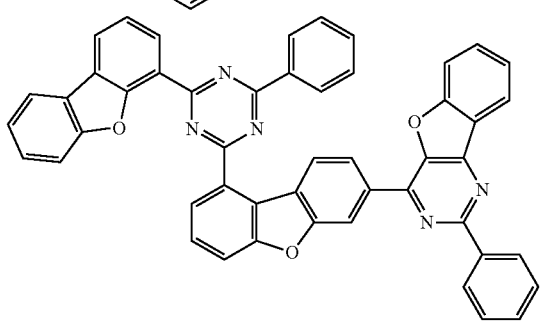

13

Formula F-3 and subsequently Compound 13 (5.8 g, yield 68%, MS:[M+H]$^+$=734) were prepared in the same manner as in the preparation of Compound 5 of Example 5, except that Formula C-10 and 2,4-dichlorobenzofuro [3,2-d]pyrimidine were used instead of Formula A-6 and 2,4-dichlorobenzothieno[3,2-d]pyrimidine.

Example 14: Preparation of Compound 14

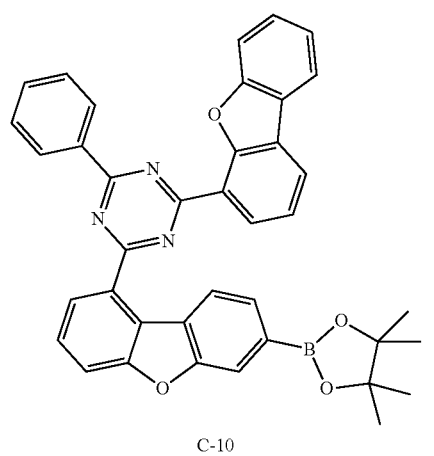

C-10

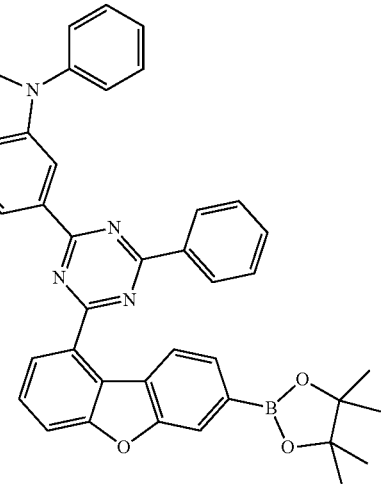

C-12

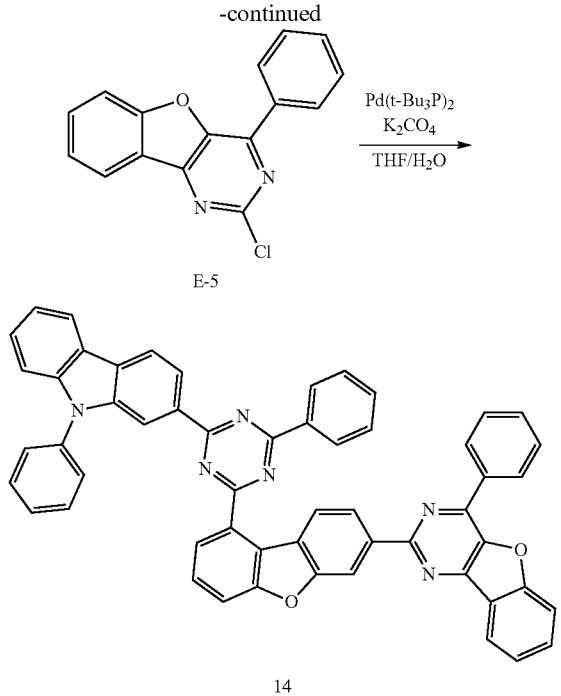

14

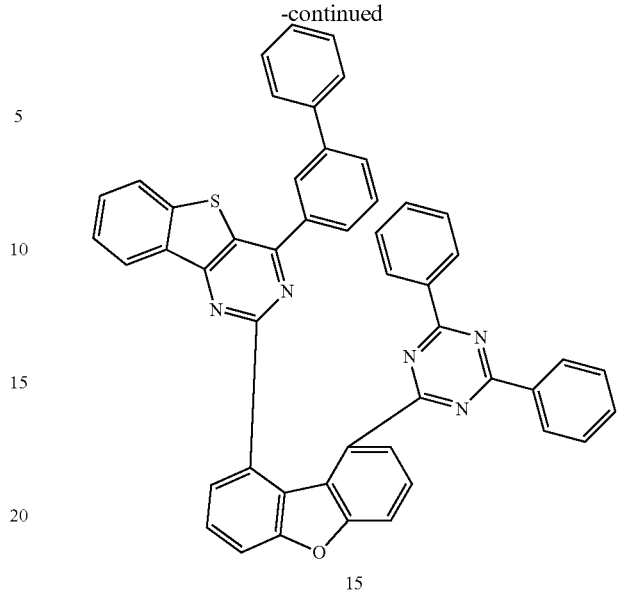

15

Compound 14 (7.9 g, yield 67%, MS:[M+H]$^+$=809) were prepared in the same manner as in the preparation of Compound 1 of Example 1, except that Formula C-12 and Formula E-5 were used instead of Formula A-6 and Formula E-1.

Example 15: Preparation of Compound 15

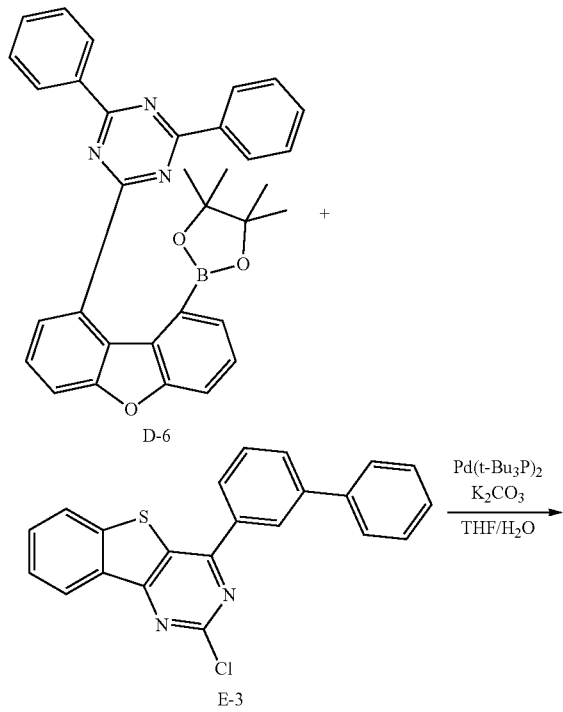

Compound 15 (8.6 g, yield 61%, MS:[M+H]$^+$=736) were prepared in the same manner as in the preparation of Compound 1 of Example 1, except that Formula D-6 and Formula E-3 were used instead of Formula A-6 and Formula E-1.

EXPERIMENTAL EXAMPLE

Experimental Example 1

A glass substrate on which a thin film of ITO (indium tin oxide) was coated at a thickness of 1300 Å was put into distilled water containing a detergent dissolved therein and washed by ultrasonic waves. In this case, the detergent used was a product commercially available from Fisher Co. and the distilled water was one which had been filtered twice by using a filter that is commercially available from Millipore Co. The ITO was washed for 30 minutes, and ultrasonic washing was then repeated twice for 10 minutes by using distilled water. After the washing with distilled water was completed, the substrate was ultrasonically washed with a solvent of isopropyl alcohol, acetone, and methanol, and dried, after which it was transported to a plasma cleaner. Then, the substrate was cleaned with oxygen plasma for 5 minutes, and then transferred to a vacuum evaporator.

On the ITO transparent electrode thus prepared, a hexanitrile hexaazatriphenylene (HAT) compound below was thermally vacuum-deposited to a thickness of 50 Å to form a hole injection layer. 4,4'-bis-(1 naphthyl)-N-phenylamino] biphenyl (NPB; HT-1) as a hole transport material was thermally vacuum-deposited thereon to a thickness of 250 Å to form a hole transport layer, and a compound of Formula HT-2 below was vacuum-deposited on the HT-1 deposited film to a thickness of 50 Å to form an electron blocking layer. Then, a Compound 1 prepared as a host, a compound of Formula YGH-1 below, and a phosphorescent dopant of Formula YGD-1 below were co-deposited on the HT-2 deposited film at a weight ratio of 44:44:12 to form the light-emitting layer having a thickness of 400 Å. A material of Formula ET-1 below was vacuum-deposited on the light-emitting layer to a thickness of 250 Å, and additionally a material of Formula ET-2 below was co-deposited with 2 wt % Li to a thickness of 100 Å to form an electron transport layer and an electron injection layer. Aluminum was evaporated to a thickness of 1000 Å on the electron injection layer to form a cathode.

In the above process, the vapor deposition rate of the organic material was maintained at 0.4 to 0.7 Å/s, the vapor deposition rate of aluminum was maintained at 2 Å/s, and the degree of vacuum during vapor deposition was maintained at $1\times10^{-7}\sim5\times10^{-8}$ tor to manufacture an organic light emitting device.

HAT

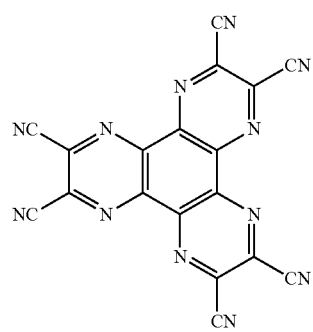

HT-1

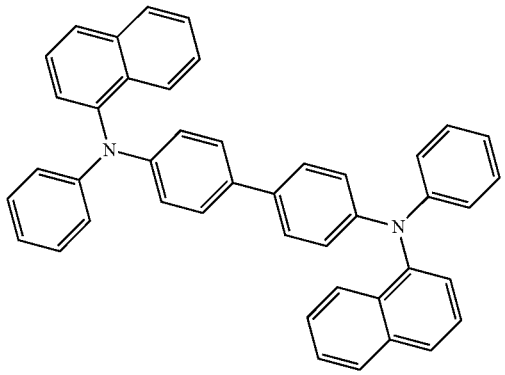

HT-2

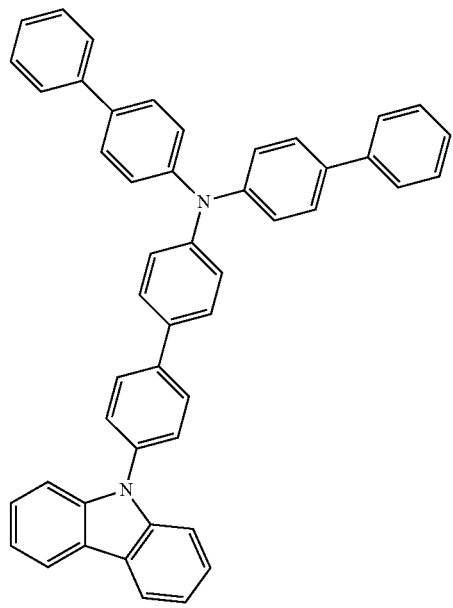

-continued

YGH-1

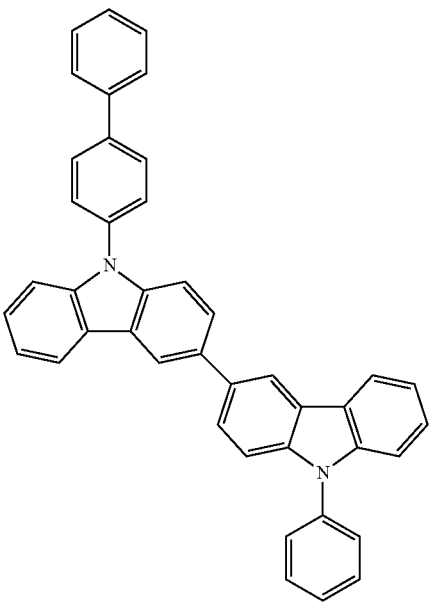

YGD-1

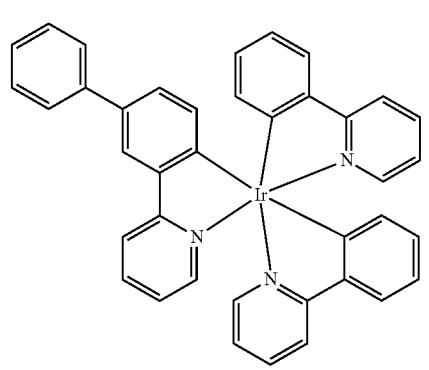

ET-1

-continued

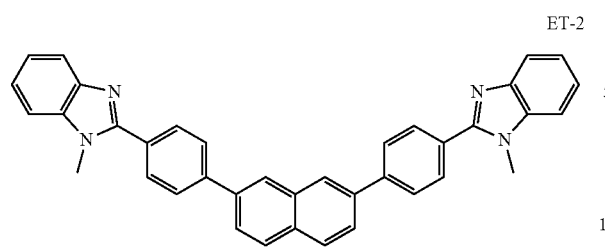
ET-2

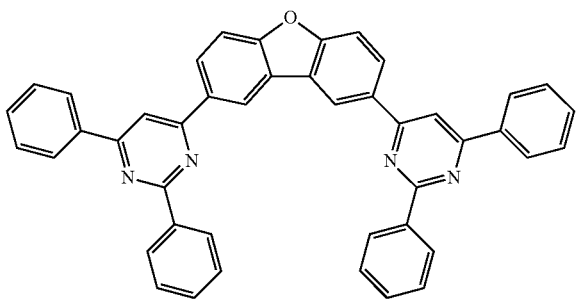
C2

Experimental Examples 2 to 9

The organic light emitting device was manufactured in the same manner as in Experimental Example 1, except that the compounds shown in Table 1 below were used instead of Compound 1 as a phosphorescent host during the formulation of the light emitting layer in Experimental Example 1.

Comparative Examples 1 to 4

The organic light emitting devices of Comparative Examples 1 to 4 were respectively manufactured in the same manner as in Example 1, except that Compounds C1 to C4 shown in Table 1 below were used instead of Compound 1 as a host during the formulation of the light emitting layer.

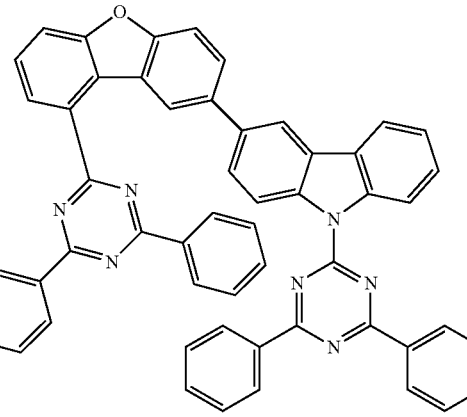
C3

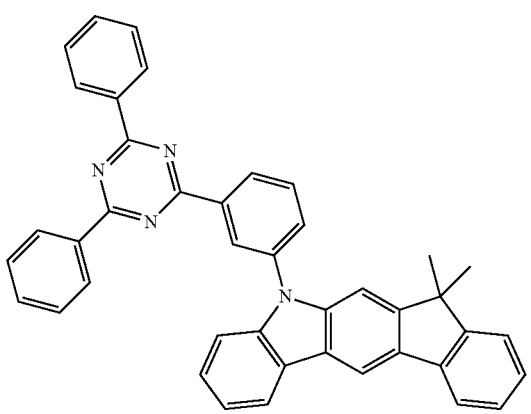
C1

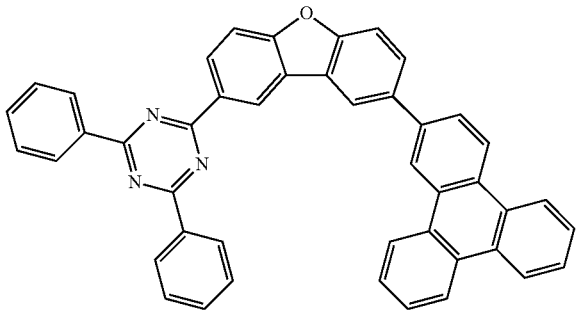
C4

The voltage, efficiency, color coordinates, and lifetime were measured by applying a current to the organic light emitting devices manufactured in Experimental Examples 1 to 9 and Comparative Examples 1 to 4, and the results are shown in Table 1 below. T95 means the time required for the luminance to be reduced to 95% of the initial luminance.

TABLE 1

| Category | Compound | Voltage (V) (@ 10 mA/cm$^2$) | Efficiency (Cd/A) (@ 10 mA/cm$^2$) | Color coordinates (x, y) | Lifetime (h) (LT$_{95}$ at 50 mA/cm$^2$) |
|---|---|---|---|---|---|
| Experimental Example 1 | Compound 1 | 3.3 | 72 | 0.45, 0.52 | 130 |
| Experimental Example 2 | Compound 2 | 3.3 | 73 | 0.45, 0.53 | 140 |
| Experimental Example 3 | Compound 4 | 3.5 | 71 | 0.46, 0.52 | 105 |
| Experimental Example 4 | Compound 6 | 3.2 | 69 | 0.45, 0.53 | 110 |
| Experimental Example 5 | Compound 7 | 3.6 | 73 | 0.45, 0.54 | 135 |
| Experimental Example 6 | Compound 10 | 3.6 | 73 | 0.46, 0.54 | 130 |

TABLE 1-continued

| Category | Compound | Voltage (V) (@ 10 mA/cm$^2$) | Efficiency (Cd/A) (@ 10 mA/cm$^2$) | Color coordinates (x, y) | Lifetime (h) (LT$_{95}$ at 50 mA/cm$^2$) |
|---|---|---|---|---|---|
| Experimental Example 7 | Compound 12 | 3.4 | 75 | 0.45, 0.52 | 120 |
| Experimental Example 8 | Compound 13 | 3.6 | 74 | 0.46, 0.53 | 125 |
| Experimental Example 9 | Compound 14 | 3.4 | 70 | 0.45, 0.54 | 110 |
| Comparative Experimental Example 1 | C1 | 3.6 | 68 | 0.45, 0.54 | 91 |
| Comparative Experimental Example 2 | C2 | 4.2 | 60 | 0.45, 0.53 | 65 |
| Comparative Experimental Example 3 | C3 | 4.4 | 65 | 0.46, 0.53 | 88 |
| Comparative Experimental Example 4 | C4 | 4.1 | 70 | 0.45, 0.53 | 94 |

As shown in Table 1, it can be confirmed that the organic light emitting devices manufactured using the compound according to the present disclosure as a host of the light emitting layer exhibit superior performance in terms of driving voltage and lifetime as compared with the organic light emitting devices of the comparative examples.

In particular, it can be confirmed that, compared with Compound C1 which is a fluorescent host material commonly used in the art, the organic light emitting devices according to the examples have low voltage characteristic as the driving voltage decreased to 10% and they have a long lifetime characteristic as the lifetime increased by about 15 to 54%. In addition, it can be confirmed that the device characteristics differ depending on the kind of the substituents other than triazine on dibenzofuran. It can be confirmed that, compared with Comparative Example C3 which is substituted with carbazole and Comparative Example C4 which is substituted with aryl substituent, the compounds of the present disclosure have low voltage and long lifetime characteristics. Further, it can be confirmed that when comparing Comparative Experimental Example 2 of Comparative Example C2 which is substituted with pyrimidine substituent, and Experimental Example 1 (or Experimental Example 4) of Compound 1 (or Compound 6) which is substituted with benzothienopyrimidine (or benzopyrimidine) which is a condensed pyrimidine, the voltage is as low as about 8%, while the lifetime is improved by 40% or more. It can be confirmed that the benzothienopyrimidine (or benzofuropyrimidine) substituent, which is the substituent of the compound of the present disclosure, is electronically stable as compared with the pyrimidine substituent.

EXPERIMENTAL EXAMPLE

Experimental Example 10

On the ITO transparent electrode prepared as in Experimental Example 1, a hexanitrile hexaazatriphenylene (HAT) compound below was thermally vacuum-deposited to a thickness of 500 Å to form a hole injection layer. A compound of Formula HT-1 below was thermally vacuum-deposited on the hole injection layer to a thickness of 800 Å, and sequentially a compound of Formula HT-3 below was vacuum-deposited to a thickness of 500 Å to form a hole transport layer. Then, Compound 1 prepared as a host, a compound of formula H2 below, and a phosphorescent dopant of formula GD below were co-deposited on the hole transport layer at a weight ratio of 47:47:6 to form a light emitting layer having a thickness of 350 Å. A material of Formula ET-3 below was vacuum-deposited on the light emitting layer to a thickness of 50 Å to form a hole blocking layer, and a material of Formula ET-4 below and LiQ (lithium quinolate) were vacuum-deposited on the hole blocking layer at a weight ratio of 1:1 to form an electron transport layer having a thickness of 250 Å. Lithium fluoride (LiF) was deposited on the electron transport layer to a thickness of 10 Å, and sequentially aluminum was deposited thereon to a thickness of 1000 Å to form a cathode.

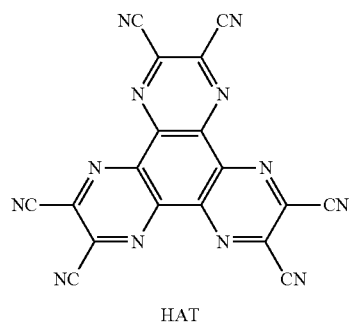

HAT

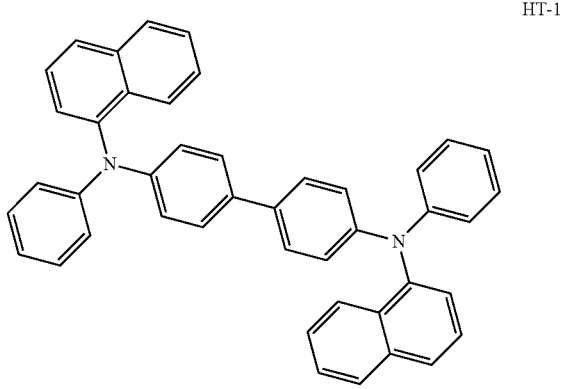

HT-1

-continued

HT-3

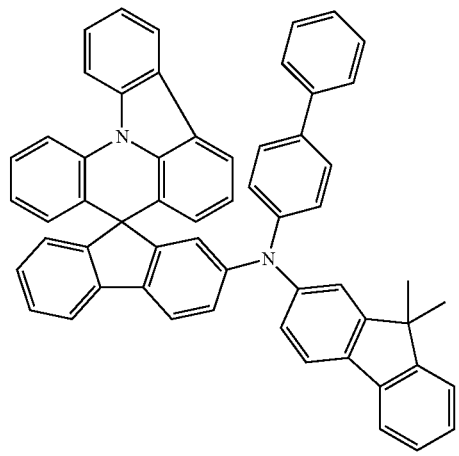

H2

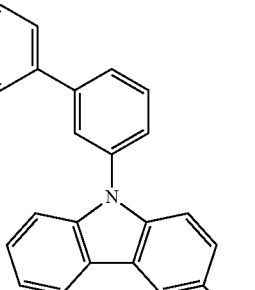

ET-3

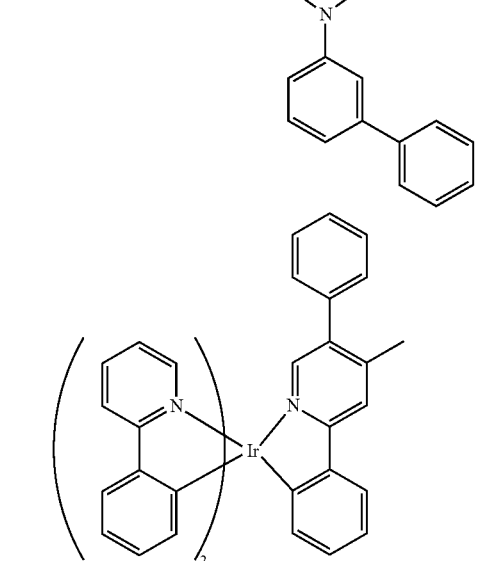

GD

ET-4

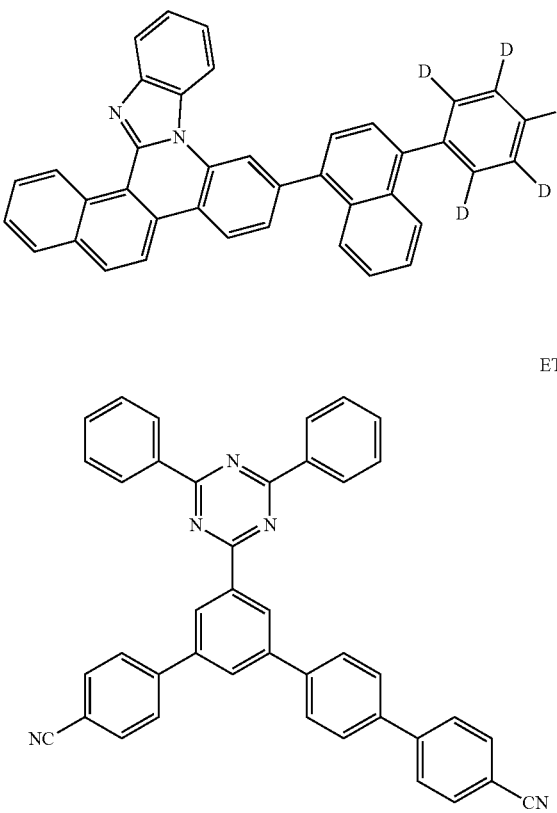

LiQ

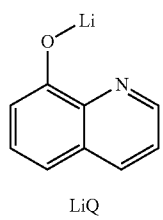

In the above process, the vapor deposition rate of the organic material was maintained at 0.4 to 0.7 Å/s, the vapor deposition rate of lithium fluoride of the cathode was maintained at 0.3 Å/s, and the vapor deposition rate of aluminum was maintained at 2 Å/s. The degree of vacuum during vapor deposition was maintained at $1\times10^{-7}\sim5\times10^{-8}$ tor.

Experimental Examples 11 to 19

The organic light emitting devices of Experimental Examples 11 to 19 were respectively manufactured in the same manner as in Experimental Example 2, except that the compounds shown in Table 2 were used instead of Compound 1 as a host during the formulation of the light emitting layer. In this case, when a mixture of two kinds of compounds is used as the host, the parentheses mean the weight ratio between the host compounds.

Comparative Examples 5 to 8

The organic light emitting devices of Comparative Examples 5 to 8 were respectively manufactured in the same manner as in Experimental Example 11, except that the compounds shown in Table 2 were used instead of Compound 1 as a host during the formulation of the light emitting layer. The compounds shown in Table 2 are the same as the compounds used in Experimental Example 1 described above.

The voltage, efficiency, and lifetime were measured by applying a current to the organic light emitting devices manufactured in Experimental Examples 10 to 19 and Comparative Examples 5 to 8, and the results are shown in Table 2 below. T95 means the time required for the luminance to be reduced to 95% of the initial luminance.

4: cathode
5: hole injection layer
6: hole transport layer
7: light emitting layer
8: electron transport layer

TABLE 2

| Category | Compund | Voltage (V) (@ 10 mA/cm$^2$) | Efficiency (Cd/A) (@ 10 mA/cm$^2$) | Color coordinates (x, y) | Lifetime (h) (LT$_{95}$ at 50 mA/cm$^2$) |
|---|---|---|---|---|---|
| Experimental Example 10 | Compound 1 | 3.8 | 65 | 0.46, 0.52 | 115 |
| Experimental Example 11 | Compound 2 | 3.9 | 70 | 0.45, 0.52 | 120 |
| Experimental Example 12 | Compound 3 | 3.8 | 68 | 0.46, 0.53 | 110 |
| Experimental Example 13 | Compound 5 | 3.9 | 67 | 0.45, 0.54 | 105 |
| Experimental Example 14 | Compound 8 | 3.8 | 64 | 0.45, 0.53 | 100 |
| Experimental Example 15 | Compound 9 | 3.7 | 67 | 0.46, 0.53 | 110 |
| Experimental Example 16 | Compound 10 | 3.9 | 69 | 0.46, 0.53 | 105 |
| Experimental Example 17 | Compound 11 | 3.8 | 70 | 0.46, 0.53 | 95 |
| Experimental Example 18 | Compound 12 | 3.9 | 66 | 0.46, 0.53 | 100 |
| Experimental Example 19 | Compound 14 | 3.8 | 71 | 0.46, 0.53 | 90 |
| Comparative Experimental Example 5 | C1 | 4.2 | 55 | 0.35, 0.61 | 55 |
| Comparative Experimental Example 6 | C2 | 4.9 | 56 | 0.35, 0.63 | 55 |
| Comparative Experimental Example 7 | C3 | 4.7 | 65 | 0.34, 0.63 | 45 |
| Comparative Experimentalt Example 8 | C4 | 4.4 | 66 | 0.35, 0.62 | 65 |

In addition, as can be seen in Table 2, it is confirmed that the case of using the compounds of the present disclosure as a light emitting layer material exhibits low voltage and long lifetime characteristics, similar to Experimental Examples 1 to 9, as compared with the case of using the materials of the comparative examples.

Further, when comparing Experimental Examples 10, 11, 14, 18, and 19 with Comparative Experimental Example 7, it can be confirmed that the difference in lifetime is displayed depending on the substitution position and substituent type of benzopyrimidine (or benzothienopyrimidine) in the dibenzofuran of the compound of the examples.

As described above, it can be confirmed that the compounds of the present disclosure exhibit superior characteristics in terms of driving voltage and lifetime according to the substituent position and substituent type, as compared with the compounds of the comparative examples.

DESCRIPTION OF SYMBOLS

1: substrate
2: anode
3: light emitting layer

The invention claimed is:
1. A compound represented by the following Formula 1:

[Formula 1]

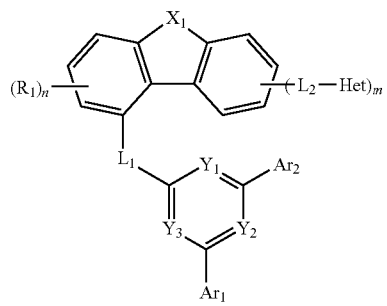

in Formula 1,
X$_1$ is O or S,
R$_1$ is hydrogen or a substituted or unsubstituted C$_{1-60}$ alkyl,
L$_1$ and L$_2$ are each independently a direct bond or a substituted or unsubstituted C$_{6-60}$ arylene,
Y$_1$, Y$_2$, and Y$_3$ are each independently N or CR$_2$, provided that at least one of them is N, R$_2$ is hydrogen or a substituted or unsubstituted C$_{1-60}$ alkyl,
Ar$_1$ and Ar$_2$ are each independently a substituted or unsubstituted C$_{6-60}$ aryl, or a substituted or unsubstituted C$_{5-60}$ heteroaryl containing at least one of N, O, and S, or combined with adjacent Y$_1$, Y$_2$, and Y$_3$ to form a ring,
n is independently 0 or 1,
m and l are independently 1 or 2, and
Het is any one selected from the group consisting of the following Formulas 1-1-1 to 1-1-4:

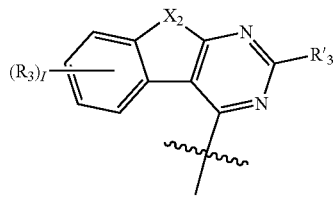

[Formula 1-1-1]

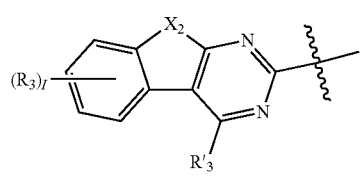

[Formula 1-1-2]

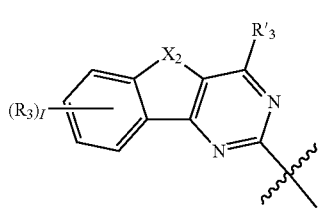

[Formula 1-1-3]

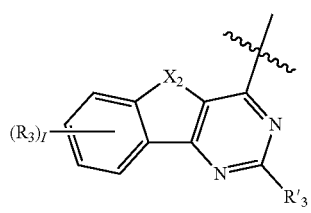

[Formula 1-1-4]

wherein, in Formulas 1-1-1 to 1-1-4,
X$_2$ is O, S, or CR'R",
R' and R" are each independently hydrogen, or a substituted or unsubstituted C$_{1-60}$ alkyl, and
R$_3$ and R'$_3$ are each independently hydrogen, a substituted or unsubstituted C$_{1-60}$ alkyl, a substituted or unsubstituted C$_{6-60}$ aryl, or a substituted or unsubstituted C$_{5-60}$ heteroaryl containing at least one of N, O, and S.

2. The compound of claim 1, wherein Het is any one selected from the group consisting of the following formulas:

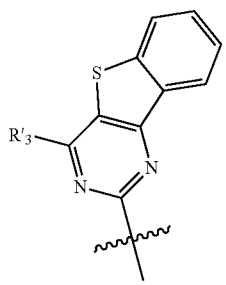 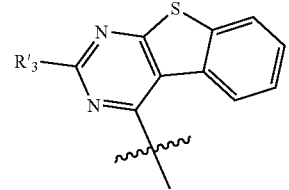

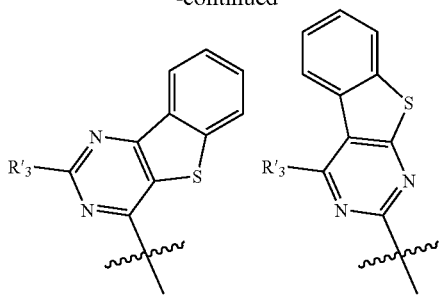

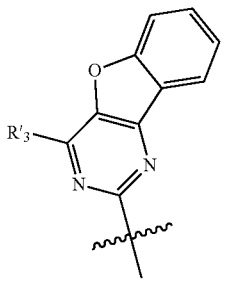 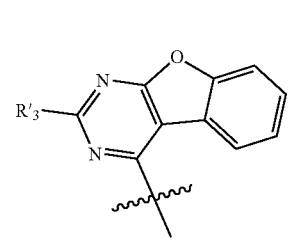

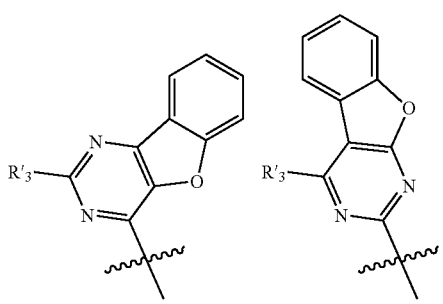

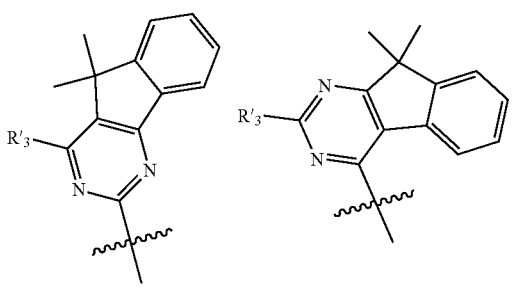

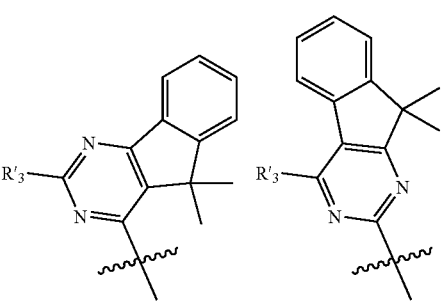

wherein
R'$_3$ and l are as defined in claim 1.

3. The compound of claim 1, wherein the compound represented by Formula 1 is any one selected from the compounds represented by the following Formulas 2 to 6:

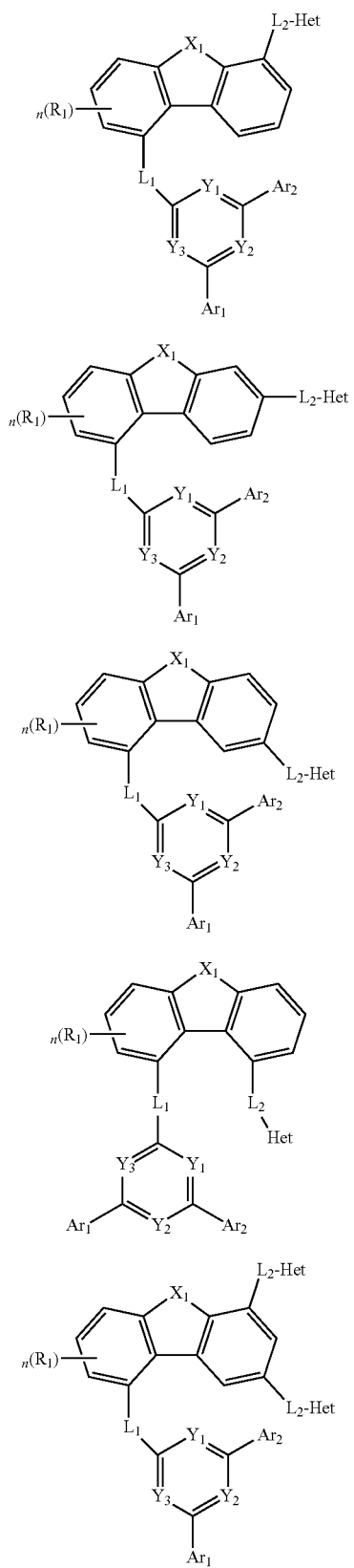
wherein, in Formulas 2 to 6 above,
$X_1$, $L_1$, $L_2$, Het, $Y_1$, $Y_2$, $Y_3$, $R_1$, $Ar_1$, $Ar_2$, and n are as defined in claim 1.
4. The compound of claim 1, wherein the compound represented by Formula 1 is any one selected from compounds represented by the following Formulas 7 to 11:
[Formula 7]
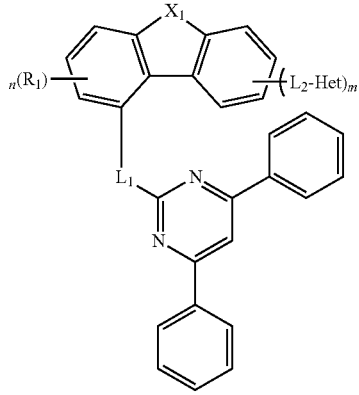
[Formula 8]
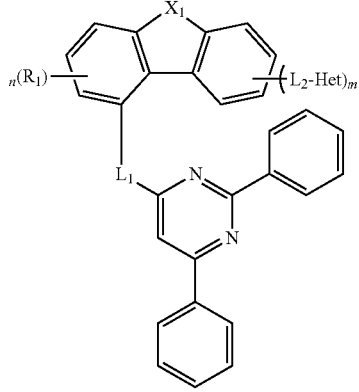
[Formula 9]
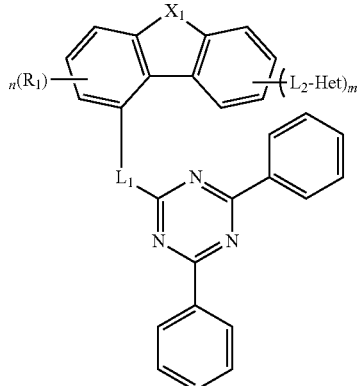
[Formula 10]
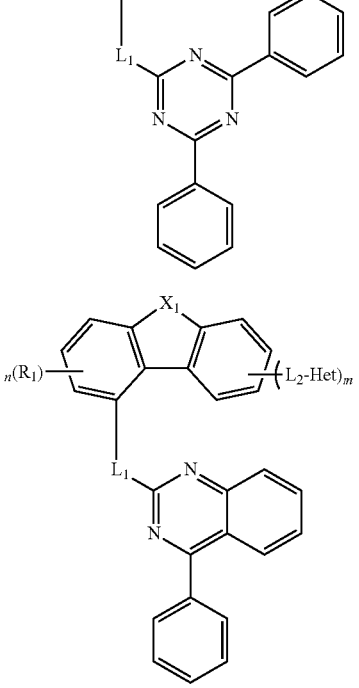

[Formula 11]

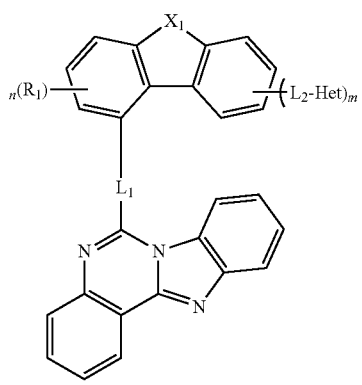

wherein, in Formulas 7 to 11 above, $X_1$, $L_1$, $L_2$, Het, $R_1$, n, and m are as defined in claim 1.

5. The compound of claim 1, wherein $R_1$ is hydrogen or a substituted or unsubstituted $C_{1-10}$ to alkyl.

6. The compound of claim 1, wherein $R_3$ is hydrogen or any one selected f group consisting of the following formulas:

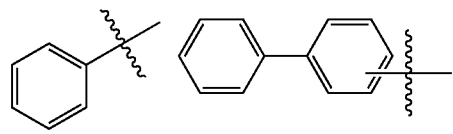

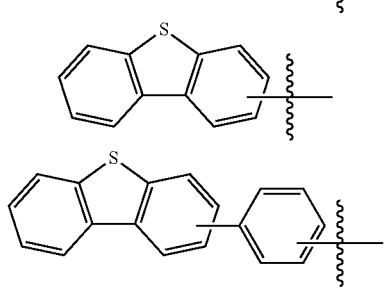

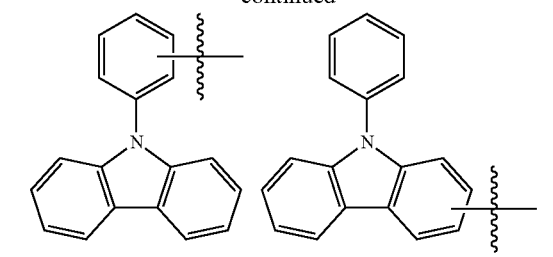

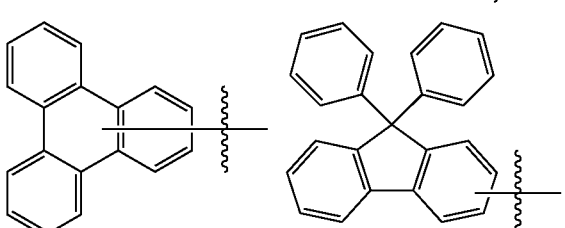

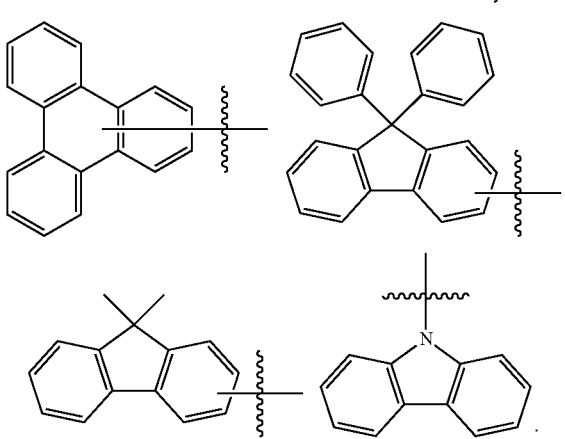

7. The compound of claim 1, wherein $L_1$ and $L_2$ are each independently a direct bond or

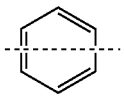

8. The compound of claim 1, wherein $Ar_1$ and $Ar_2$ are combined with adjacent $Y_1$, $Y_2$, and $Y_3$ to form a ring, or are each independently any one selected from the group consisting of the following formulas:

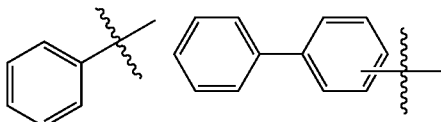

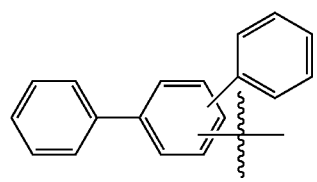

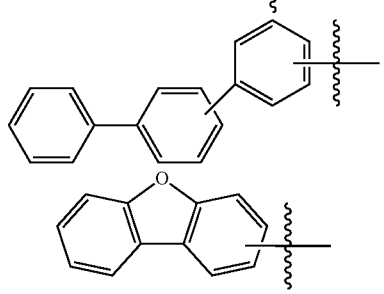

355
-continued
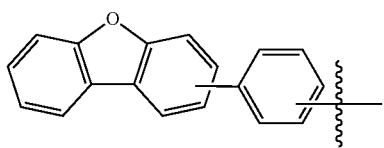
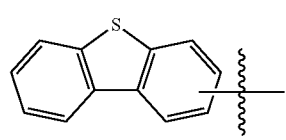
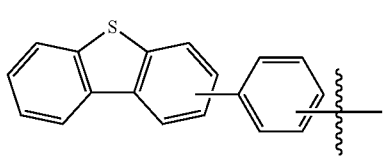
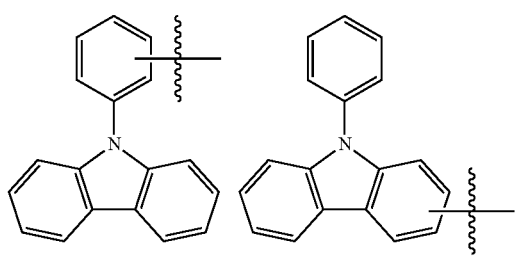
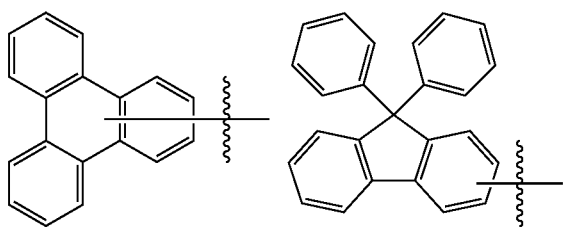
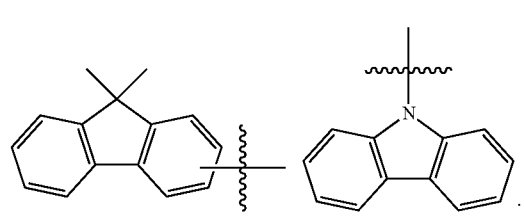
356
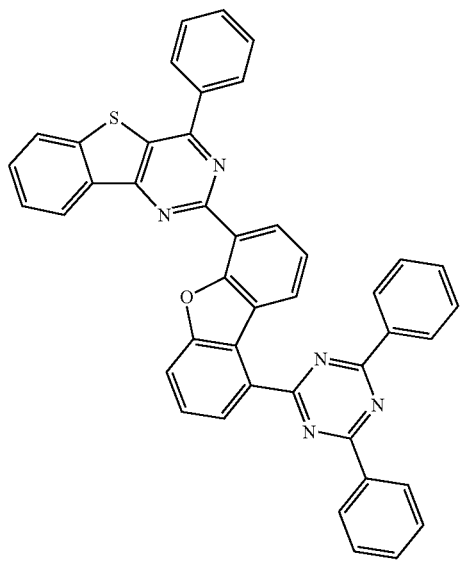
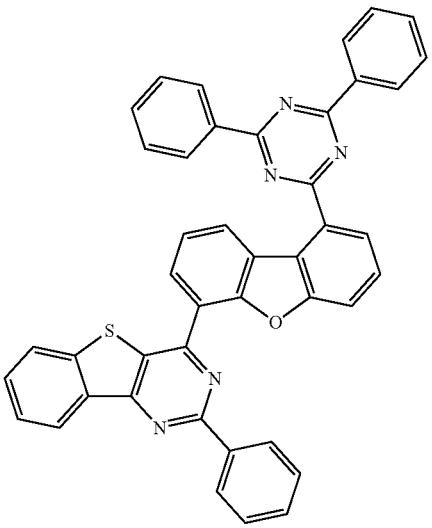
9. The compound of claim 1, wherein the compound represented by Formula 1 is any one selected from the group consisting of the following formulas:

357
-continued
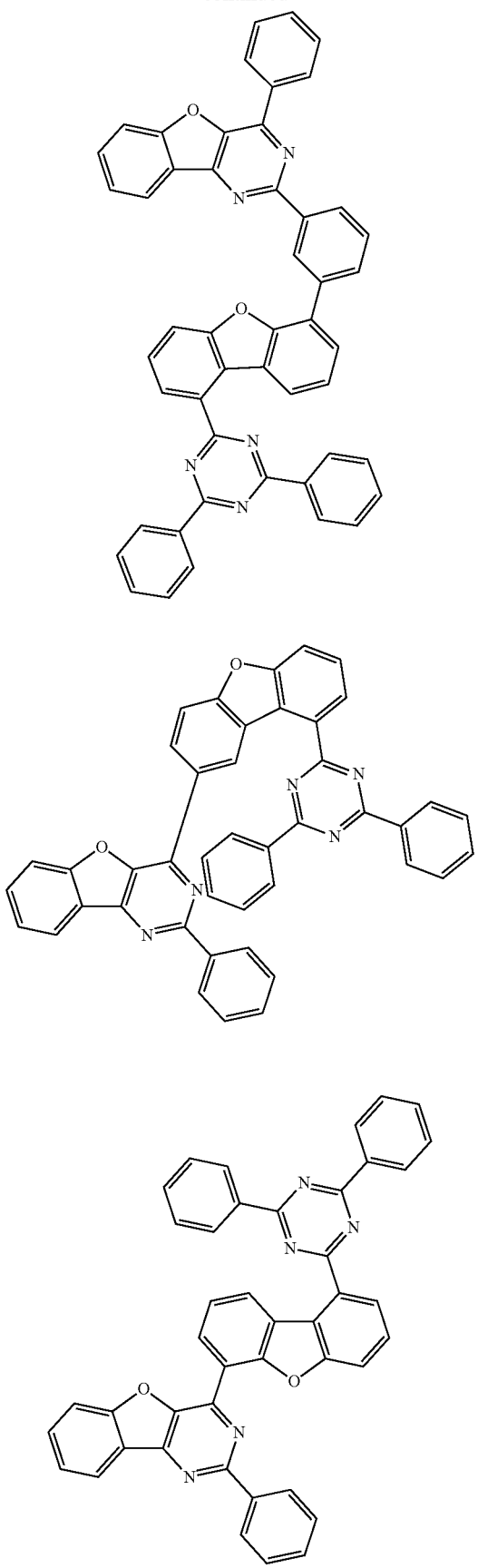
358
-continued
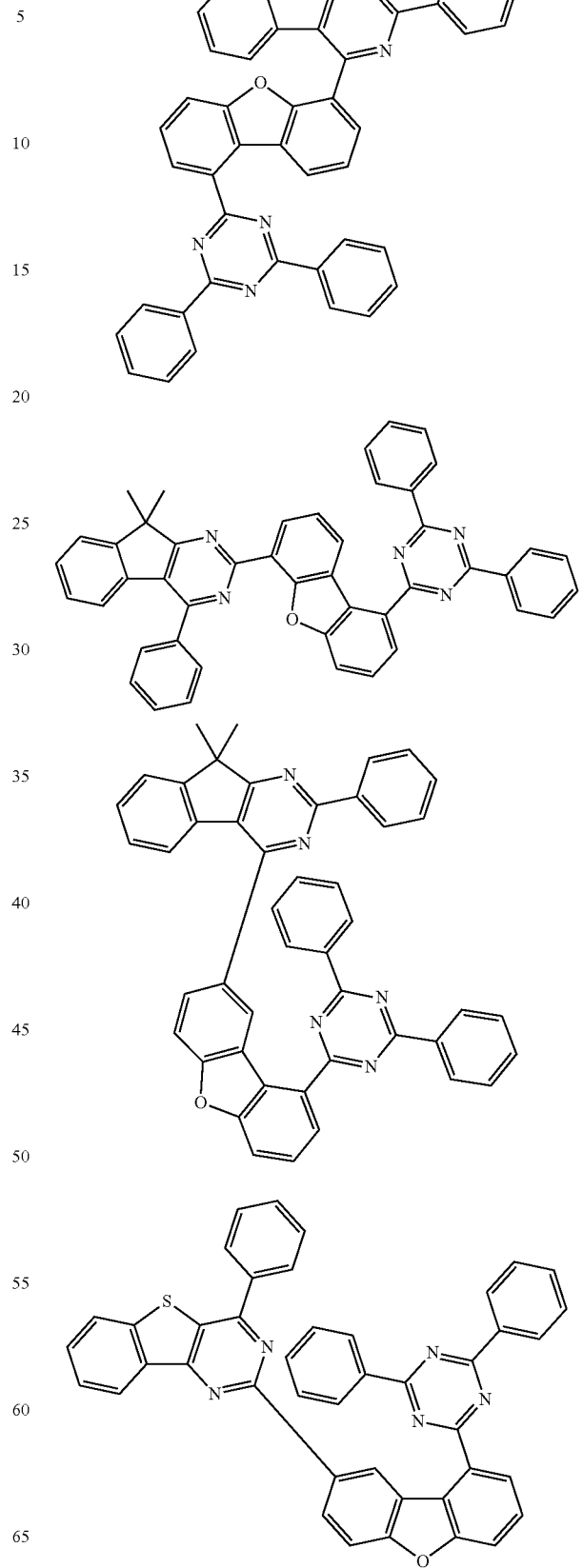

359
-continued
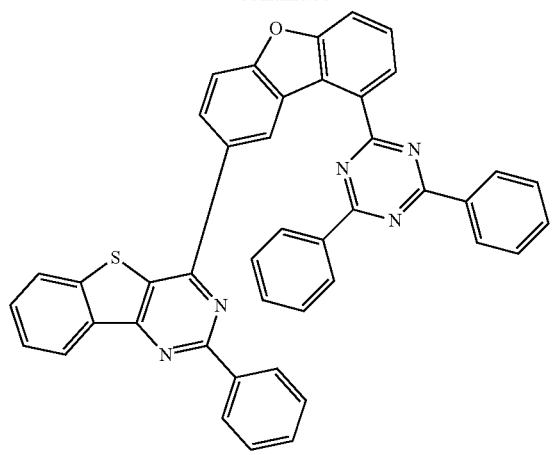
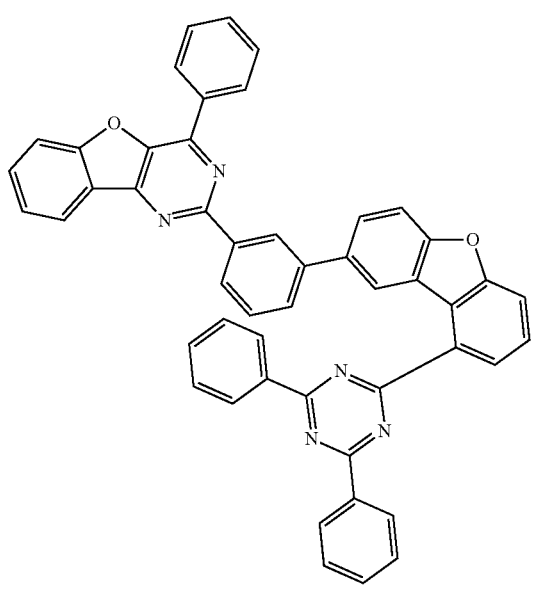
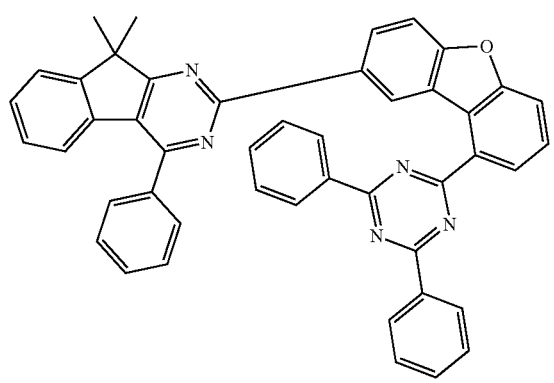
360
-continued
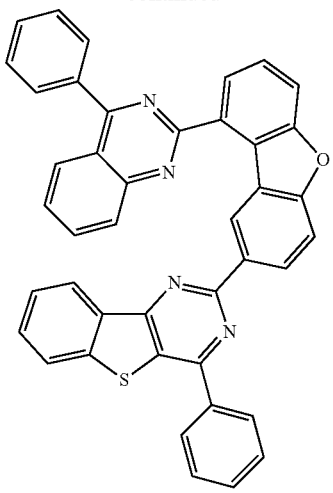
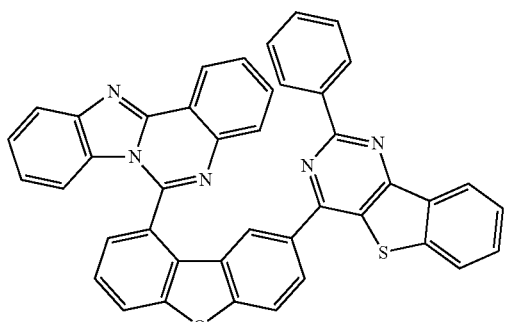
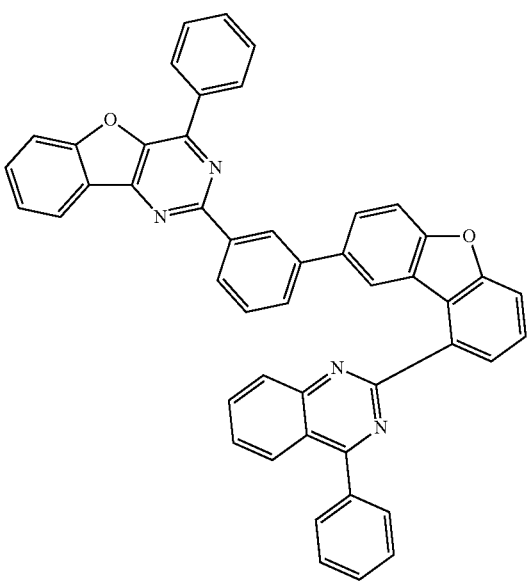

361
-continued
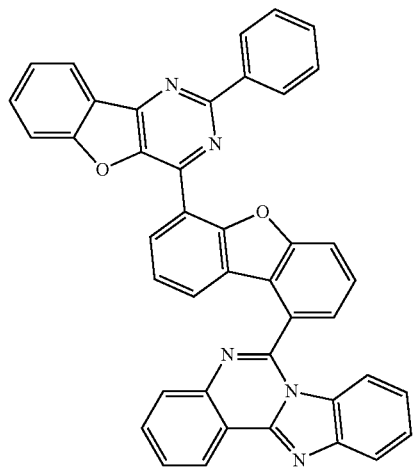
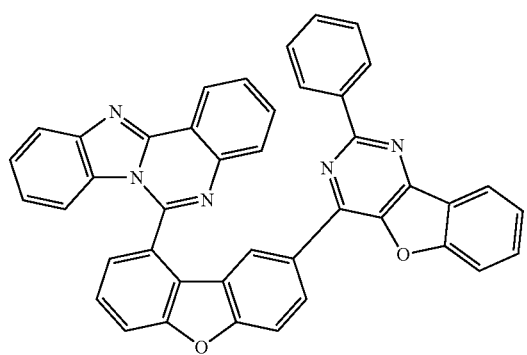
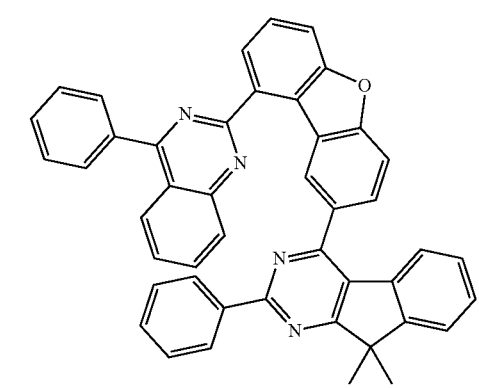
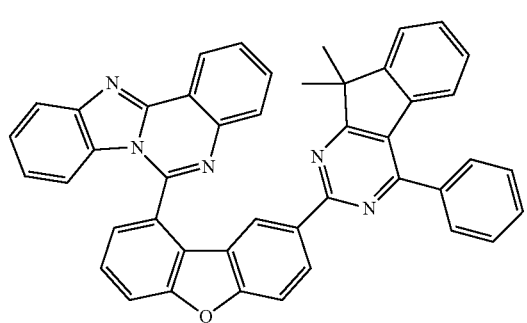
362
-continued
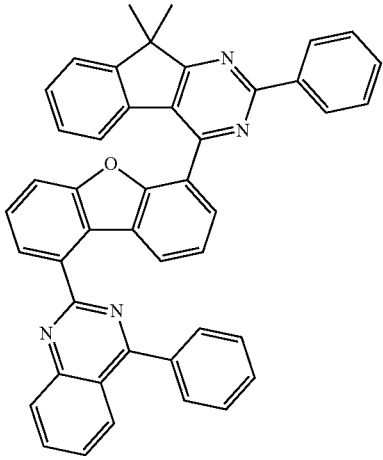
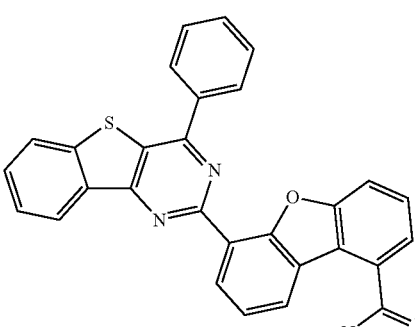
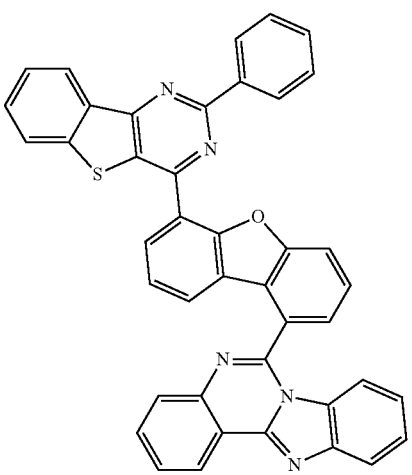

363
-continued
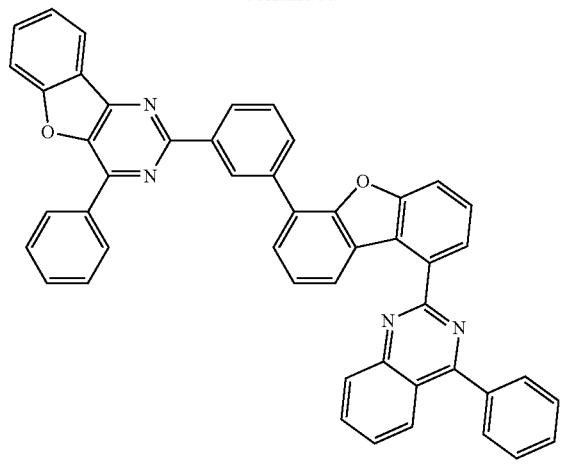
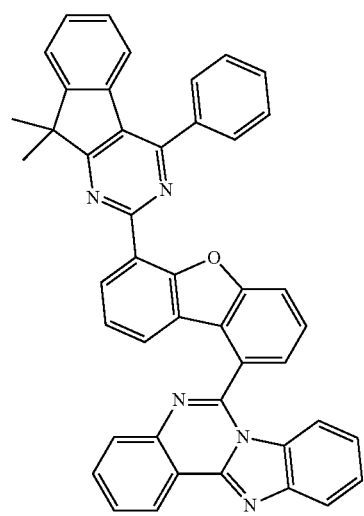
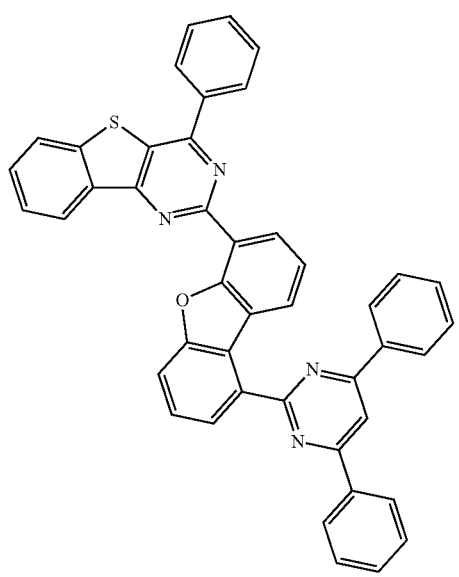
364
-continued
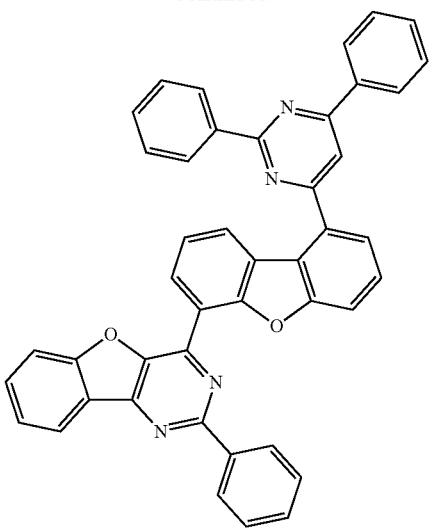
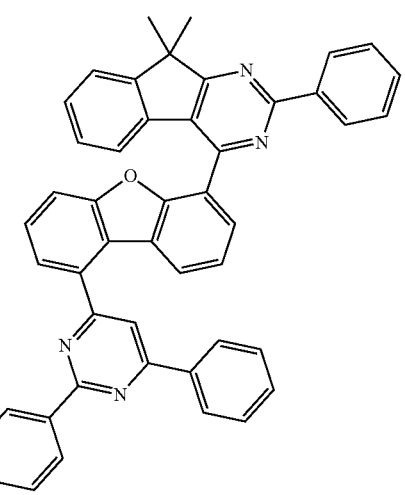
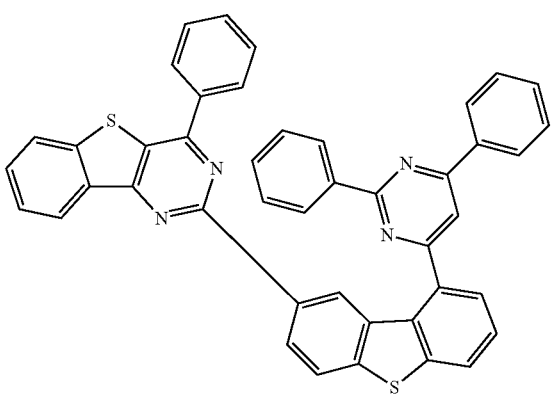

365
-continued
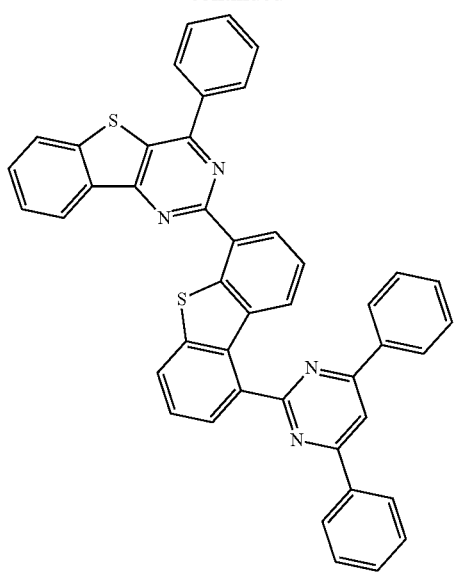
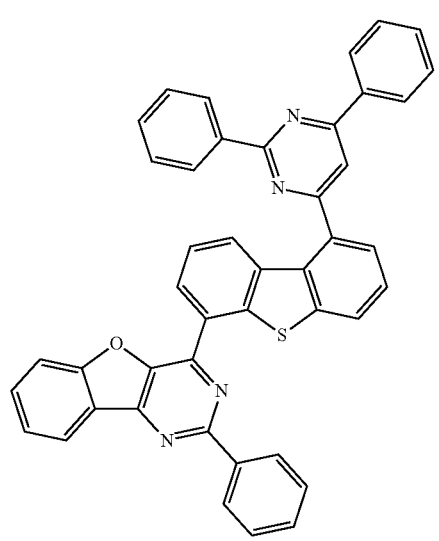
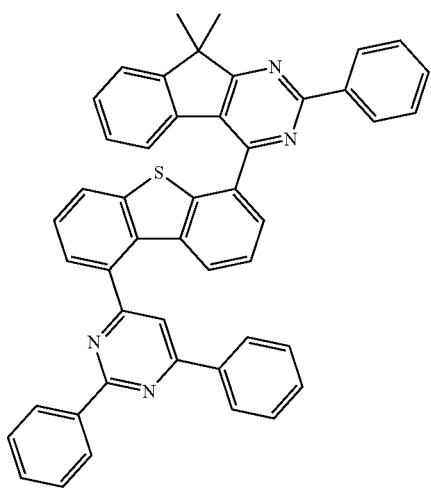
366
-continued
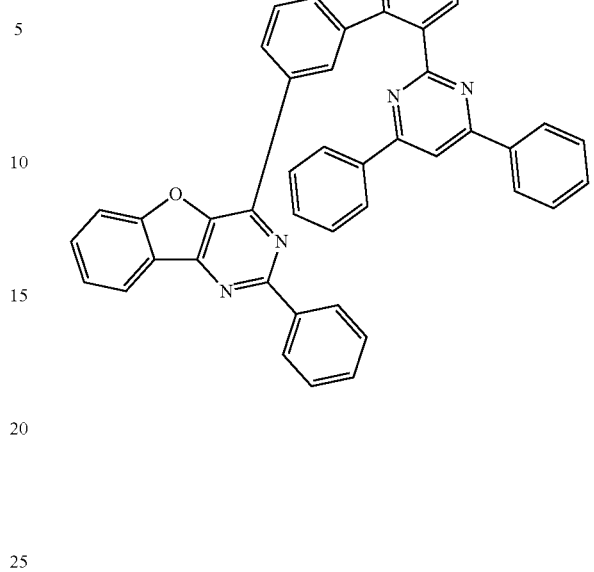
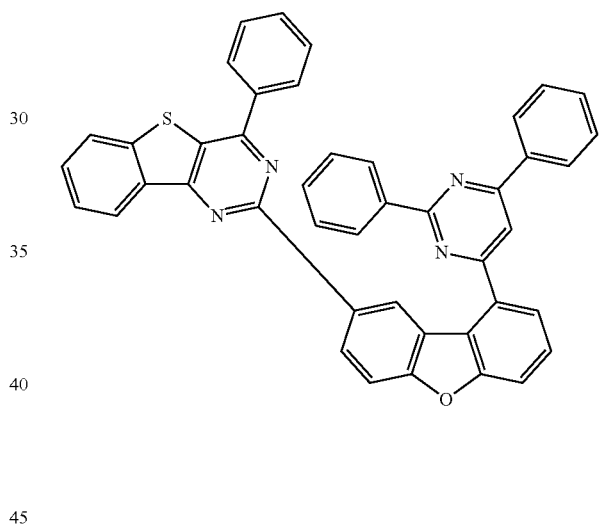
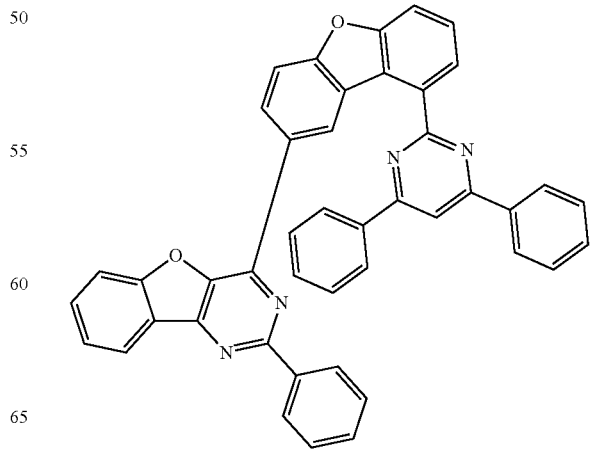

367
-continued
368
-continued
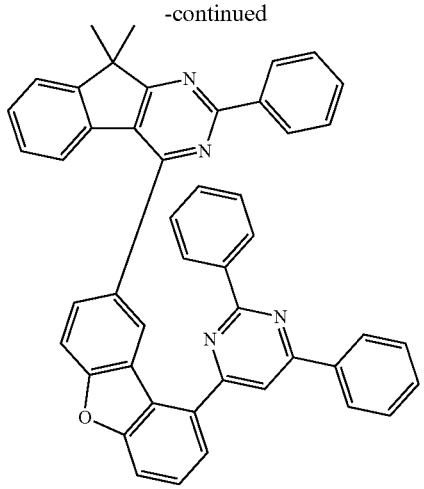
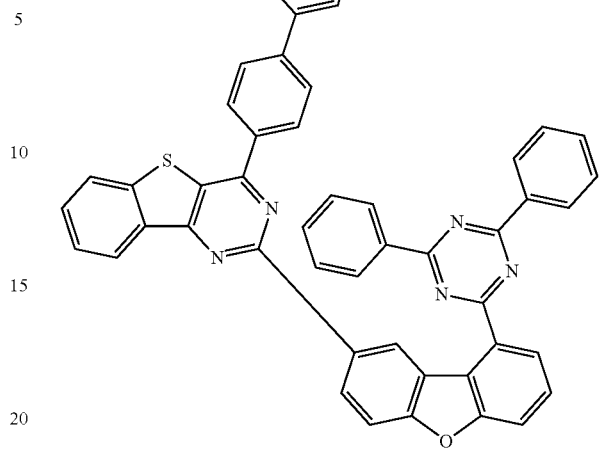
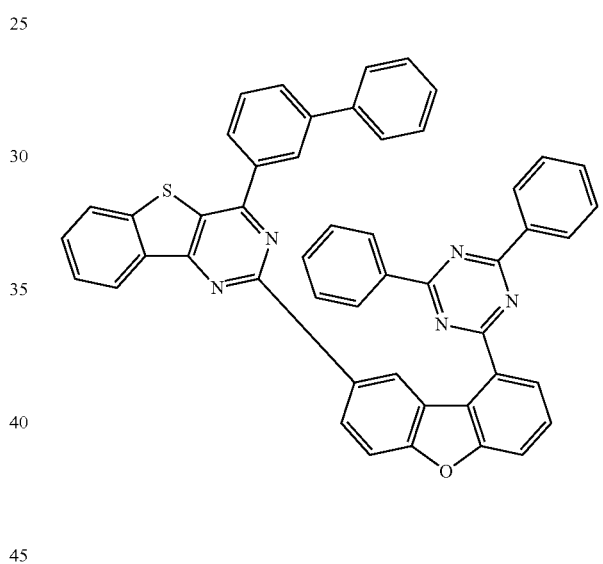
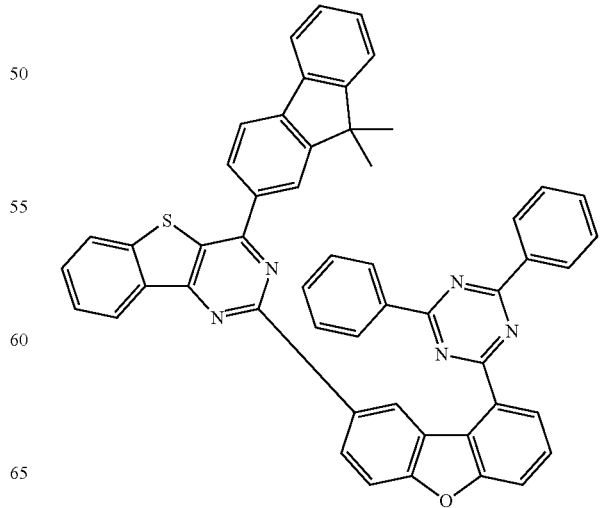

369
-continued
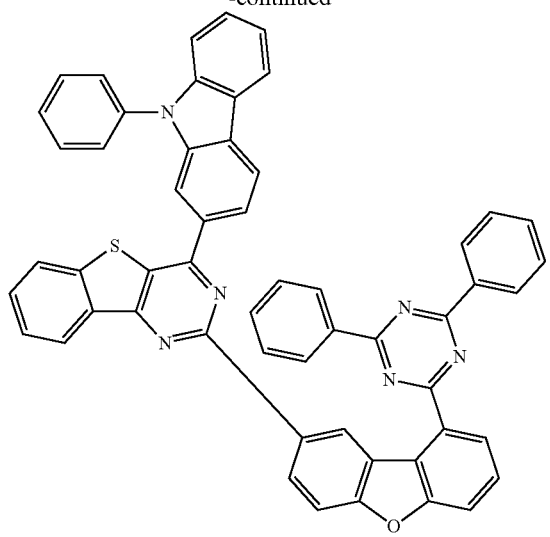
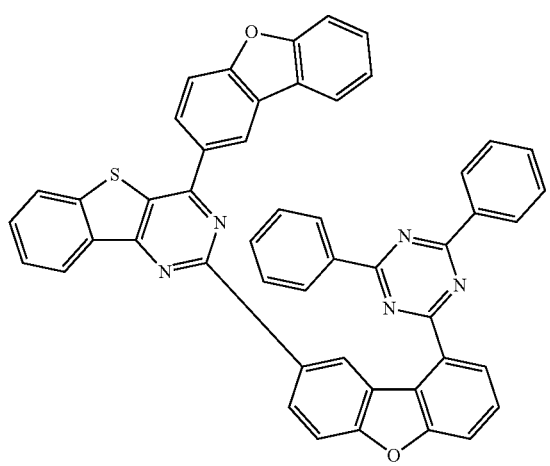
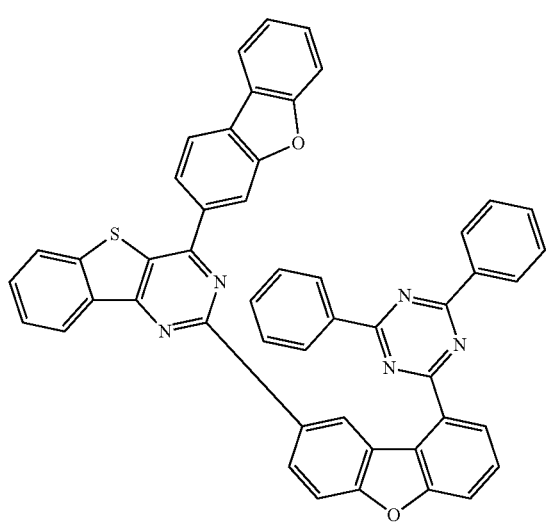
370
-continued
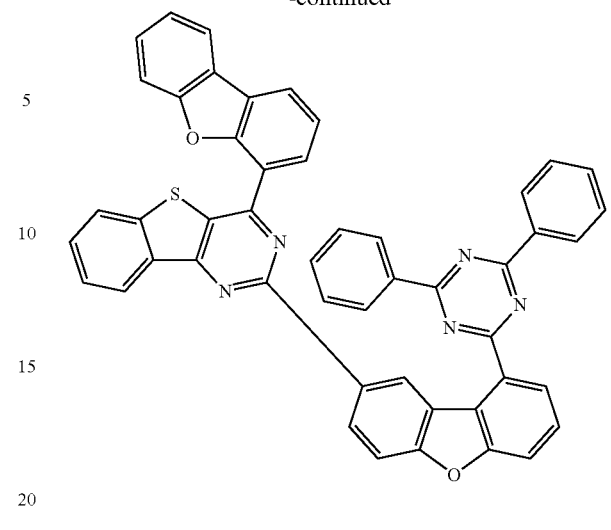
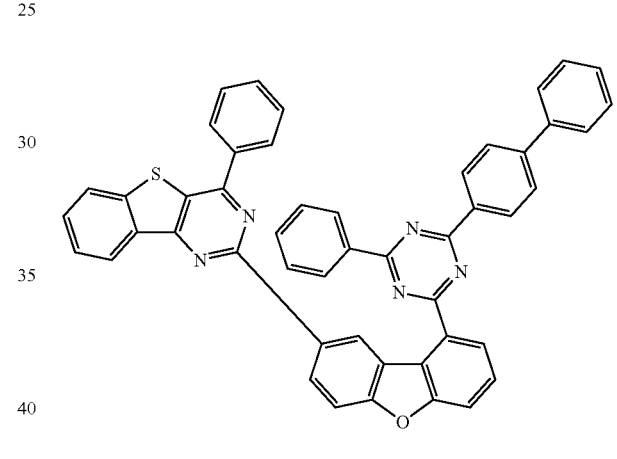
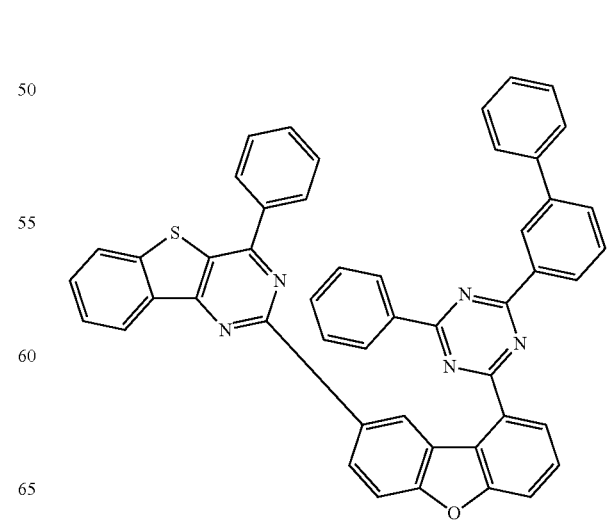

371
-continued
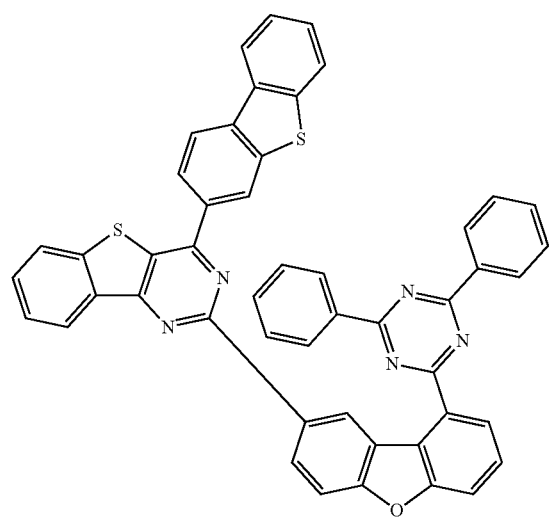
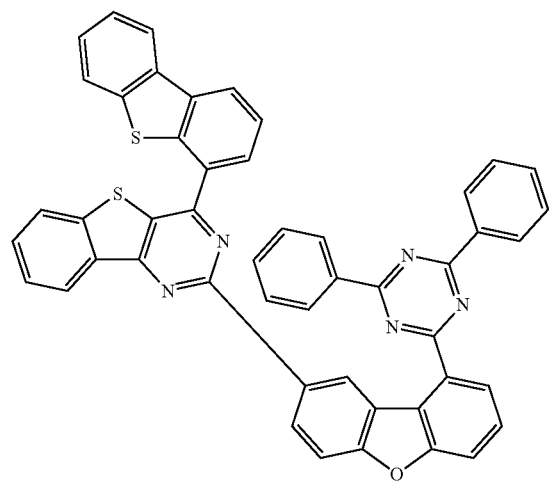
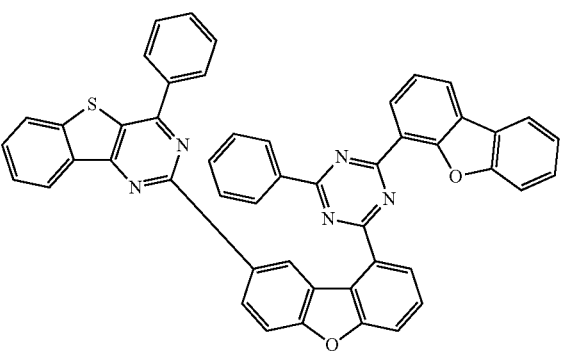
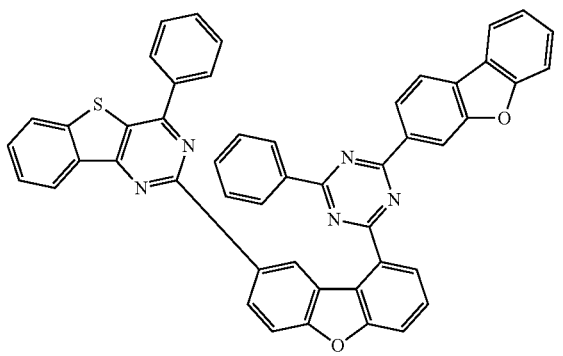
372
-continued
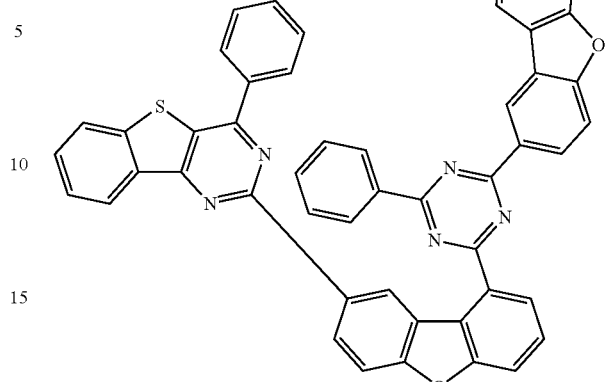
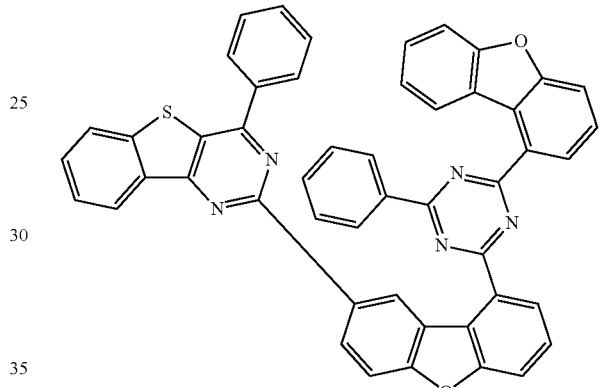
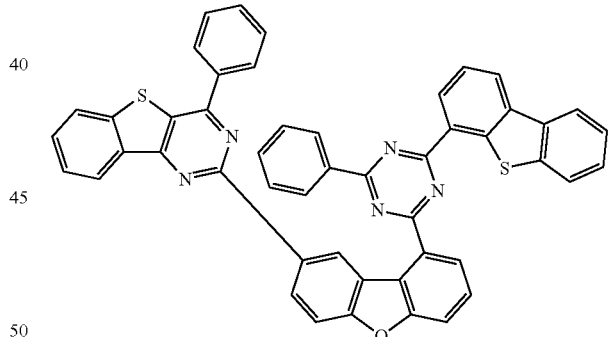
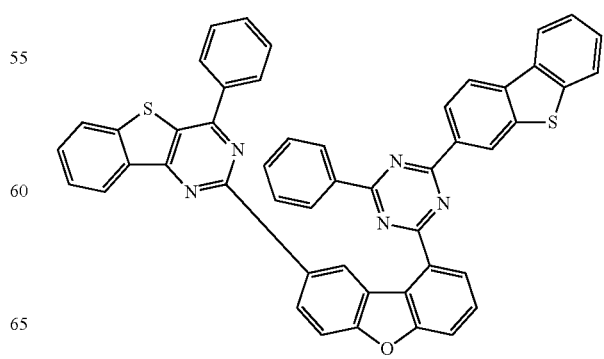

373
-continued
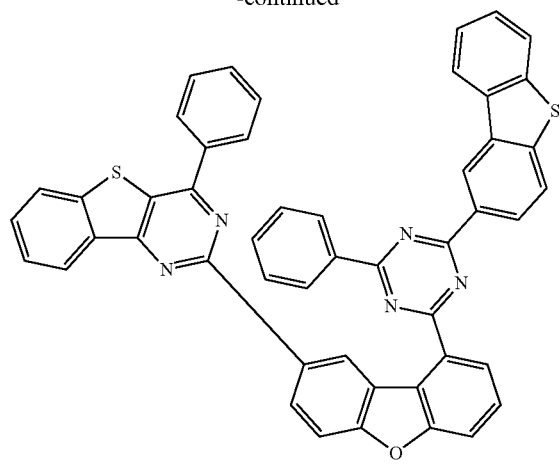
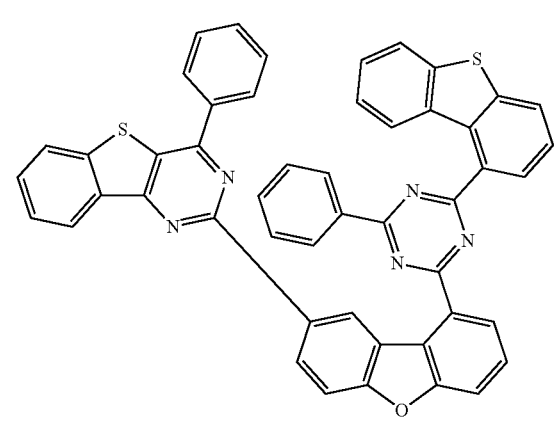
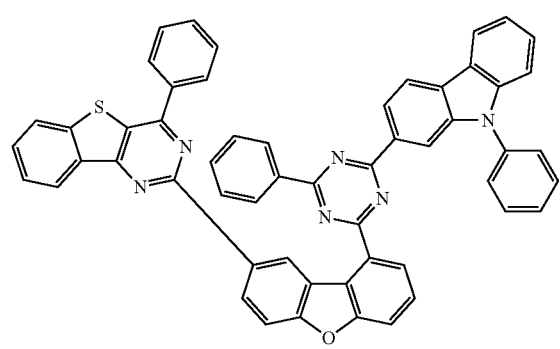
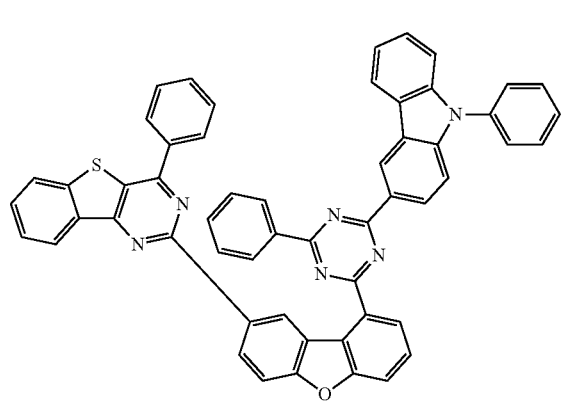
374
-continued
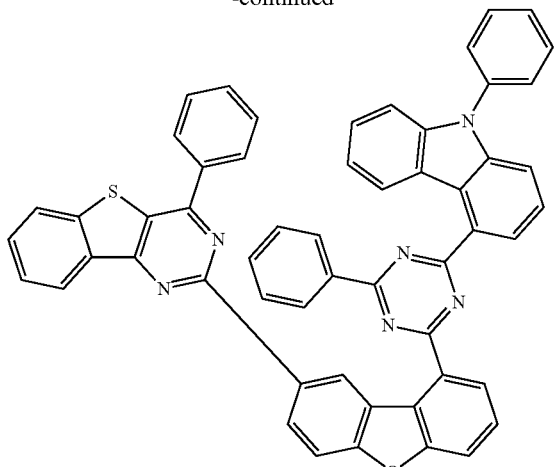
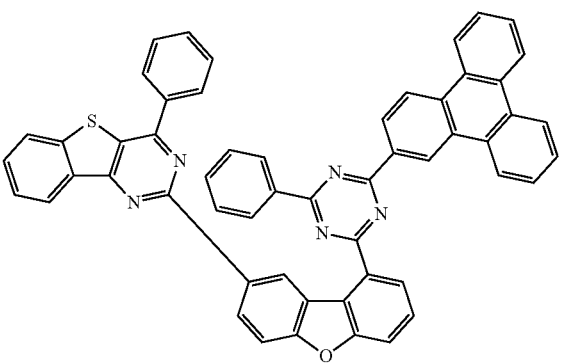
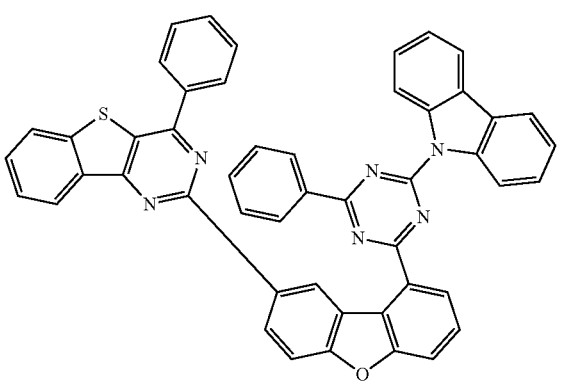
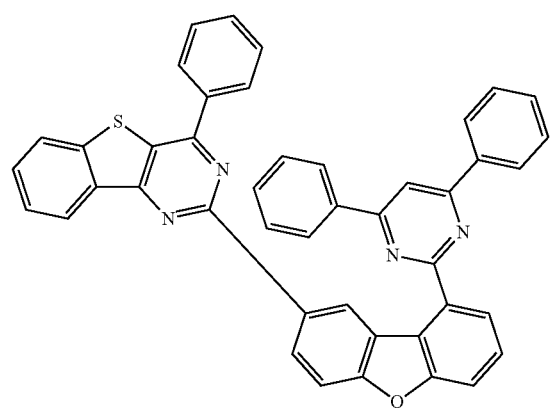

375
-continued
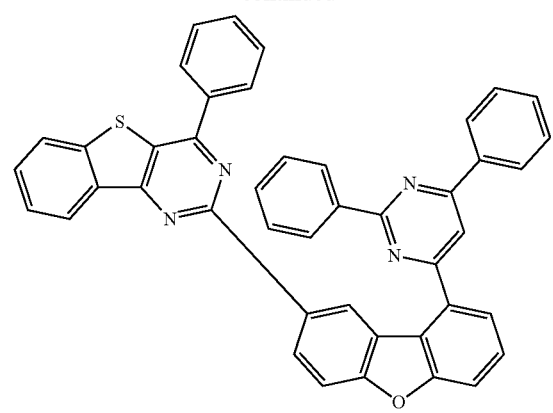
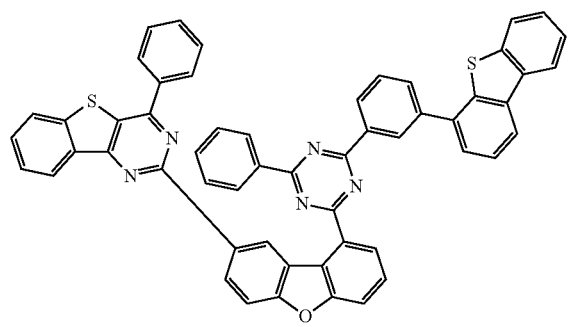
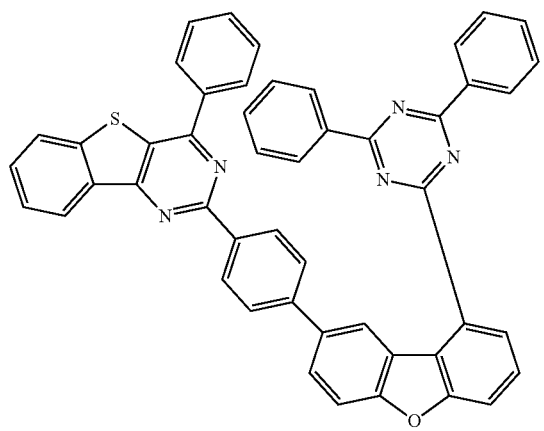
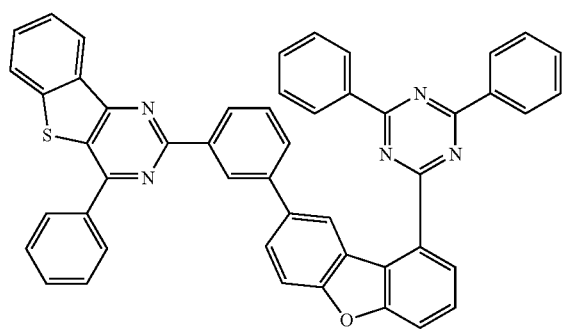
376
-continued
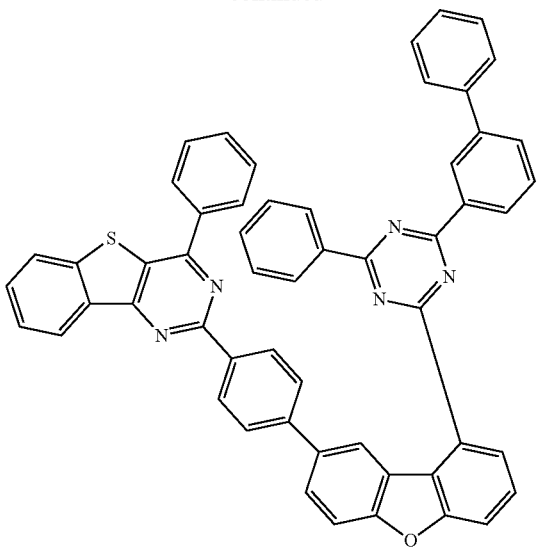
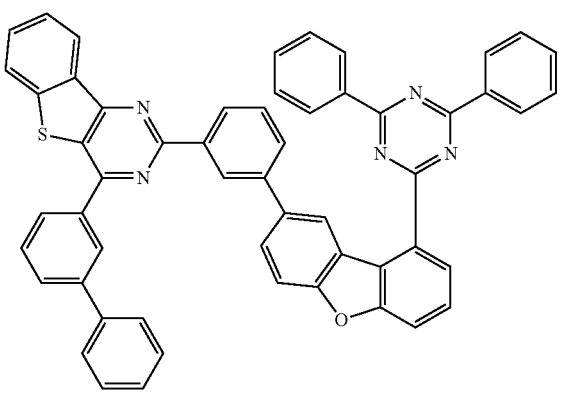
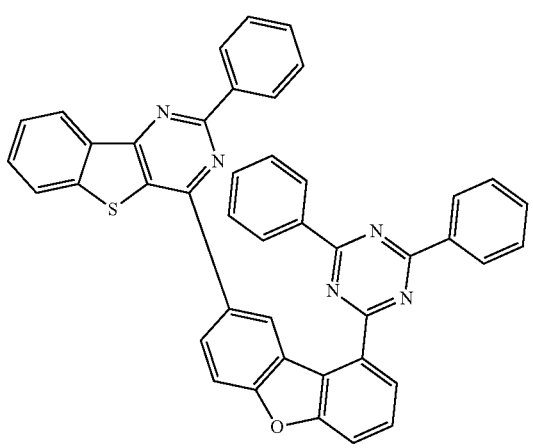

377
-continued
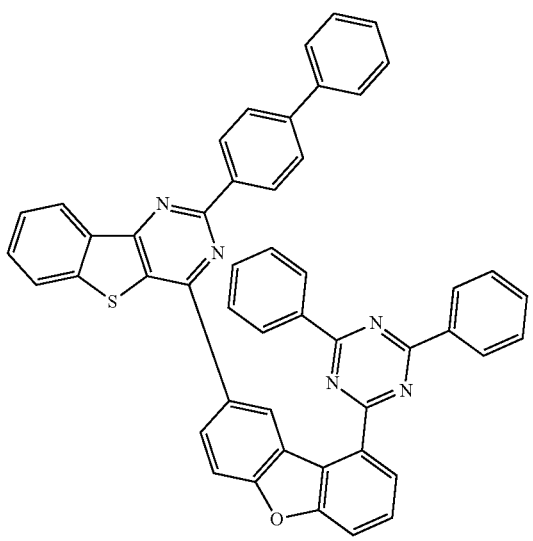
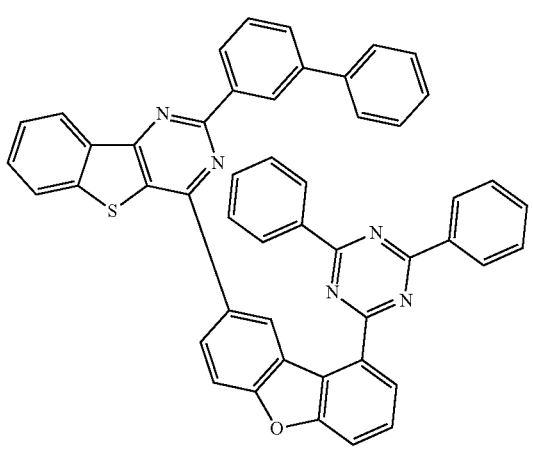
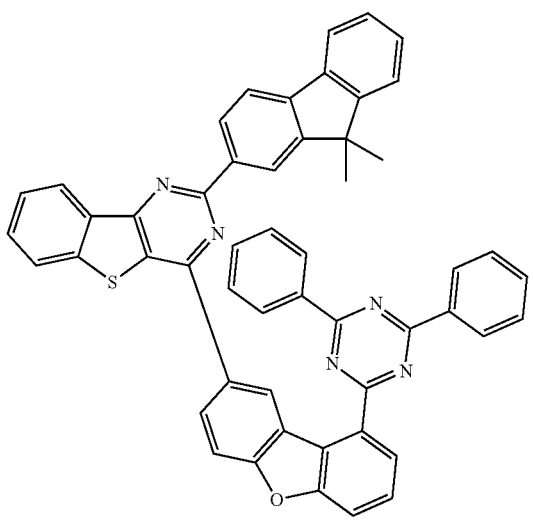
378
-continued
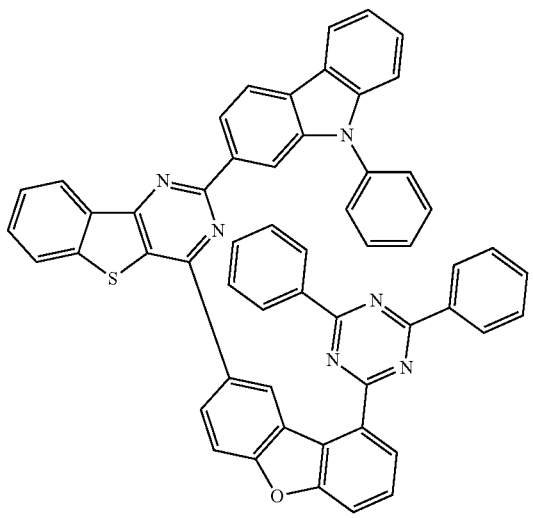
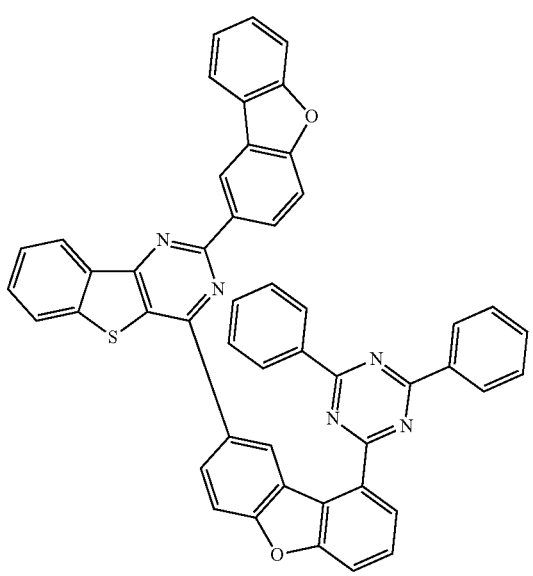

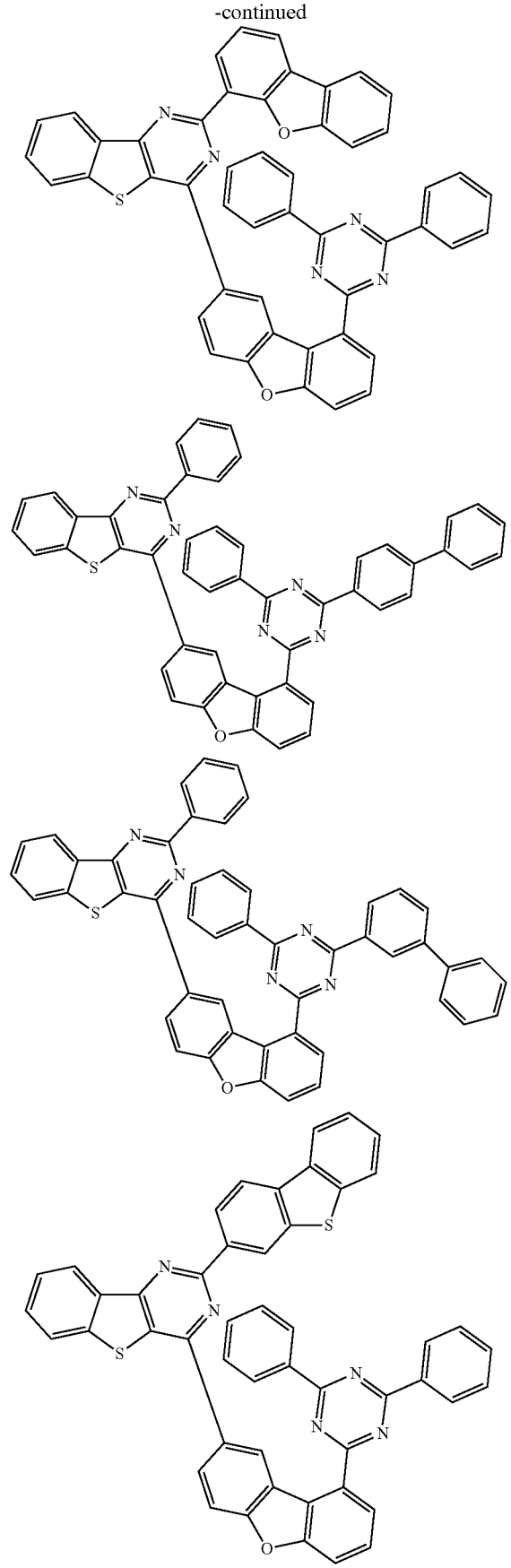
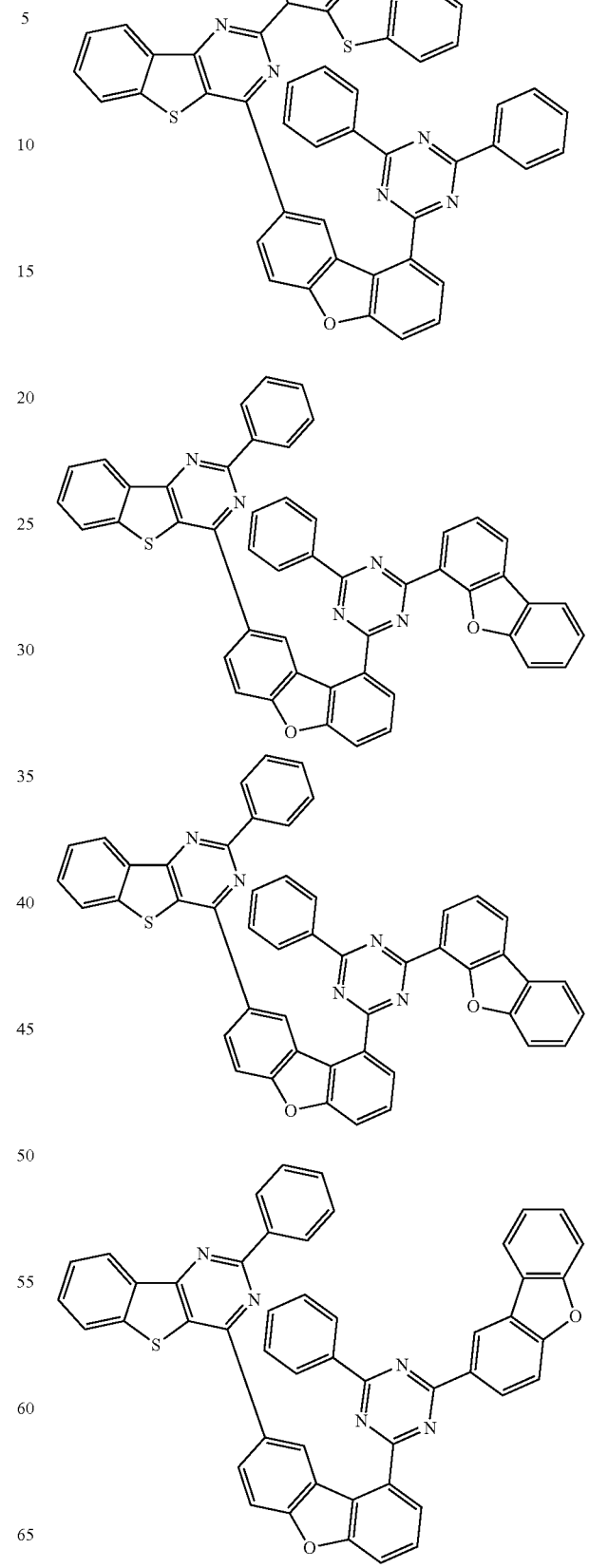

381
-continued
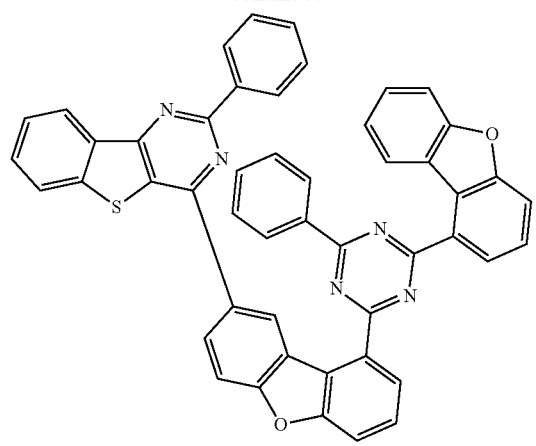
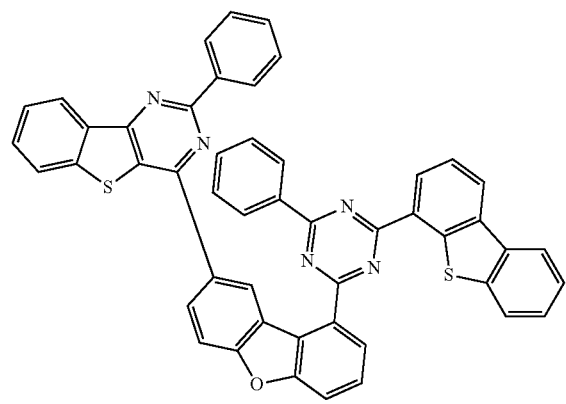
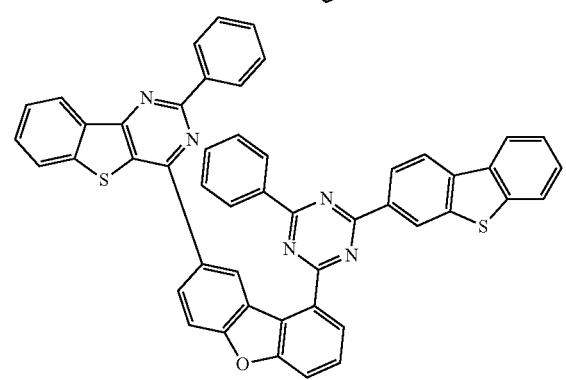
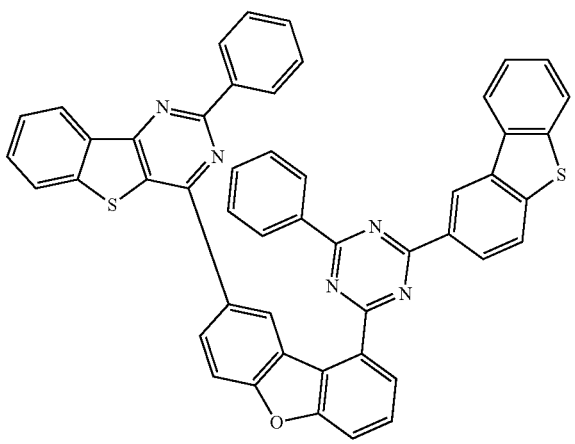
382
-continued
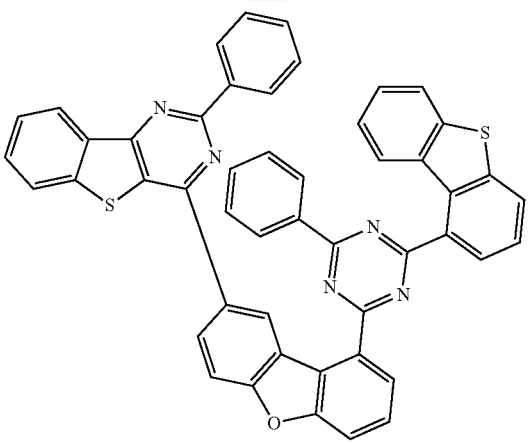
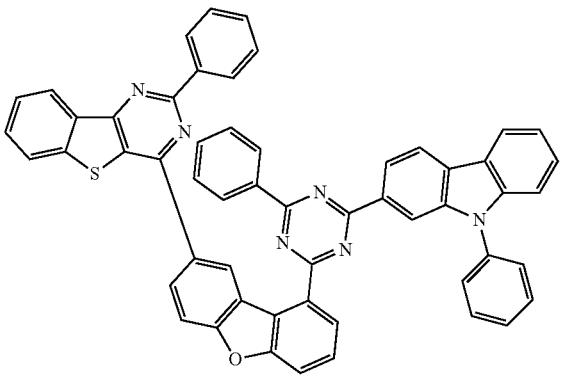
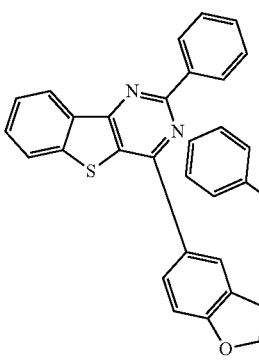
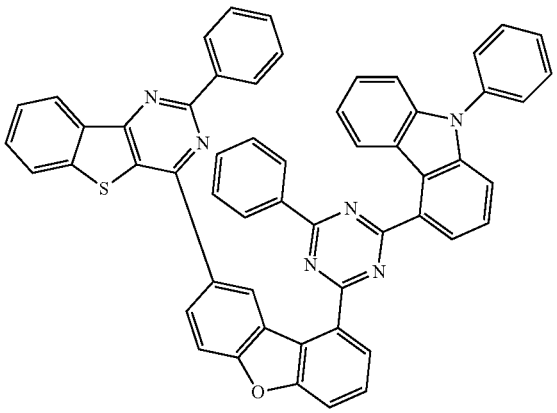

383
-continued
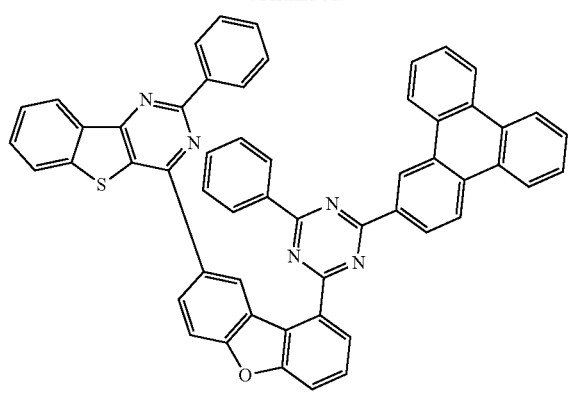
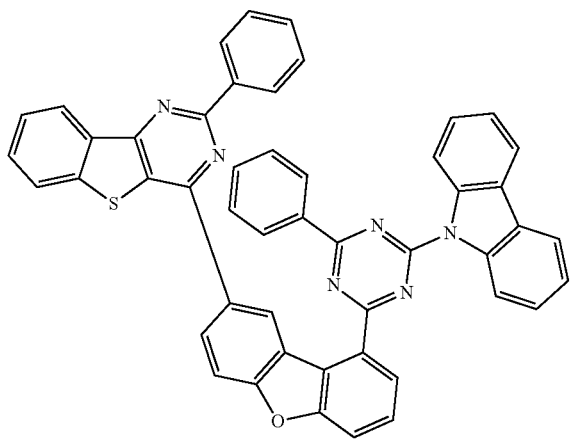
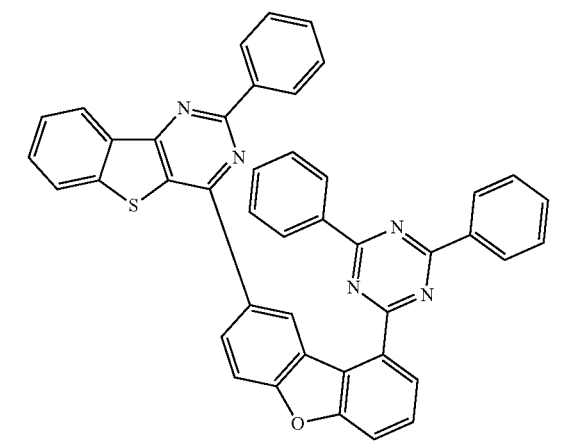
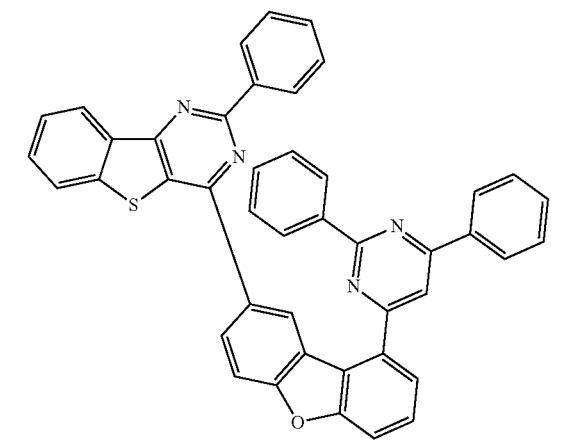
384
-continued
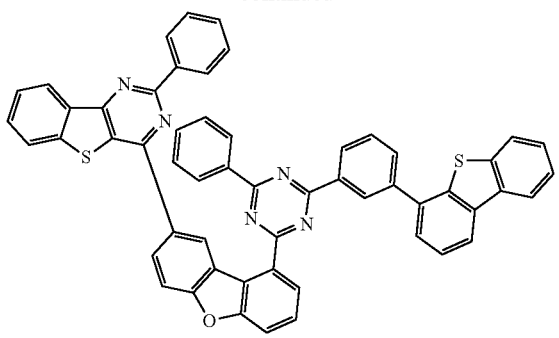
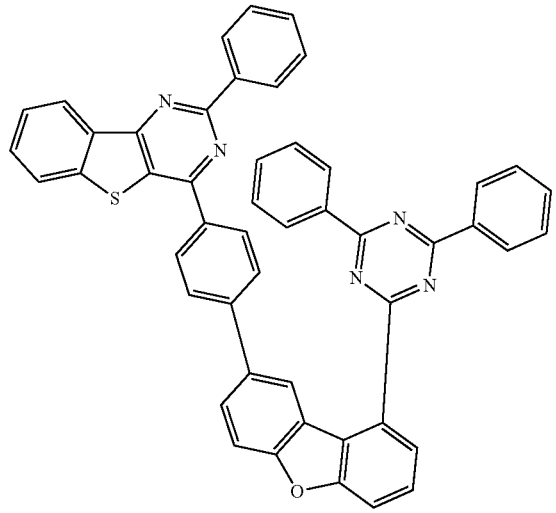
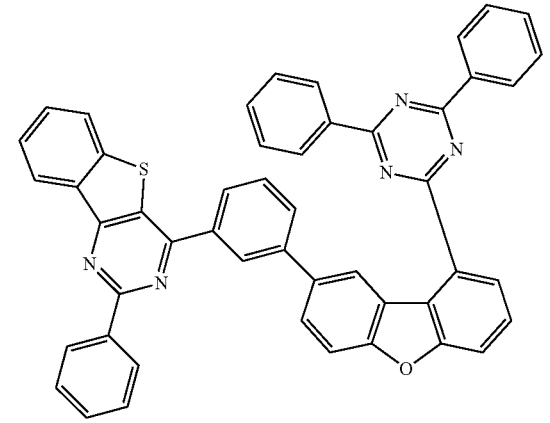

-continued
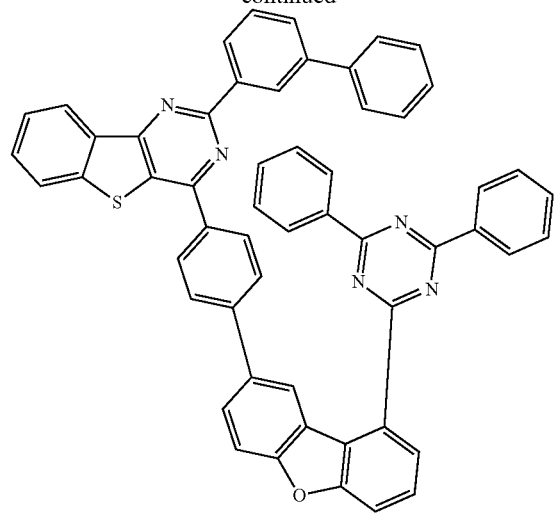
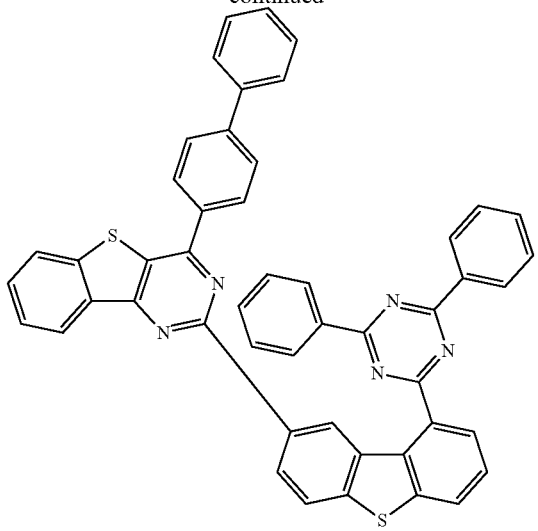
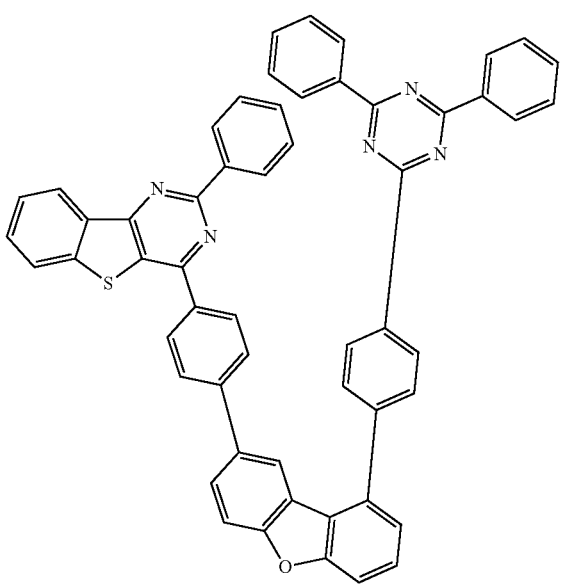
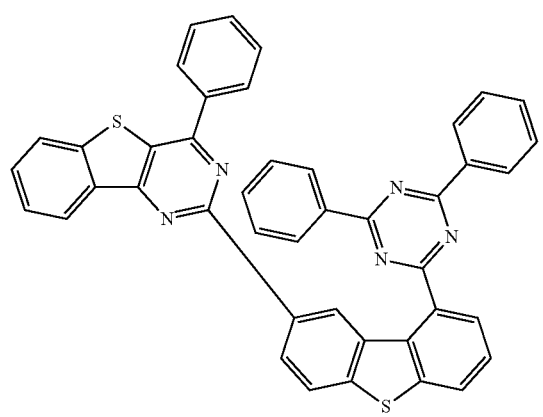
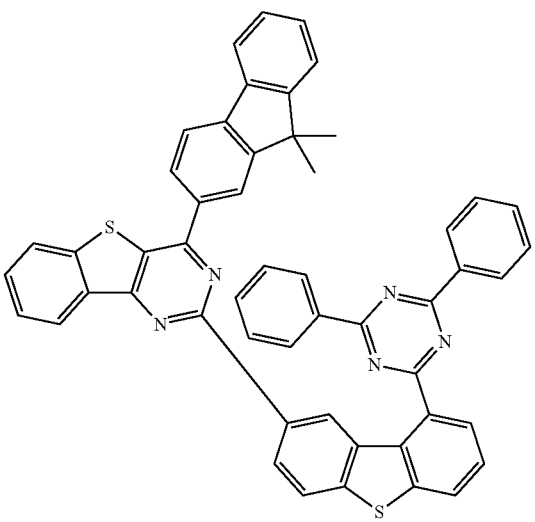

387
-continued
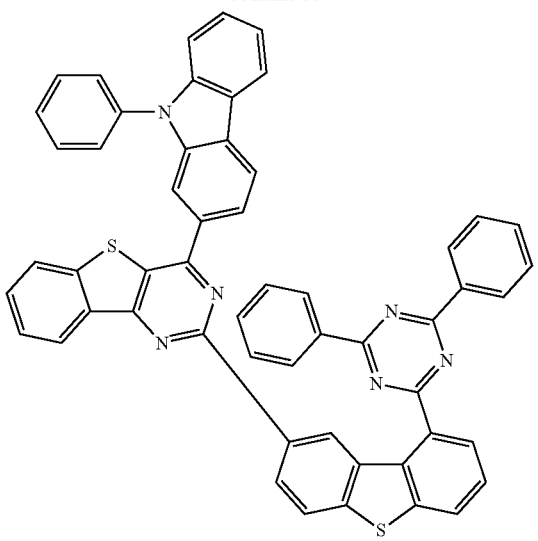
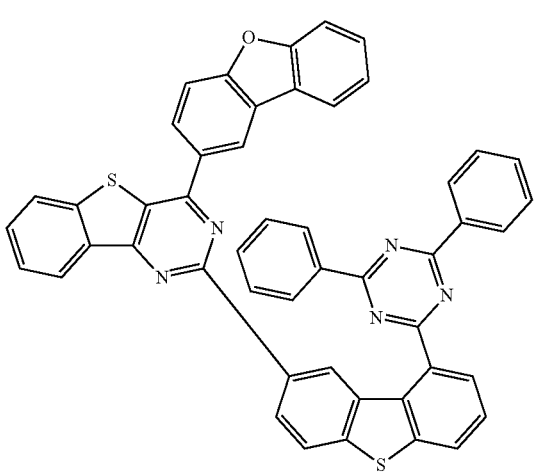
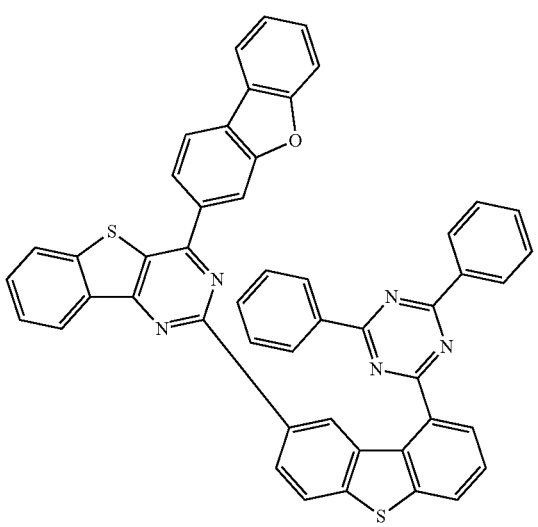
388
-continued
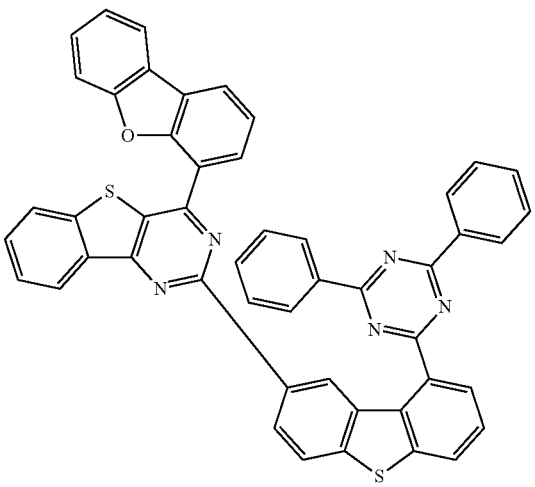
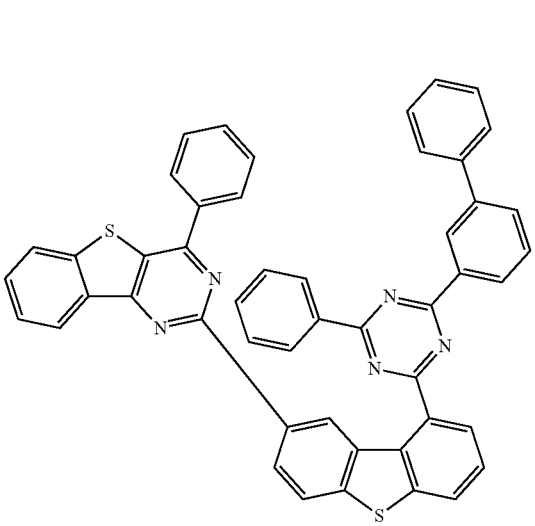

-continued
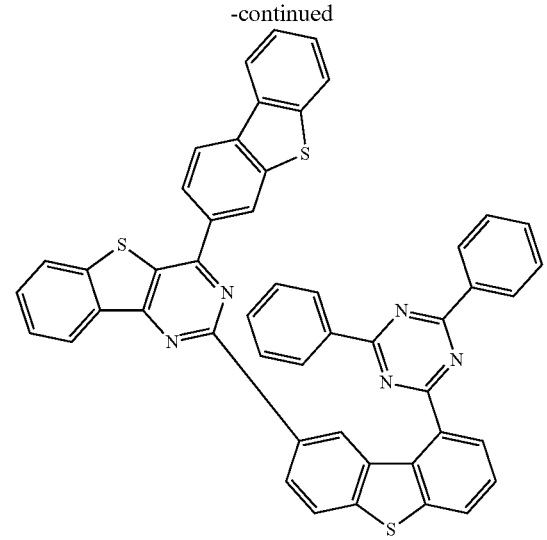
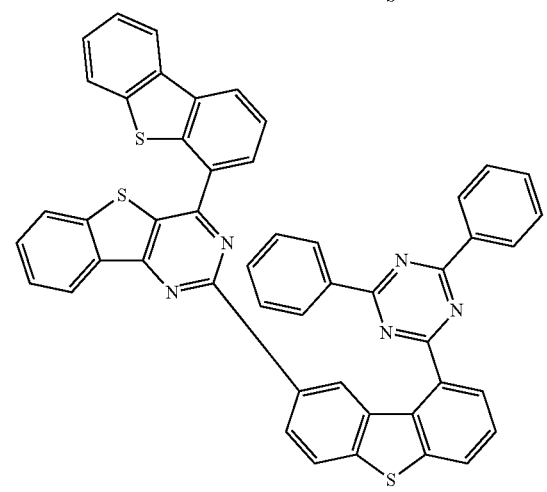
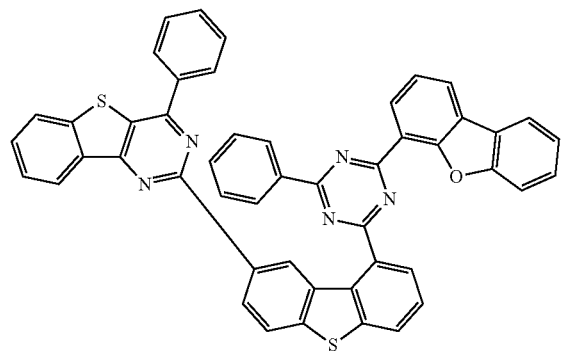
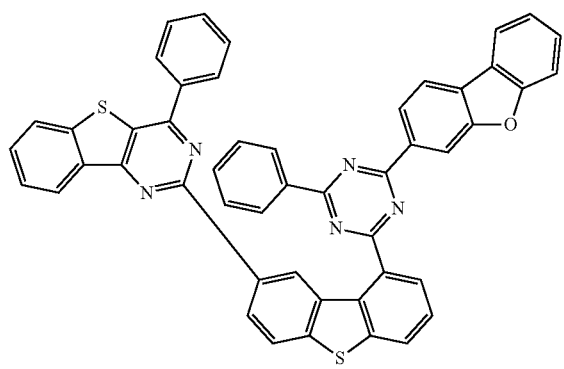
-continued
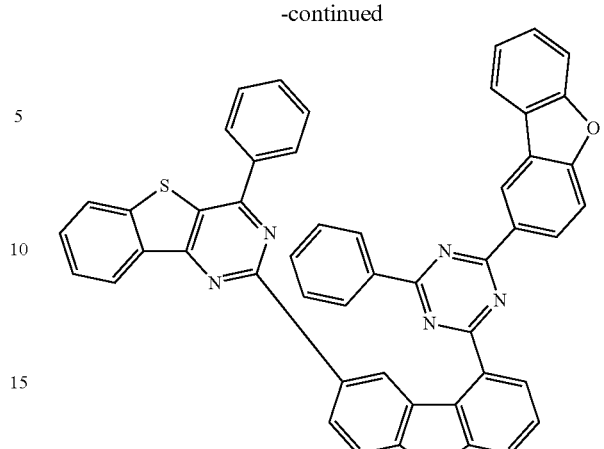
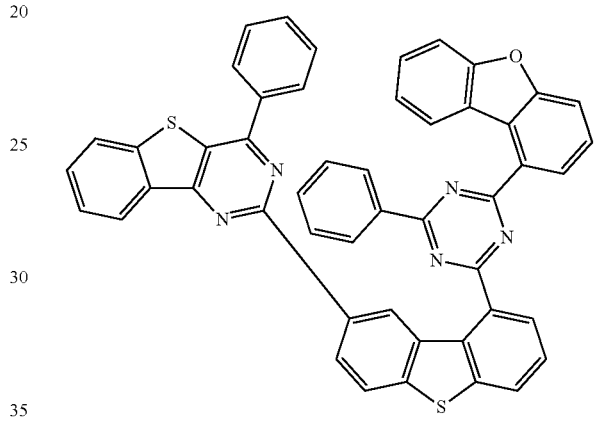
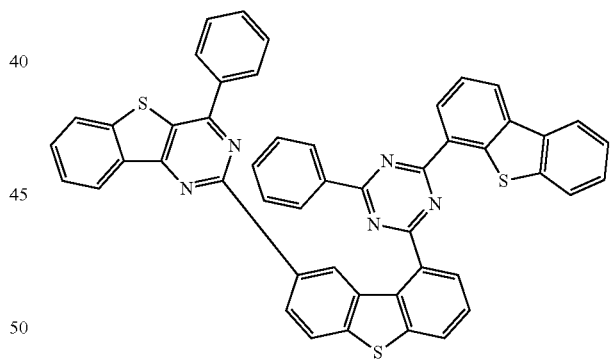
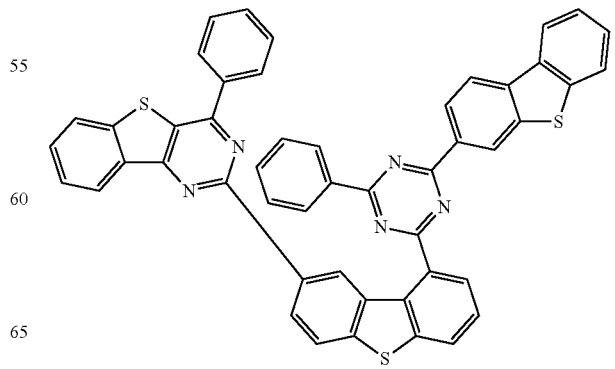

391
-continued
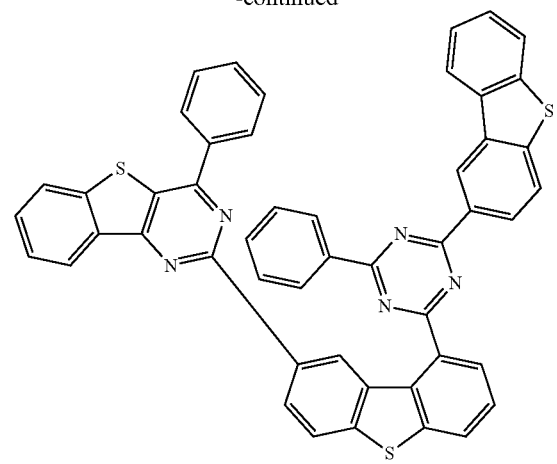
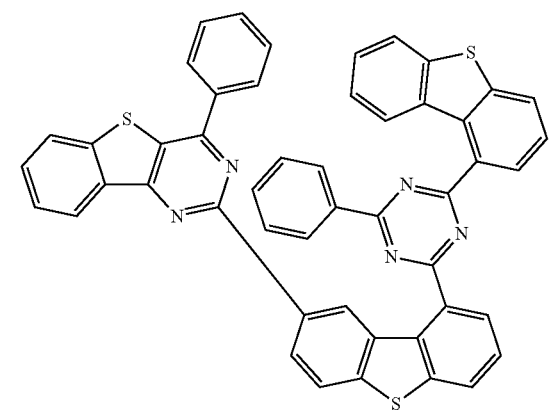
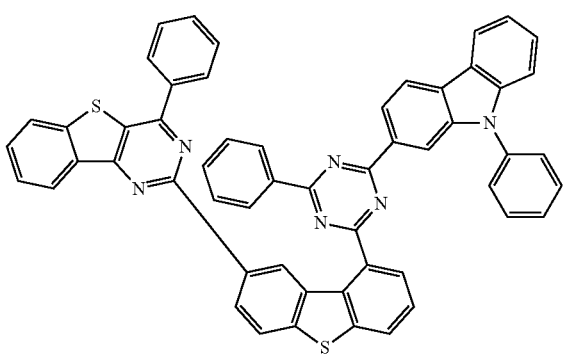
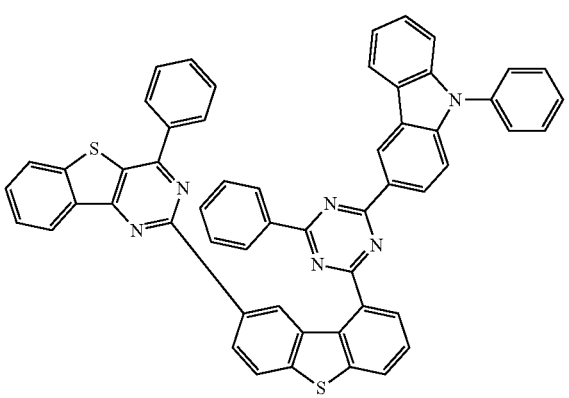
392
-continued
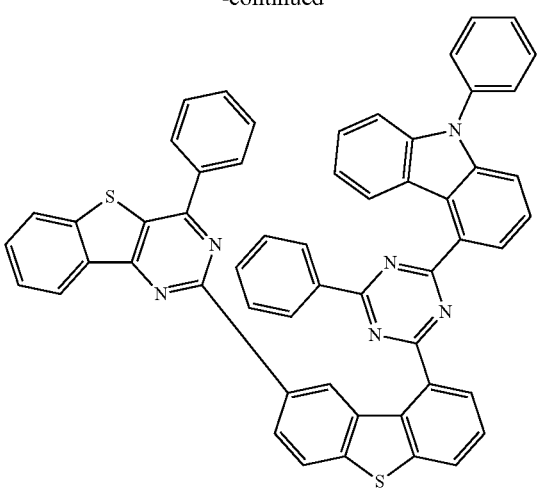
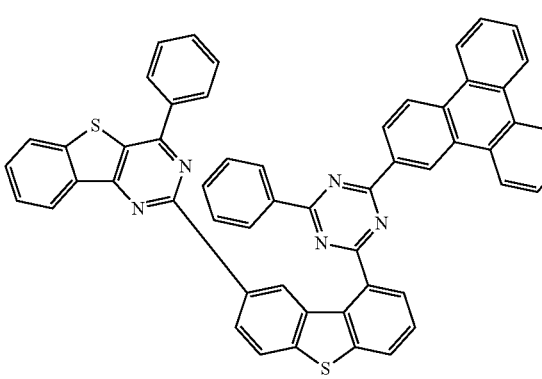
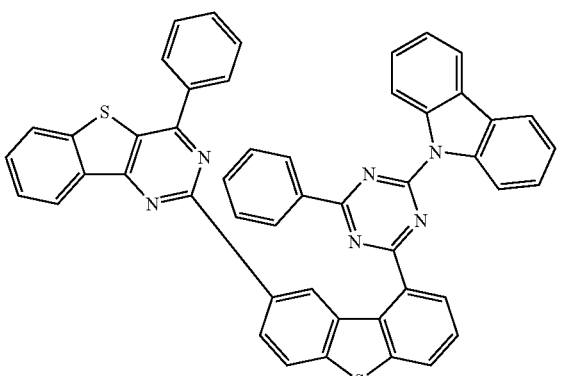
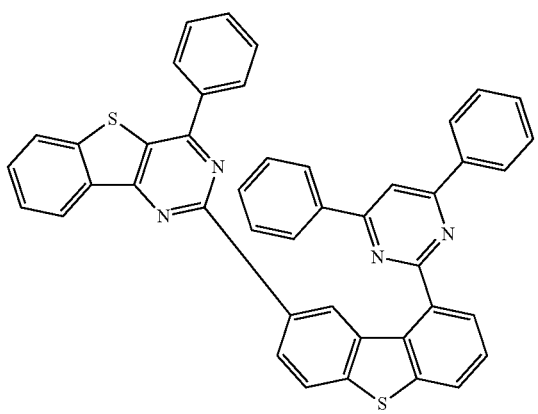

393
-continued
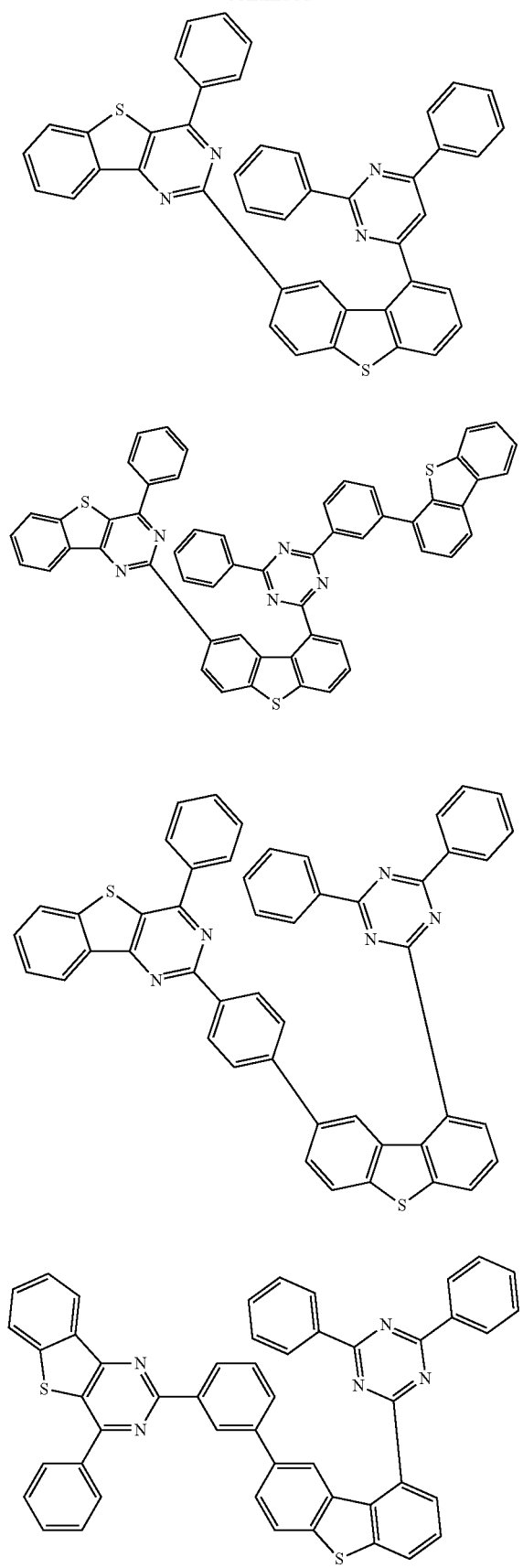
394
-continued
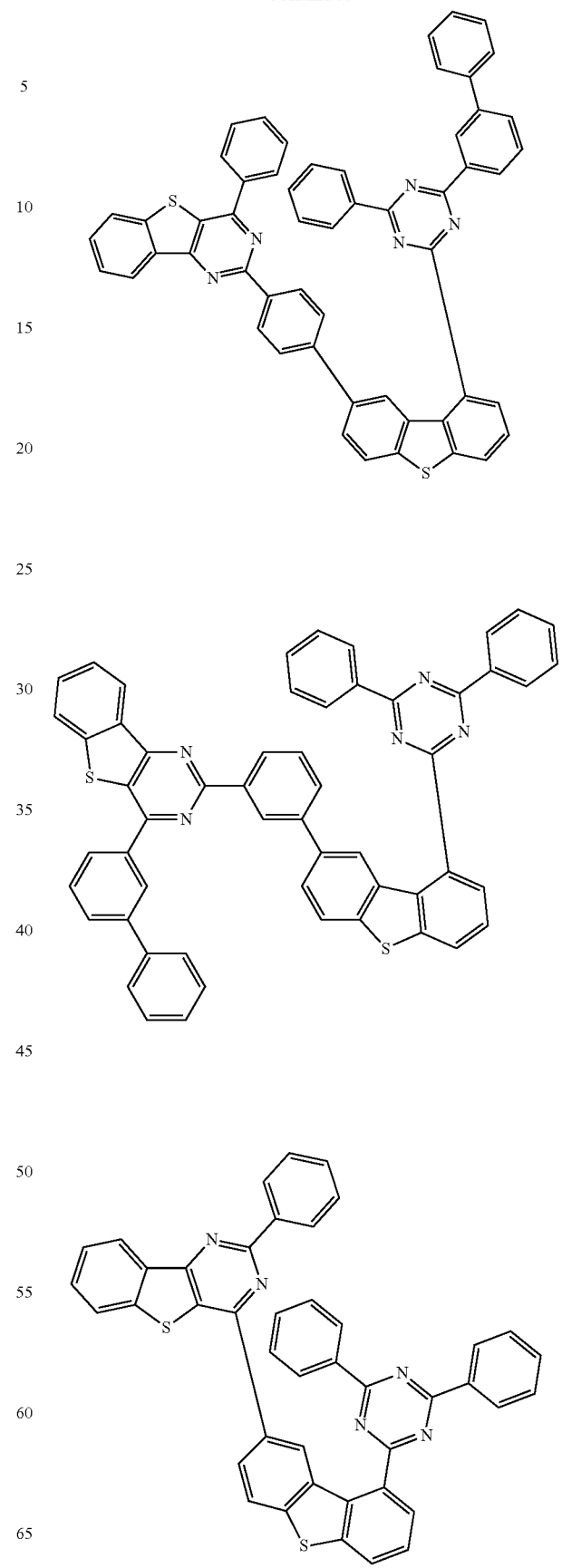

395
-continued
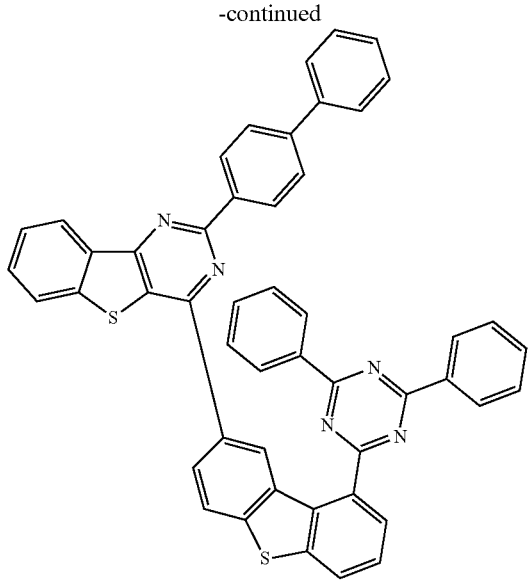
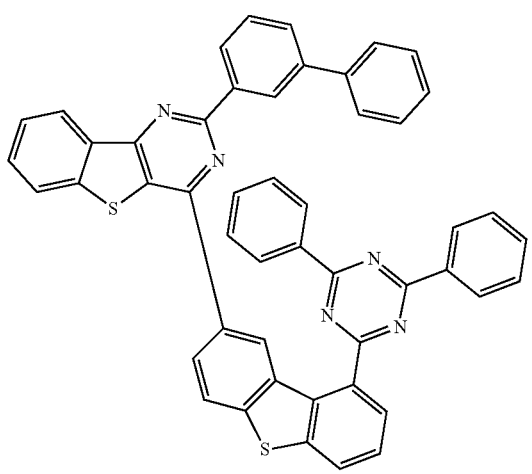
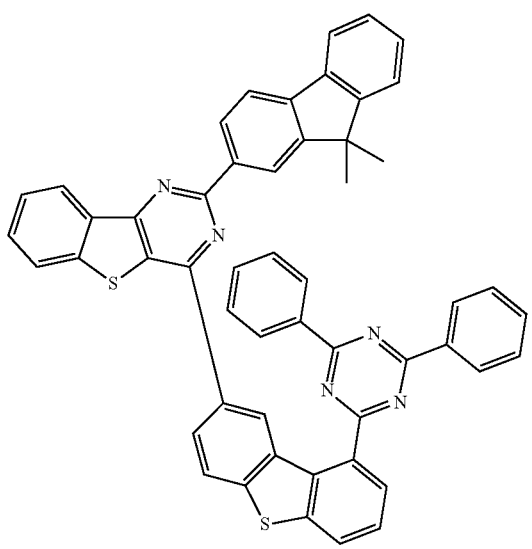
396
-continued
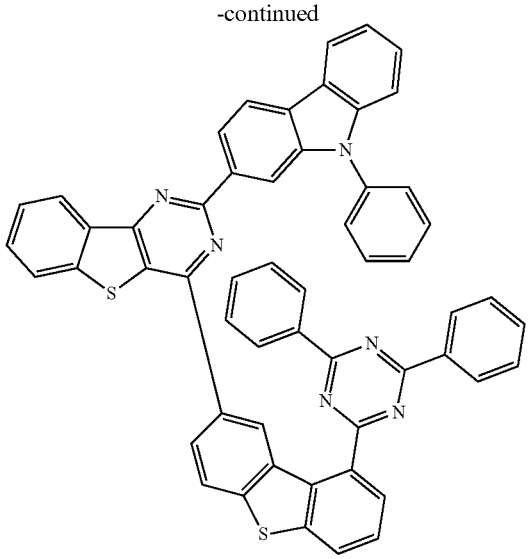
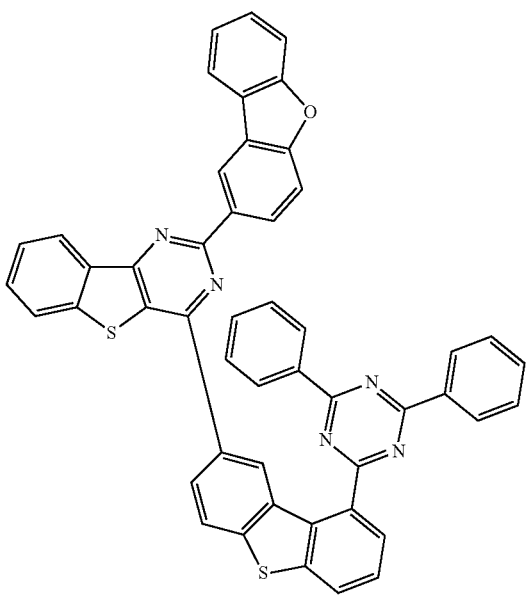
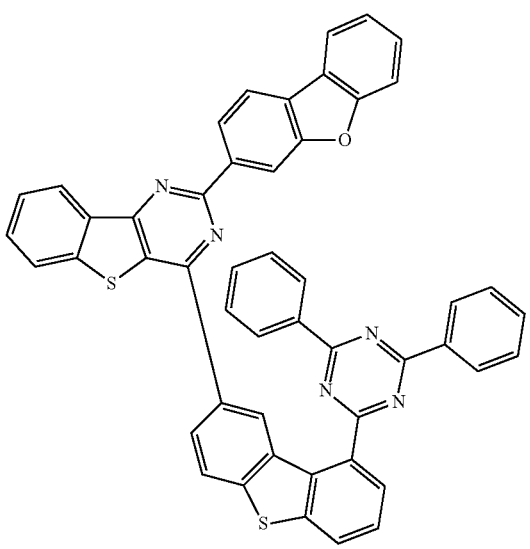

397
-continued
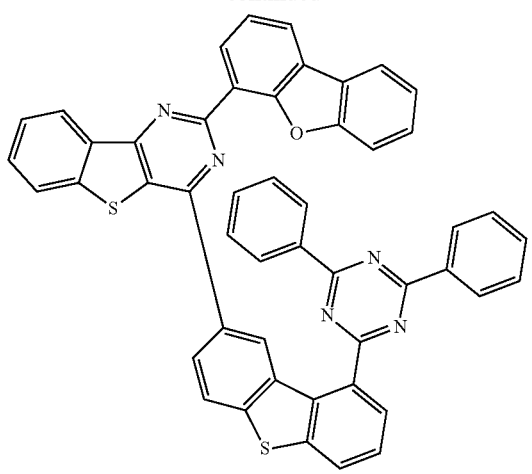
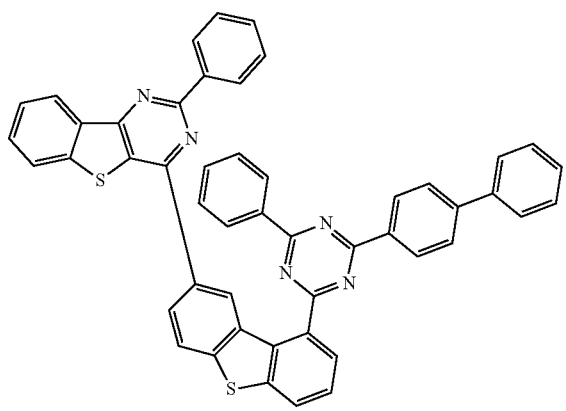
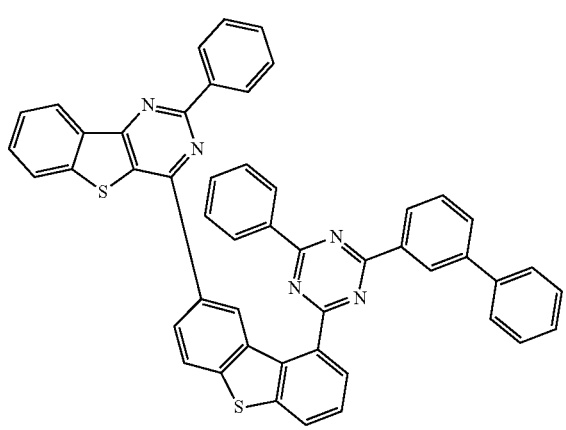
398
-continued
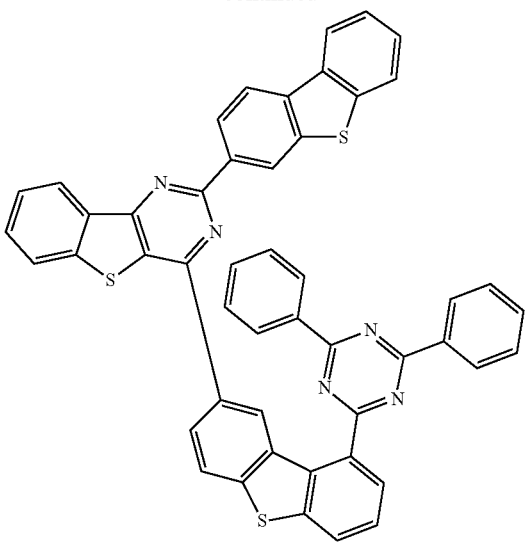
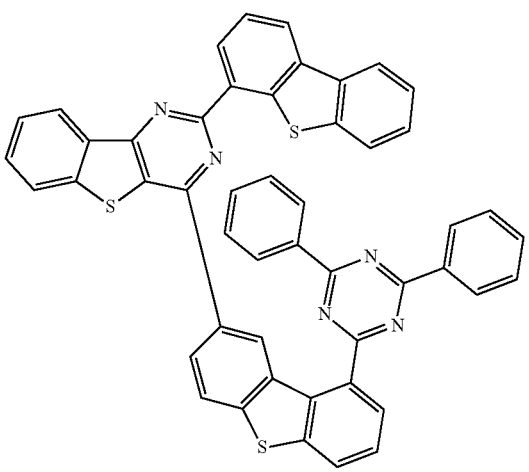
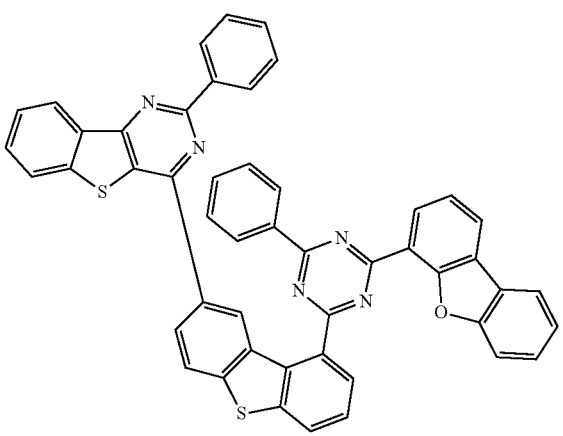

399
-continued
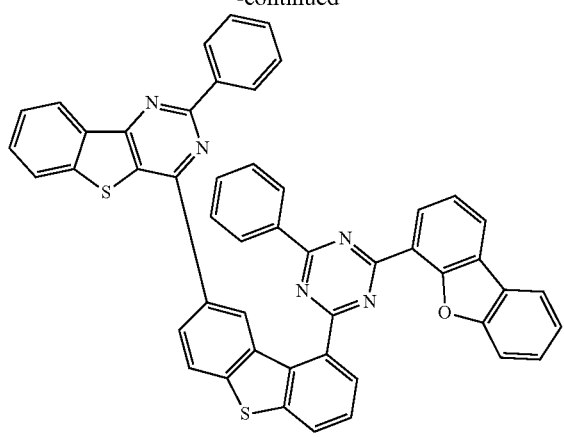
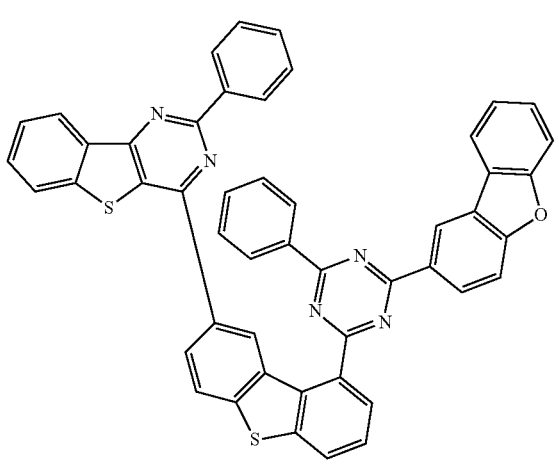
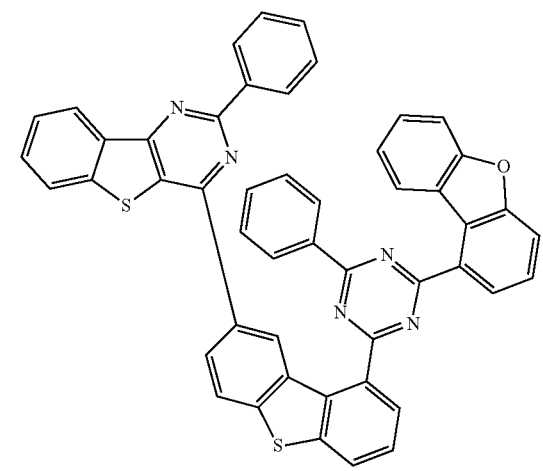
400
-continued
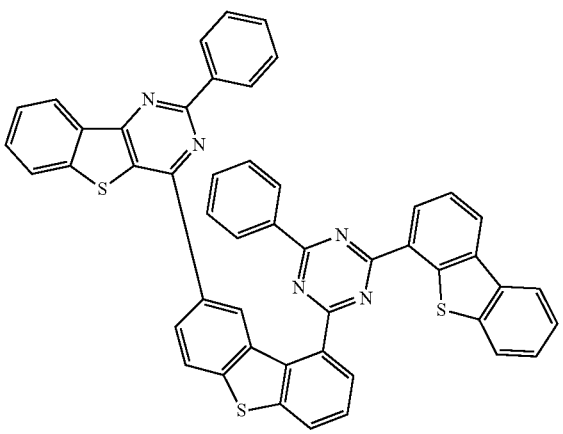
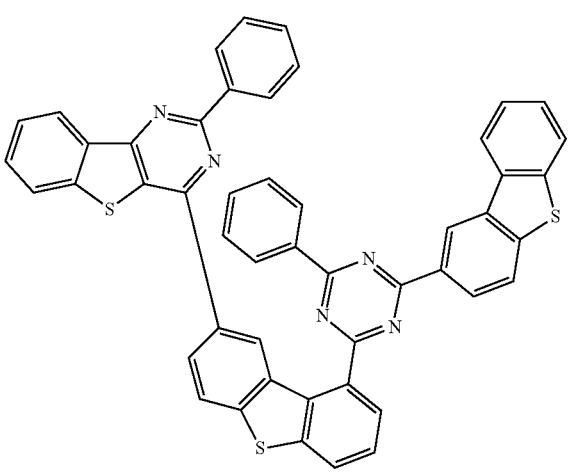

401
-continued
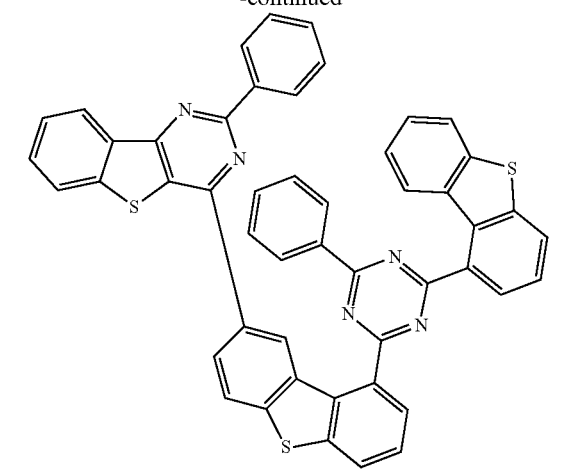
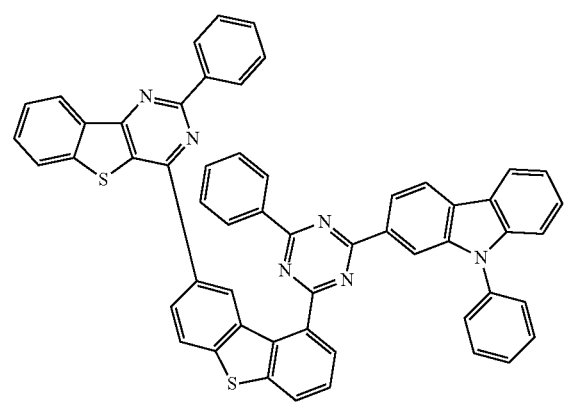
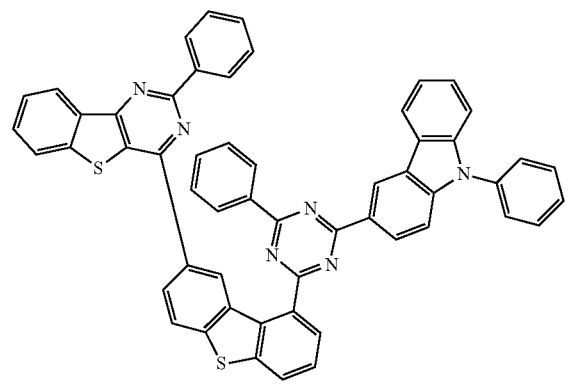
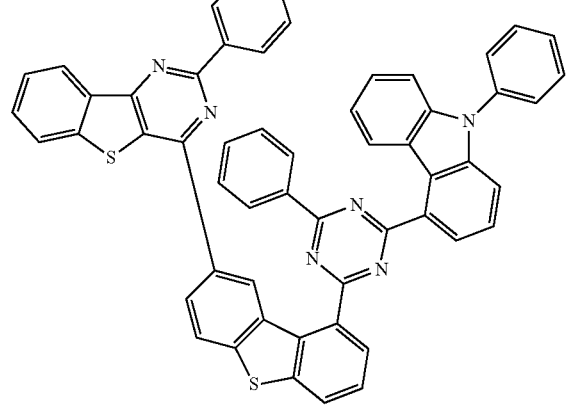
402
-continued
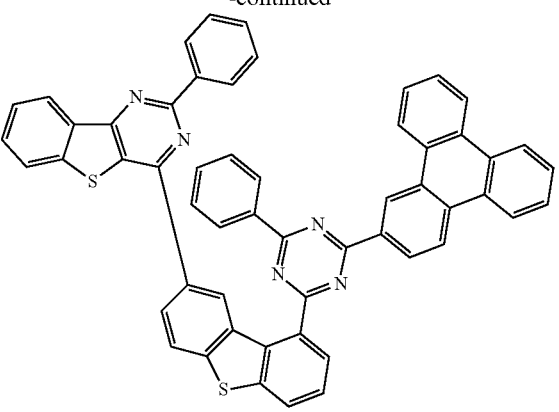
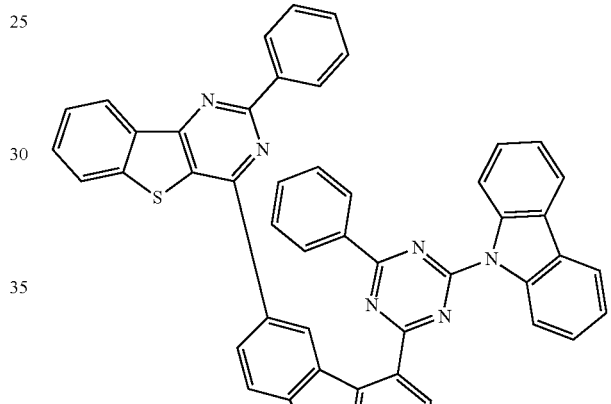
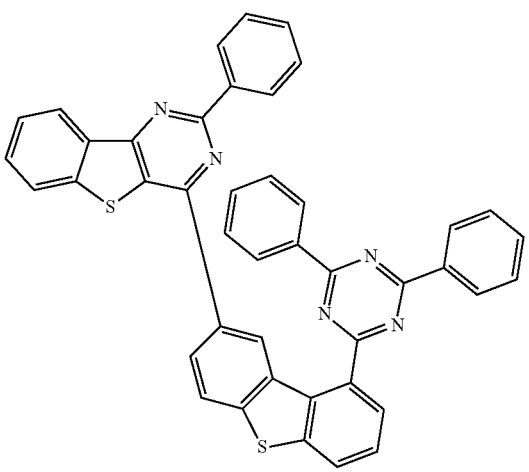

403
-continued
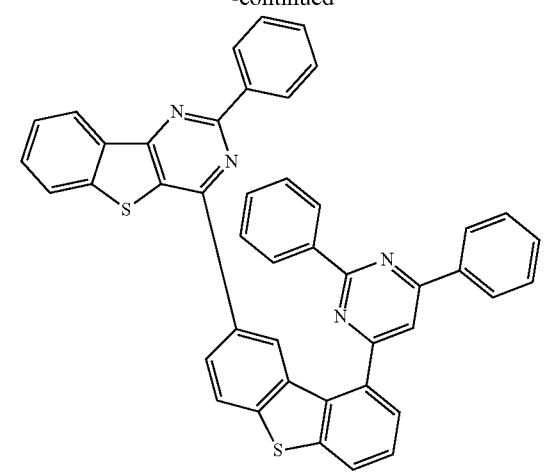

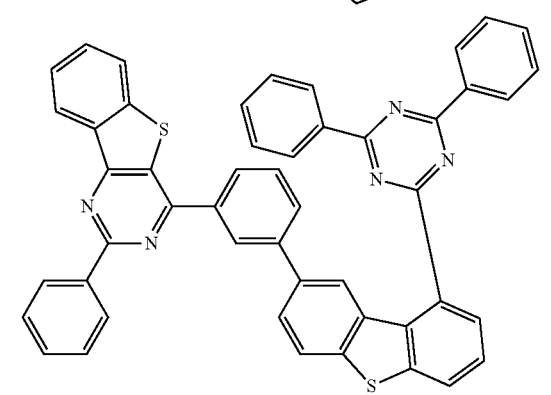
404
-continued
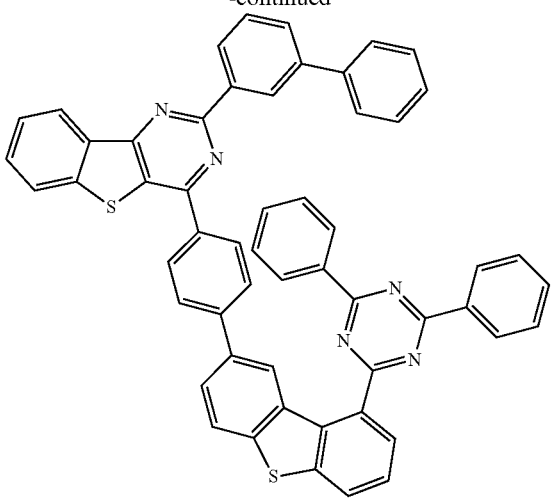
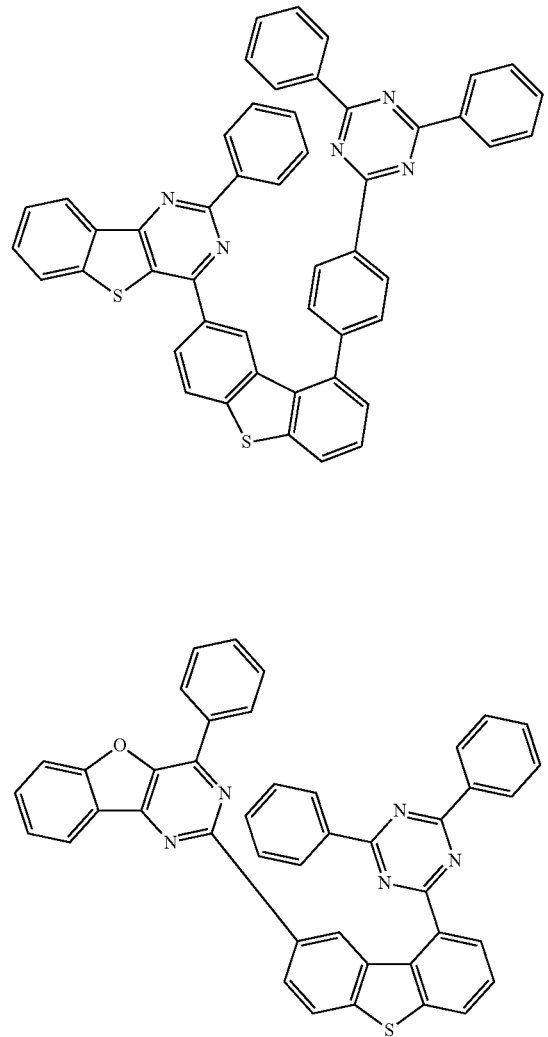

405
-continued
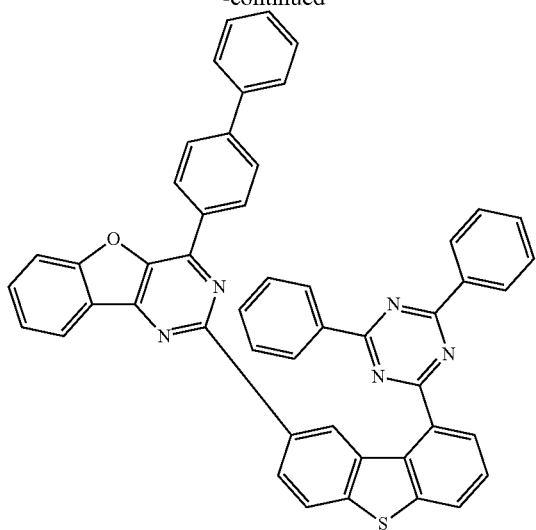
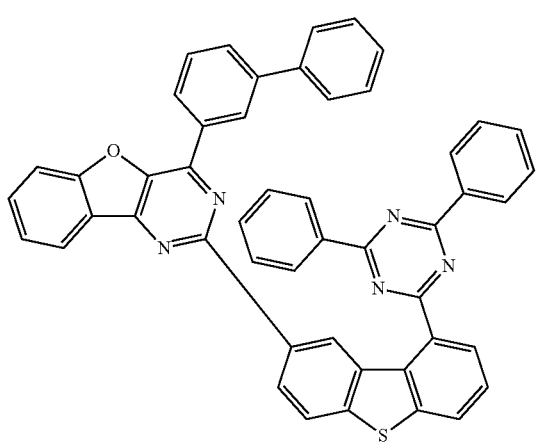
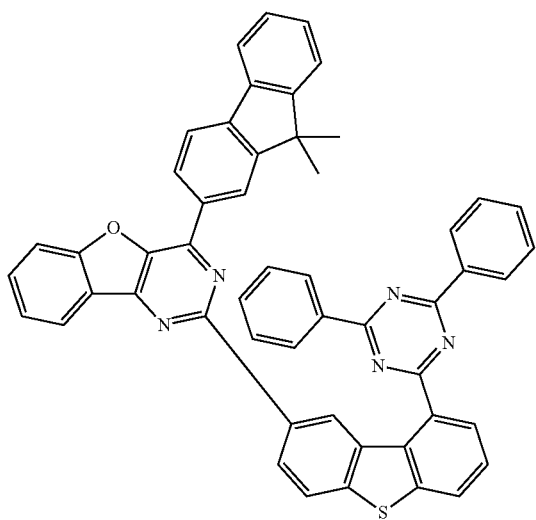
406
-continued
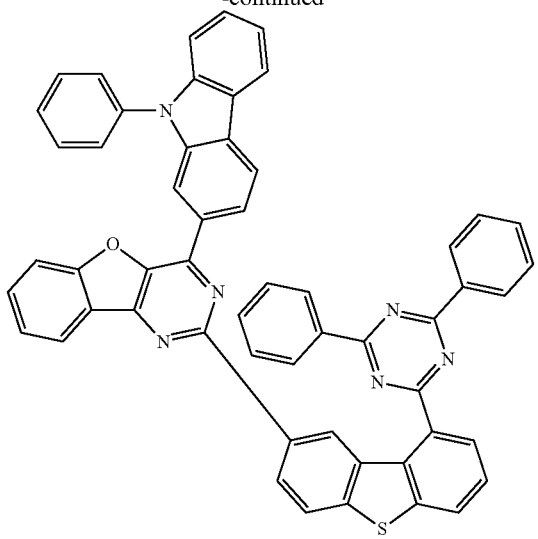
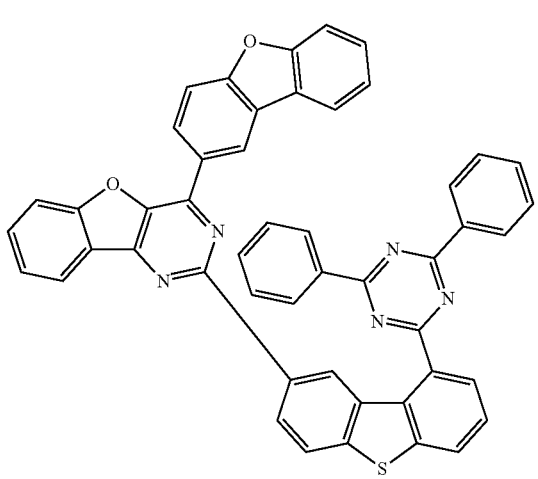
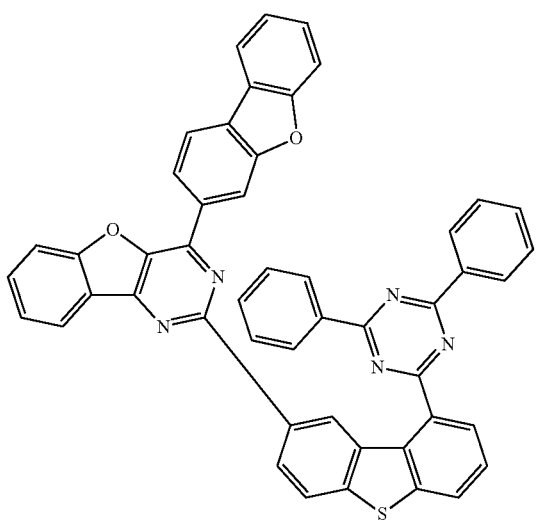

407
-continued
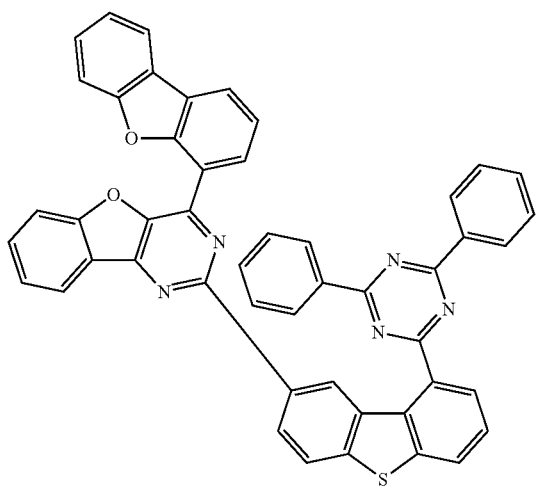
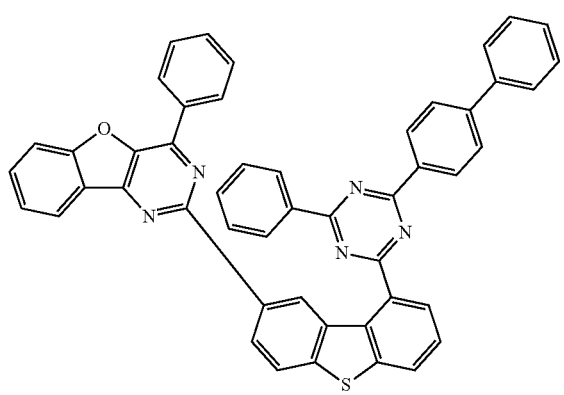
408
-continued
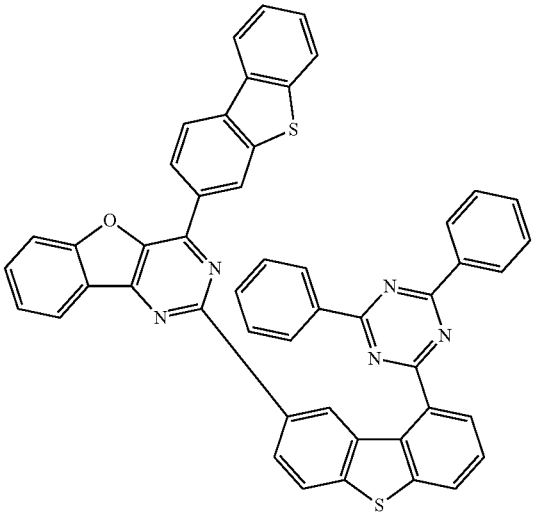
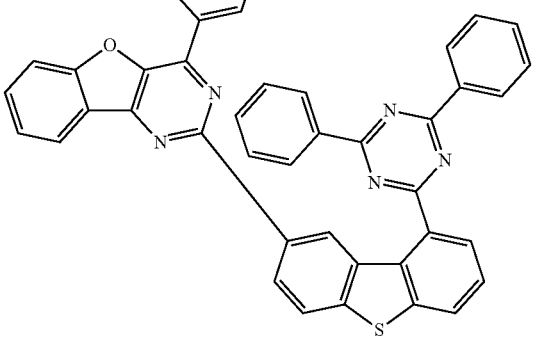
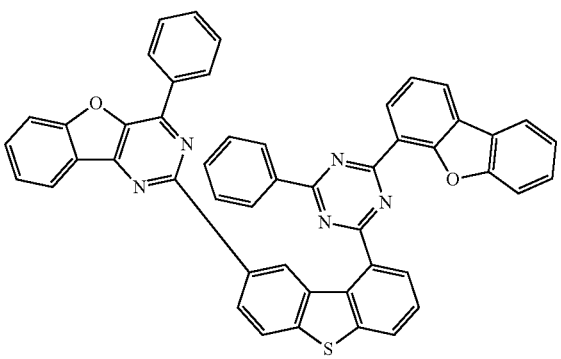
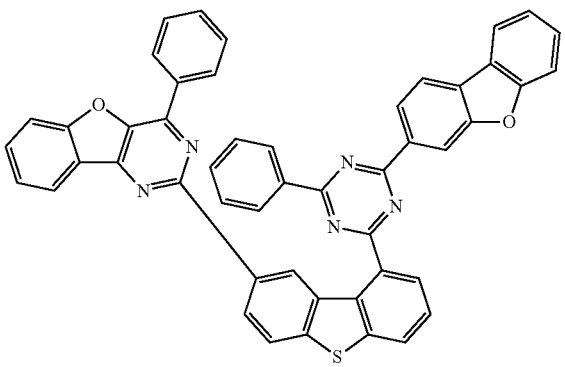

409
-continued
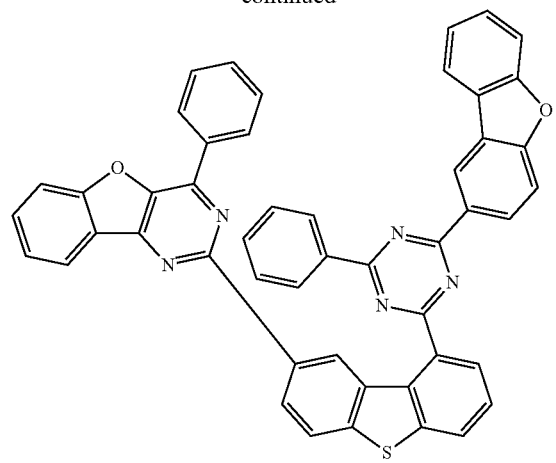
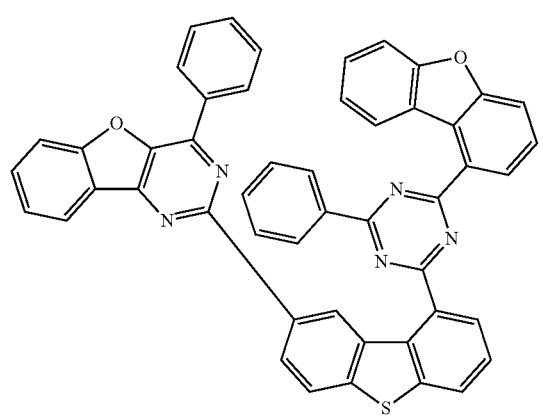 [SMILES: c1ccc(-c2nc(-c3cccc4oc5ccccc5c34)nc(-c3cccc4sc5ccc(-c6nc(-c7ccccc7)c7oc8ccccc8c7n6)cc5c34)n2)cc1]
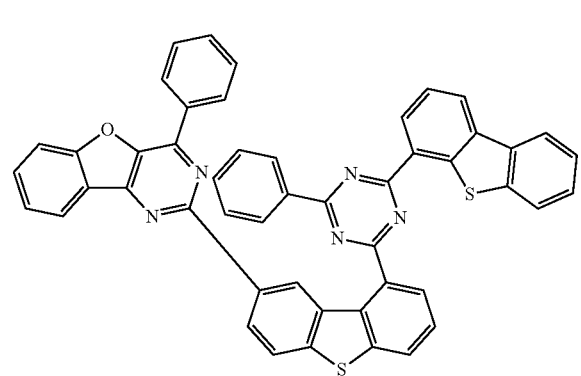
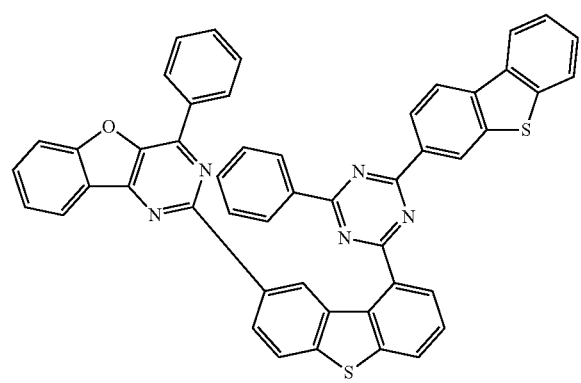
410
-continued
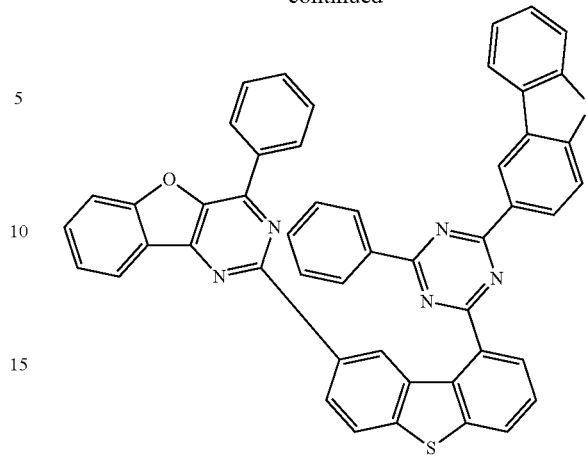
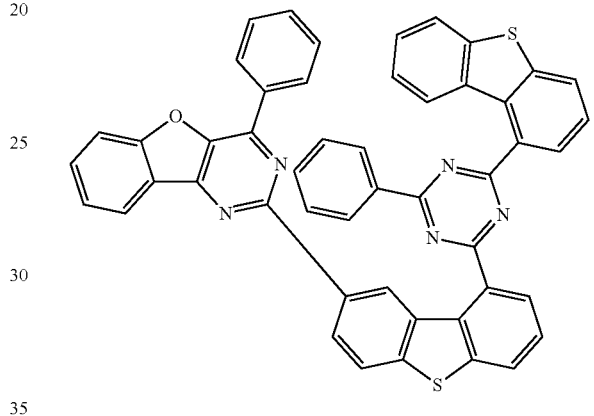
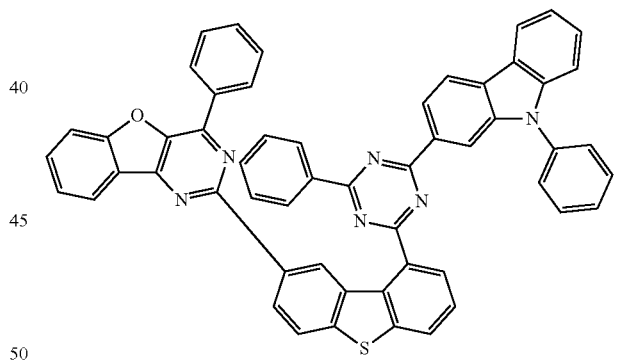
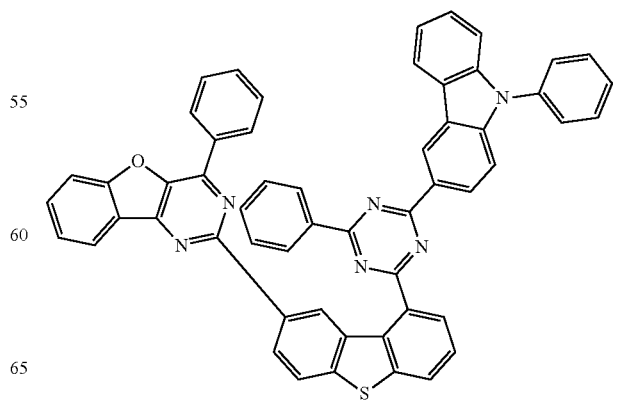

411
-continued
412
-continued
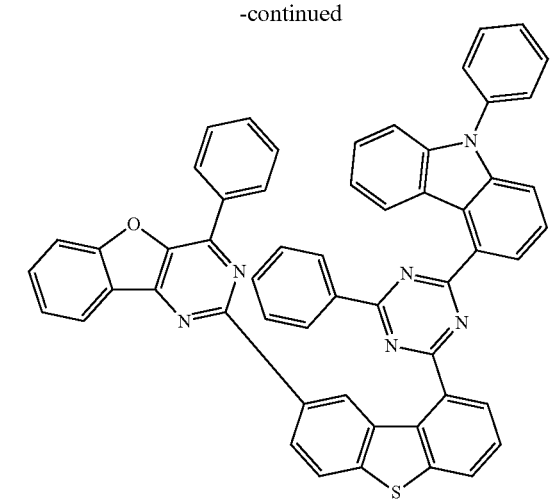
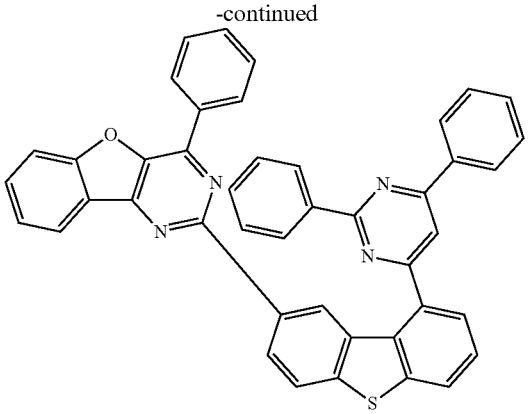
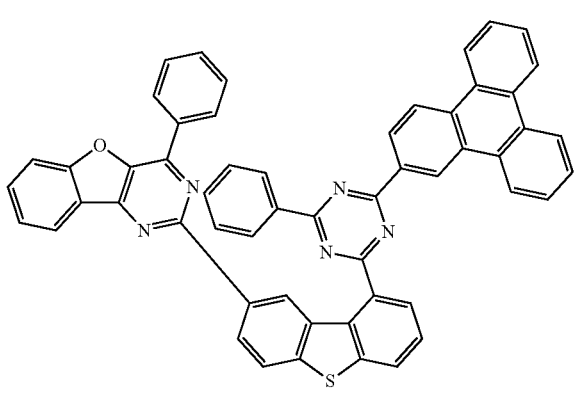
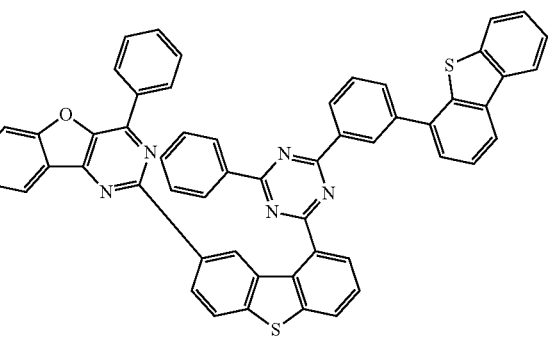
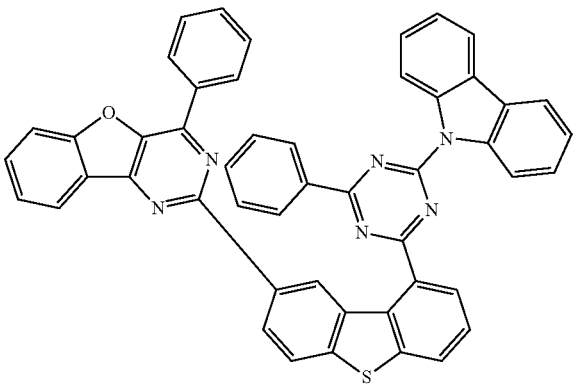
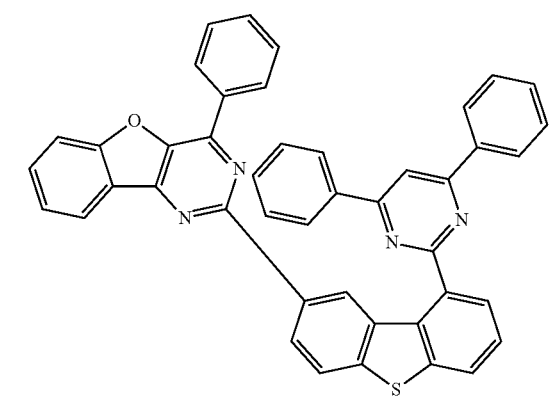

413
-continued
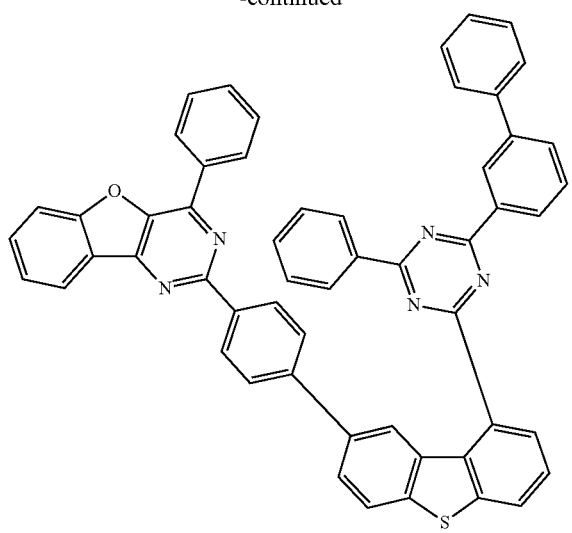
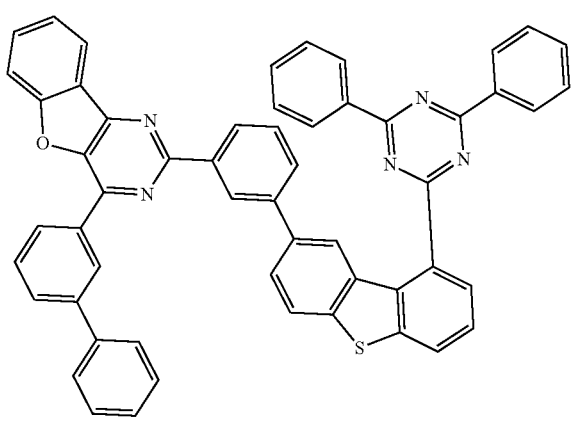 [SMILES: c1ccc(-c2cccc(-c3nc(-c4cccc(-c5ccc6sc7cccc(-c8nc(-c9ccccc9)nc(-c9ccccc9)n8)c7c6c5)c4)nc4c3oc3ccccc34)c2)cc1]
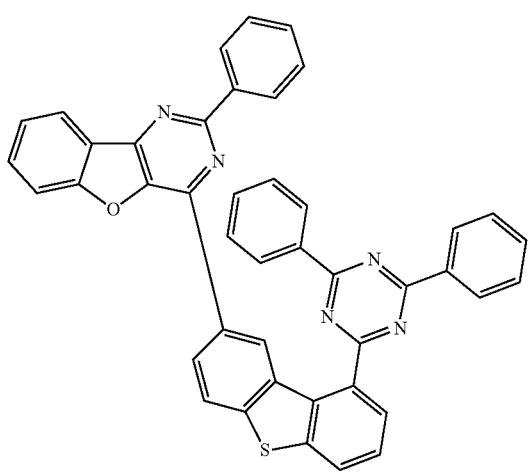
414
-continued
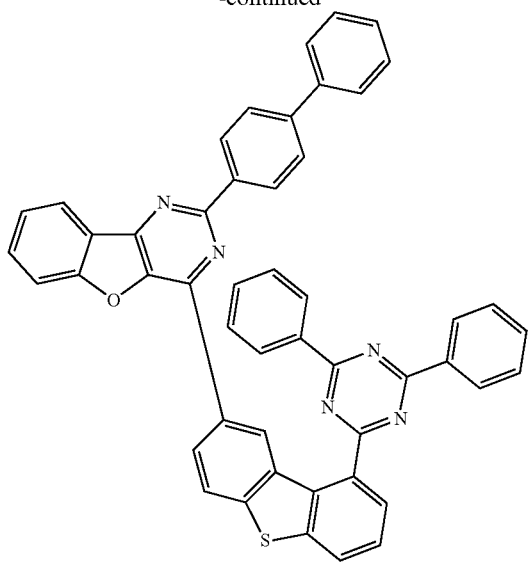
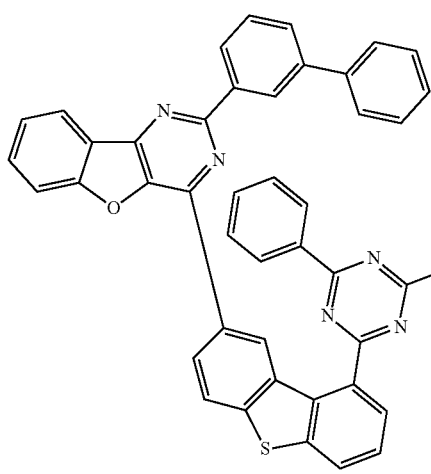
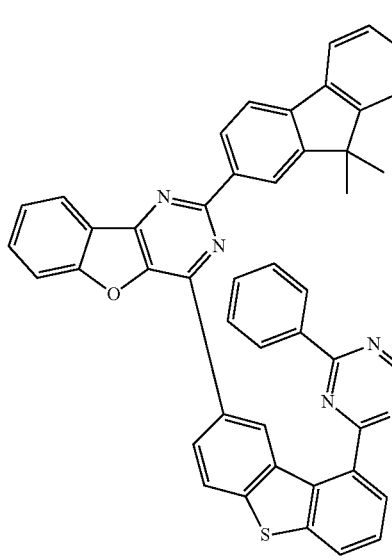

415
-continued
416
-continued
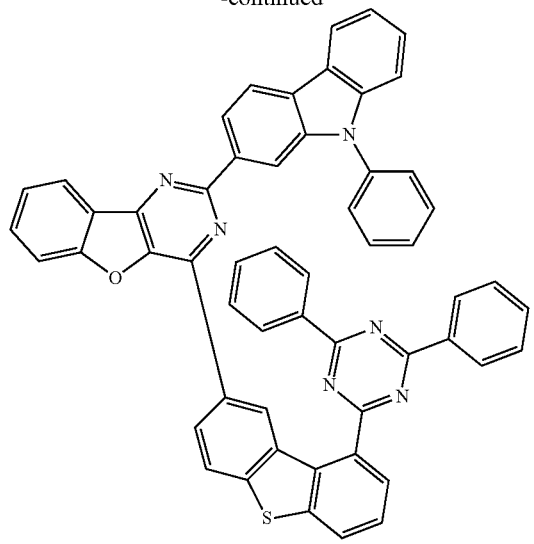
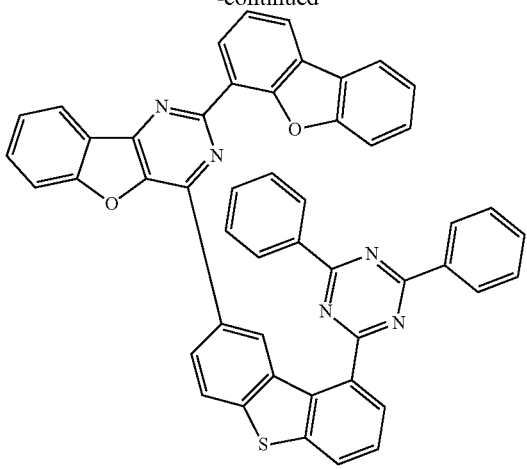
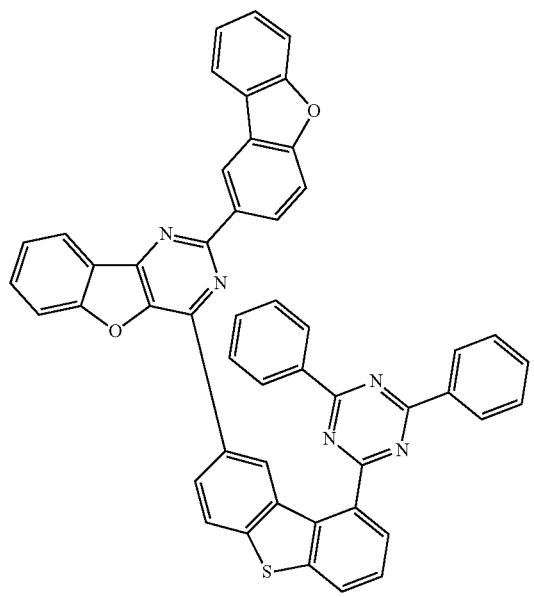
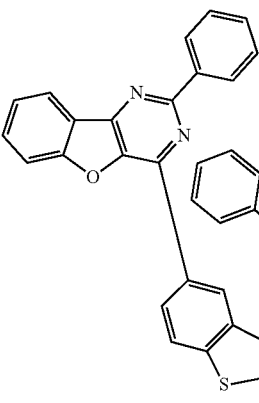
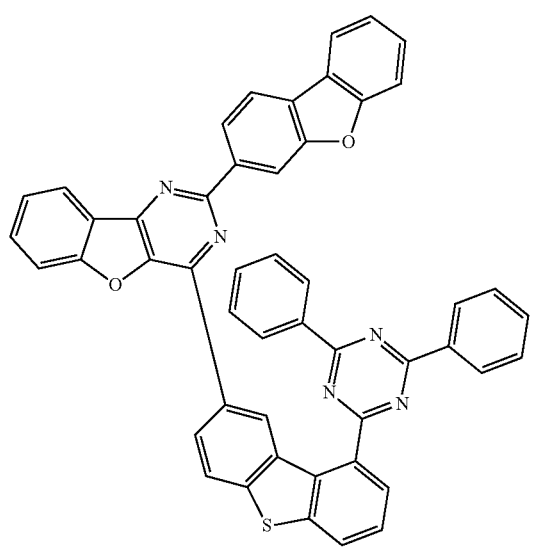
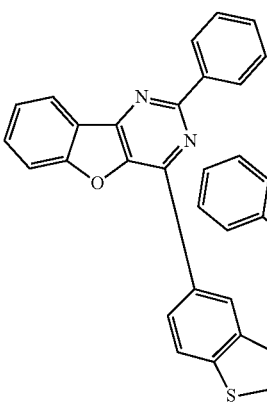

417
-continued
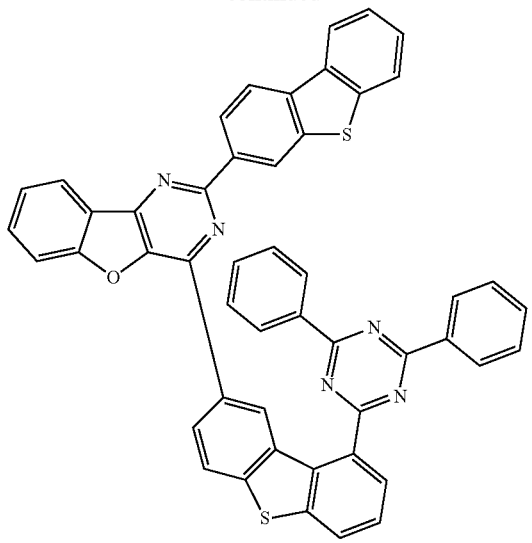
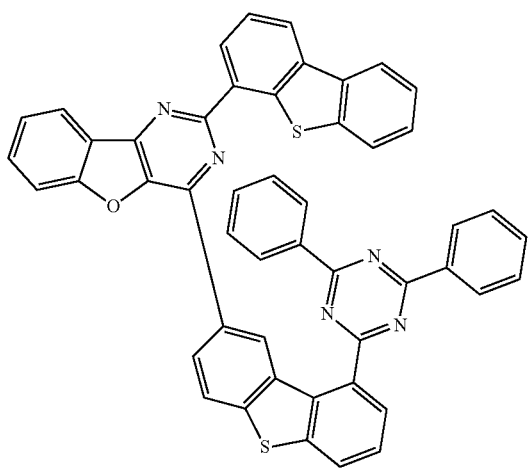
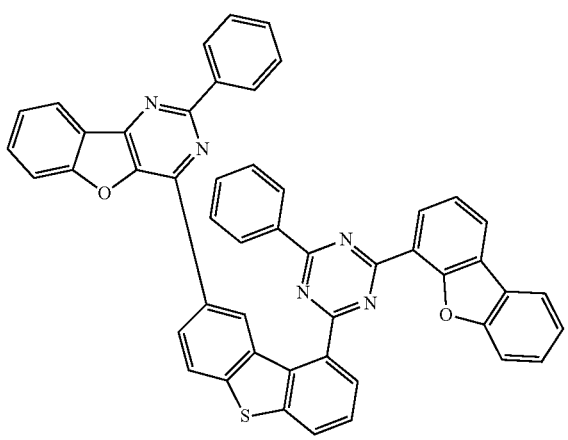
418
-continued
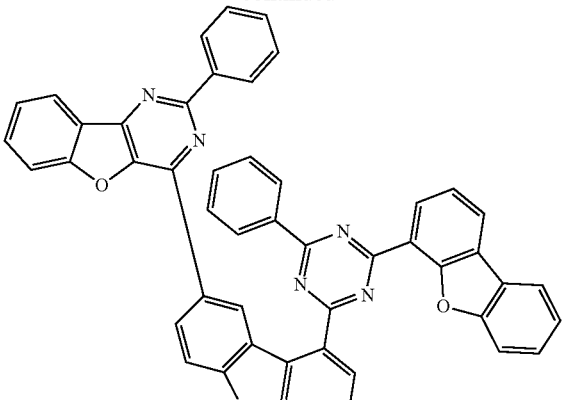
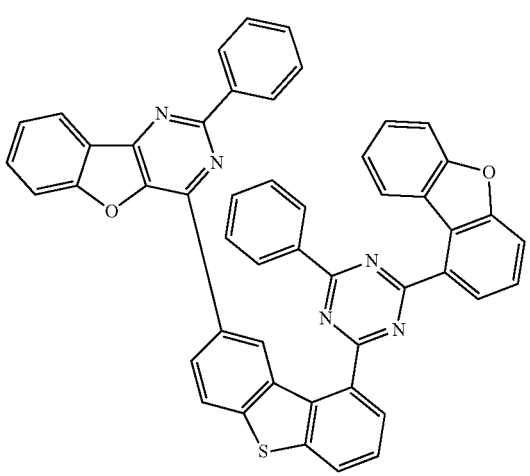

419
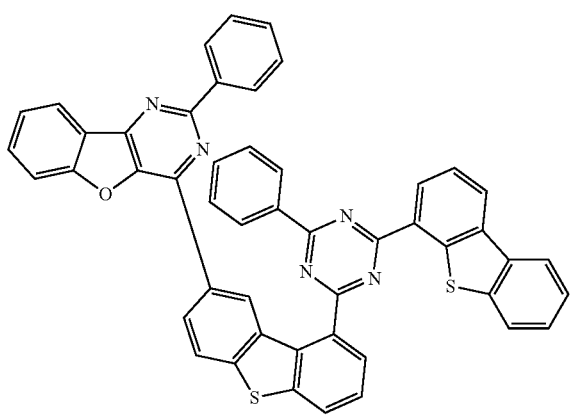
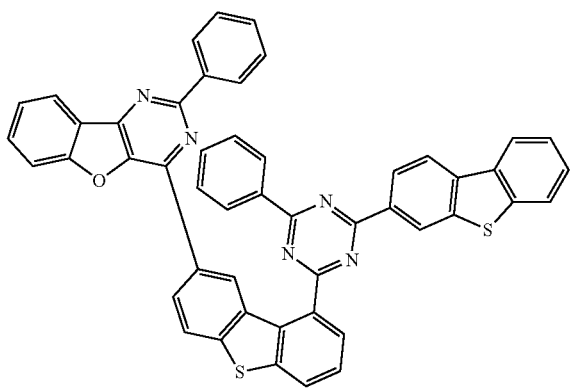
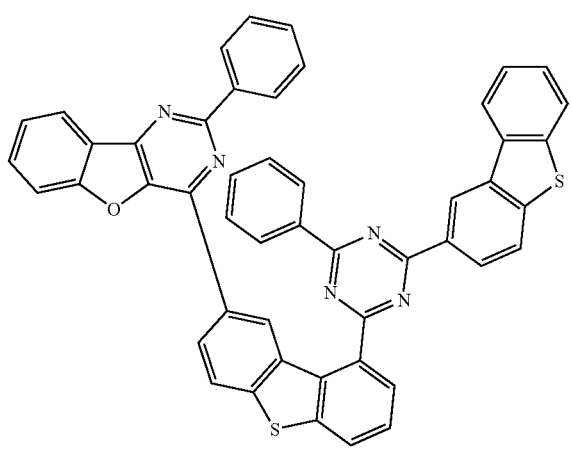
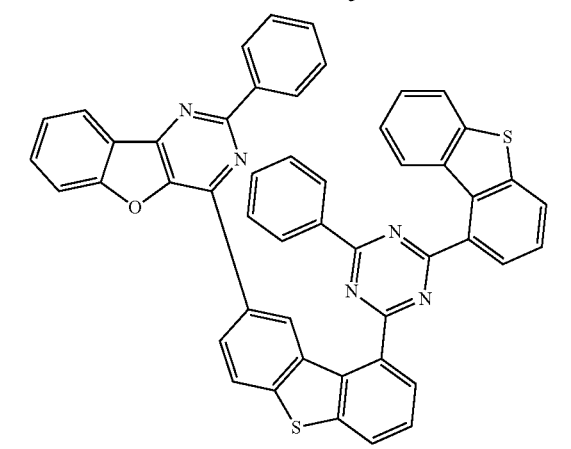
420
-continued
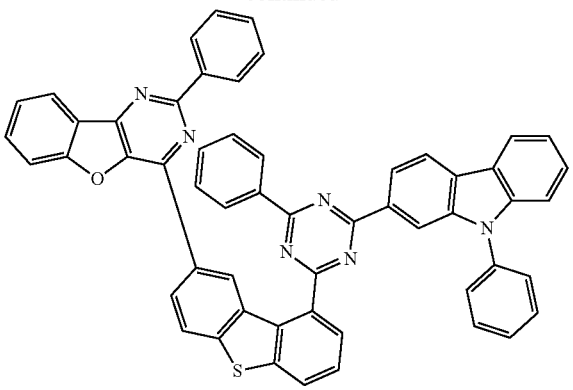
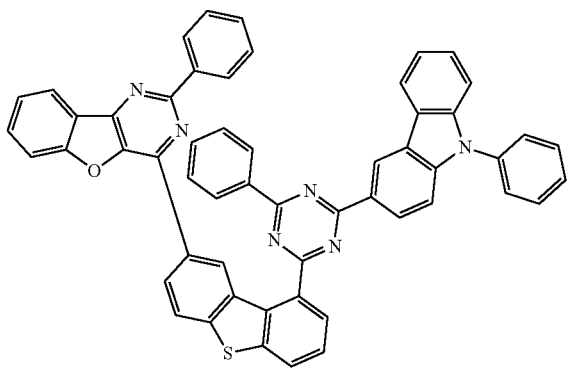
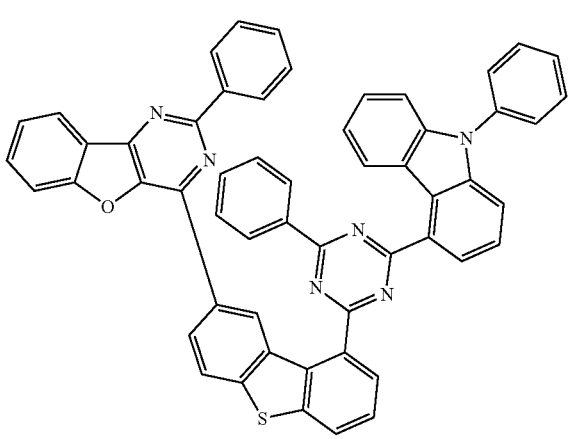
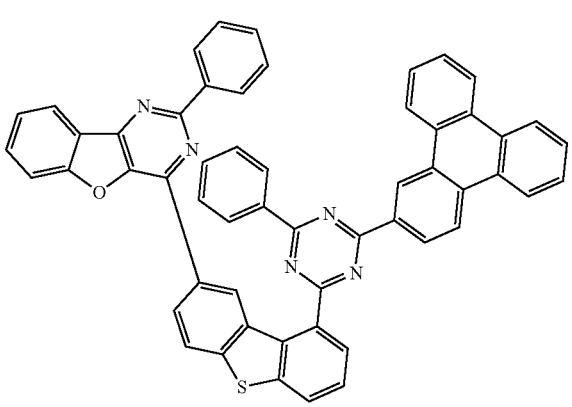

421
-continued
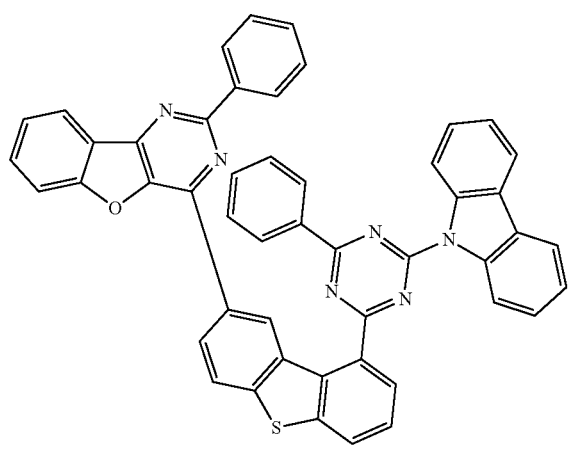
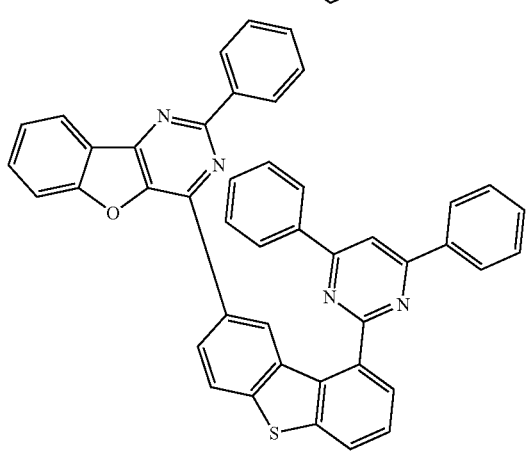
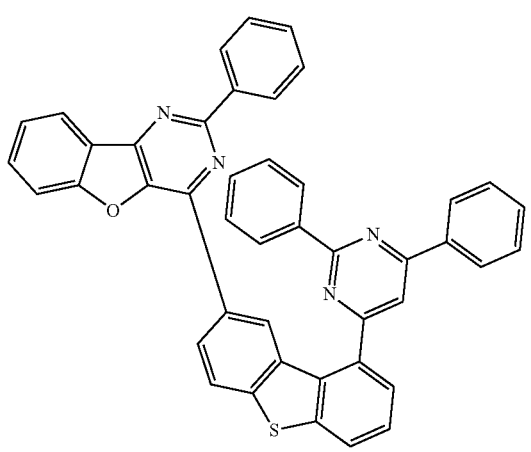
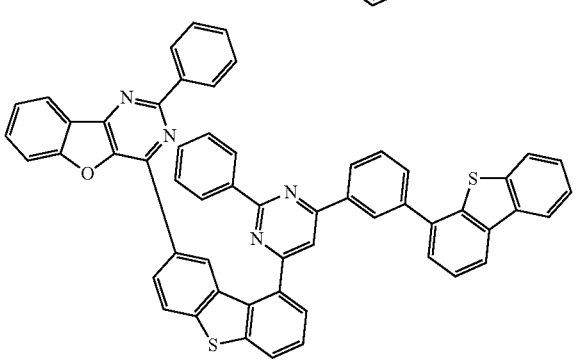
422
-continued
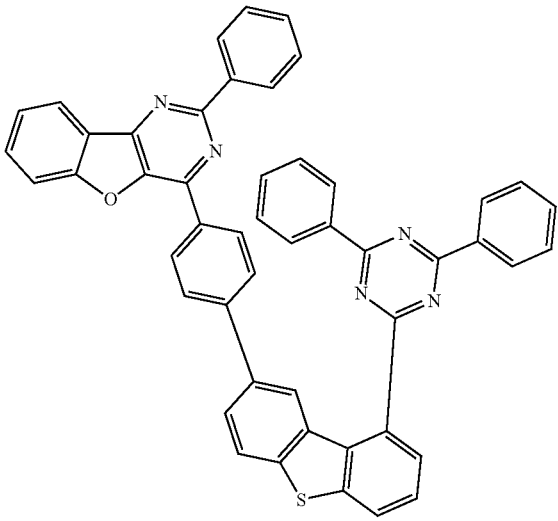
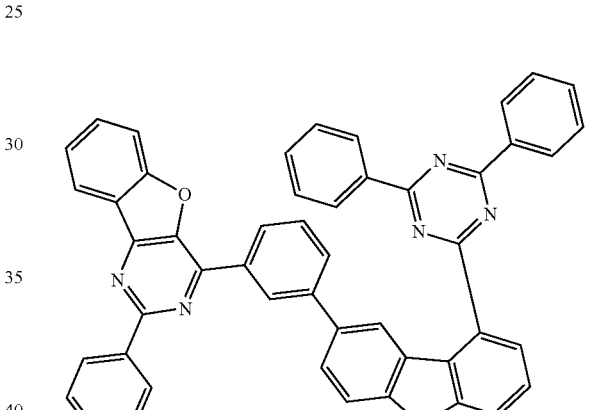
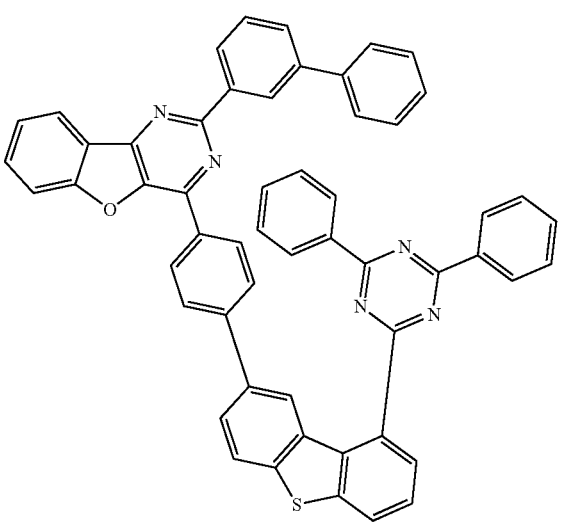

423
-continued
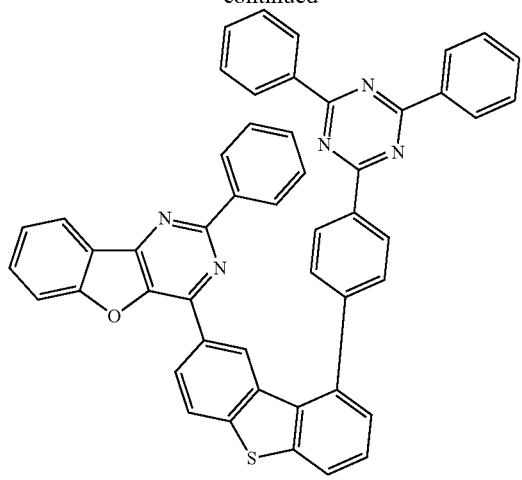
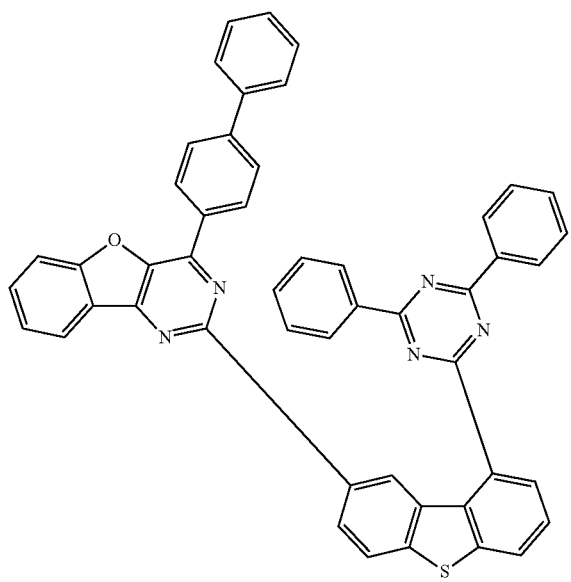
424
-continued
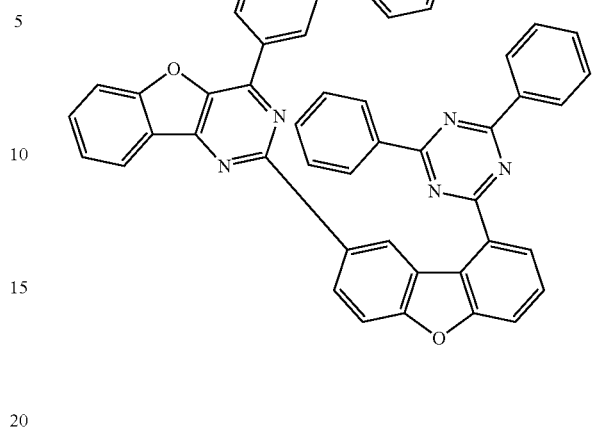
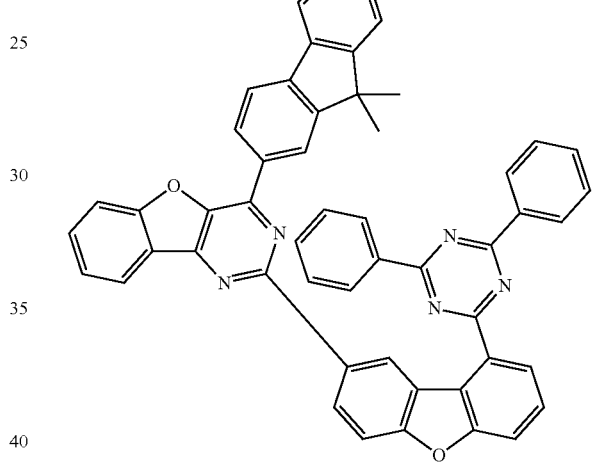
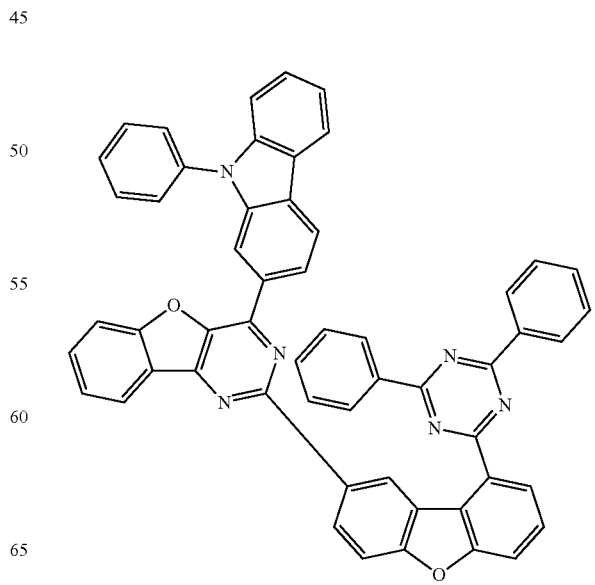

425
-continued
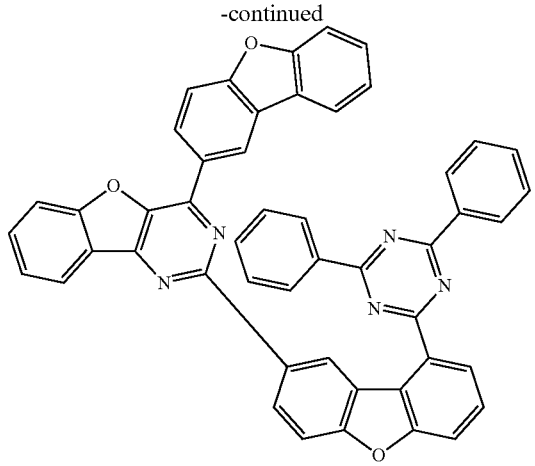
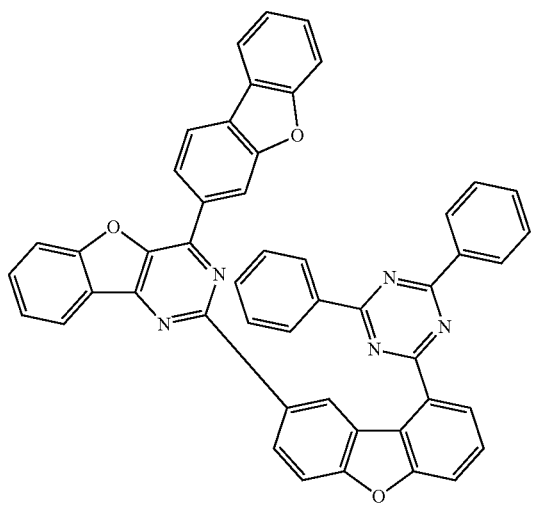
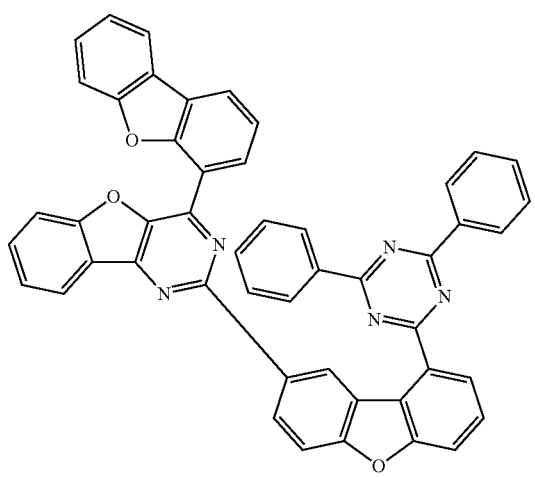
426
-continued
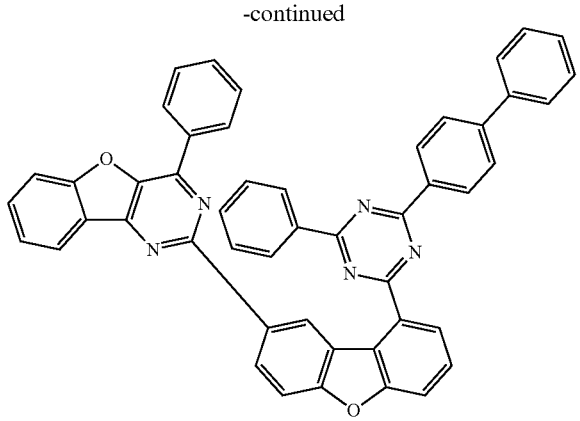
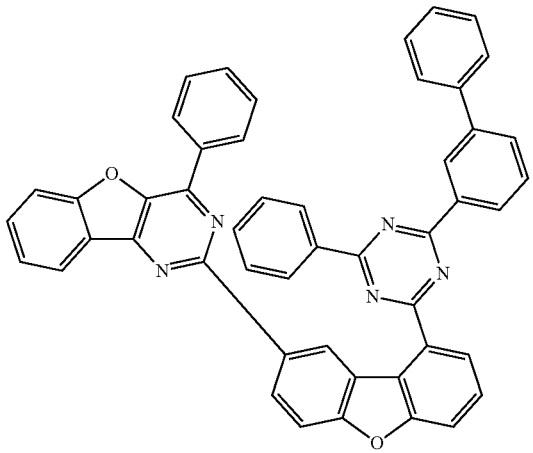
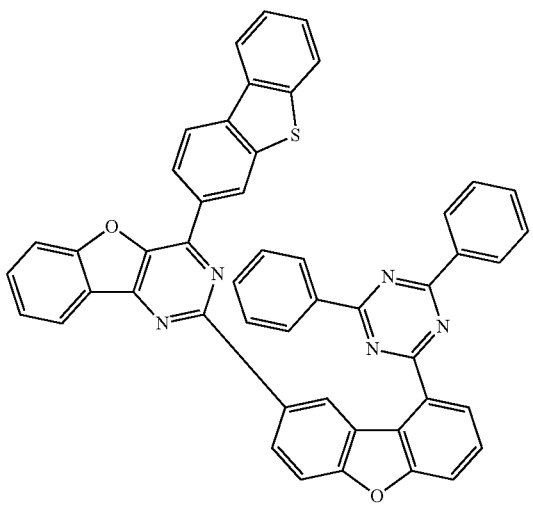

427
-continued
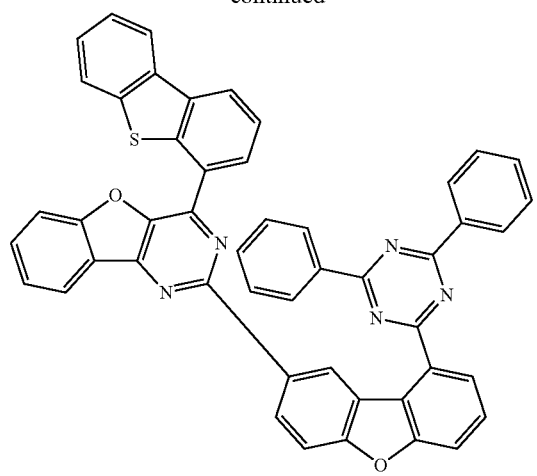
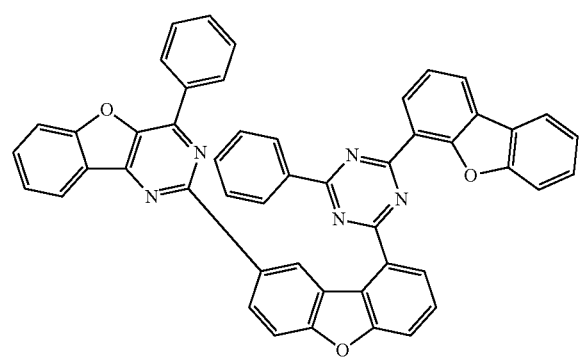
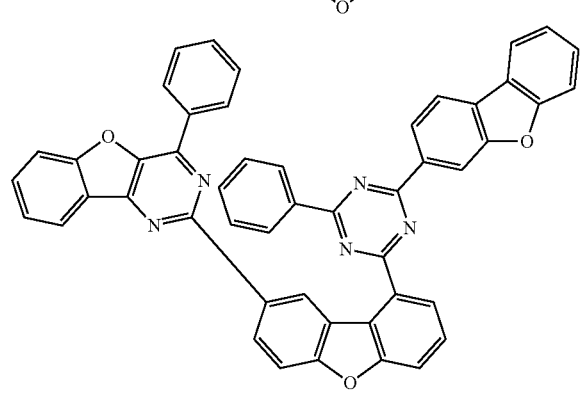
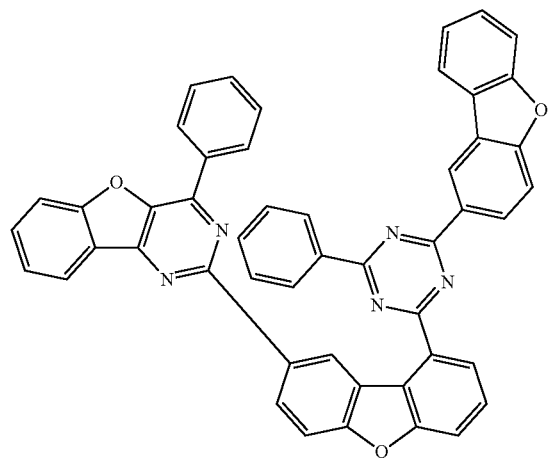
428
-continued
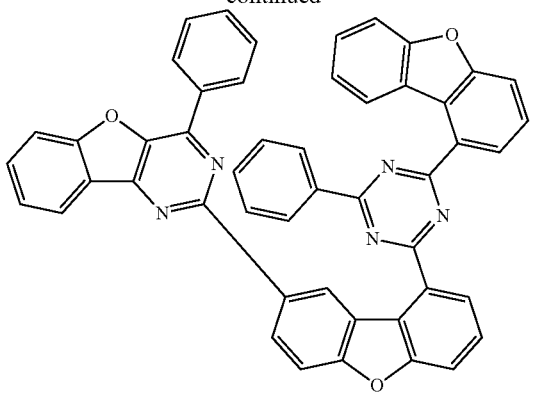
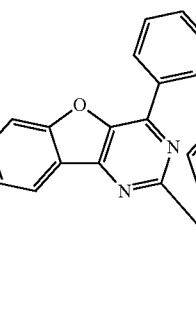
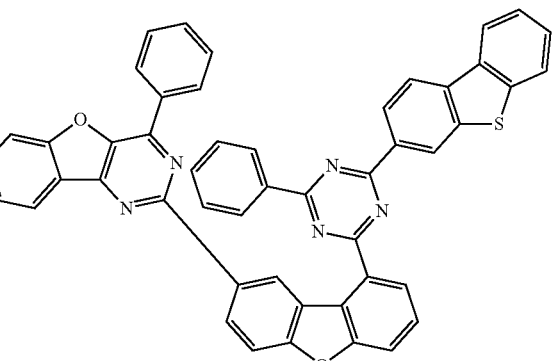
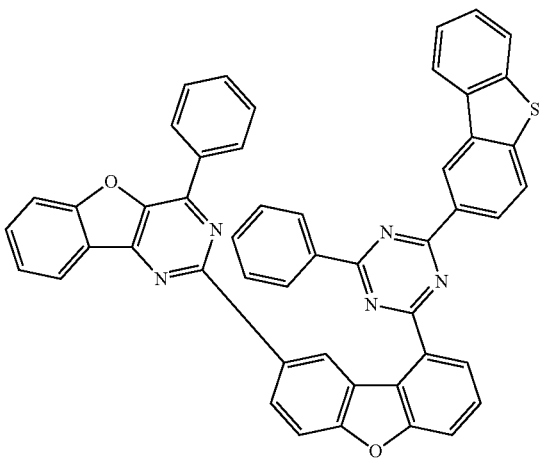

429
-continued
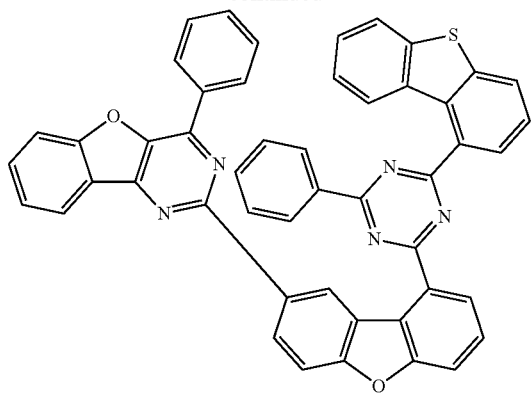
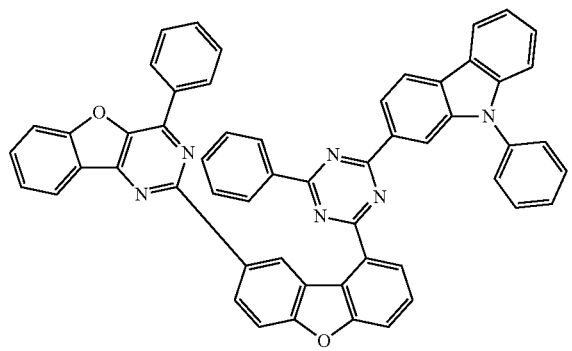
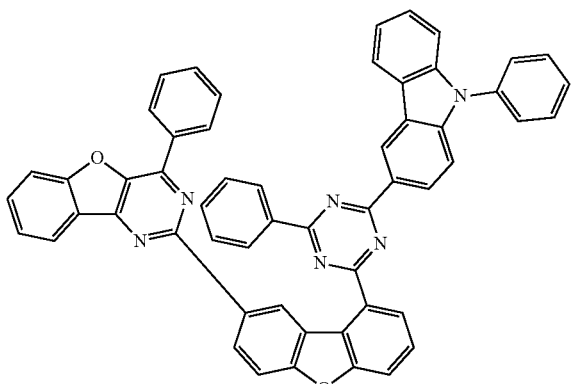
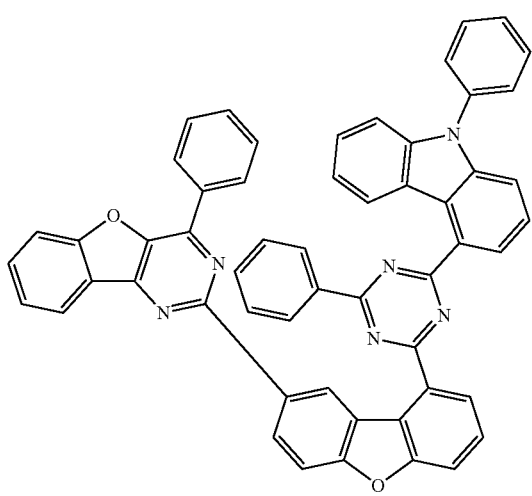
430
-continued
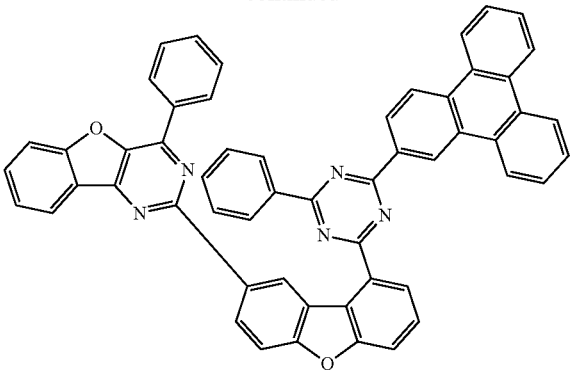
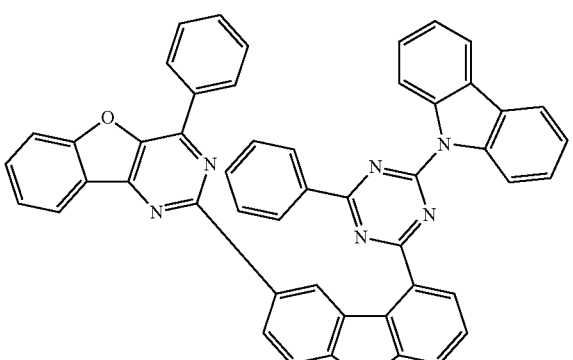
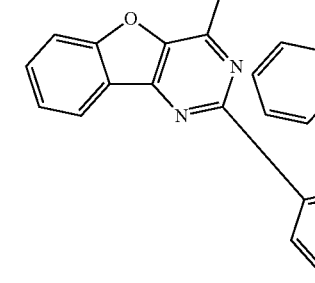
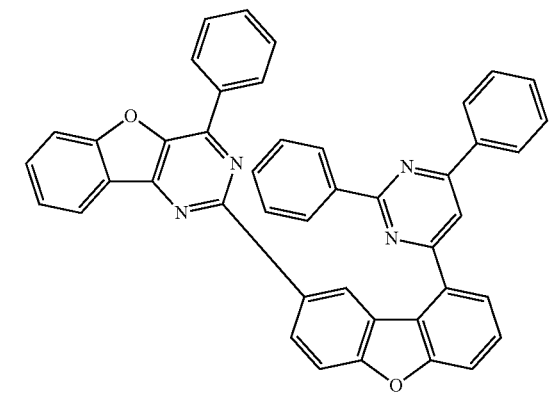

| 431 -continued | 432 -continued |
|---|---|
| 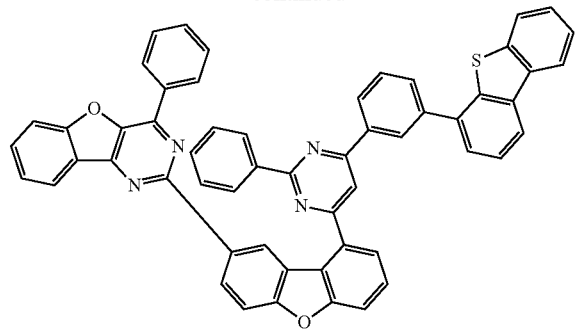 | 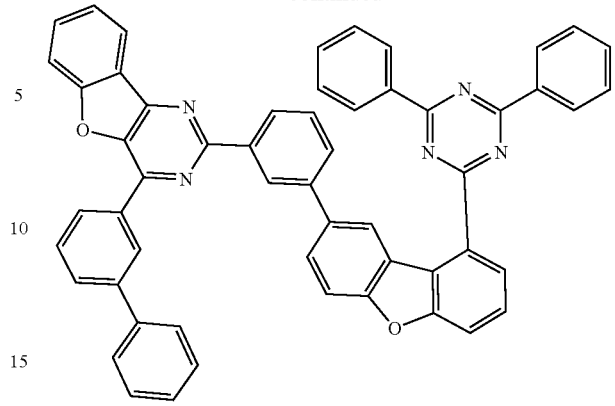 |
| 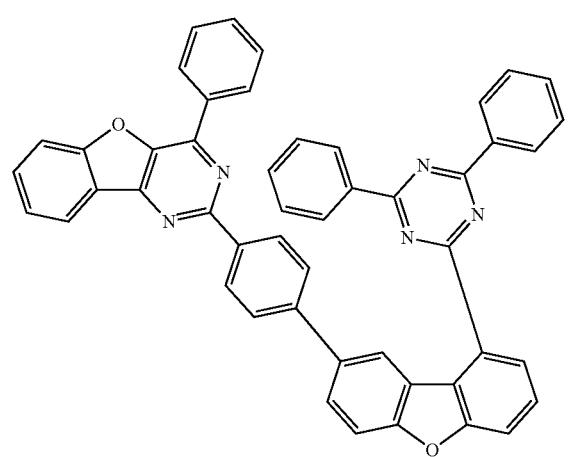 | 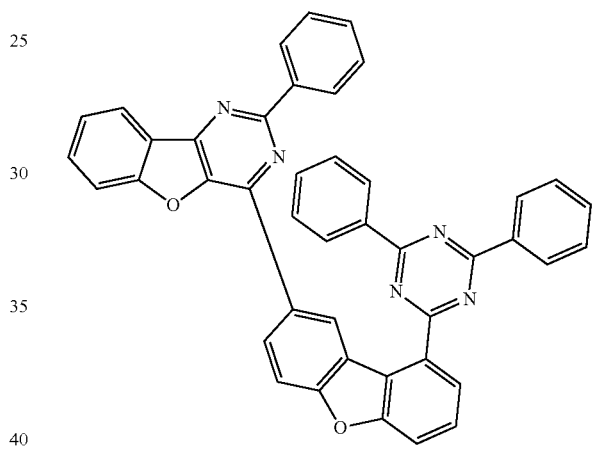 |
| 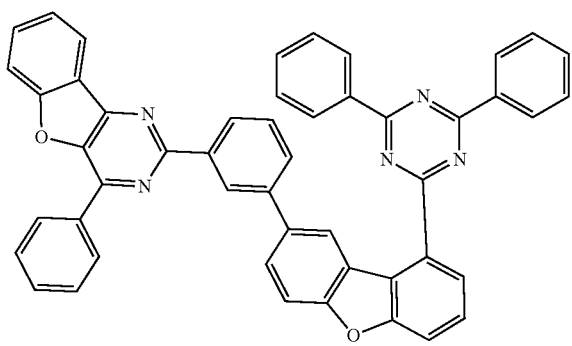 | 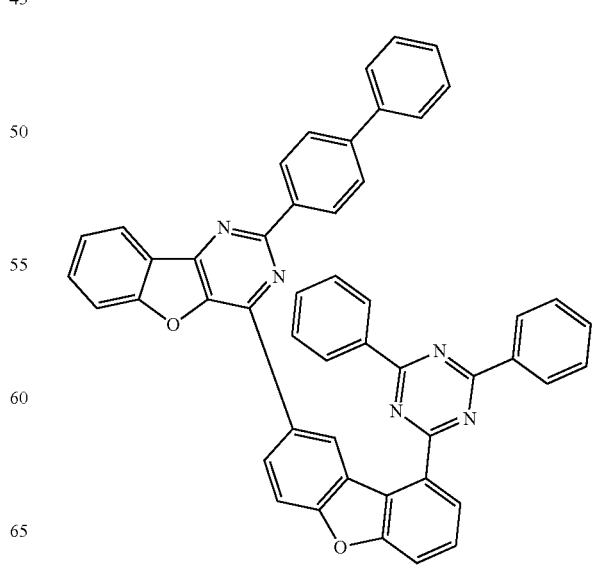 |
| 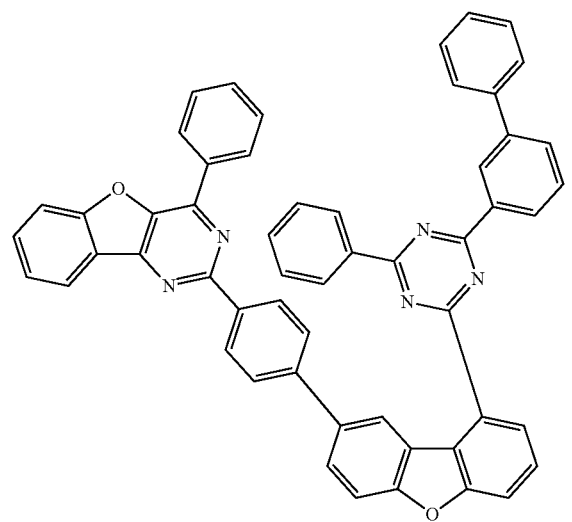 | |

433
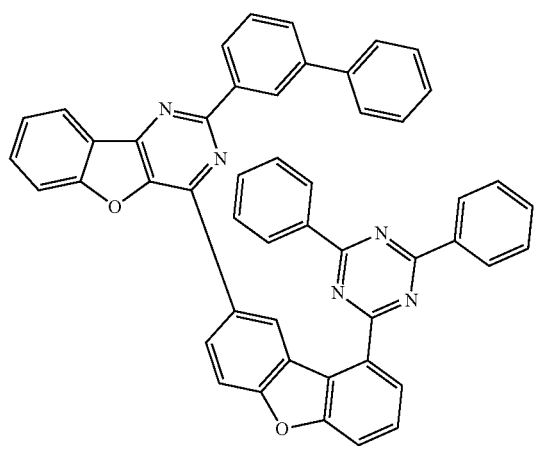
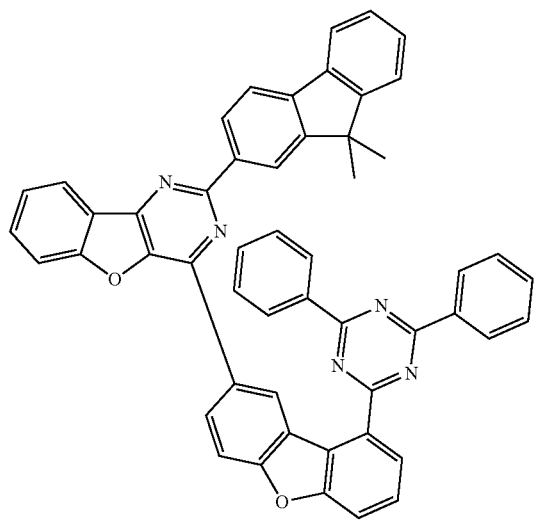
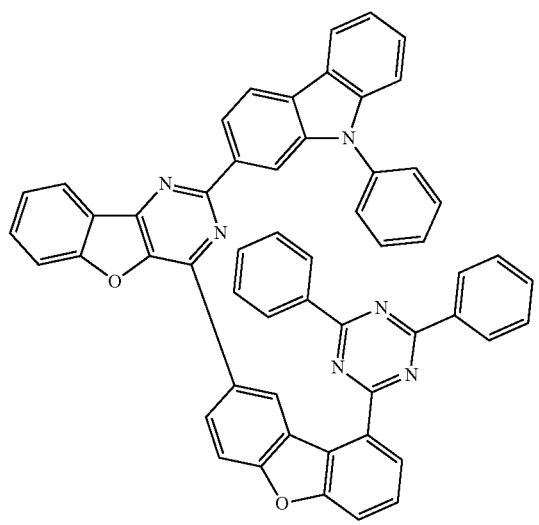
434
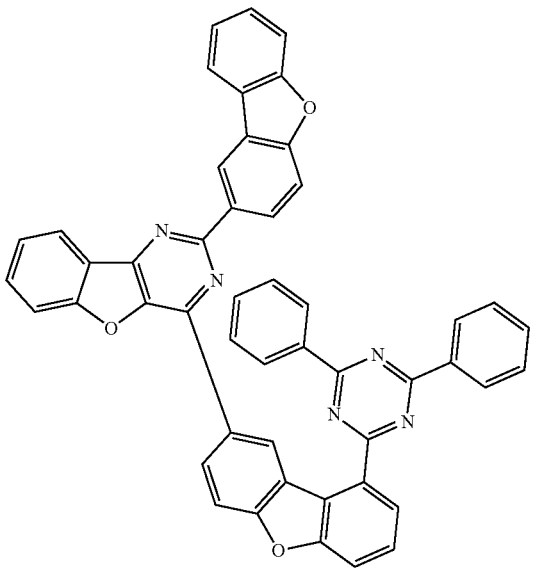
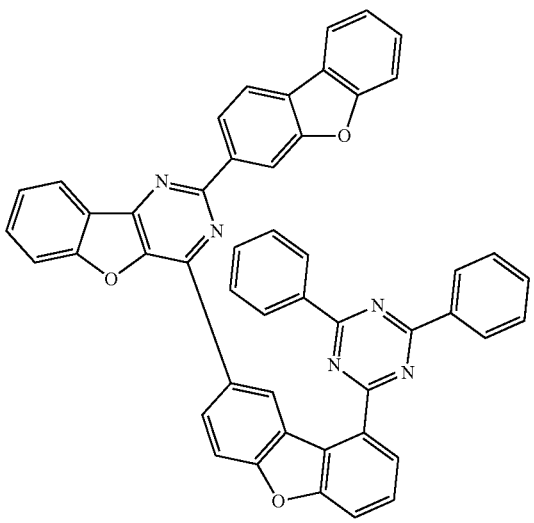
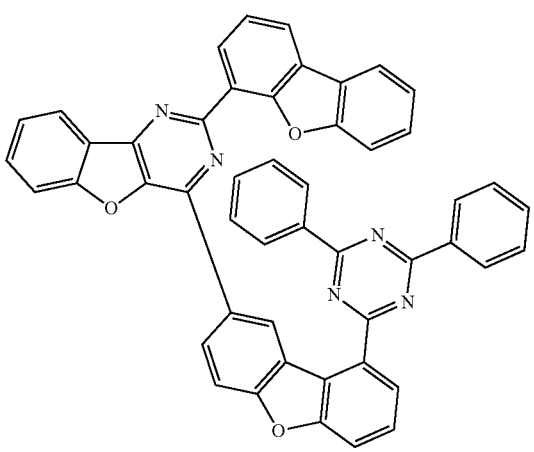

435
-continued
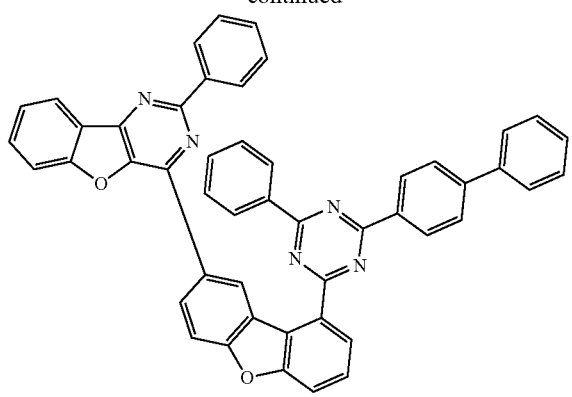
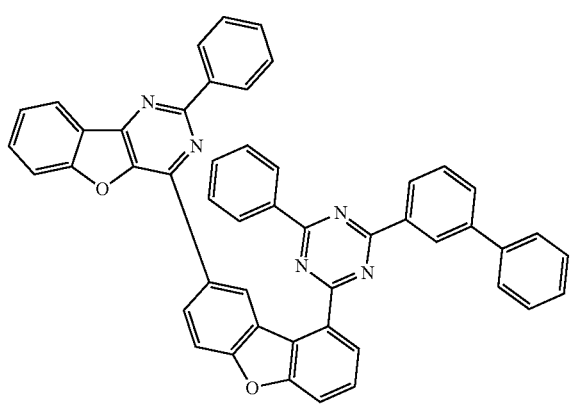
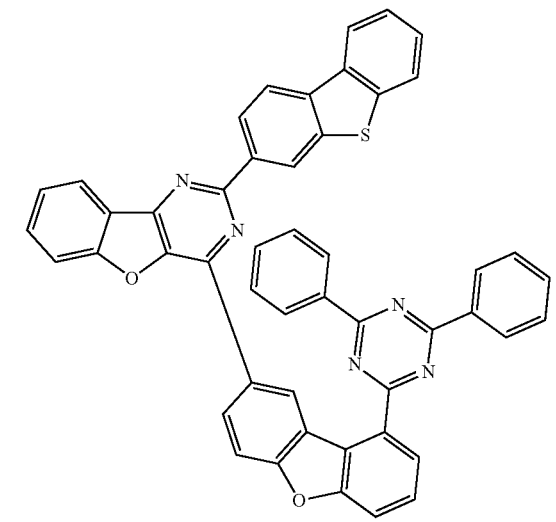
436
-continued
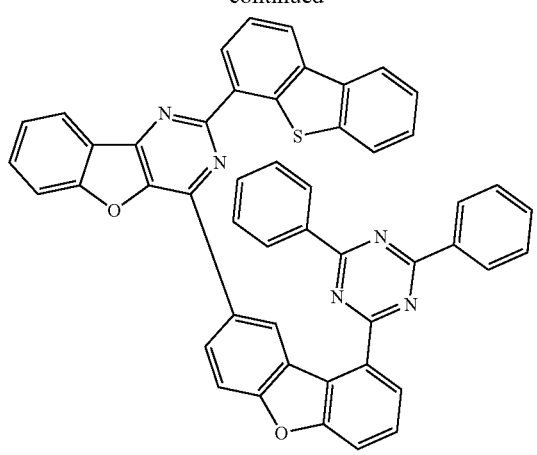
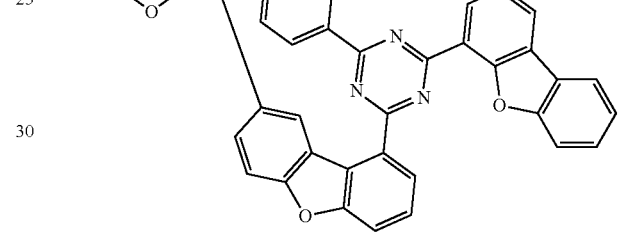
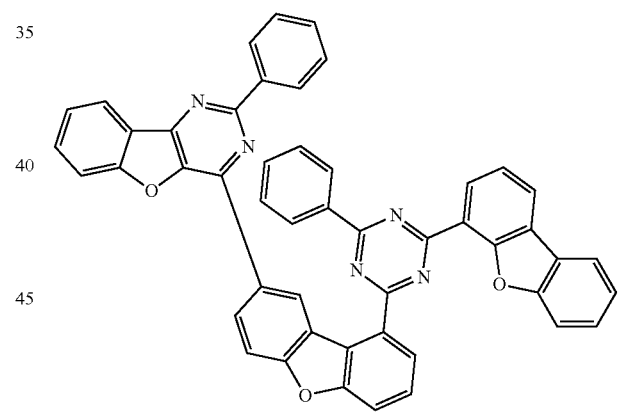
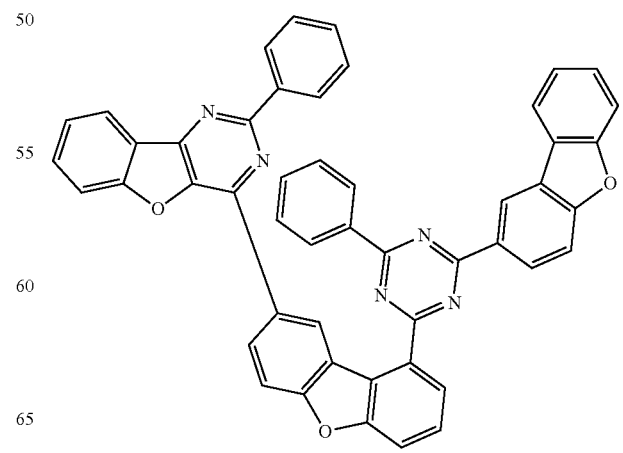

437
-continued
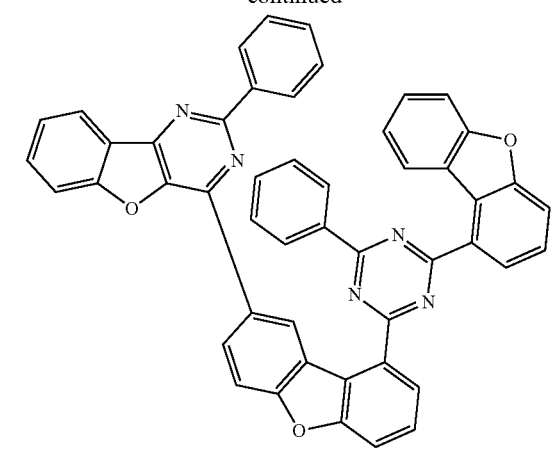
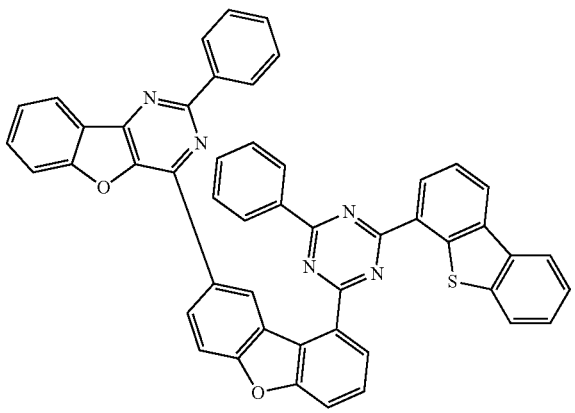
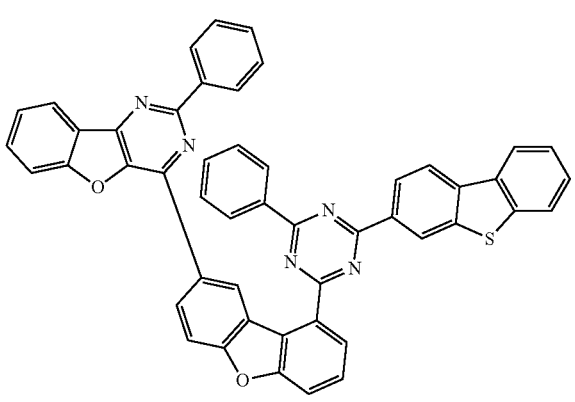
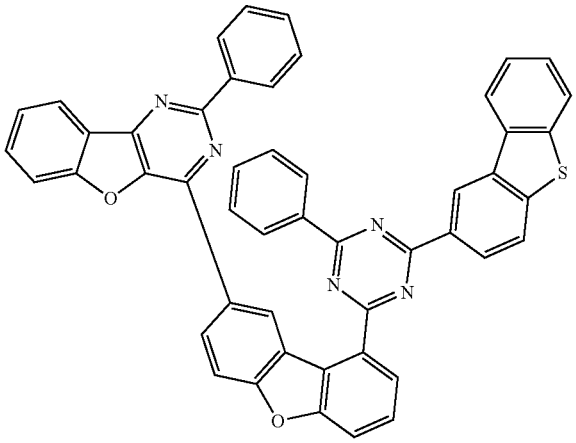
438
-continued
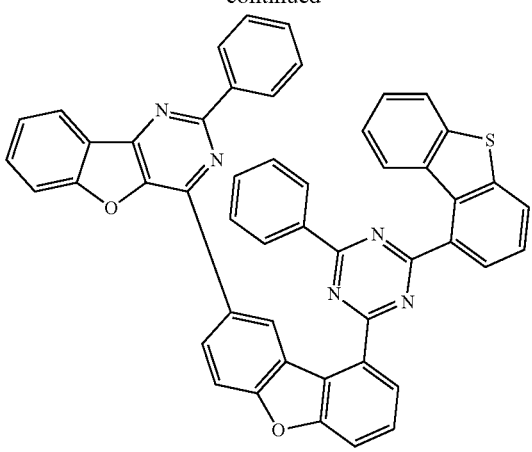
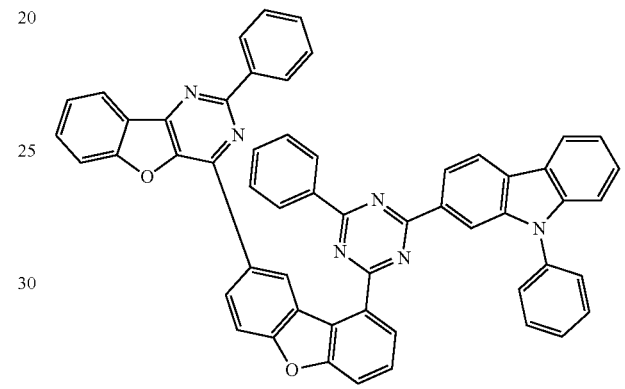
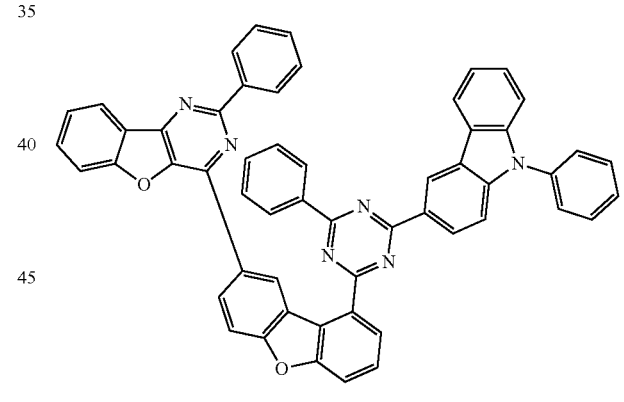
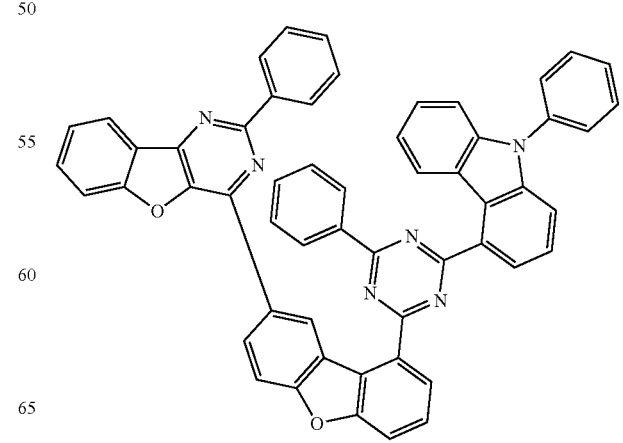

439
-continued
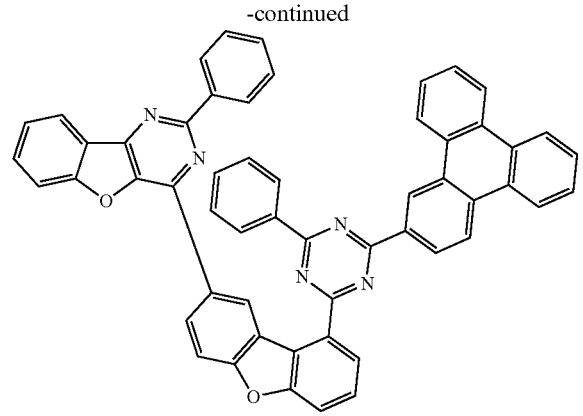
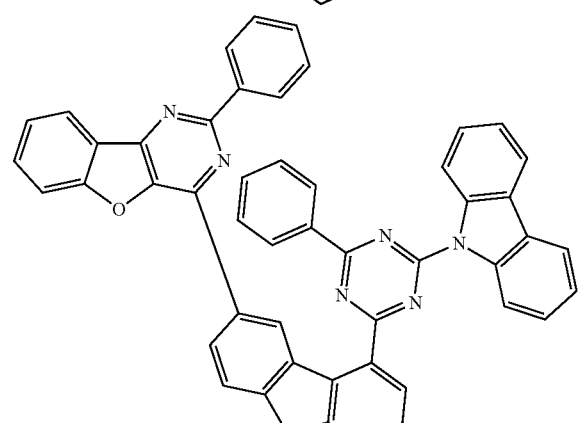
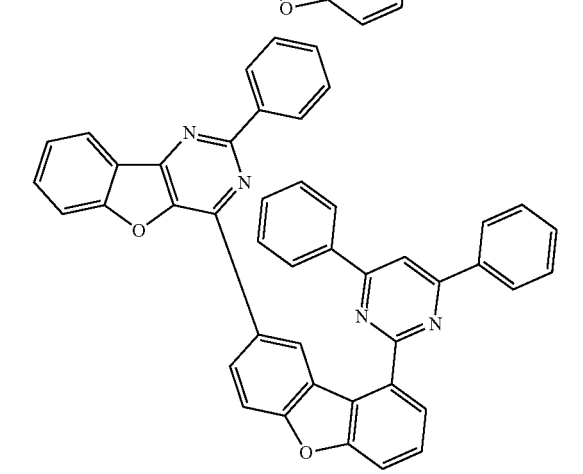
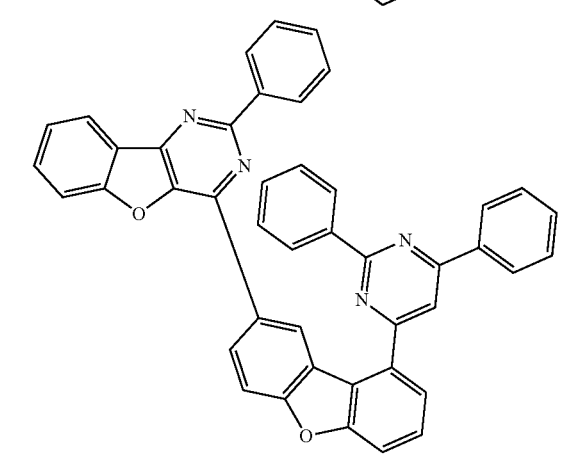
440
-continued
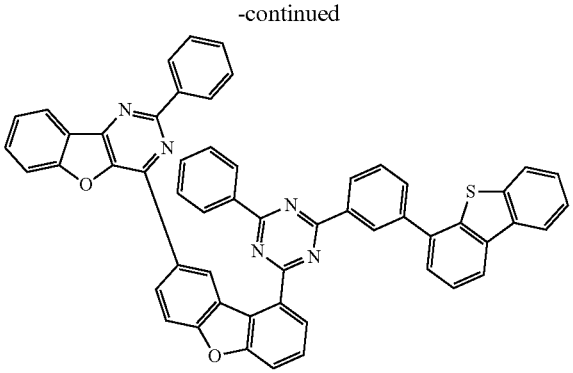
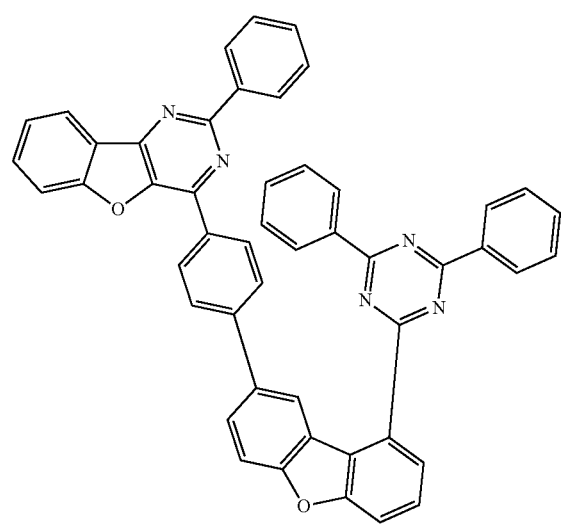
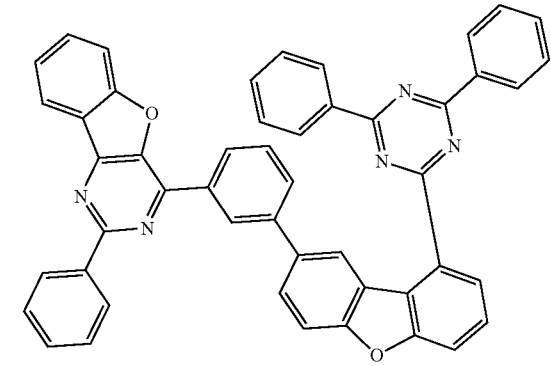

441
-continued
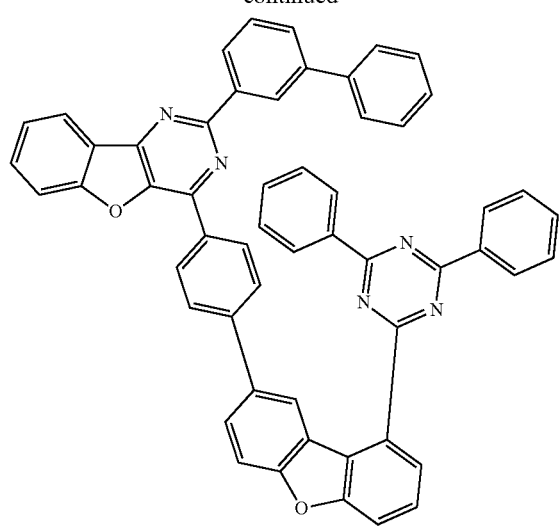
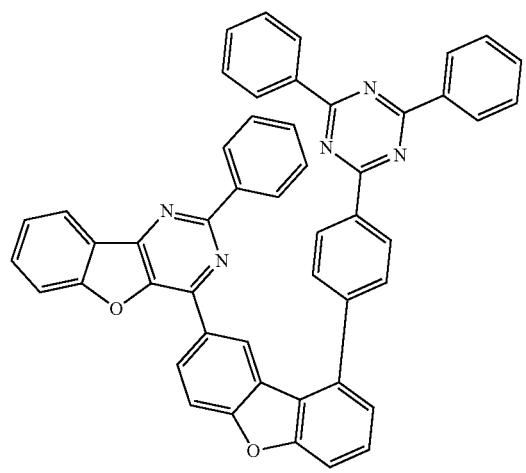
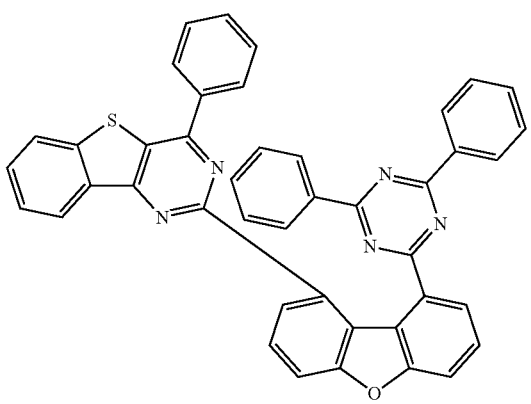
442
-continued
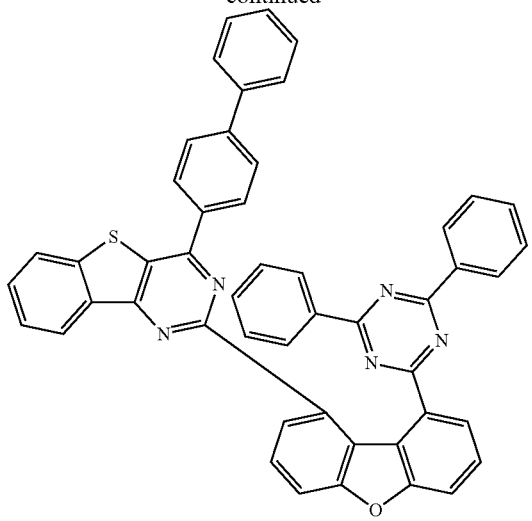
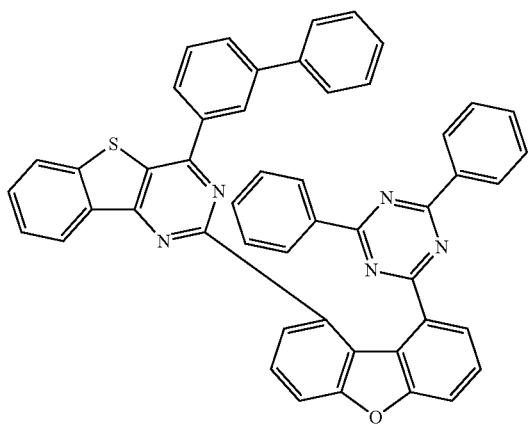
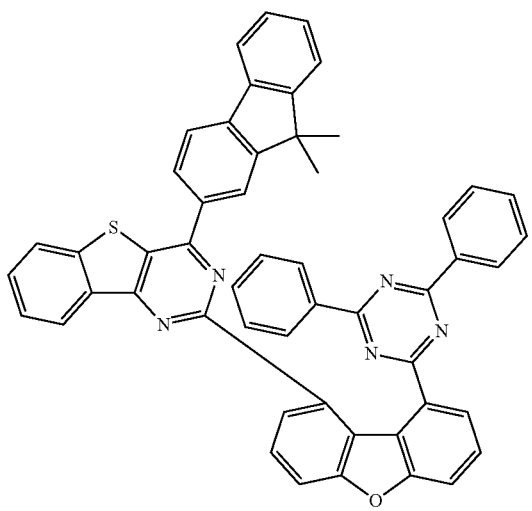

443
-continued
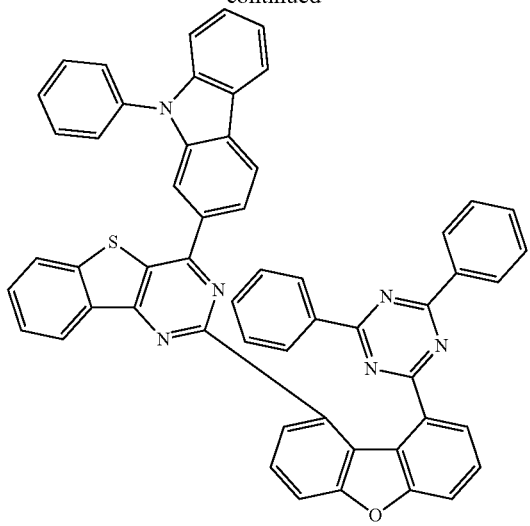
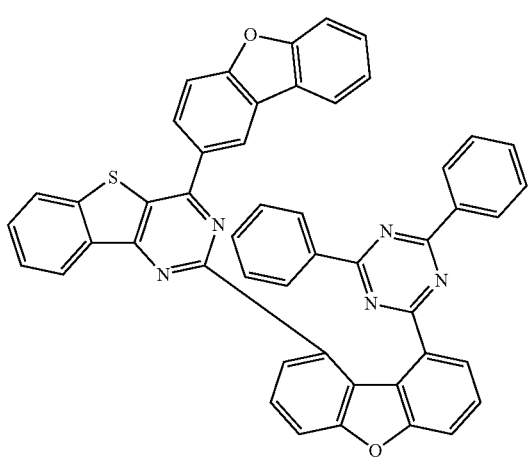
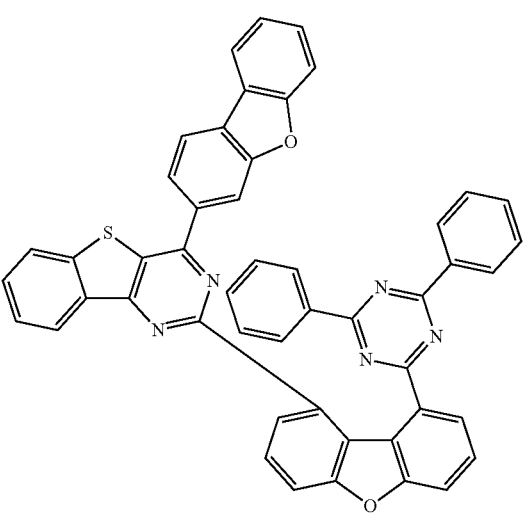
444
-continued
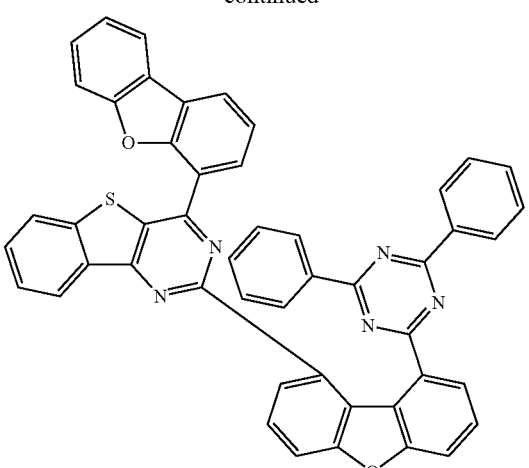
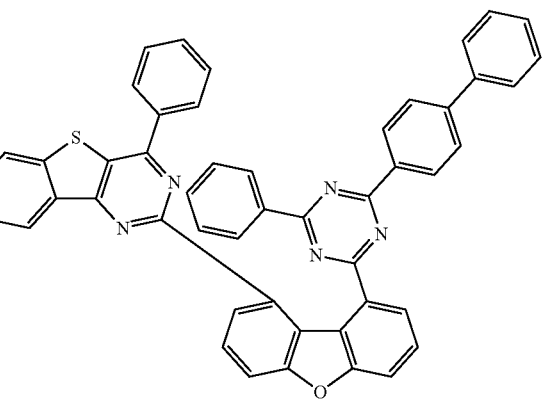
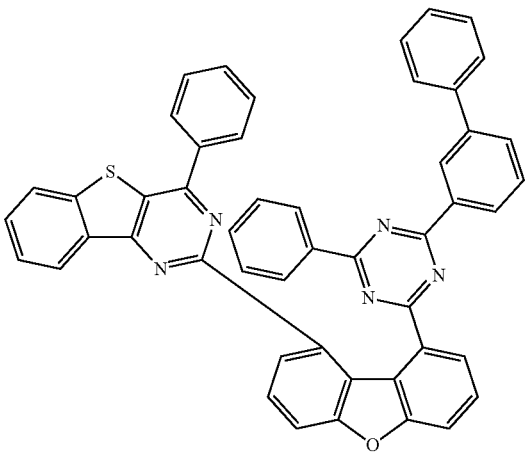

-continued
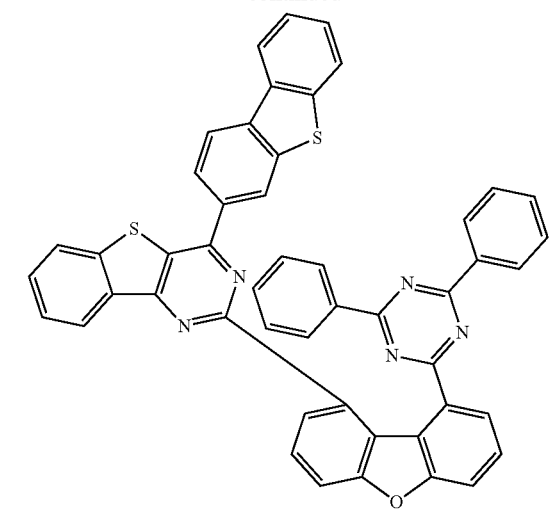
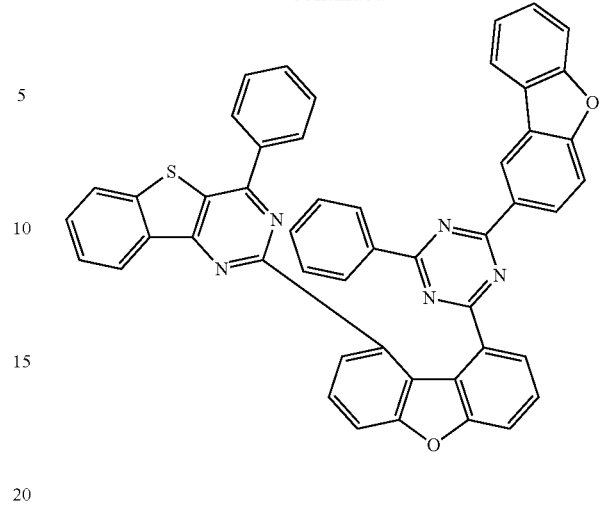
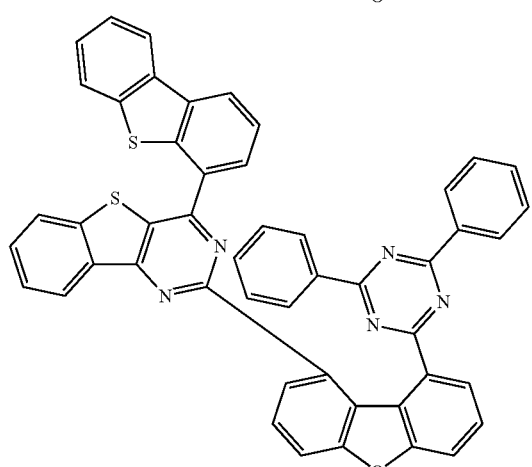
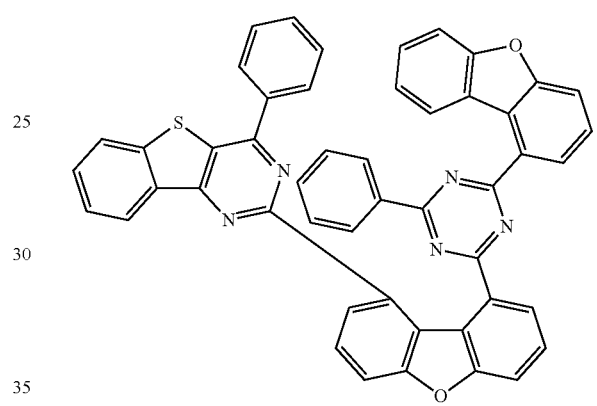
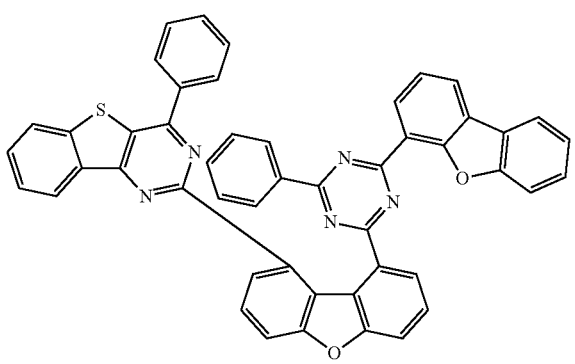
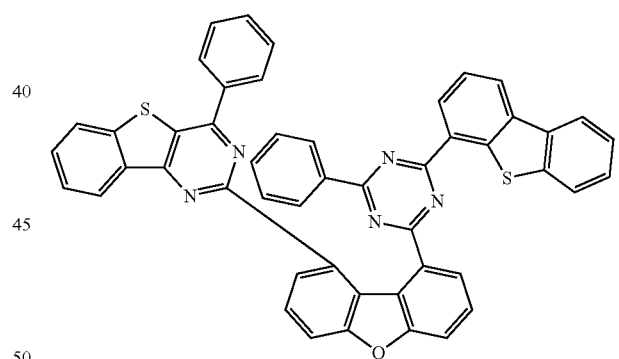
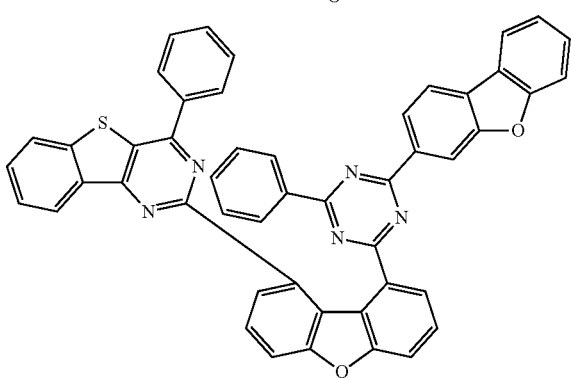
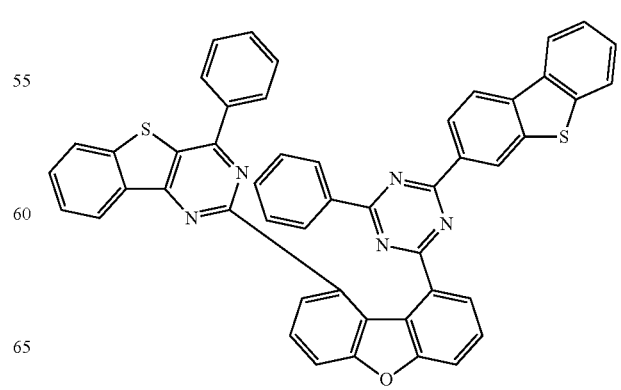

447
-continued
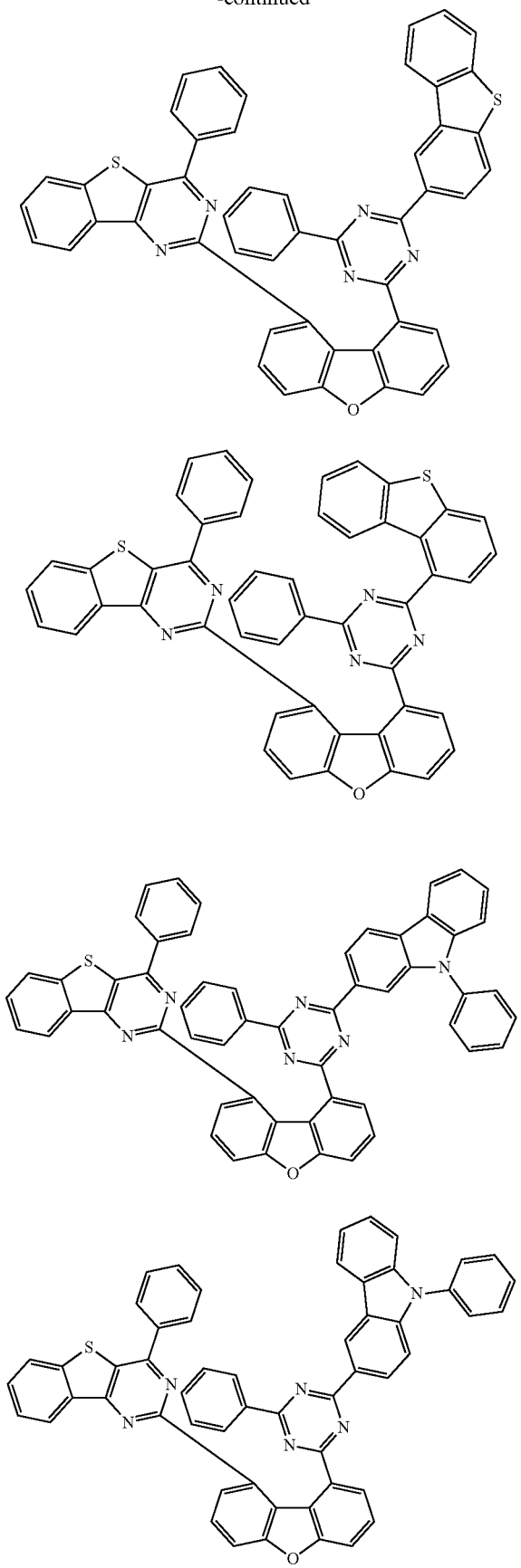
448
-continued
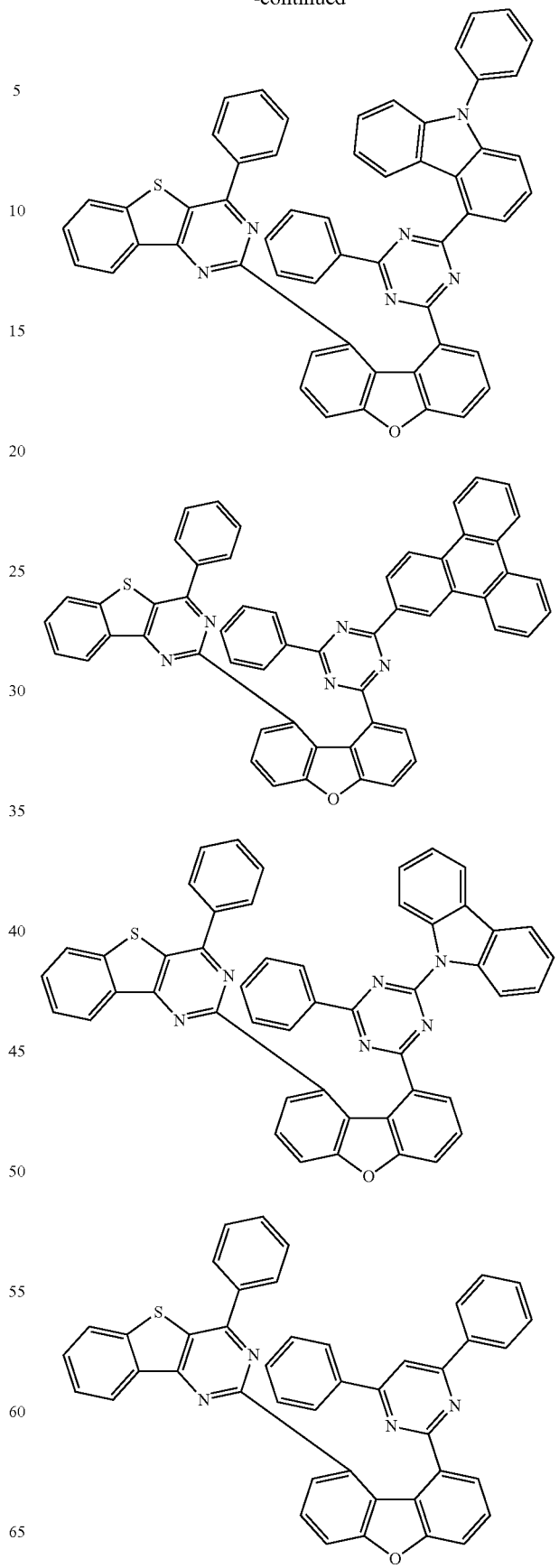

449
-continued
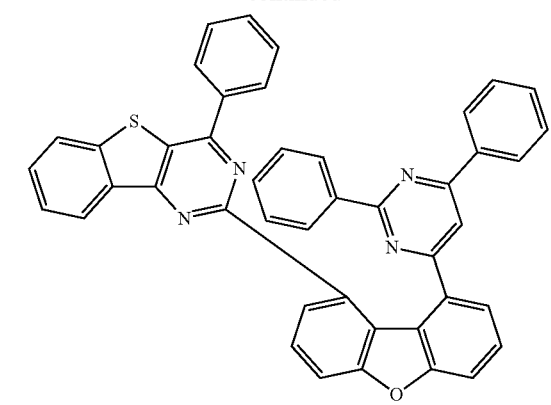
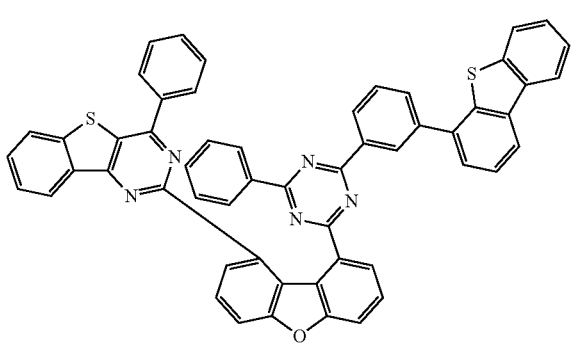
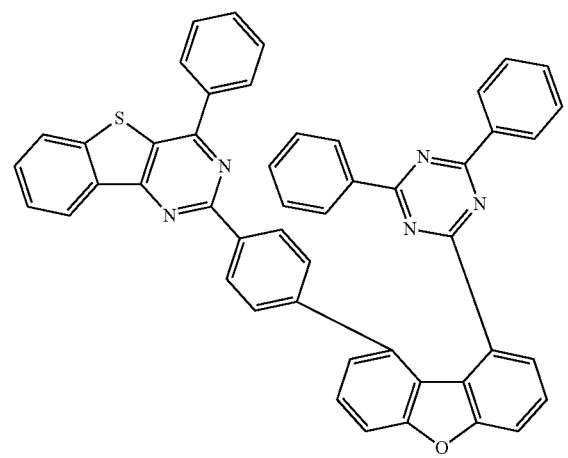
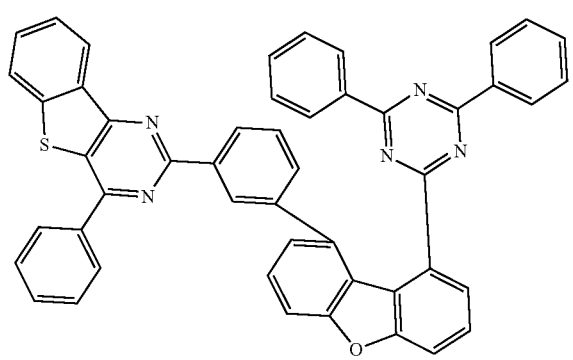
450
-continued
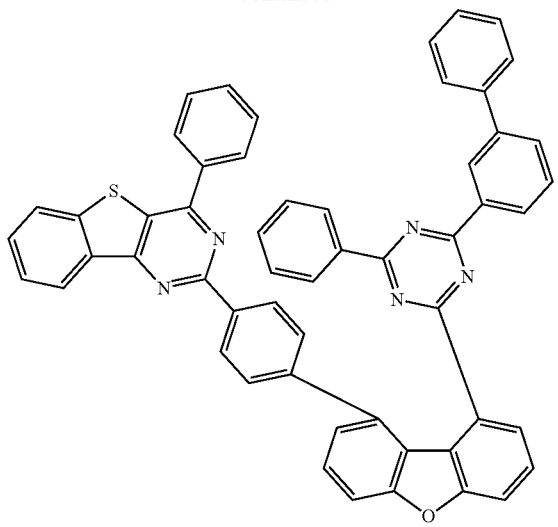
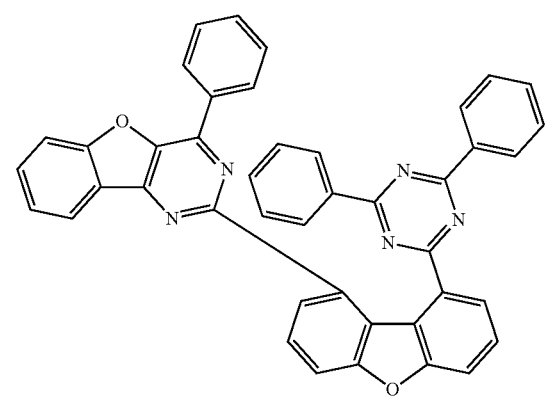

451 452
-continued -continued
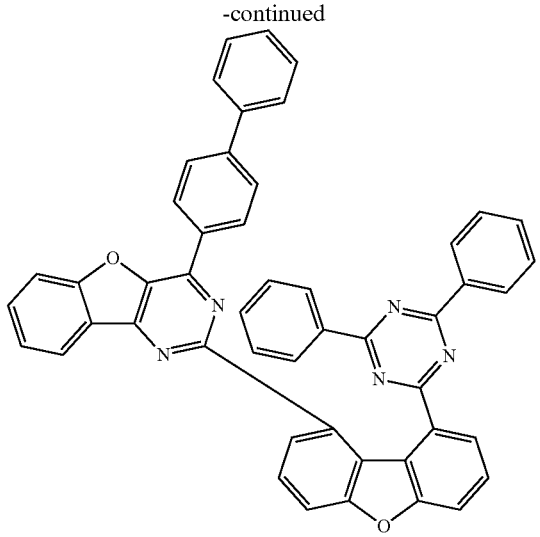
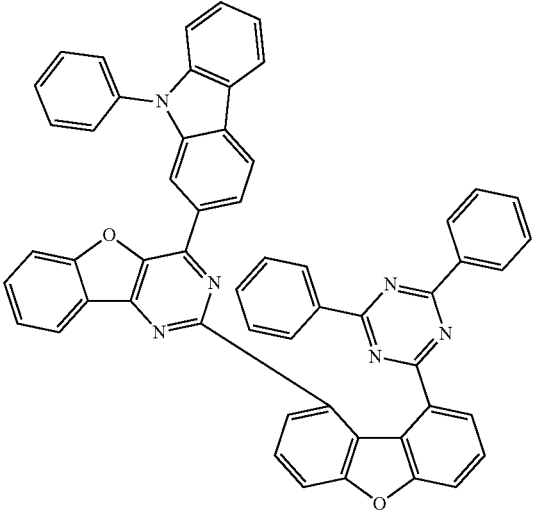
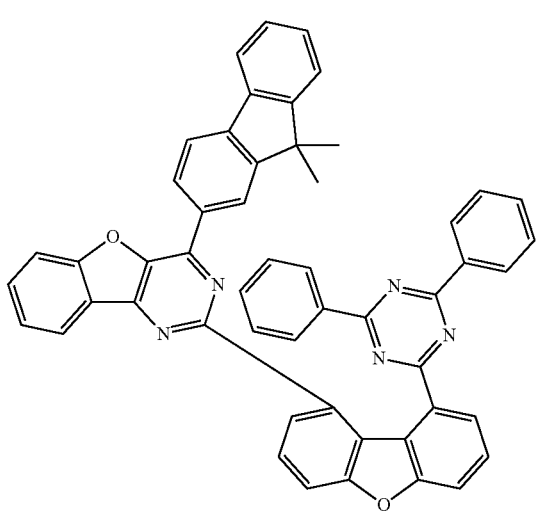
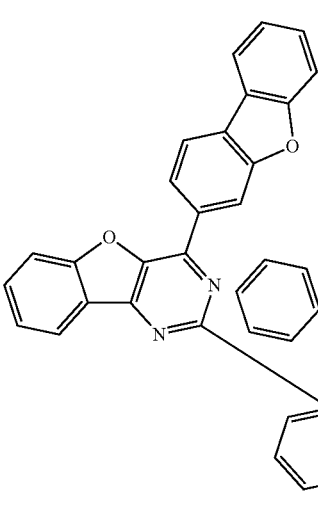

453
-continued
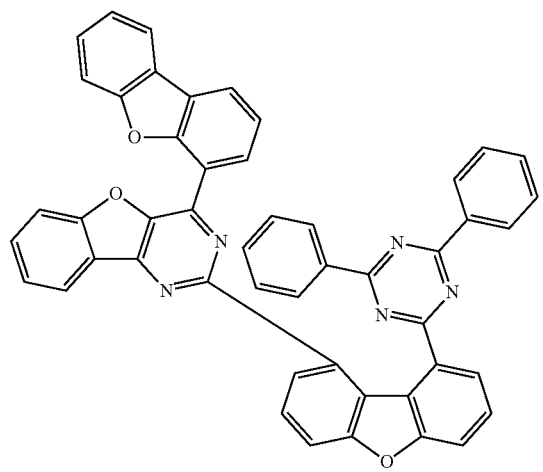
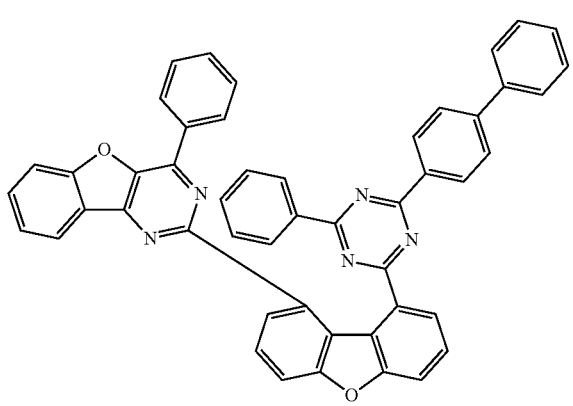
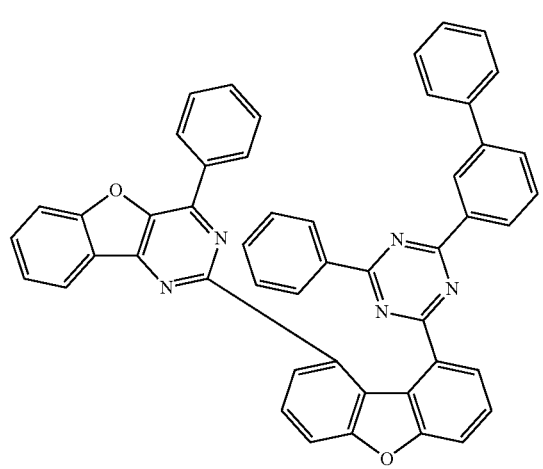
454
-continued
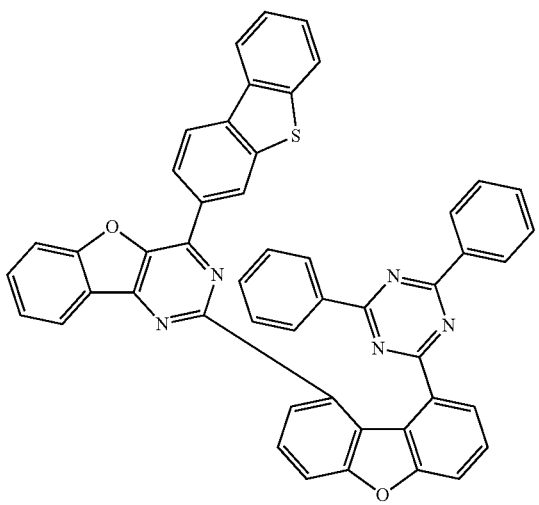
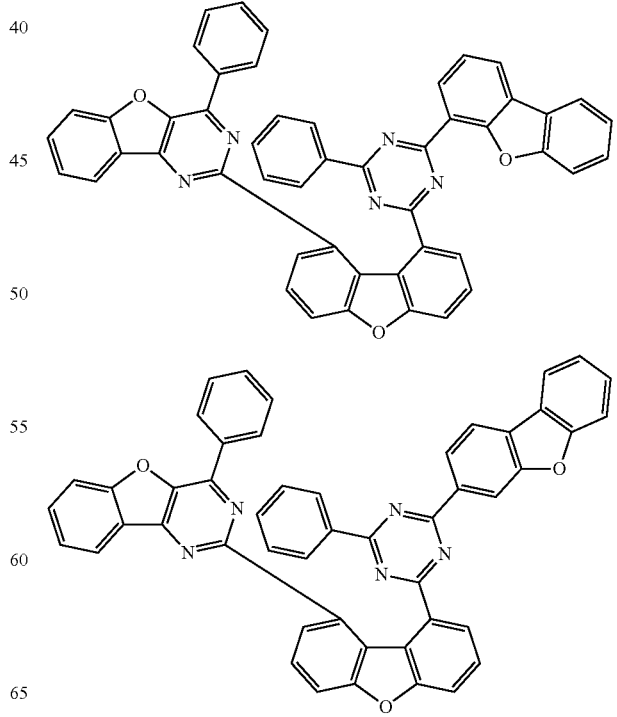

455
-continued
456
-continued
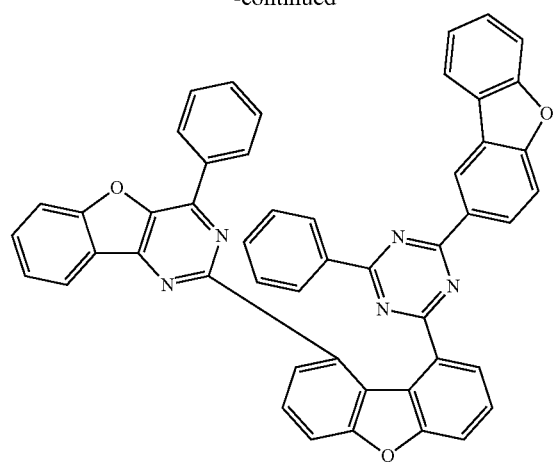
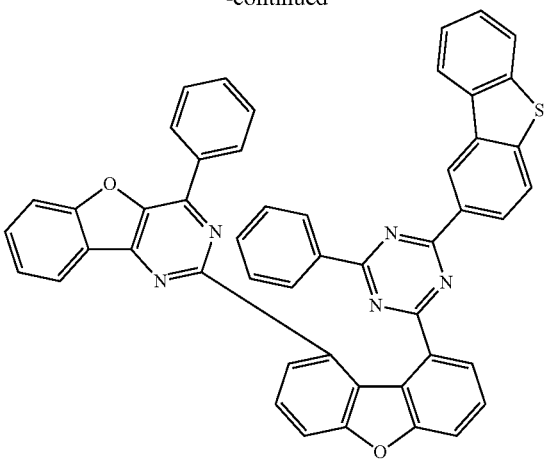

457
-continued
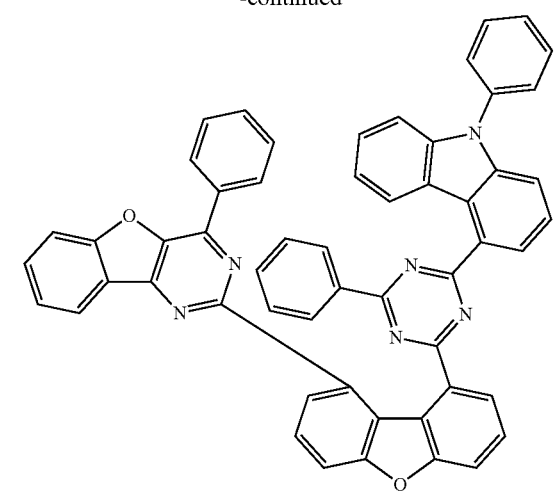
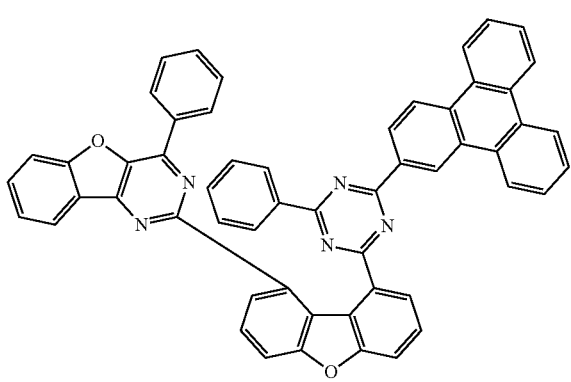
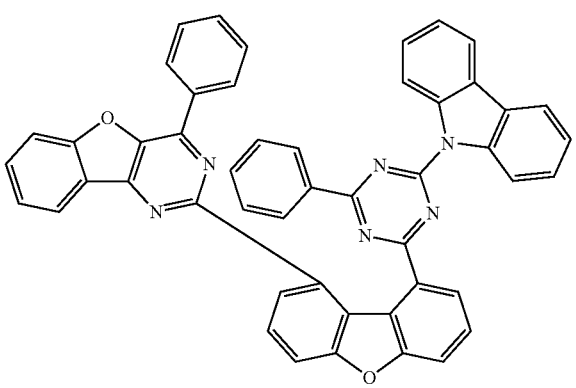
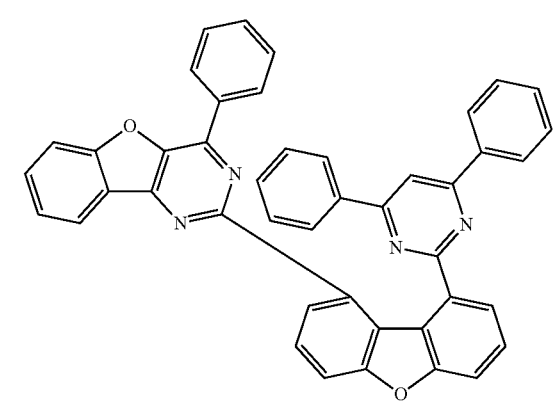
458
-continued
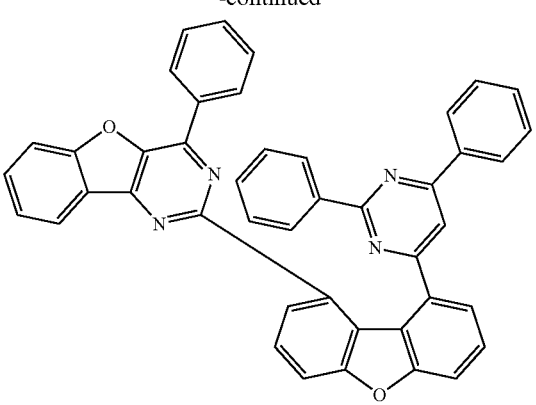
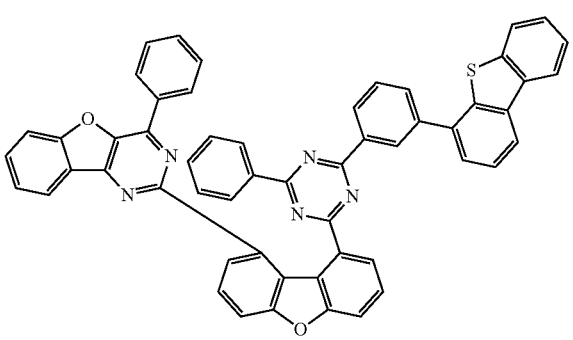
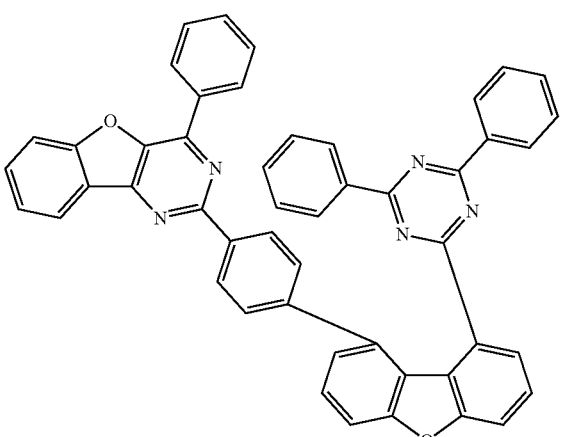
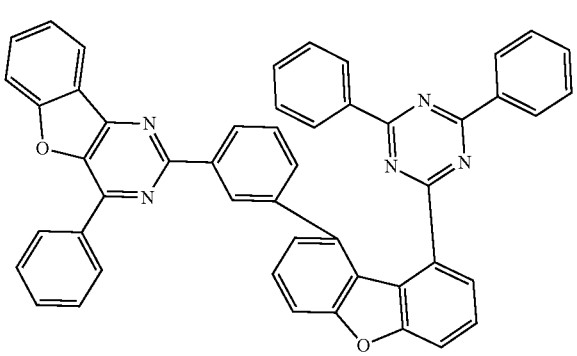

| 459 -continued | 460 -continued |
|---|---|
| 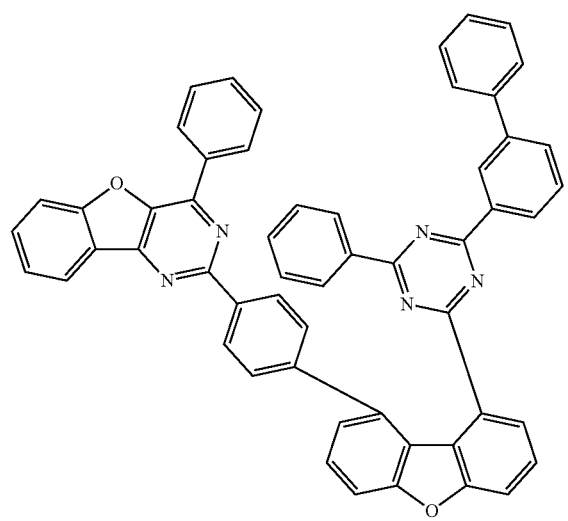 | 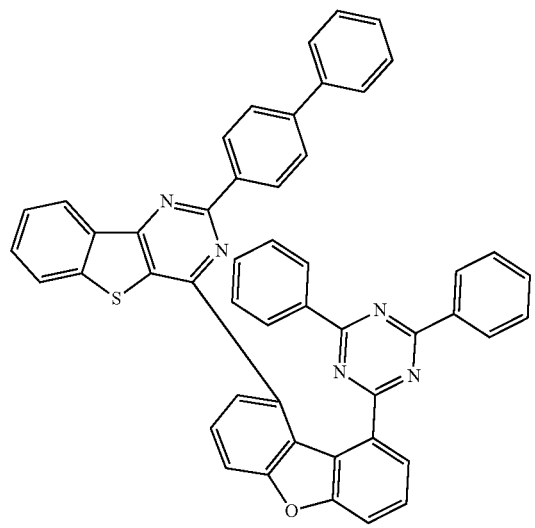 |
| 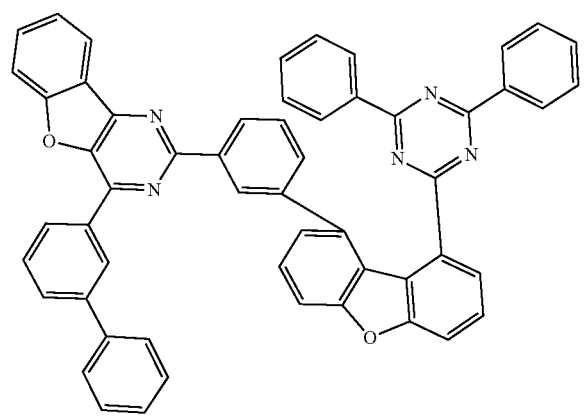 | 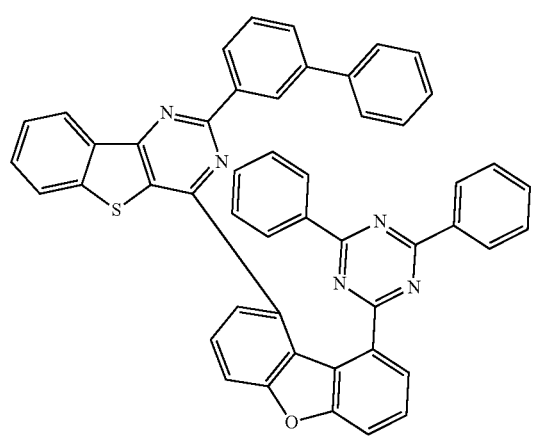 |
| 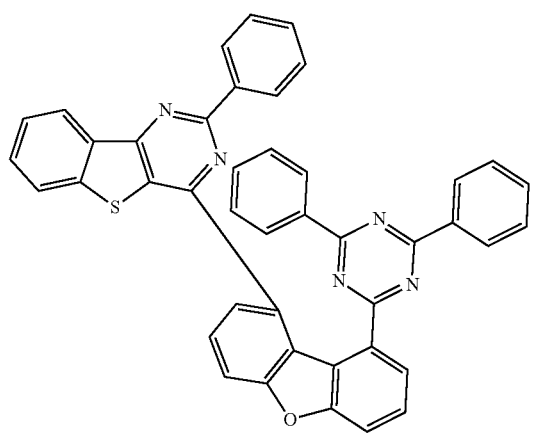 | 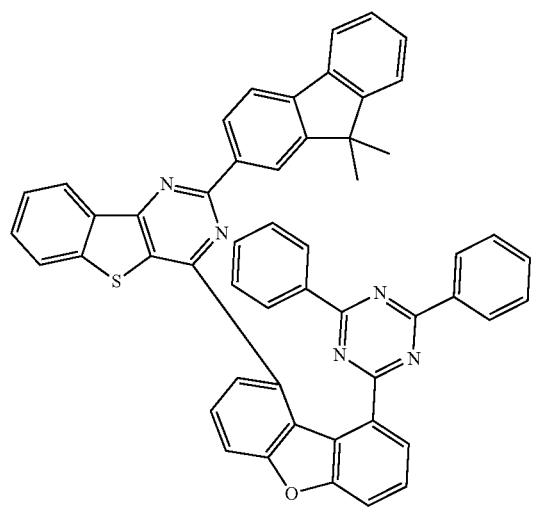 |

461
-continued
462
-continued
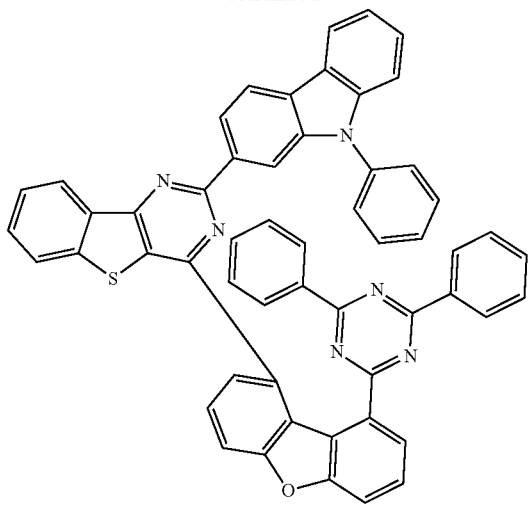
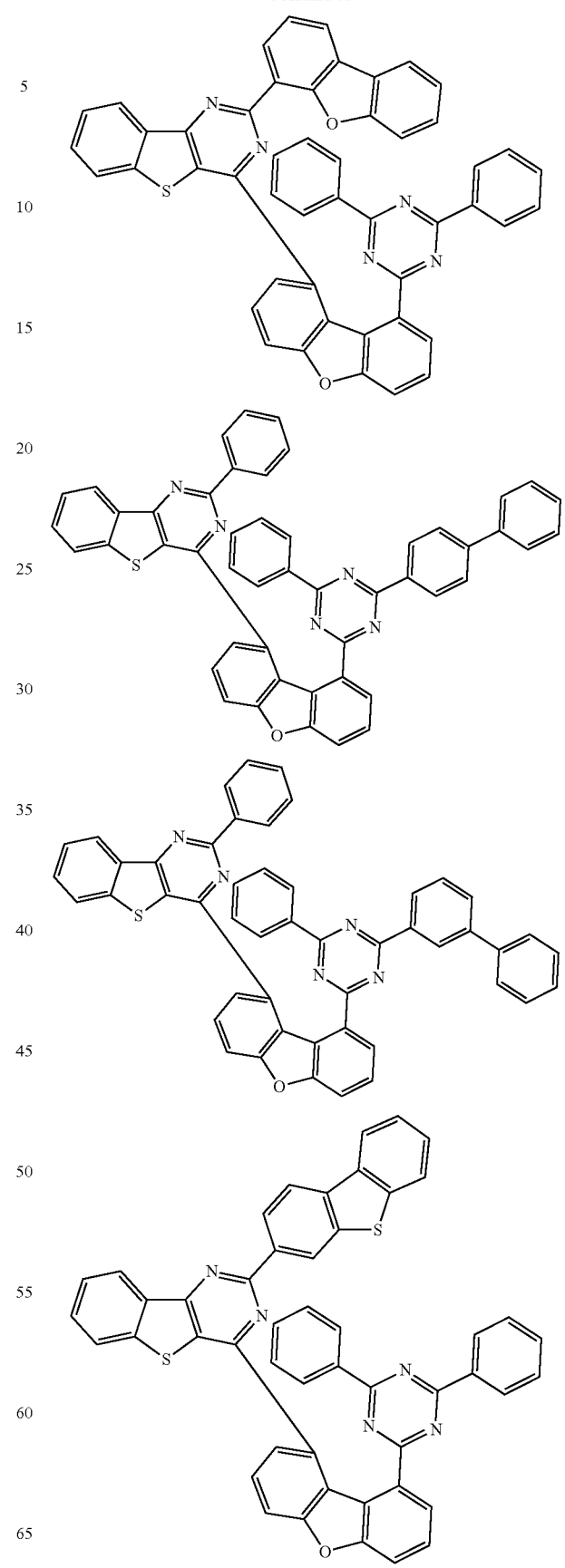

463
-continued
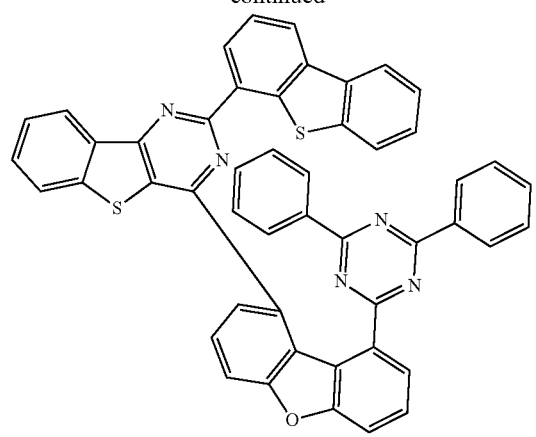
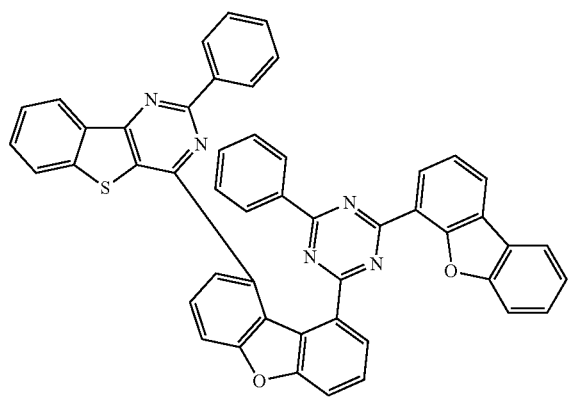
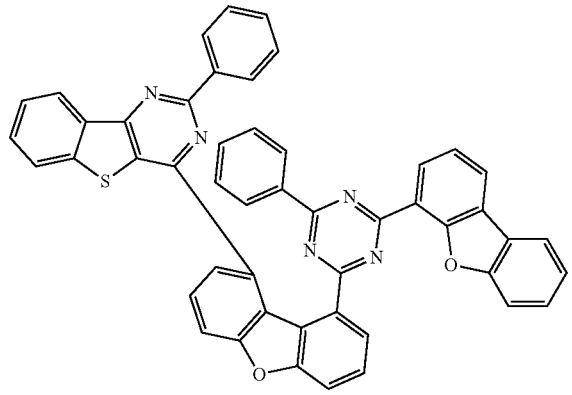
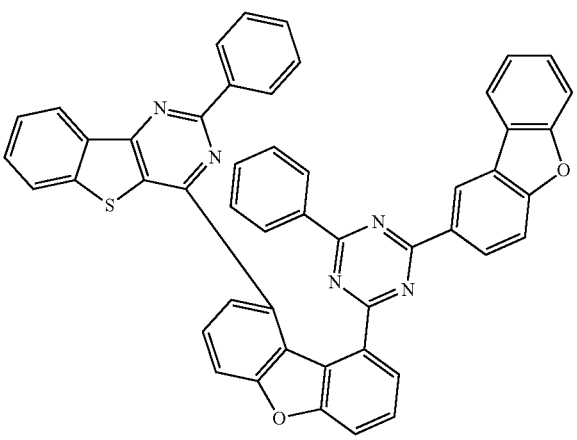
464
-continued
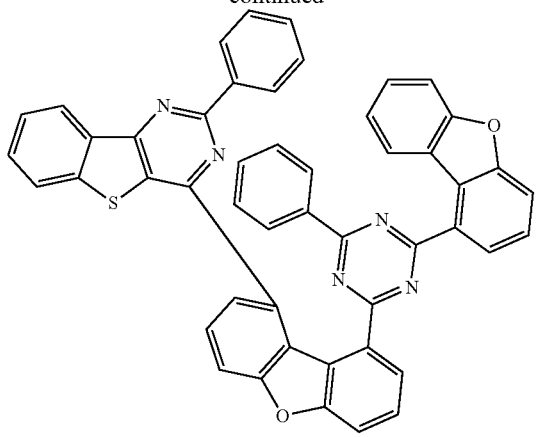
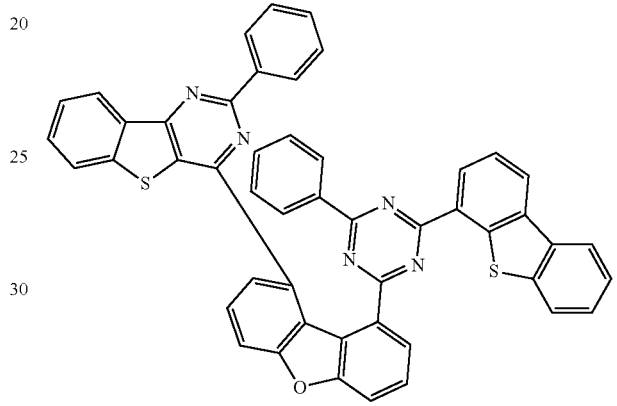
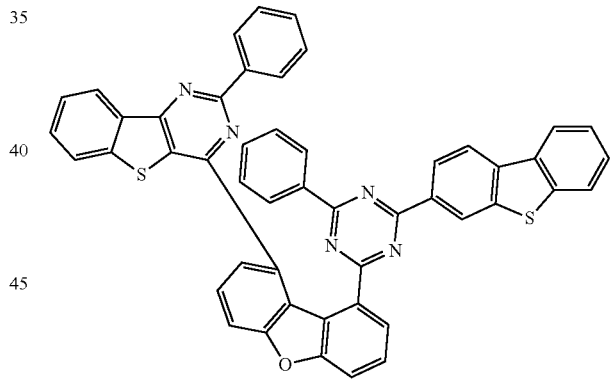
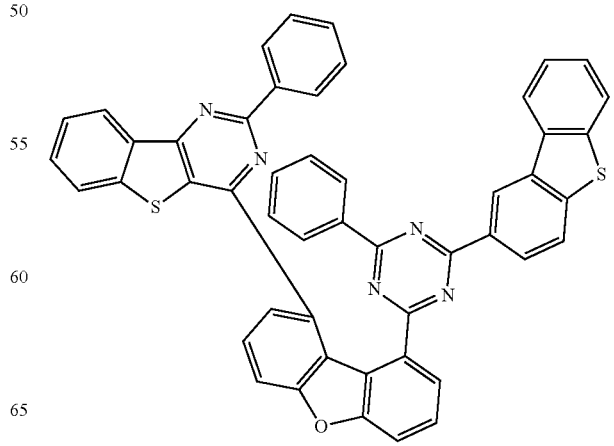

465
-continued
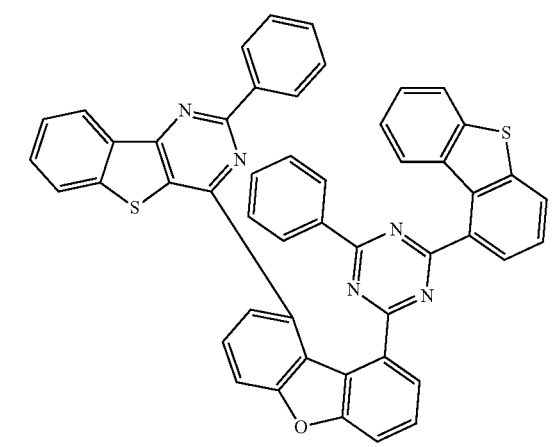
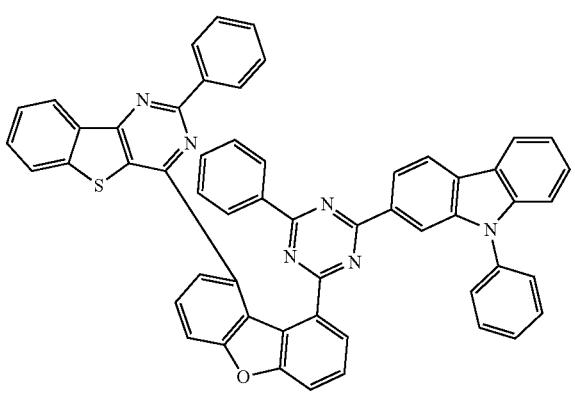
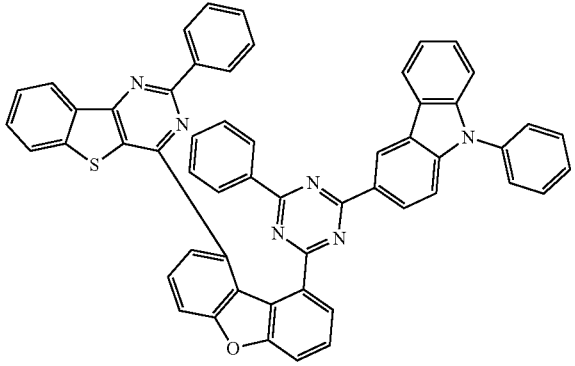
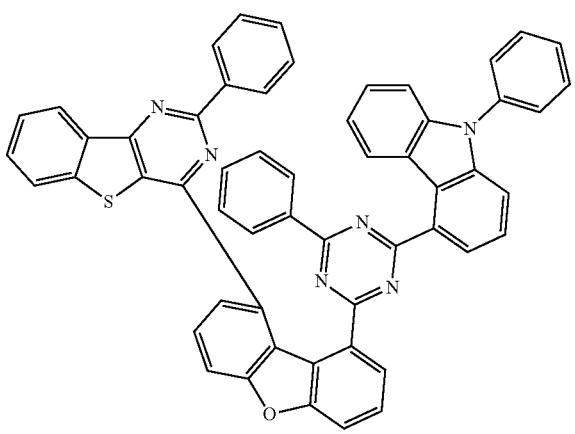
466
-continued
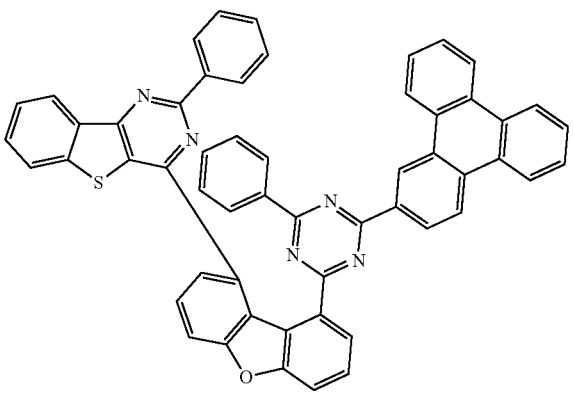
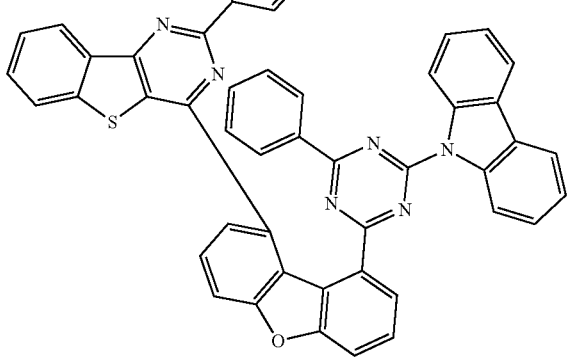
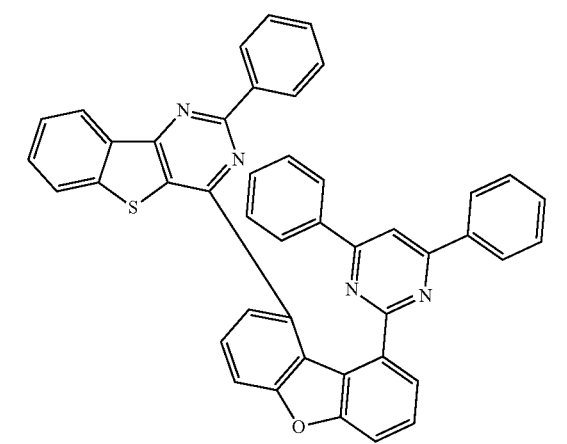
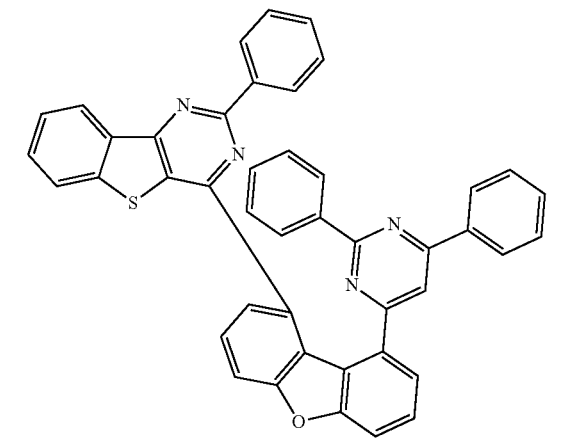

467
-continued
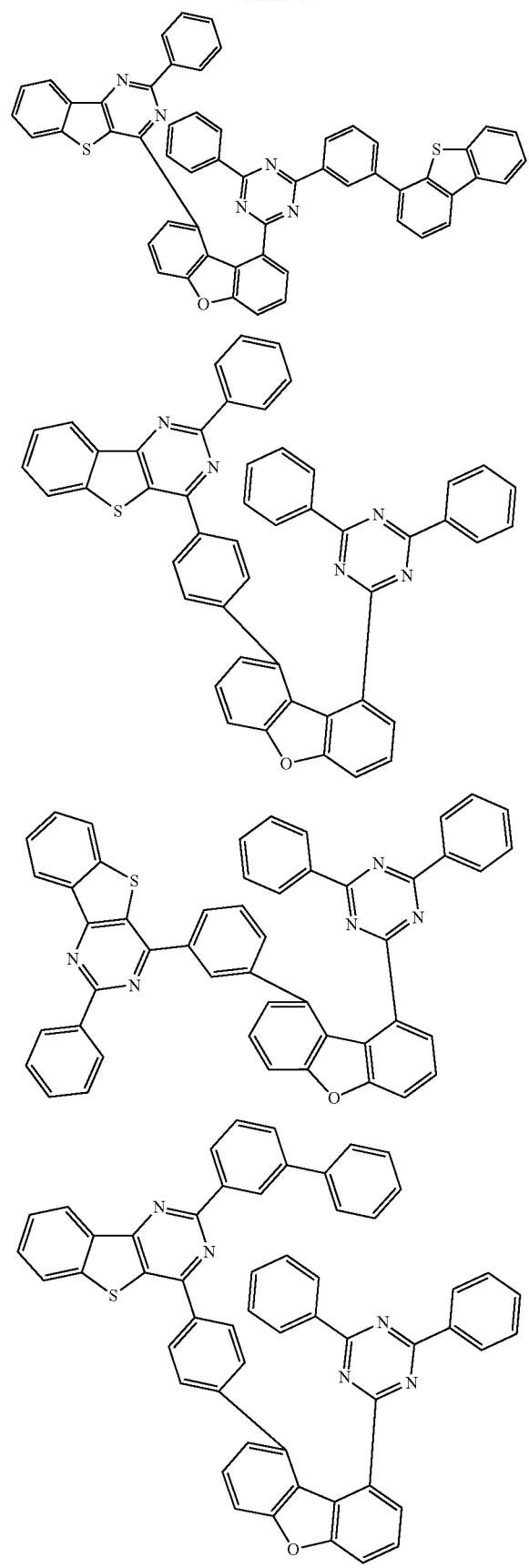
468
-continued
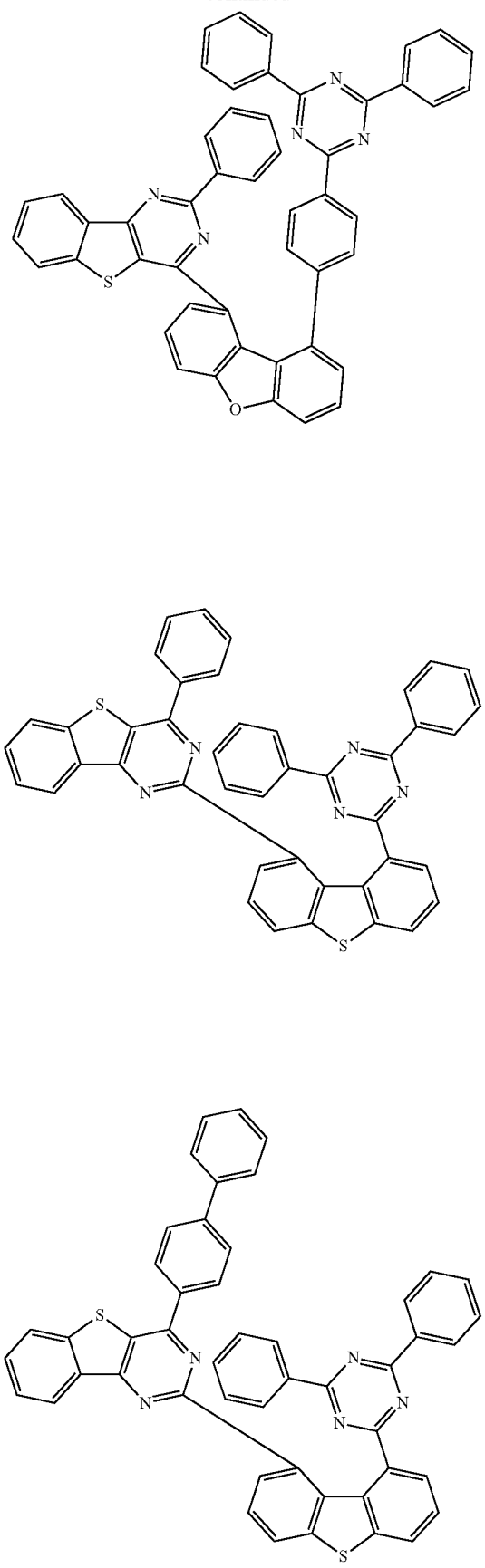

469
-continued
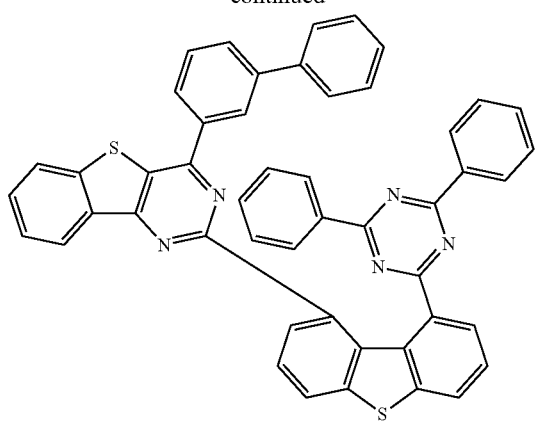
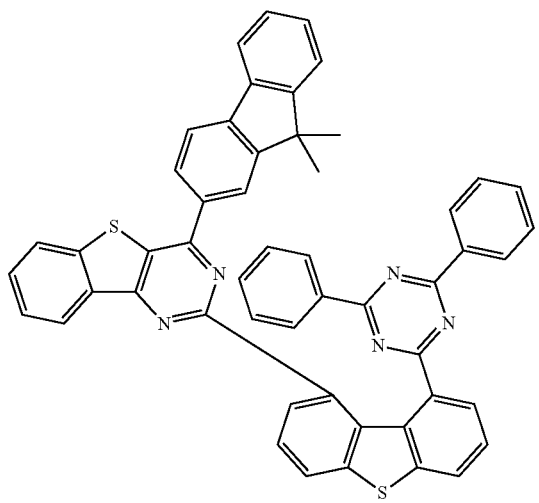
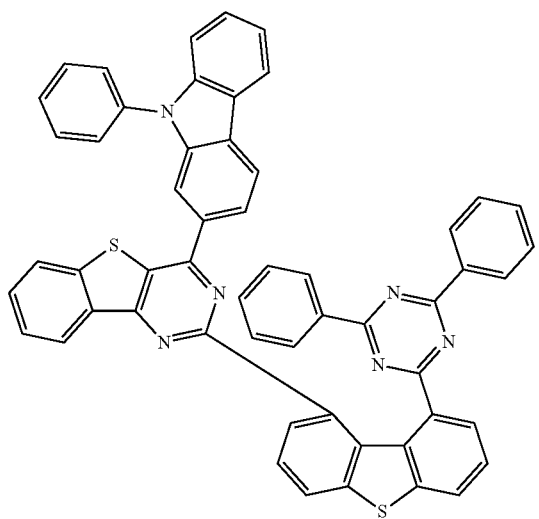
470
-continued
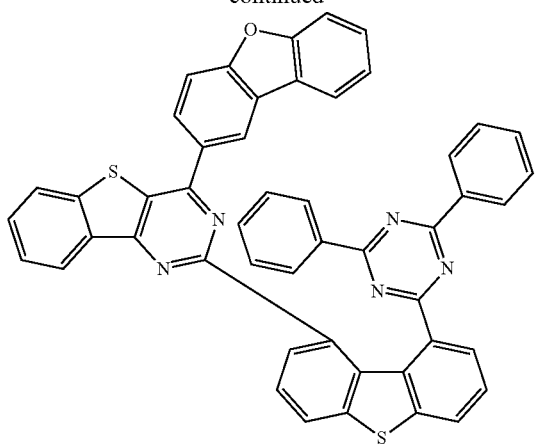
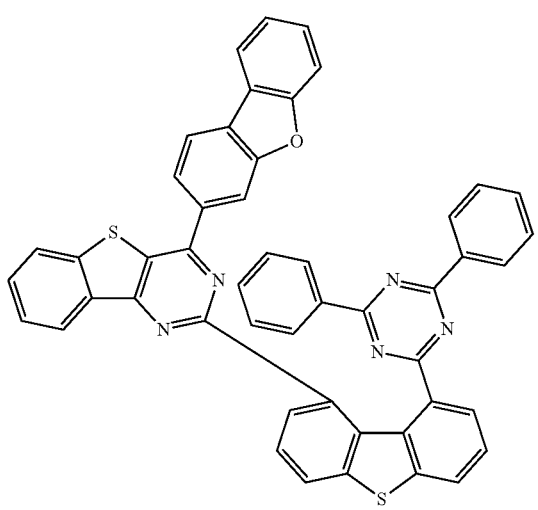
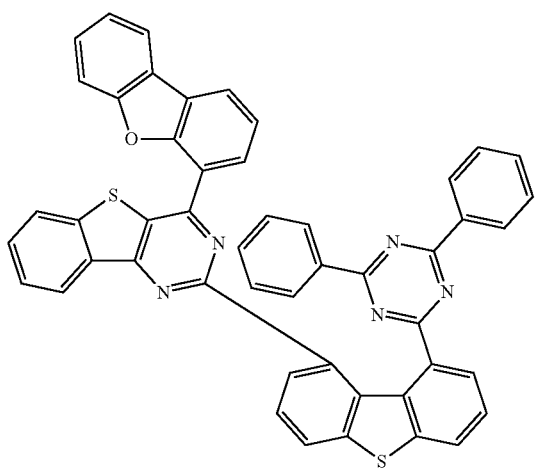

471
-continued
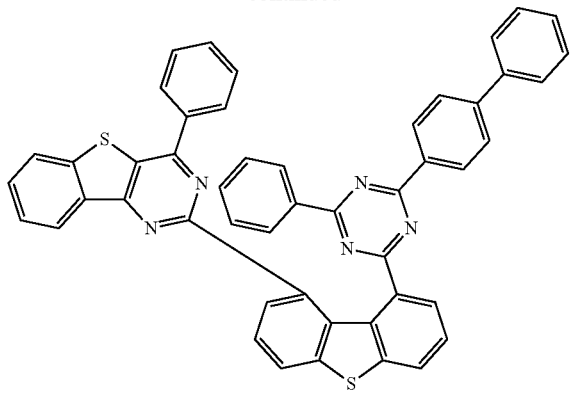
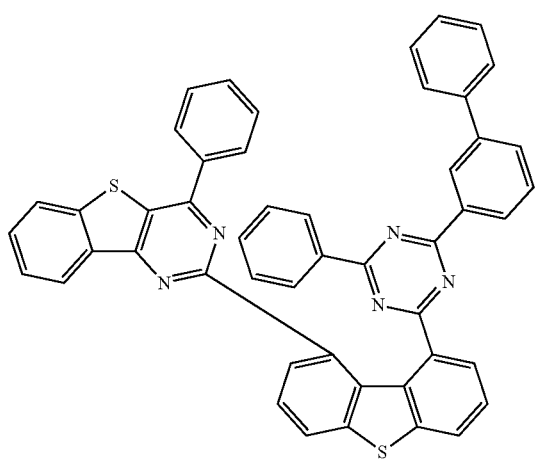
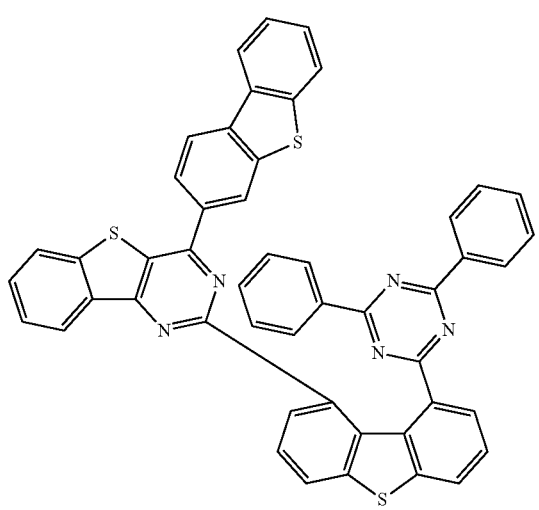
472
-continued
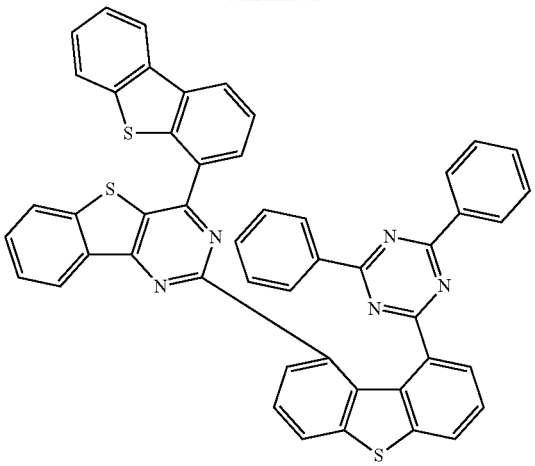
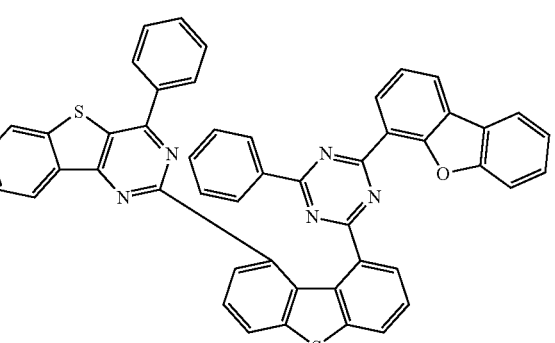
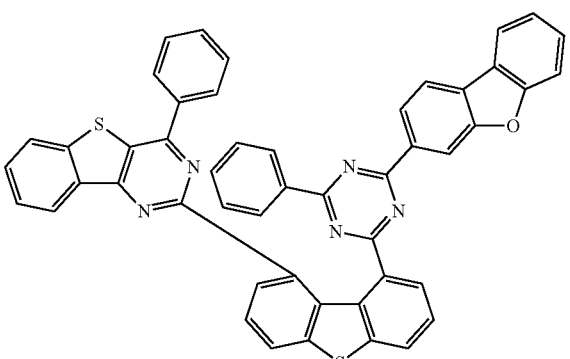
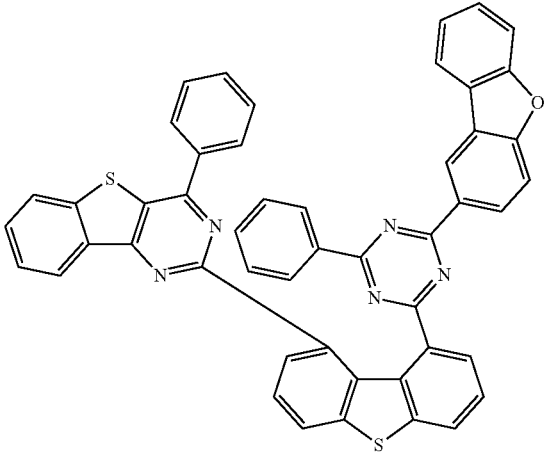

473
-continued
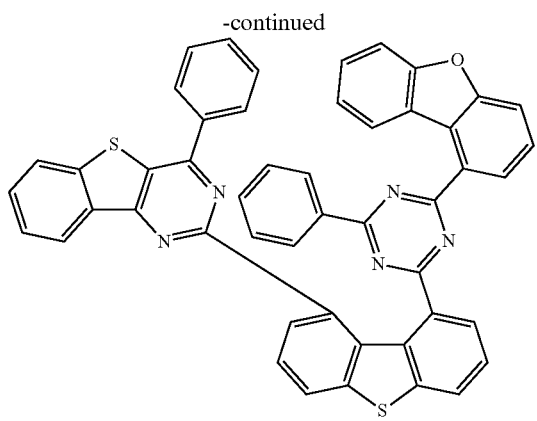
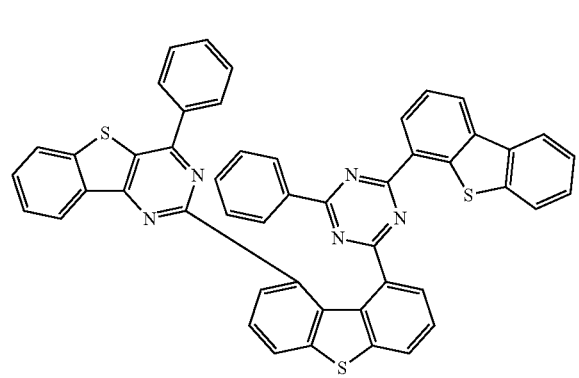
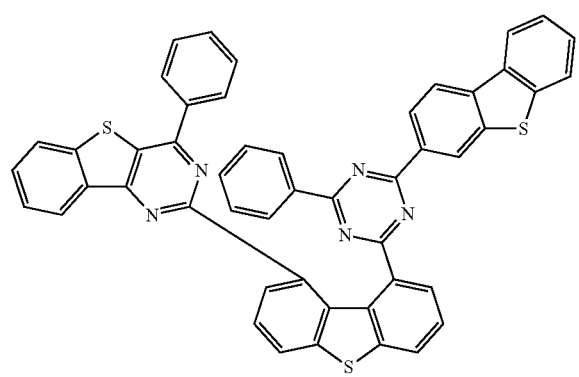
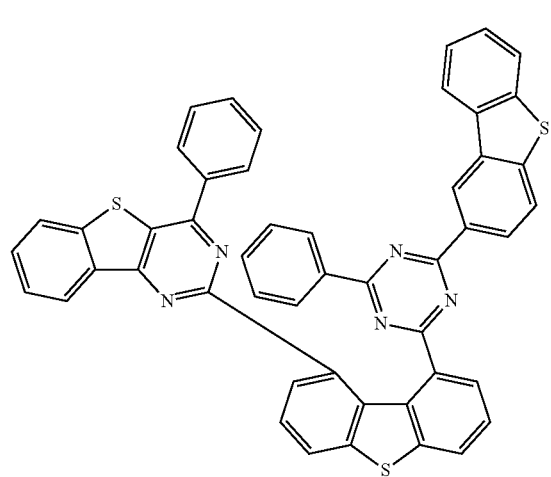
474
-continued
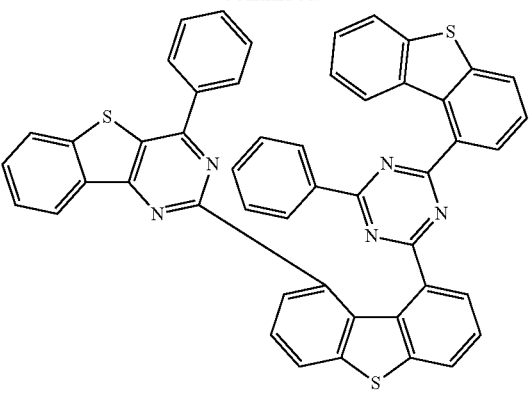
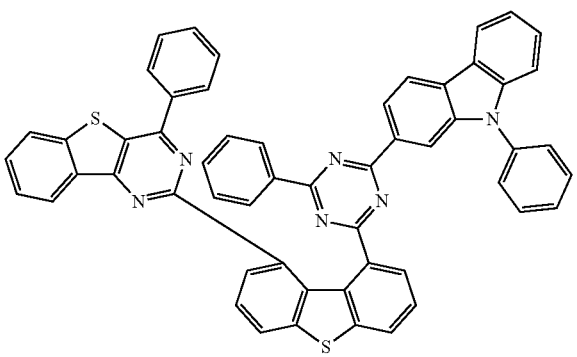
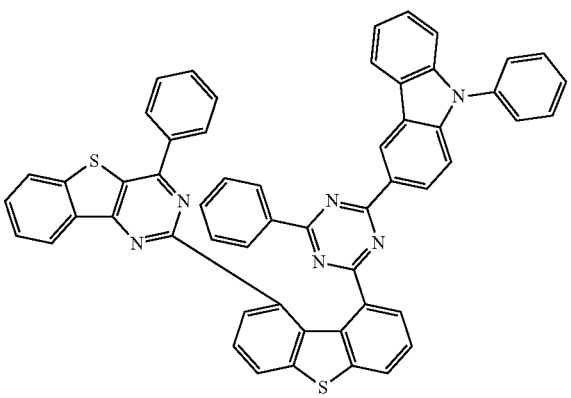
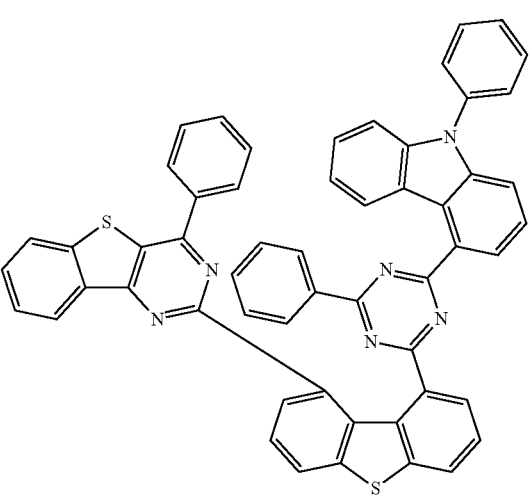

475
-continued
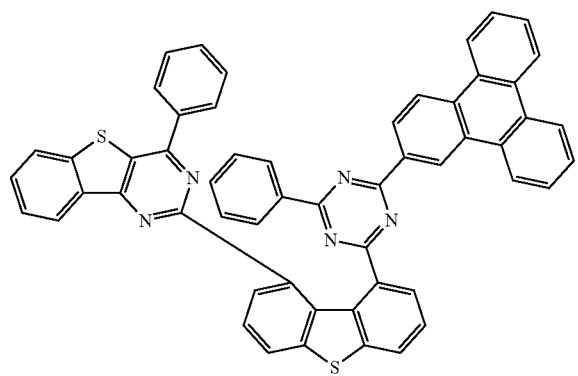
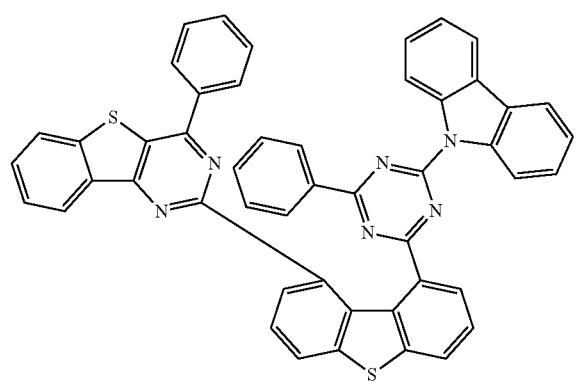
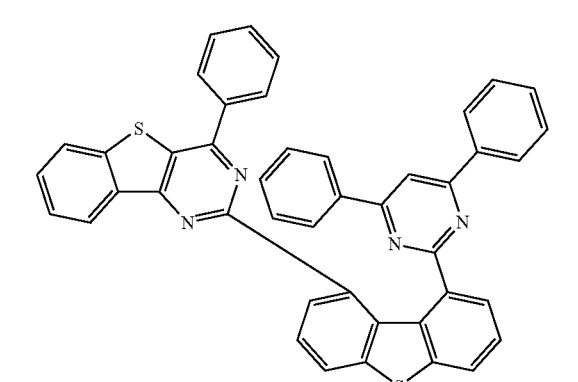
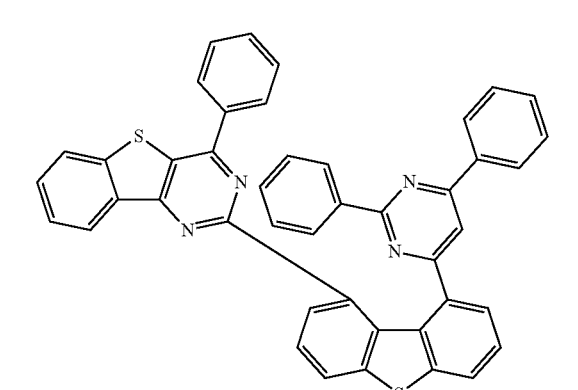
476
-continued
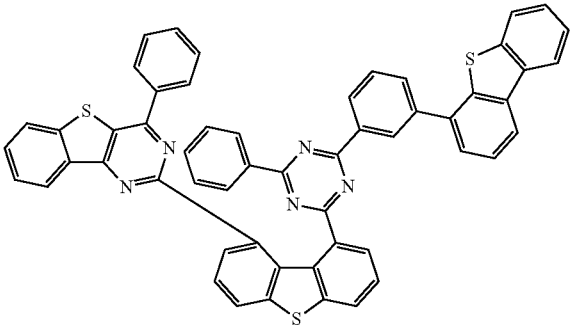
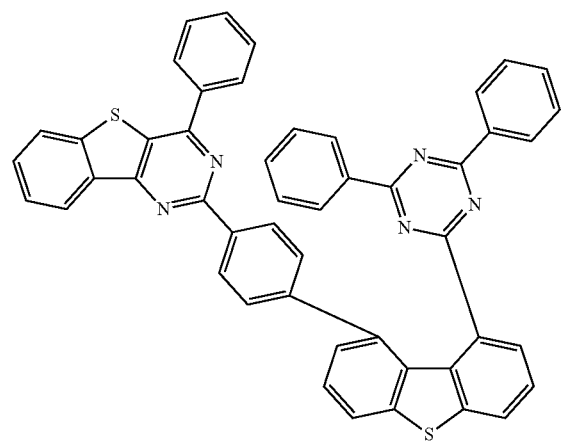
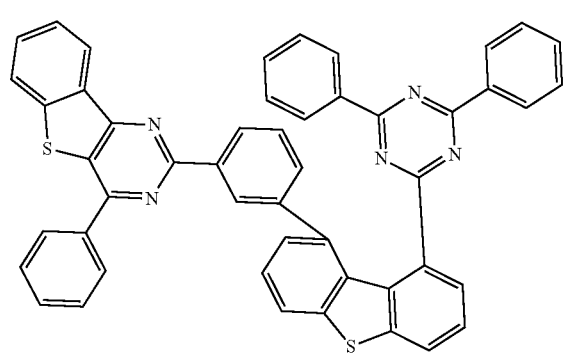
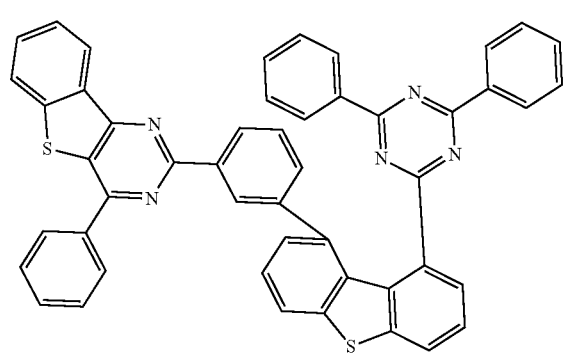

477
-continued
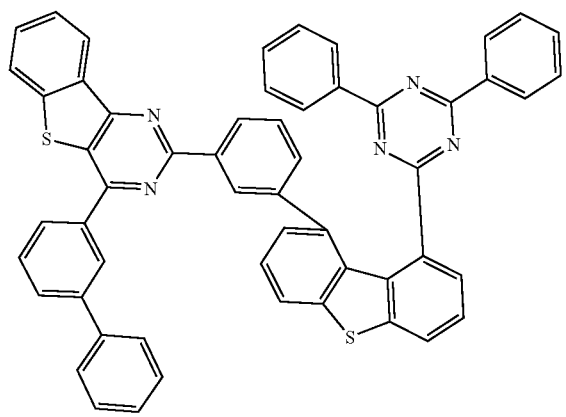
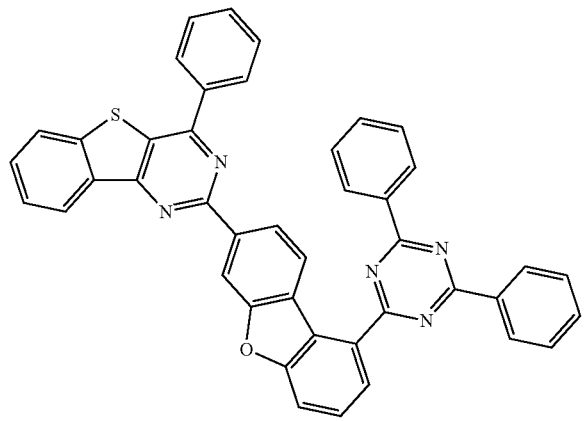
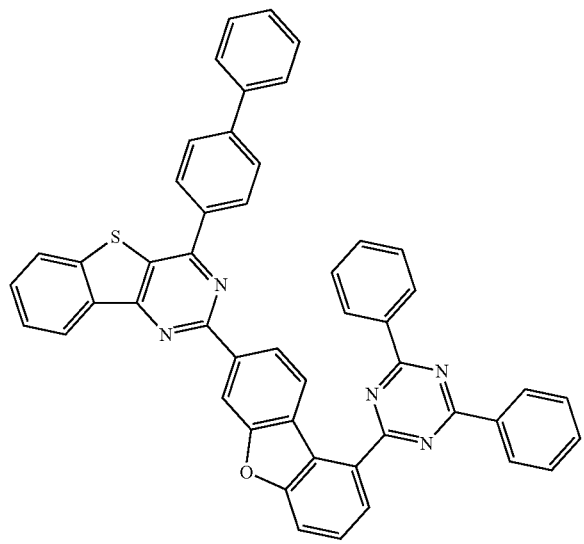
478
-continued
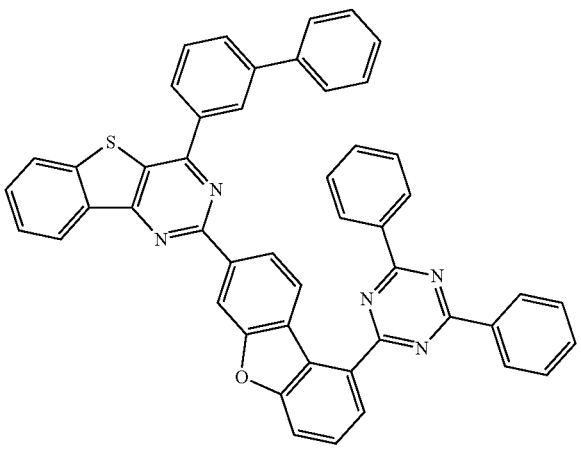
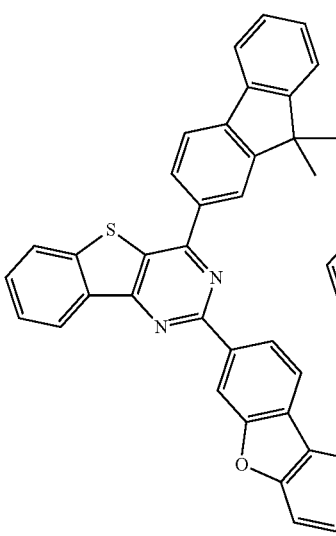
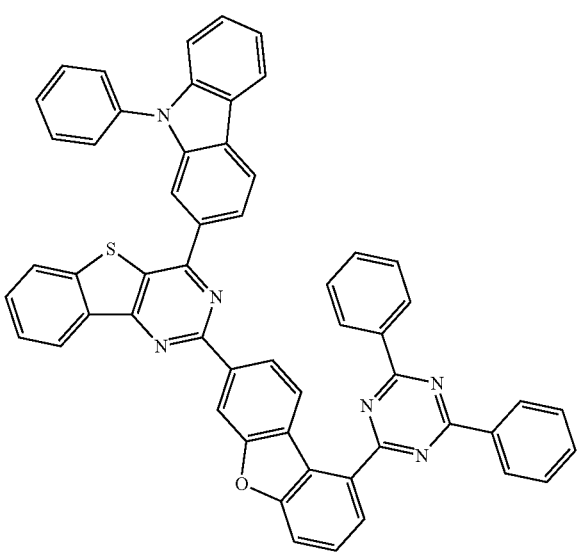

479
-continued
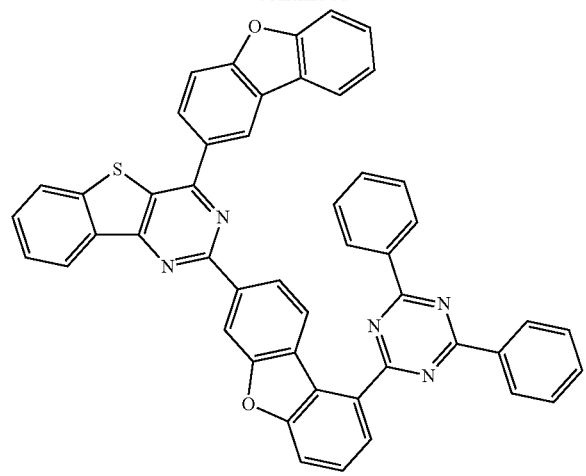
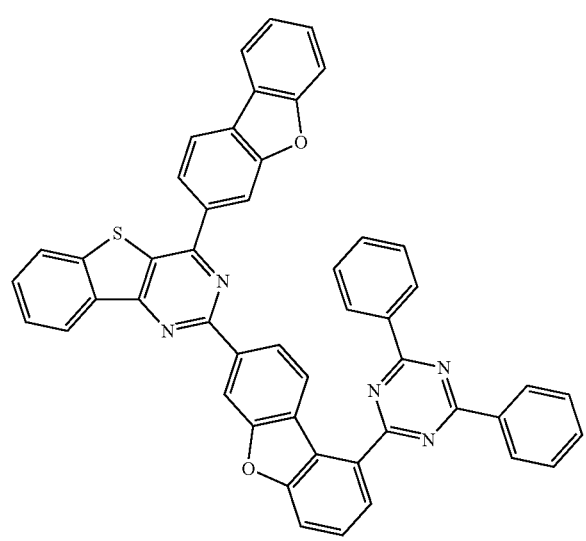
480
-continued
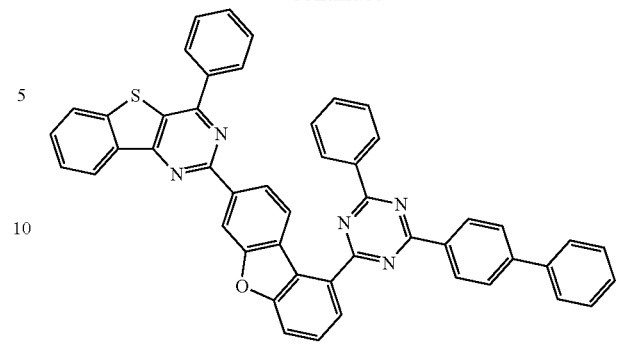
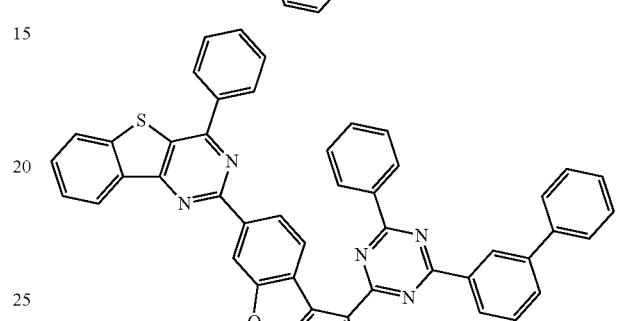
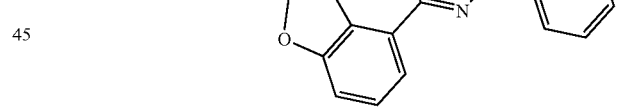
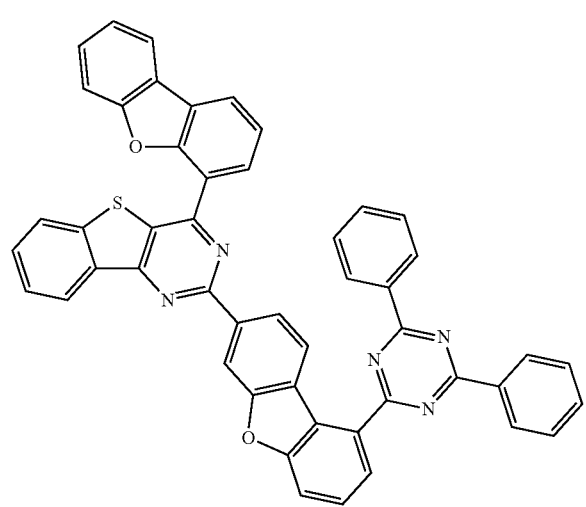

481
-continued
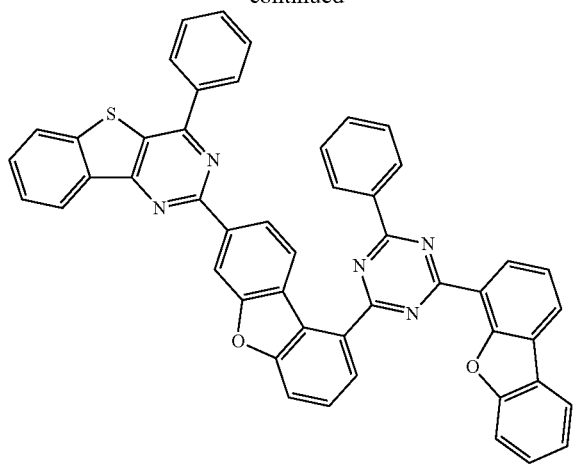
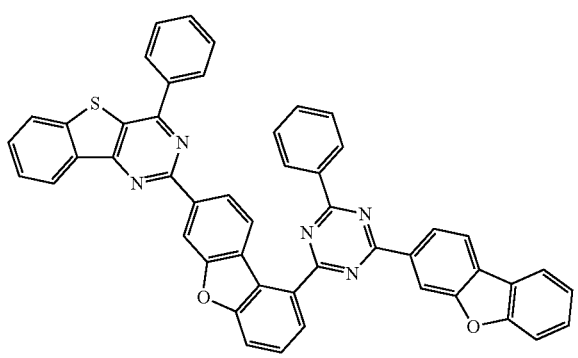
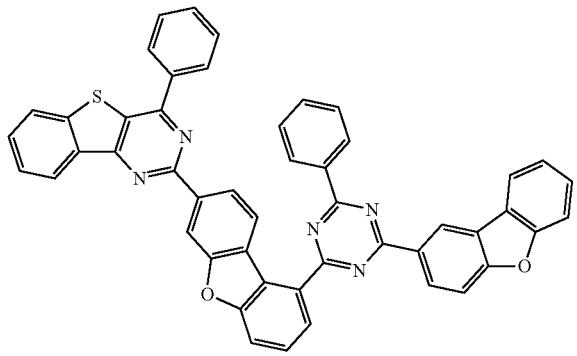
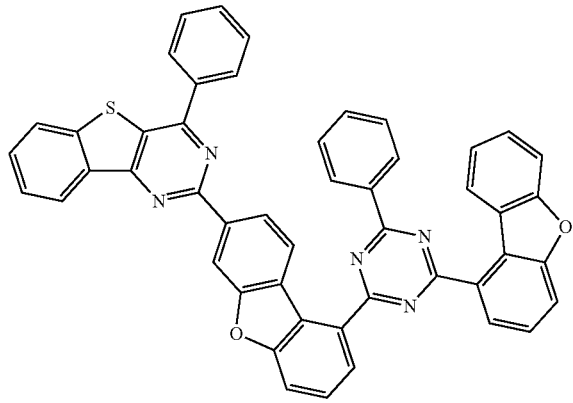
482
-continued
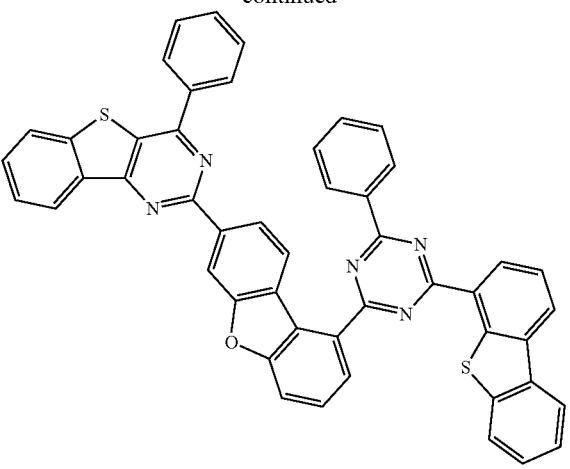
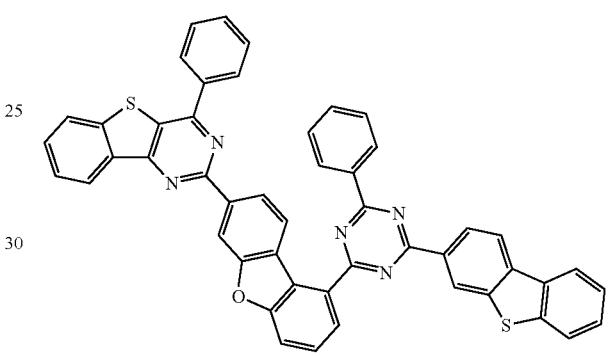
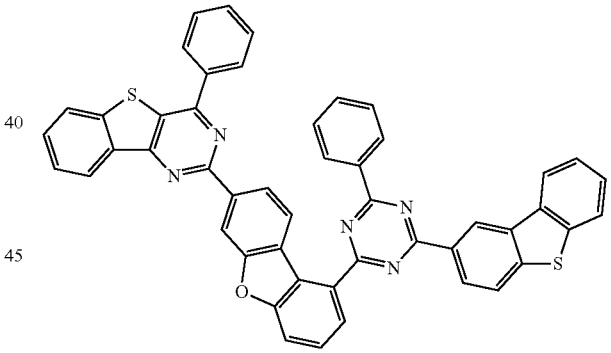
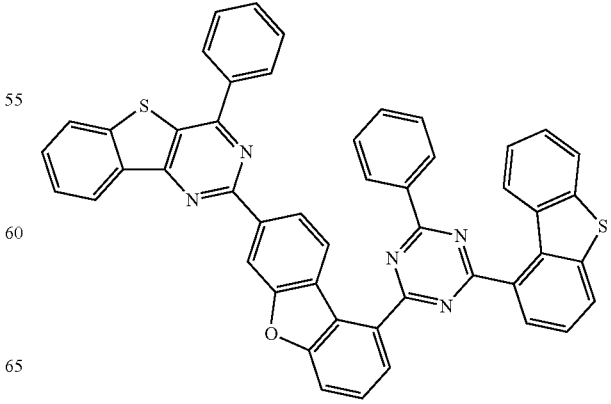

483
-continued
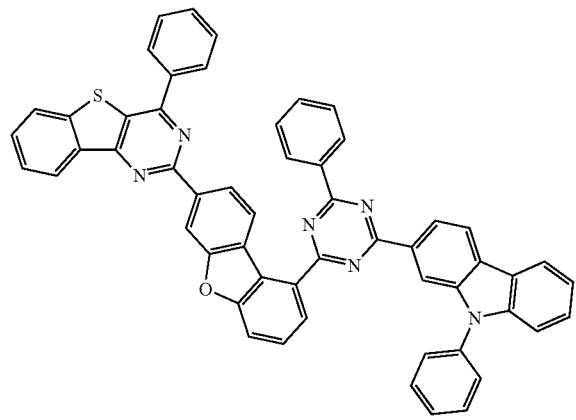
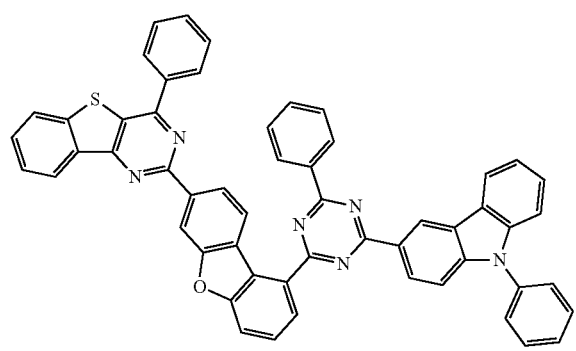
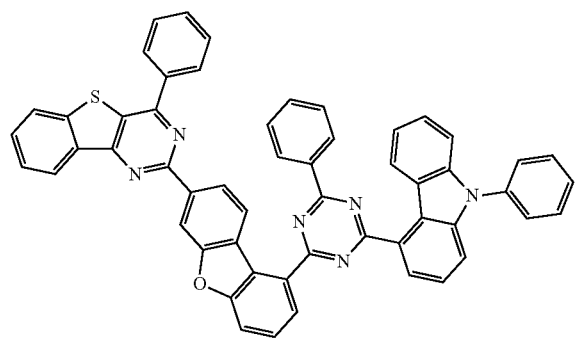
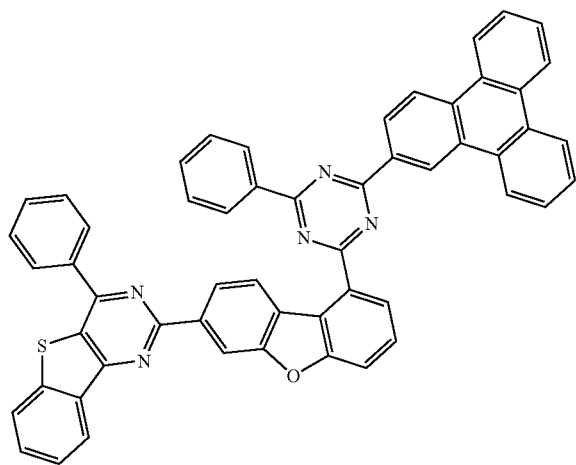
484
-continued
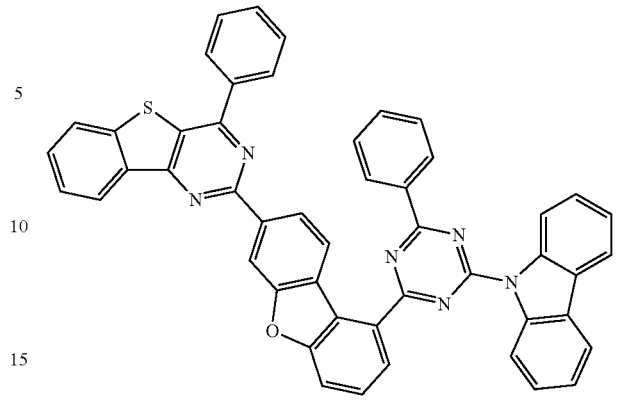
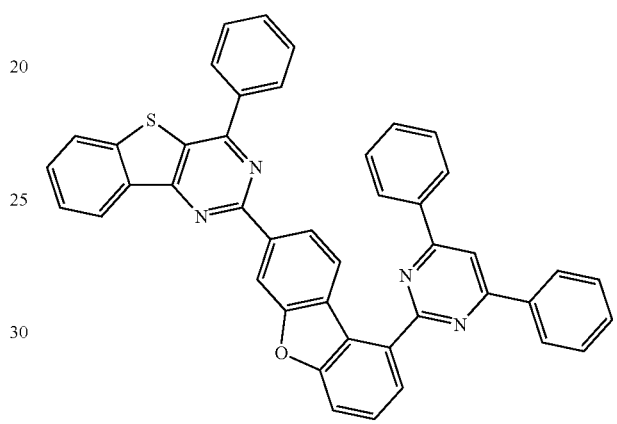
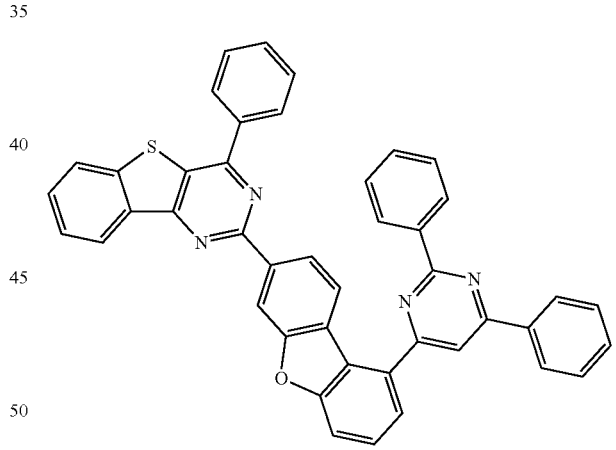
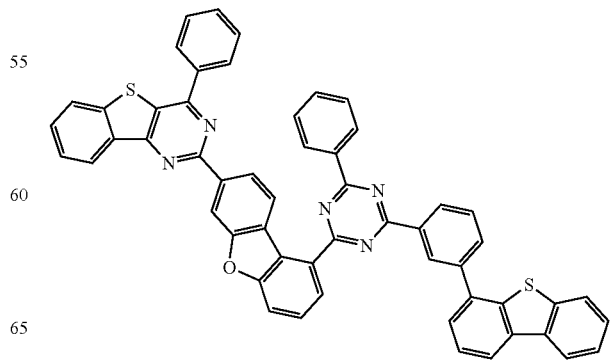

485
-continued
486
-continued
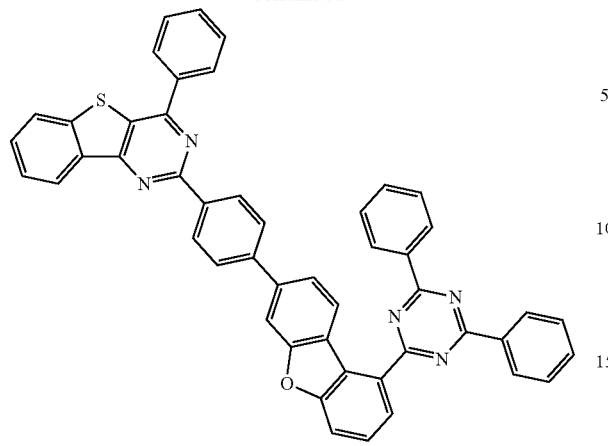
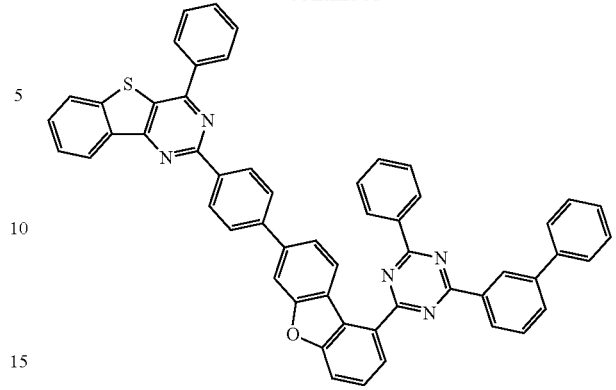
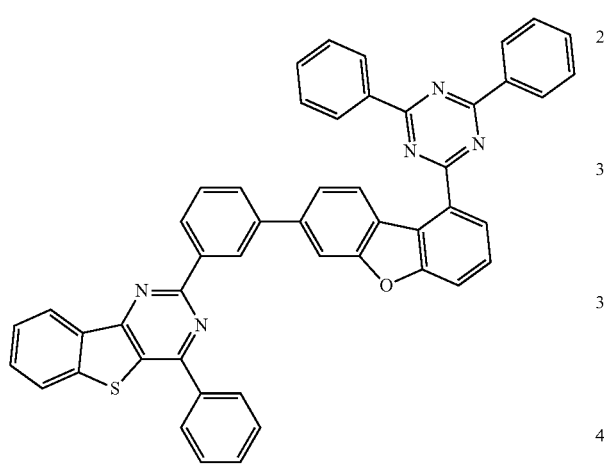
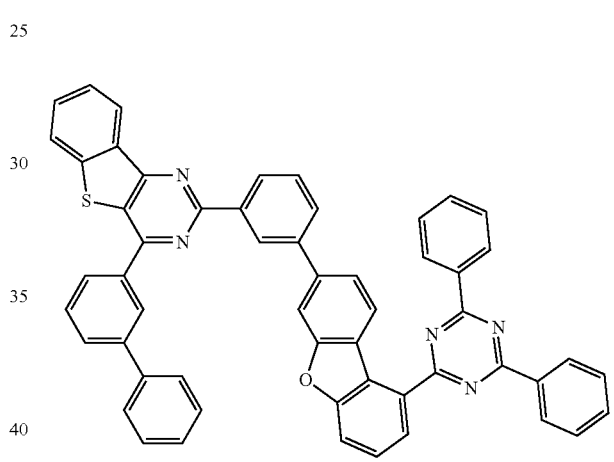
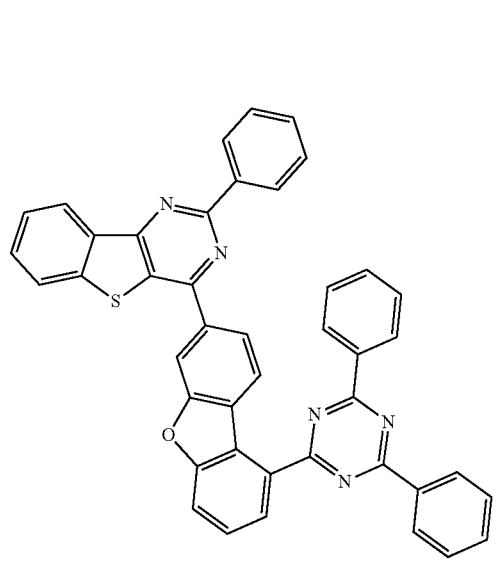
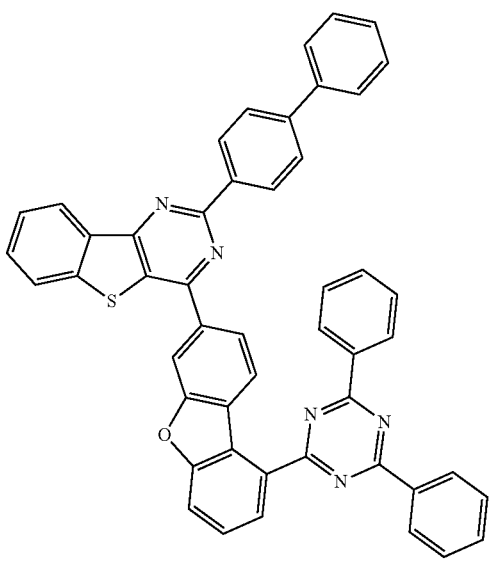

-continued
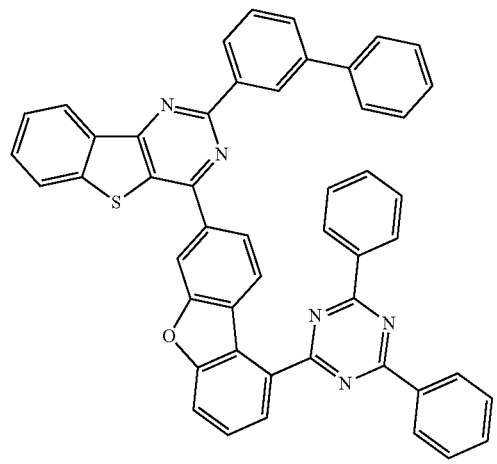
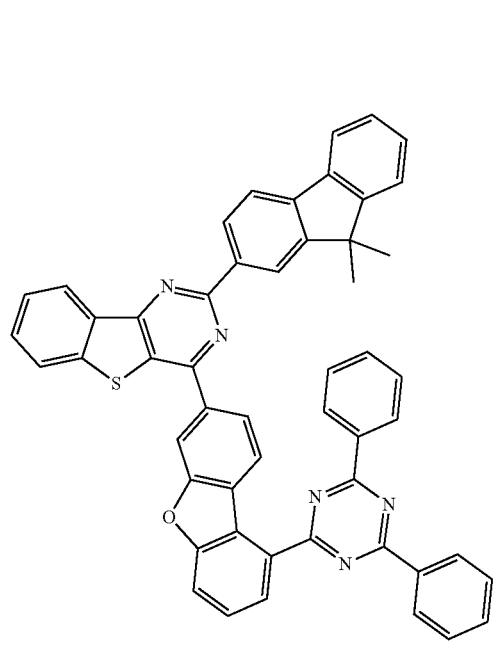
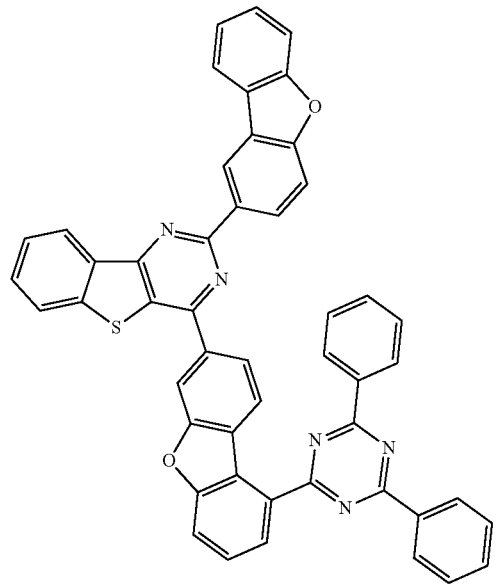

-continued
489
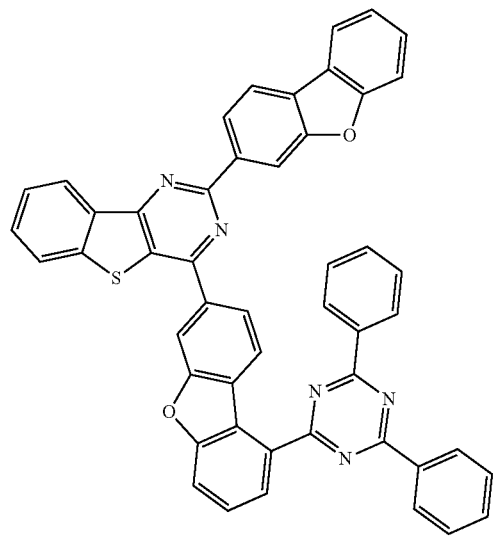
490
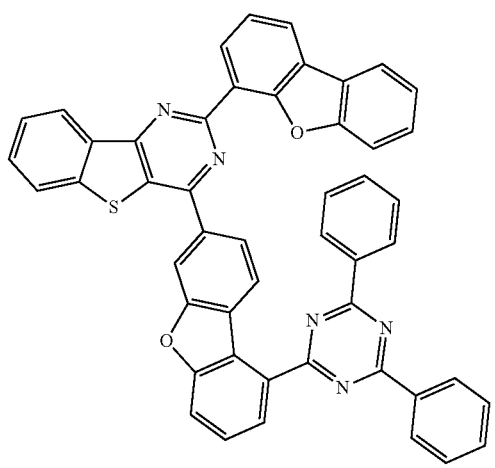
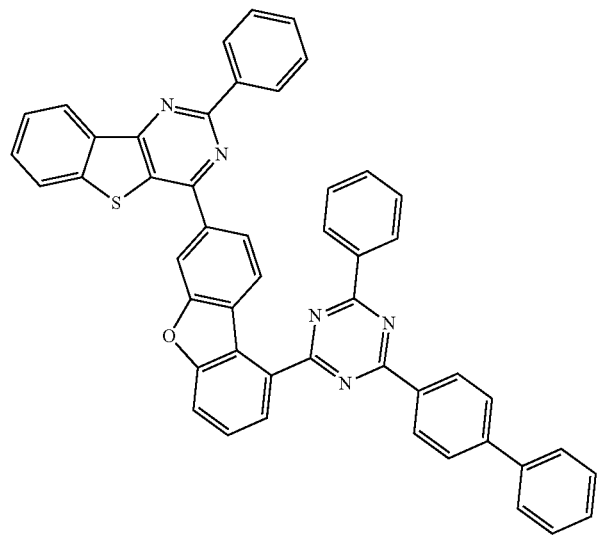
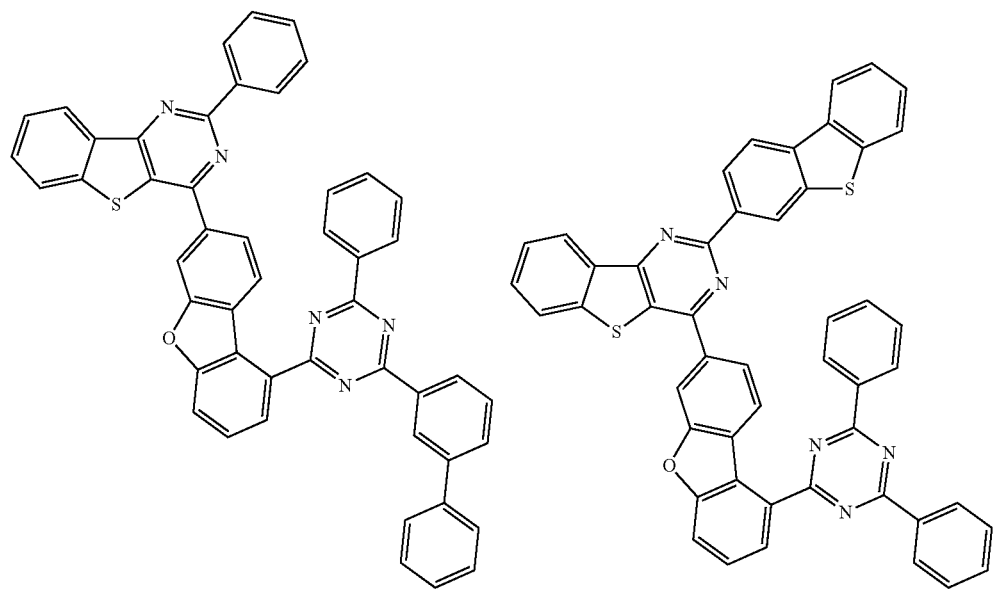

491
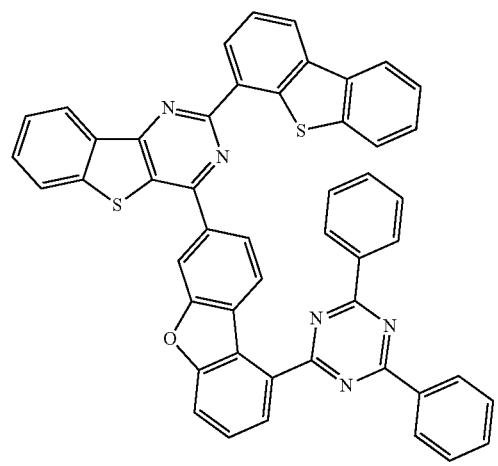
492
-continued
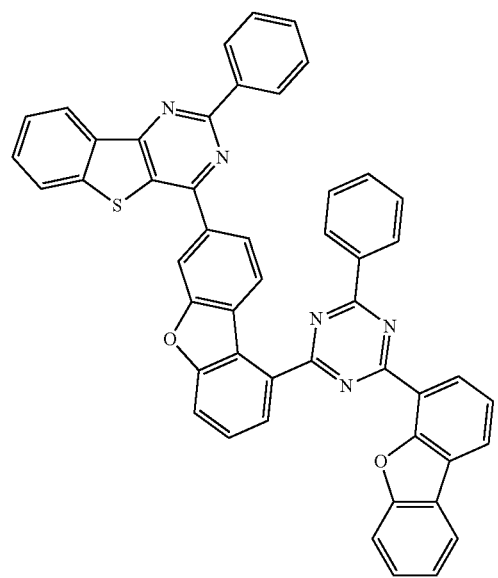
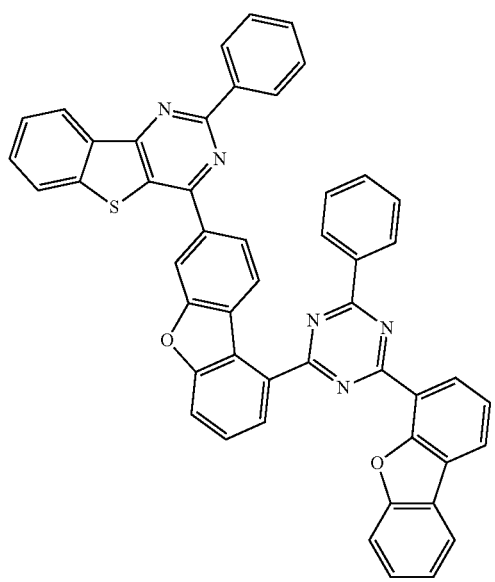
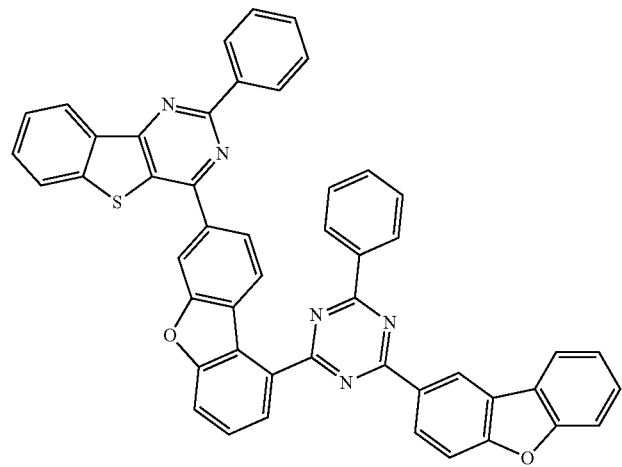

-continued
493
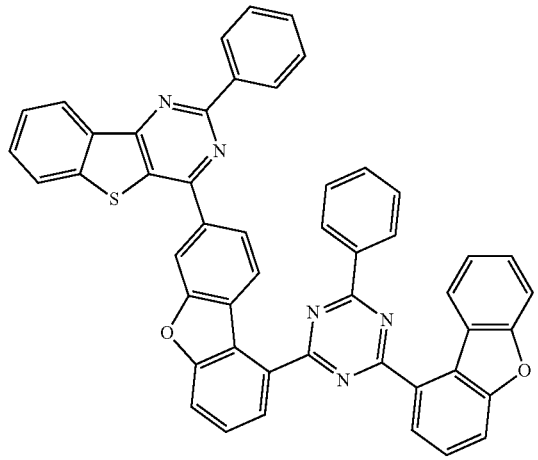
494
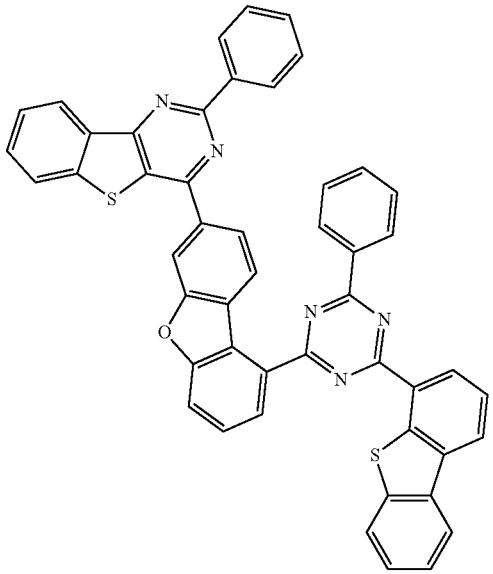
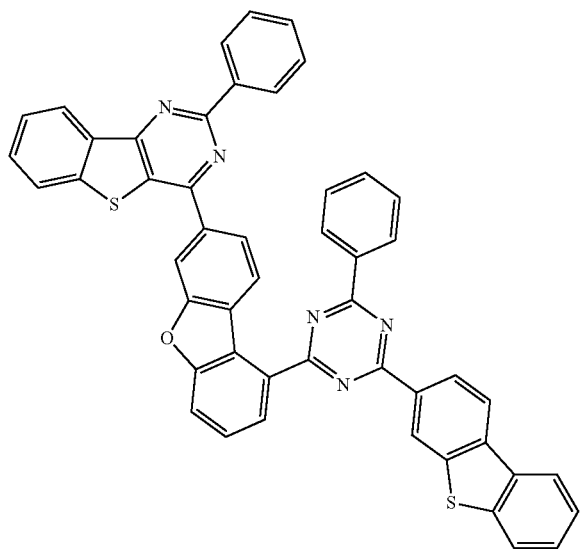
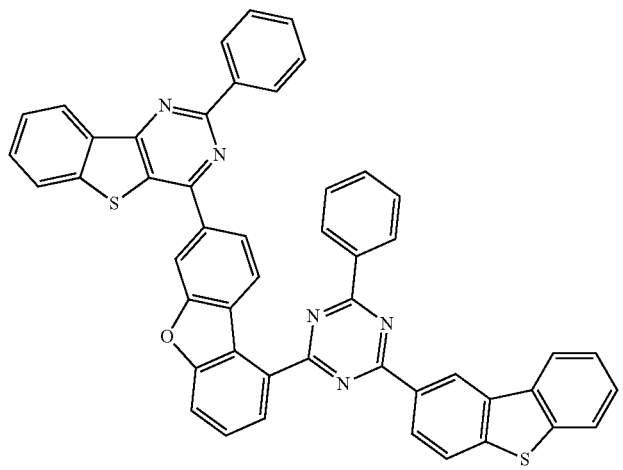
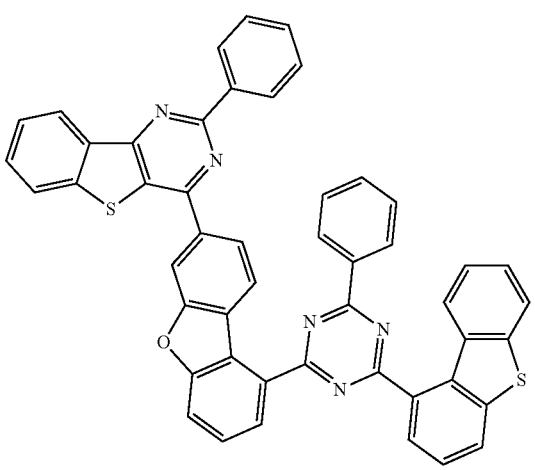

-continued
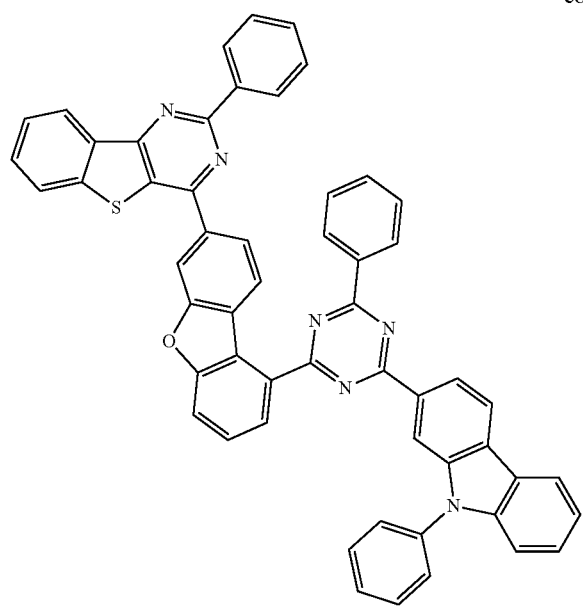
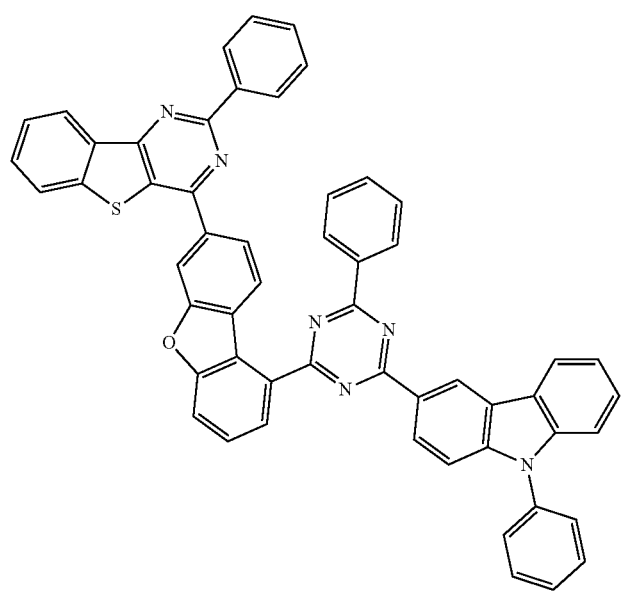
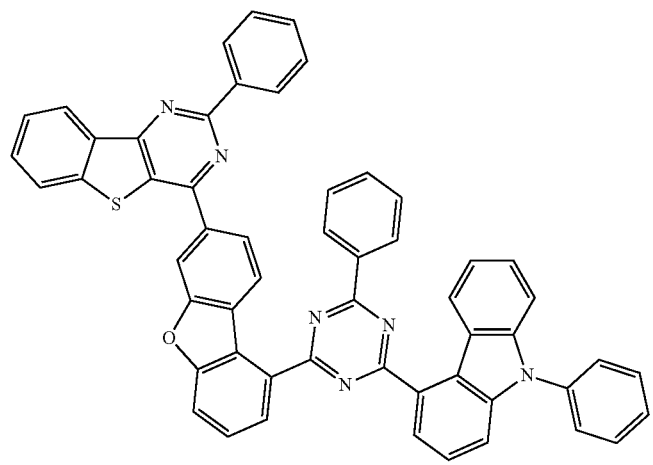

-continued
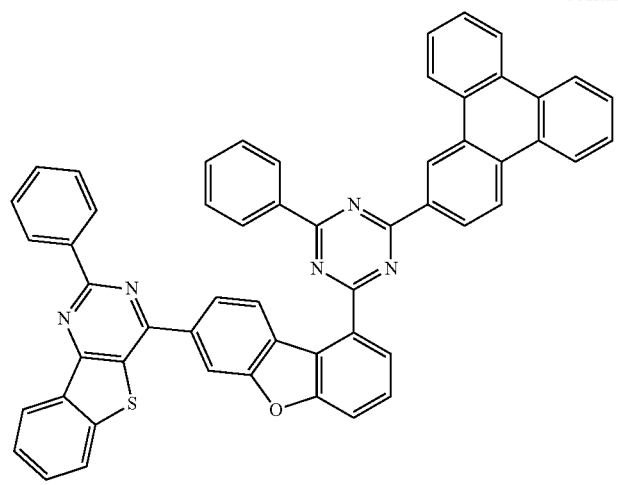
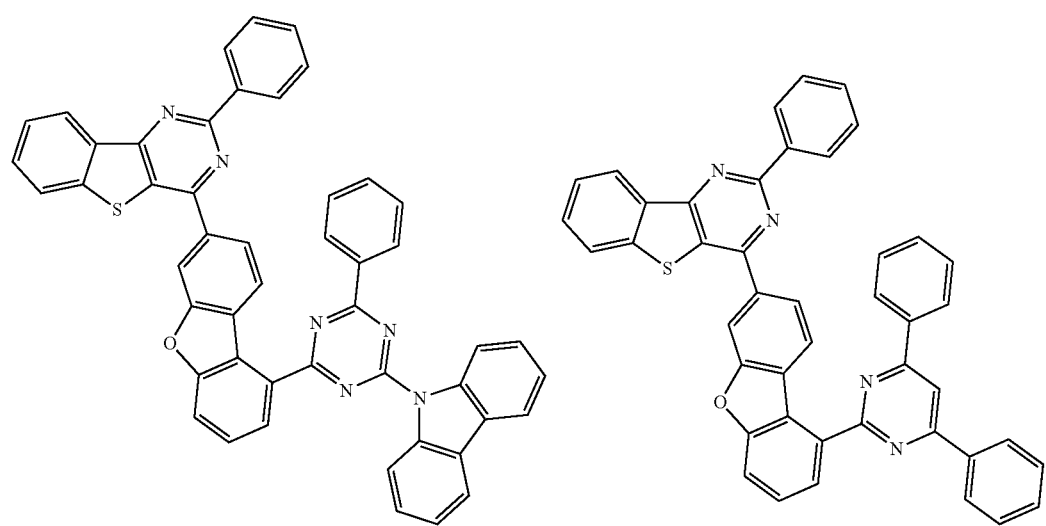
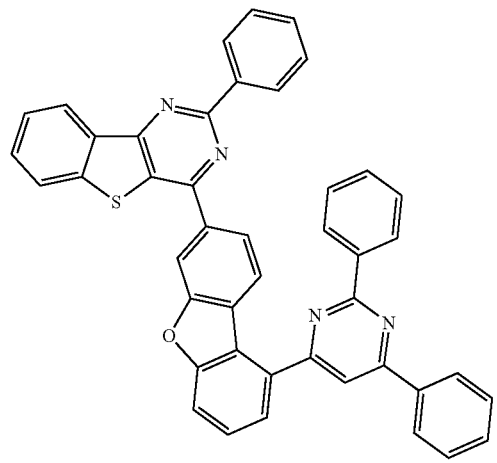

499
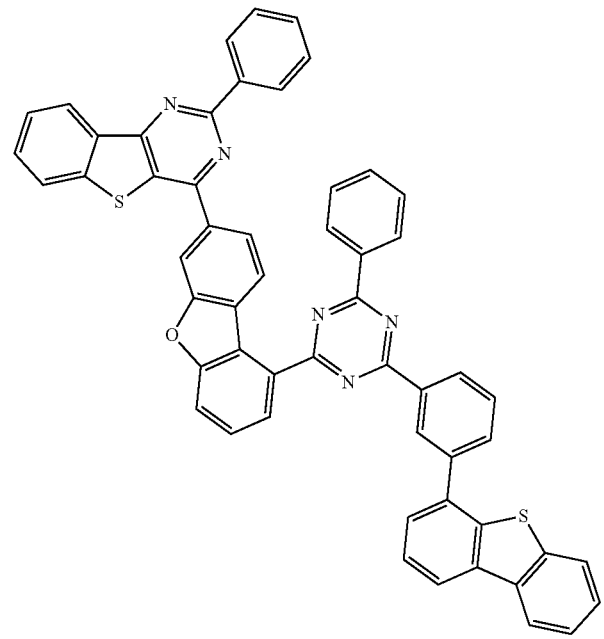
500
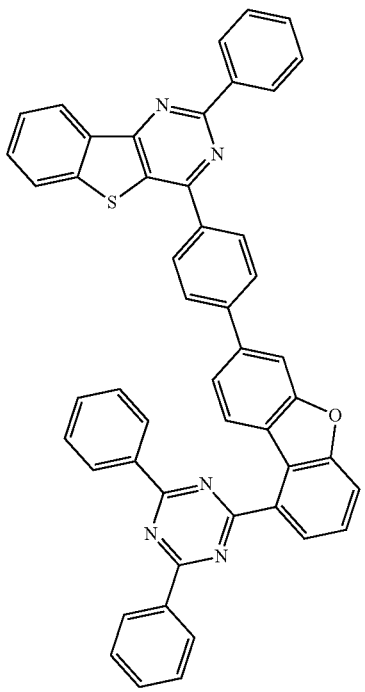
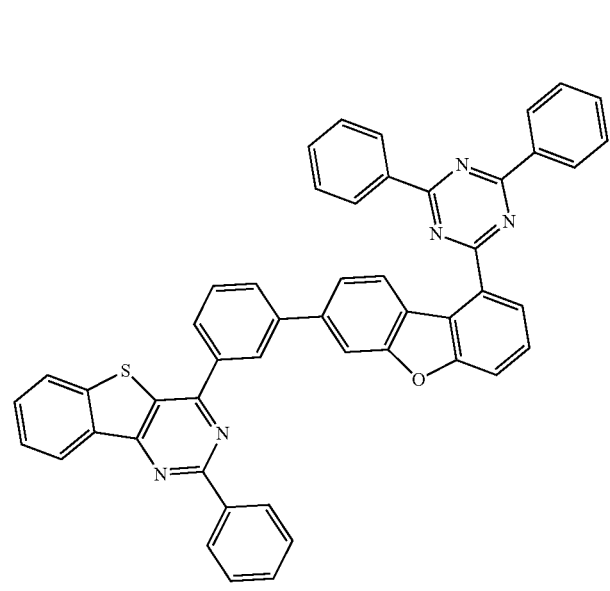
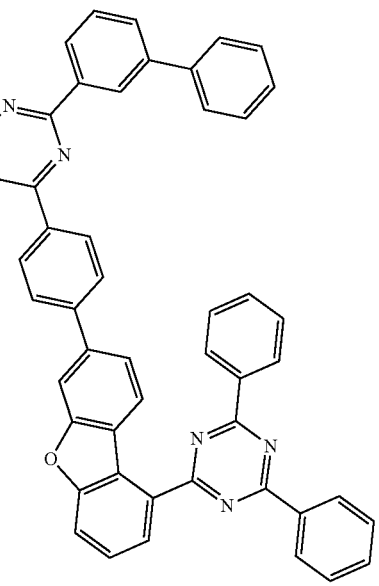
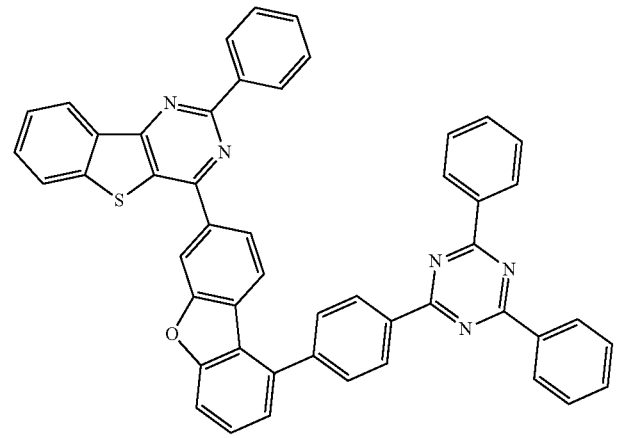

-continued
501
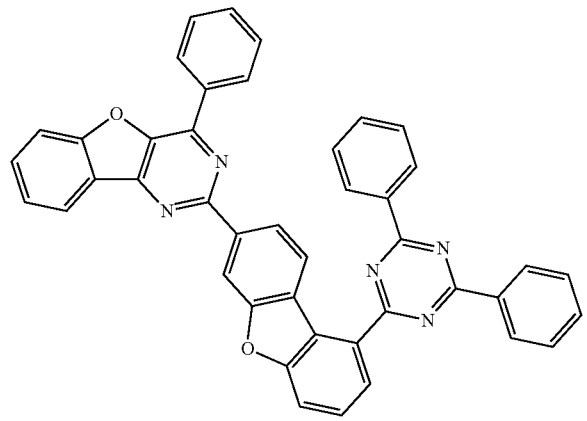
502
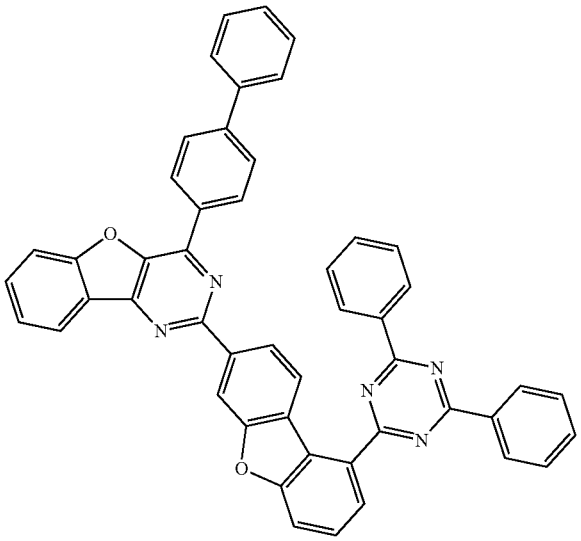
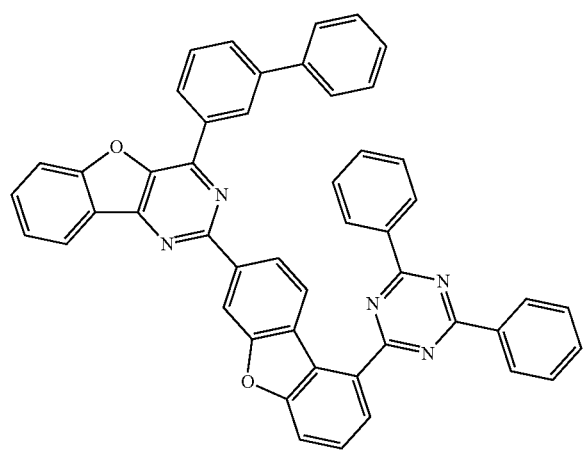
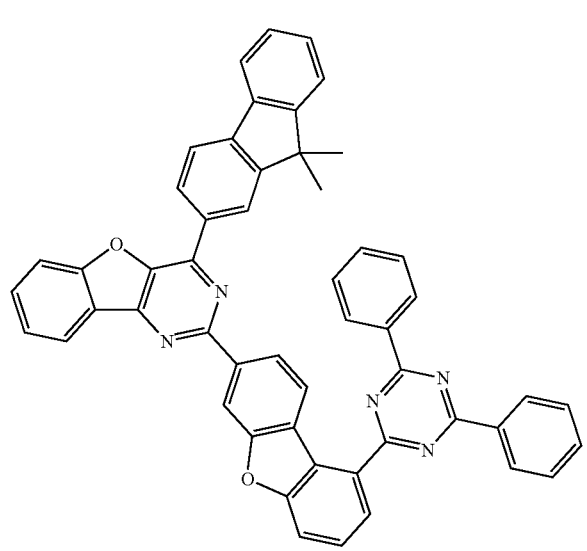
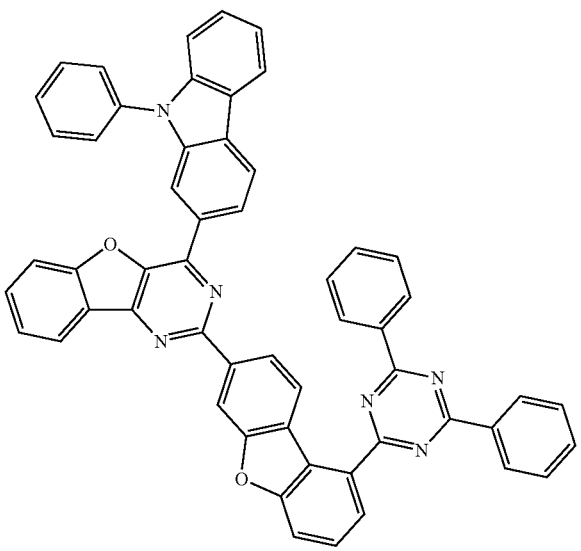

503
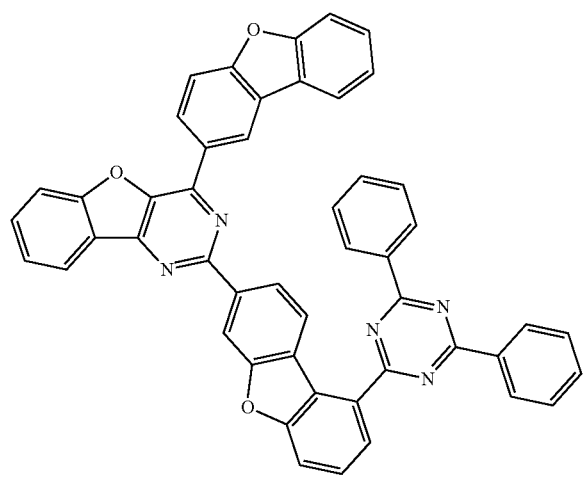
504
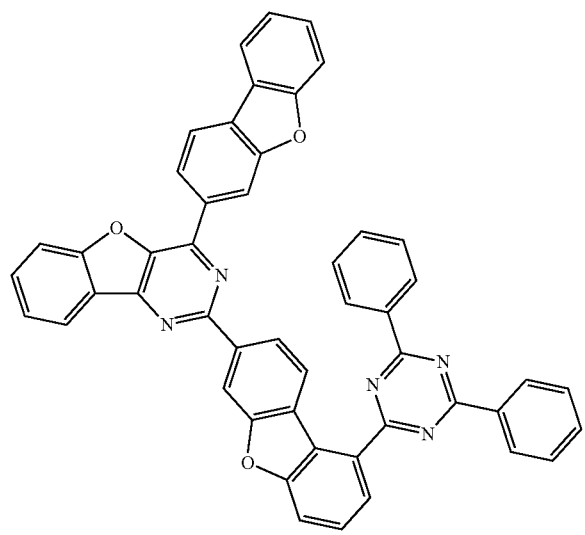
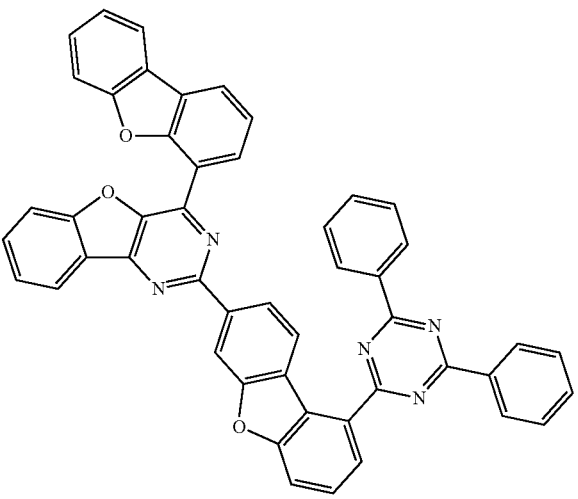
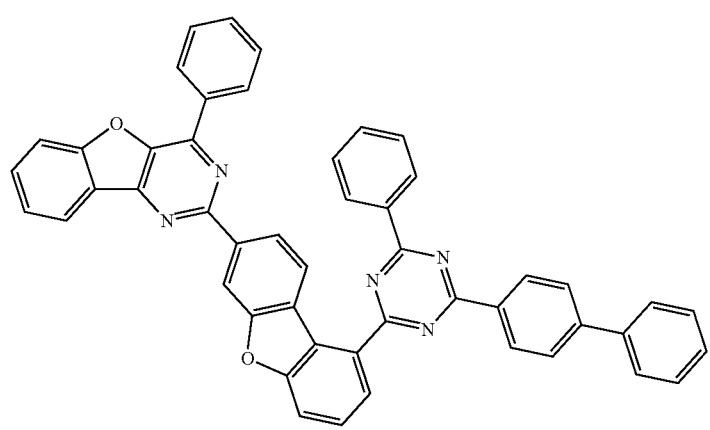

-continued
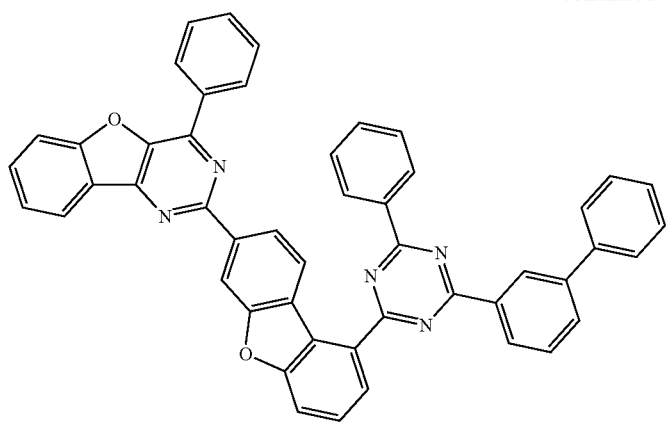
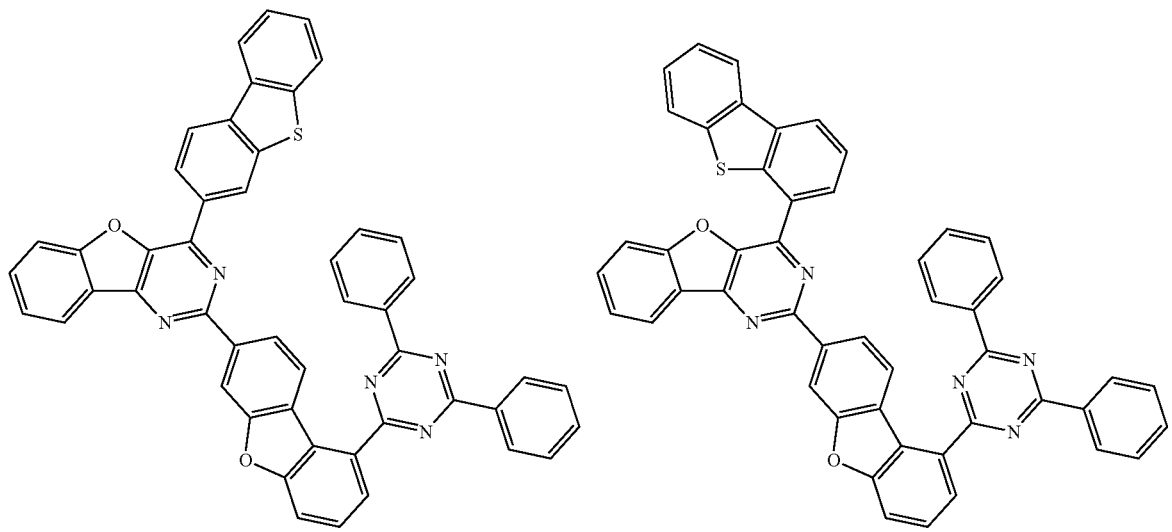
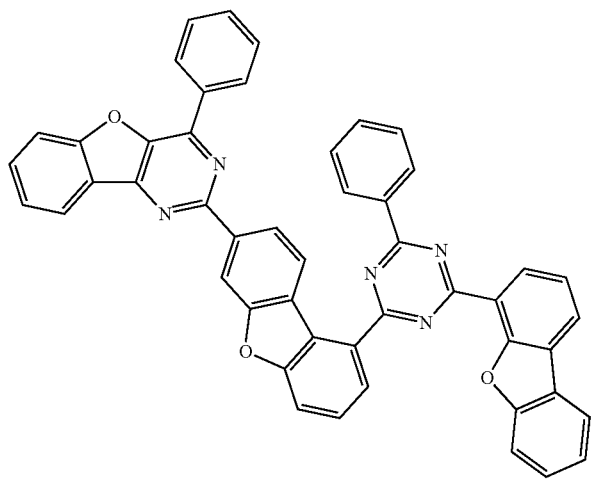

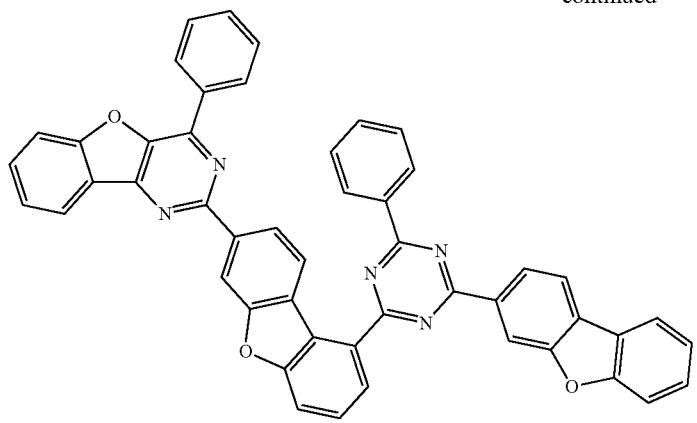
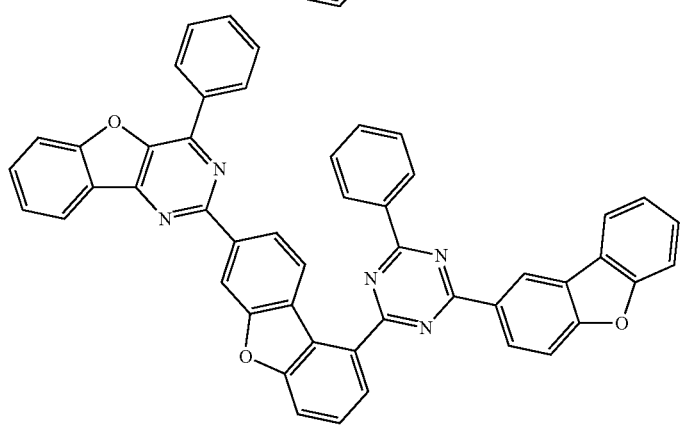
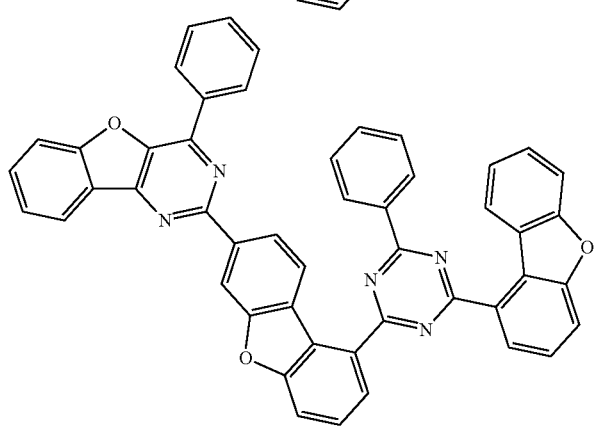
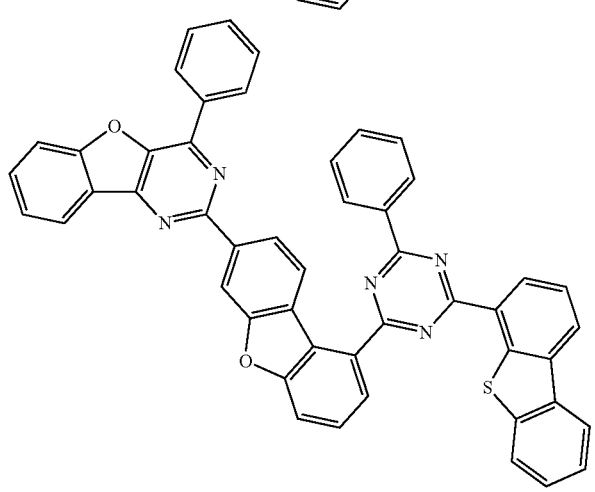

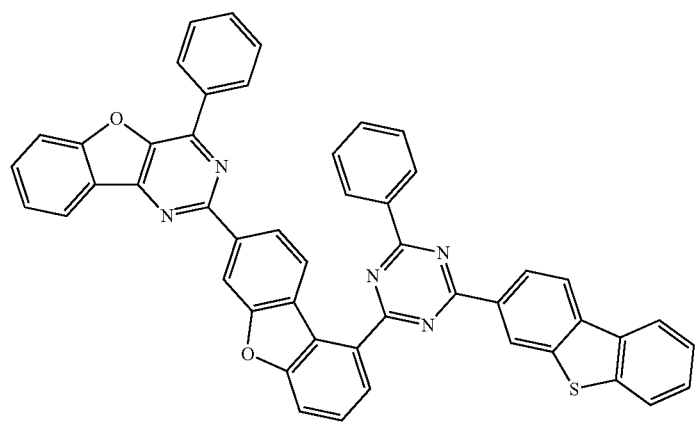
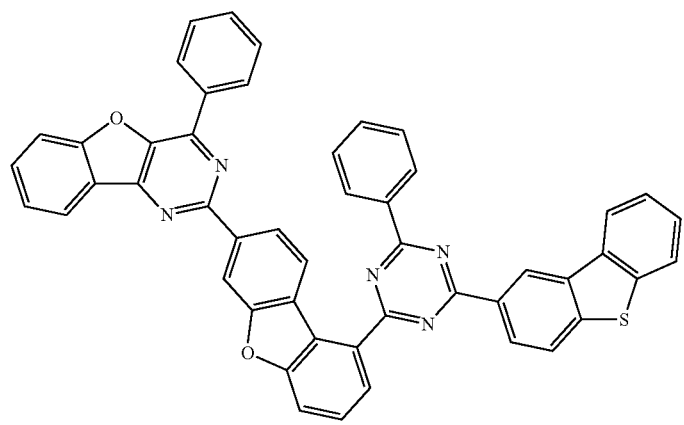
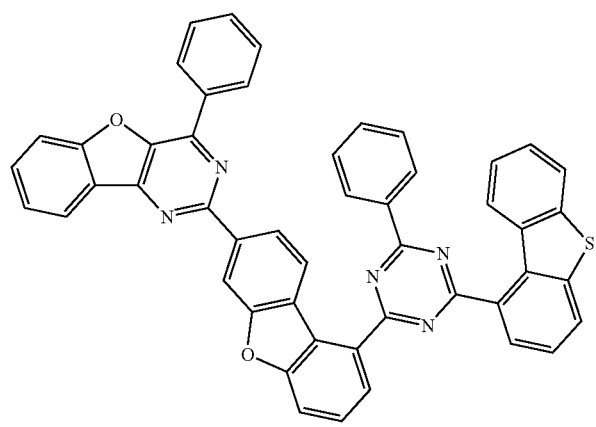

511
512
-continued
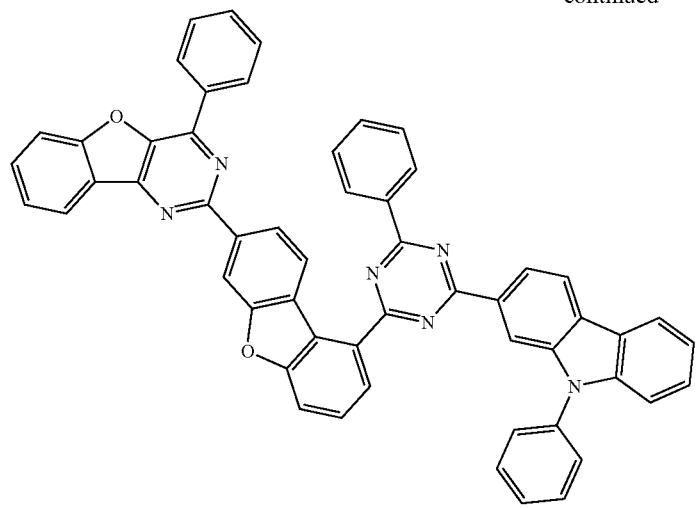
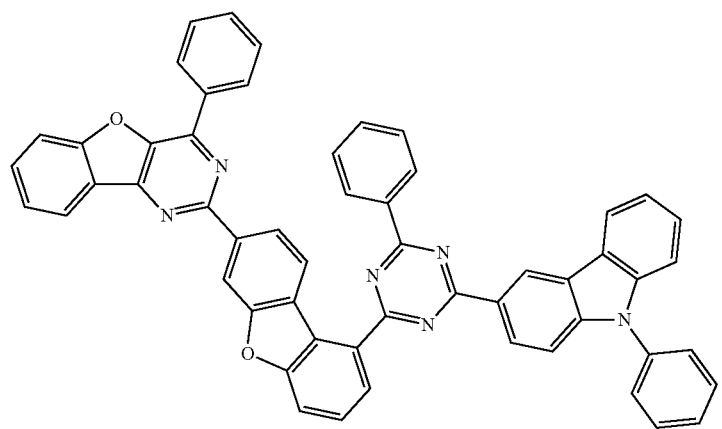
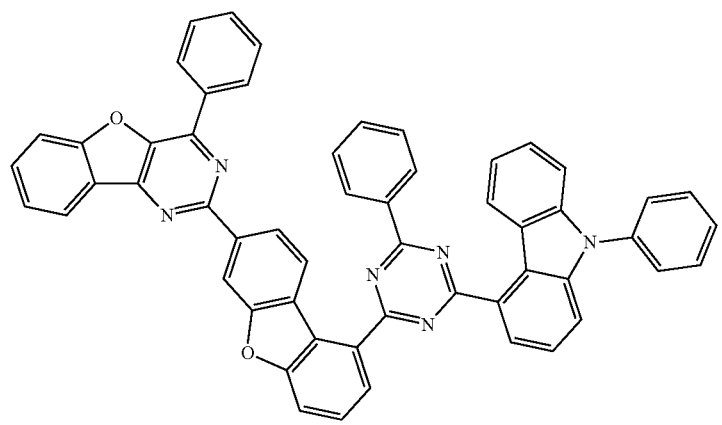

513
-continued
514
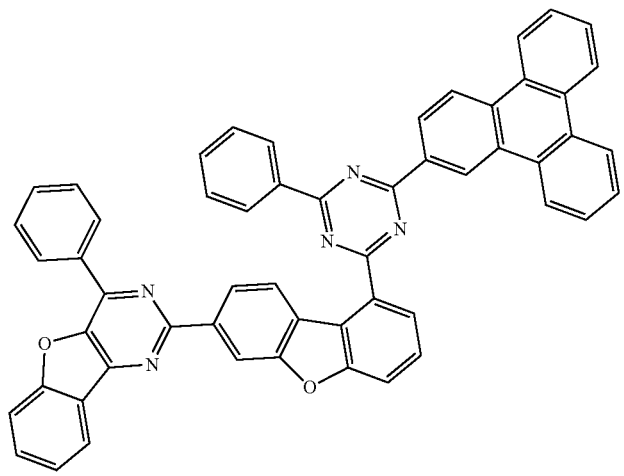
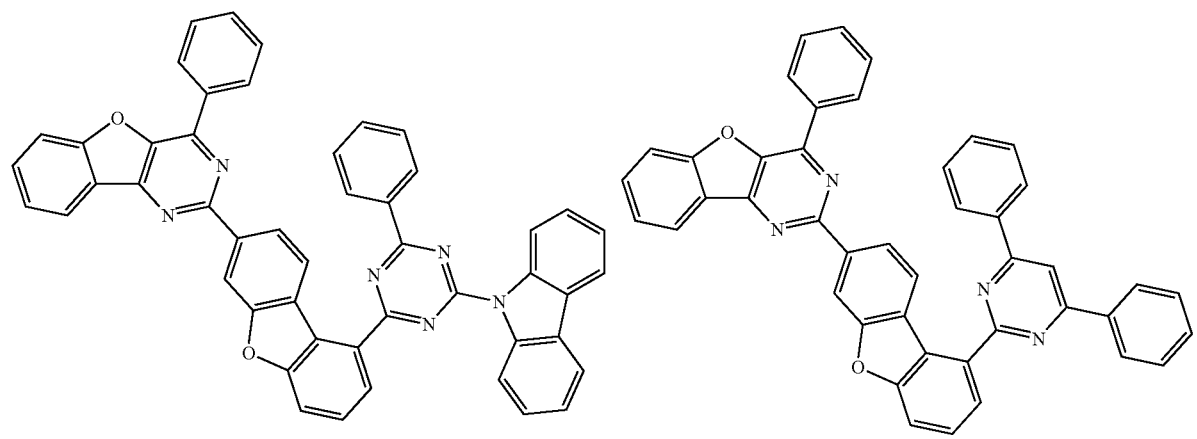
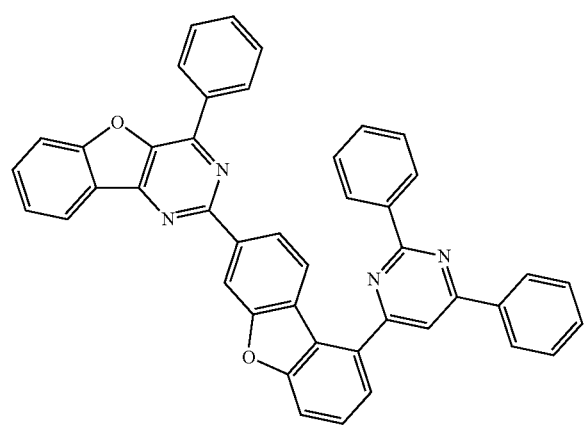

-continued
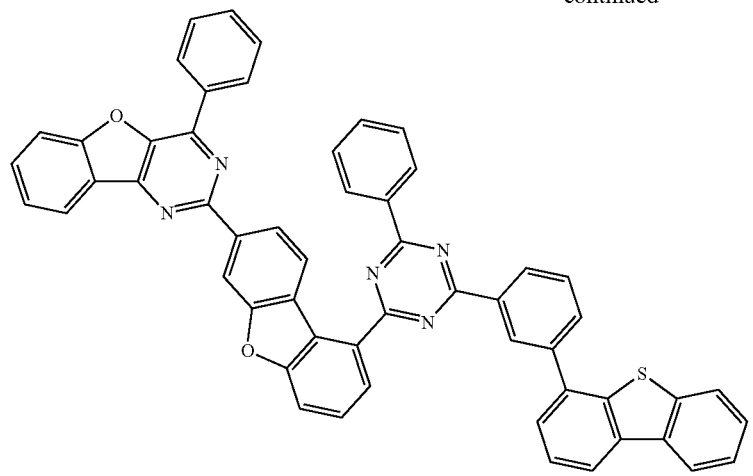
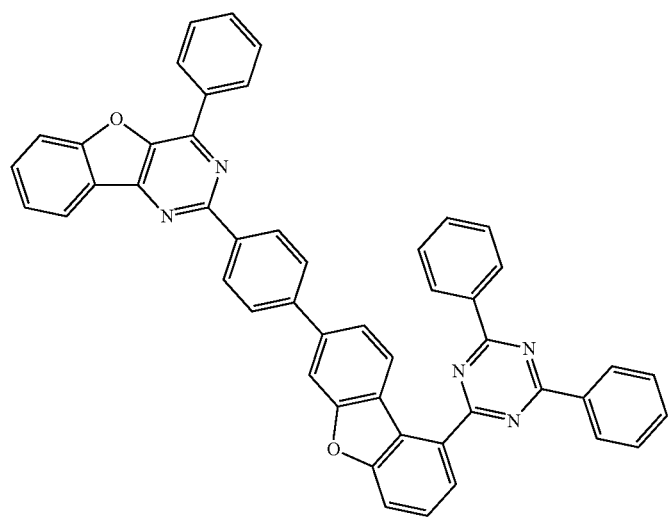
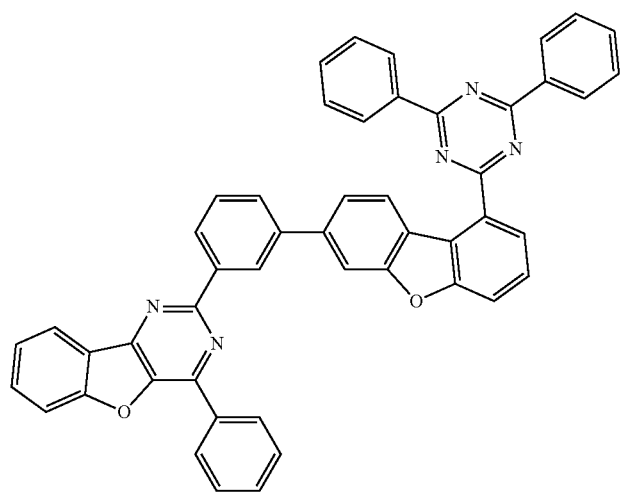

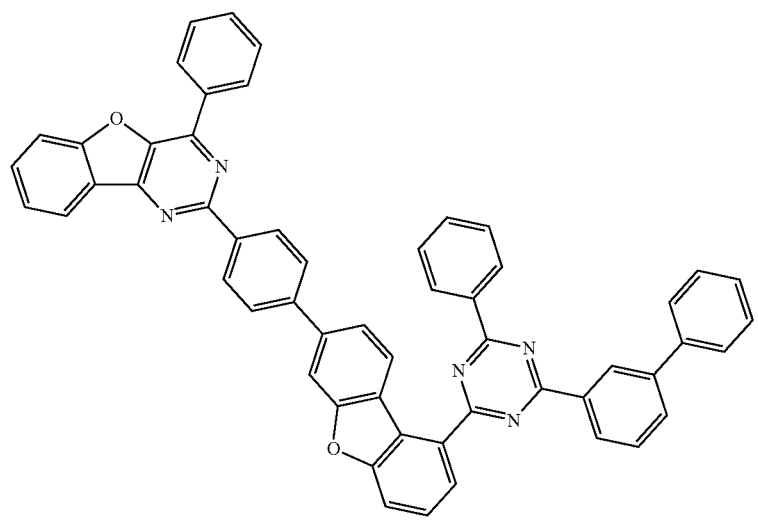
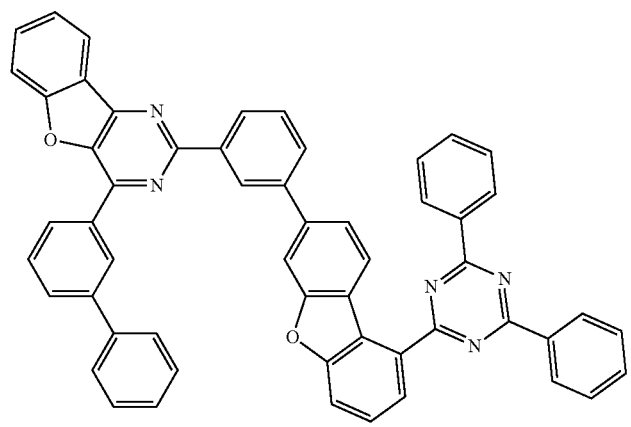
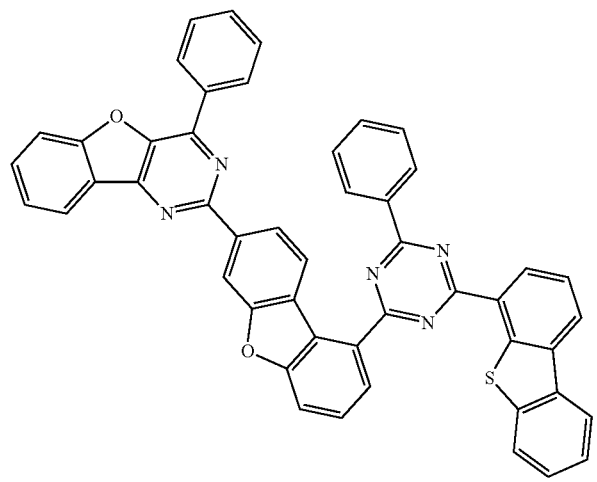

-continued
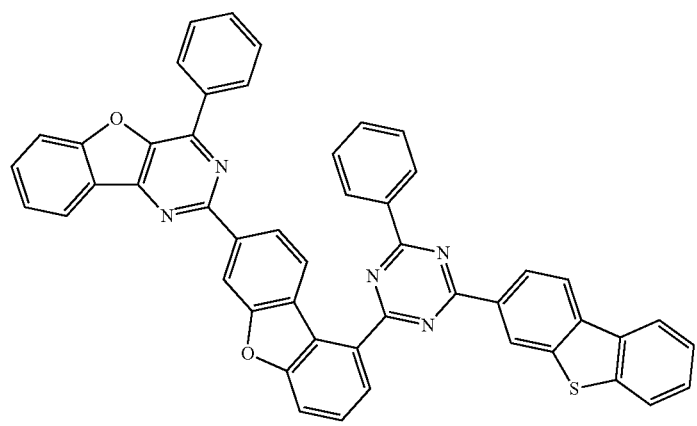
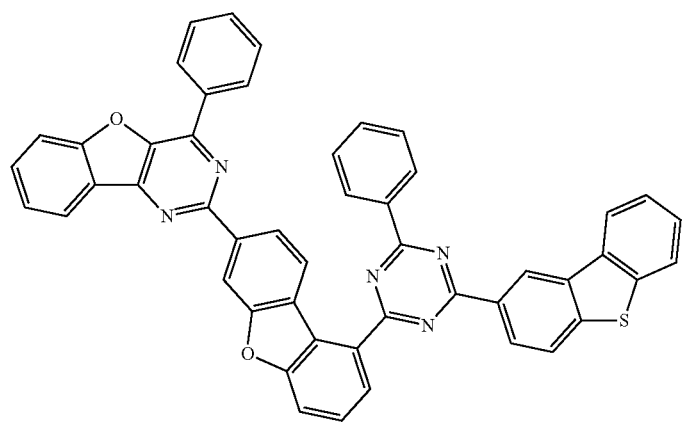
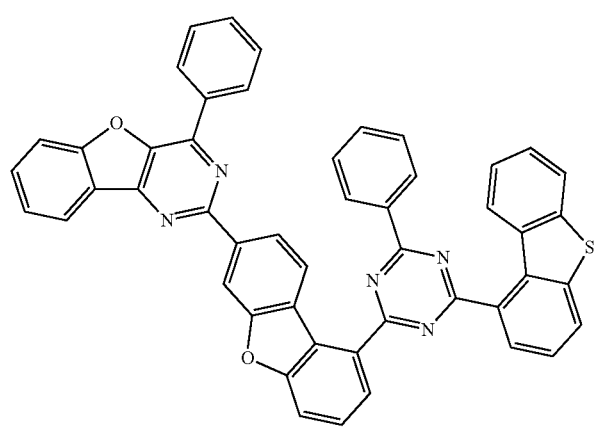

-continued
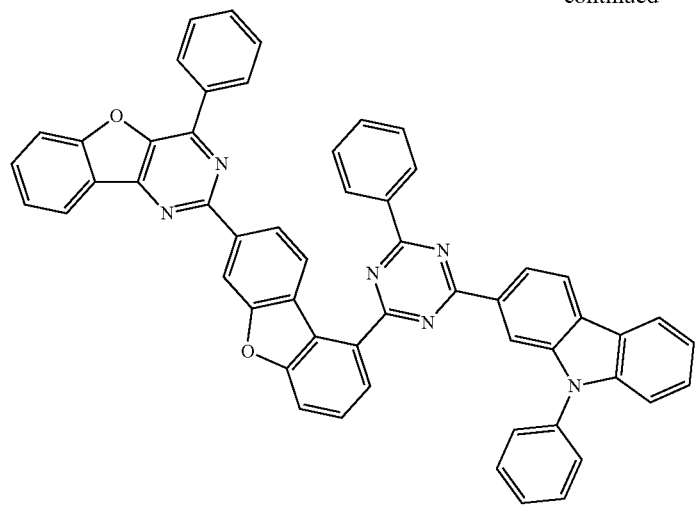
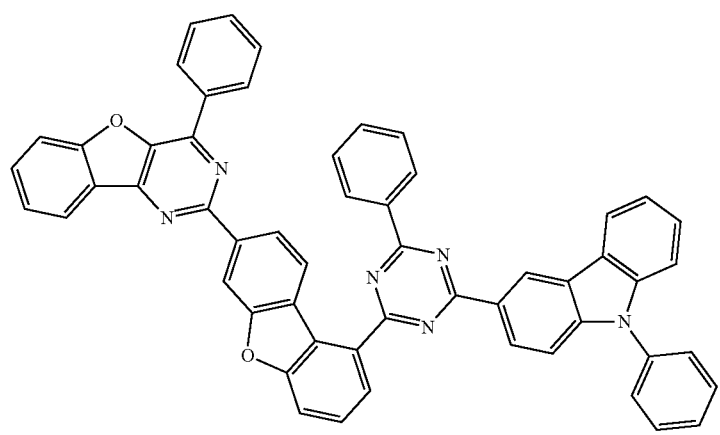
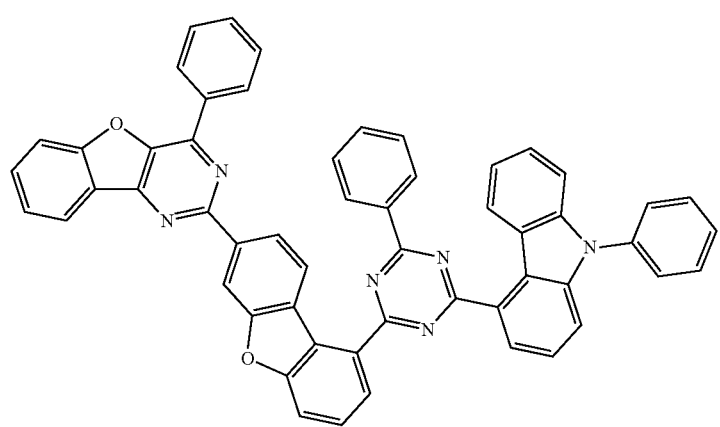

-continued
523
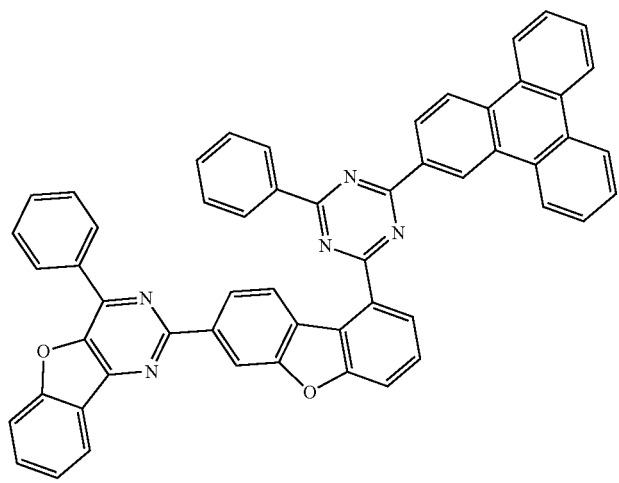
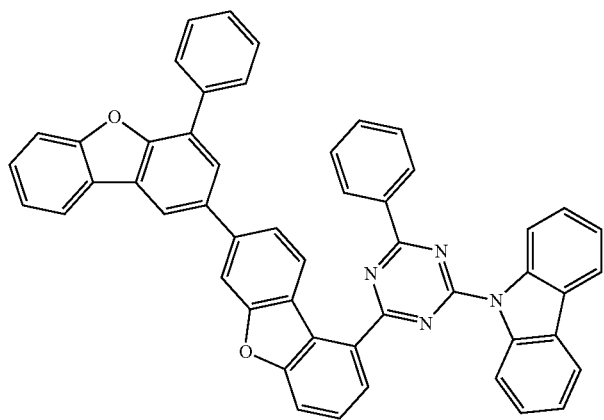
524
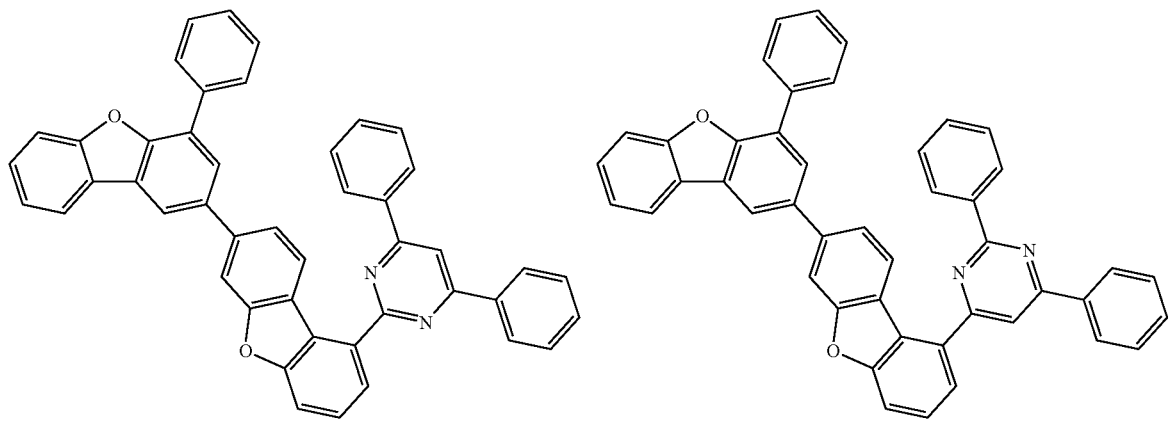

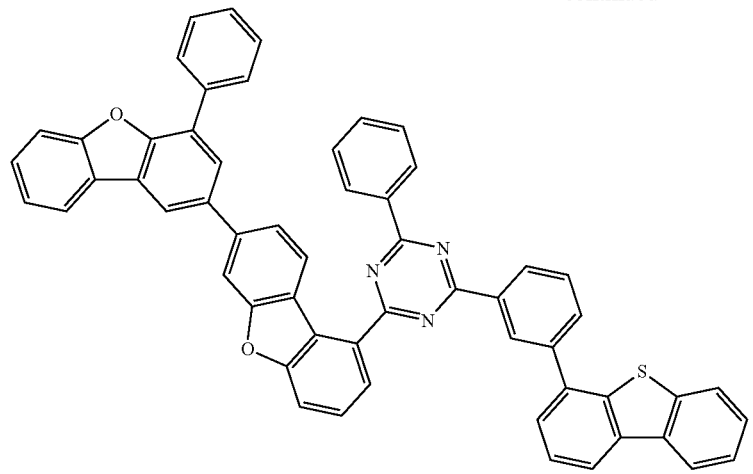
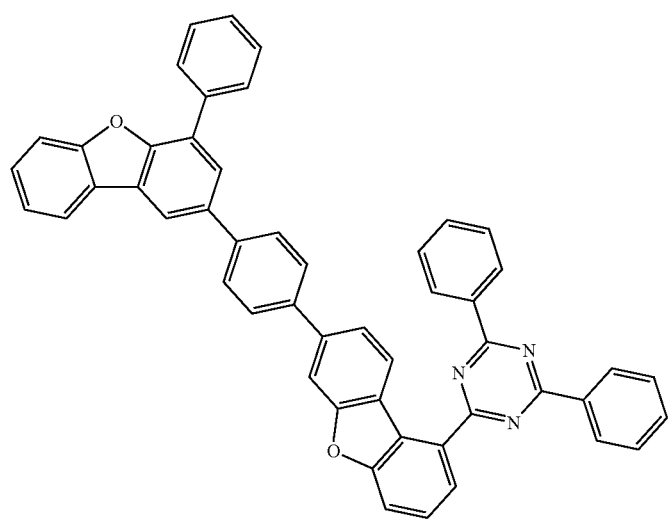
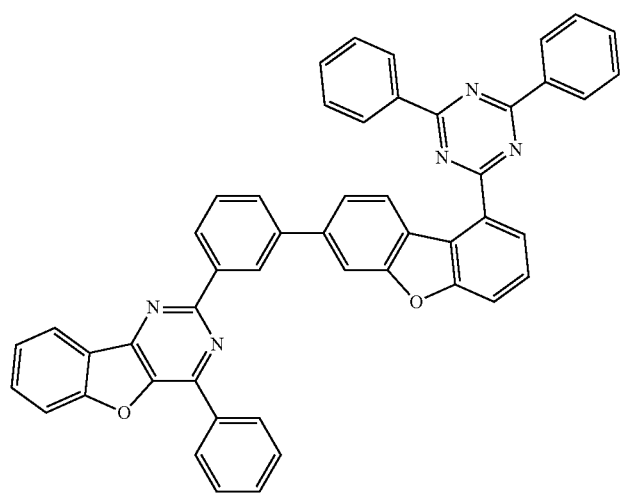

-continued
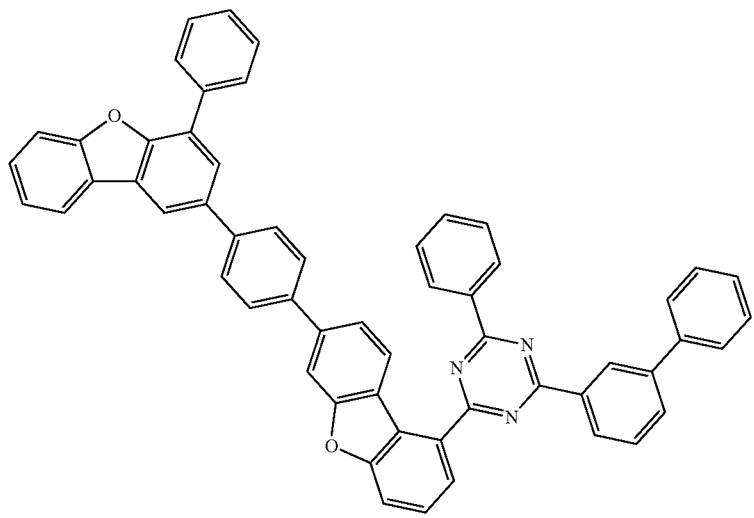
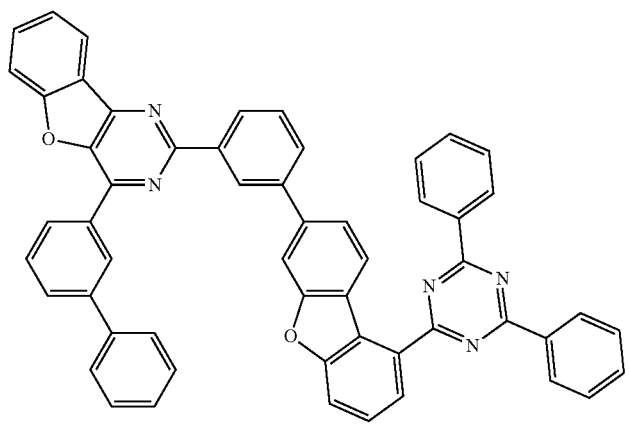 [SMILES: c1ccc(-c2cccc(-c3nc(-c4cccc(-c5ccc6c(c5)oc5cccc(-c7nc(-c8ccccc8)nc(-c8ccccc8)n7)c56)c4)nc4c3sc3ccccc34)c2)cc1]
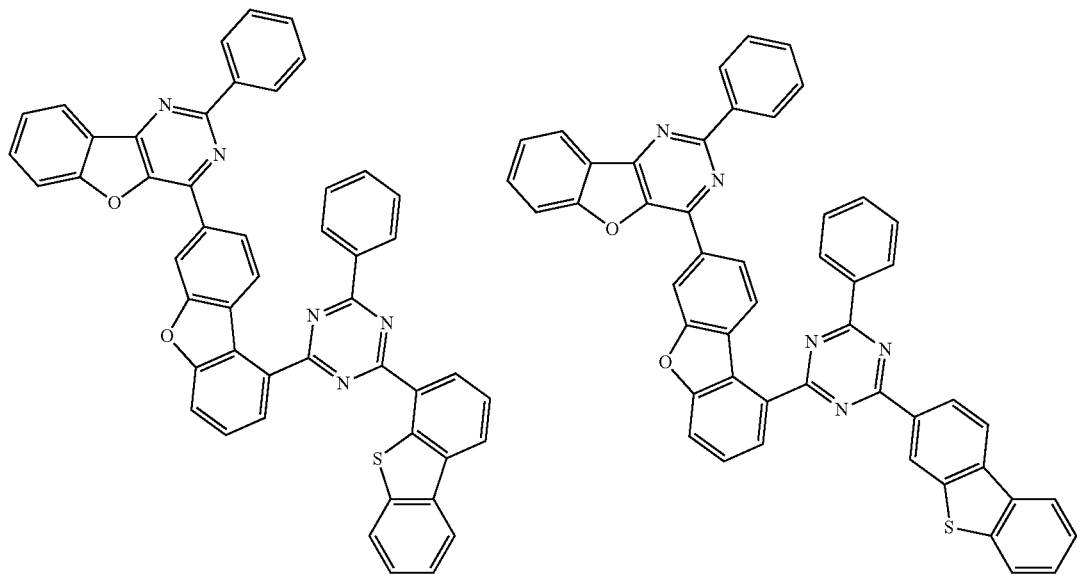

-continued
| 529 | 530 |
|---|---|
| 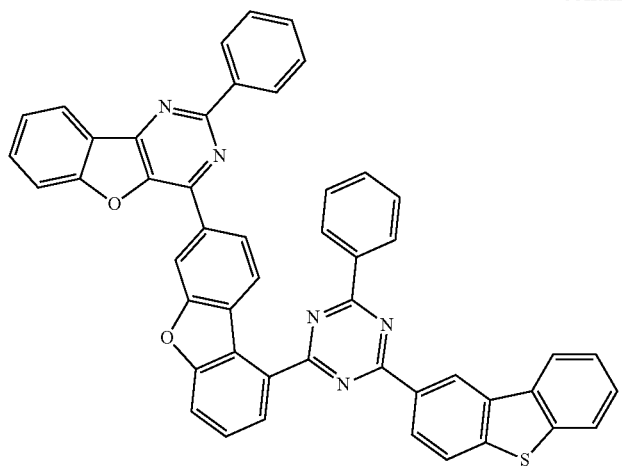 | 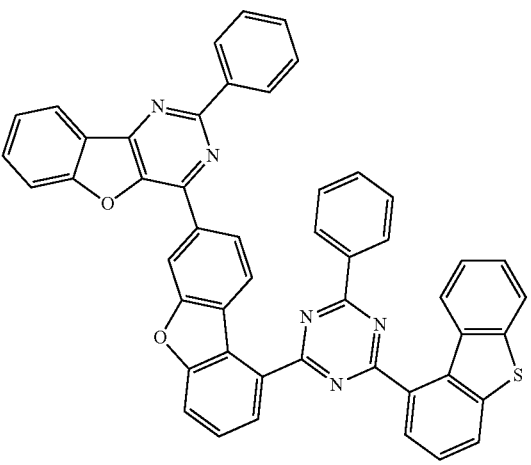 |
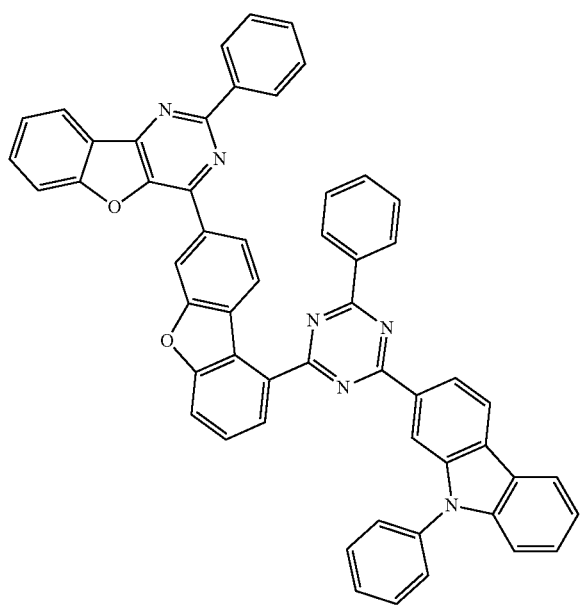
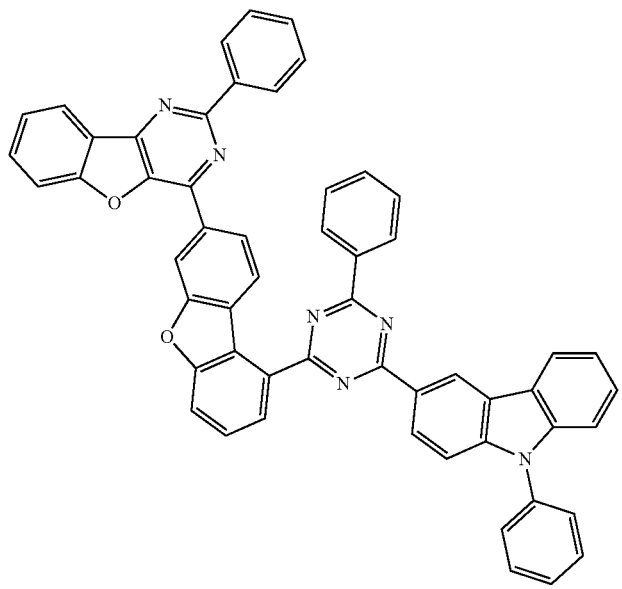

-continued
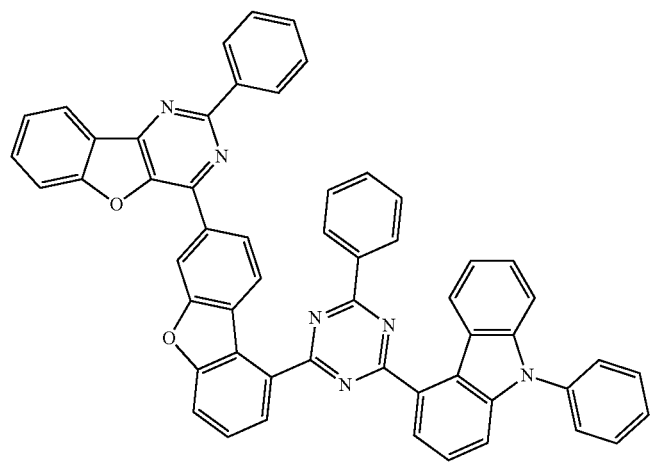
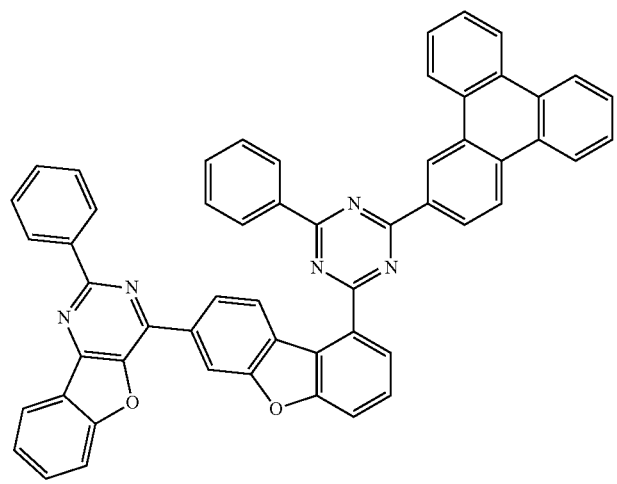
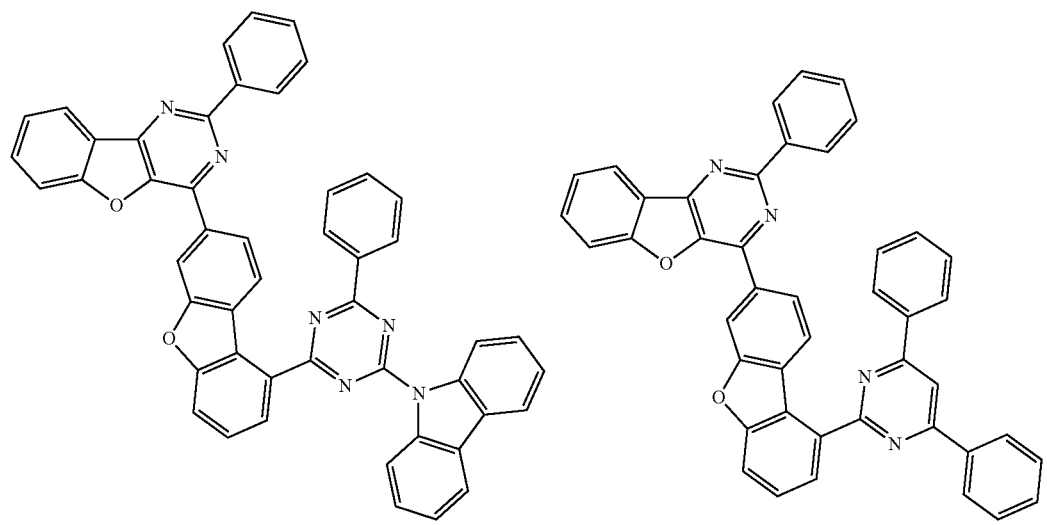

533
534
-continued
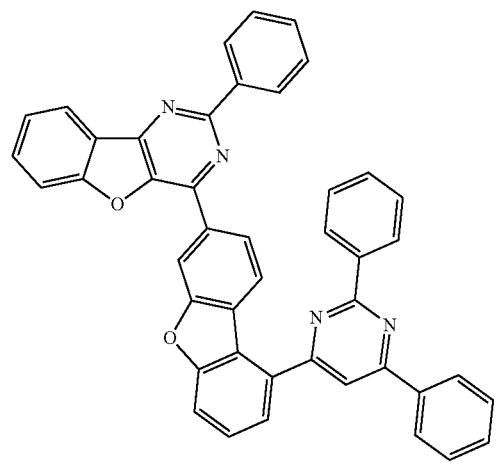
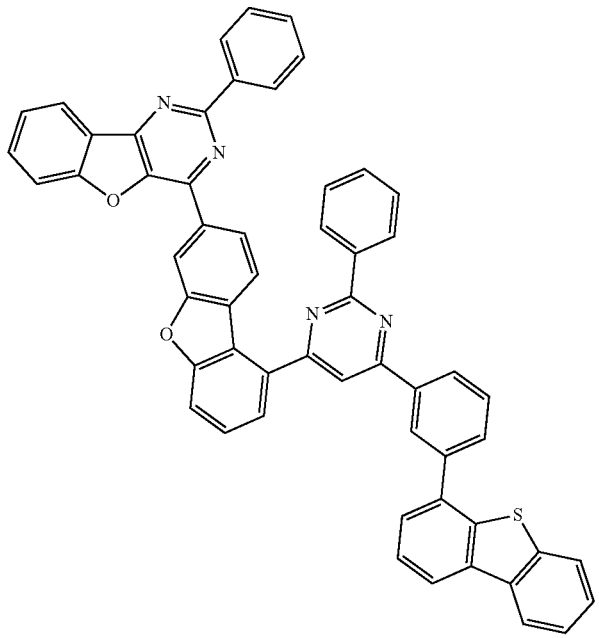
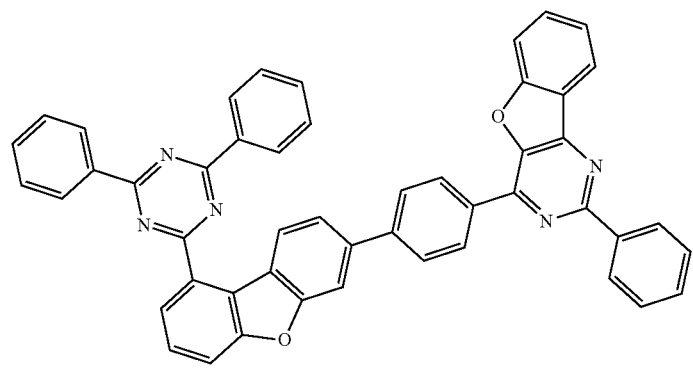
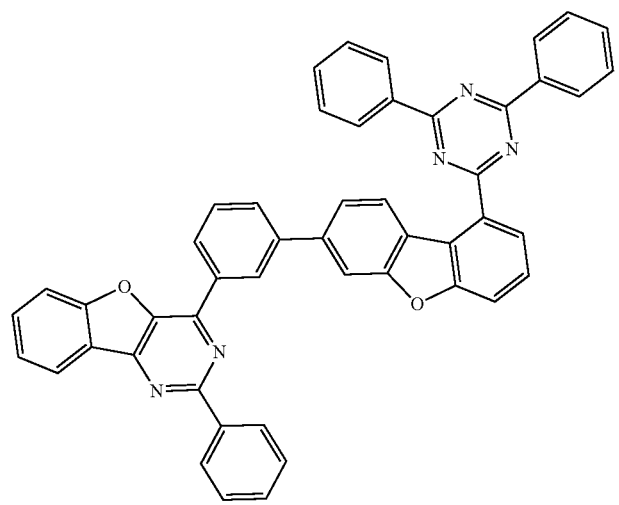

-continued
535
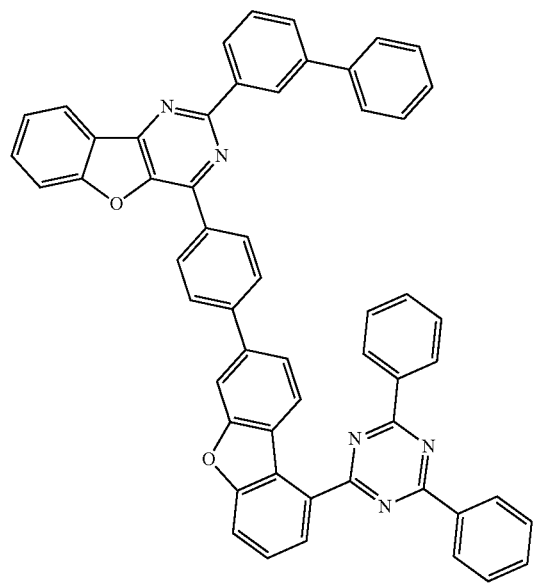
536
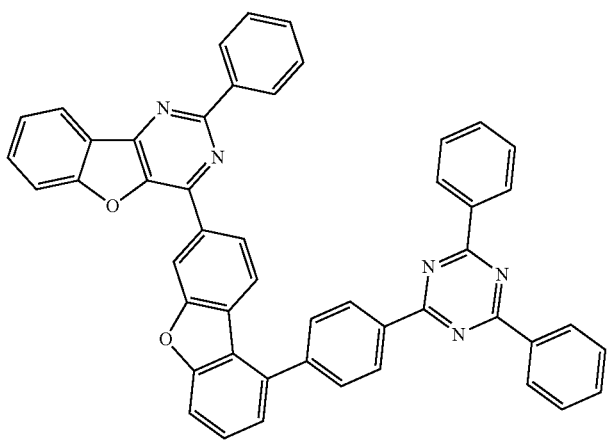
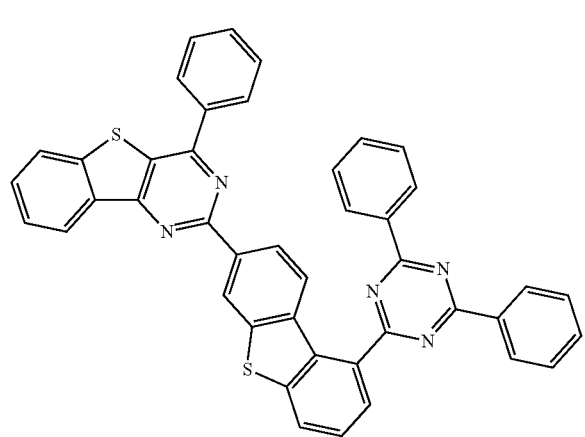
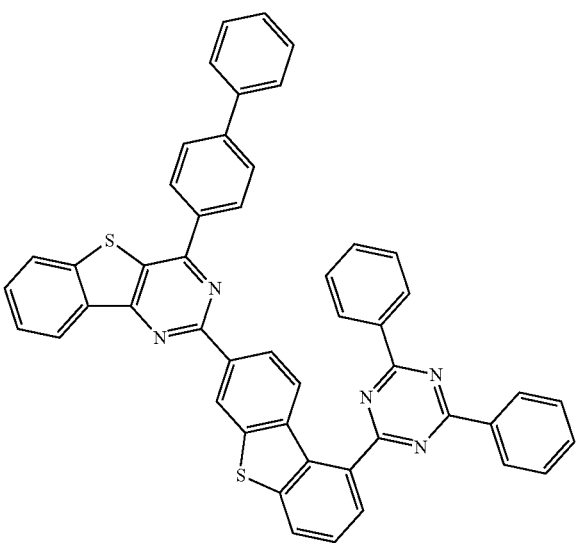
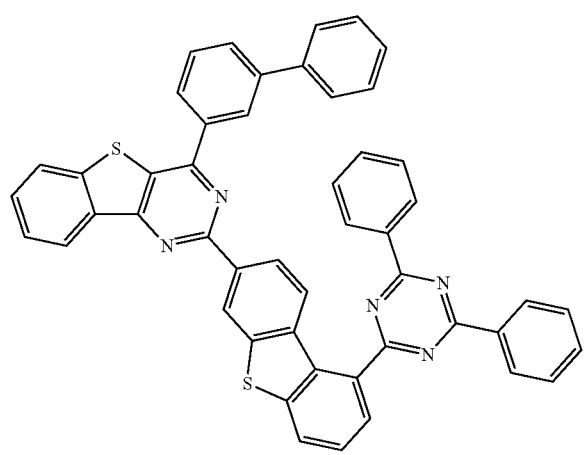
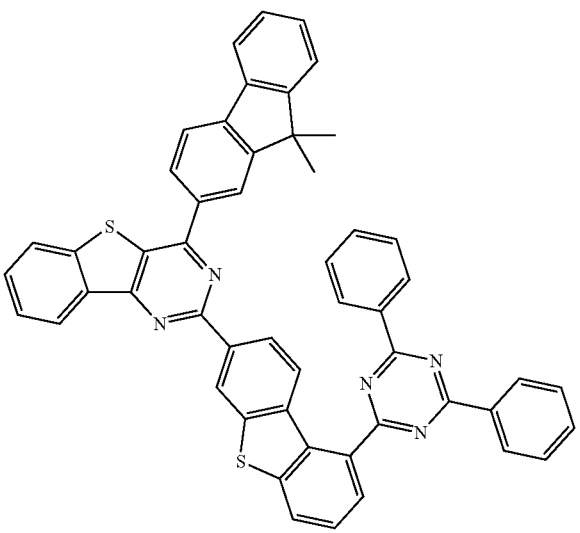

-continued
537
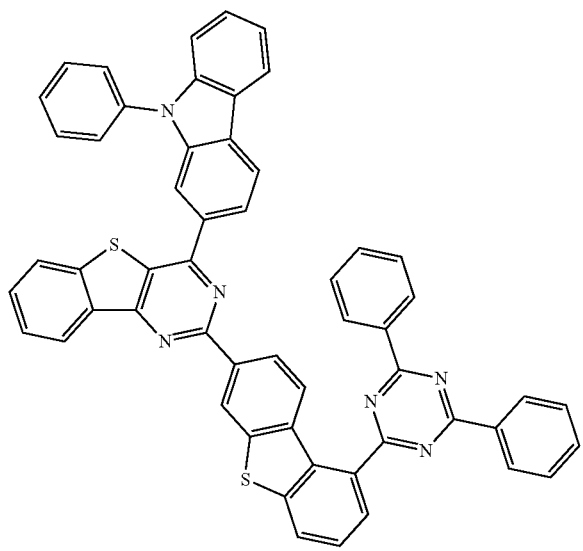
538
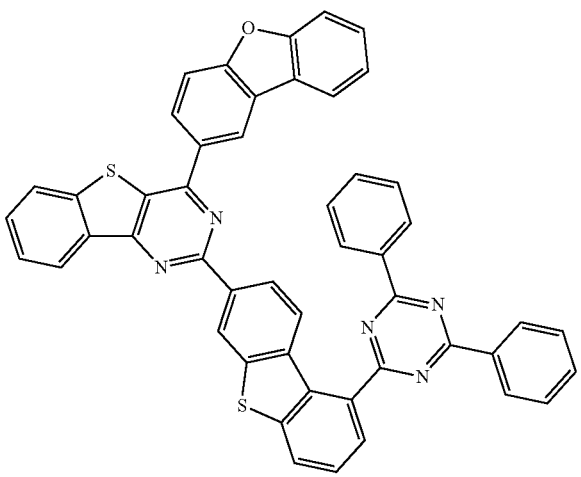
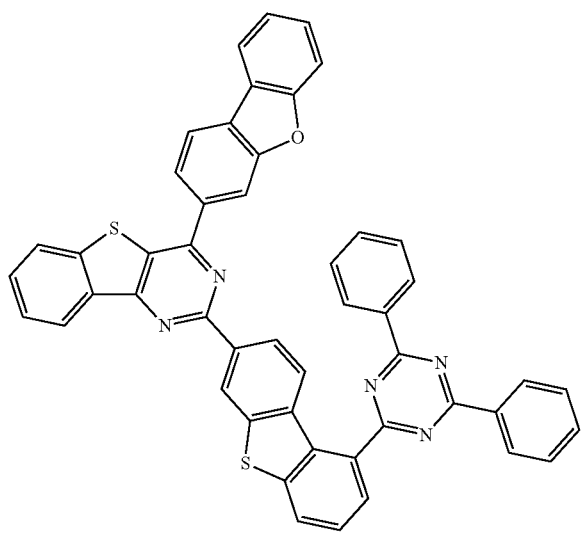
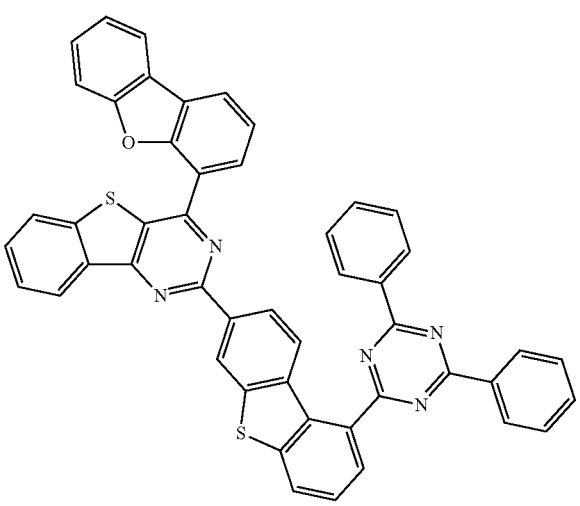
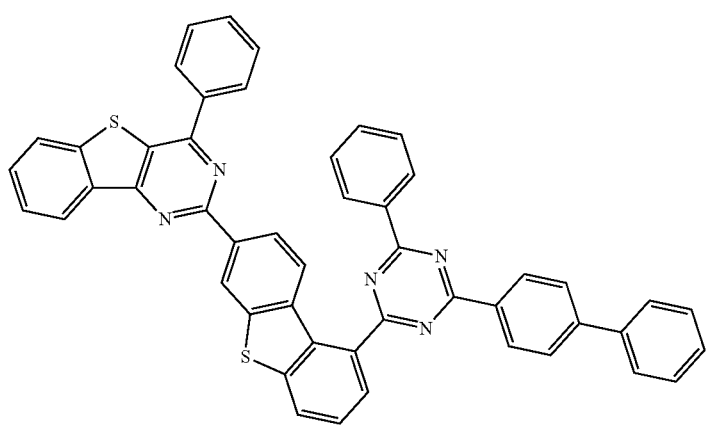

539
540
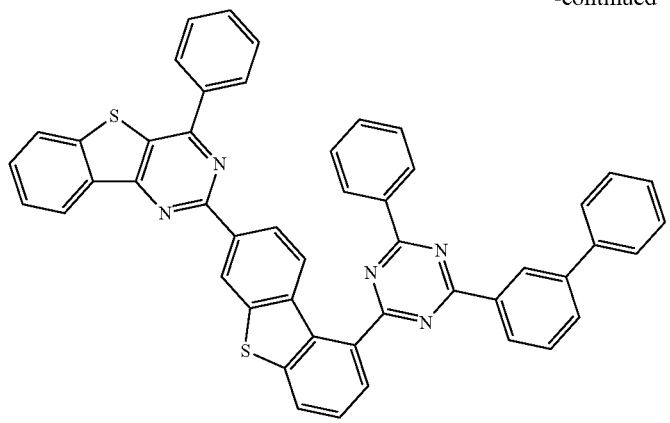
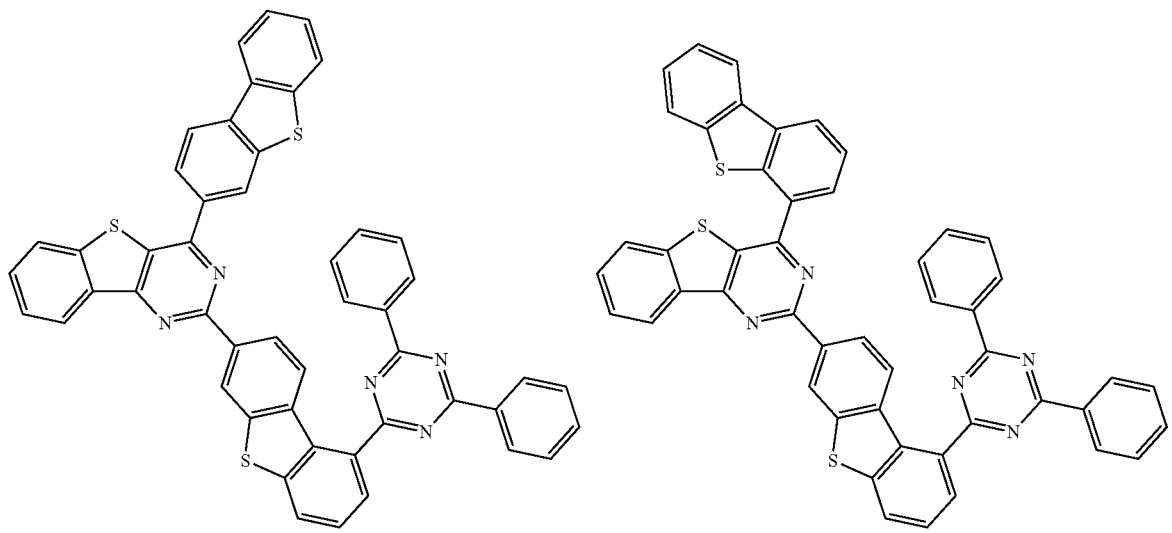
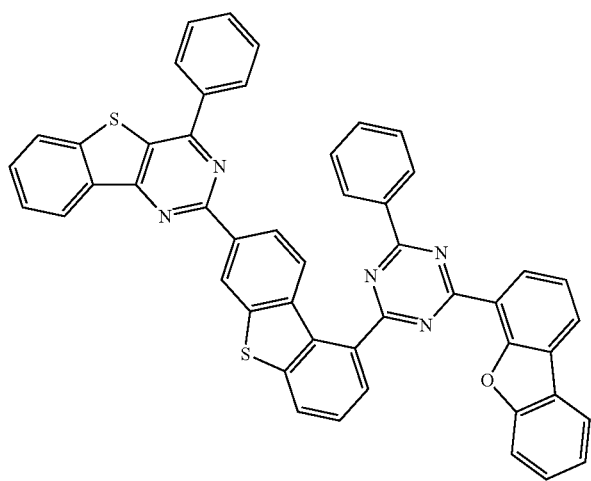

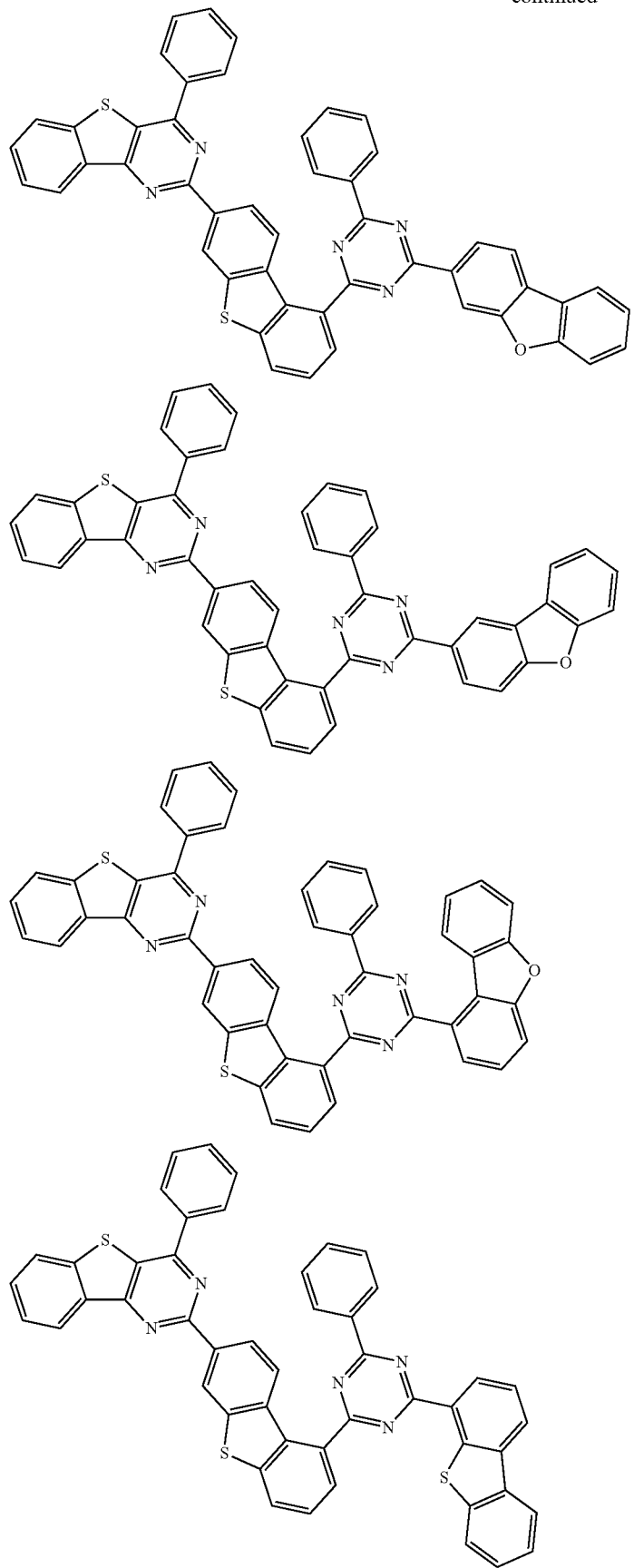

-continued
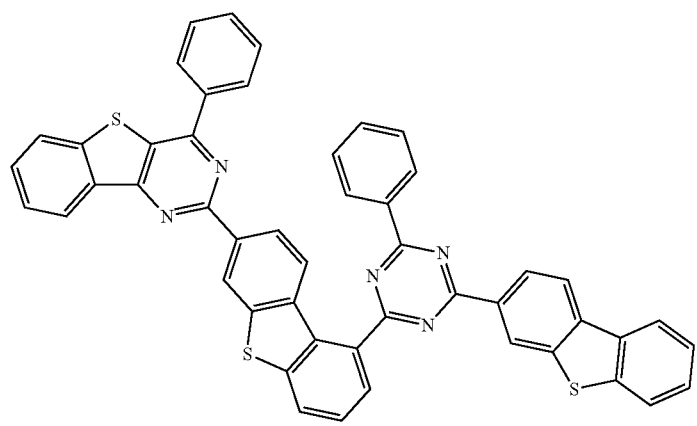
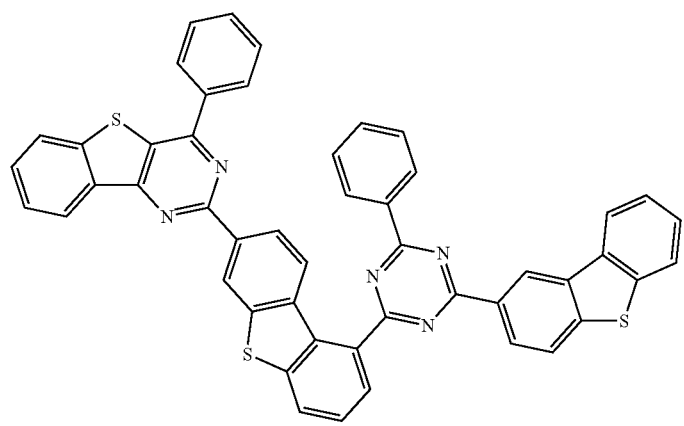
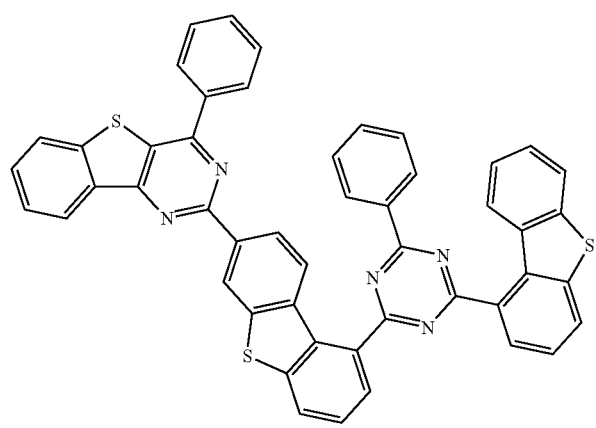

-continued
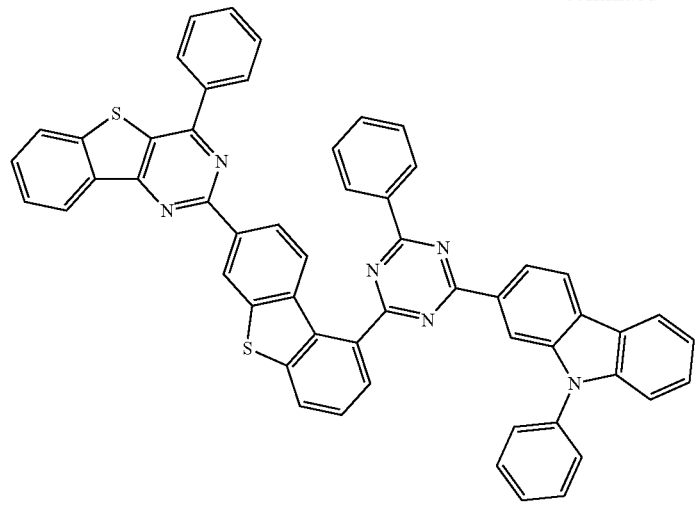
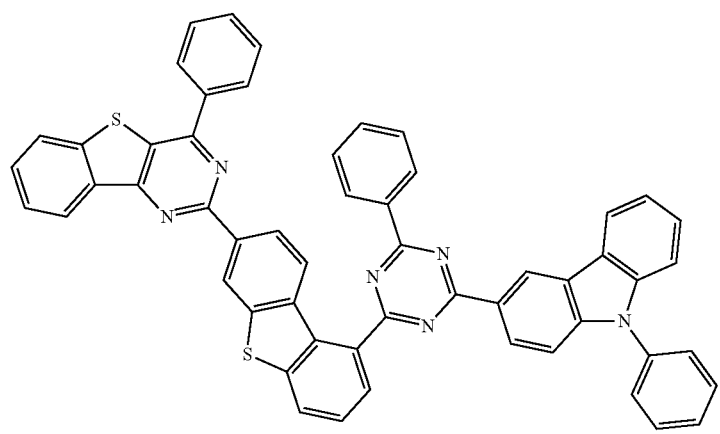
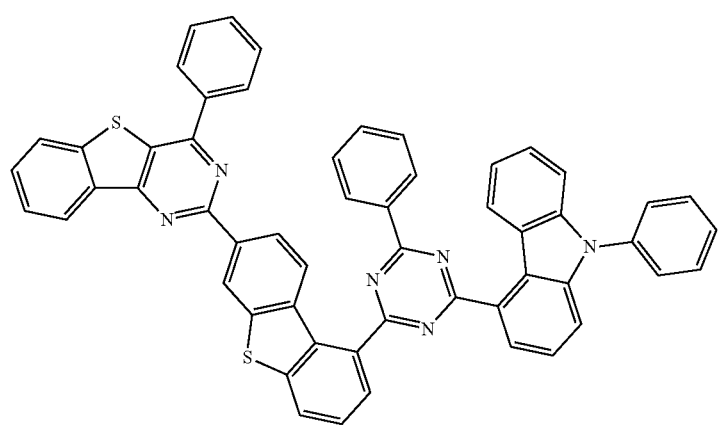

-continued
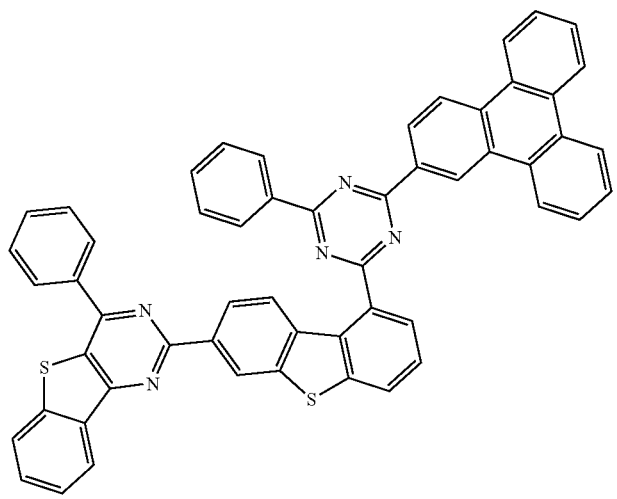
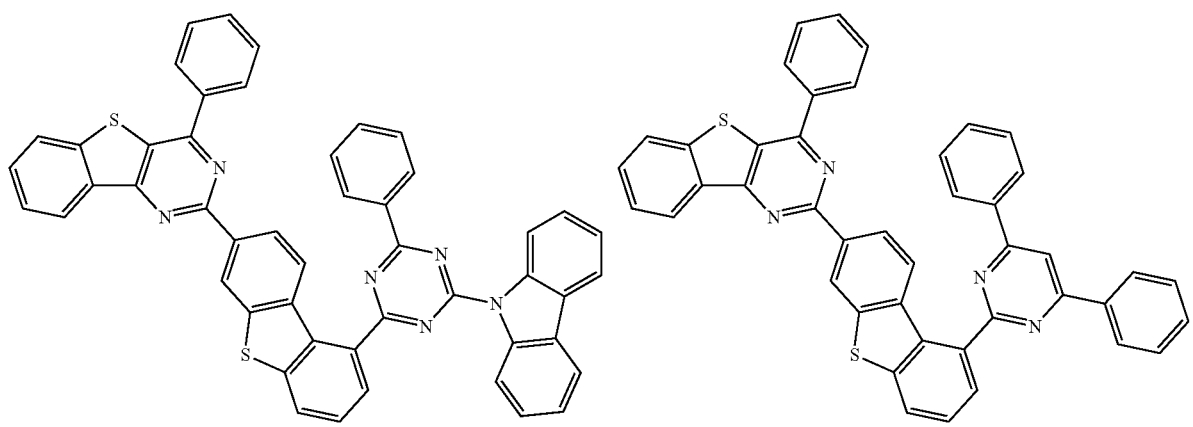
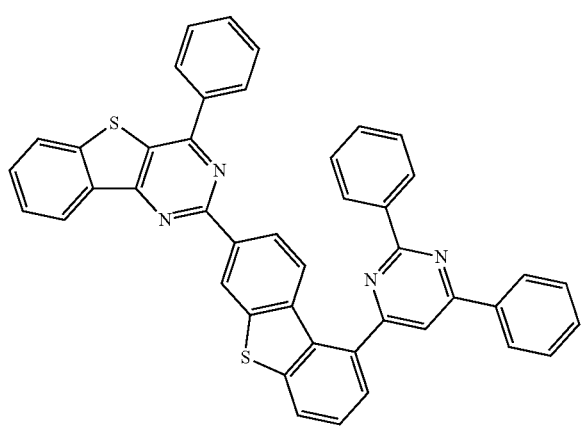

-continued
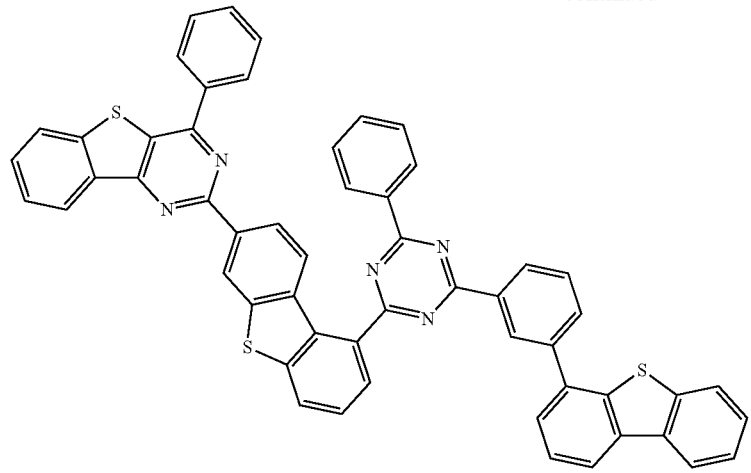
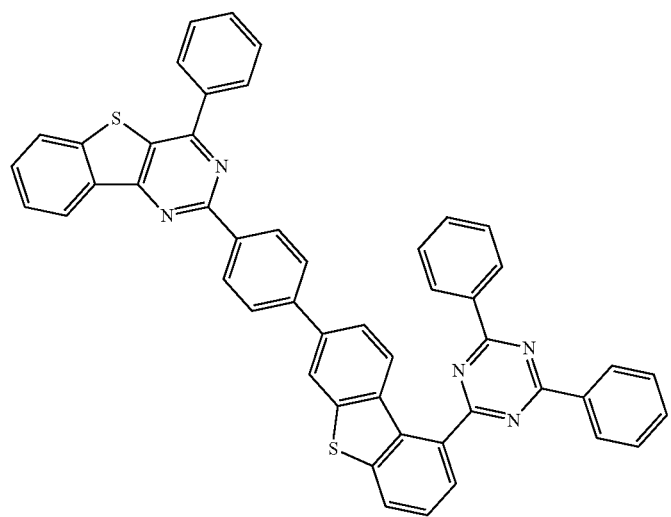
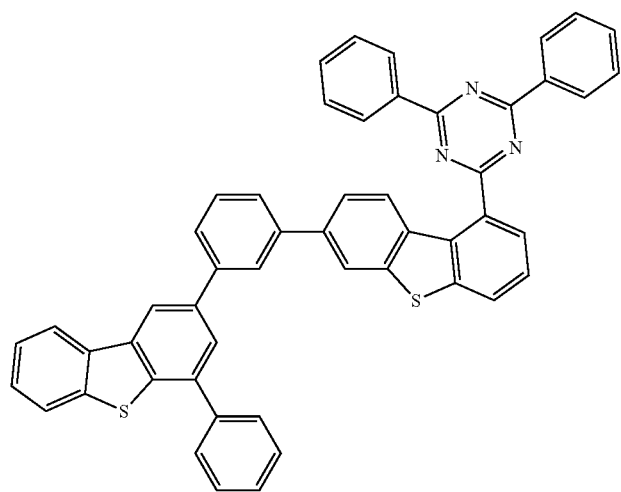

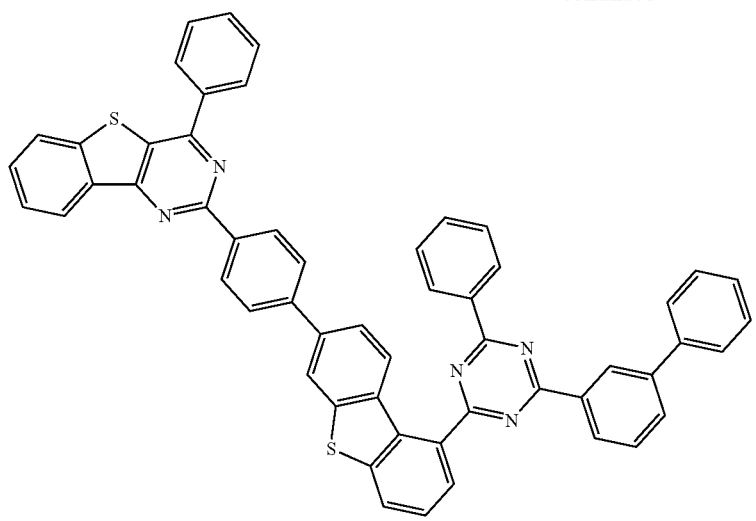
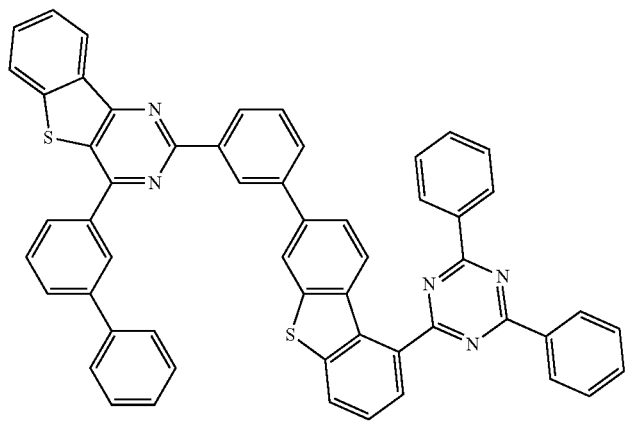
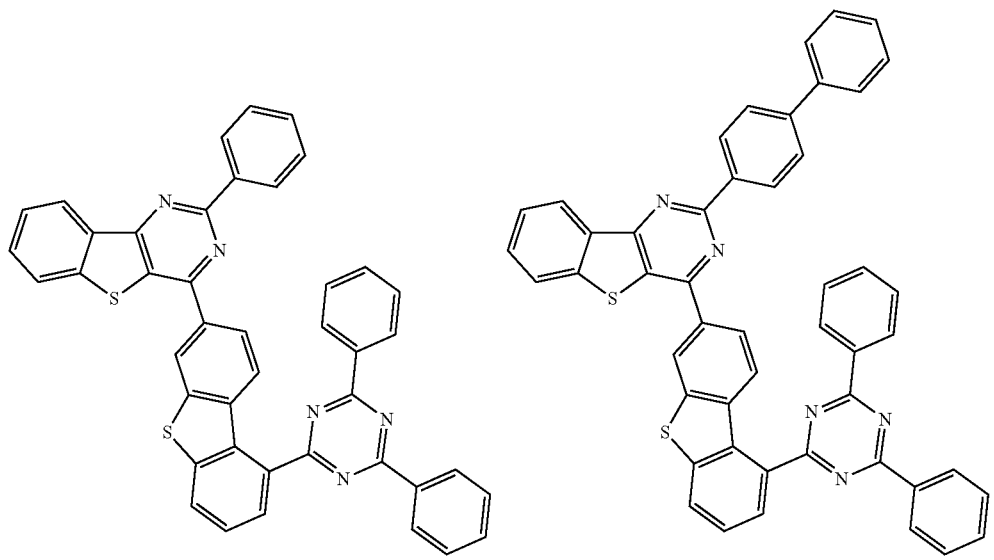

-continued
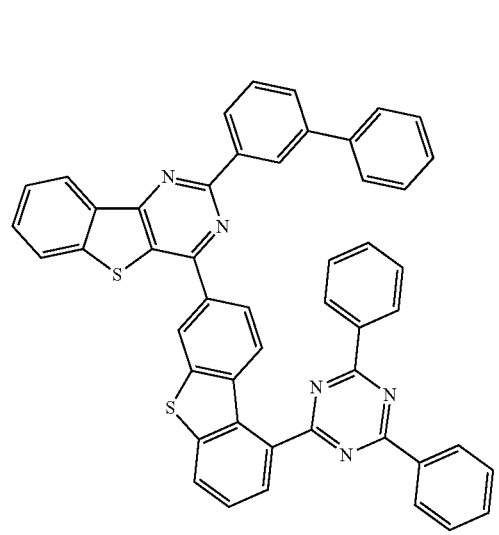
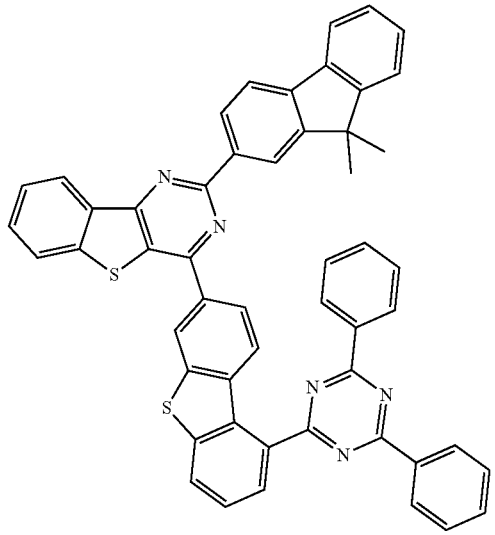
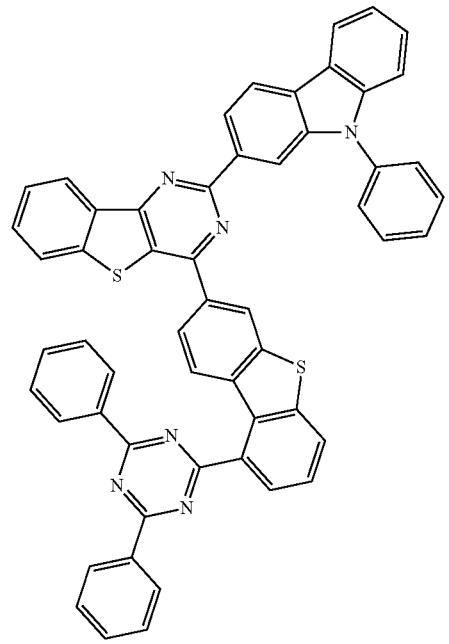
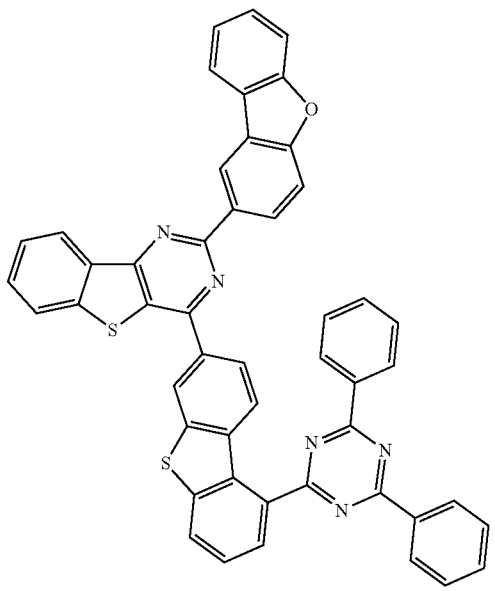
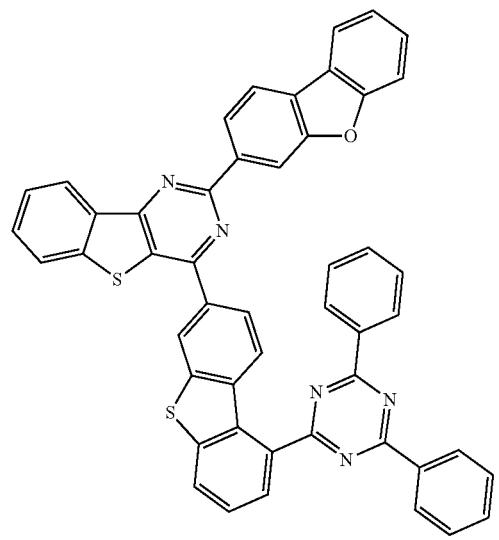
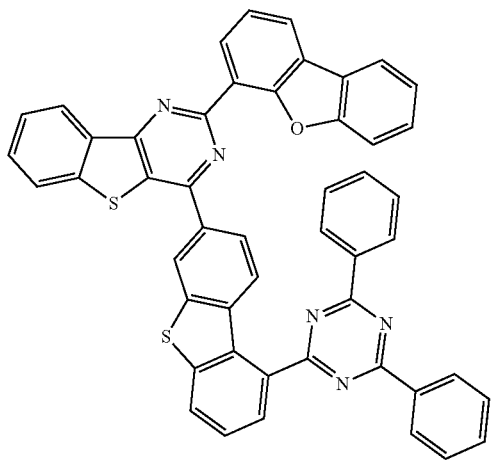

555
556
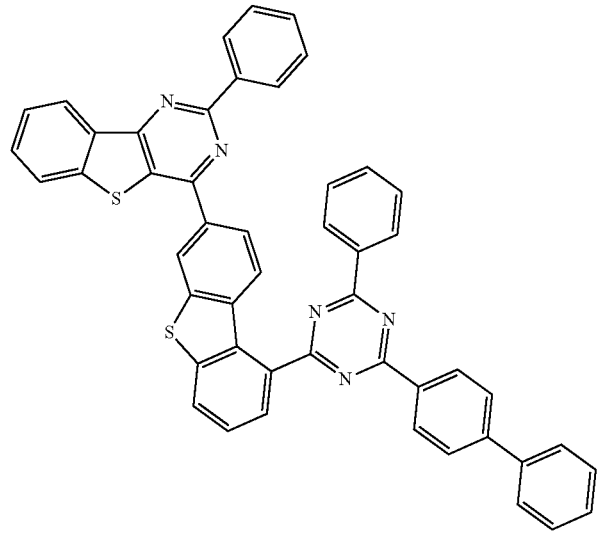
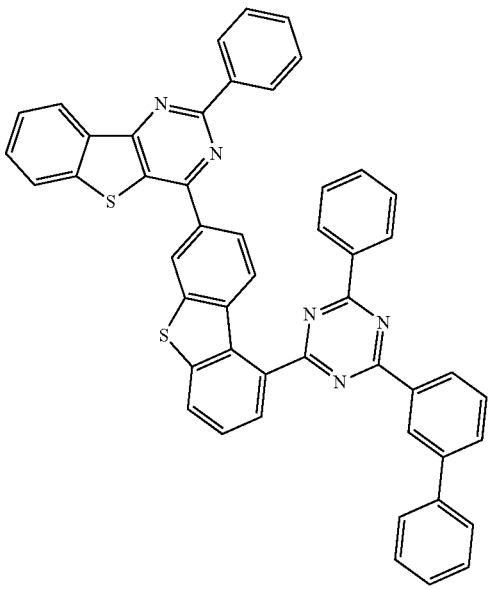
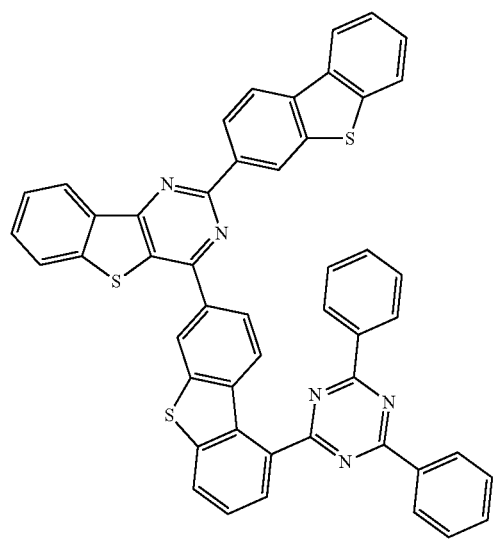
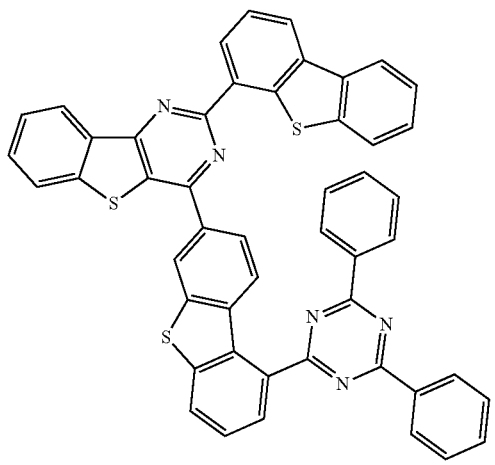
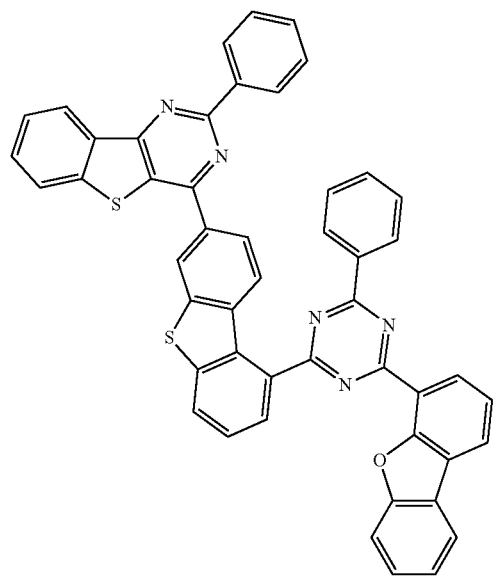
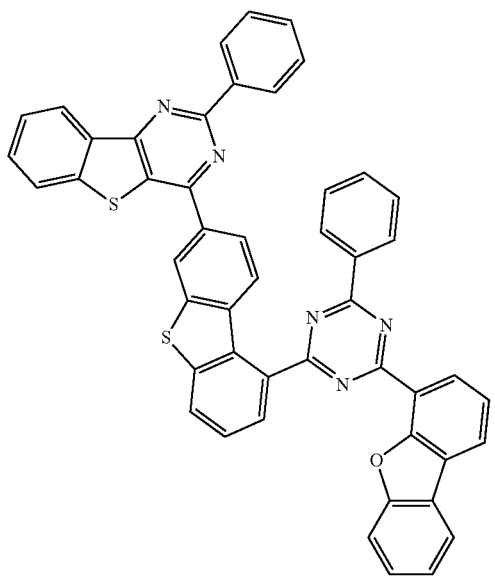

557
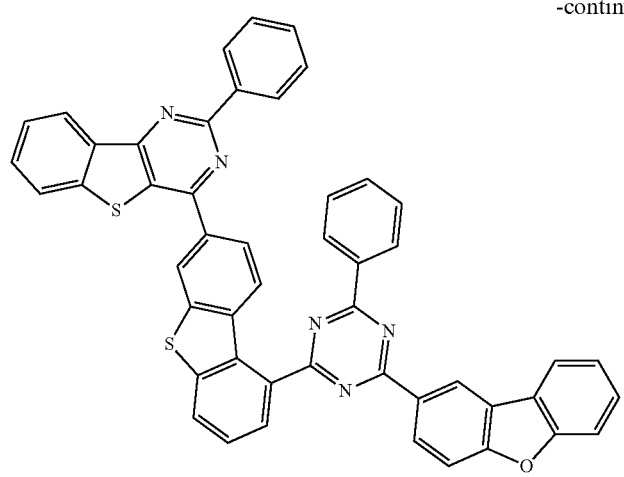
558
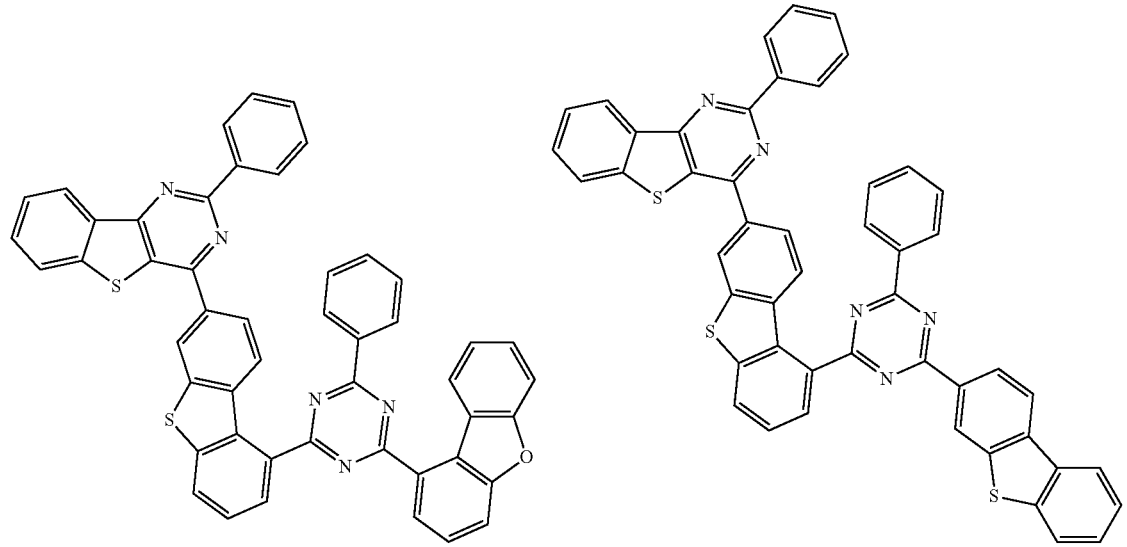
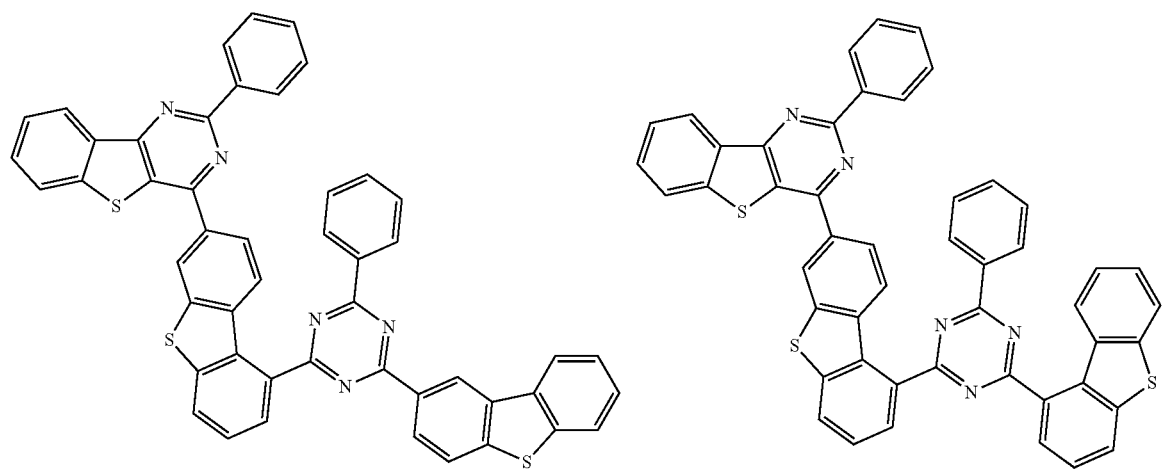

-continued
559
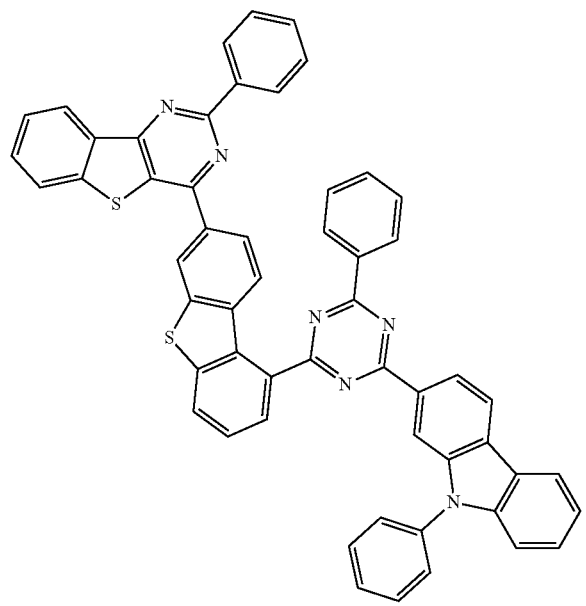
560
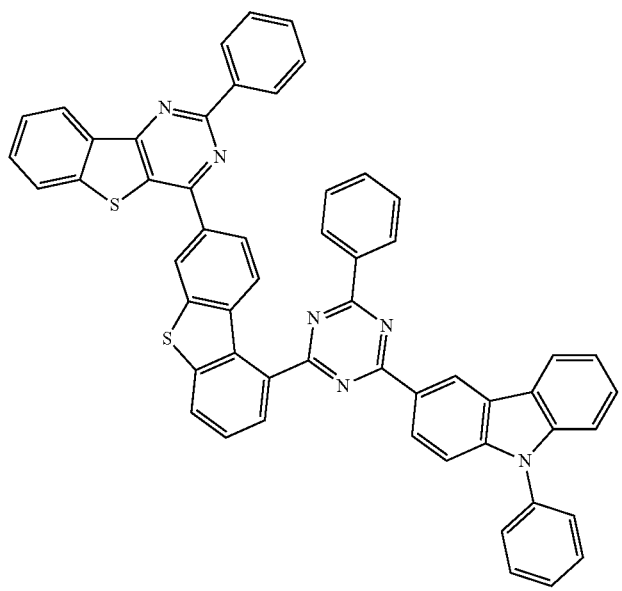
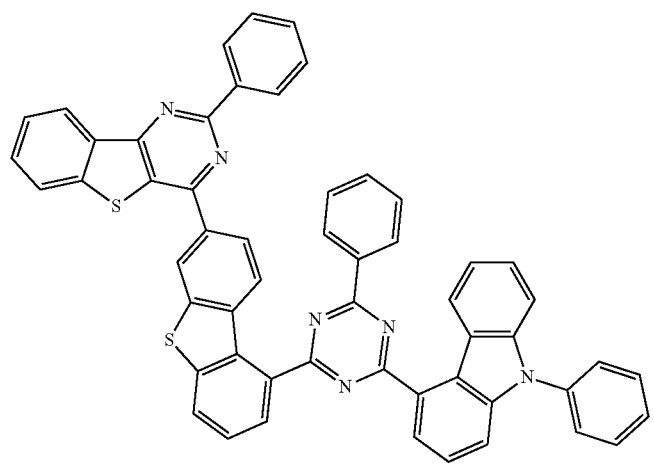
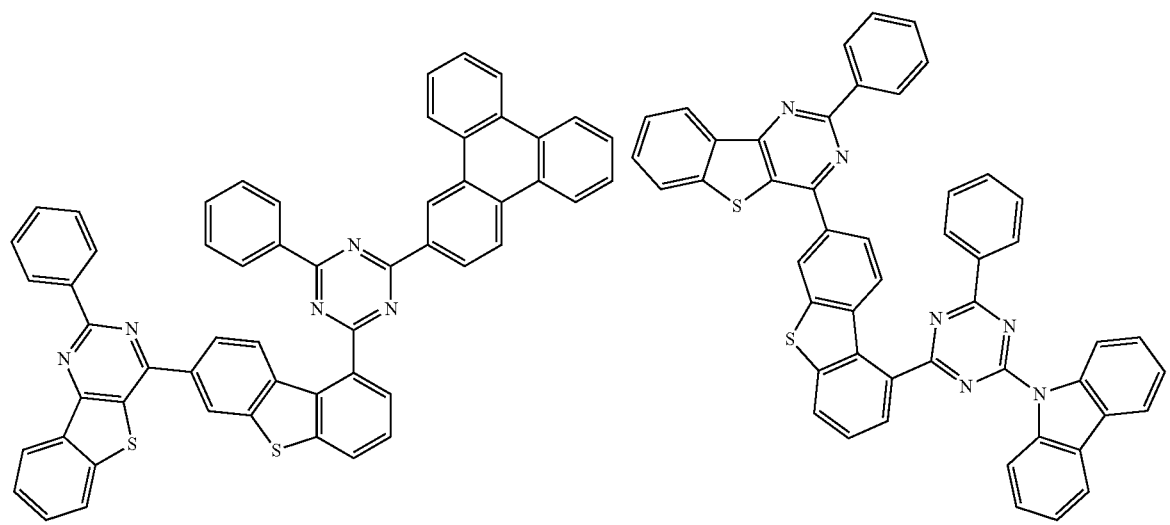

561 562
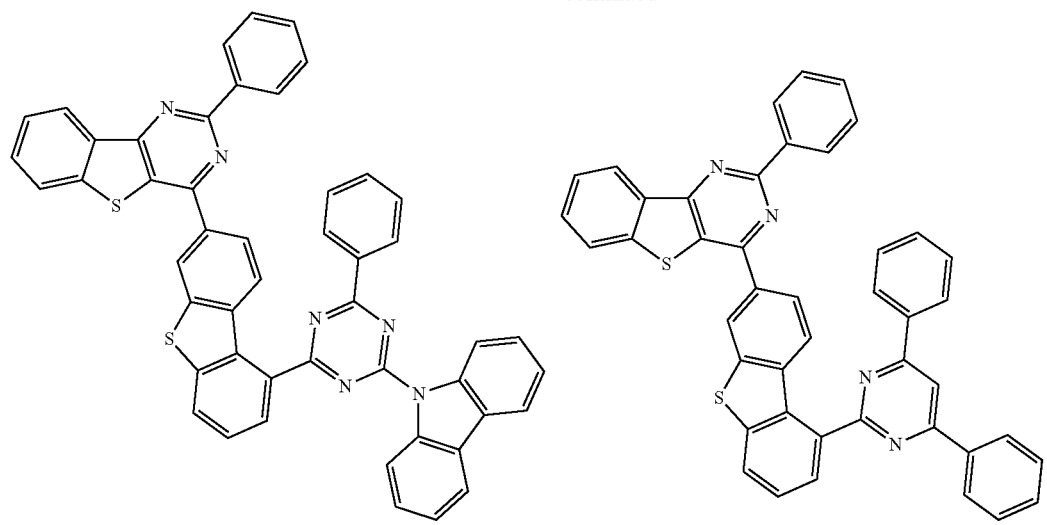
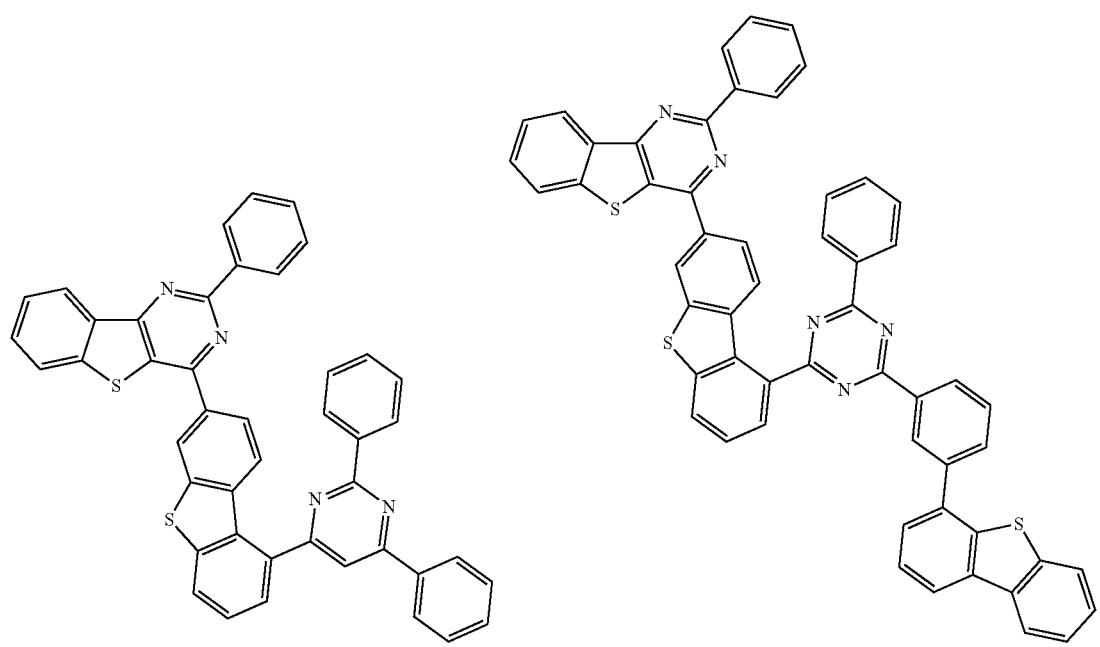
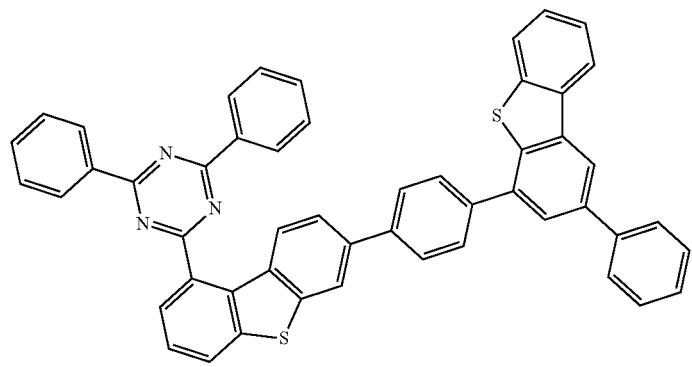

563 564
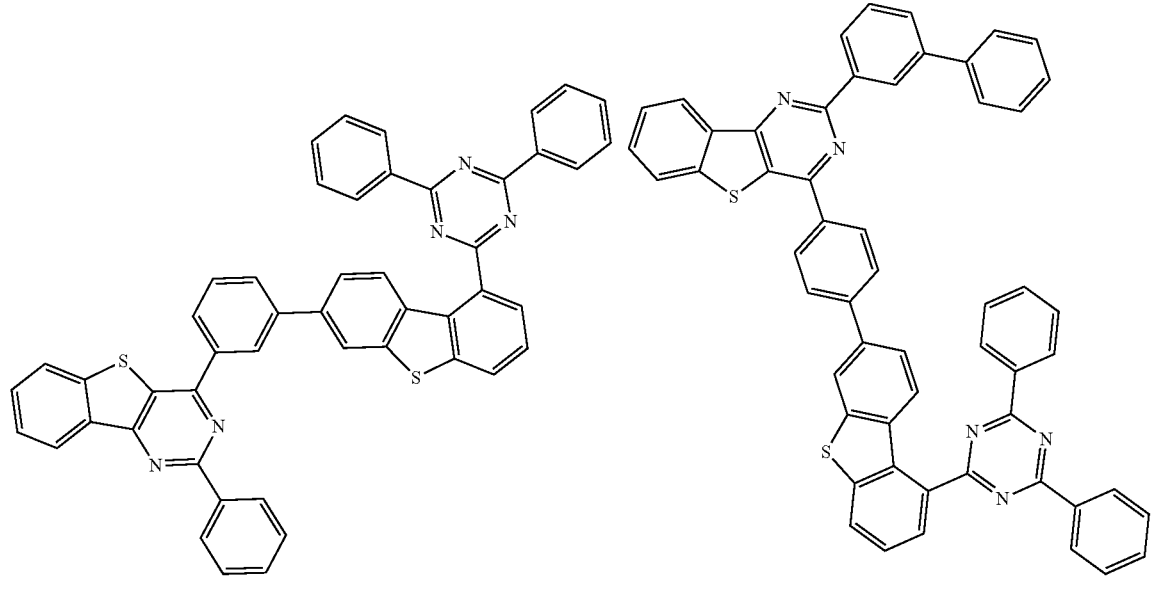
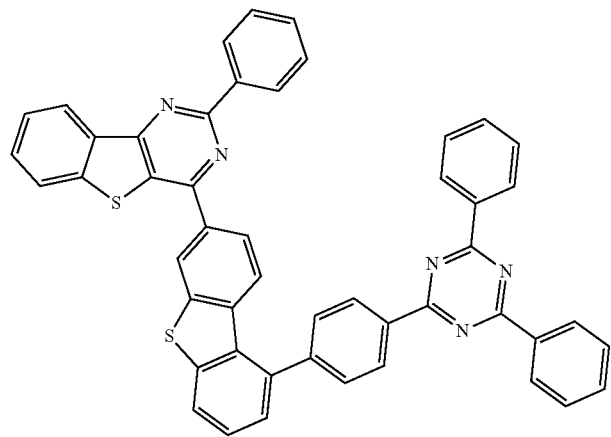
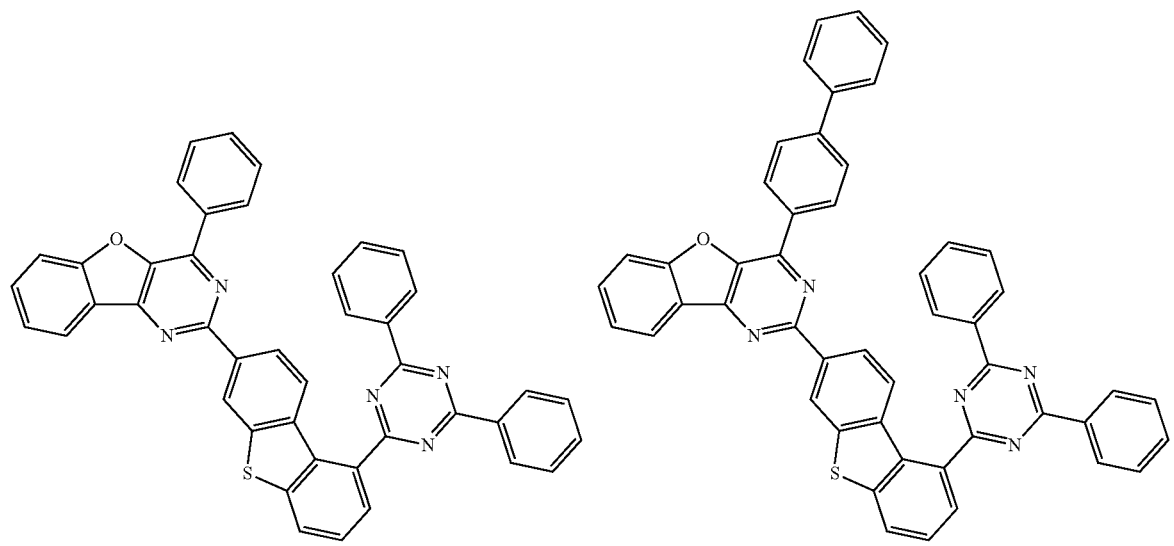

565
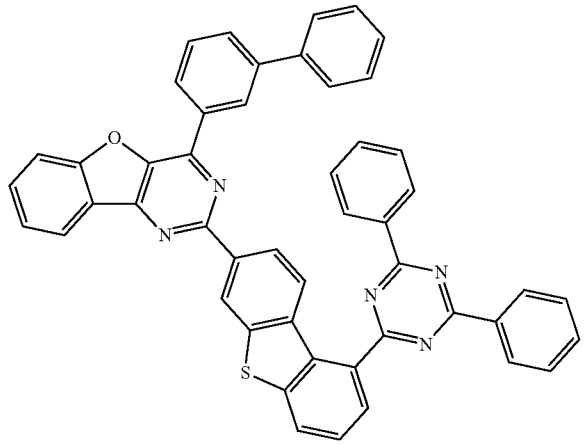
566
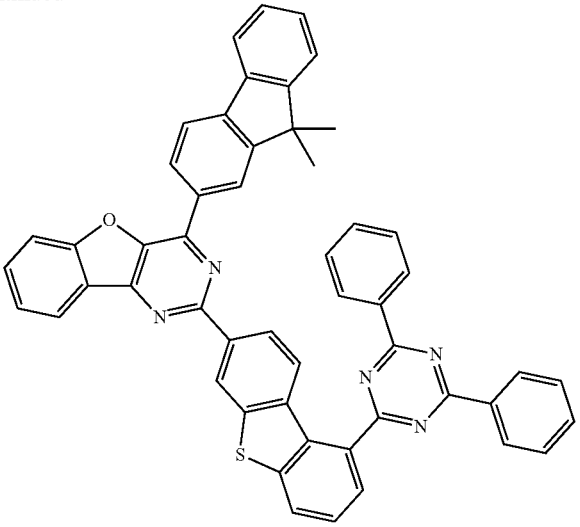
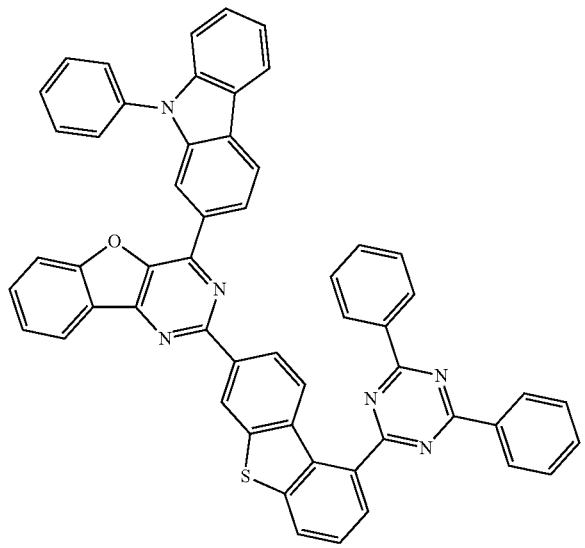
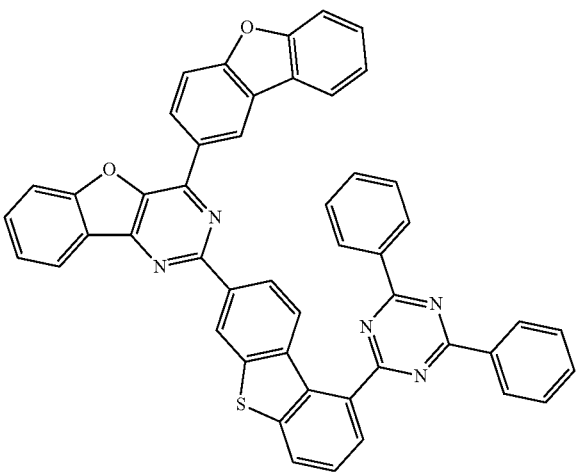
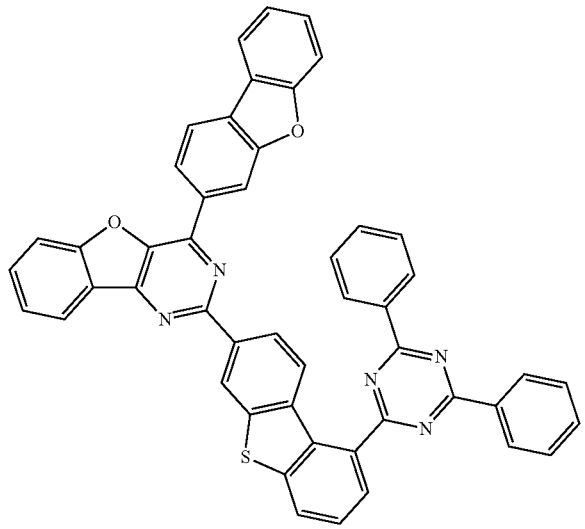
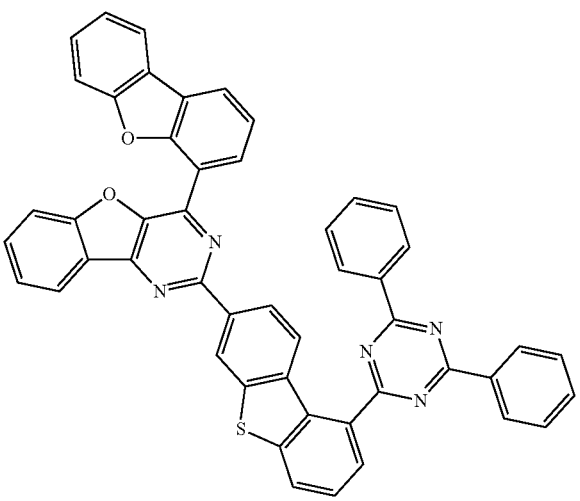

-continued
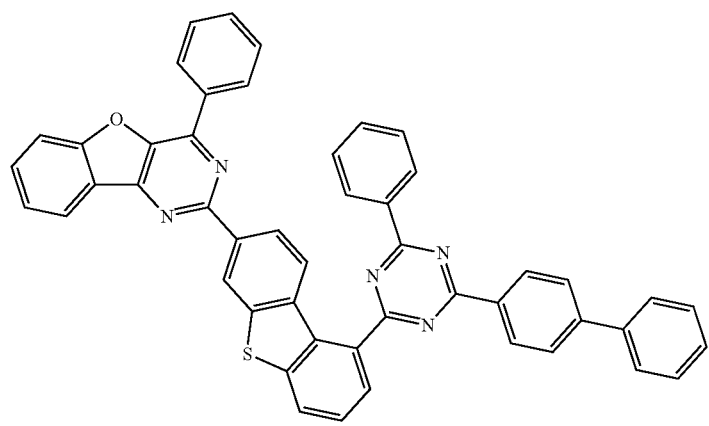
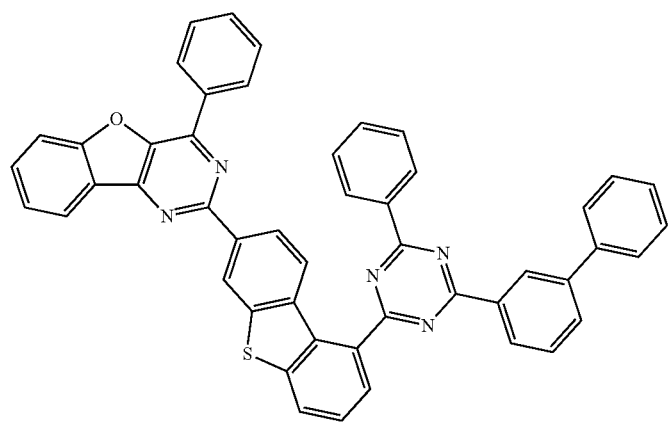
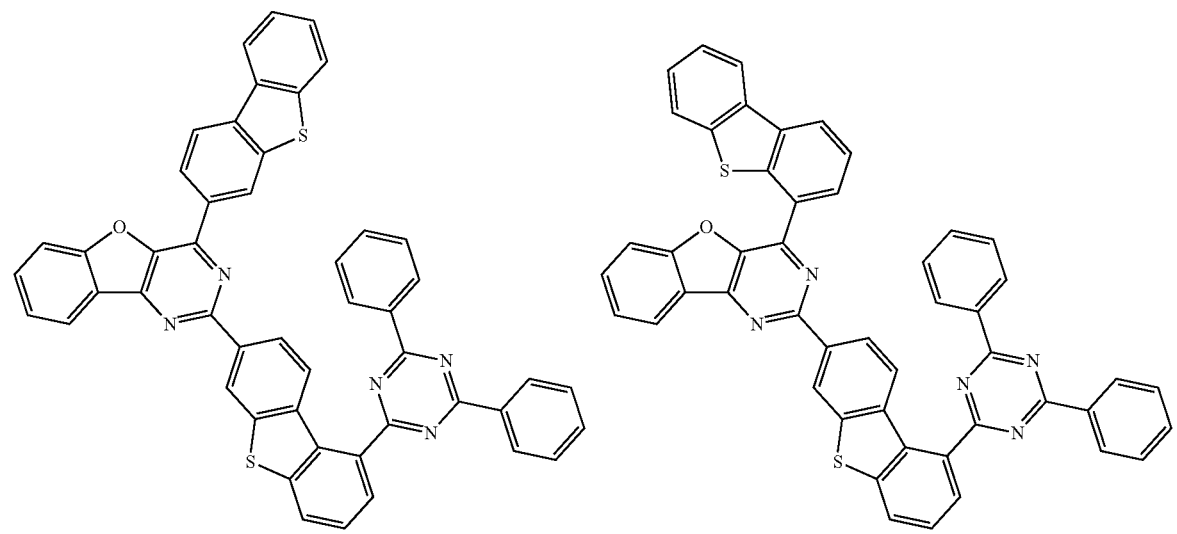

-continued
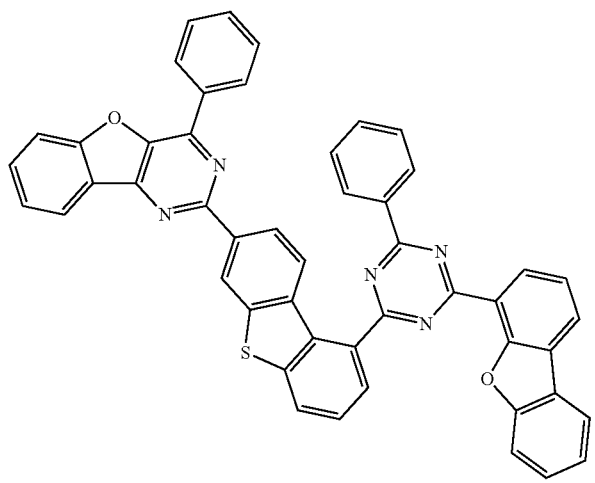
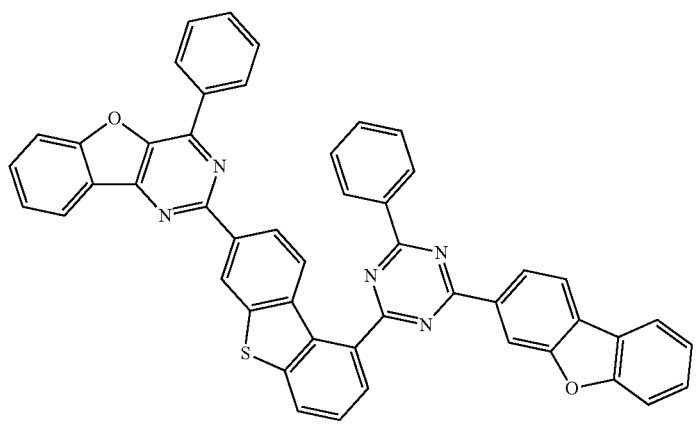
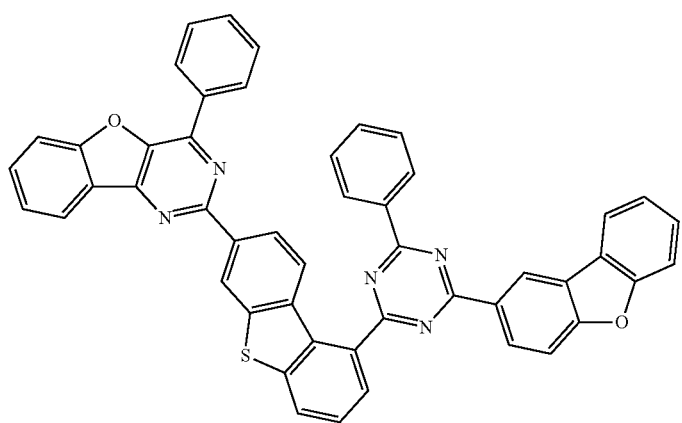

571
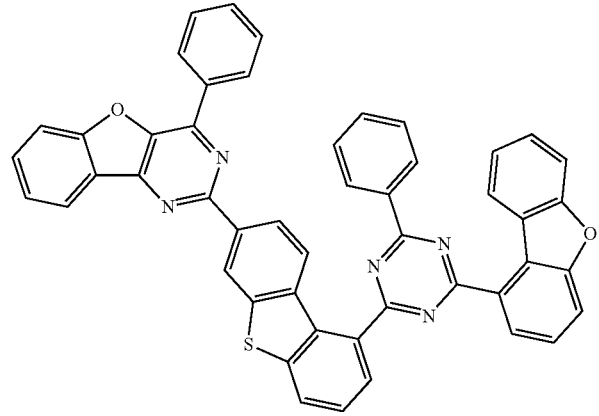
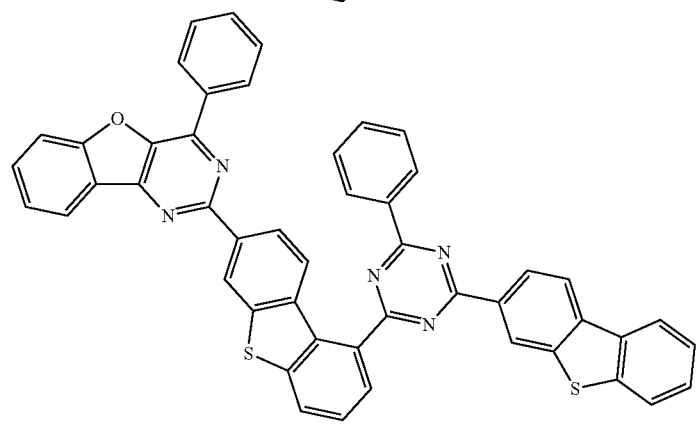
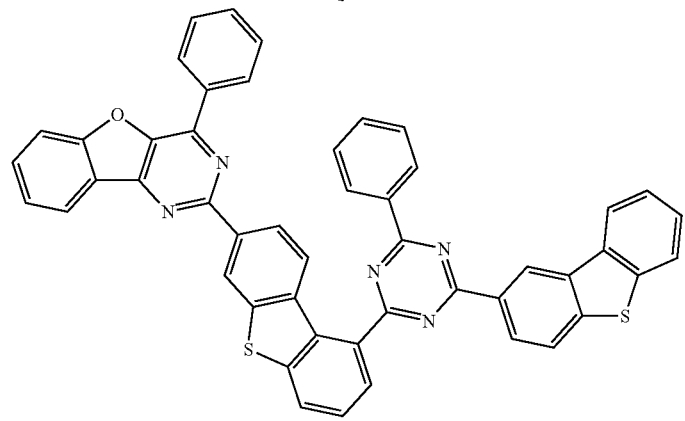
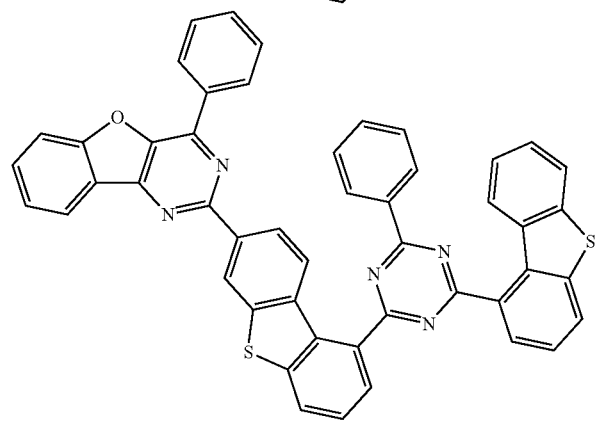
572
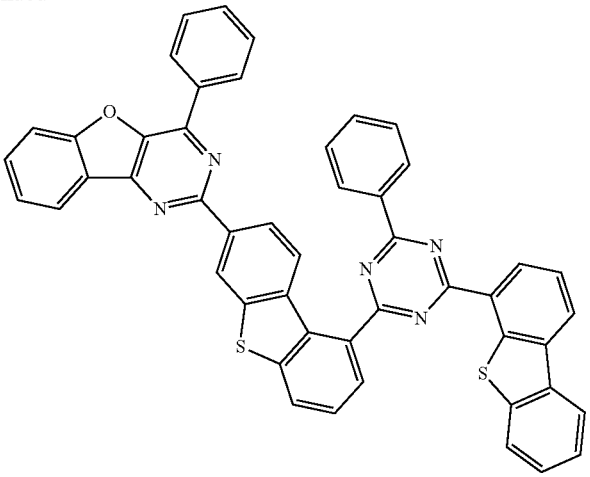

-continued
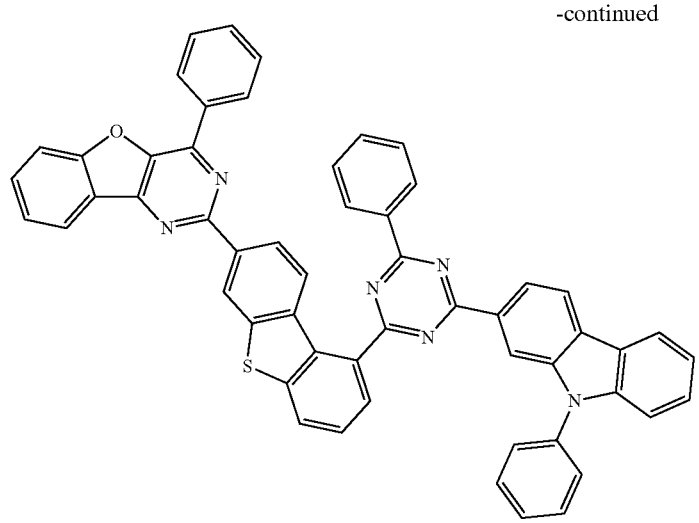
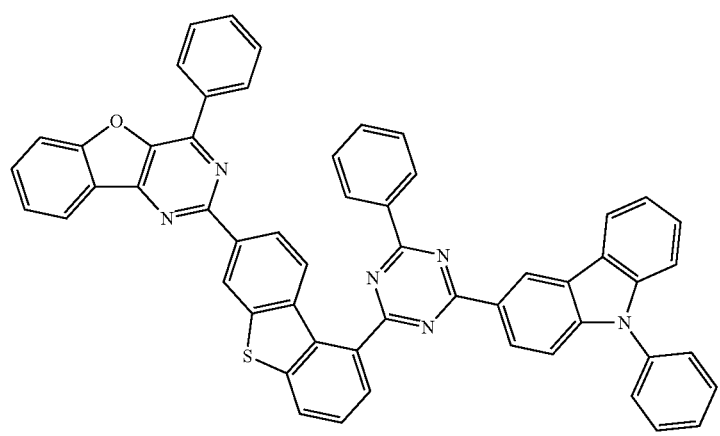
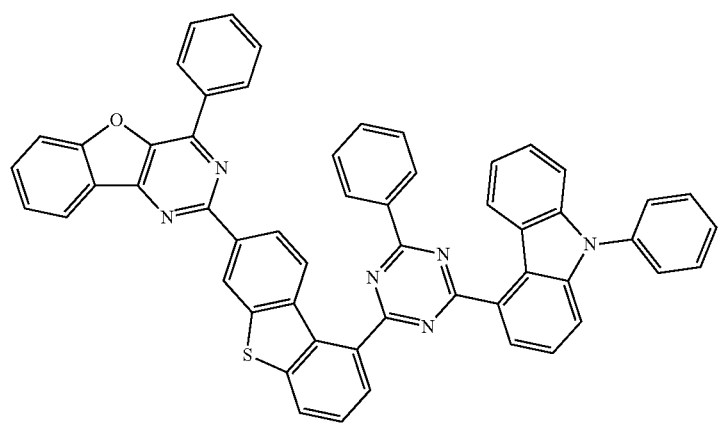

-continued
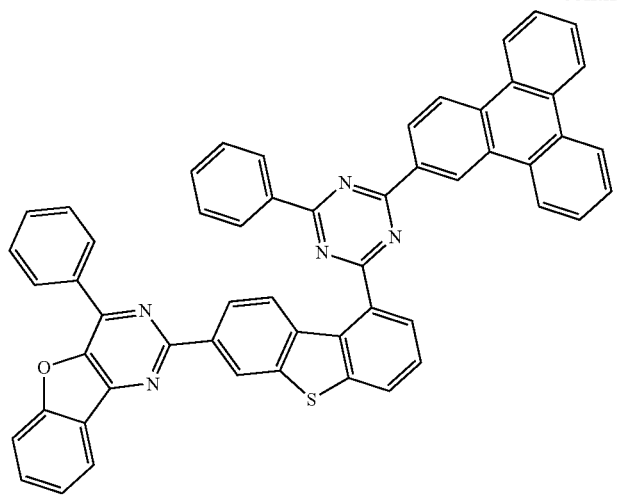
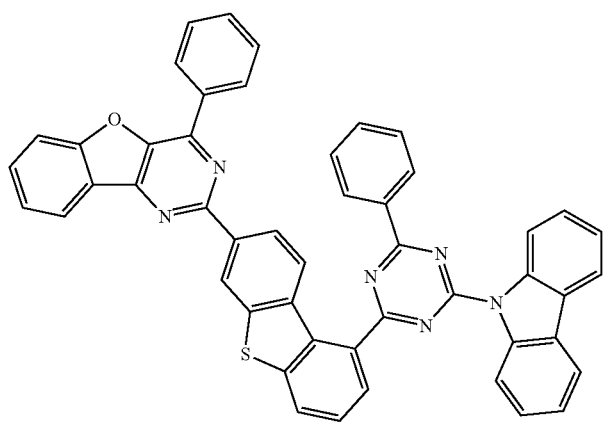
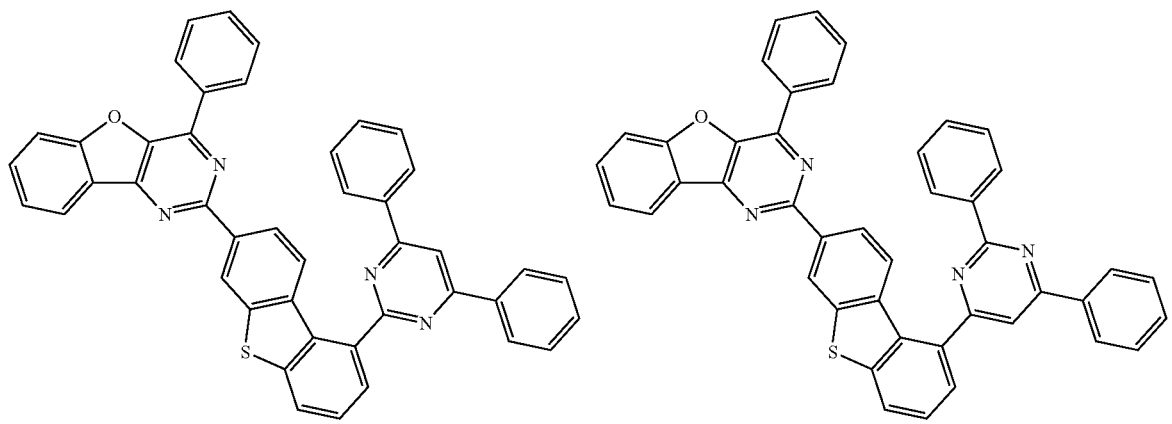

-continued
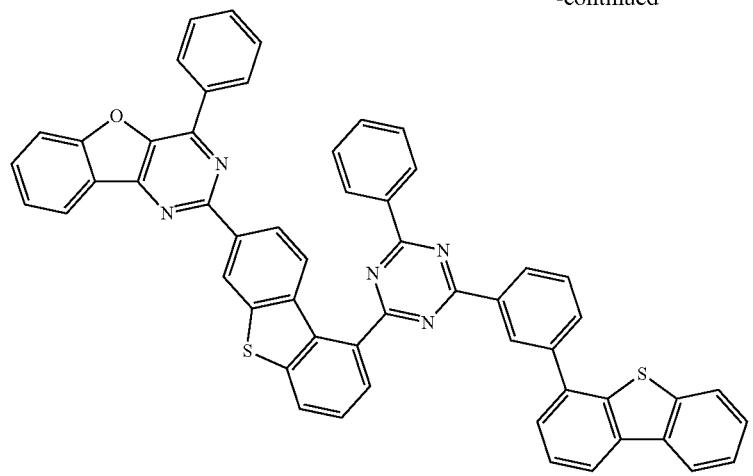
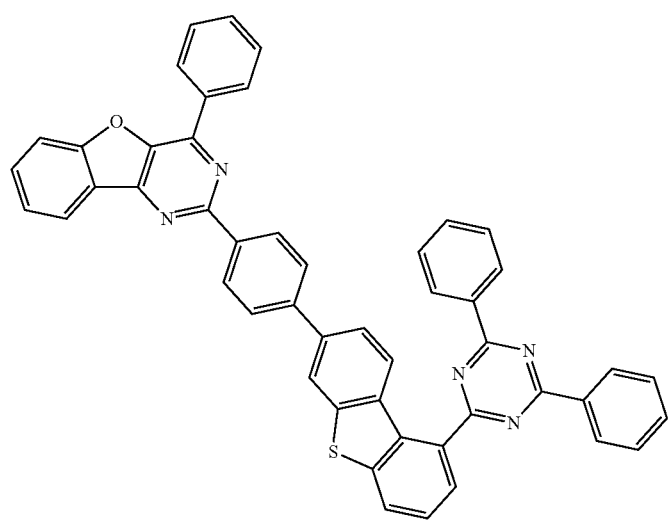
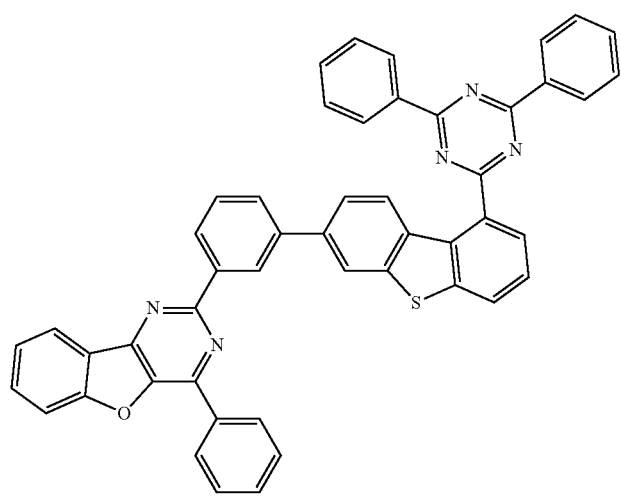

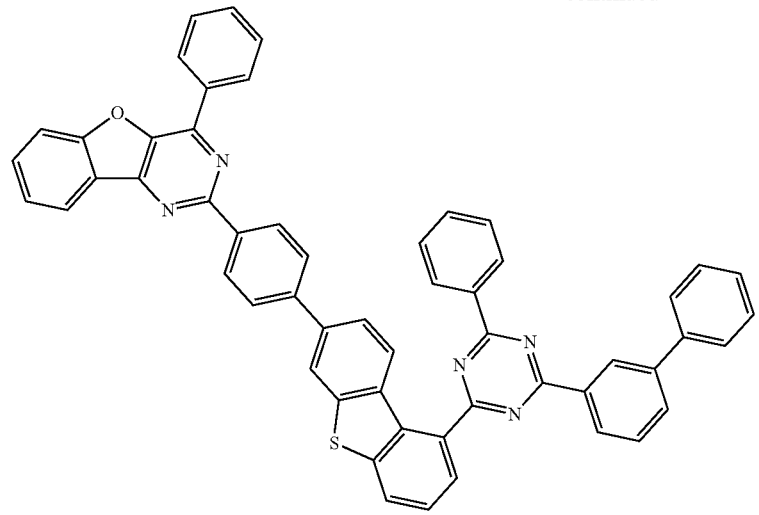
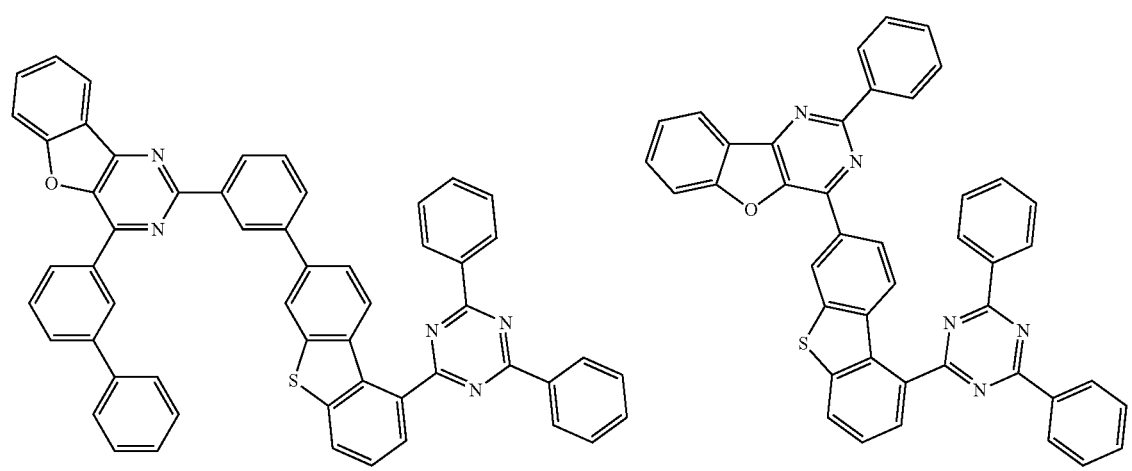
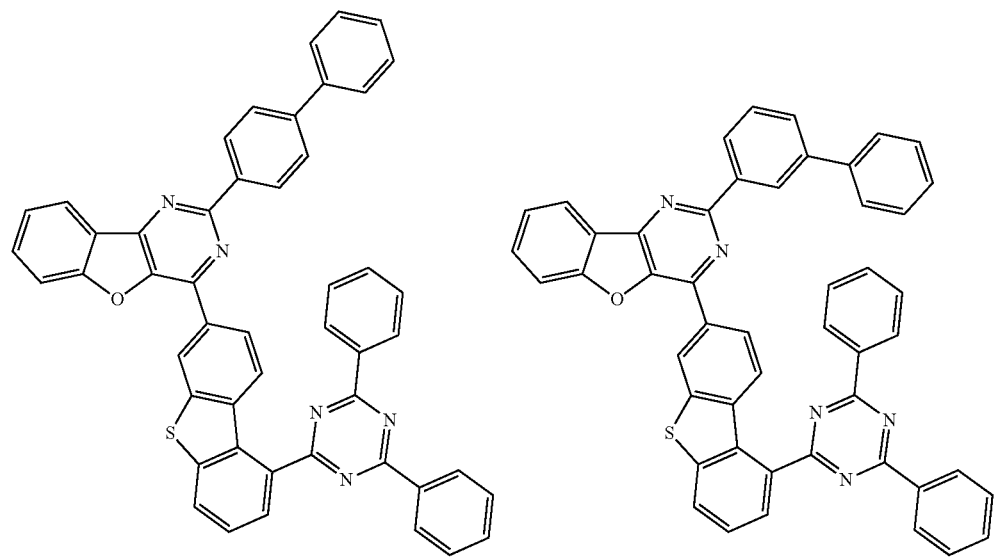

581
582
-continued
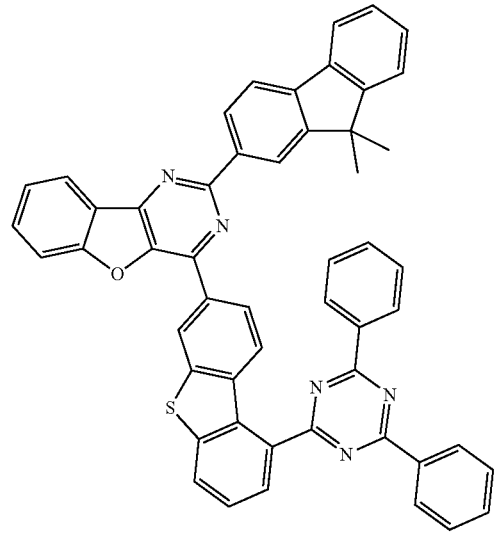
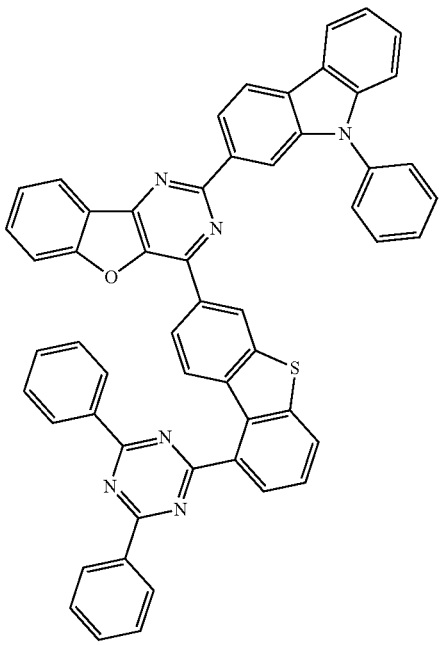
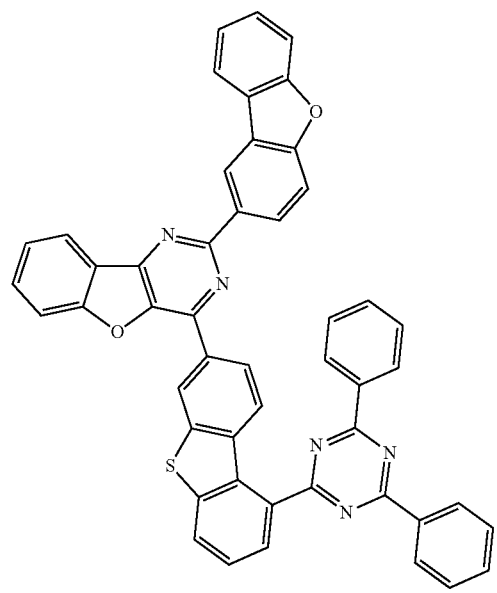
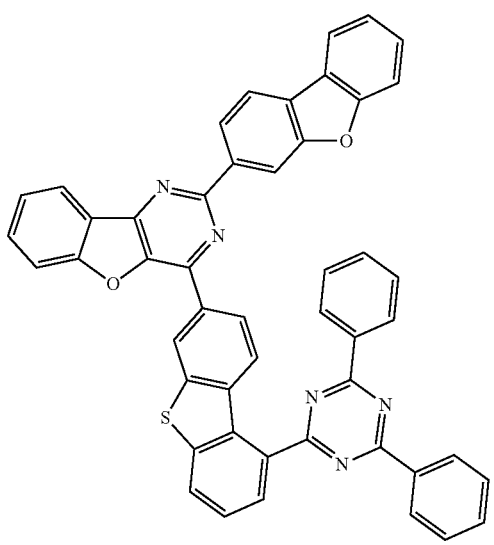

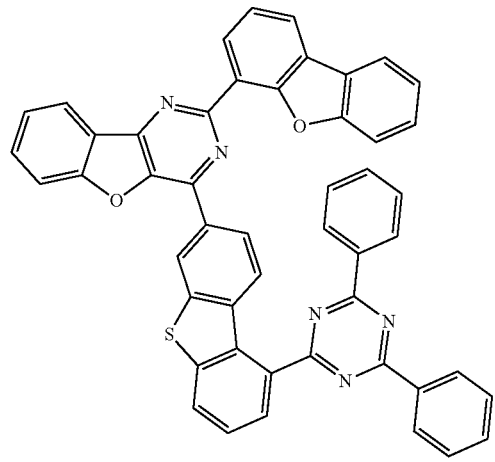
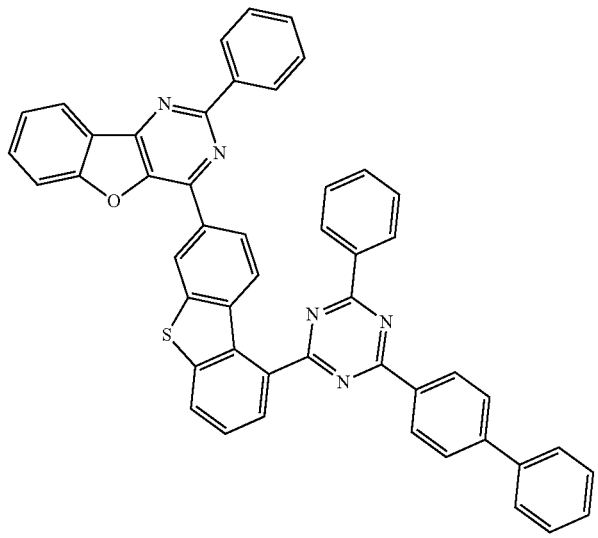
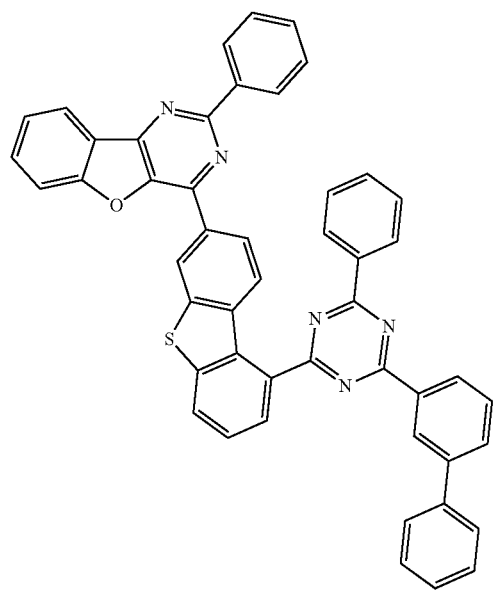
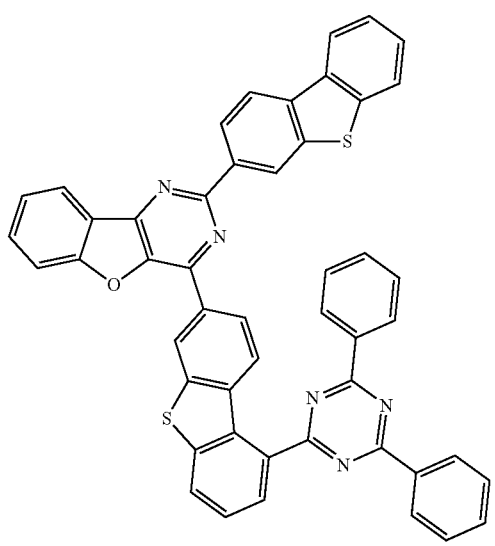
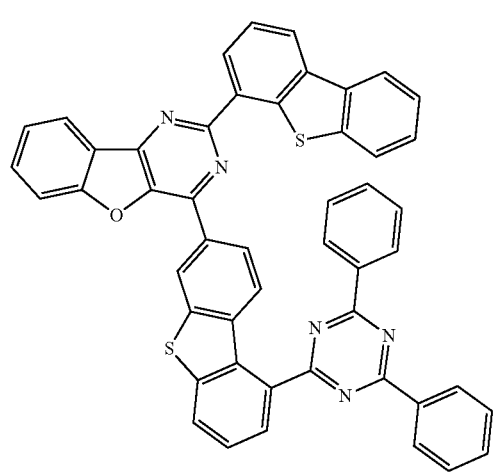
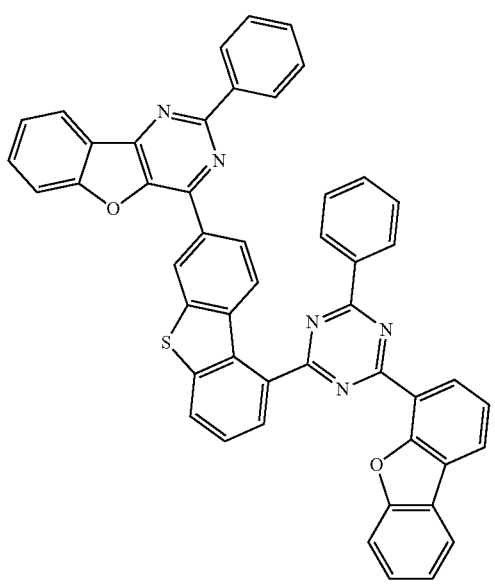

-continued
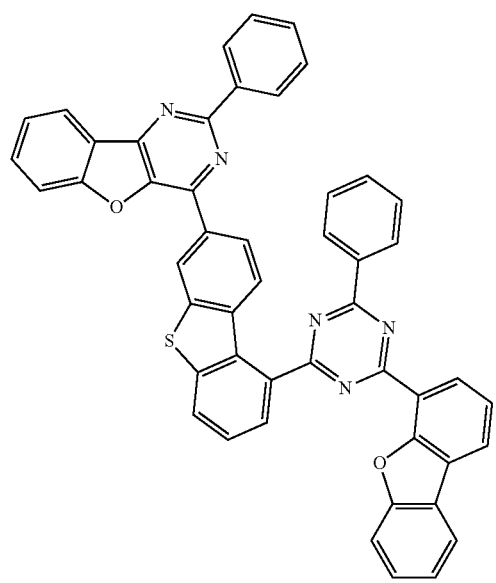
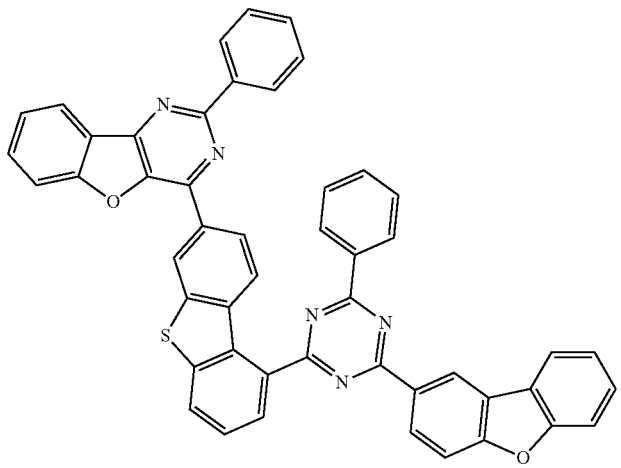
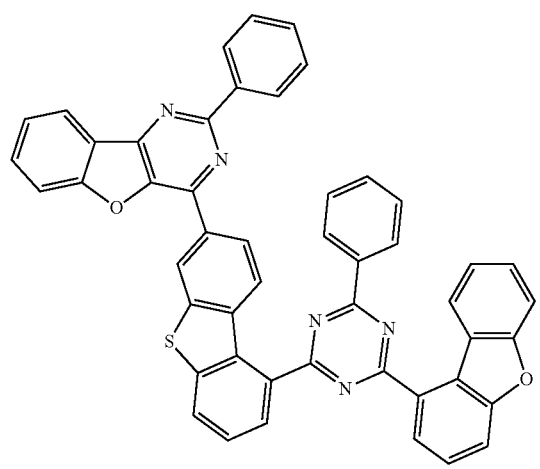
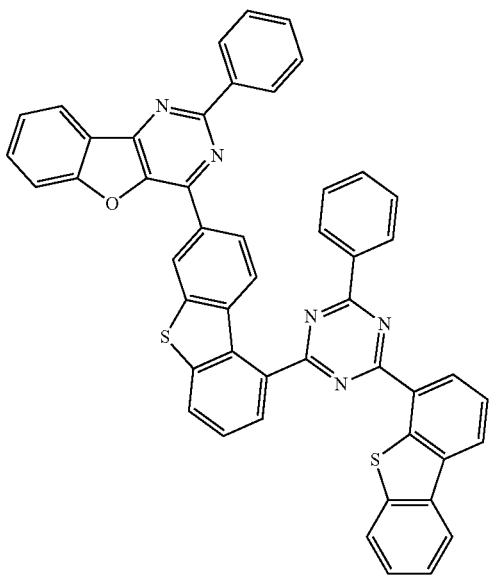
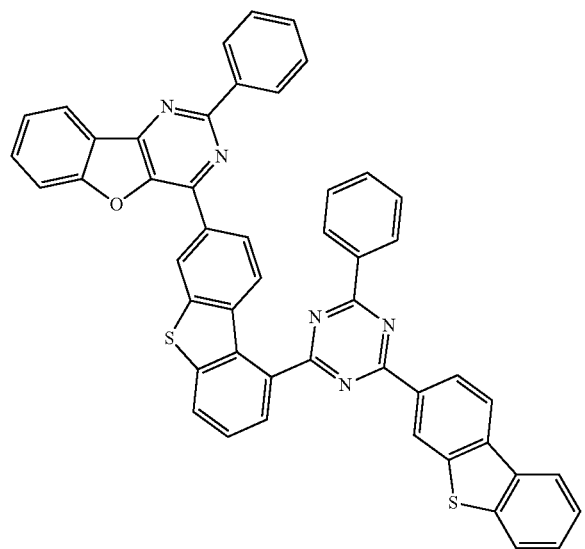
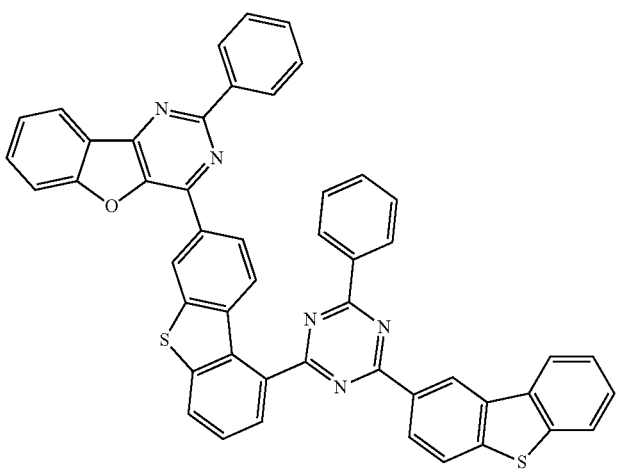

587
588
-continued
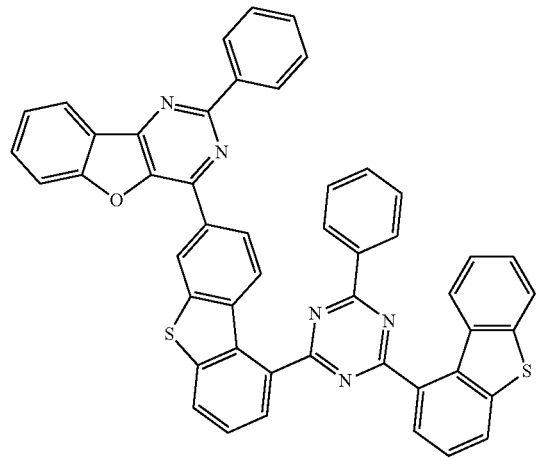
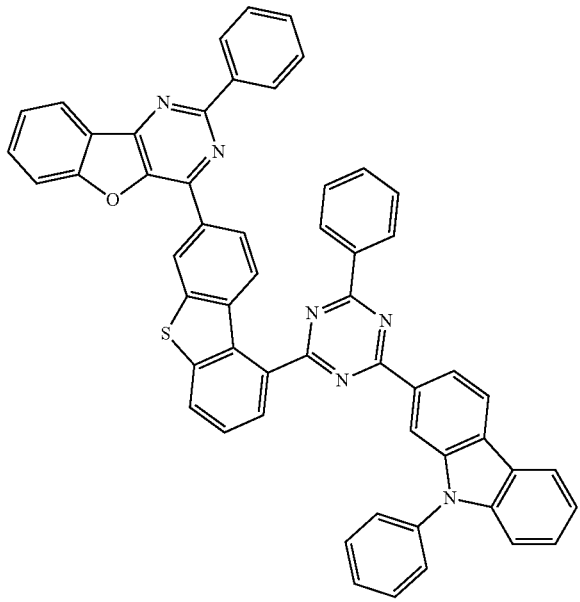
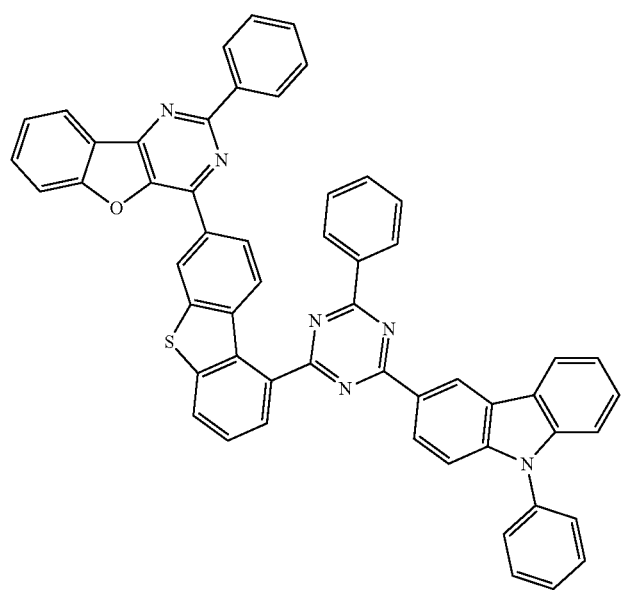
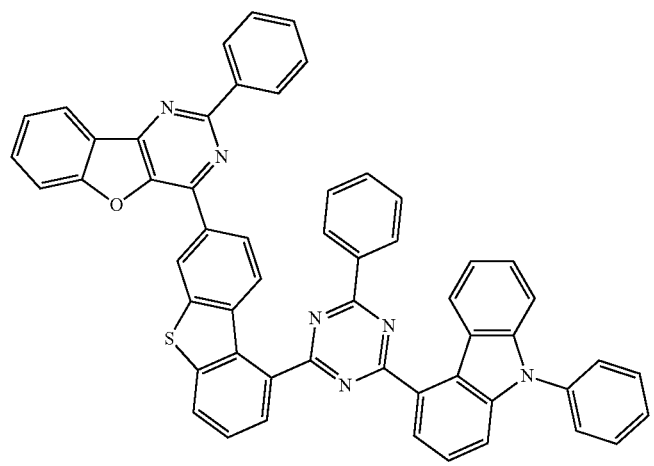

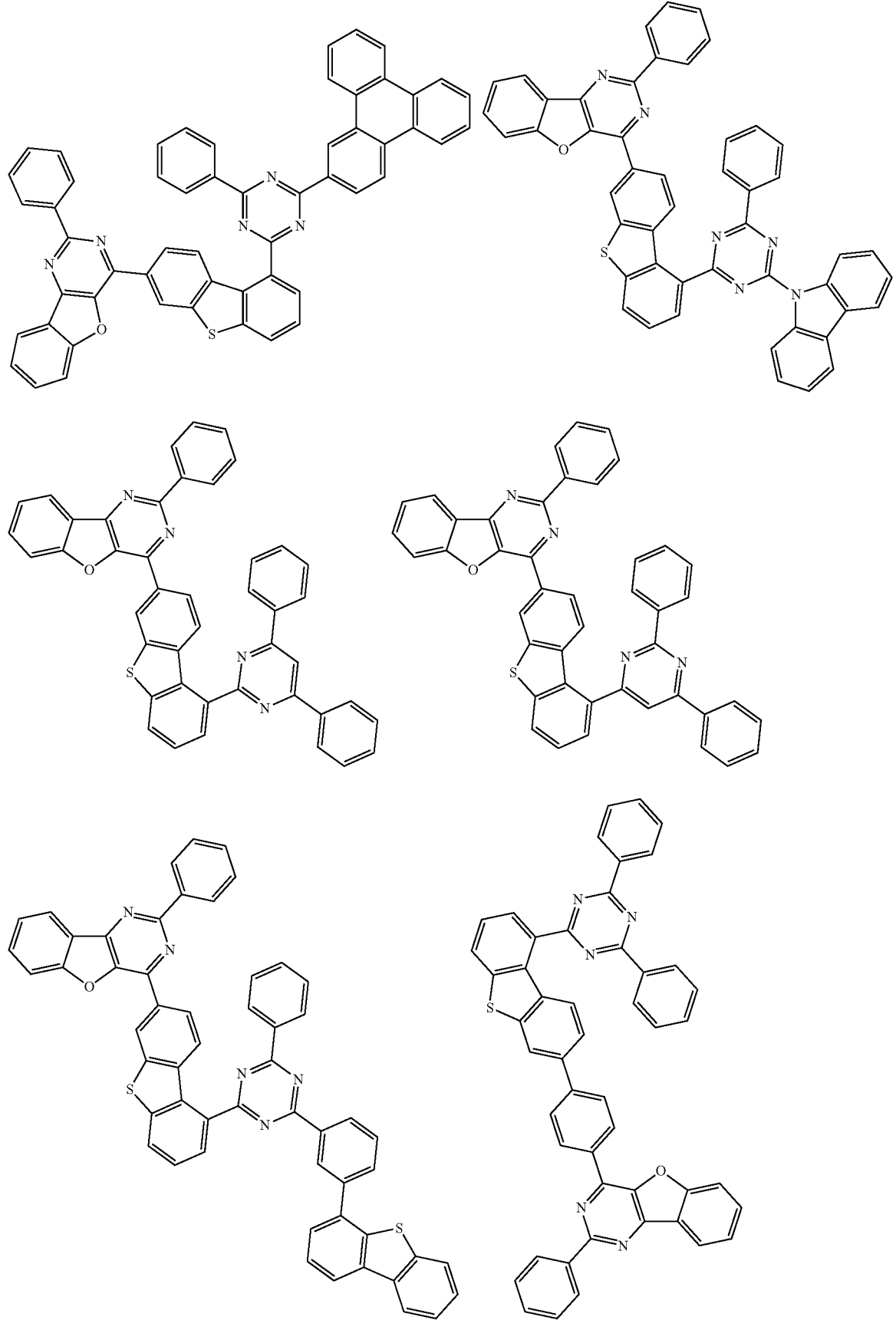

-continued
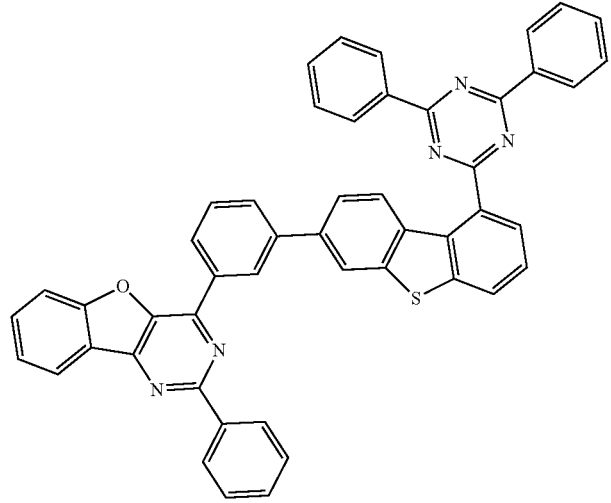
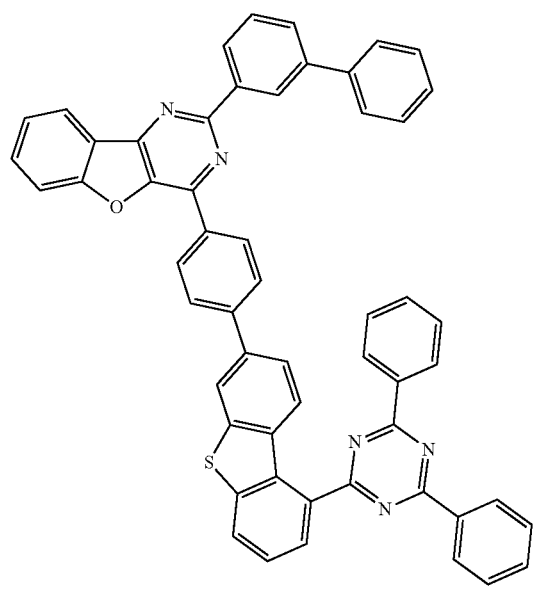
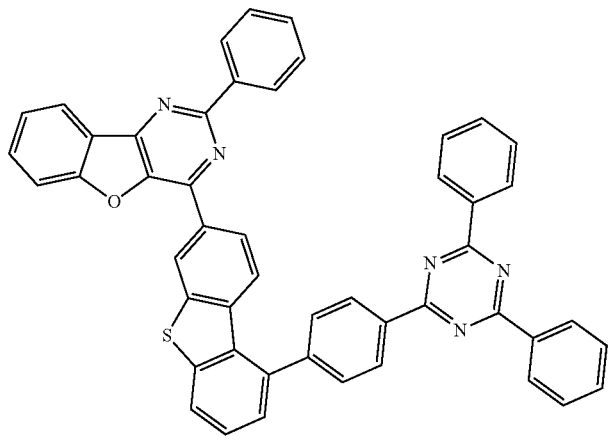
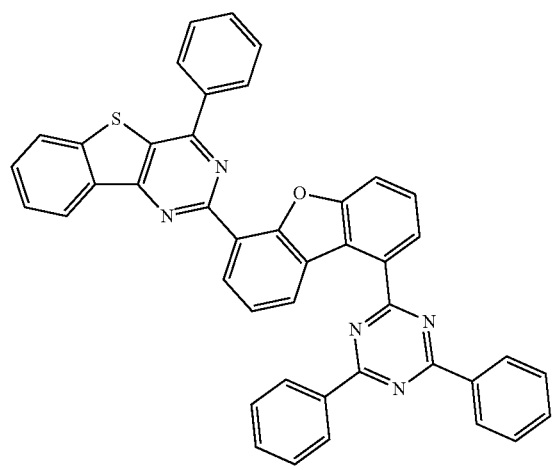
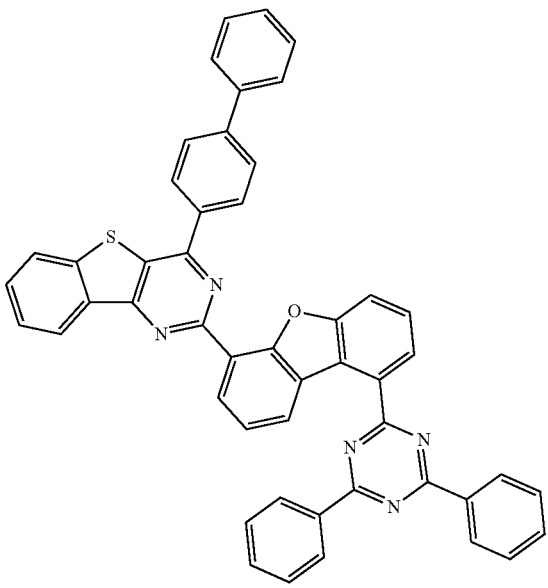

593
594
-continued
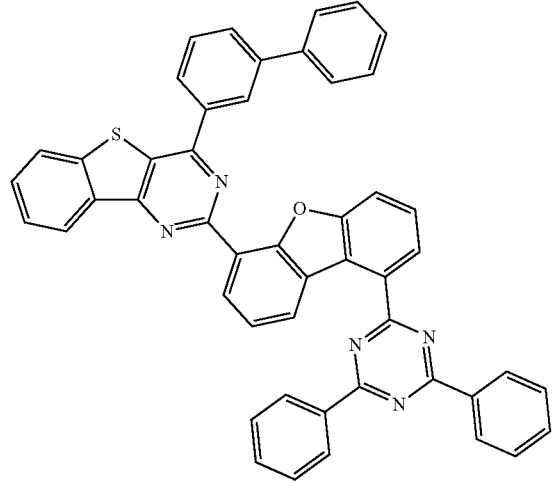
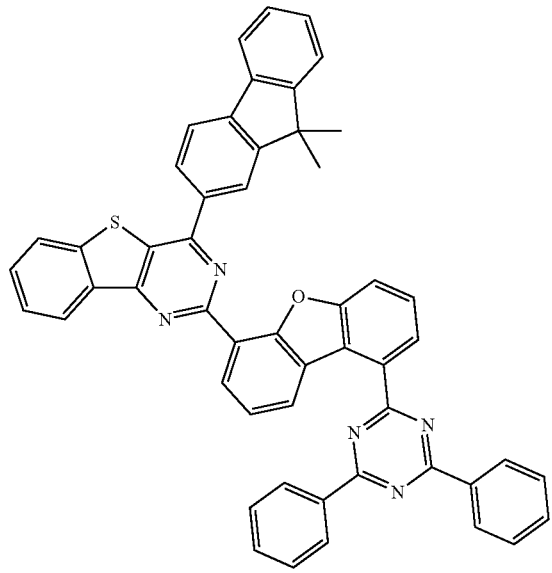
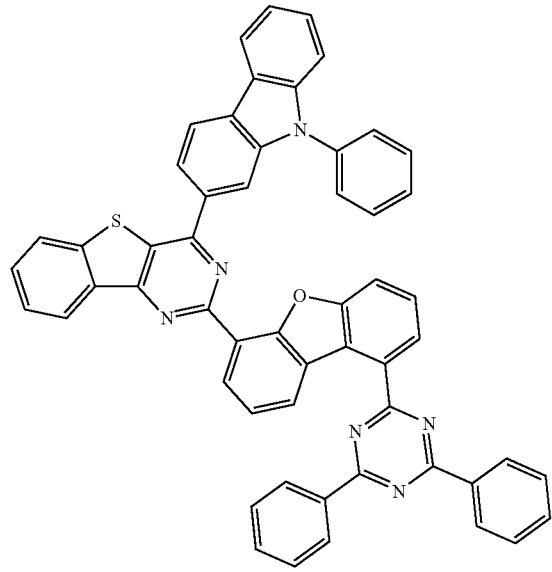
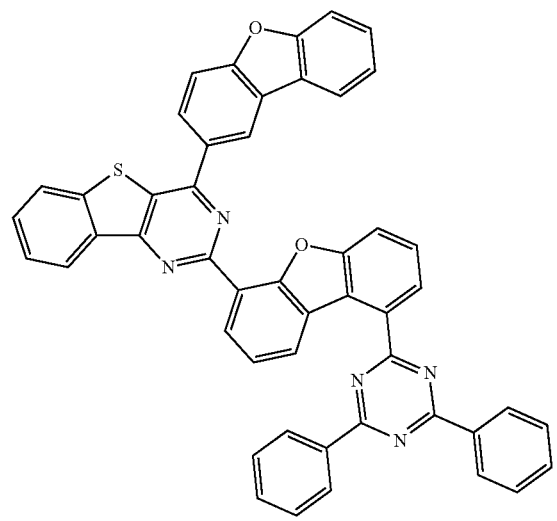
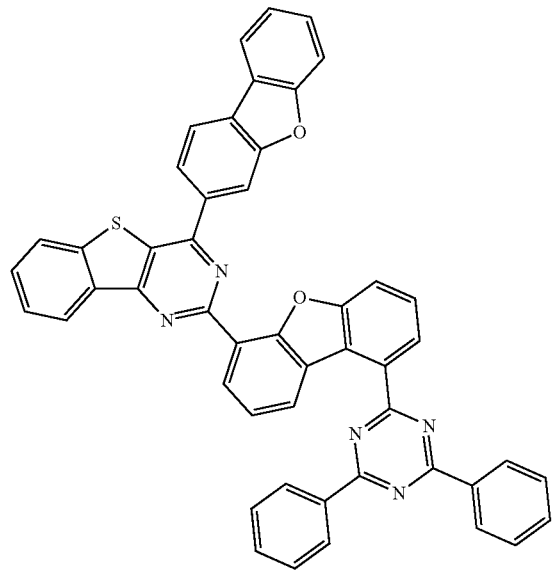
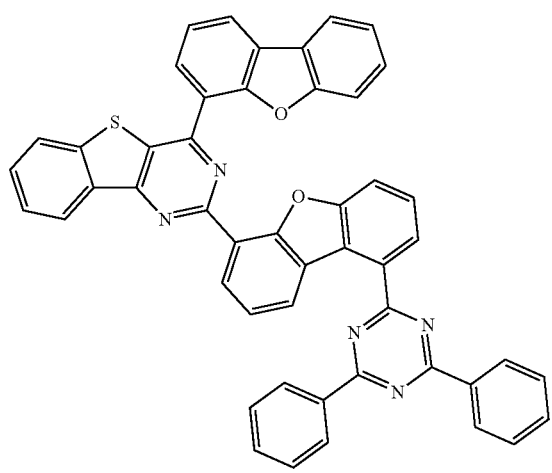

595
596
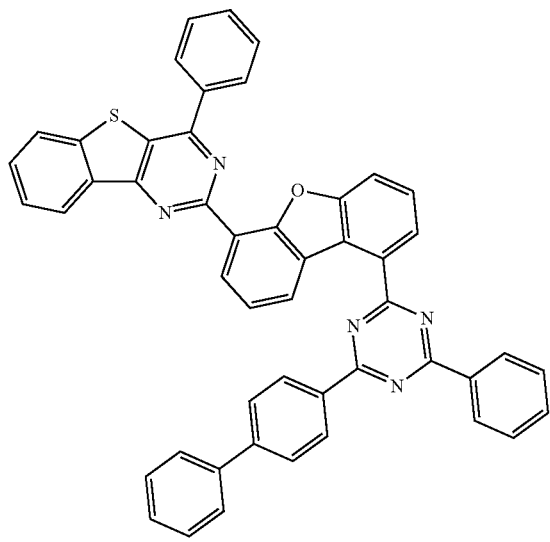
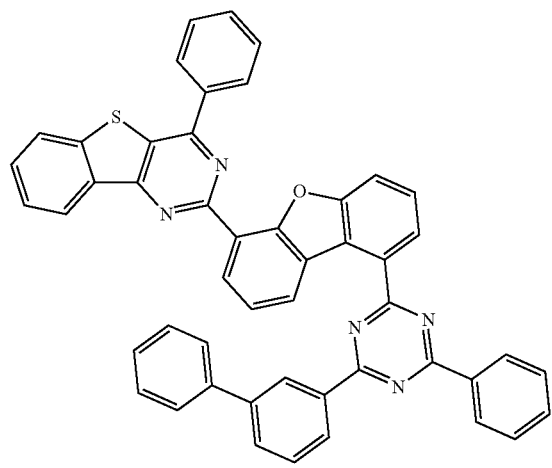
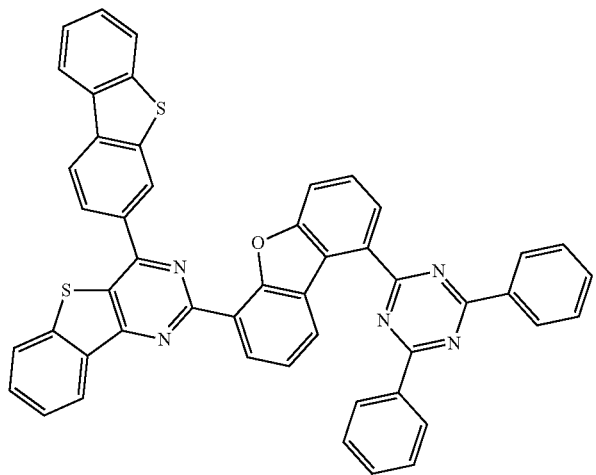
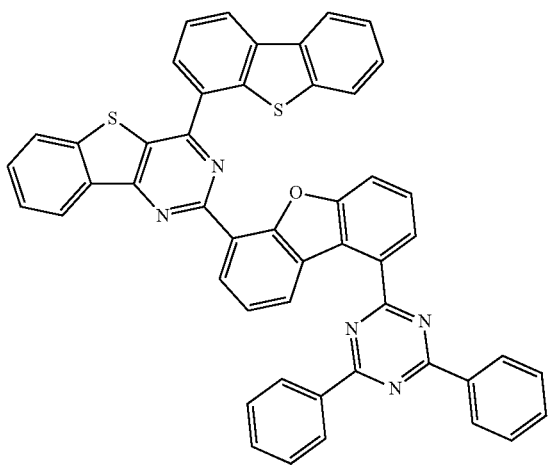
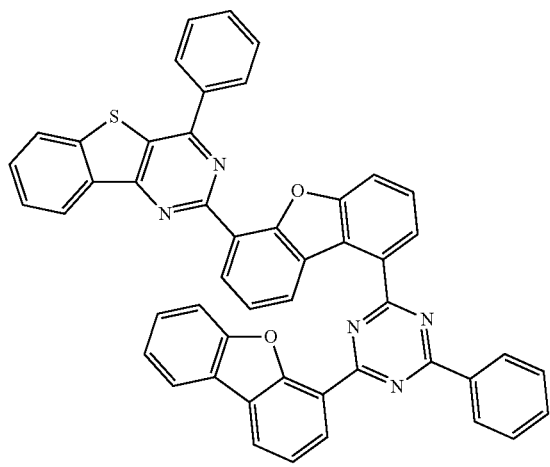
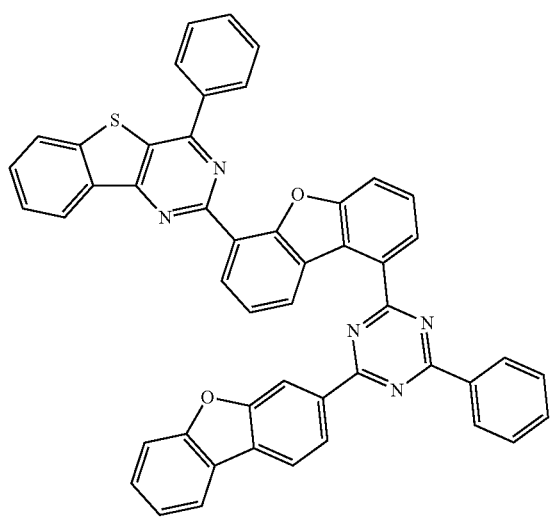

597
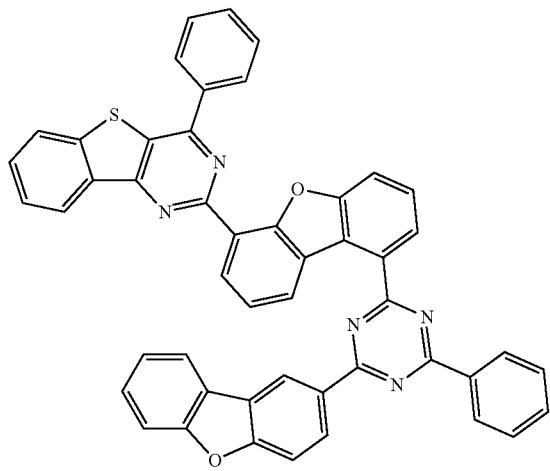
598
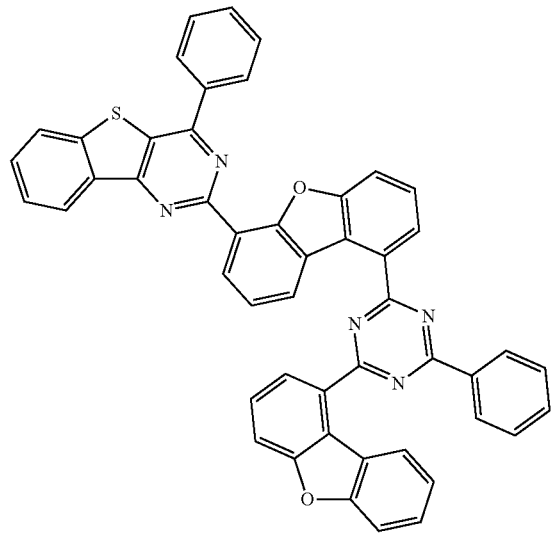
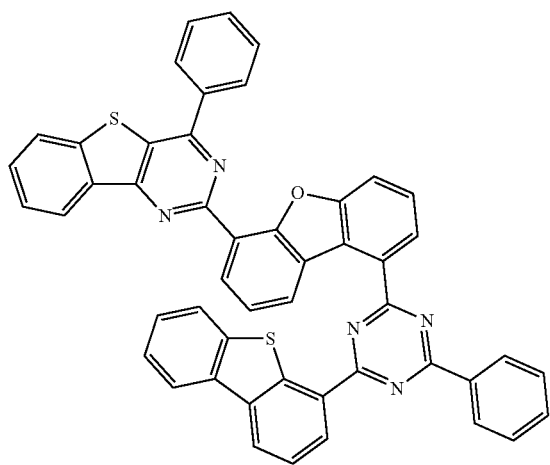
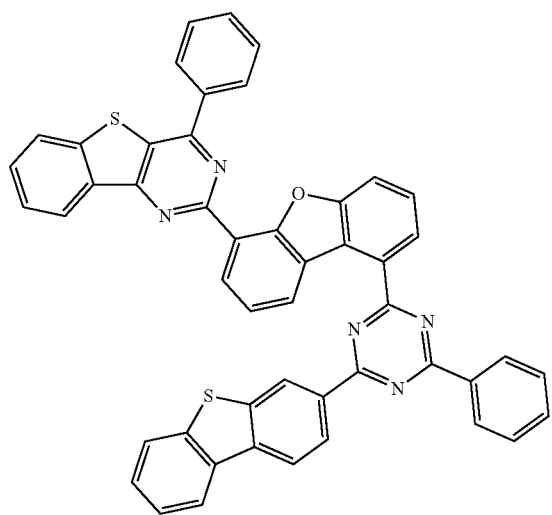
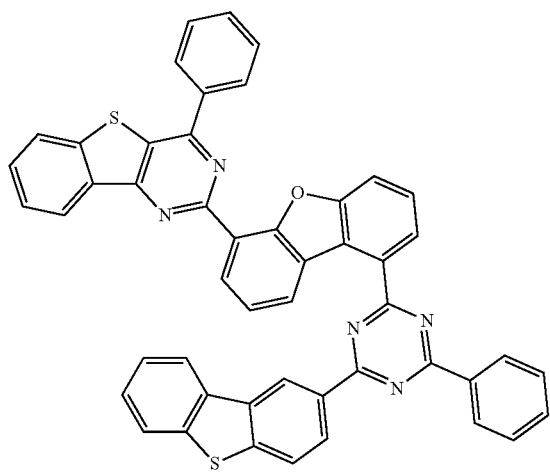
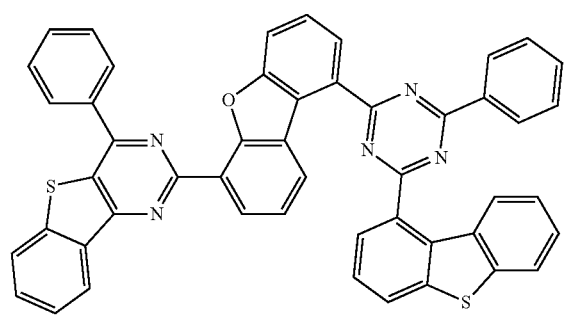

599
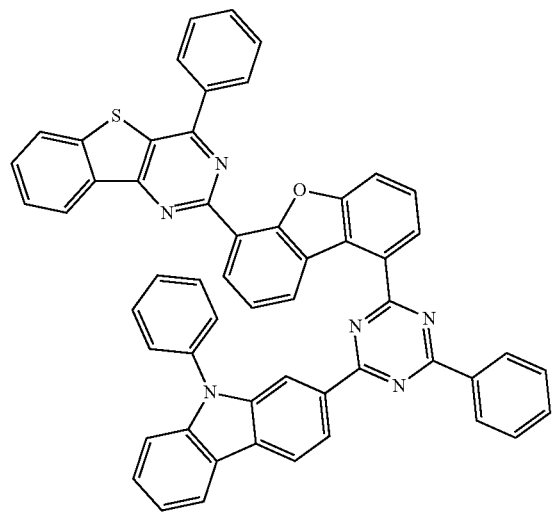
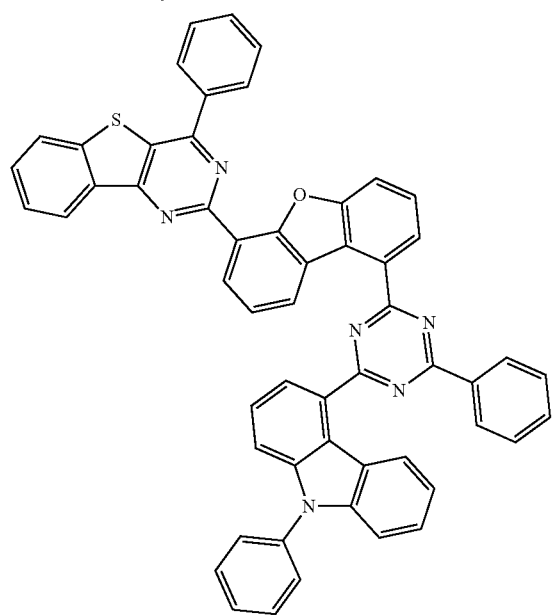
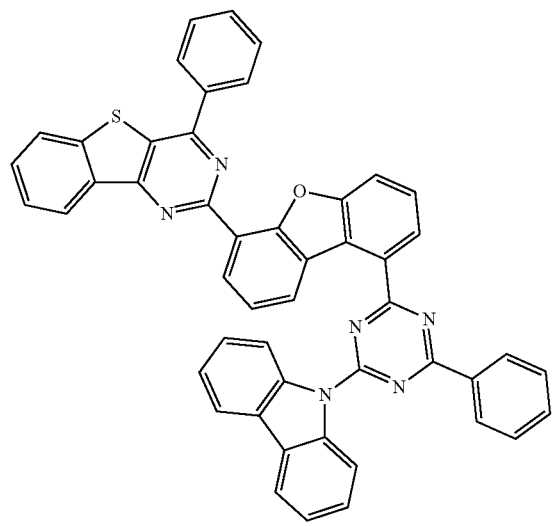
600
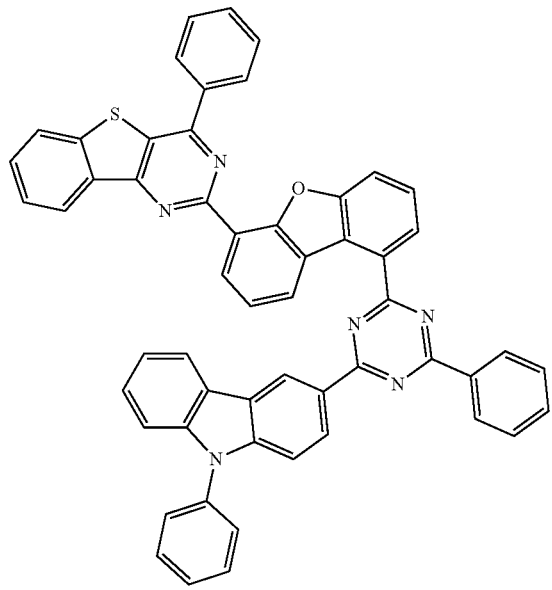
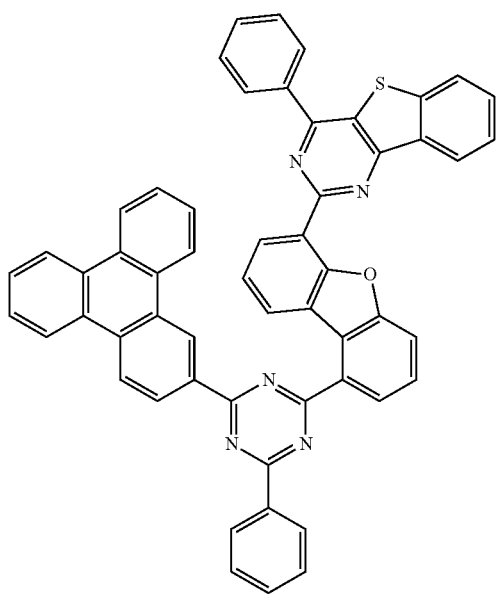
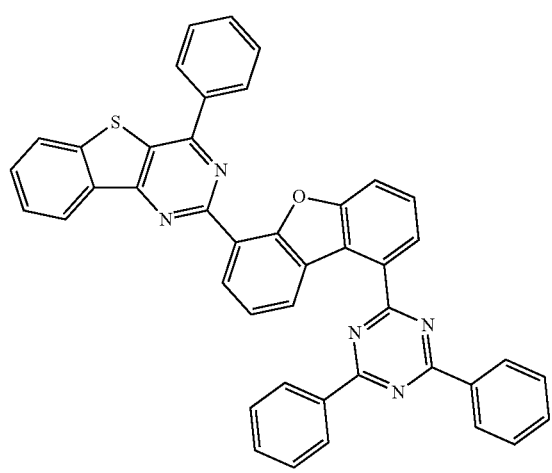

-continued
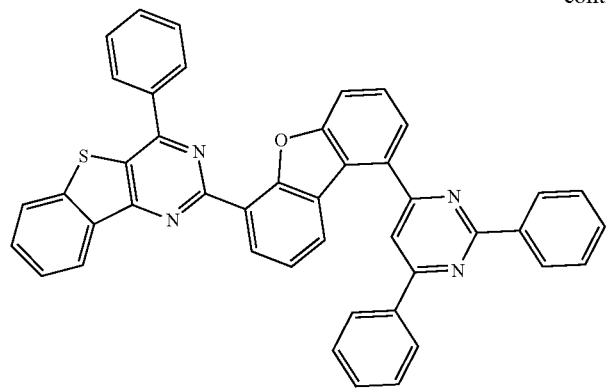
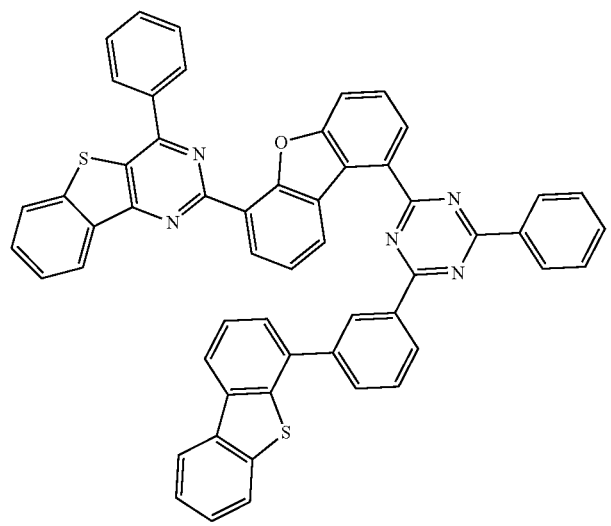
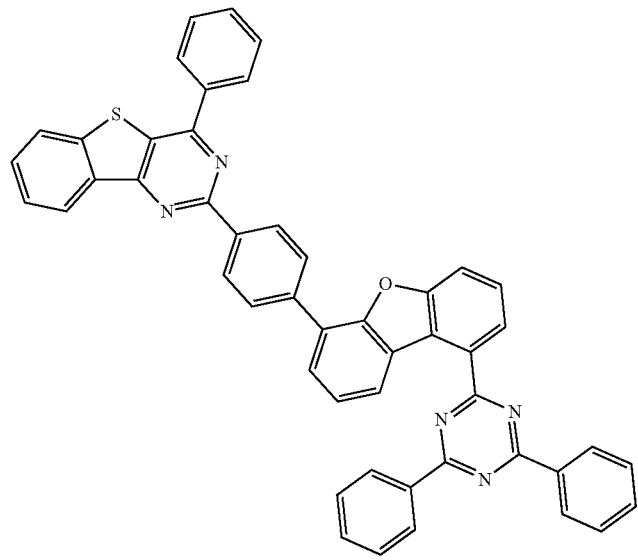

-continued
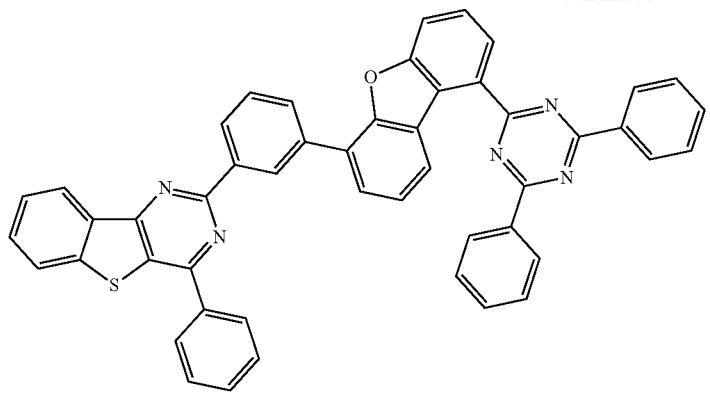
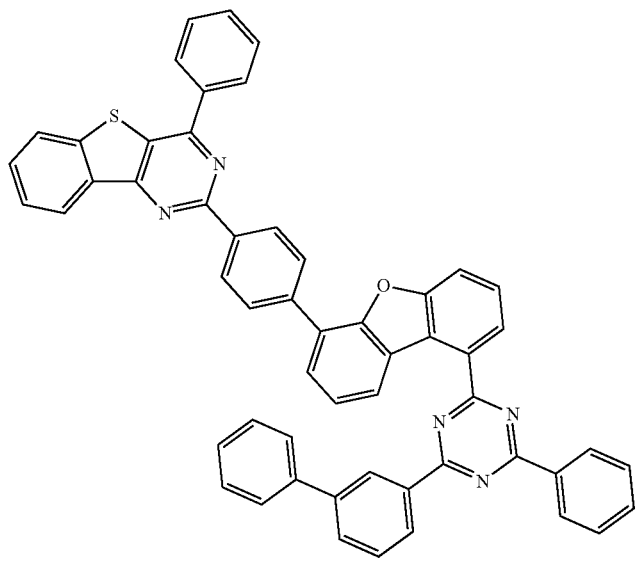
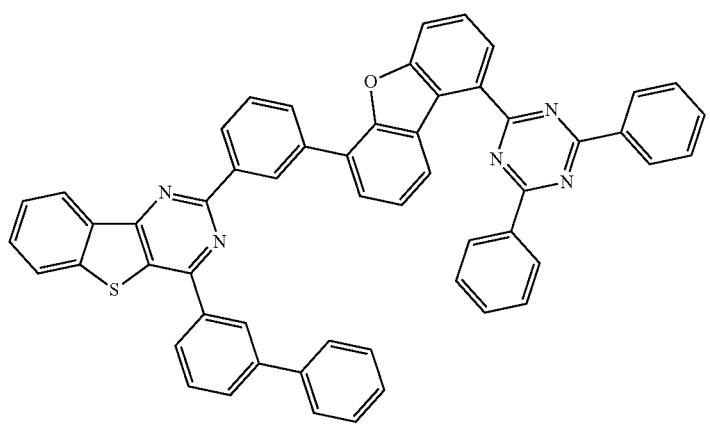

605
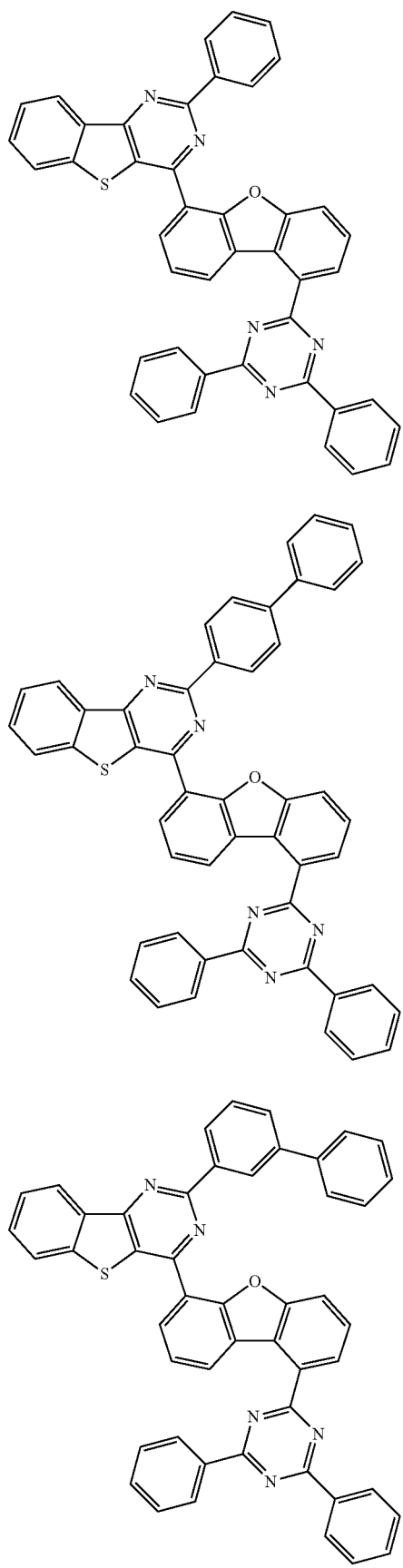
606
-continued
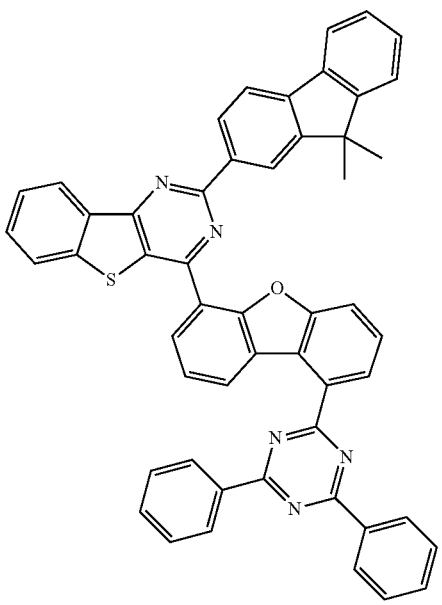
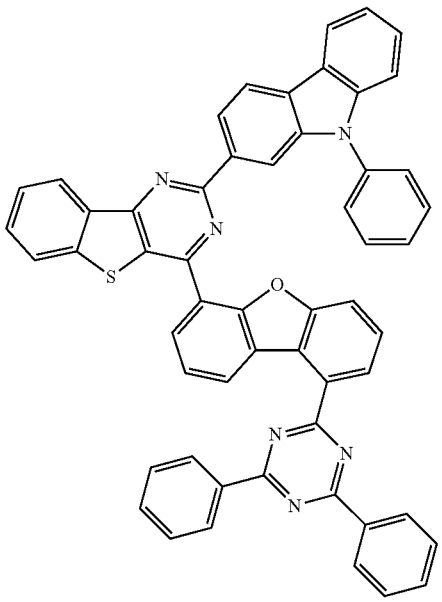

607
-continued
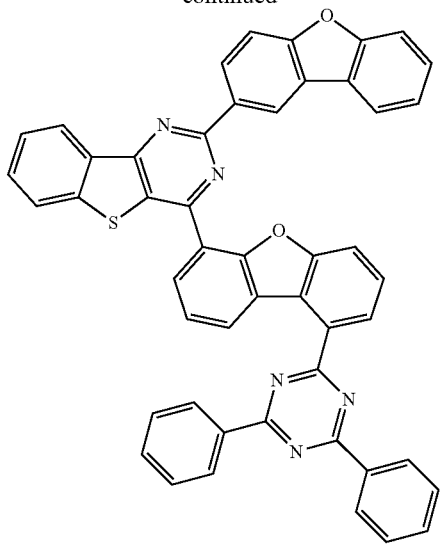
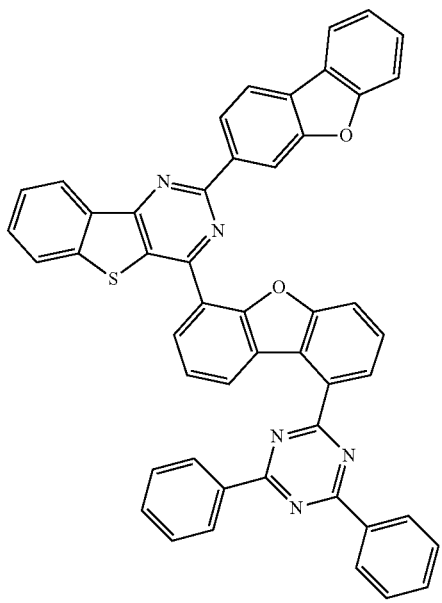
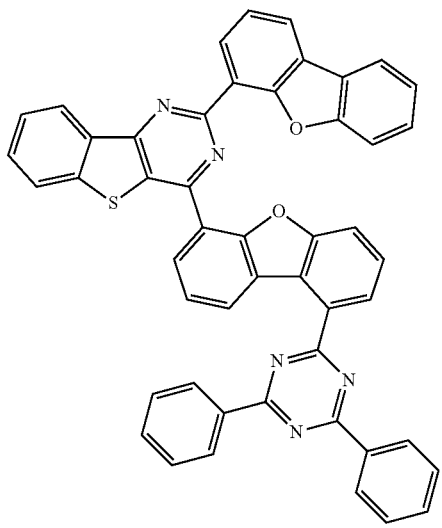
608
-continued
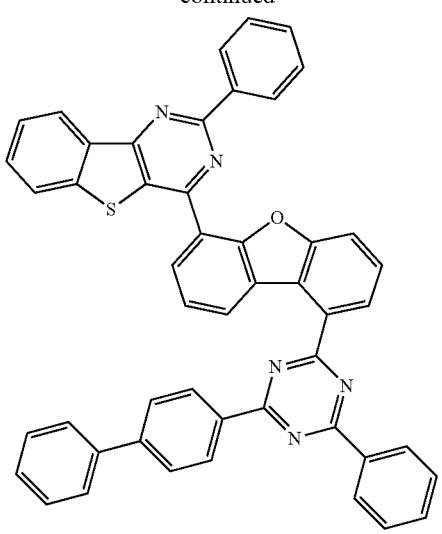
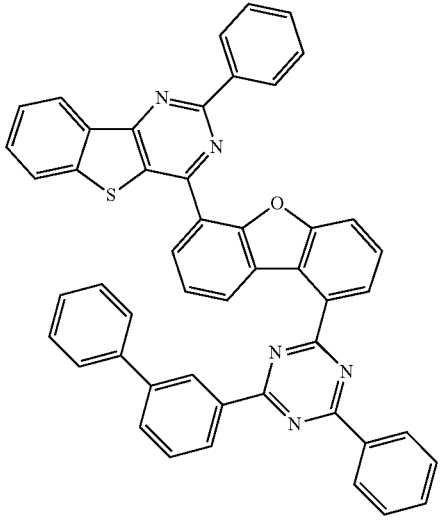
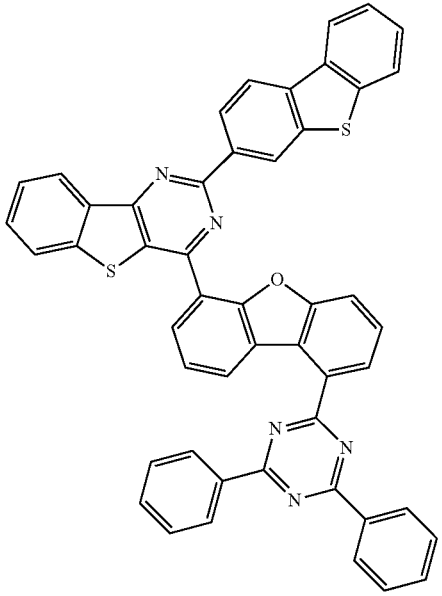

609
-continued
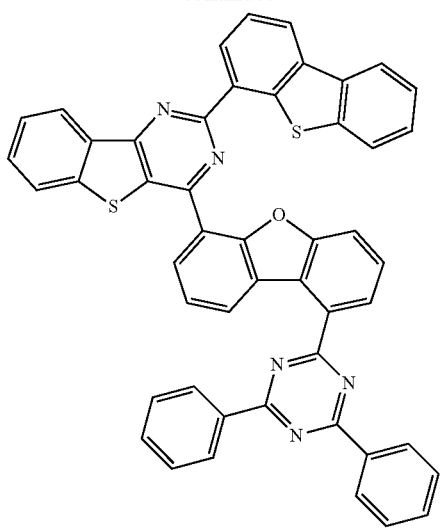
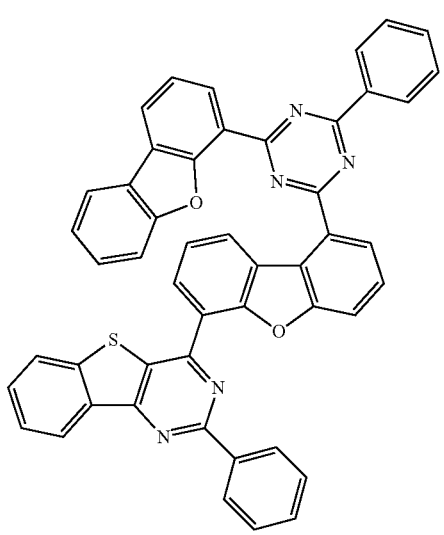
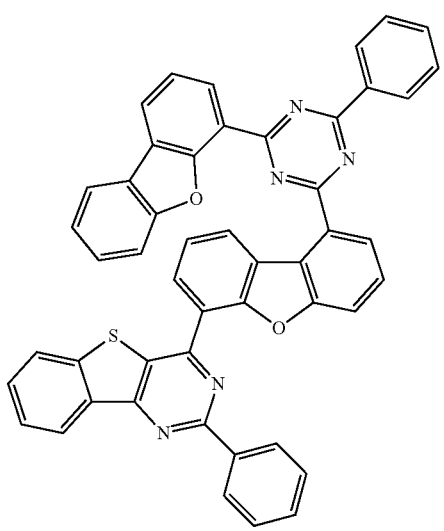
610
-continued
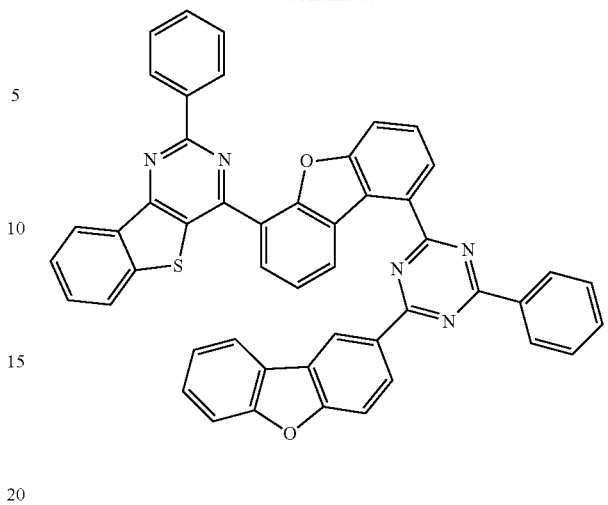
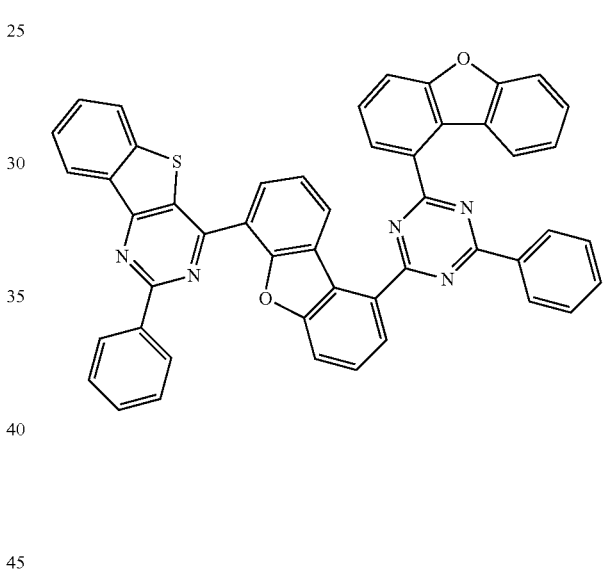
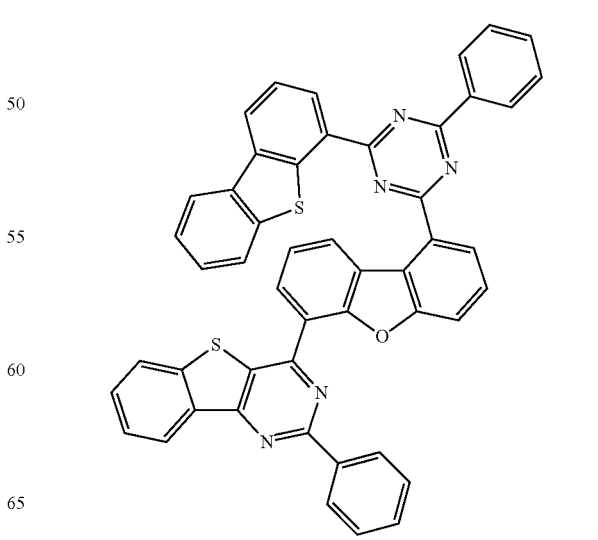

| 611 -continued | 612 -continued |
|---|---|
| 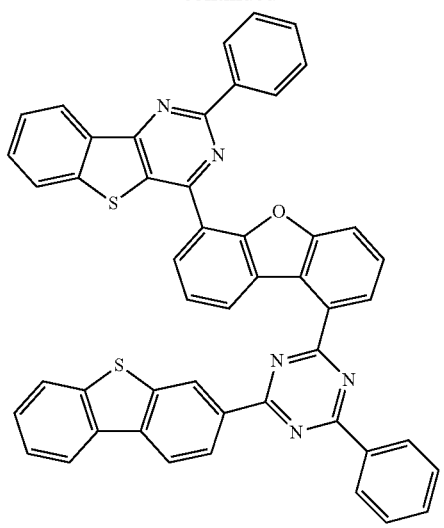 | 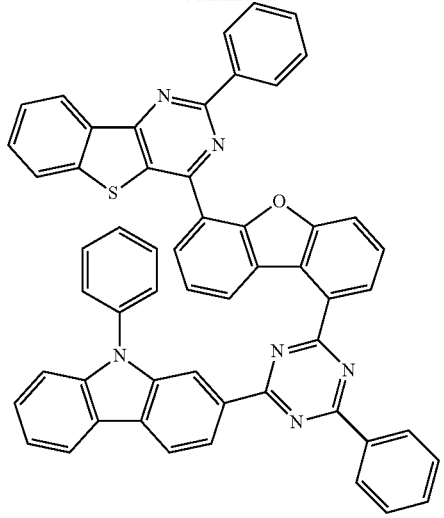 |
| 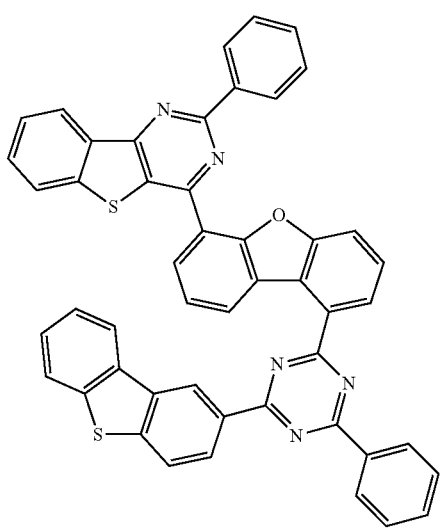 | 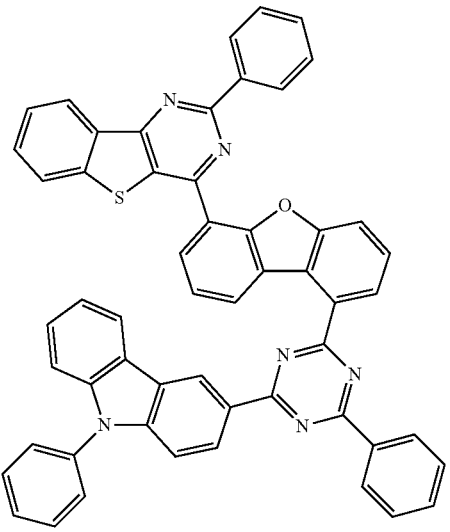 |
| 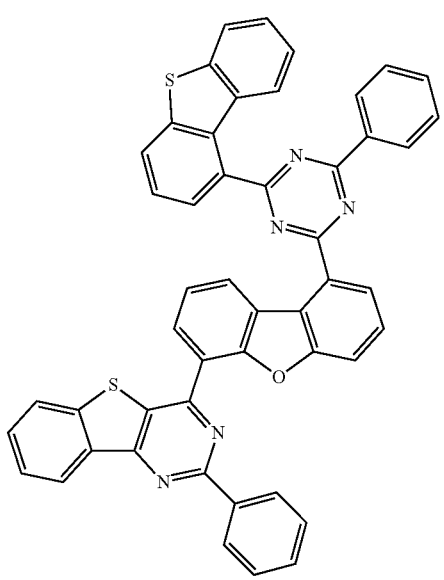 | 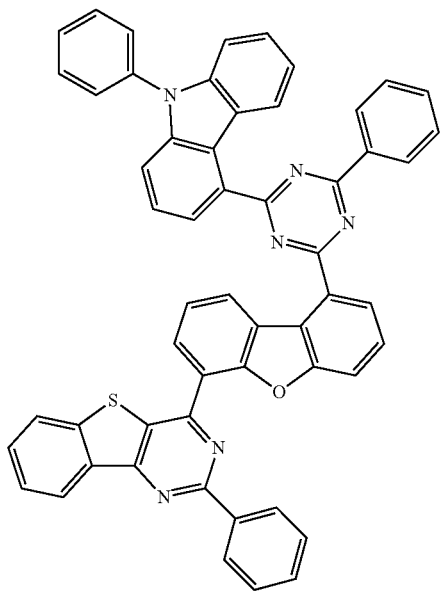 |

613
-continued
614
-continued
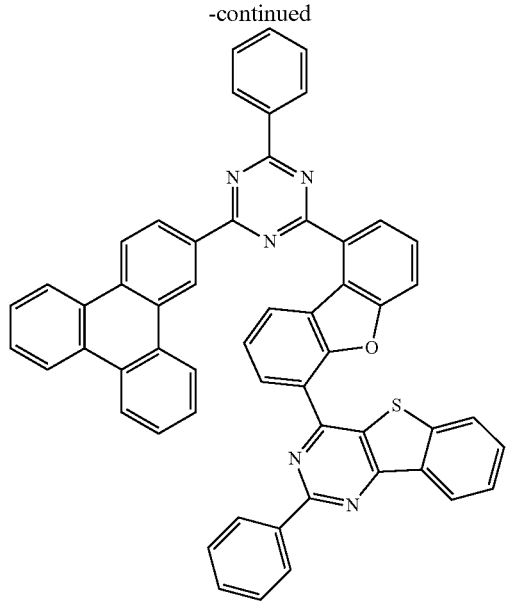
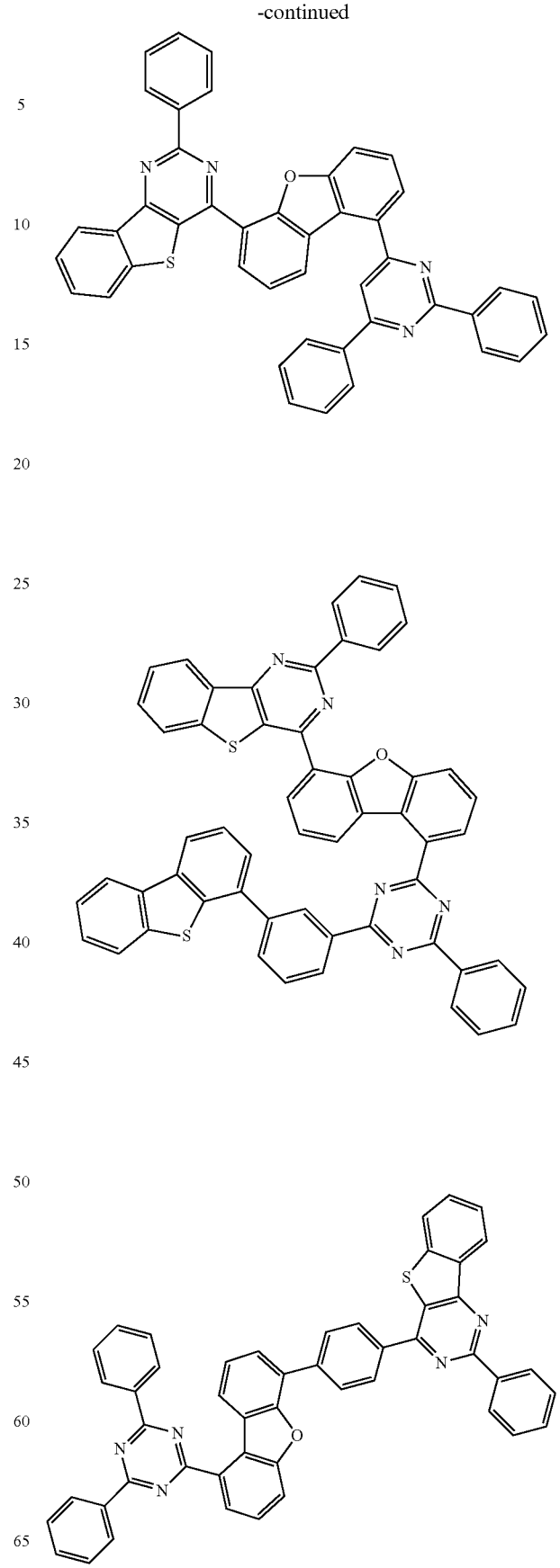

615
-continued
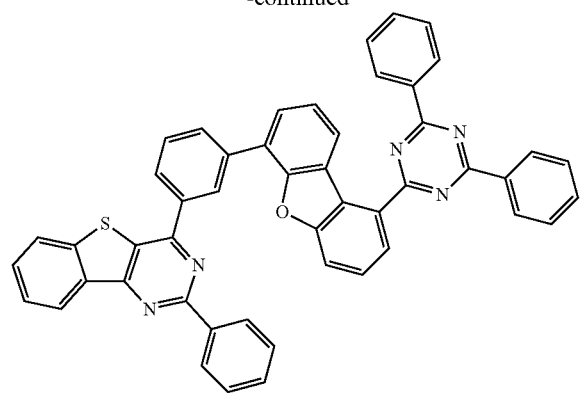
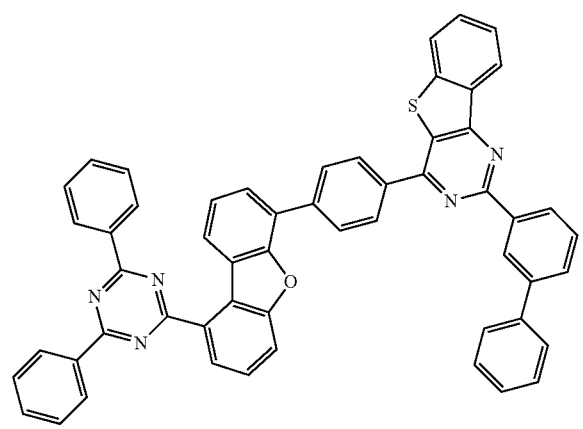
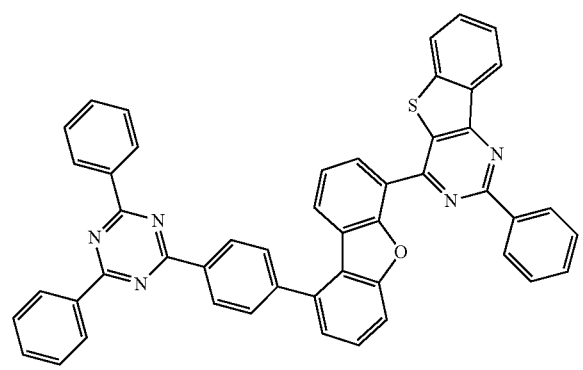
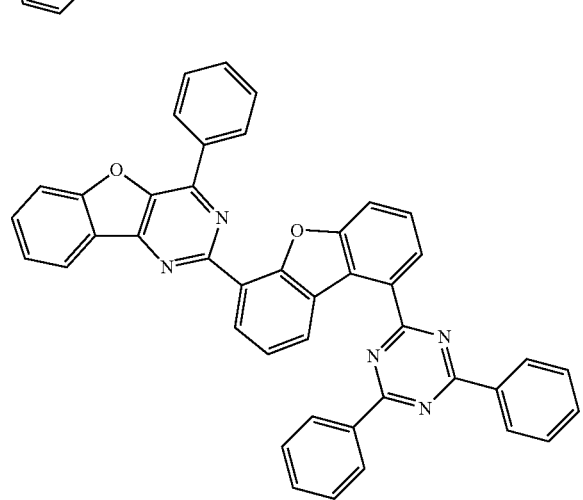
616
-continued
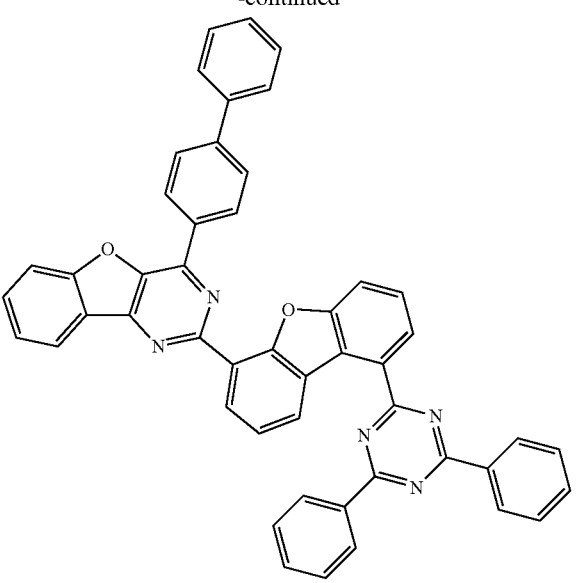
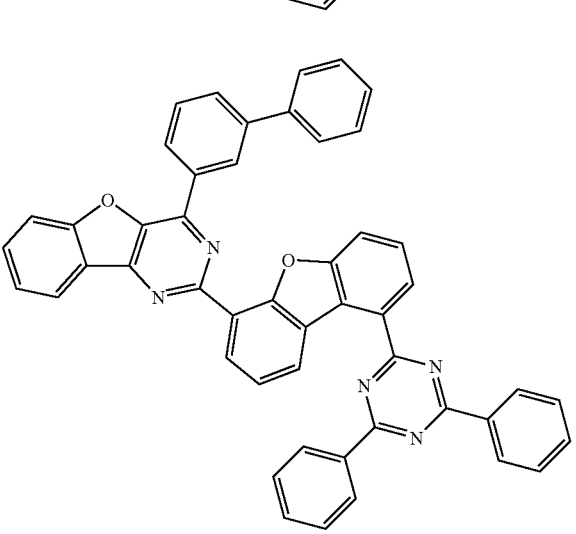
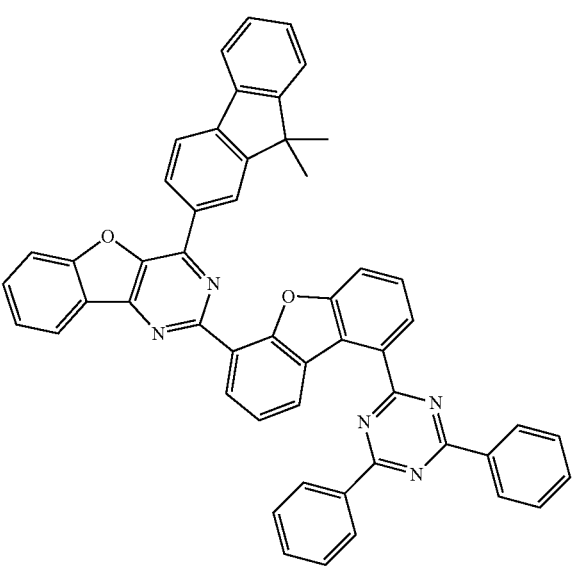
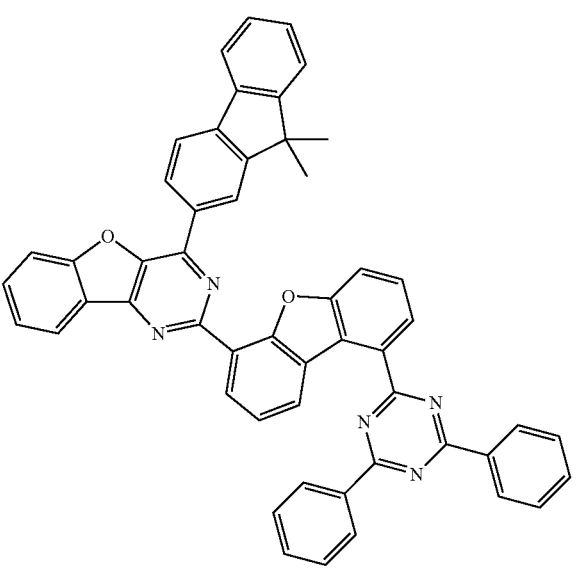

617
-continued
618
-continued
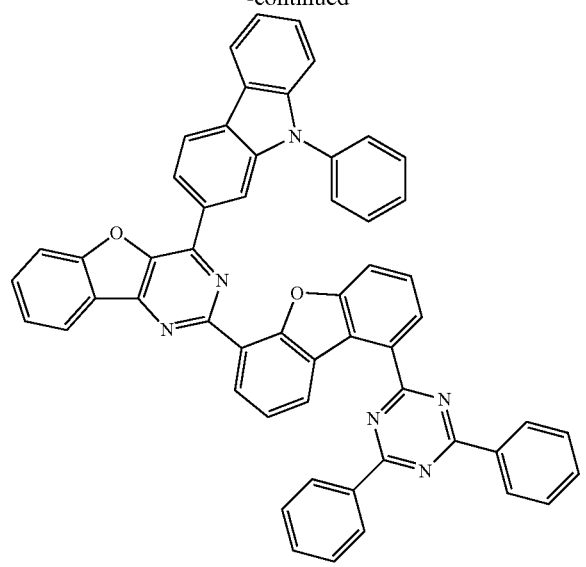
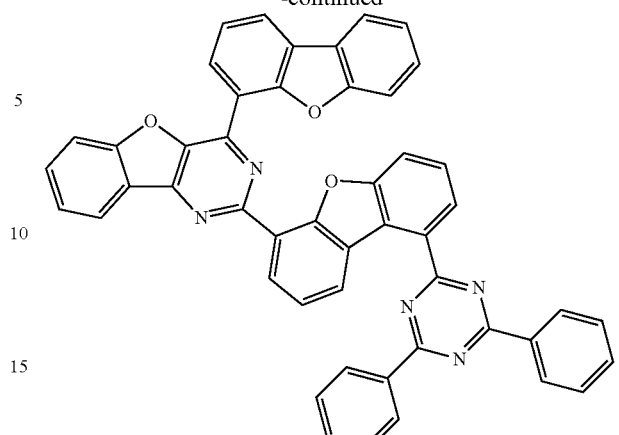
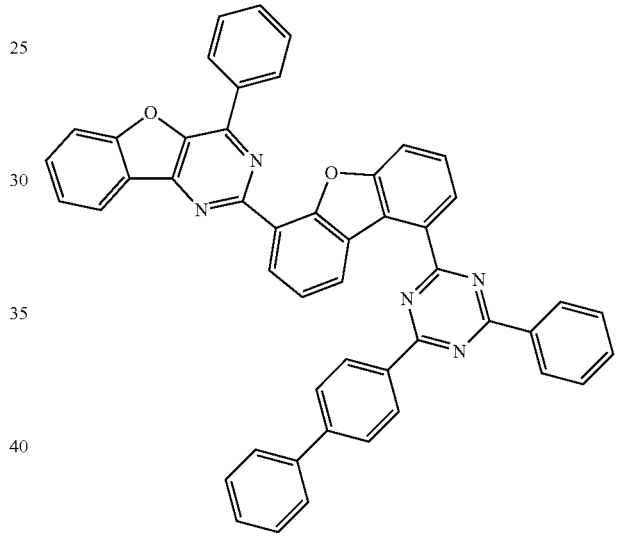
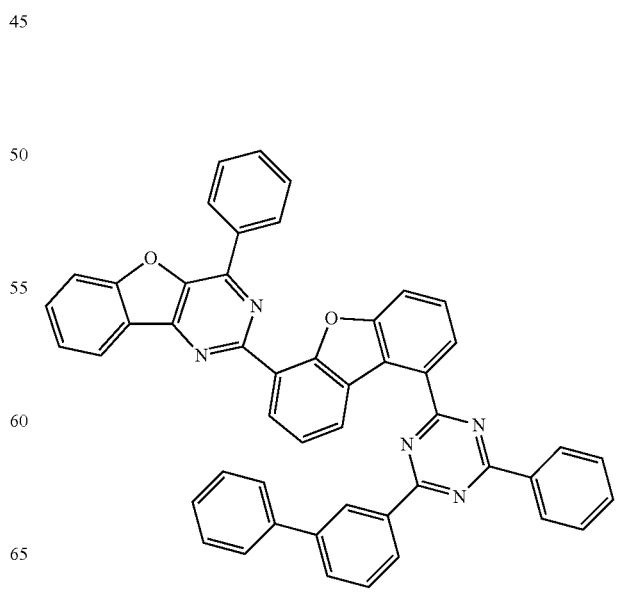

619
-continued
620
-continued
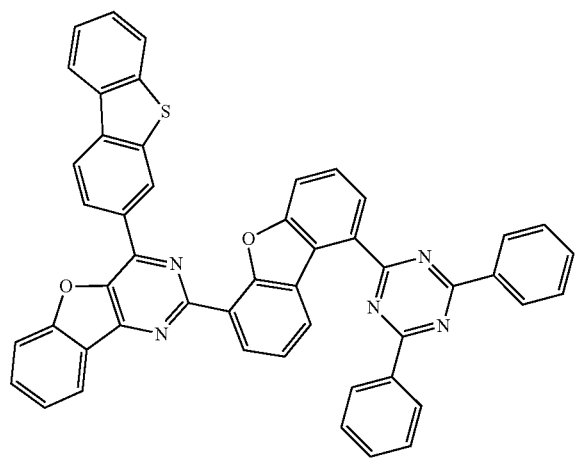
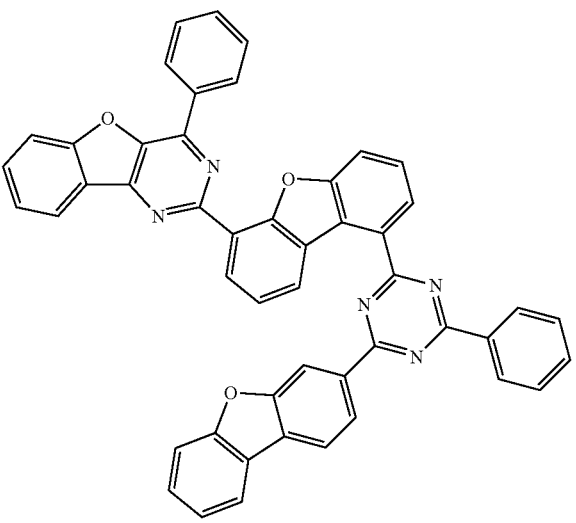
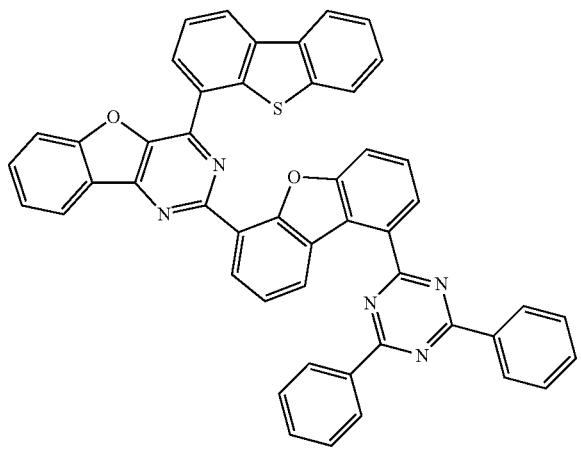
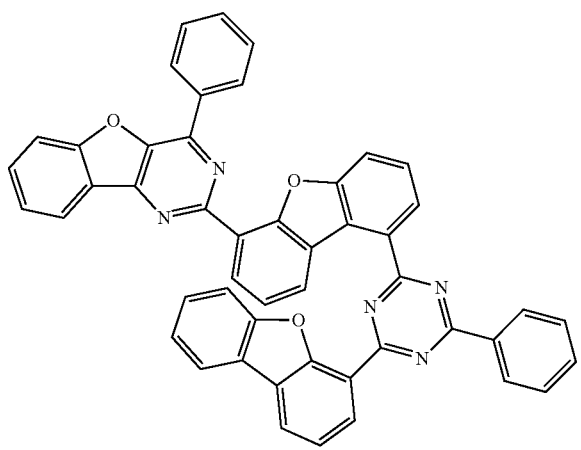
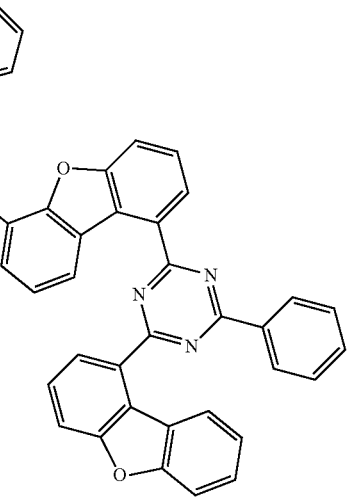

621
-continued
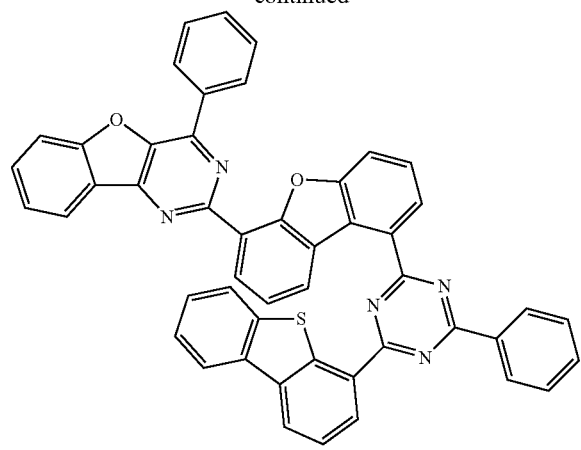
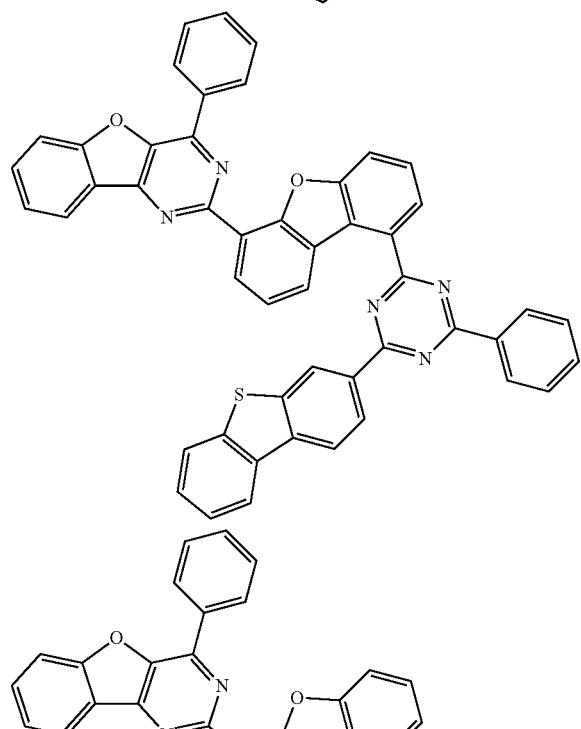
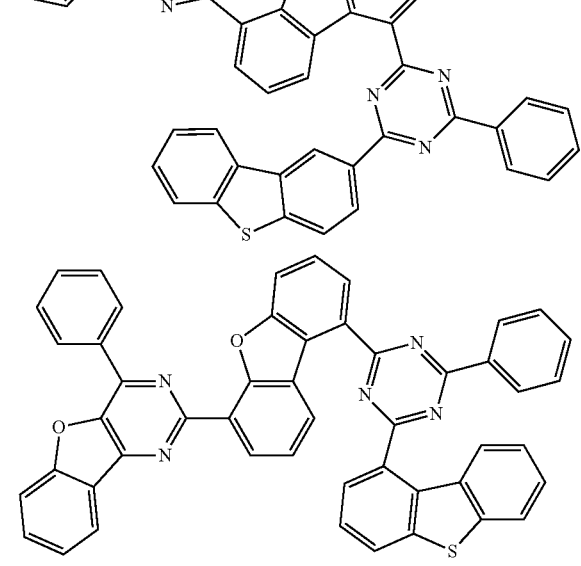
622
-continued
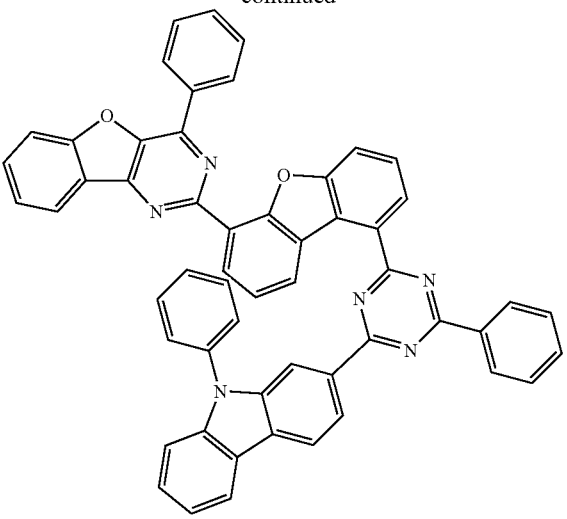
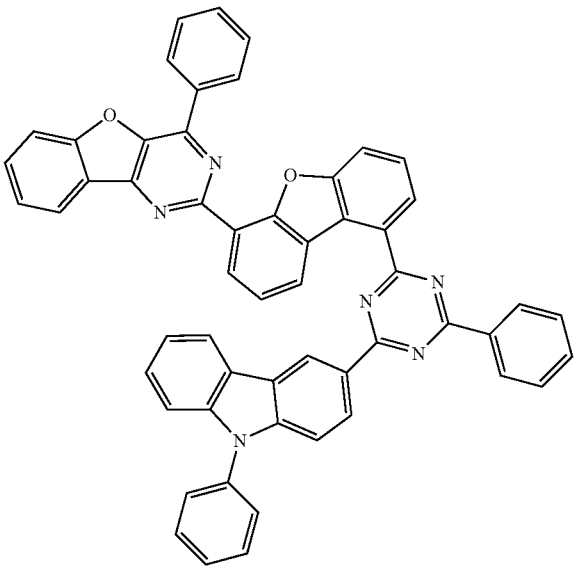
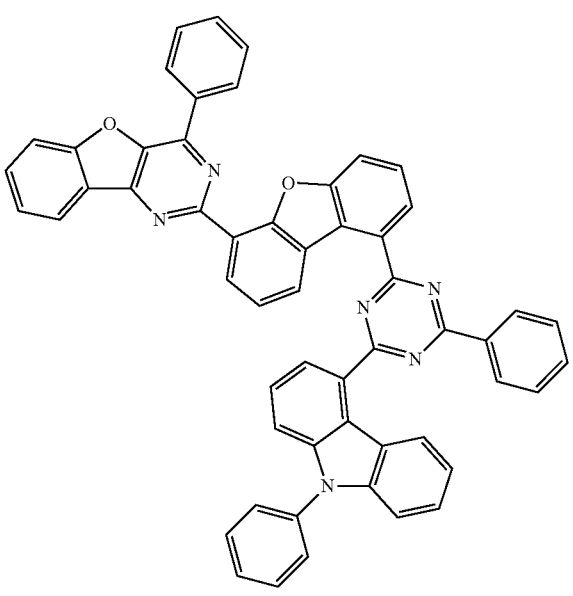

623
-continued
624
-continued
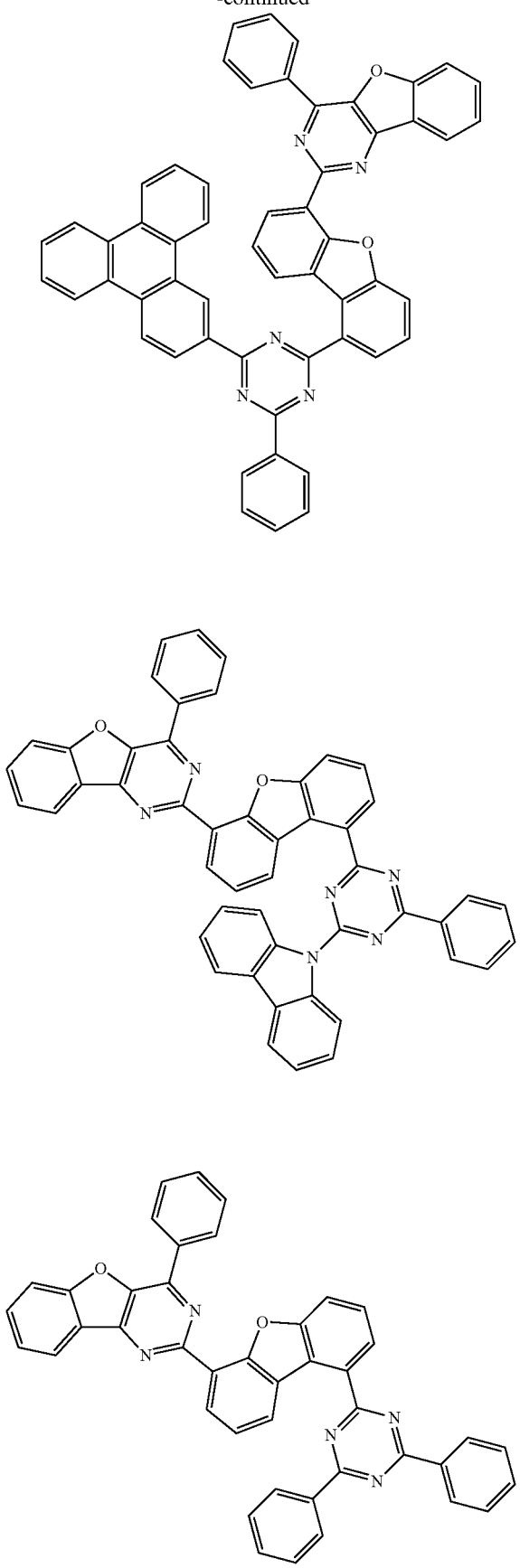
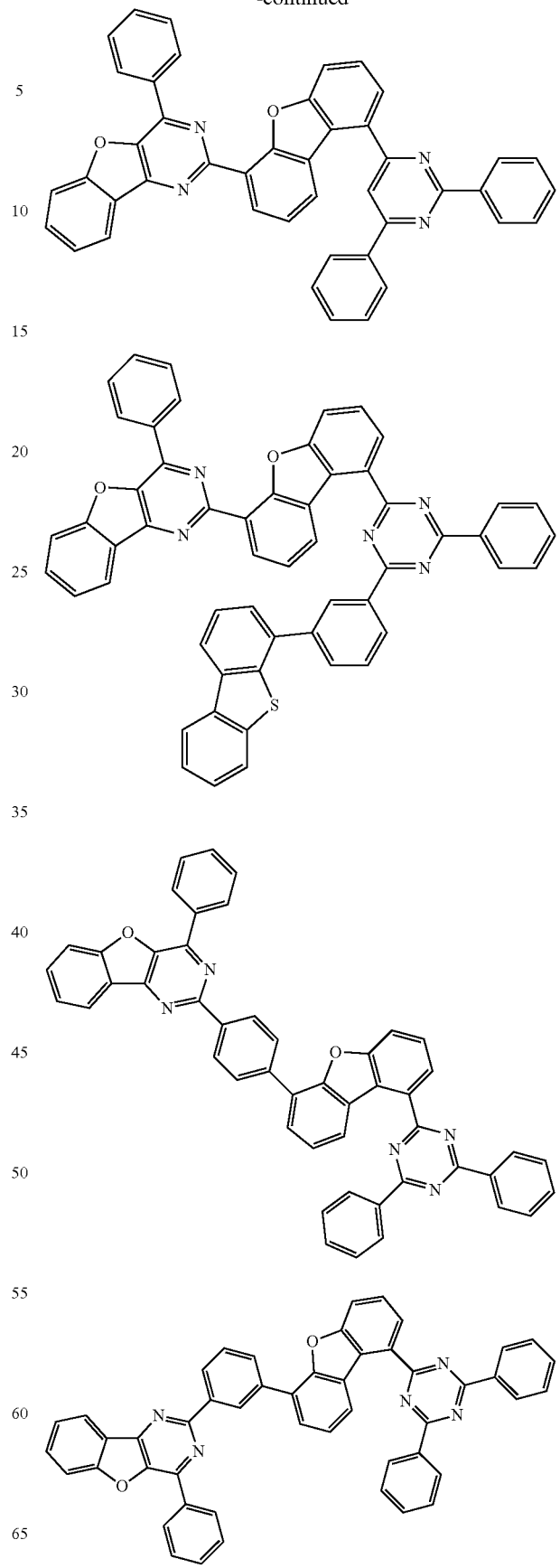

625
-continued
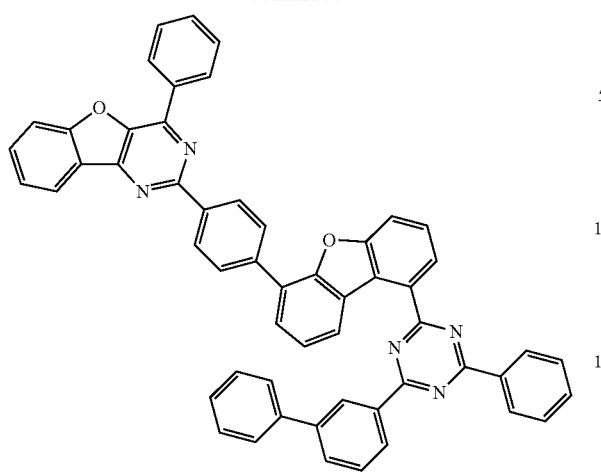
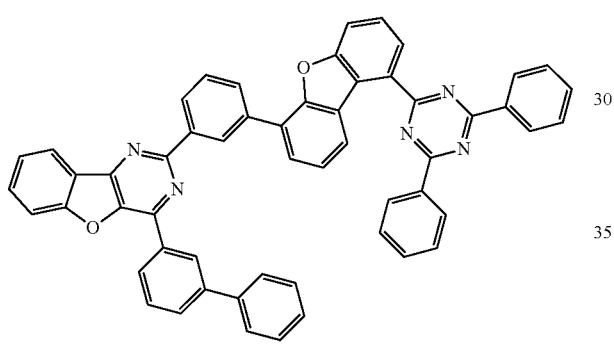
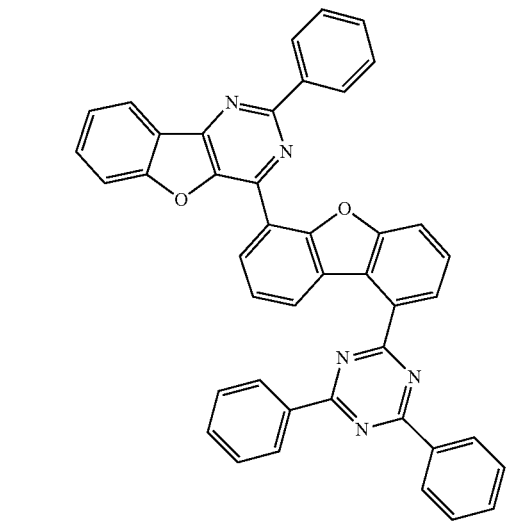
626
-continued
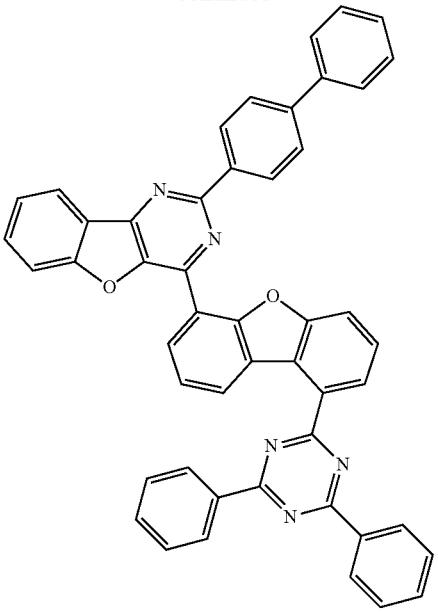
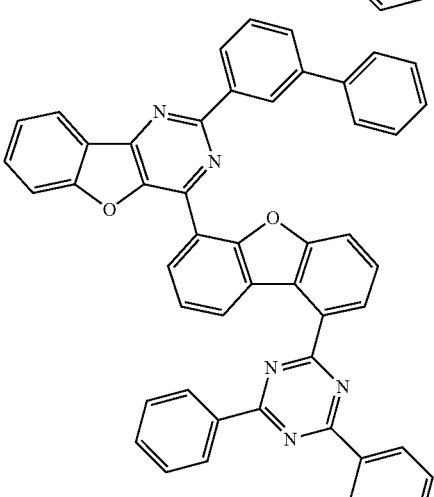
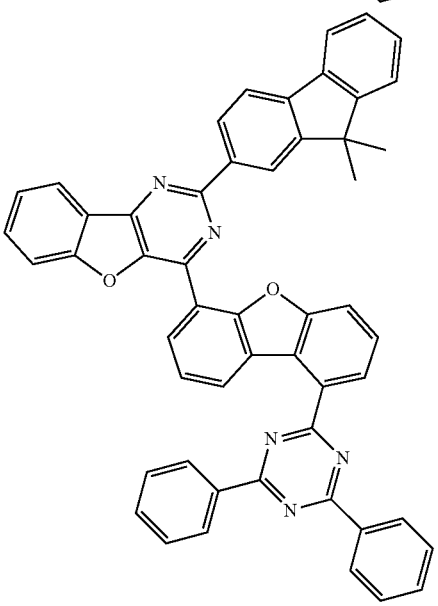

627
-continued
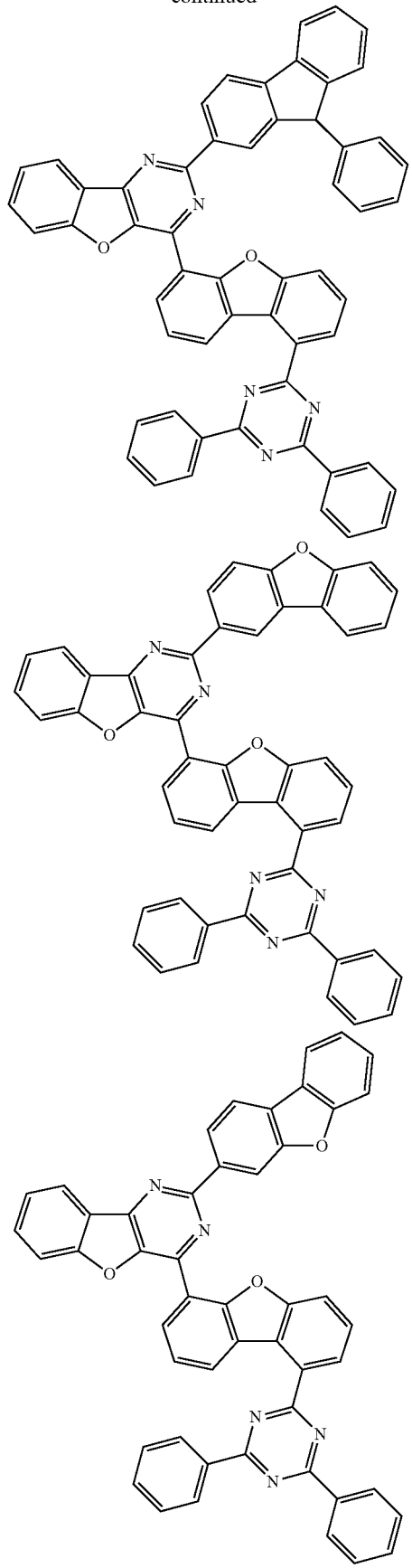
628
-continued
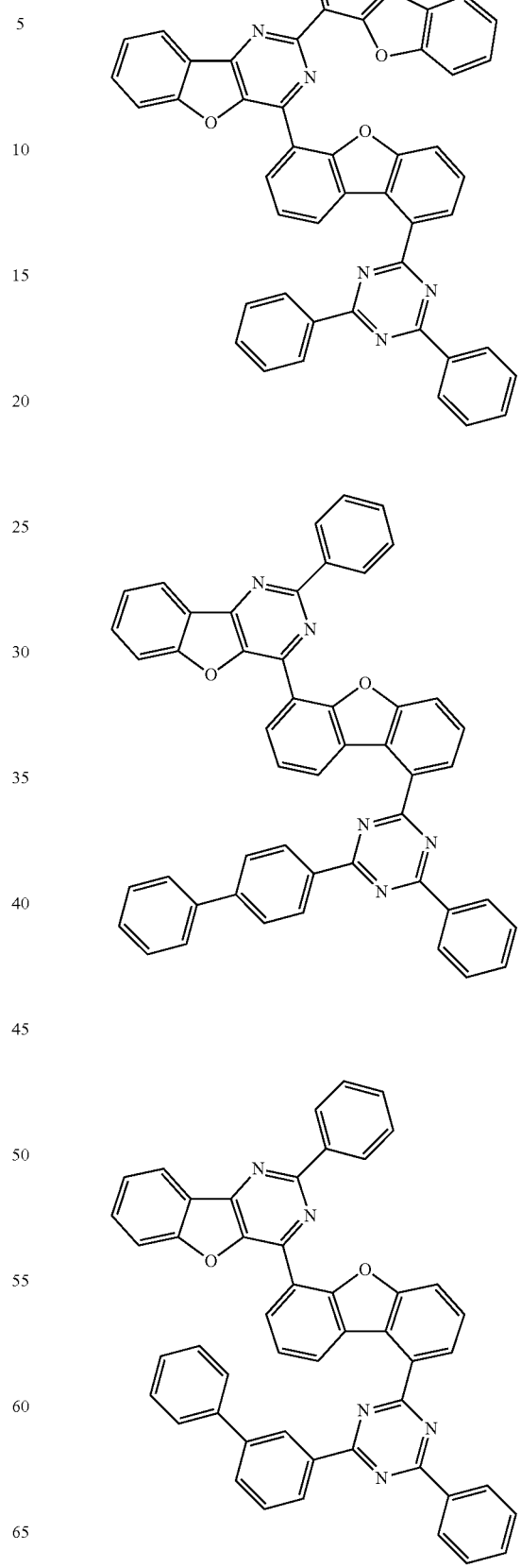

629 -continued
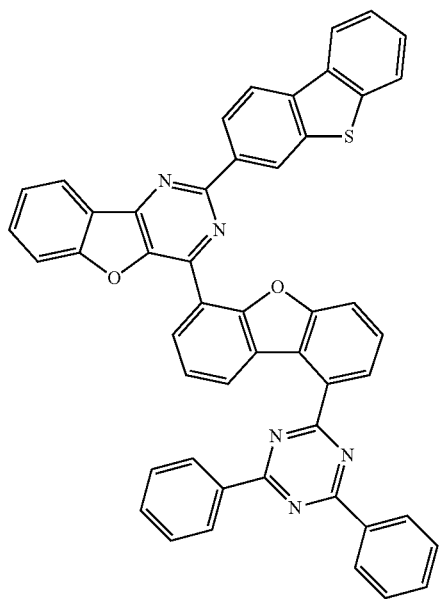
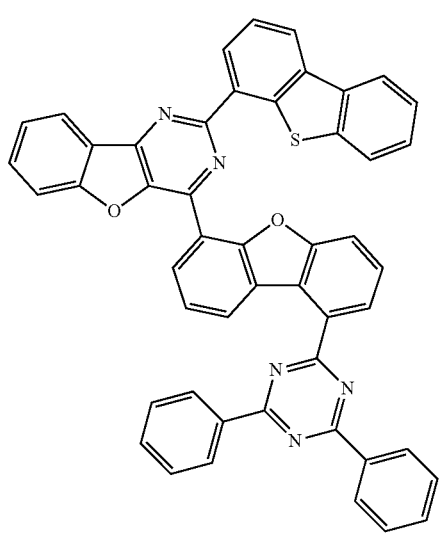
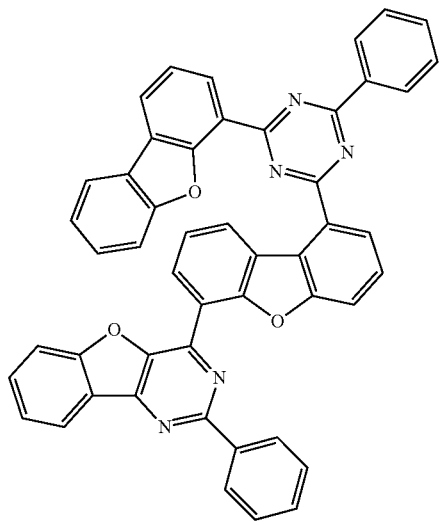
630 -continued
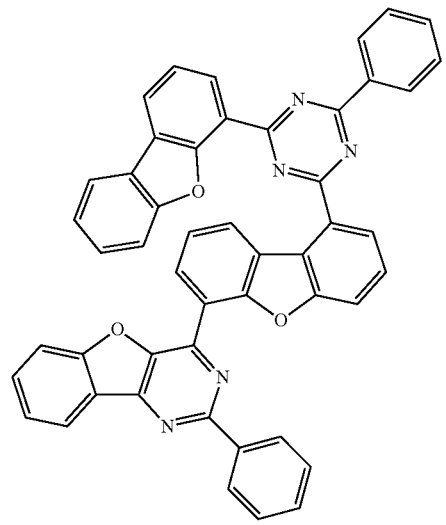
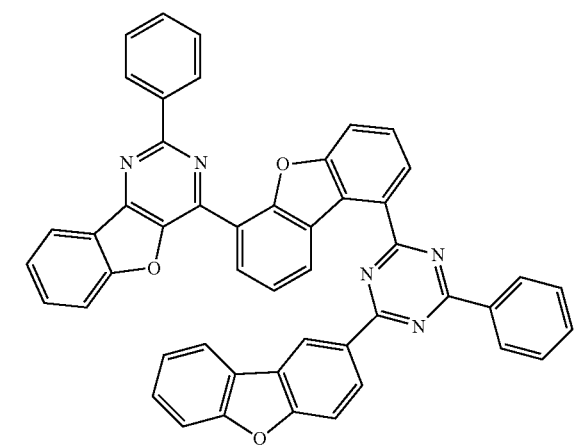
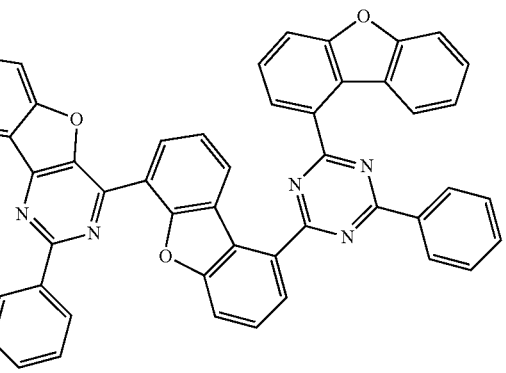

631
-continued
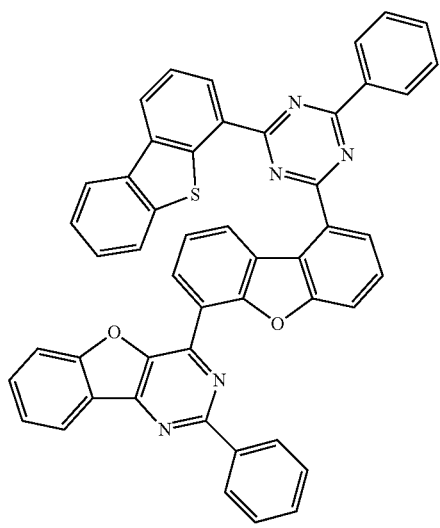
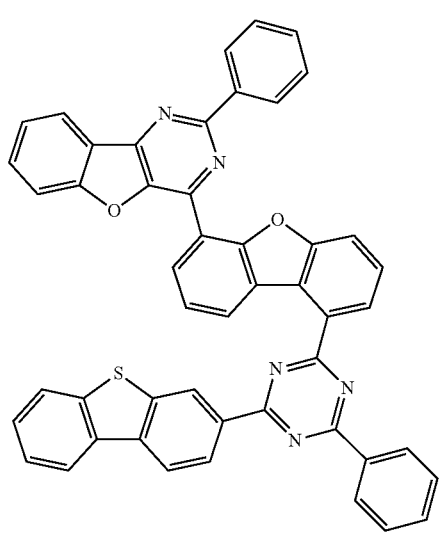
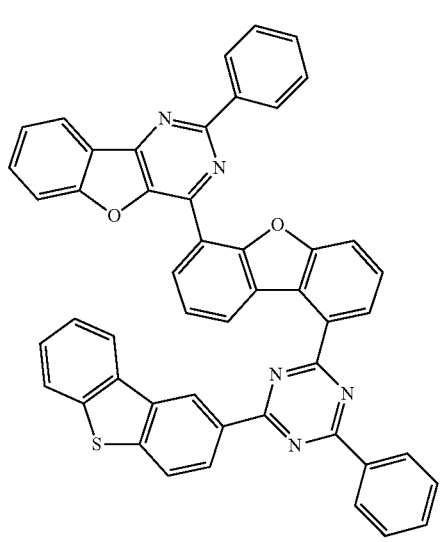
632
-continued
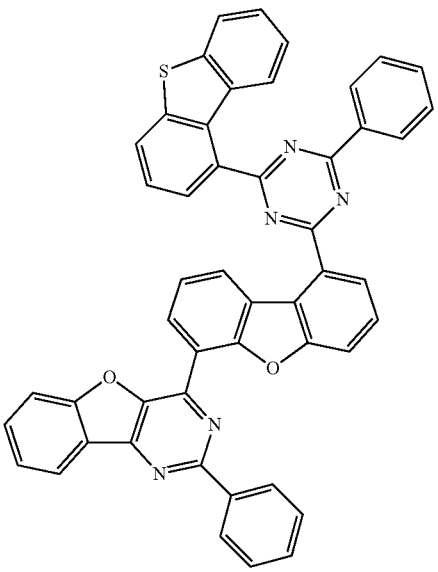
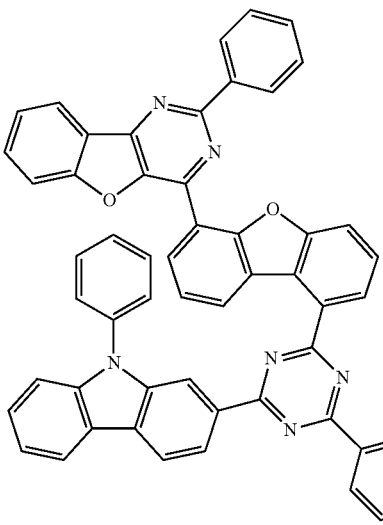
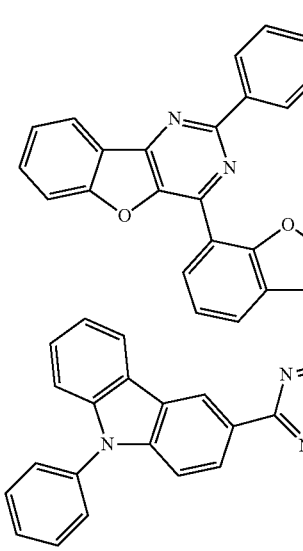

633
-continued
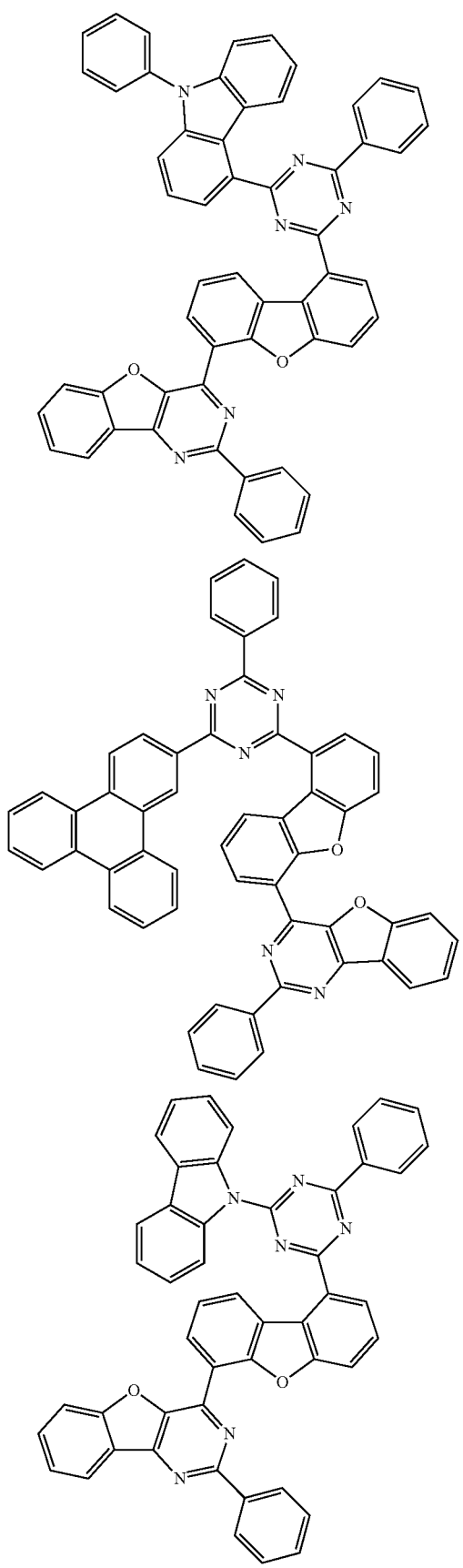
634
-continued
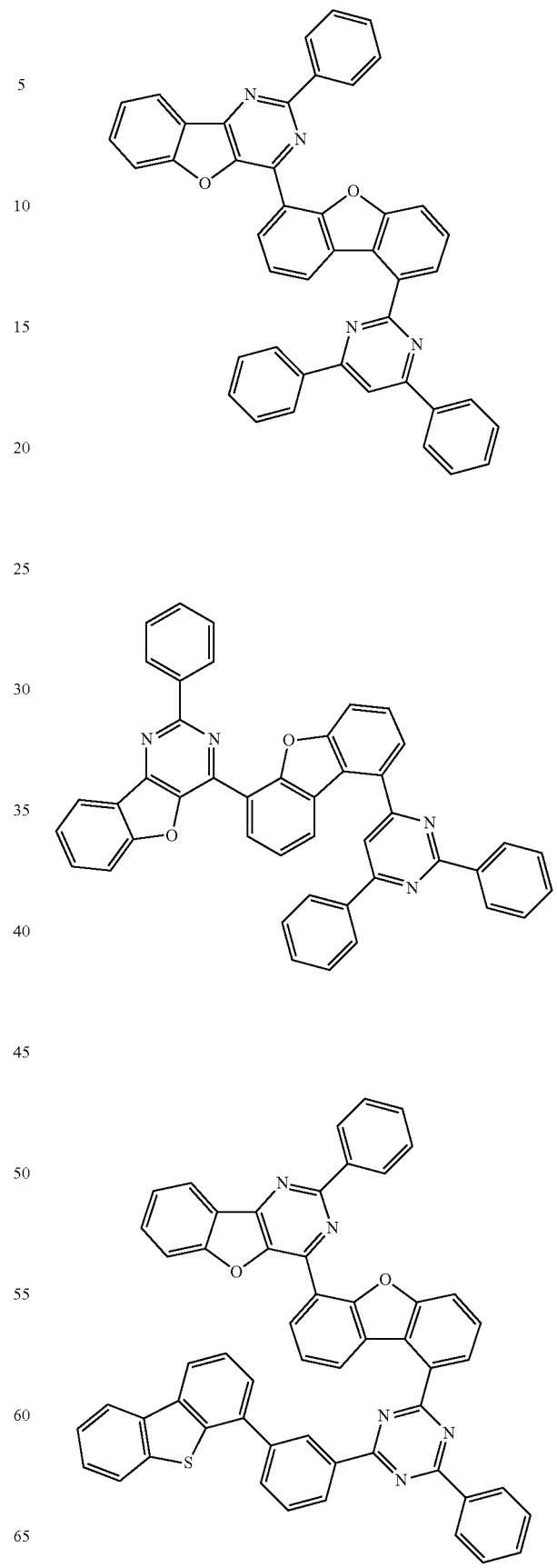

635
-continued
636
-continued
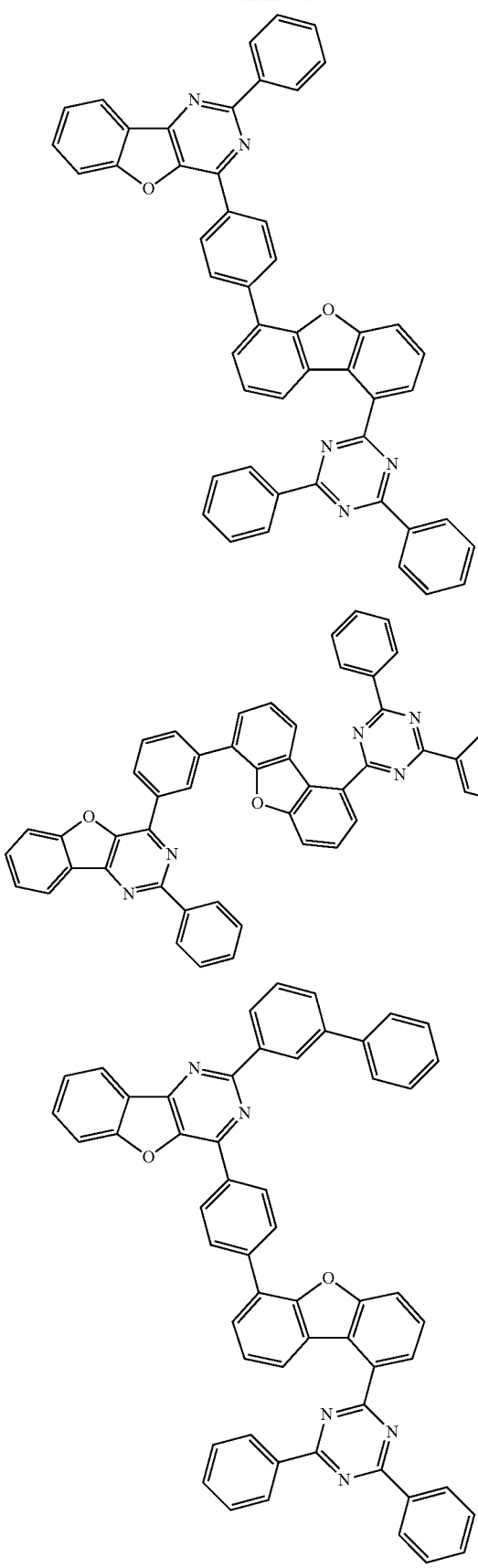
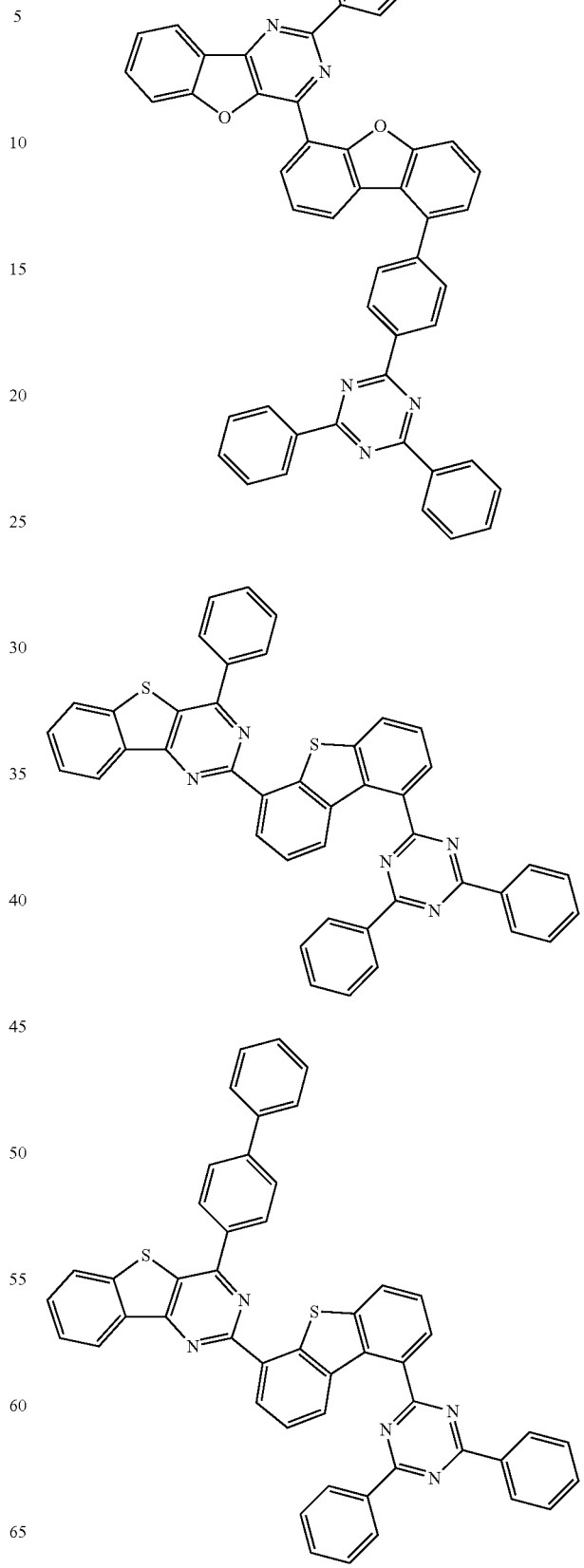

637
-continued
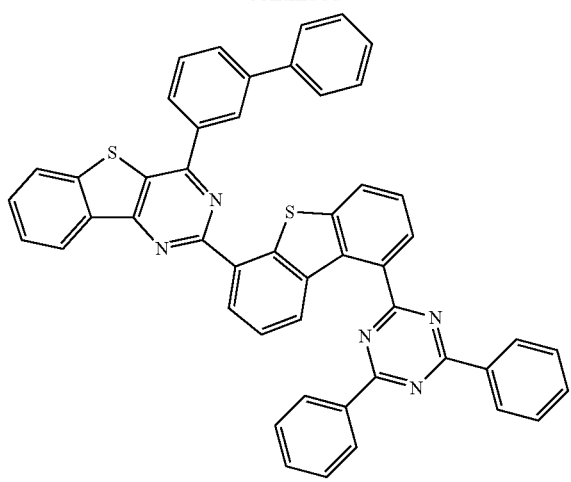
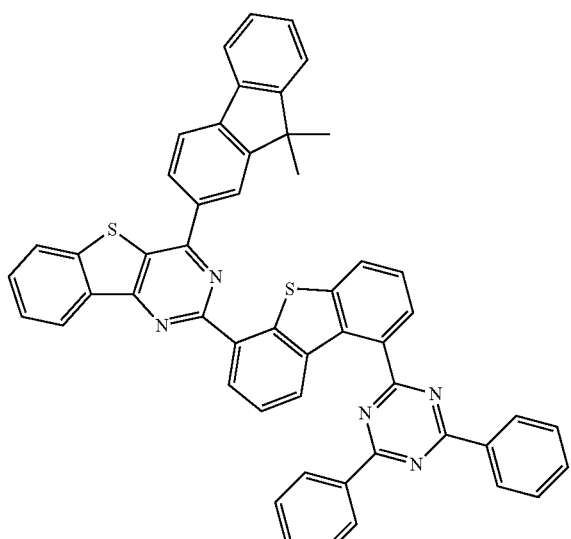
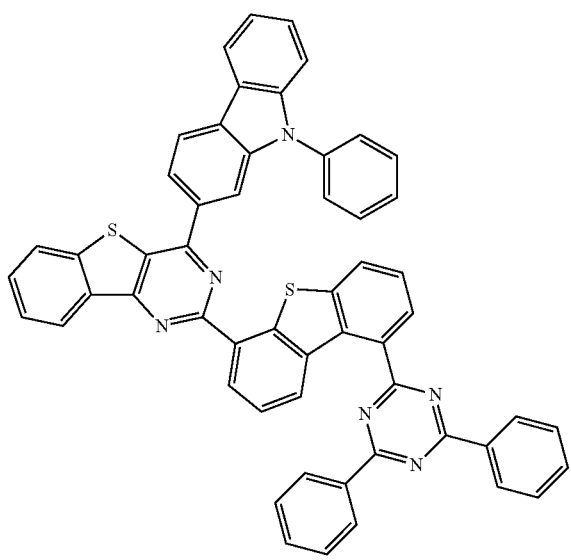
638
-continued
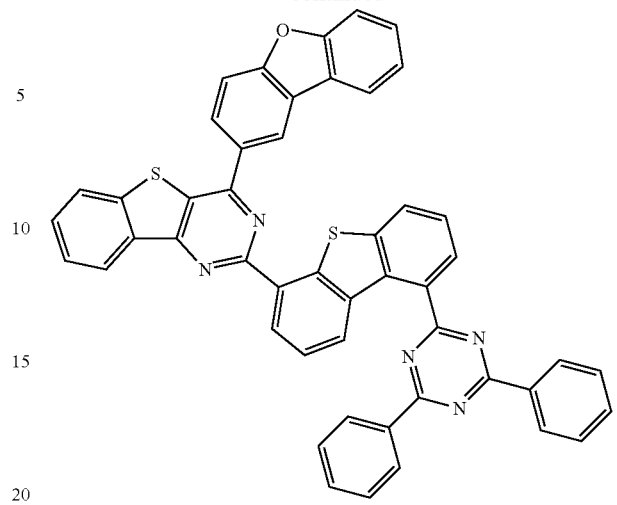
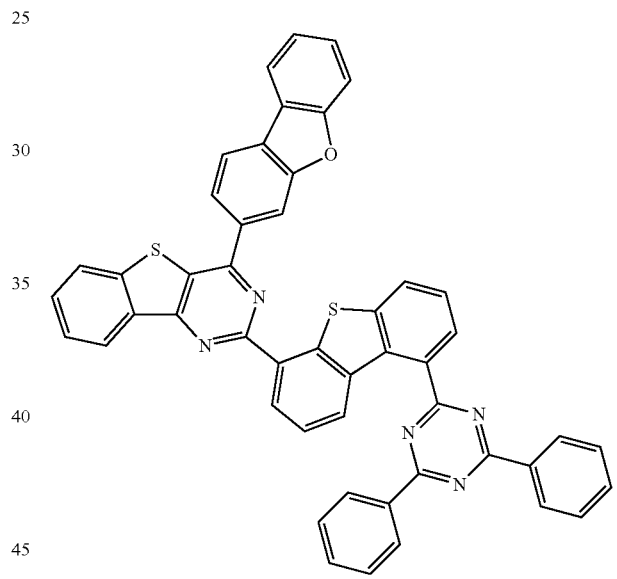
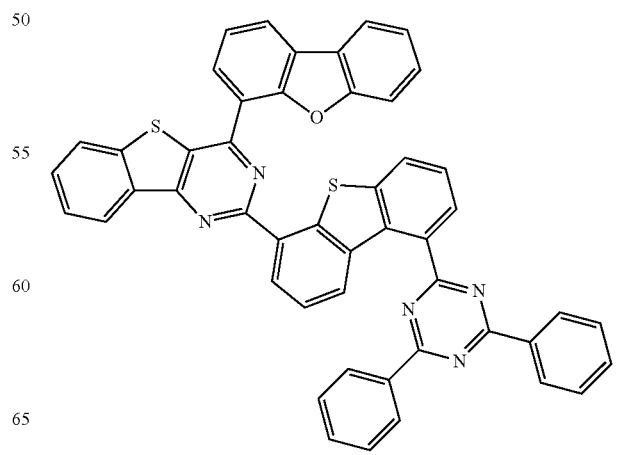

639
-continued
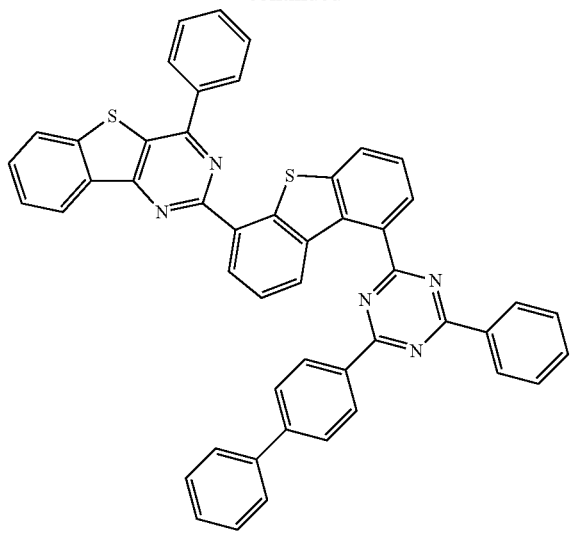
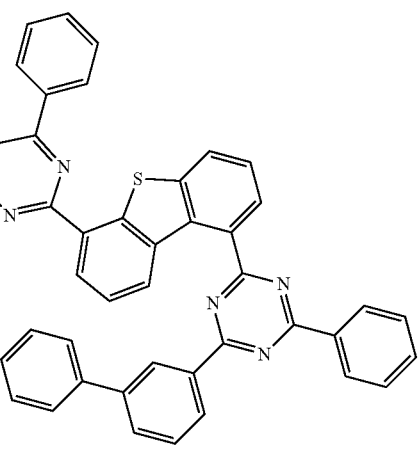
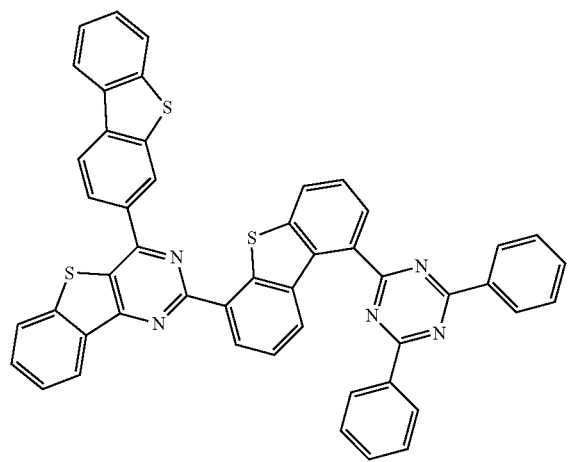
640
-continued
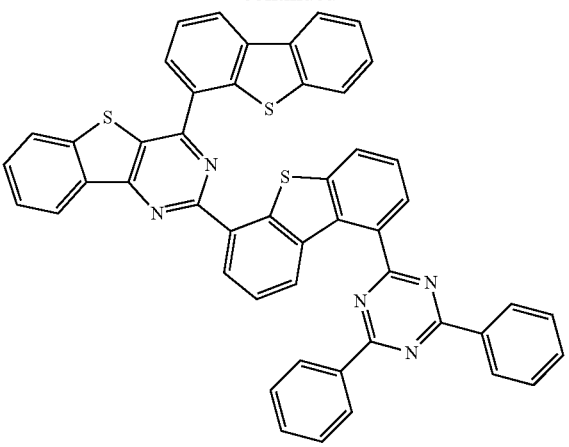
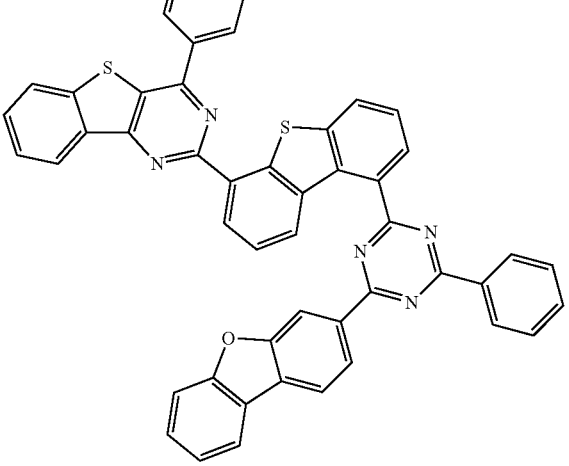

| 641 | 642 |
|---|---|
| -continued | -continued |
| 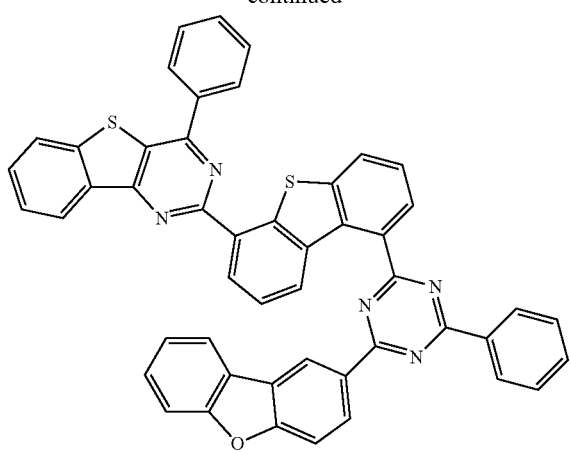 | 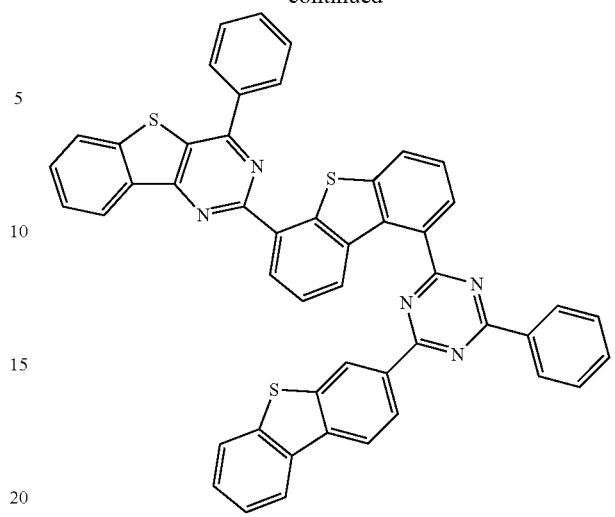 |
| 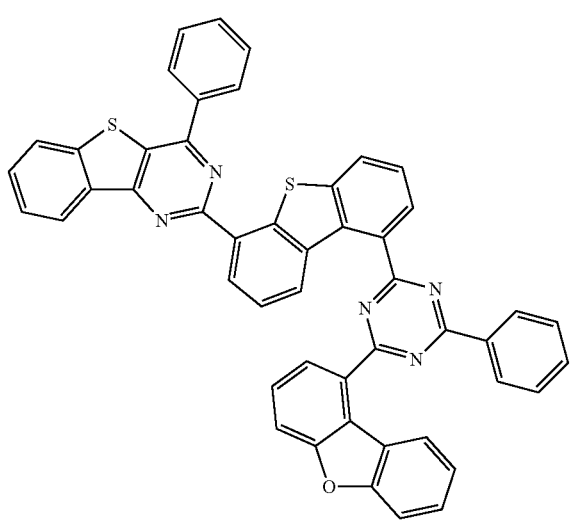 | 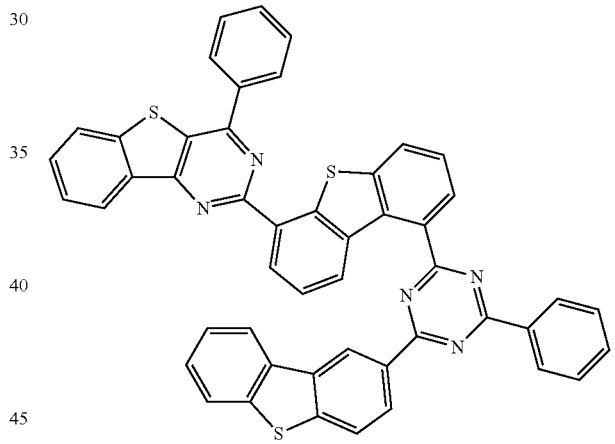 |
| 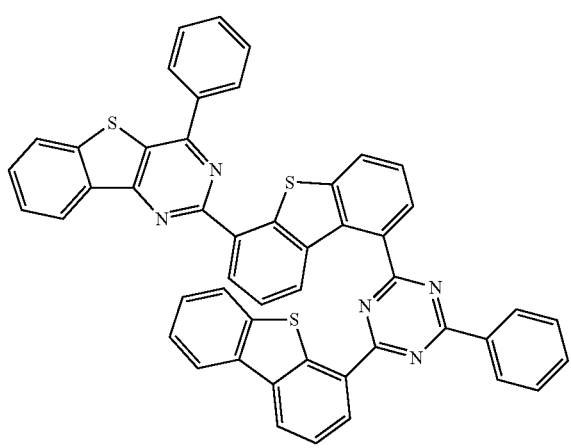 | 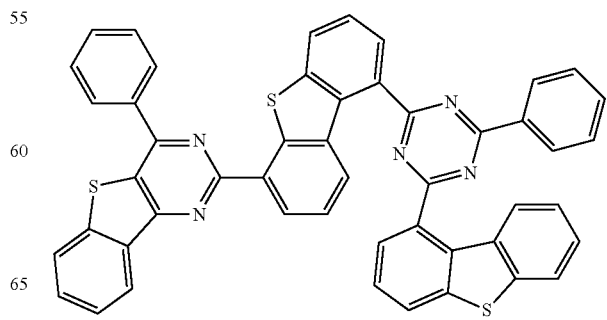 |

643
-continued
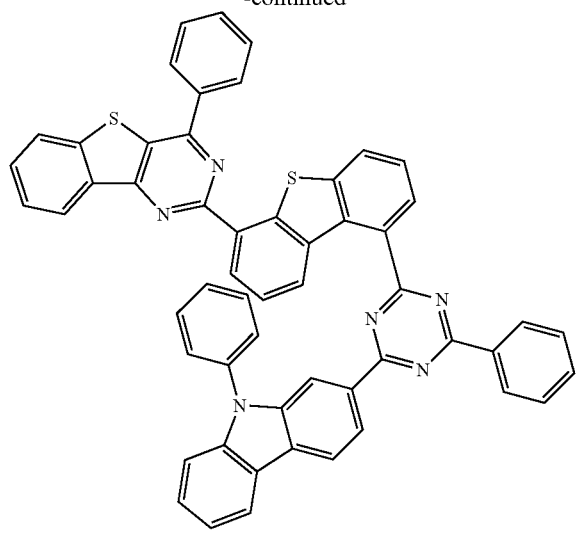
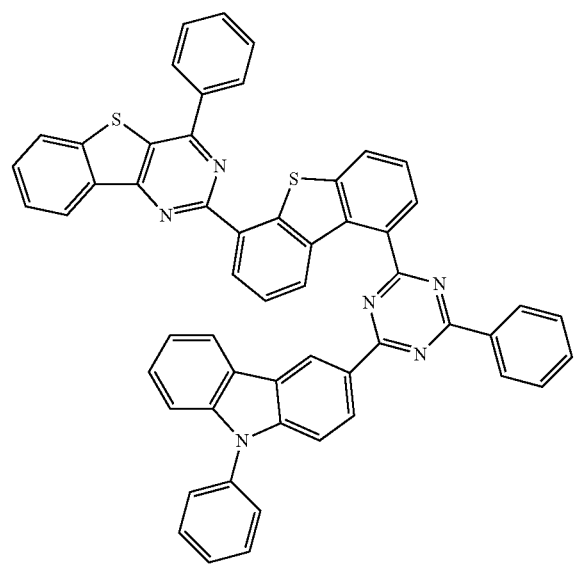
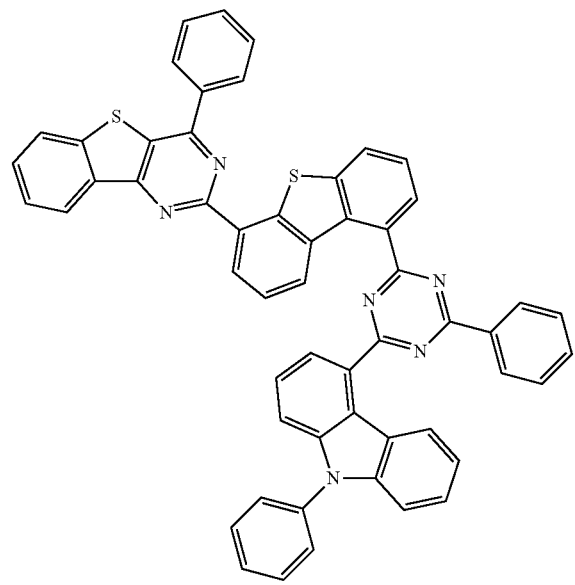
644
-continued
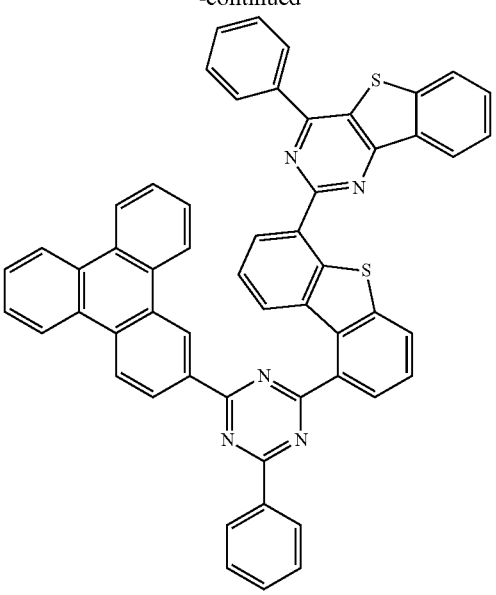
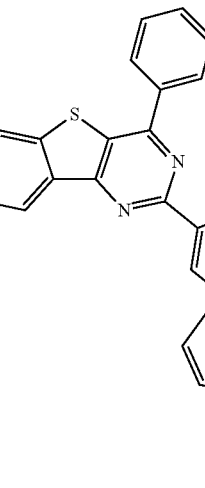
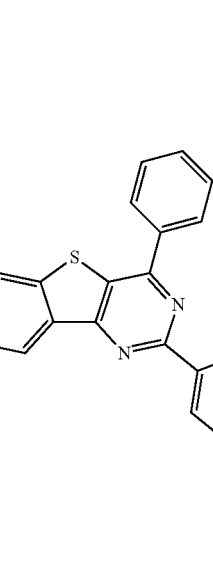

645
-continued
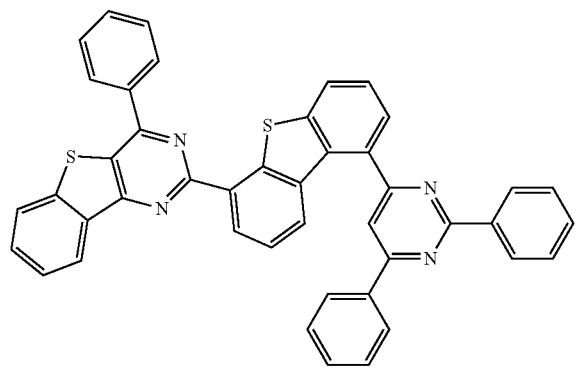
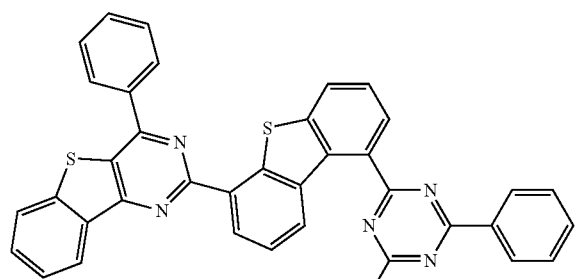
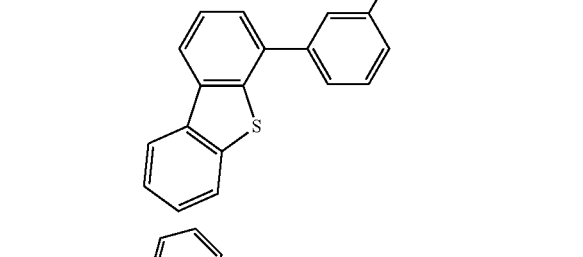
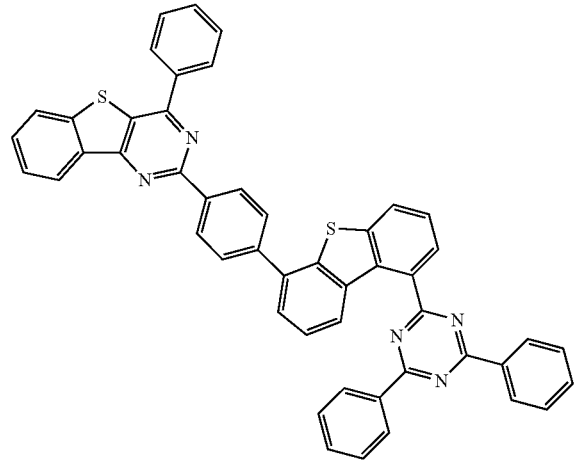
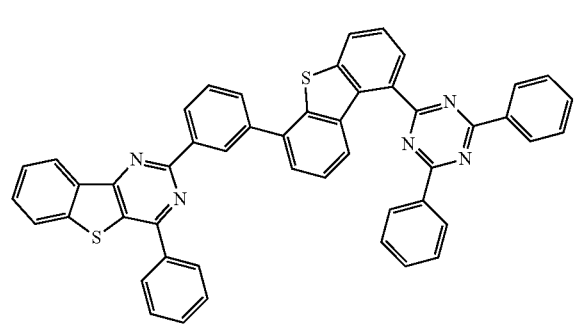
646
-continued
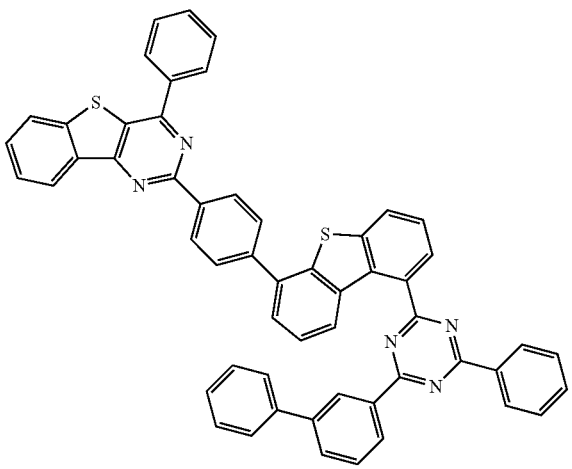
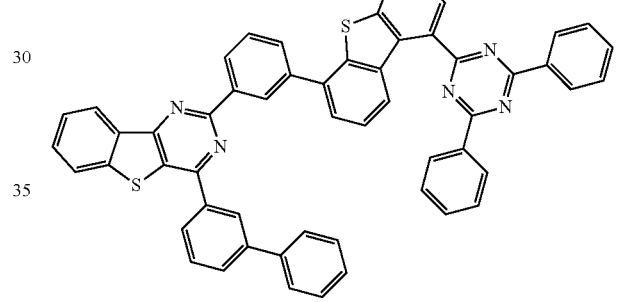
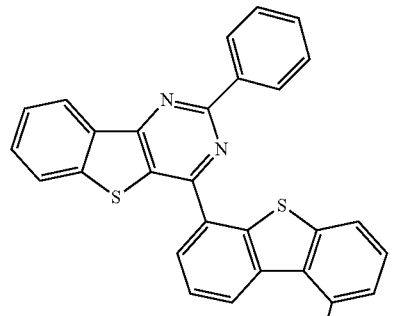

647
-continued
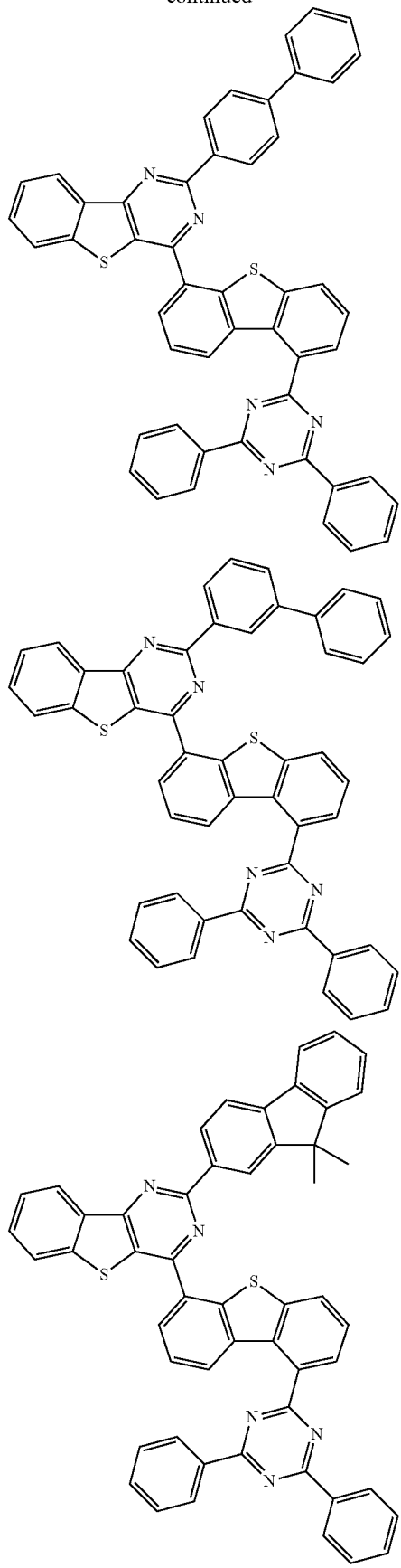
648
-continued

649
-continued
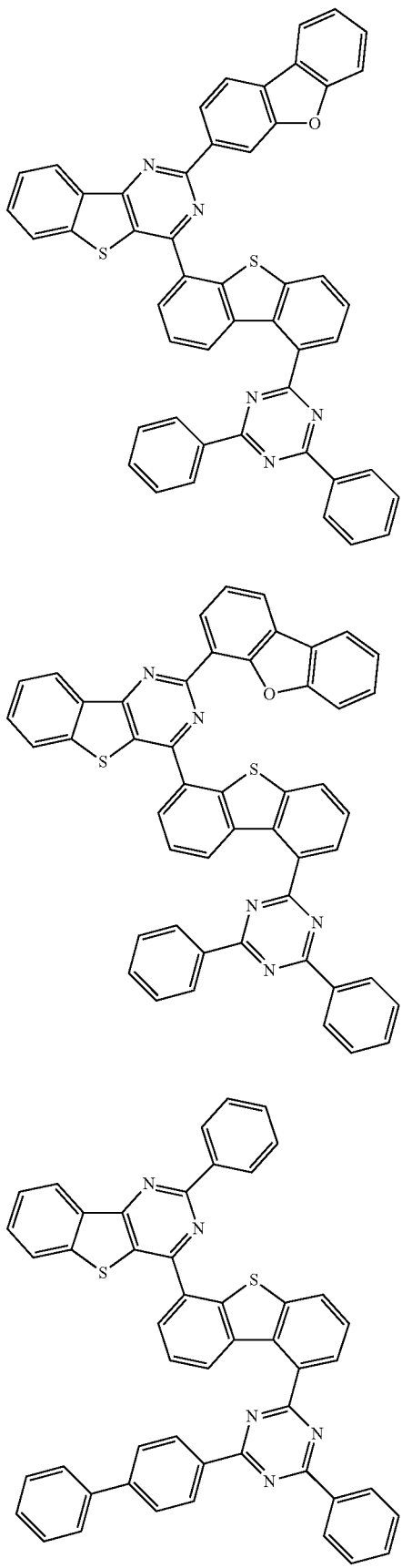
650
-continued
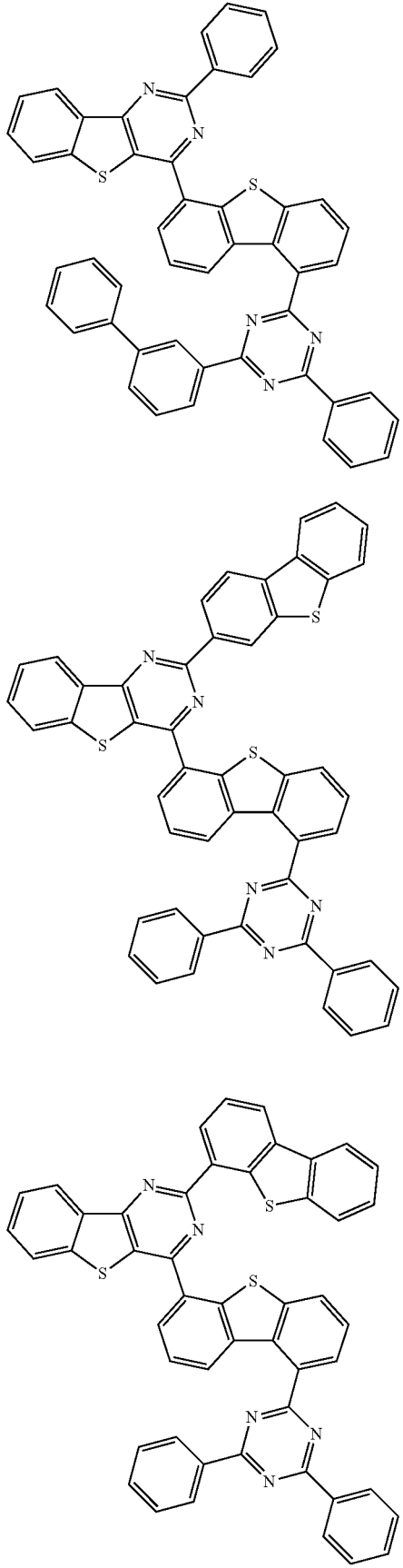

651
-continued
652
-continued
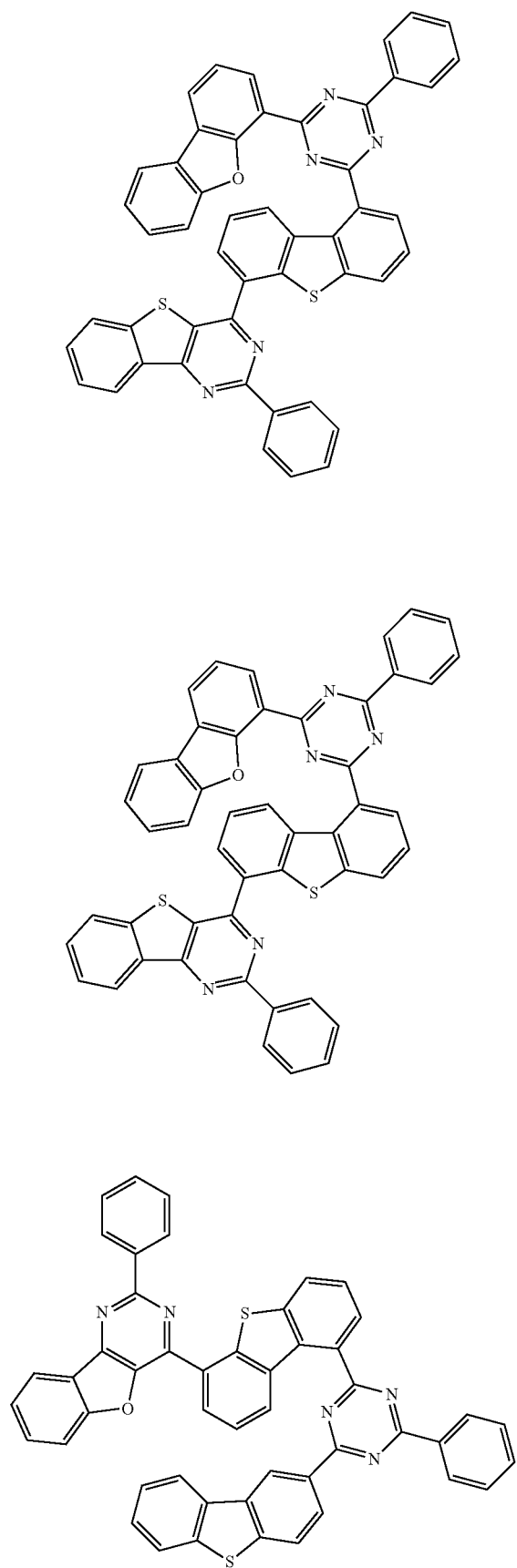
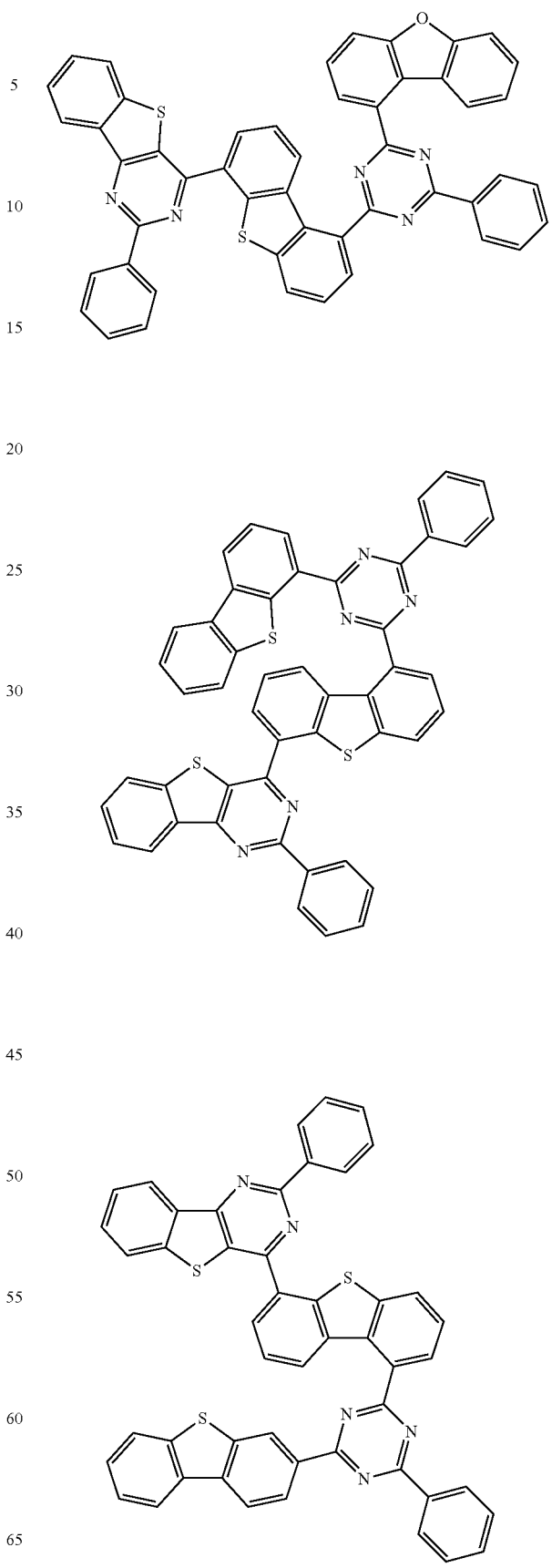

653
-continued
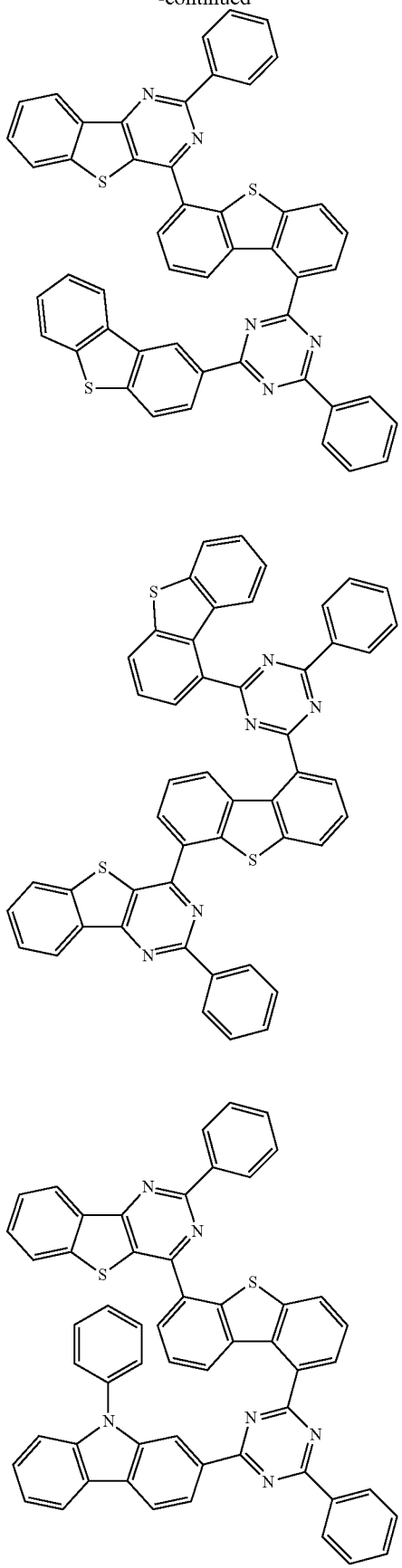
654
-continued
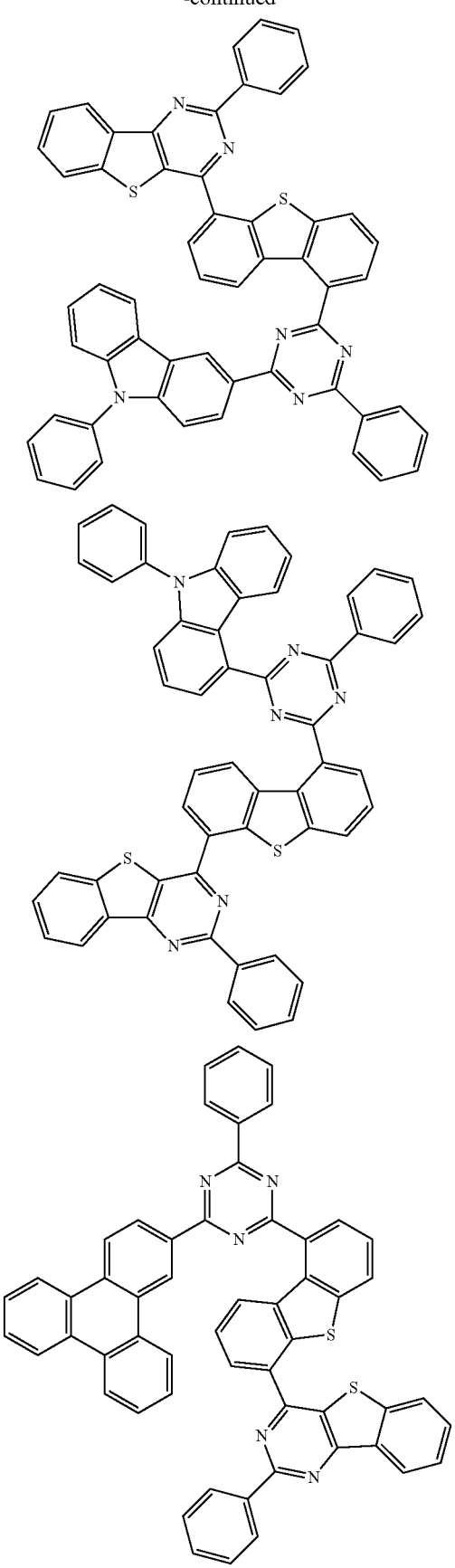

655
-continued
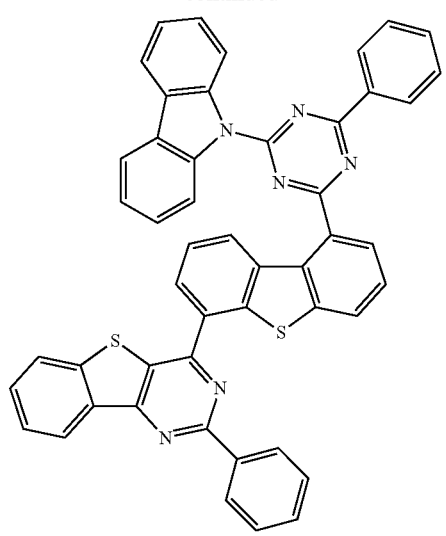
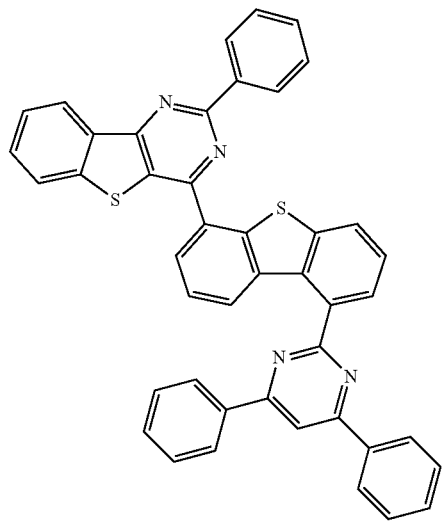
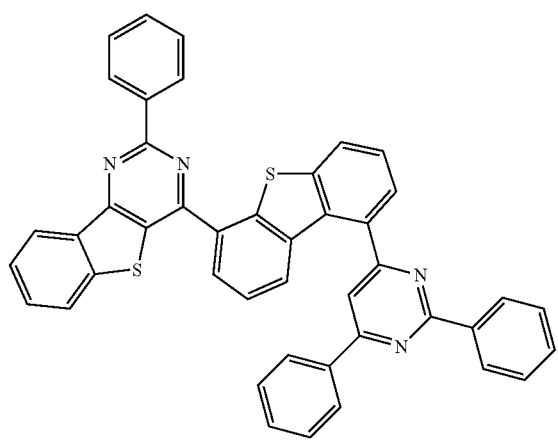
656
-continued
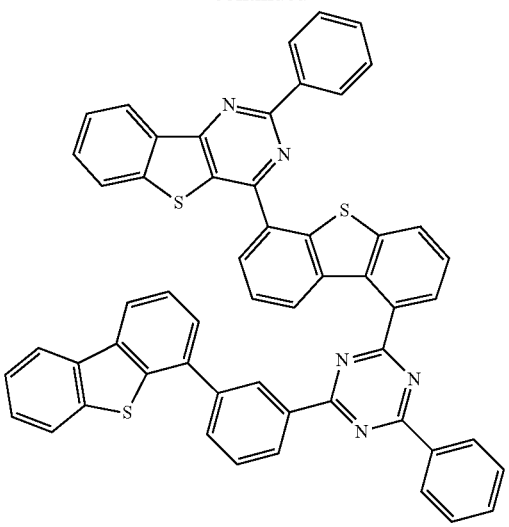
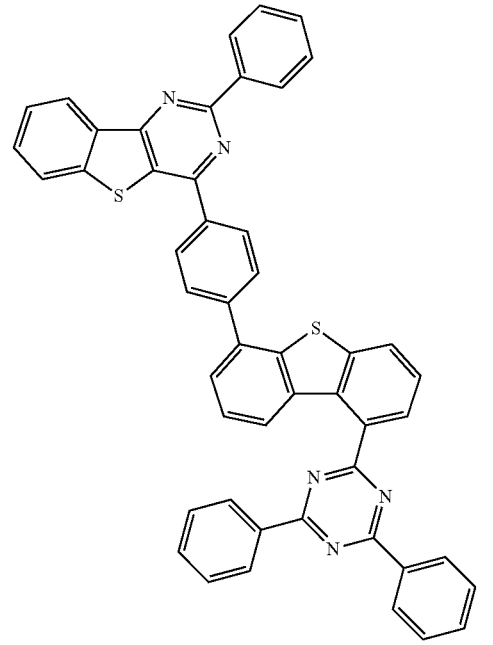
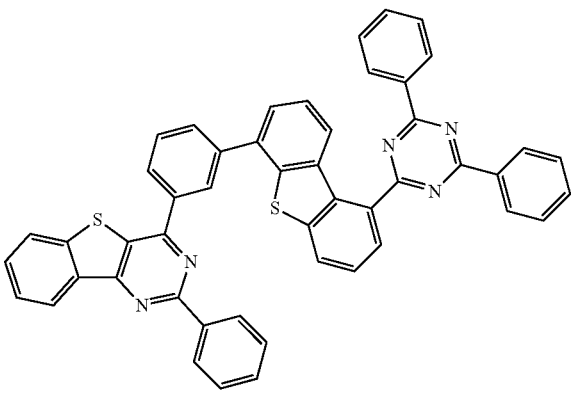

657
-continued
658
-continued
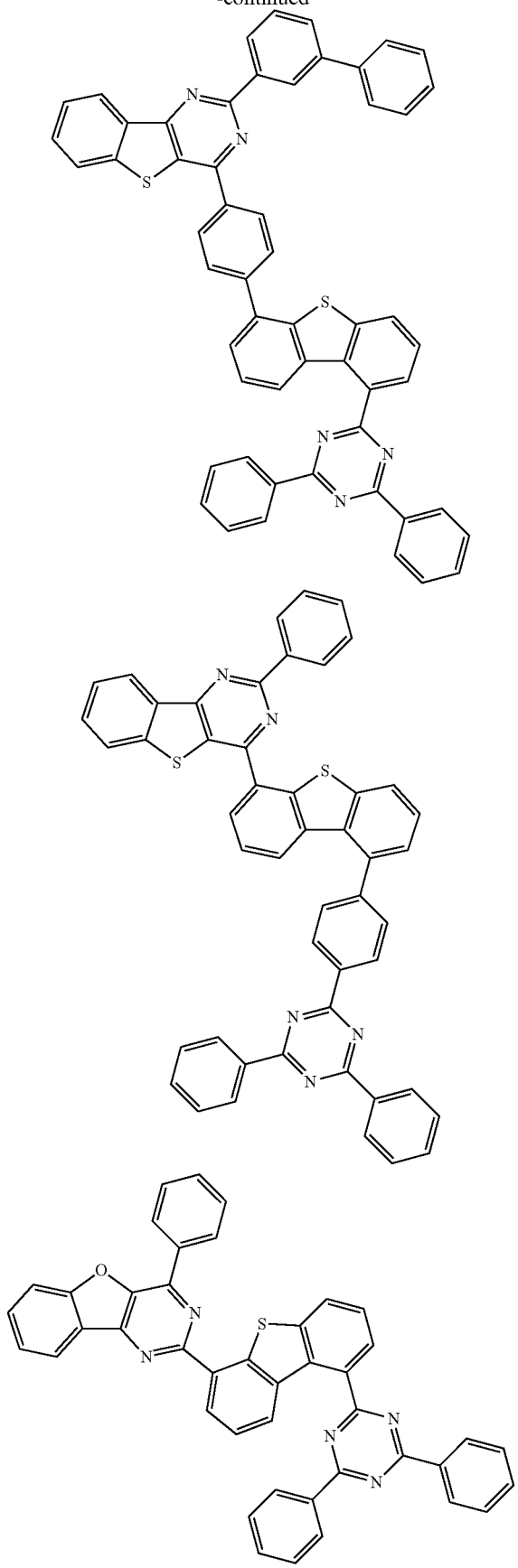
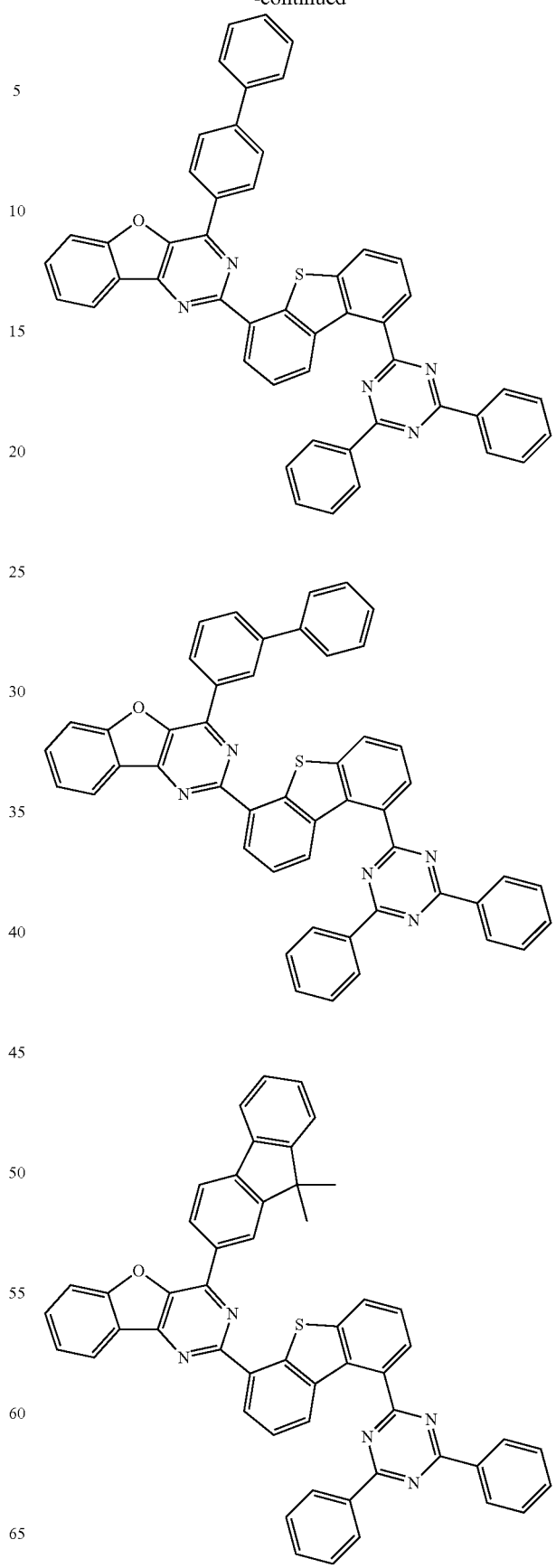

659
-continued
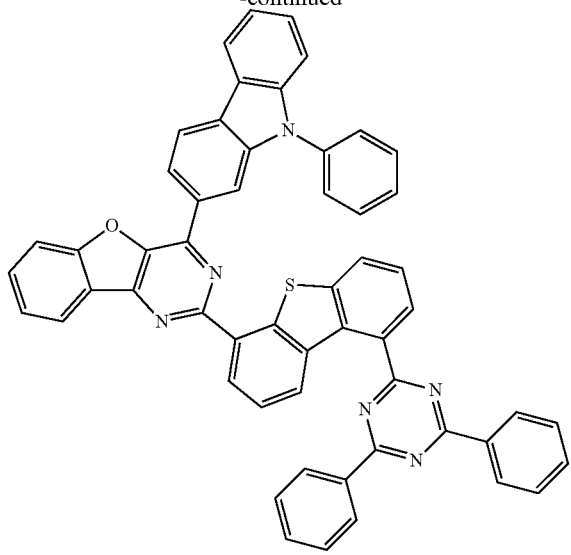
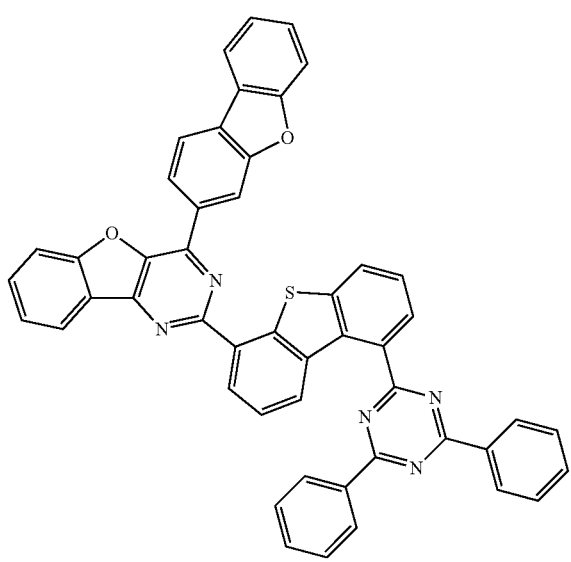
660
-continued
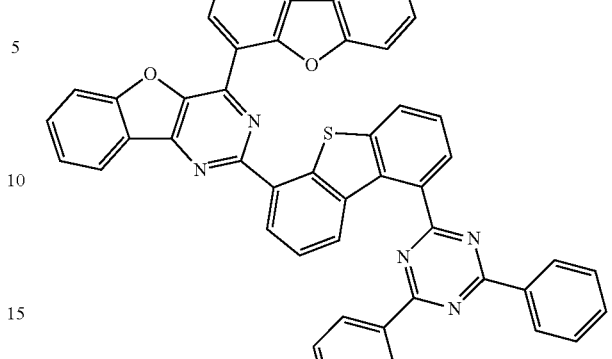
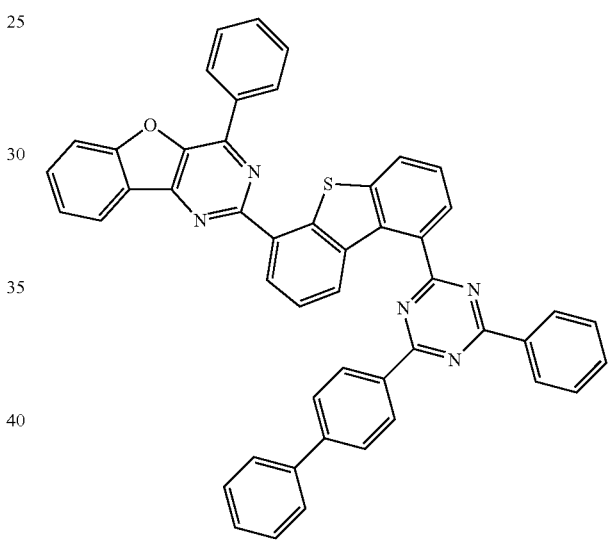
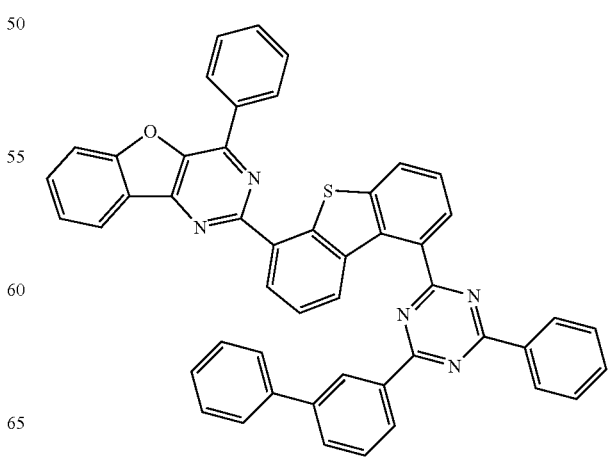

661
-continued
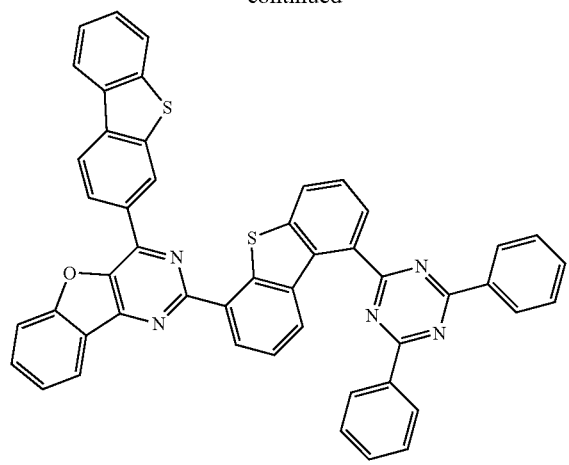
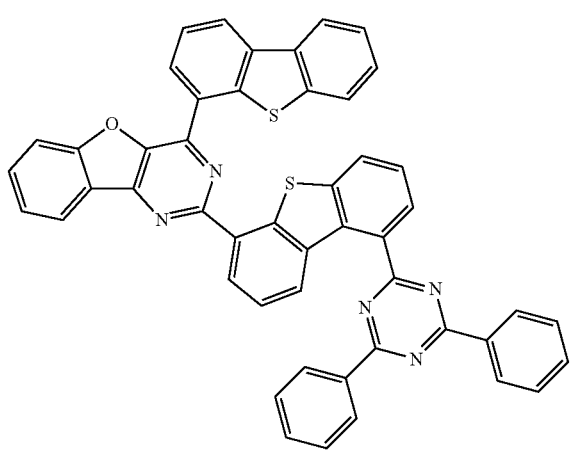
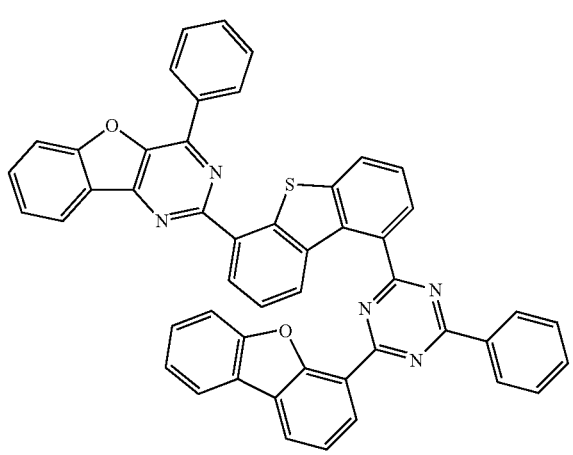
662
-continued
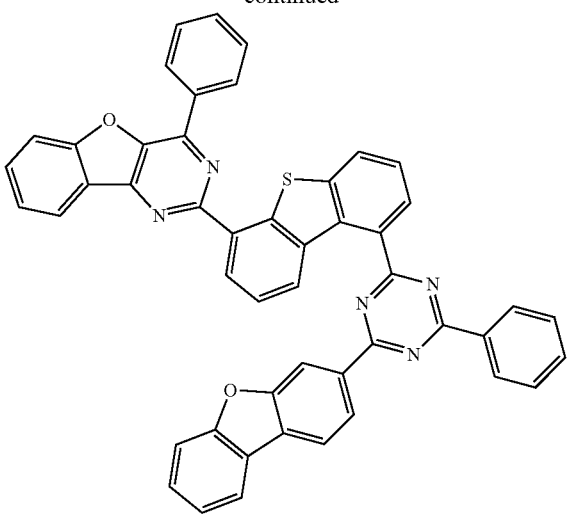
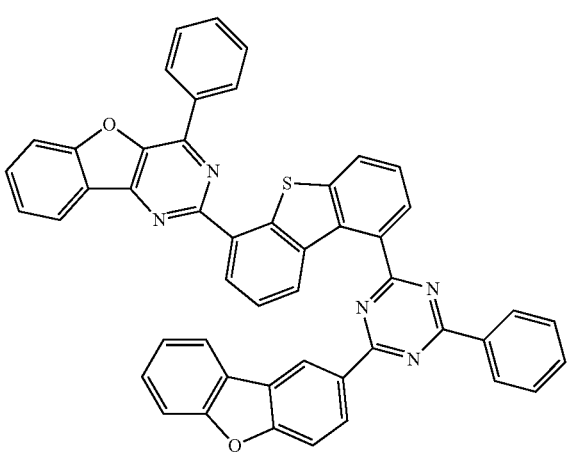
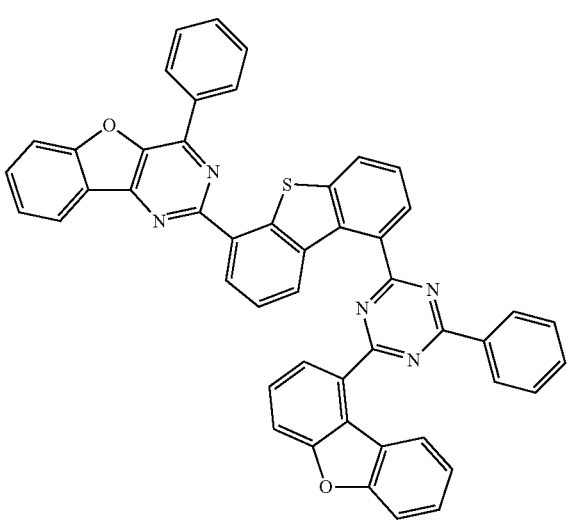

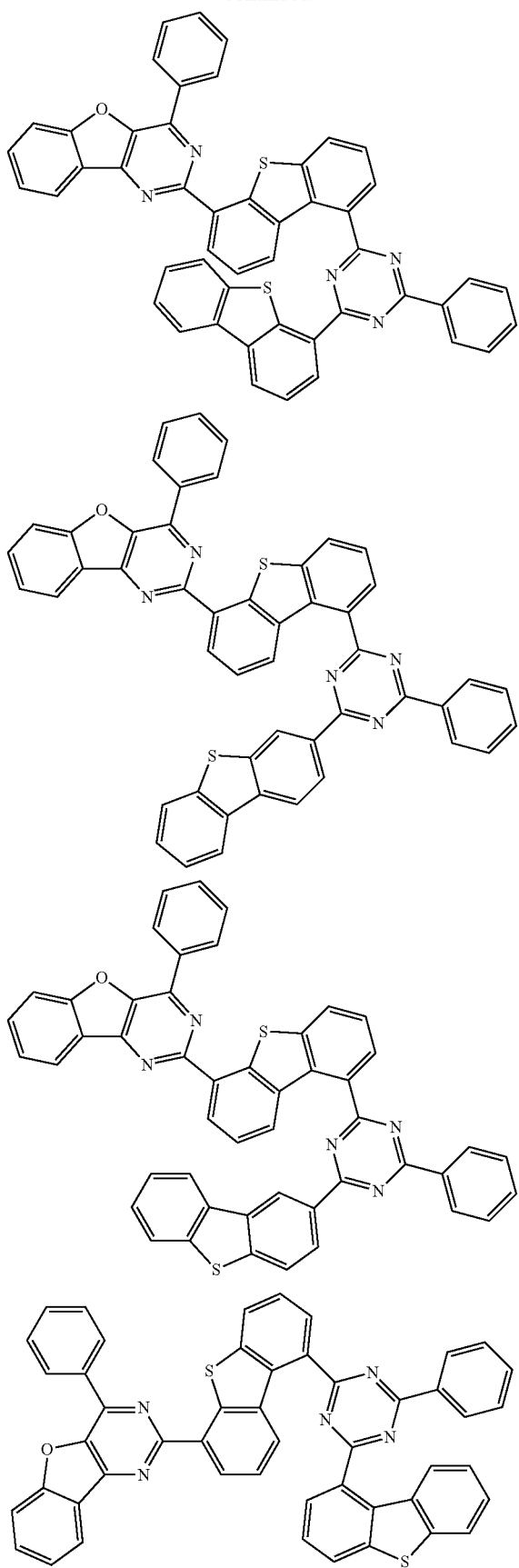
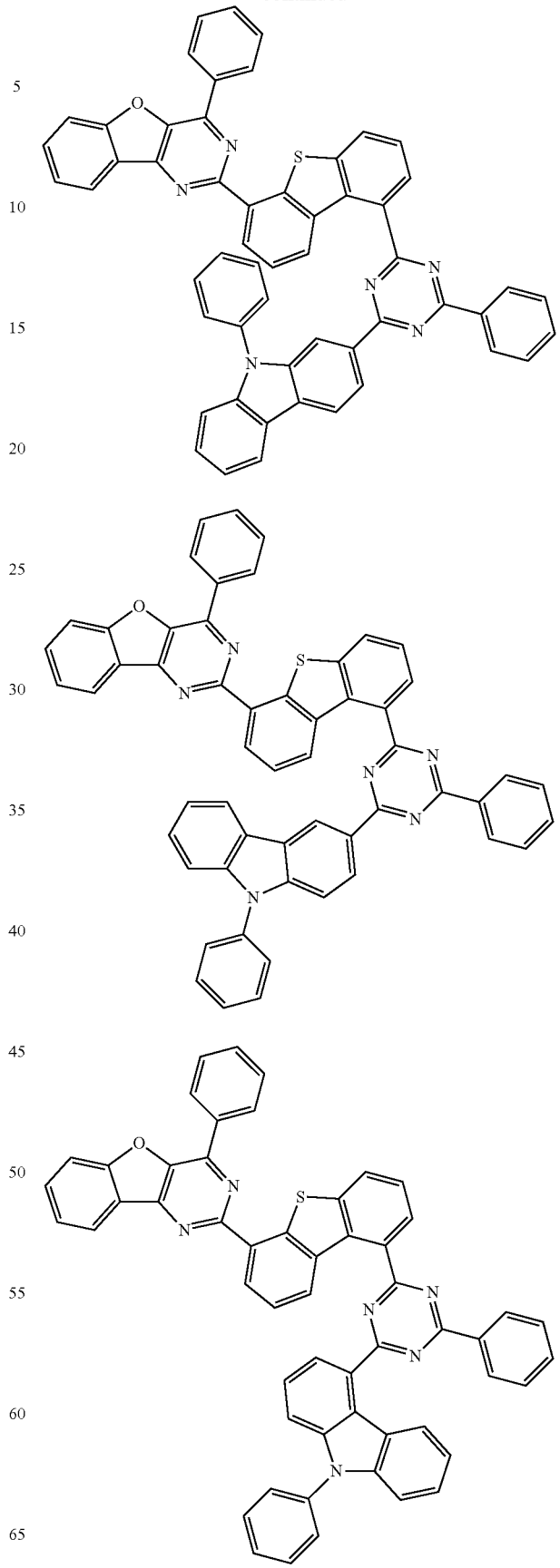

665
-continued
666
-continued
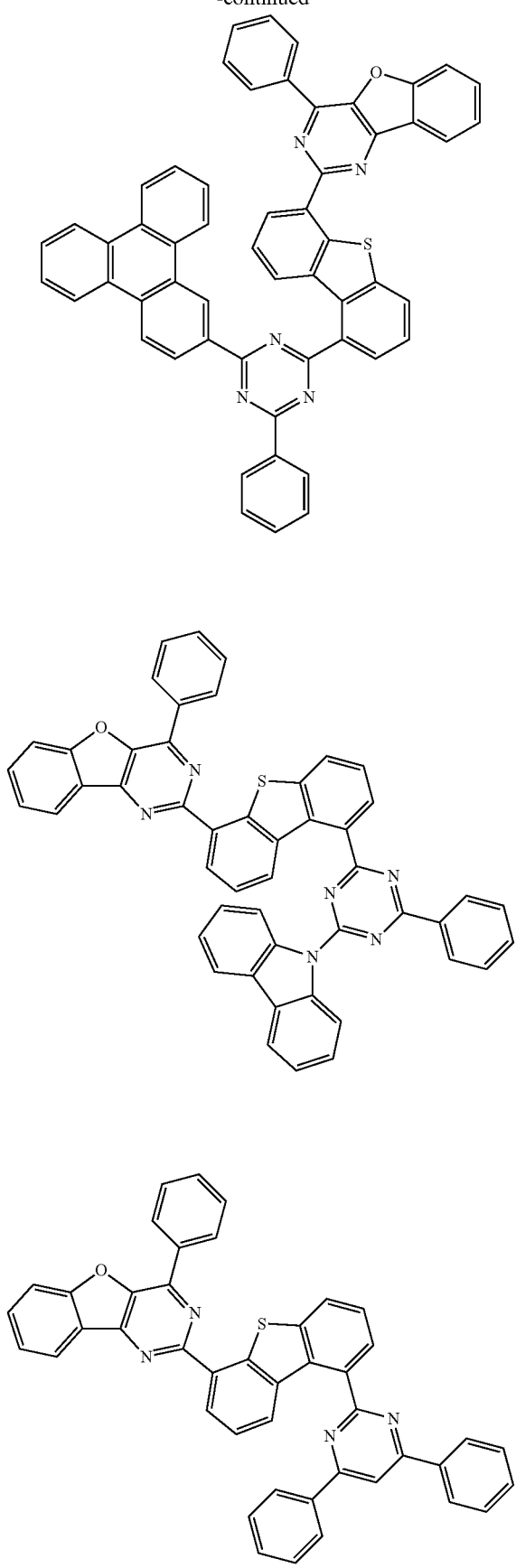
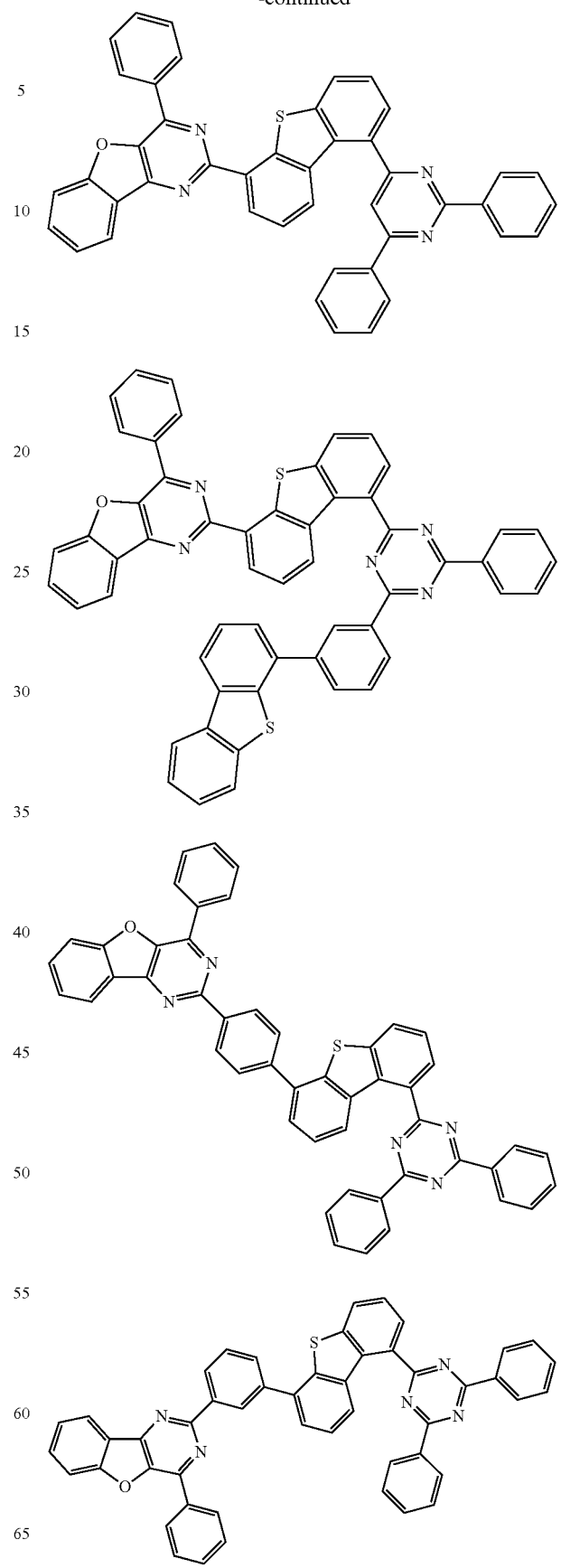

667
-continued
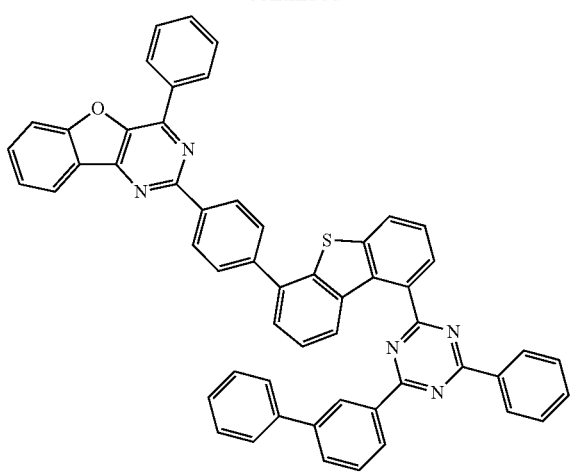
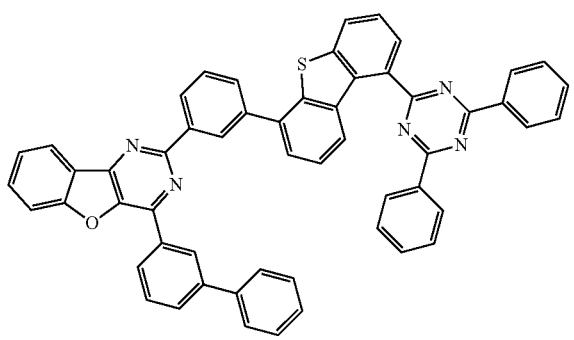
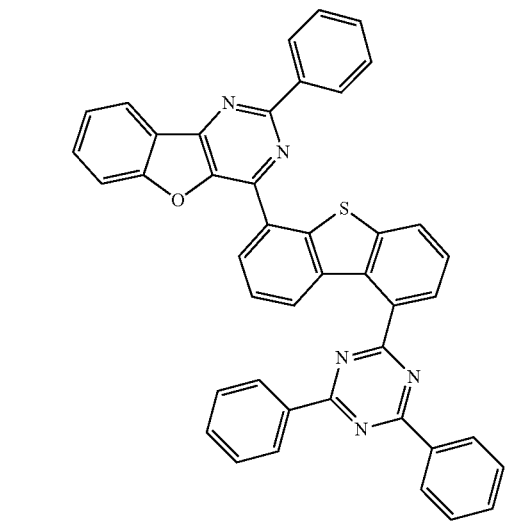
668
-continued
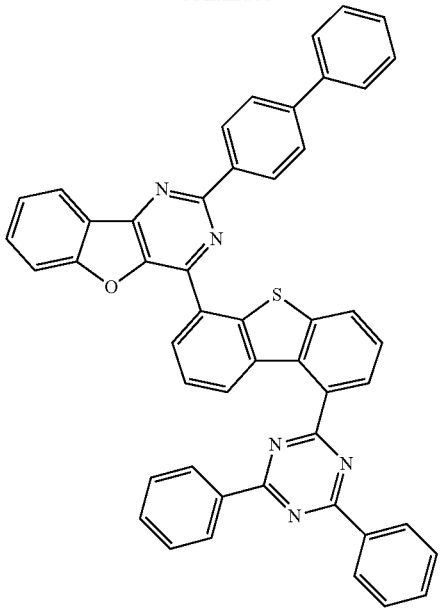
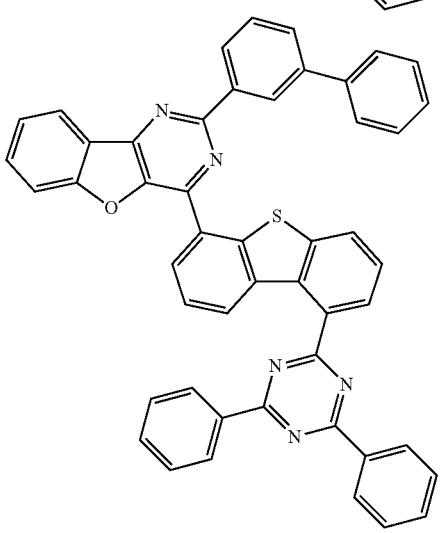
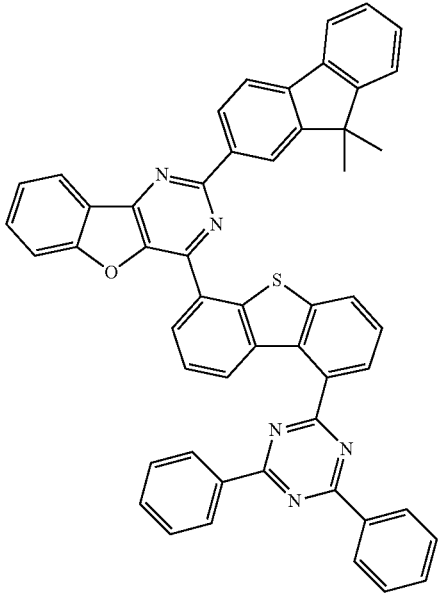

669
-continued
670
-continued
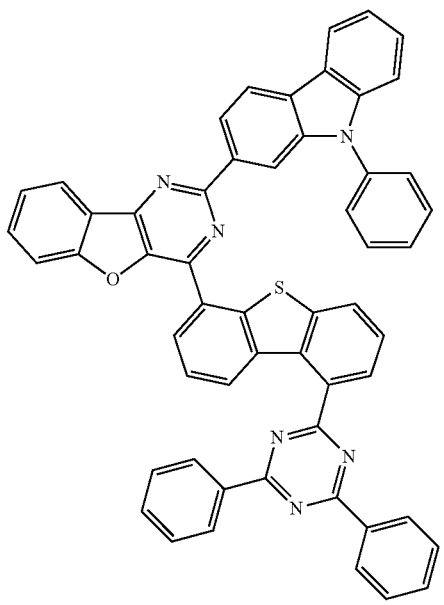
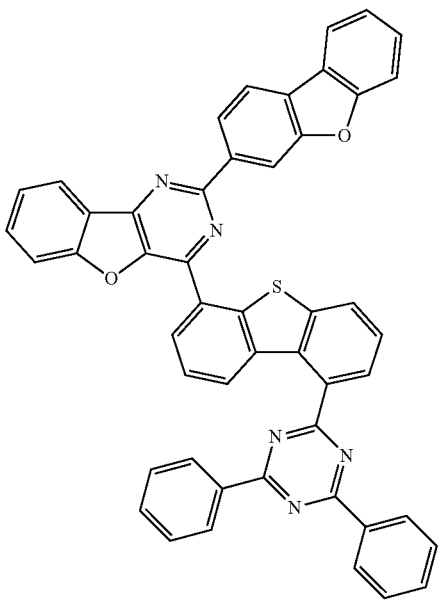
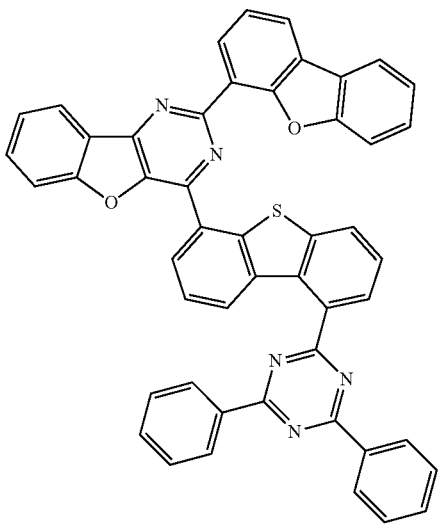
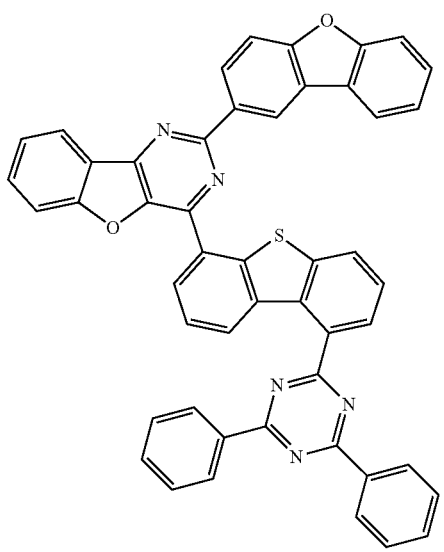
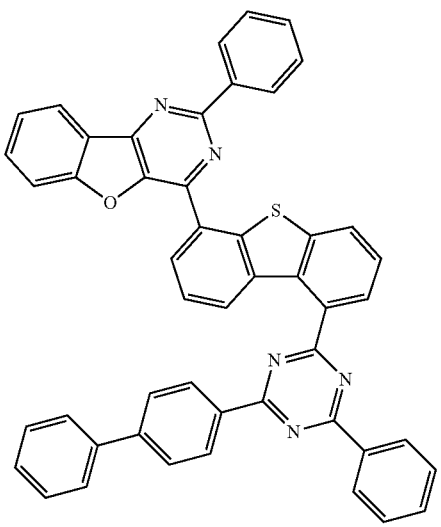

671
-continued
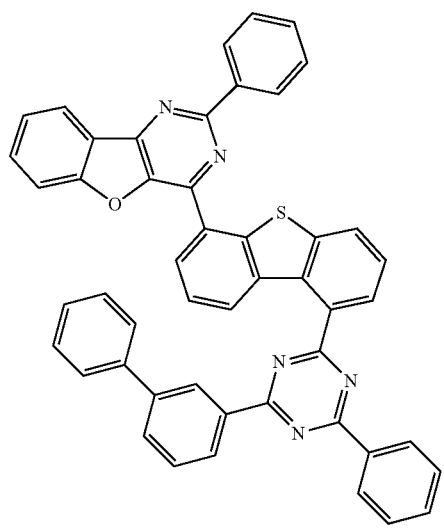
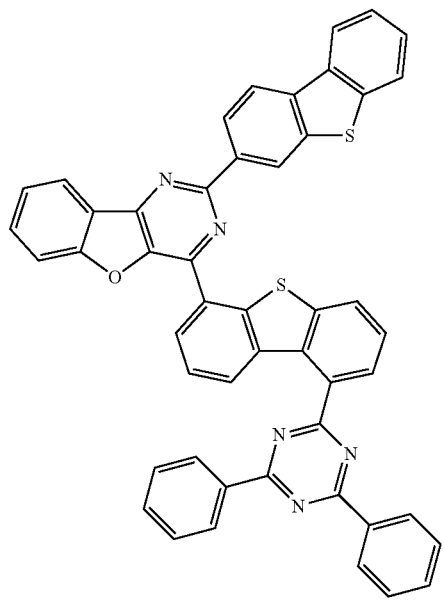
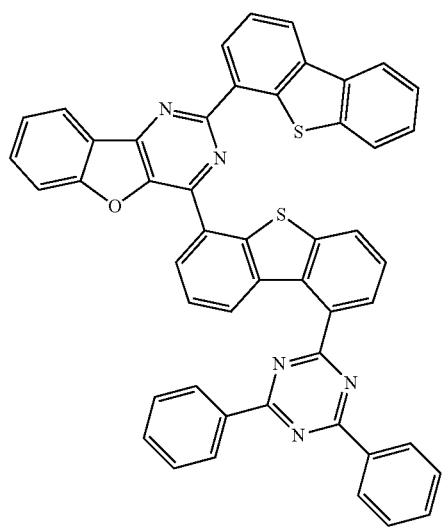
672
-continued
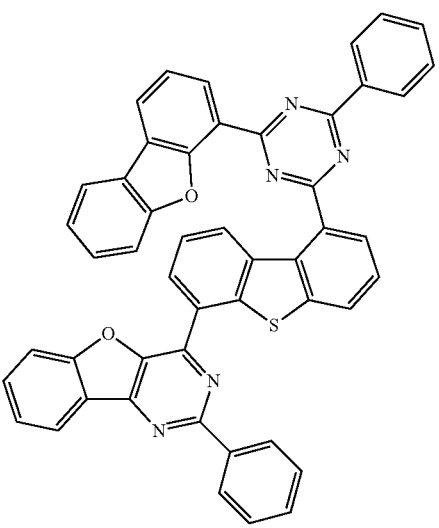
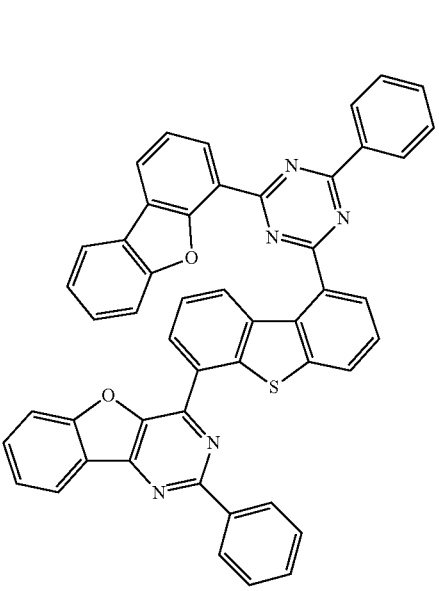
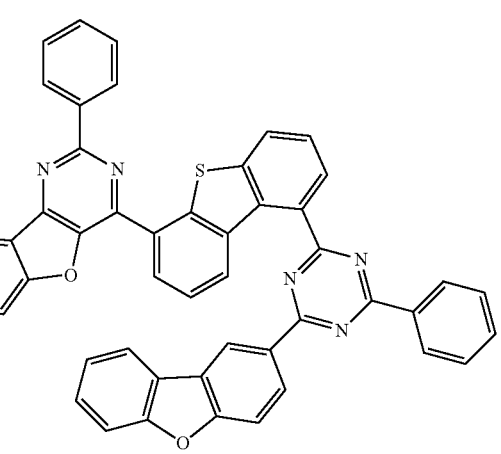

673
-continued
674
-continued
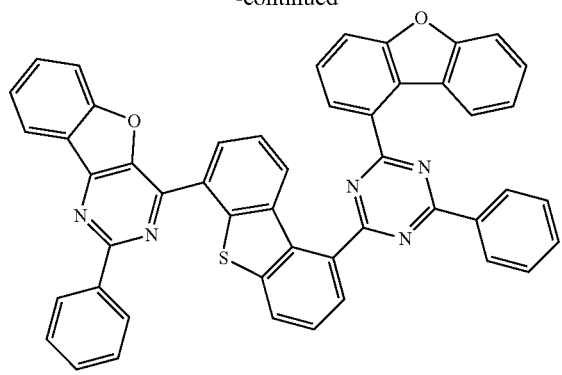
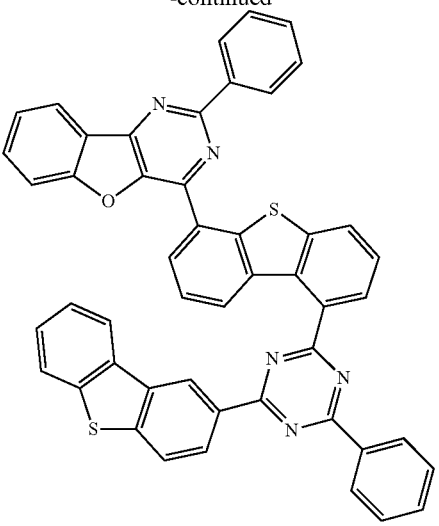
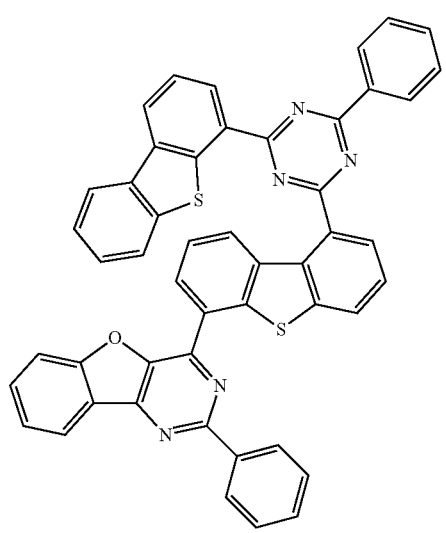
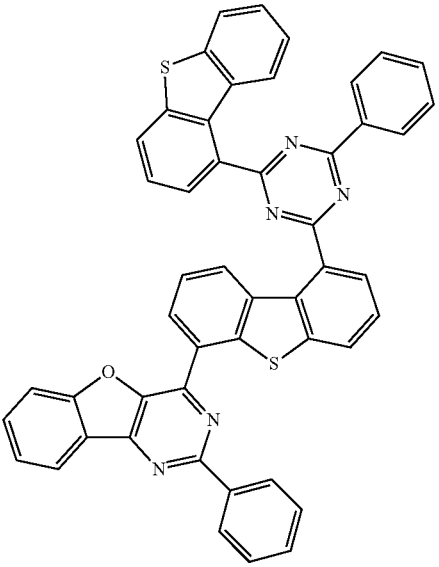
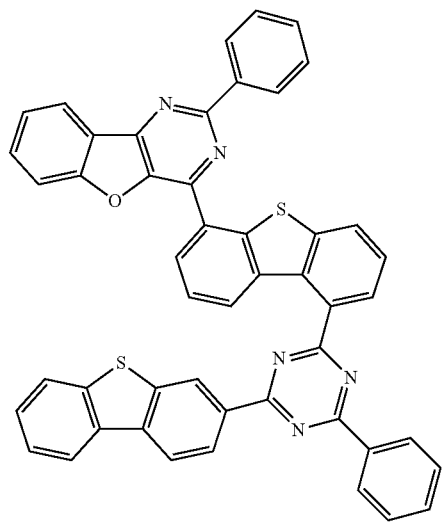
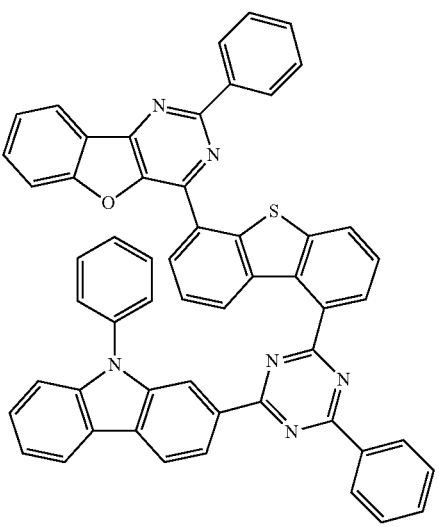

675
-continued
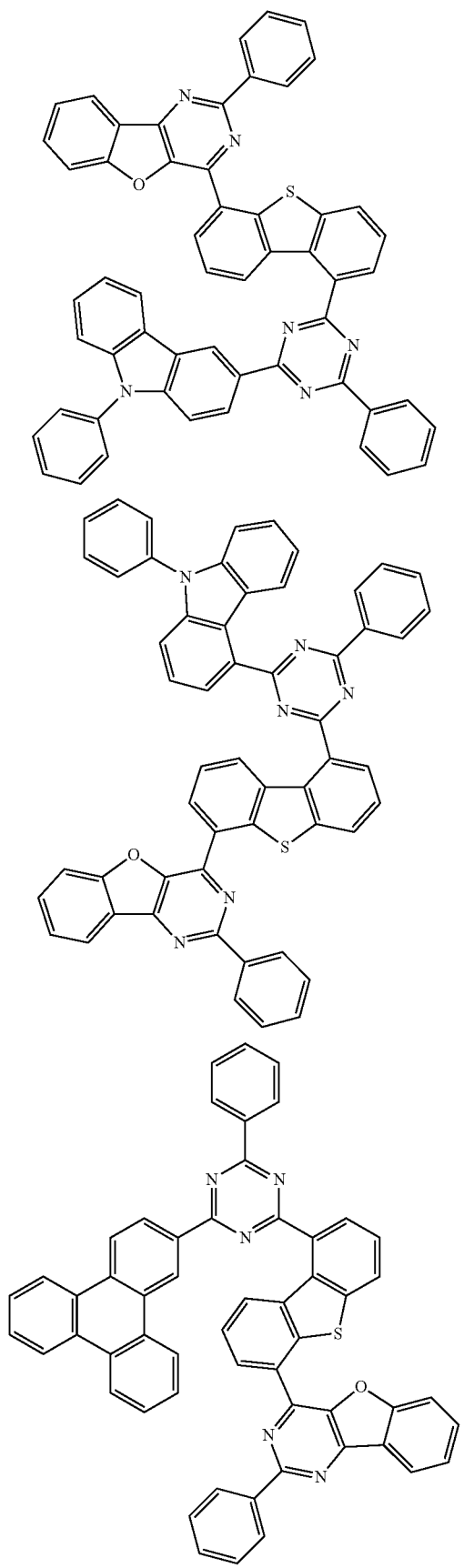
676
-continued
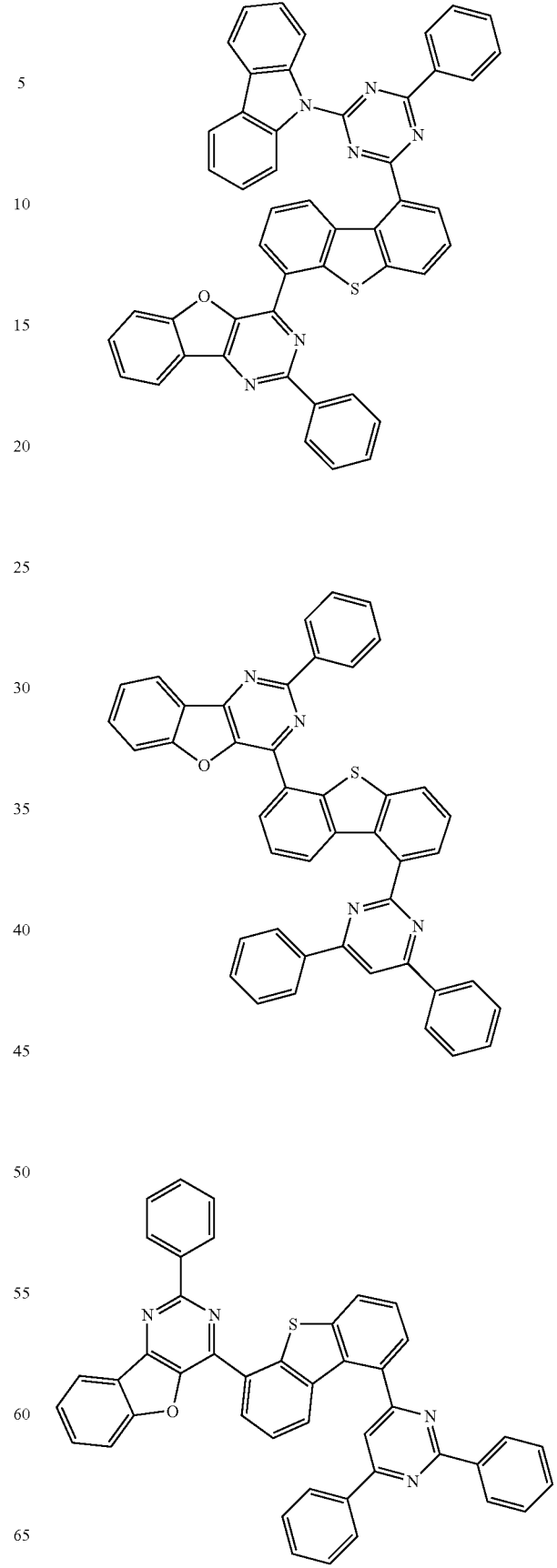

677
-continued

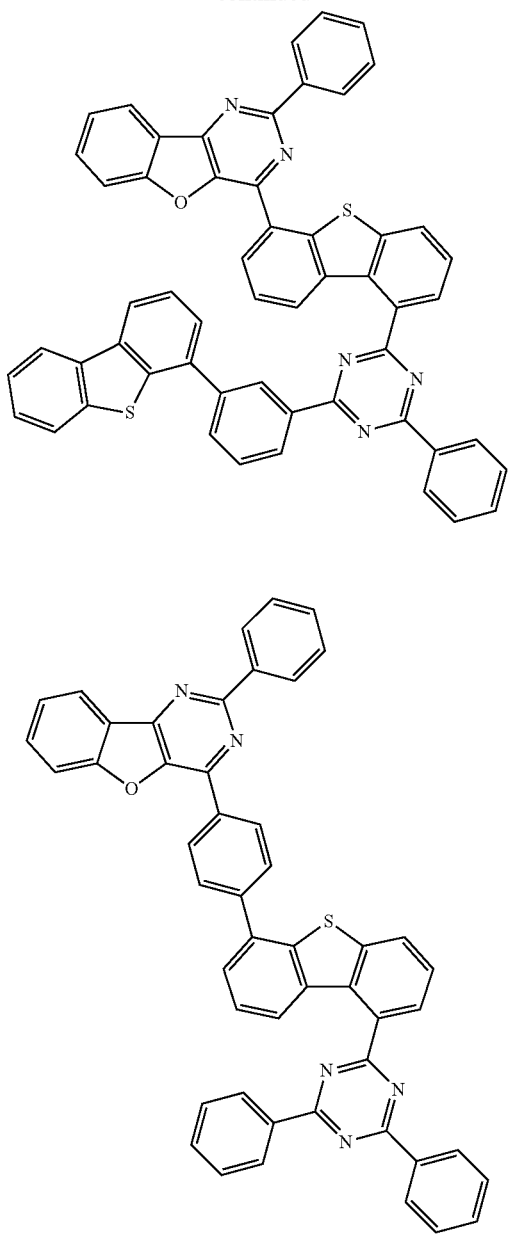

678
-continued

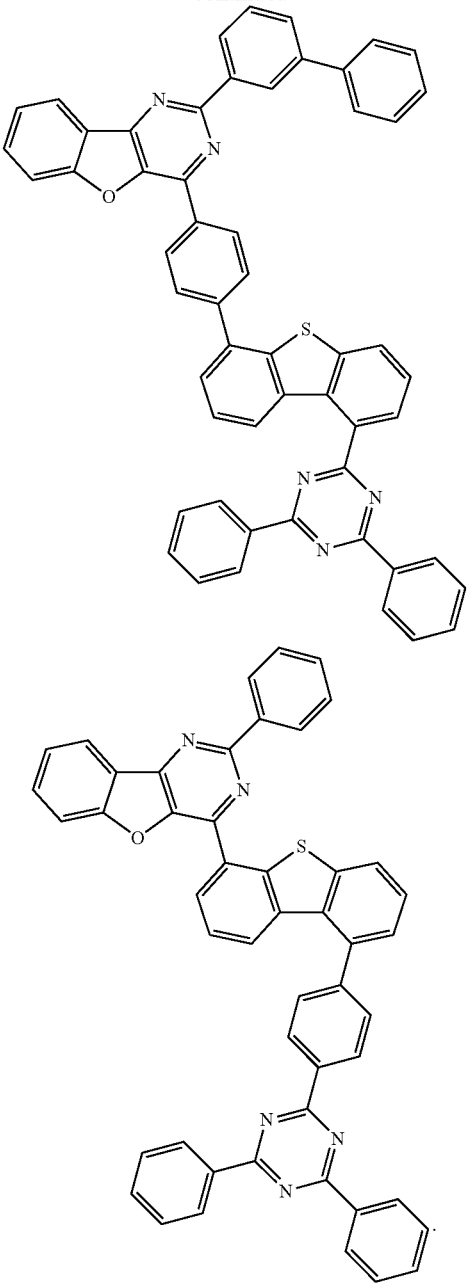

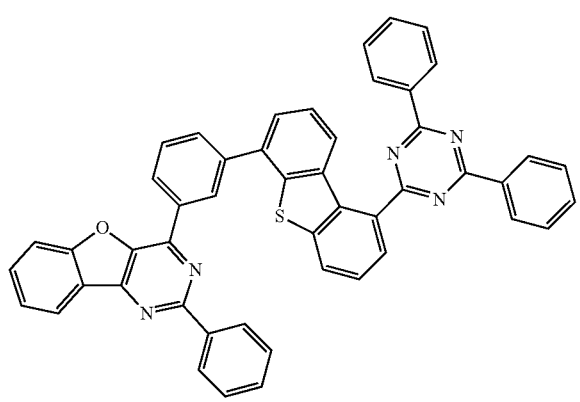

10. An organic light emitting device comprising: a first electrode; a second electrode provided to face the first electrode; and at least one layer of an organic material layer provided between the first electrode and the second electrode, wherein the at least one layer of the organic material layer includes the compound according to claim 1.

11. The organic light emitting device of claim 10, wherein the organic material layer including said compound is a light emitting layer.

12. The organic light emitting device of claim 11, wherein the compound is a host material in the light emitting layer.

13. The organic light emitting device of claim 12, wherein the light emitting layer further includes a dopant material.

14. The organic light emitting device of claim 10, wherein the organic material layer including said compound is an electron injection layer; an electron transport layer; or a layer simultaneously performing electron injection and electron transport.

* * * * *